(12) United States Patent
Jones et al.

(10) Patent No.: US 11,186,577 B2
(45) Date of Patent: Nov. 30, 2021

(54) VASOPRESSIN RECEPTOR ANTAGONISTS AND PRODUCTS AND METHODS RELATED THERETO

(71) Applicant: BlackThorn Therapeutics, Inc., South San Francisco, CA (US)

(72) Inventors: Robert M. Jones, South San Francisco, CA (US); Mariangela Urbano, Del Mar, CA (US); Gary Brandt, South San Francisco, CA (US); David Hardick, Saffron Walden (GB); Chris Knight, Saffron Walden (GB); Jason Tierney, Saffron Walden (GB)

(73) Assignee: BLACKTHORN THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 16/000,869

(22) Filed: Jun. 5, 2018

(65) Prior Publication Data

US 2019/0048013 A1     Feb. 14, 2019

Related U.S. Application Data

(60) Provisional application No. 62/515,473, filed on Jun. 5, 2017.

(51) Int. Cl.

| | | |
|---|---|---|
| *C07D 487/04* | (2006.01) | |
| *A61P 15/08* | (2006.01) | |
| *A61P 15/10* | (2006.01) | |
| *A61P 25/20* | (2006.01) | |
| *A61P 25/24* | (2006.01) | |
| *A61P 9/06* | (2006.01) | |
| *A61P 25/18* | (2006.01) | |
| *A61P 25/22* | (2006.01) | |
| *C07D 491/04* | (2006.01) | |
| *C07D 498/04* | (2006.01) | |

(52) U.S. Cl.
CPC .............. *C07D 487/04* (2013.01); *A61P 9/06* (2018.01); *A61P 15/08* (2018.01); *A61P 15/10* (2018.01); *A61P 25/18* (2018.01); *A61P 25/20* (2018.01); *A61P 25/22* (2018.01); *A61P 25/24* (2018.01); *C07D 491/04* (2013.01); *C07D 498/04* (2013.01)

(58) Field of Classification Search
CPC .......... A61P 15/08; A61P 15/10; A61P 25/18; A61P 25/20; A61P 25/22; A61P 25/24; A61P 9/06; C07D 487/04; C07D 491/04; C07D 498/04

See application file for complete search history.

(56) References Cited

FOREIGN PATENT DOCUMENTS

| WO | WO-2004074291 A1 * | 9/2004 | ........... C07D 401/04 |
| WO | 2010/054961 A1 | 5/2010 | |

* cited by examiner

*Primary Examiner* — Kara R McMillian
(74) *Attorney, Agent, or Firm* — Seed IP Law Group LLP

(57) ABSTRACT

Compounds are provided that antagonize vasopressin receptors, particularly the V1a receptor products containing such compounds, as well as to methods of their use and synthesis. Such compounds have the structure of Formula (I), or a pharmaceutically acceptable isomer, racemate, hydrate, solvate, isotope, or salt thereof:

(I)

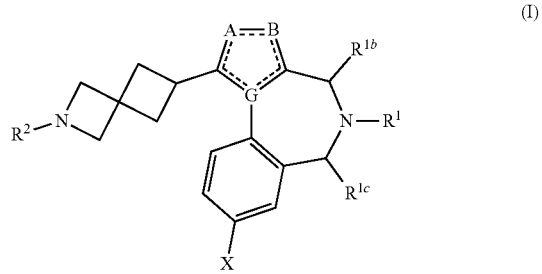

wherein A, B, G, $R^1$, $R^{1b}$, $R^{1c}$, $R^2$ and X are as defined herein.

11 Claims, No Drawings

VASOPRESSIN RECEPTOR ANTAGONISTS AND PRODUCTS AND METHODS RELATED THERETO

FIELD OF THE INVENTION

The invention relates to vasopressin receptor antagonists and to products containing the same, as well as to methods of their use and preparation.

BACKGROUND

Arginine vasopressin (AVP) is a naturally occurring neurohormone released in the brain and the blood stream. AVP is important in regulating water conservation, blood pressure and pituitary adrenocorticotropic hormone (ACTH) secretion and exerts its effects on physiology and behavior by binding to specific G protein-coupled receptors in the central nervous system and certain peripheral sites or tissues. Within the brain, AVP regulates circadian rhythms, facilitates hippocampal learning and memory and plays an important role in mediating social behaviors by acting in limbic circuits that are dysregulated in neurobehavioral disorders.

Three distinct AVP receptor subtypes have been identified on pharmacological and functional bases: V1a, V1b and V2. These receptors are located in the liver, vessels (coronary, renal, cerebral), platelets, kidney, uterus, adrenal glands, pancreas, central nervous system or pituitary gland. AVP is involved in the regulation of several functions, such as cardiovascular, hepatic, pancreatic, antidiuretic, and platelet-aggregating effects, and effects on the central and peripheral nervous system and on the uterine sphere. The effects of the AVP receptors depends on where they are located. The V1a receptor is found throughout the limbic system and cortex of the brain, and in the smooth muscle of blood vessels, uterus, and heart muscle. The V1b receptor is also located in limbic system and the pituitary gland. V2 receptors are located on the collecting ducts of nephrons in the kidney and have been a target for therapeutic approaches to the treatment of cardiovascular conditions.

Vasopressin functions as a neurochemical signal in the brain to affect social behavior. The V1a receptor is extensively expressed in the brain and particularly in limbic areas like the amygdala, lateral septum and hippocampus which are known to have an important role in the regulation of majority of the known effects of AVP, including anxiety, memory and learning, social cognition, aggressive behavior, affiliation, depression and the like. The V1a receptor is implicated in other neuropsychological disorders such as autistic spectrum disorders, schizophrenia, aggression, aggressive behavior and obsessive-compulsive disorders. The V1a receptor also mediates the cardiovascular effects of vasopressin in the brain by centrally regulating blood pressure and heart rate in the solitary tract nucleus and peripherally by inducing the contraction of vascular smooth muscles.

Use of vasopressin receptor antagonists, particularly V1a receptor antagonists, provides significant promise for the treatment of a variety of disorders which may benefit from antagonism of the V1a receptor. As a result, a number of V1a antagonists have been taken forward for clinical use and/or development. However, despite the advances made in this field, there remains a significant need for new and/or improved V1a receptor antagonists, as well as for pharmaceutical products containing the same, and for methods related to their use and manufacture.

SUMMARY OF THE INVENTION

The present invention is directed to compounds that antagonize vasopressin receptors, particularly the V1a receptor, to compositions containing the same, and to methods of their preparation and use for treatment of a malcondition wherein antagonism of the V1a receptor is medically indicated or beneficial.

In an embodiment, compounds are provided having the structure of Formula (I), or a pharmaceutically acceptable isomer, racemate, hydrate, solvate, isotope, or salt thereof:

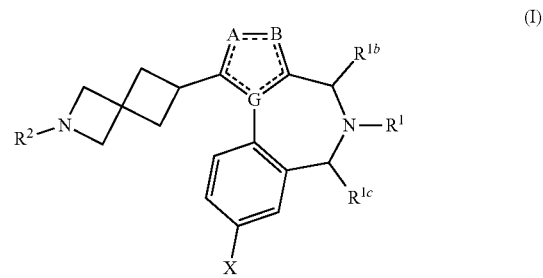

(I)

wherein A, B, G, $R^1$, $R^{1b}$, $R^{1c}$, $R^2$ and X are as defined below.

In an embodiment, a pharmaceutical composition is provided comprising a compound having the structure of Formula (I), or a pharmaceutically acceptable isomer, racemate, hydrate, solvate, isotope, or salt thereof, in combination with a pharmaceutically acceptable carrier, diluent, or excipient.

In an embodiment, use of a compound having the structure of Formula (I), or a pharmaceutically acceptable isomer, racemate, hydrate, solvate, isotope, or salt thereof, for the manufacture of a medicament is provided.

In an embodiment, a method is provided for antagonizing the V1a receptor, the method comprising contacting the receptor with an effective amount of a compound having the structure of Formula (I), or a pharmaceutically acceptable isomer, racemate, hydrate, solvate, isotope, or salt thereof, or a pharmaceutical composition comprising the same.

In an embodiment, a method is provided for treatment of a malcondition in a subject for which antagonism of the V1a receptor is medically indicated. Such method comprises administering to the subject an effective amount of a compound having the structure of Formula (I), or a pharmaceutically acceptable isomer, racemate, hydrate, solvate, isotope, or salt thereof, or a pharmaceutical composition comprising the same, at a frequency and for duration sufficient to provide a beneficial effect to the subject.

In an embodiment, a pharmaceutical composition is provided comprising a compound having the structure of Formula (I), or a pharmaceutically acceptable isomer, racemate, hydrate, solvate, isotope, or salt thereof, in combination with at least one pharmaceutically acceptable carrier, diluent, or excipient.

In an embodiment, a method of synthesis is provided for a compound having the structure of Formula (I), or a pharmaceutically acceptable isomer, racemate, hydrate, solvate, isotope, or salt thereof.

DETAILED DESCRIPTION OF THE INVENTION

As mentioned above, the invention relates to compounds that antagonize vasopressin receptors, particularly the V1a receptor, to products comprising the same, and to methods for their use and synthesis.

In one embodiment, compounds are provided having the structure of Formula (I), or a pharmaceutically acceptable isomer, racemate, hydrate, solvate, isotope, or salt thereof:

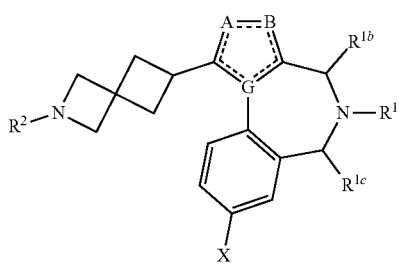

(I)

wherein
=== represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ and $R^{1c}$ are independently hydrogen, lower alkyl, or spiroalkyl;
$R^2$ is -Q-($R^4$)$_n$, —S(=O)$_2R^5$, or —C(=O)$R^5$;
$R^3$ is lower alkyl, lower haloalkyl, lower alkoxy, lower haloalkoxy, -cycloalkyl-$R^6$, —O— cycloalkyl-$R^6$, —O-heterocyclyl-$R^6$, —NHR$^5$, or —NR$^5R^5$;
or $R^{1b}$ and $R^1$ or $R^{1b}$ and $R^3$, together with the atoms to which they are attached, form a ring;
Q is aryl or heteroaryl;
each $R^4$ is independently halogen, hydroxy, lower alkyl, lower haloalkyl, lower alkoxy, lower haloalkoxyalkyl, or cyano;
each $R^5$ is independently cycloalkyl, lower alkyl, lower haloalkyl, cycloalkylalkyl, lower alkoxy, heterocyclyl, or —O-heterocyclyl;
$R^6$ is hydrogen, halo, alkyl, lower haloalkyl, or cyano; and
n is 0, 1, or 2.

As used herein, "lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 2 carbon atoms. Examples of straight chain lower alkyl groups include, but are not limited to, methyl, ethyl, n-propyl, n-butyl, n-pentyl, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

"Halo" or "halogen" refers to fluorine, chlorine, bromine, and iodine.

"Hydroxy" refers to —OH.

"Cyano" refers to —CN.

"Lower haloalkyl" refers to a lower alkyl as defined above with one or more hydrogen atoms replaced with halogen. Examples of lower haloalkyl groups include, but are not limited to, —CF$_3$, —CH$_2$CF$_3$, and the like.

"Lower alkoxy" refers to a lower alkyl as defined above joined by way of an oxygen atom (i.e., —O-(lower alkyl). Examples of lower alkoxy groups include, but are not limited to, methoxy, ethoxy, n-propoxy, n-butoxy, iso-propoxy, sec-butoxy, tert-butoxy, and the like.

"Lower haloalkoxy" refers to a lower haloalkyl as defined above joined by way of an oxygen atom (i.e., —O-(lower haloalkyl). Examples of lower haloalkoxy groups include, but are not limited to, —OCF$_3$, —OCH$_2$CF$_3$, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like "Cycloalkylalkyl" are alkyl groups as defined above in which a hydrogen or carbon bond of the alkyl group is replaced with a bond to a cycloalkyl group as defined above.

"Aryl" groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like). In one embodiment, aryl is phenyl or naphthyl, and in another embodiment aryl is phenyl.

"Heterocyclyl" or "heterocyclic" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups.

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of non-superimposable isomers that are called "enantiomers." Single enantiomers of a pure compound are optically active (i.e., they are capable of rotating the plane of plane polarized light and designated R or 5).

"Spiroalkyl" refers to a geminally substituted di-lower alkyl substituents of 1 to 3 carbon atoms that form a continuous ring of 3 to 7 carbon atoms, respectively. The number of carbon atoms of the bonded geminal substituents are independent of each other, e.g. one germinal substituent may be 2 carbon atoms and the second germinal substituent may be 3 carbon atoms, with terminal carbons bonded to make a fused spiroalkyl of 6 carbon atoms, counting the geminally substituted carbon atom.

"Isolated optical isomer" means a compound which has been substantially purified from the corresponding optical isomer(s) of the same formula. For example, the isolated isomer may be at least about 80%, at least 80% or at least 85% pure. In other embodiments, the isolated isomer is at least 90% pure or at least 98% pure, or at least 99% pure by weight.

"Substantially enantiomerically or diasteromerically" pure means a level of enantiomeric or diasteromeric enrichment of one enantiomer with respect to the other enantiomer or diasteromer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out).

A "hydrate" is a compound that exists in combination with water molecules. The combination can include water in stoichiometric quantities, such as a monohydrate or a dehydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

Co-crystal forms of compounds having the structure of Formula (I) are also included within the scope of this invention; namely, solids that are crystalline single phase materials composed of two or more different molecular and/or ionic compounds generally in a stoichiometric ratio which are neither solvates nor simple salts.

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int J. Pharm.*, 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In one embodiment, compounds are provided having the structure of Formula (I), or a pharmaceutically acceptable isomer, racemate, hydrate, solvate, isotope, or salt thereof:

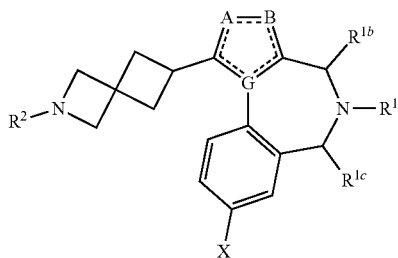

(I)

wherein

--- represents an optional double bond;

A and B are independently nitrogen or oxygen, with the proviso that A and B are not both oxygen;

G is nitrogen or carbon;

X is halogen, lower alkyl, lower haloalkyl, lower alkoxy, or cyano;

$R^1$ is hydrogen, lower alkyl, lower alkoxyalkyl, cycloalkyl, heterocyclyl, lower haloalkyl, or —C(=O)R$^3$;

$R^{1b}$ and $R^{1c}$ are independently hydrogen or lower alkyl;

$R^2$ is -Q-(R$^4$)$_n$, —S(=O)$_2$R$^5$, or —C(=O)R$^5$;

$R^3$ is lower alkyl, lower haloalkyl, lower alkoxy, lower haloalkoxy, or cycloalkyl-R$^6$;

Q is aryl or heteroaryl;

each $R^4$ is independently halogen, hydroxy, lower alkyl, lower alkoxy, or cyano;

$R^5$ is cycloalkyl, lower alkyl, lower haloalkyl, cycloalkylalkyl, lower alkoxy, heterocyclyl, or —O-heterocyclyl;

$R^6$ is hydrogen, halo, alkyl, lower haloalkyl, or cyano; and n is 0, 1, or 2.

In one embodiment, compounds are provided having the structure of Formula (I-A), or a pharmaceutically acceptable isomer, racemate, hydrate, solvate, isotope, or salt thereof:

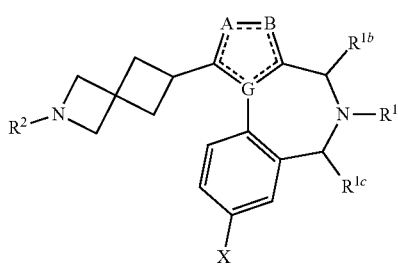

(I-A)

wherein

--- represents an optional double bond;

A and B are independently nitrogen or oxygen, with the proviso that A and B are not both oxygen;

G is nitrogen or carbon;

X is halogen, lower alkyl, lower haloalkyl, lower alkoxy, or cyano;

$R^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, or -alkyl-C(=O)R$^3$;

$R^{1b}$ and $R^{1c}$ are independently hydrogen or lower alkyl; or $R^{1b}$ and $R^1$, together with the atoms to which they are attached, form a ring;

$R^2$ is -Q-(R$^4$)$_n$, —S(=O)$_2$R$^5$, or —C(=O)R$^5$;

Q is heteroaryl;

each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O— heterocyclyl;

$R^6$ is hydrogen, halo, alkyl, lower haloalkyl, or cyano; and n is 0, 1, or 2.

In one embodiment, compounds are provided having the structure of Formula (I-B), or a pharmaceutically acceptable isomer, racemate, hydrate, solvate, isotope, or salt thereof:

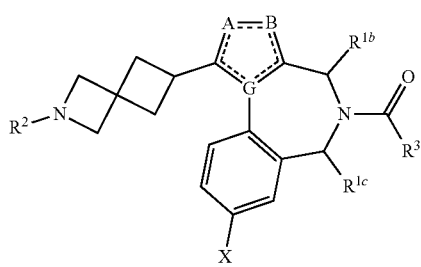

(I-B)

wherein

--- represents an optional double bond;

A and B are independently nitrogen or oxygen, with the proviso that A and B are not both oxygen;

G is nitrogen or carbon;

X is halogen, lower alkyl, lower haloalkyl, lower alkoxy, or cyano;

$R^{1b}$ and $R^{1c}$ are independently hydrogen or lower alkyl;

$R^2$ is -Q-(R$^4$)$_n$, —S(=O)$_2$R$^5$, or —C(=O)R$^5$;

$R^3$ is lower alkyl, lower haloalkyl, lower alkoxy, lower haloalkoxy, -cycloalkyl-R$^6$, —O— cycloalkyl-R$^6$, or —O— heterocyclyl-R$^6$; or R$^{1b}$ and R$^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O— heterocyclyl;

$R^6$ is hydrogen, halo, alkyl, lower haloalkyl, or cyano; and n is 0, 1, or 2.

In a more specific embodiment, $R^{1c}$ is hydrogen and compounds are provided having the structure of Formula (II), or a pharmaceutically acceptable isomer, racemate, hydrate, solvate, isotope or salt thereof:

(II)

wherein
=== represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^2$ is -Q-$(R^4)_n$, —S(=O)$_2R^5$, or —C(=O)$R^5$;
$R^3$ lower alkyl, lower haloalkyl, alkoxy, lower haloalkoxy, -cycloalkyl-$R^6$, —O— cycloalkyl-$R^6$, or —O— heterocyclyl-$R^6$;
or $R^{1b}$ and $R^1$ or $R^{1b}$ and $R^3$, together with the atoms to which they are attached, form a ring
Q is aryl or heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, lower haloalkoxy, heterocyclyl, or —O— heterocyclyl;
$R^6$ is hydrogen, halo, alkyl, lower haloalkyl, or cyano; and
n is 0, 1, or 2.

In a more specific embodiment, compounds are provided having the structure of Formula (II-A), or a pharmaceutically acceptable isomer, racemate, hydrate, solvate, isotope, or salt thereof:

(II-A)

wherein
=== represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
$R^{1b}$ is hydrogen or lower alkyl;
or $R^{1b}$ and $R^1$, together with the atoms to which they are attached, form a ring
$R^2$ is -Q-$(R^4)_n$, —S(=O)$_2R^5$, or —C(=O)$R^5$;
Q is heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, heterocyclyl, or —O— heterocyclyl;
$R^6$ is hydrogen, halo, alkyl, lower haloalkyl, or cyano; and
n is 0, 1, or 2.

In a more specific embodiment, compounds are provided having the structure of Formula (II-B), or a pharmaceutically acceptable isomer, racemate, hydrate, solvate, isotope, or salt thereof:

(II-B)

wherein
=== represents an optional double bond;
A and B are independently nitrogen or oxygen, with the proviso that A and B are not both oxygen;
G is nitrogen or carbon;
X is halogen, lower alkyl, lower haloalkyl, lower alkoxy, or cyano;
$R^{1b}$ is hydrogen or lower alkyl;
$R^2$ is -Q-$(R^4)_n$, —S(=O)$_2R^5$, or —C(=O)$R^5$;
$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;
or $R^{1b}$ and $R^3$, together with the atoms to which they are attached, form a ring Q is heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, heterocyclyl, or —O— heterocyclyl;
$R^6$ is hydrogen, halo, alkyl, lower haloalkyl, or cyano; and
n is 0, 1, or 2.

In a more specific embodiment, compounds are provided having the structure of Formula (III), or a pharmaceutically acceptable isomer, racemate, hydrate, solvate, isotope, or salt thereof:

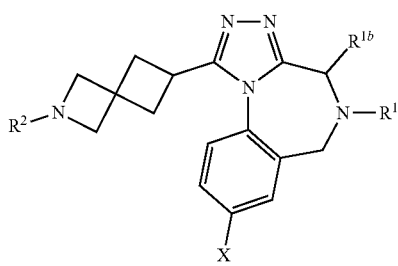

(III)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^2$ is -Q-($R^4$)$_n$, —S(=O)$_2$$R^5$, or —C(=O)$R^5$;

$R^3$ is lower alkyl, lower haloalkyl, alkoxy, lower haloalkoxy, -cycloalkyl-$R^6$, —O— cycloalkyl-$R^6$, or —O— heterocyclyl-$R^6$;

or $R^{1b}$ and $R^1$ or $R^{1b}$ and $R^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O— heterocyclyl;

$R^6$ is hydrogen, halo, alkyl, lower haloalkyl, or cyano; and n is 0, 1, or 2.

In a more specific embodiment, compounds are provided having the structure of Formula (III-A), or a pharmaceutically acceptable isomer, racemate, hydrate, solvate, isotope, or salt thereof:

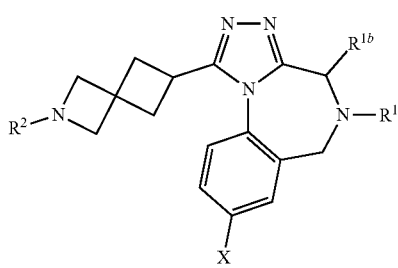

(III-A)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;

$R^{1b}$ is hydrogen or lower alkyl;

or $R^{1b}$ and $R^1$, together with the atoms to which they are attached, form a ring;

$R^2$ is -Q-($R^4$)$_n$, —S(=O)$_2$$R^5$, or —C(=O)$R^5$;

Q is heteroaryl;

each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O— heterocyclyl;

$R^6$ is hydrogen, halo, alkyl, lower haloalkyl, or cyano; and n is 0, 1, or 2.

In another embodiment, compounds are provided having the structure of Formula (III-B), or a pharmaceutically acceptable isomer, racemate, hydrate, solvate, isotope, or salt thereof:

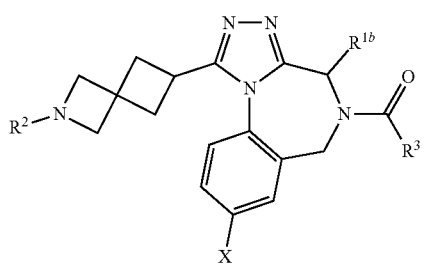

(III-B)

wherein

X is halogen, lower alkyl, lower haloalkyl, lower alkoxy, or cyano;

$R^{1b}$ is hydrogen or lower alkyl;

$R^2$ is -Q-($R^4$)$_n$, —S(=O)$_2$$R^5$, or —C(=O)$R^5$;

$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O— heterocyclyl;

$R^6$ is hydrogen, halo, alkyl, lower haloalkyl, or cyano; and n is 0, 1, or 2.

In a more specific embodiment, compounds are provided having the structure of Formula (IV), or a pharmaceutically acceptable isomer, racemate, hydrate, solvate, isotope, or salt thereof:

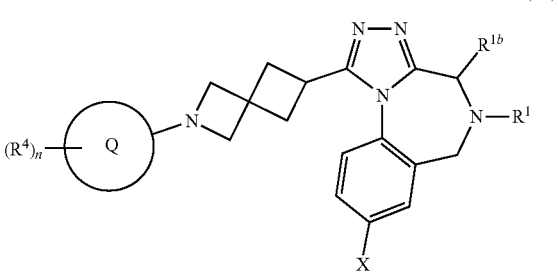

(IV)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O— cycloalkyl-$R^6$, or —O— heterocyclyl-$R^6$;

or $R^{1b}$ and $R^1$ or $R^{1b}$ and $R^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (IV-A), or a pharmaceutically acceptable isomer, racemate, hydrate, solvate, isotope, or salt thereof:

(IV-A)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;

$R^{1b}$ is hydrogen or lower alkyl;

or $R^{1b}$ and $R^1$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (IV-B), or a pharmaceutically acceptable isomer, racemate, hydrate, solvate, isotope, or salt thereof:

(IV-B)

wherein

X is halogen, lower alkyl, lower haloalkyl, lower alkoxy, or cyano;

$R^{1b}$ is hydrogen or lower alkyl;

$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (V), or a pharmaceutically acceptable isomer, racemate, hydrate, solvate, isotope, or salt thereof:

(V)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O— cycloalkyl-$R^6$, or —O— heterocyclyl-$R^6$;

or $R^{1b}$ and $R^1$ or $R^{1b}$ and $R^3$, together with the atoms to which they are attached, form a ring;

$Q^1$, $Q^2$, $Q^3$, $Q^4$, and $Q^5$ are independently N, CH, or CR$^4$;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (V-A), or a pharmaceutically acceptable isomer, racemate, hydrate, solvate, isotope, or salt thereof:

(V-A)

wherein
X is halogen, lower alkyl, lower haloalkyl, lower alkoxy, or cyano;
R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, or -alkyl-C(=O)R³;
R¹ᵇ is hydrogen or lower alkyl;
or R¹ᵇ and R¹, together with the atoms to which they are attached, form a ring;
Q¹, Q², Q³, Q⁴, and Q⁵ are independently N, CH, or CR⁴;
each R⁴ is independently halogen, hydroxy, lower alkyl, lower haloalkyl, lower alkoxy, lower haloalkoxyalkyl, or cyano;
R⁶ is hydrogen, halo, alkyl, lower haloalkyl, or cyano; and
n is 0, 1, or 2.

In a more specific embodiment, compounds are provided having the structure of Formula (V-B), or a pharmaceutically acceptable isomer, racemate, hydrate, solvate, isotope, or salt thereof:

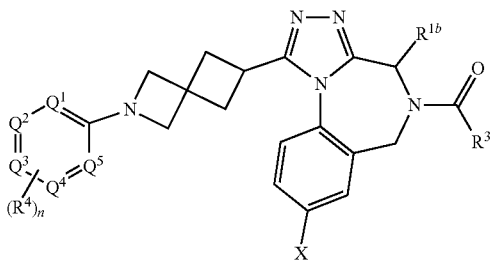

(V-B)

wherein
X is halogen, lower alkyl, lower haloalkyl, lower alkoxy, or cyano;
R¹ᵇ is hydrogen or lower alkyl;
R³ is lower alkyl, lower haloalkyl, lower alkoxy, lower haloalkoxy, -cycloalkyl-R⁶, —O— cycloalkyl-R⁶, or —O— heterocyclyl-R⁶;
or R¹ᵇ and R³, together with the atoms to which they are attached, form a ring;
Q¹, Q², Q³, Q⁴, and Q⁵ are independently N, CH, or CR⁴;
each R⁴ is independently halogen, hydroxy, lower alkyl, lower haloalkyl, lower alkoxy, lower haloalkoxyalkyl, or cyano;
R⁶ is hydrogen, halo, alkyl, lower haloalkyl, or cyano; and
n is 0, 1, or 2.

In a more specific embodiment, compounds are provided having the structure of Formula (VI), or a pharmaceutically acceptable isomer, racemate, hydrate, solvate, isotope, or salt thereof:

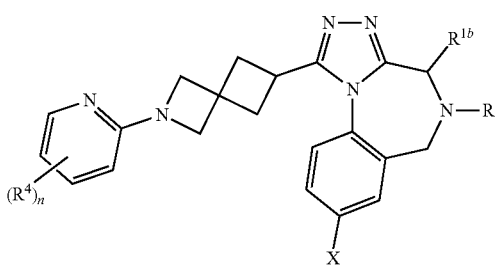

(VI)

wherein
X is halogen, lower alkyl, lower haloalkyl, lower alkoxy, or cyano;
R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;
R¹ᵇ is hydrogen or lower alkyl;
R³ is lower alkyl, lower haloalkyl, alkoxy, lower haloalkoxy, -cycloalkyl-R⁶, —O— cycloalkyl-R⁶, or —O— heterocyclyl-R⁶;
or R¹ᵇ and R¹ or R¹ᵇ and R³, together with the atoms to which they are attached, form a ring;
each R⁴ is independently halogen, hydroxy, lower alkyl, lower haloalkyl, lower alkoxy, lower haloalkoxyalkyl, or cyano;
R⁶ is hydrogen, halo, alkyl, lower haloalkyl, or cyano; and
n is 0, 1, or 2.

In a more specific embodiment, compounds are provided having the structure of Formula (VI-A), or a pharmaceutically acceptable isomer, racemate, hydrate, solvate, isotope, or salt thereof:

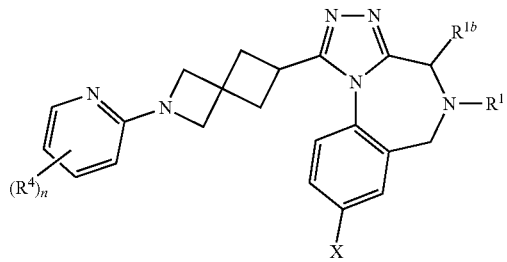

(VI-A)

wherein
X is halogen, lower alkyl, lower haloalkyl, lower alkoxy, or cyano;
R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, or -alkyl-C(=O)R³;
R¹ᵇ is hydrogen or lower alkyl;
or R¹ᵇ and R¹, together with the atoms to which they are attached, form a ring;
each R⁴ is independently halogen, hydroxy, lower alkyl, lower haloalkyl, lower alkoxy, lower haloalkoxyalkyl, or cyano;
R⁶ is hydrogen, halo, alkyl, lower haloalkyl, or cyano; and
n is 0, 1, or 2.

In a more specific embodiment, compounds are provided having the structure of Formula (VI-B), or a pharmaceutically acceptable isomer, racemate, hydrate, solvate, isotope, or salt thereof:

(VI-B)

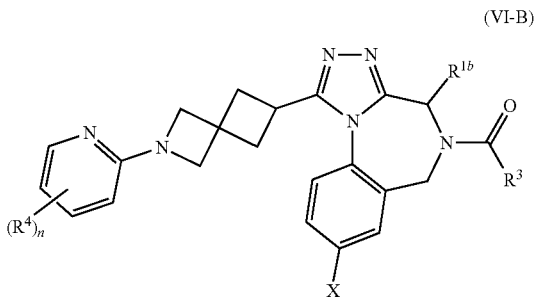

wherein

X is halogen, lower alkyl, lower haloalkyl, lower alkoxy, or cyano;

$R^{1b}$ is hydrogen or lower alkyl;

$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (VII), or a pharmaceutically acceptable isomer, racemate, hydrate, solvate, isotope, or salt thereof:

(VII)

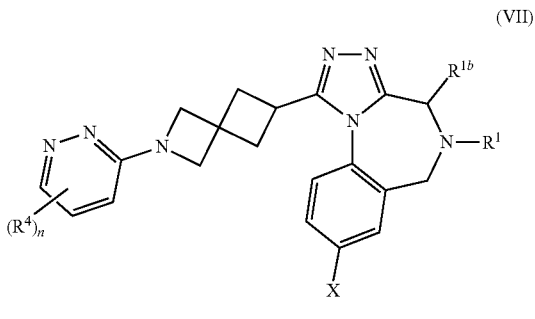

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O— cycloalkyl-$R^6$, or —O— heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (VII-A), or a pharmaceutically acceptable isomer, racemate, hydrate, solvate, isotope, or salt thereof:

(VII-A)

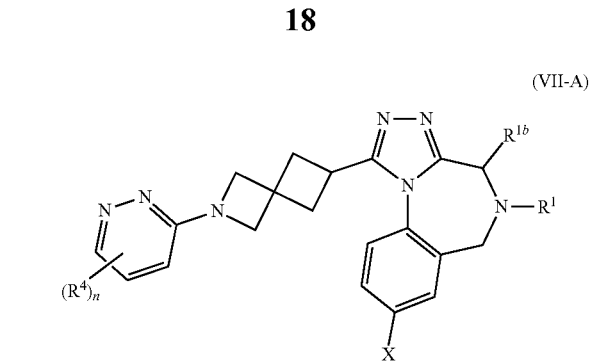

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;

$R^{1b}$ is hydrogen or lower alkyl;

or $R^{1b}$ and $R^1$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (VII-B), or a pharmaceutically acceptable isomer, racemate, hydrate, solvate, isotope, or salt thereof:

(VII-B)

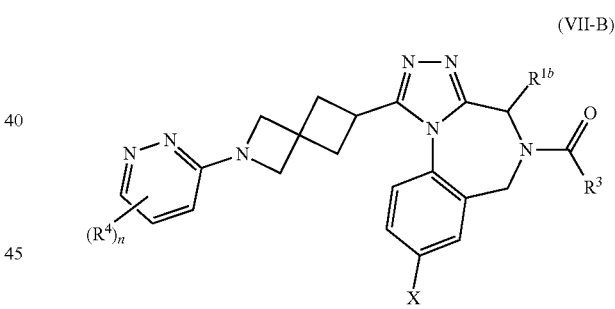

wherein

X is halogen, lower alkyl, lower haloalkyl, lower alkoxy, or cyano;

$R^{1b}$ is hydrogen or lower alkyl;

$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (VIII), or a pharmaceutically acceptable isomer, racemate, hydrate, solvate, isotope, or salt thereof:

(VIII)

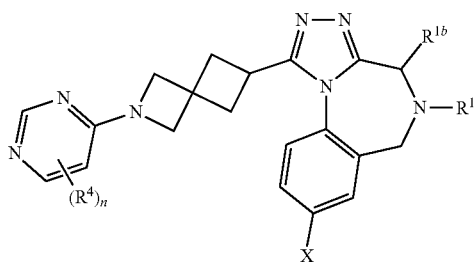

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^3$ is lower alkyl, lower haloalkyl, alkoxy, lower haloalkoxy, -cycloalkyl-R$^6$, —O— cycloalkyl-R$^6$, or —O— heterocyclyl-R$^6$;
or R$^{1b}$ and R$^1$ or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and n is 0, 1, or 2.

In a more specific embodiment, compounds are provided having the structure of Formula (VIII-A), or a pharmaceutically acceptable isomer, racemate, hydrate, solvate, isotope, or salt thereof:

(VIII-A)

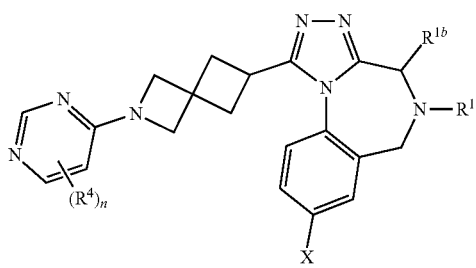

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, or -alkyl-C(=O)R$^3$;
R$^{1b}$ is hydrogen or lower alkyl;
or R$^{1b}$ and R$^1$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and n is 0, 1, or 2.

In a more specific embodiment, compounds are provided having the structure of Formula (VIII-B), or a pharmaceutically acceptable isomer, racemate, hydrate, solvate, isotope, or salt thereof:

(VIII-B)

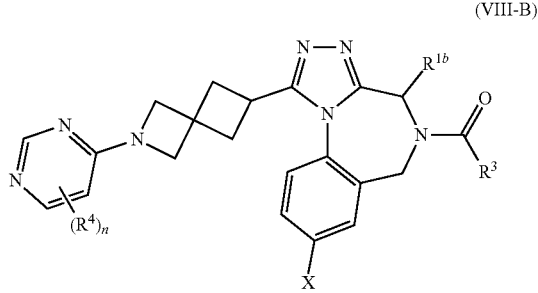

wherein
X is halogen, lower alkyl, lower haloalkyl, lower alkoxy, or cyano;
R$^{1b}$ is hydrogen or lower alkyl;
R$^3$ is lower alkyl, lower haloalkyl, lower alkoxy, lower haloalkoxy, -cycloalkyl-R$^6$, —O— cycloalkyl-R$^6$, or —O— heterocyclyl-R$^6$;
or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;
R$^6$ is hydrogen, halo, alkyl, lower haloalkyl, or cyano; and n is 0, 1, or 2.

In a more specific embodiment, compounds are provided having the structure of Formula (IX), or a pharmaceutically acceptable isomer, racemate, hydrate, solvate, isotope, or salt thereof:

(IX)

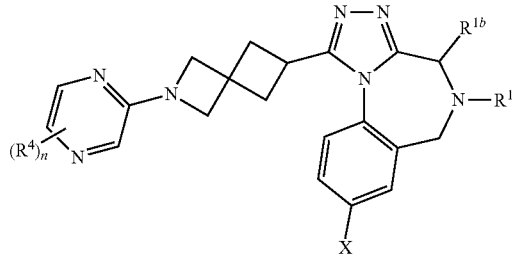

wherein
X is halogen, lower alkyl, lower haloalkyl, lower alkoxy, or cyano;
R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, -alkyl-C(=O)R$^3$, or —C(=O)R$^3$;
R$^{1b}$ is hydrogen or lower alkyl;
R$^3$ is lower alkyl, lower haloalkyl, alkoxy, lower haloalkoxy, -cycloalkyl-R$^6$, —O— cycloalkyl-R$^6$, or —O— heterocyclyl-R$^6$;
or R$^{1b}$ and R$^1$ or R$^{1b}$ and R$^3$, together with the atoms to which they are attached, form a ring;
each R$^4$ is independently halogen, hydroxy, lower alkyl, lower haloalkyl, lower alkoxy, lower haloalkoxyalkyl, or cyano;

R[6] is hydrogen, halo, alkyl, lower haloalkyl, or cyano; and n is 0, 1, or 2.

In a more specific embodiment, compounds are provided having the structure of Formula (IX-A), or a pharmaceutically acceptable isomer, racemate, hydrate, solvate, isotope, or salt thereof:

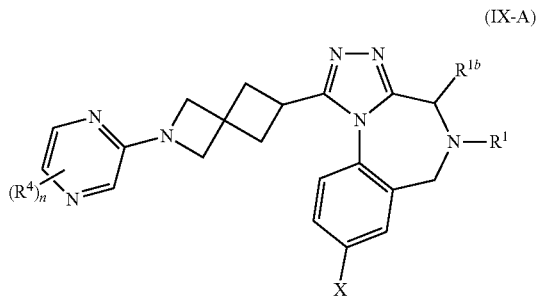

(IX-A)

wherein

X is halogen, lower alkyl, lower haloalkyl, lower alkoxy, or cyano;

R[1] is hydrogen, lower alkyl-R[6], haloalkyl, lower alkoxyalkyl, -cycloalkyl-R[6], -alkyl-cycloalkyl-R[6], -aryl-R[6], -alkyl-aryl-R[6], -heterocyclyl-R[6], -alkyl-heterocyclyl-R[6], lower haloalkyl, or -alkyl-C(=O)R[3];

R[1b] is hydrogen or lower alkyl;

or R[1b] and R[1], together with the atoms to which they are attached, form a ring;

each R[4] is independently halogen, hydroxy, lower alkyl, lower haloalkyl, lower alkoxy, lower haloalkoxyalkyl, or cyano;

R[6] is hydrogen, halo, alkyl, lower haloalkyl, or cyano; and n is 0, 1, or 2.

In a more specific embodiment, compounds are provided having the structure of Formula (IX-B), or a pharmaceutically acceptable isomer, racemate, hydrate, solvate, isotope, or salt thereof:

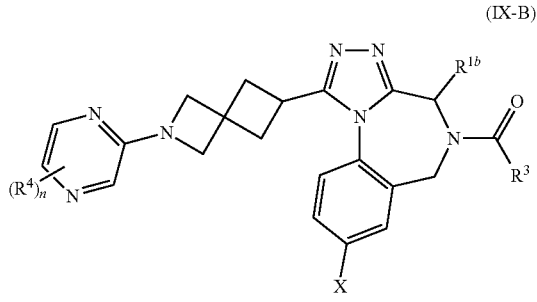

(IX-B)

wherein

X is halogen, lower alkyl, lower haloalkyl, lower alkoxy, or cyano;

R[1b] is hydrogen or lower alkyl;

R[3] is lower alkyl, lower haloalkyl, lower alkoxy, lower haloalkoxy, -cycloalkyl-R[6], —O— cycloalkyl-R[6], or —O— heterocyclyl-R[6];

or R[1b] and R[3], together with the atoms to which they are attached, form a ring;

each R[4] is independently halogen, hydroxy, lower alkyl, lower haloalkyl, lower alkoxy, lower haloalkoxyalkyl, or cyano;

R[6] is hydrogen, halo, alkyl, lower haloalkyl, or cyano; and n is 0, 1, or 2.

In a more specific embodiment, compounds are provided having the structure of Formula (X), or a pharmaceutically acceptable isomer, racemate, hydrate, solvate, isotope, or salt thereof:

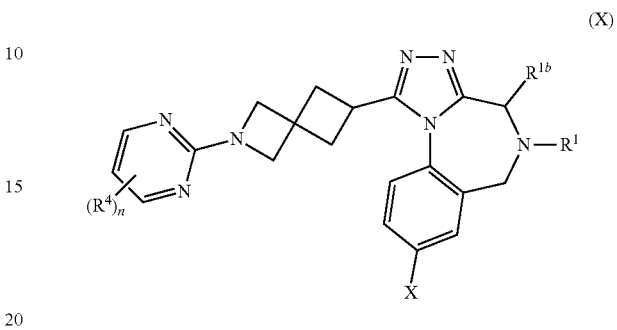

(X)

wherein

X is halogen, lower alkyl, lower haloalkyl, lower alkoxy, or cyano;

R[1] is hydrogen, lower alkyl-R[6], haloalkyl, lower alkoxyalkyl, -cycloalkyl-R[6], -alkyl-cycloalkyl-R[6], -aryl-R[6], -alkyl-aryl-R[6], -heterocyclyl-R[6], -alkyl-heterocyclyl-R[6], lower haloalkyl, -alkyl-C(=O)R[3], or —C(=O)R[3];

R[1b] is hydrogen or lower alkyl;

R[3] is lower alkyl, lower haloalkyl, alkoxy, lower haloalkoxy, -cycloalkyl-R[6], —O— cycloalkyl-R[6], or —O— heterocyclyl-R[6];

or R[1b] and R[1] or R[1b] and R[3], together with the atoms to which they are attached, form a ring;

each R[4] is independently halogen, hydroxy, lower alkyl, lower haloalkyl, lower alkoxy, lower haloalkoxyalkyl, or cyano;

R[6] is hydrogen, halo, alkyl, lower haloalkyl, or cyano; and n is 0, 1, or 2.

In a more specific embodiment, compounds are provided having the structure of Formula (X-A), or a pharmaceutically acceptable isomer, racemate, hydrate, solvate, isotope, or salt thereof:

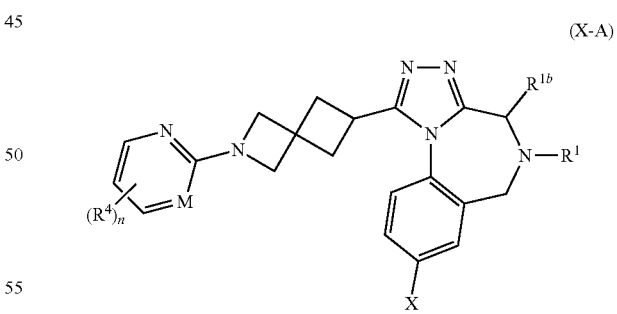

(X-A)

wherein

X is halogen, lower alkyl, lower haloalkyl, lower alkoxy, or cyano;

R[1] is hydrogen, lower alkyl-R[6], haloalkyl, lower alkoxyalkyl, -cycloalkyl-R[6], -alkyl-cycloalkyl-R[6], -aryl-R[6], -alkyl-aryl-R[6], -heterocyclyl-R[6], -alkyl-heterocyclyl-R[6], lower haloalkyl, or -alkyl-C(=O)R[3];

R[1b] is hydrogen or lower alkyl;

or R[1b] and R[1], together with the atoms to which they are attached, form a ring;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

In a more specific embodiment, compounds are provided having the structure of Formula (X-B), or a pharmaceutically acceptable isomer, racemate, hydrate, solvate, isotope, or salt thereof:

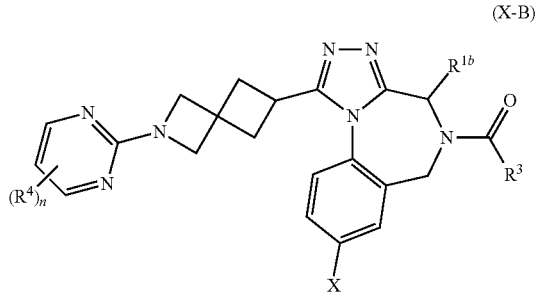

(X-B)

wherein

X is halogen, lower alkyl, lower haloalkyl, lower alkoxy, or cyano;

R¹ᵇ is hydrogen or lower alkyl;

R³ is lower alkyl, lower haloalkyl, lower alkoxy, lower haloalkoxy, -cycloalkyl-R⁶, —O— cycloalkyl-R⁶, or —O— heterocyclyl-R⁶;

or R¹ᵇ and R³, together with the atoms to which they are attached, form a ring;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

In a more specific embodiment, compounds are provided having the structure of Formula (XI), or a pharmaceutically acceptable isomer, racemate, hydrate, solvate, isotope, or salt thereof:

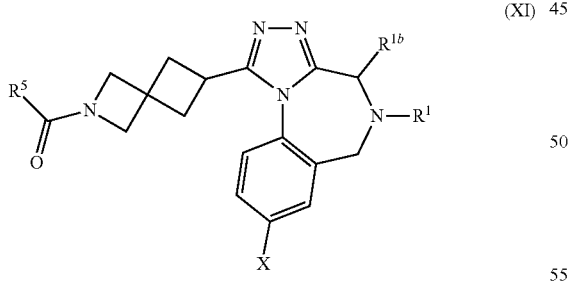

(XI)

wherein

X is halogen, lower alkyl, lower haloalkyl, lower alkoxy, or cyano;

R¹ is hydrogen, lower alkyl-R⁶, haloalkyl, lower alkoxy-alkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;

R¹ᵇ is hydrogen or lower alkyl;

R³ is lower alkyl, lower haloalkyl, alkoxy, lower haloalkoxy, -cycloalkyl-R⁶, —O— cycloalkyl-R⁶, or —O— heterocyclyl-R⁶;

or R¹ᵇ and R¹ or R¹ᵇ and R³, together with the atoms to which they are attached, form a ring;

R⁵ is cycloalkyl, lower alkyl, lower haloalkyl, cycloalkylalkyl, lower alkoxy, heterocyclyl, or —O— heterocyclyl; and R⁶ is hydrogen, halo, alkyl, lower haloalkyl, or cyano; and In a more specific embodiment, compounds are provided having the structure of Formula (XI-A), or a pharmaceutically acceptable isomer, racemate, hydrate, solvate, isotope, or salt thereof:

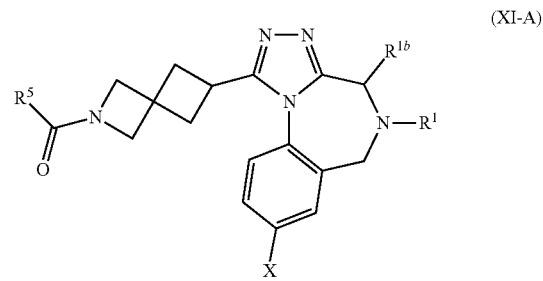

(XI-A)

wherein

X is halogen, lower alkyl, lower haloalkyl, lower alkoxy, or cyano;

R¹ is hydrogen, lower alkyl-R⁶, haloalkyl, lower alkoxy-alkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, or -alkyl-C(=O)R³;

R¹ᵇ is hydrogen or lower alkyl;

or R¹ᵇ and R¹, together with the atoms to which they are attached, form a ring;

R⁵ is cycloalkyl, lower alkyl, lower haloalkyl, cycloalkylalkyl, lower alkoxy, heterocyclyl, or —O— heterocyclyl; and R⁶ is hydrogen, halo, alkyl, lower haloalkyl, or cyano.

In a more specific embodiment, compounds are provided having the structure of Formula (XI-B), or a pharmaceutically acceptable isomer, racemate, hydrate, solvate, isotope, or salt thereof:

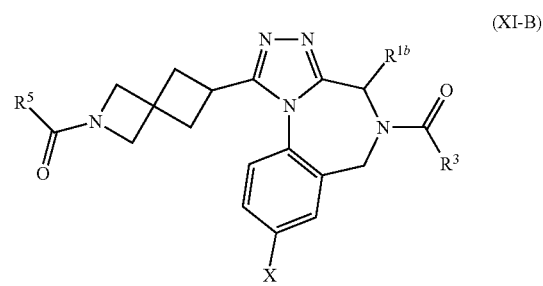

(XI-B)

wherein

X is halogen, lower alkyl, lower haloalkyl, lower alkoxy, or cyano;

R¹ᵇ is hydrogen or lower alkyl;

R³ is lower alkyl, lower haloalkyl, alkoxy, lower haloalkoxy, -cycloalkyl-R⁶, —O— cycloalkyl-R⁶, or —O— heterocyclyl-R⁶;

or R¹ᵇ and R³, together with the atoms to which they are attached, form a ring;

R⁵ is cycloalkyl, lower alkyl, lower haloalkyl, cycloalkylalkyl, alkoxy, heterocyclyl, or —O-heterocyclyl; and R⁶ is hydrogen, halo, alkyl, lower haloalkyl, or cyano.

In another embodiment, compounds are provided having the structure of Formula (XII), or a pharmaceutically acceptable isomer, racemate, hydrate, solvate, isotope, or salt thereof:

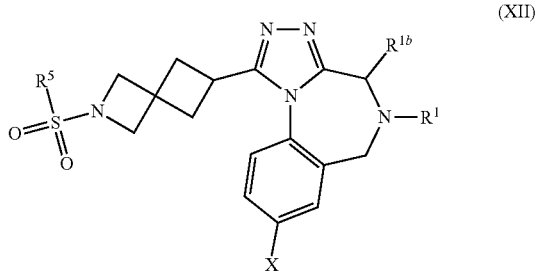

(XII)

wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^3$ is lower alkyl, lower haloalkyl, alkoxy, lower haloalkoxy, -cycloalkyl-$R^6$, —O— cycloalkyl-$R^6$, or —O— heterocyclyl-$R^6$;
or $R^{1b}$ and $R^1$ or $R^{1b}$ and $R^3$, together with the atoms to which they are attached, form a ring;
$R^5$ is cycloalkyl, lower alkyl, lower haloalkyl, cycloalkylalkyl, lower alkoxy, heterocyclyl, or —O— heterocyclyl; and
$R^6$ is hydrogen, halo, alkyl, lower haloalkyl, or cyano.

In a more specific embodiment, compounds are provided having the structure of Formula (XII-A), or a pharmaceutically acceptable isomer, racemate, hydrate, solvate, isotope, or salt thereof:

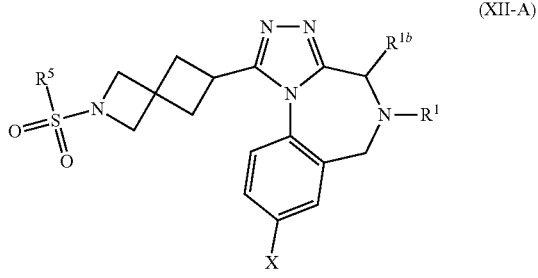

(XII-A)

wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
$R^{1b}$ is hydrogen or lower alkyl;
or $R^{1b}$ and $R^1$, together with the atoms to which they are attached, form a ring;
$R^5$ is cycloalkyl, lower alkyl, lower haloalkyl, cycloalkylalkyl, heterocyclyl, lower alkoxy, or —O— heterocyclyl
$R^6$ is hydrogen, halo, alkyl, lower haloalkyl, or cyano.

In a more specific embodiment, compounds are provided having the structure of Formula (XII-B), or a pharmaceutically acceptable isomer, racemate, hydrate, solvate, isotope, or salt thereof:

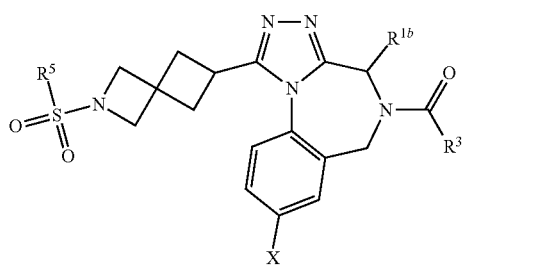

(XII-B)

wherein
X is halogen, lower alkyl, lower haloalkyl, lower alkoxy, or cyano;
$R^{1b}$ is hydrogen or lower alkyl;
$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;
or $R^{1b}$ and $R^3$, together with the atoms to which they are attached, form a ring;
$R^5$ is cycloalkyl, lower alkyl, lower haloalkyl, cycloalkylalkyl, lower alkoxy, heterocyclyl, or —O-heterocyclyl; and
$R^6$ is hydrogen, halo, alkyl, lower haloalkyl, or cyano.

In a more specific embodiment, compounds are provided having the structure of Formula (XIII), or a pharmaceutically acceptable isomer, racemate, hydrate, solvate, isotope, or salt thereof:

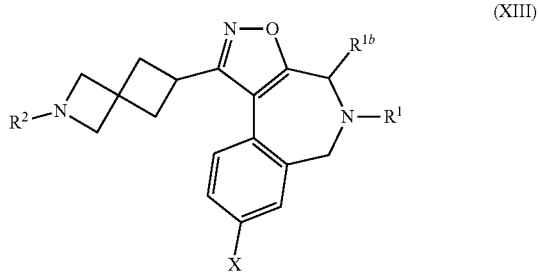

(XIII)

wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^2$ is -Q-($R^4$)$_n$, —S(=O)$_2R^5$, or —C(=O)$R^5$;
$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;
or $R^{1b}$ and $R^1$ or $R^{1b}$ and $R^3$, together with the atoms to which they are attached, form a ring;
Q is heteroaryl;
each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O— heterocyclyl;

$R^6$ is hydrogen, halo, alkyl, lower haloalkyl, or cyano; and n is 0, 1, or 2.

In a more specific embodiment, compounds are provided having the structure of Formula (XIII-A), or a pharmaceutically acceptable isomer, racemate, hydrate, solvate, isotope, or salt thereof:

(XIII-A)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;

$R^{1b}$ is hydrogen or lower alkyl;

or $R^{1b}$ and $R^1$, together with the atoms to which they are attached, form a ring;

$R^2$ is -Q-$(R^4)_n$, —S(=O)$_2R^5$, or —C(=O)$R^5$;

Q is heteroaryl;

each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O— heterocyclyl;

$R^6$ is hydrogen, halo, alkyl, lower haloalkyl, or cyano; and n is 0, 1, or 2.

In a more specific embodiment, compounds are provided having the structure of Formula (XIII-B), or a pharmaceutically acceptable isomer, racemate, hydrate, solvate, isotope, or salt thereof:

(XIII-B)

wherein

X is halogen, lower alkyl, lower haloalkyl, lower alkoxy, or cyano;

$R^{1b}$ is hydrogen or lower alkyl;

$R^2$ is -Q-$(R^4)_n$, —S(=O)$_2R^5$, or —C(=O)$R^5$;

$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^5$ is cycloalkyl, lower alkyl, lower haloalkyl, cycloalkylalkyl, lower alkoxy, heterocyclyl, or —O— heterocyclyl;

$R^6$ is hydrogen, halo, alkyl, lower haloalkyl, or cyano; and n is 0, 1, or 2.

In a more specific embodiment, compounds are provided having the structure of Formula (XIV), or a pharmaceutically acceptable isomer, racemate, hydrate, solvate, isotope, or salt thereof:

(XIV)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^1$ or $R^{1b}$ and $R^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XIV-A), or a pharmaceutically acceptable isomer, racemate, hydrate, solvate, isotope, or salt thereof:

(XIV-A)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;

$R^{1b}$ is hydrogen or lower alkyl;

or $R^{1b}$ and $R^1$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XIV-B), or a pharmaceutically acceptable isomer, racemate, hydrate, solvate, isotope, or salt thereof:

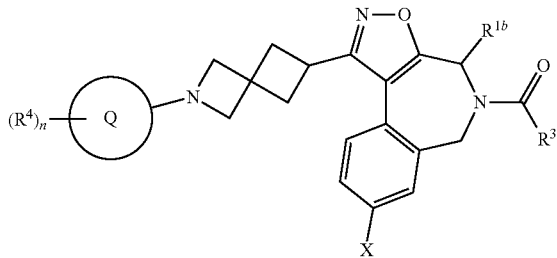

(XIV-B)

wherein

X is halogen, lower alkyl, lower haloalkyl, lower alkoxy, or cyano;

$R^{1b}$ is hydrogen or lower alkyl;

$R^3$ is lower alkyl lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^3$, together with the atoms to which they are attached, form a ring;

Q is heteroaryl;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XV), or a pharmaceutically acceptable isomer, racemate, hydrate, solvate, isotope, or salt thereof:

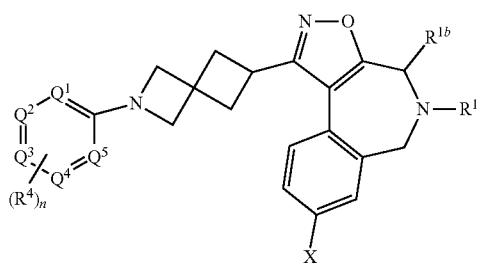

(XV)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O— cycloalkyl-$R^6$, or —O— heterocyclyl-$R^6$;

or $R^{1b}$ and $R^1$ or $R^{1b}$ and $R^3$, together with the atoms to which they are attached, form a ring;

$Q^1$, $Q^2$, $Q^3$, $Q^4$, and $Q^5$ are independently N, CH, or CR$^4$;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XV-A), or a pharmaceutically acceptable isomer, racemate, hydrate, solvate, isotope, or salt thereof:

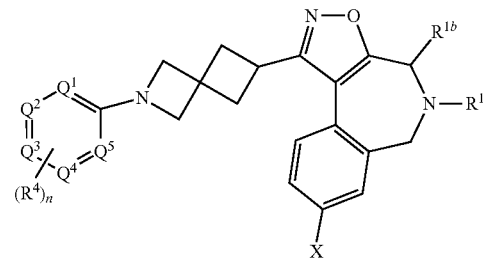

(XV-A)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;

$R^{1b}$ is hydrogen or lower alkyl;

or $R^{1b}$ and $R^1$, together with the atoms to which they are attached, form a ring;

$Q^1$, $Q^2$, $Q^3$, $Q^4$, and $Q^5$ are independently N, CH, or CR$^4$;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XV-B), or a pharmaceutically acceptable isomer, racemate, hydrate, solvate, isotope, or salt thereof:

(XV-B)

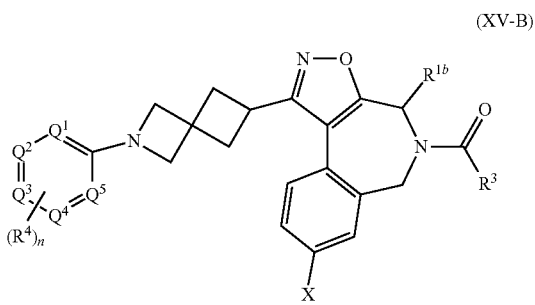

wherein

X is halogen, lower alkyl, lower haloalkyl, lower alkoxy, or cyano;

$R^{1b}$ is hydrogen or lower alkyl;

$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^3$, together with the atoms to which they are attached, form a ring;

$Q^1$, $Q^2$, $Q^3$, $Q^4$, and $Q^5$ are independently N, CH, or $CR^4$;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XVI), or a pharmaceutically acceptable isomer, racemate, hydrate, solvate, isotope, or salt thereof:

(XVI)

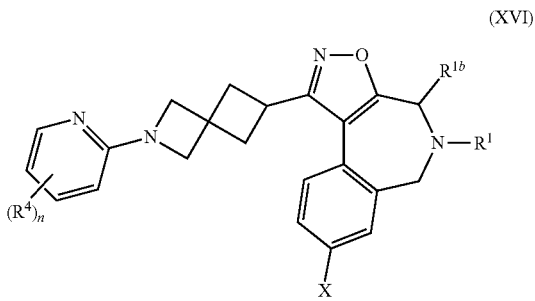

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O— cycloalkyl-$R^6$, or —O— heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XVI-A), or a pharmaceutically acceptable isomer, racemate, hydrate, solvate, isotope, or salt thereof:

(XVI-A)

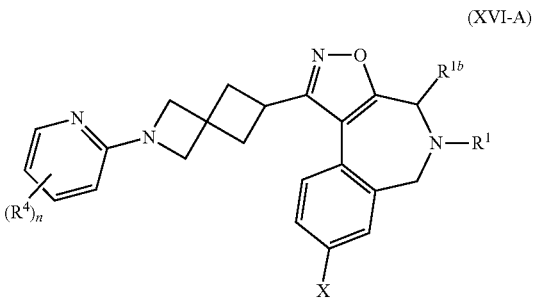

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;

$R^{1b}$ is hydrogen or lower alkyl;

or $R^{1b}$ and $R^1$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XVI-B), or a pharmaceutically acceptable isomer, racemate, hydrate, solvate, isotope, or salt thereof:

(XVI-B)

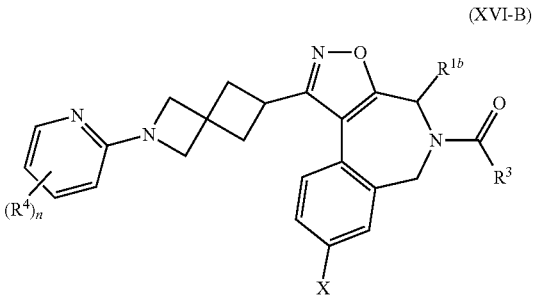

wherein

X is halogen, lower alkyl, lower haloalkyl, lower alkoxy, or cyano;

$R^{1b}$ is hydrogen or lower alkyl;

$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XVII), or a pharmaceutically acceptable isomer, racemate, hydrate, solvate, isotope, or salt thereof:

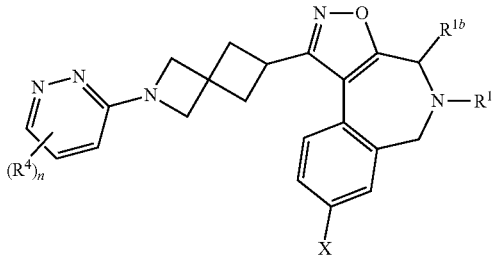

(XVII)

wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^3$ is lower alkyl, lower haloalkyl, alkoxy, lower haloalkoxy, -cycloalkyl-$R^6$, —O— cycloalkyl-$R^6$, or —O— heterocyclyl-$R^6$;
or $R^{1b}$ and $R^1$ or $R^{1b}$ and $R^3$, together with the atoms to which they are attached, form a ring;
each $R^4$ is independently halogen, hydroxy, lower alkyl, lower haloalkyl, lower alkoxy, lower haloalkoxyalkyl, or cyano;
$R^6$ is hydrogen, halo, alkyl, lower haloalkyl, or cyano; and n is 0, 1, or 2.

In a more specific embodiment, compounds are provided having the structure of Formula (XVII-A), or a pharmaceutically acceptable isomer, racemate, hydrate, solvate, isotope, or salt thereof:

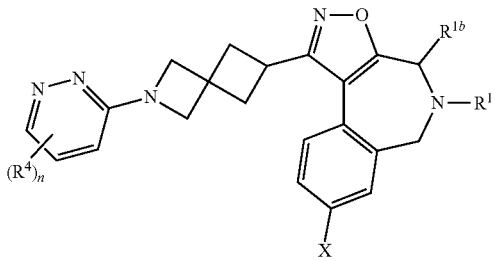

(XVII-A)

wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;
$R^{1b}$ is hydrogen or lower alkyl;
or $R^{1b}$ and $R^1$, together with the atoms to which they are attached, form a ring;
each $R^4$ is independently halogen, hydroxy, lower alkyl, lower haloalkyl, lower alkoxy, lower haloalkoxyalkyl, or cyano;
$R^6$ is hydrogen, halo, alkyl, lower haloalkyl, or cyano; and n is 0, 1, or 2.

In a more specific embodiment, compounds are provided having the structure of Formula (XVII-B), or a pharmaceutically acceptable isomer, racemate, hydrate, solvate, isotope, or salt thereof:

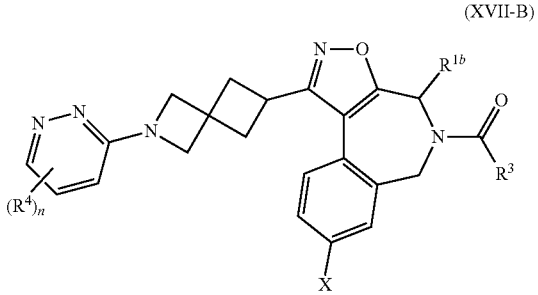

(XVII-B)

wherein
X is halogen, lower alkyl, lower haloalkyl, lower alkoxy, or cyano;
$R^{1b}$ is hydrogen or lower alkyl;
$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;
or $R^{1b}$ and $R^3$, together with the atoms to which they are attached, form a ring;
each $R^4$ is independently halogen, hydroxy, lower alkyl, lower haloalkyl, lower alkoxy, lower haloalkoxyalkyl, or cyano;
$R^6$ is hydrogen, halo, alkyl, lower haloalkyl, or cyano; and n is 0, 1, or 2.

In a more specific embodiment, compounds are provided having the structure of Formula (XVIII), or a pharmaceutically acceptable isomer, racemate, hydrate, solvate, isotope, or salt thereof:

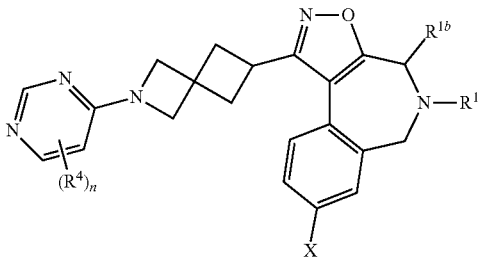

(XVIII)

wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^3$ is lower alkyl, lower haloalkyl, alkoxy, lower haloalkoxy, -cycloalkyl-$R^6$, —O— cycloalkyl-$R^6$, or —O— heterocyclyl-$R^6$;
or $R^{1b}$ and $R^1$ or $R^{1b}$ and $R^3$, together with the atoms to which they are attached, form a ring;

each R⁴ is independently halogen, hydroxy, lower alkyl, lower haloalkyl, lower alkoxy, lower haloalkoxyalkyl, or cyano;
R⁶ is hydrogen, halo, alkyl, lower haloalkyl, or cyano; and n is 0, 1, or 2.

In a more specific embodiment, compounds are provided having the structure of Formula (XVIII-A), or a pharmaceutically acceptable isomer, racemate, hydrate, solvate, isotope, or salt thereof:

(XVIII-A)

wherein
X is halogen, lower alkyl, lower haloalkyl, lower alkoxy, or cyano;
R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, or -alkyl-C(=O)R³;
R¹ᵇ is hydrogen or lower alkyl;
or R¹ᵇ and R¹, together with the atoms to which they are attached, form a ring;
each R⁴ is independently halogen, hydroxy, lower alkyl, lower haloalkyl, lower alkoxy, lower haloalkoxyalkyl, or cyano;
R⁶ is hydrogen, halo, alkyl, lower haloalkyl, or cyano; and n is 0, 1, or 2.

In a more specific embodiment, compounds are provided having the structure of Formula (XVIII-B), or a pharmaceutically acceptable isomer, racemate, hydrate, solvate, isotope, or salt thereof:

(XVIII-B)

wherein
X is halogen, lower alkyl, lower haloalkyl, lower alkoxy, or cyano;
R¹ᵇ is hydrogen or lower alkyl;
R³ is lower alkyl, lower haloalkyl, lower alkoxy, lower haloalkoxy, -cycloalkyl-R⁶, —O— cycloalkyl-R⁶, or —O— heterocyclyl-R⁶;
or R¹ᵇ and R³, together with the atoms to which they are attached, form a ring;

each R⁴ is independently halogen, hydroxy, lower alkyl, lower haloalkyl, lower alkoxy, lower haloalkoxyalkyl, or cyano;
R⁶ is hydrogen, halo, alkyl, lower haloalkyl, or cyano; and n is 0, 1, or 2.

In a more specific embodiment, compounds are provided having the structure of Formula (XIX), or a pharmaceutically acceptable isomer, racemate, hydrate, solvate, isotope, or salt thereof:

(XIX)

wherein
R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;
R¹ᵇ is hydrogen or lower alkyl;
R³ is lower alkyl, lower haloalkyl, alkoxy, lower haloalkoxy, -cycloalkyl-R⁶, —O— cycloalkyl-R⁶, or —O— heterocyclyl-R⁶;
or R¹ᵇ and R¹ or R¹ᵇ and R³, together with the atoms to which they are attached, form a ring;
each R⁴ is independently halogen, hydroxy, lower alkyl, lower haloalkyl, lower alkoxy, lower haloalkoxyalkyl, or cyano;
R⁶ is hydrogen, halo, alkyl, lower haloalkyl, or cyano; and n is 0, 1, or 2.

In a more specific embodiment, compounds are provided having the structure of Formula (XIX-A), or a pharmaceutically acceptable isomer, racemate, hydrate, solvate, isotope, or salt thereof:

(XIX-A)

wherein
X is halogen, lower alkyl, lower haloalkyl, lower alkoxy, or cyano;
R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, or -alkyl-C(=O)R³;

$R^{1b}$ is hydrogen or lower alkyl;

or $R^{1b}$ and $R^1$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XIX-B), or a pharmaceutically acceptable isomer, racemate, hydrate, solvate, isotope, or salt thereof:

(XVII-B)

wherein

X is halogen, lower alkyl, lower haloalkyl, lower alkoxy, or cyano;

$R^{1b}$ is hydrogen or lower alkyl;

$R^3$ is lower alkyl, lower haloalkyl, lower alkoxy, lower haloalkoxy, -cycloalkyl-$R^6$, —O— cycloalkyl-$R^6$, or —O— heterocyclyl-$R^6$;

or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XX), or a pharmaceutically acceptable isomer, racemate, hydrate, solvate, isotope, or salt thereof:

(XX)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;

$R^{1b}$ is hydrogen or lower alkyl;

$R^3$ is lower alkyl, lower haloalkyl, alkoxy, lower haloalkoxy, -cycloalkyl-$R^6$, —O— cycloalkyl-$R^6$, or —O— heterocyclyl-$R^6$;

or $R^{1b}$ and $R^1$ or $R^{1b}$ and $R^3$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XX-A), or a pharmaceutically acceptable isomer, racemate, hydrate, solvate, isotope, or salt thereof:

(XX-A)

wherein

X is halogen, lower alkyl, lower haloalkyl, lower alkoxy, or cyano;

$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, or -alkyl-C(=O)$R^3$;

$R^{1b}$ is hydrogen or lower alkyl;

or $R^{1b}$ and $R^1$, together with the atoms to which they are attached, form a ring;

each $R^4$ is independently halogen, hydroxy, lower alkyl, lower haloalkyl, lower alkoxy, lower haloalkoxyalkyl, or cyano;

$R^6$ is hydrogen, halo, alkyl, lower haloalkyl, or cyano; and n is 0, 1, or 2.

In a more specific embodiment, compounds are provided having the structure of Formula (XX-B), or a pharmaceutically acceptable isomer, racemate, hydrate, solvate, isotope, or salt thereof:

(XX-B)

wherein

X is halogen, lower alkyl, lower haloalkyl, lower alkoxy, or cyano;

$R^{1b}$ is hydrogen or lower alkyl;

R³ is lower alkyl, lower haloalkyl, lower alkoxy, lower haloalkoxy, -cycloalkyl-R⁶, —O— cycloalkyl-R⁶, or —O— heterocyclyl-R⁶;

or R$^{1b}$ and R³, together with the atoms to which they are attached, form a ring;

each R⁴ is independently halogen, hydroxy, lower alkyl, lower haloalkyl, lower alkoxy, lower haloalkoxyalkyl, or cyano;

R⁶ is hydrogen, halo, alkyl, lower haloalkyl, or cyano; and n is 0, 1, or 2.

In a more specific embodiment, compounds are provided having the structure of Formula (XXI), or a pharmaceutically acceptable isomer, racemate, hydrate, solvate, isotope, or salt thereof:

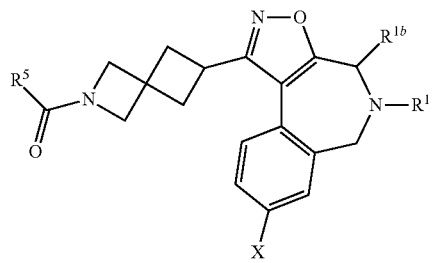

(XXI)

wherein

X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;

R$^{1b}$ is hydrogen or lower alkyl;

R³ is lower alkyl, lower haloalkyl, alkoxy, lower haloalkoxy, -cycloalkyl-R⁶, —O— cycloalkyl-R⁶, or —O— heterocyclyl-R⁶;

or R$^{1b}$ and R¹ or R$^{1b}$ and R³, together with the atoms to which they are attached, form a ring;

R⁵ is cycloalkyl, lower alkyl, lower haloalkyl, cycloalkylalkyl, lower alkoxy, heterocyclyl, or —O-heterocyclyl; and R⁶ is hydrogen, halo, alkyl, lower haloalkyl, or cyano.

In a more specific embodiment, compounds are provided having the structure of Formula (XXI-A), or a pharmaceutically acceptable isomer, racemate, hydrate, solvate, isotope, or salt thereof:

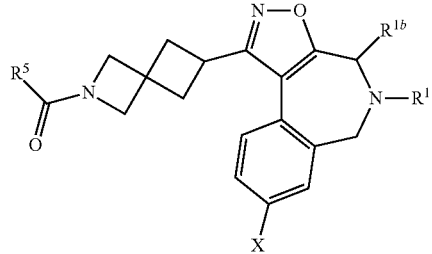

(XXI-A)

wherein

X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, or -alkyl-C(=O)R³;

R$^{1b}$ is hydrogen or lower alkyl;

or R$^{1b}$ and R¹, together with the atoms to which they are attached, form a ring;

R⁵ is cycloalkyl, lower alkyl, lower haloalkyl, cycloalkylalkyl, lower alkoxy, heterocyclyl, or —O— heterocyclyl R⁶ is hydrogen, halo, alkyl, lower haloalkyl, or cyano.

In a more specific embodiment, compounds are provided having the structure of Formula (XXI-B), or a pharmaceutically acceptable isomer, racemate, hydrate, solvate, isotope, or salt thereof:

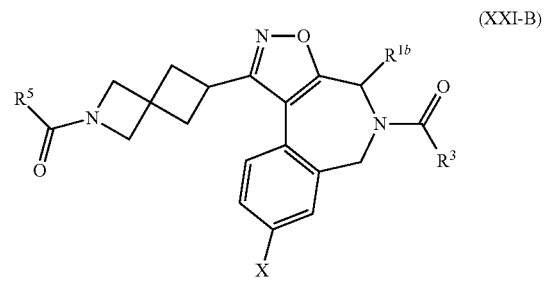

(XXI-B)

wherein

X is halogen, lower alkyl, lower haloalkyl, lower alkoxy, or cyano;

R$^{1b}$ is hydrogen or lower alkyl;

R³ is lower alkyl, lower haloalkyl, lower alkoxy, lower haloalkoxy, -cycloalkyl-R⁶, —O— cycloalkyl-R⁶, or —O— heterocyclyl-R⁶;

or R$^{1b}$ and R³, together with the atoms to which they are attached, form a ring;

R⁵ is cycloalkyl, lower alkyl, lower haloalkyl, cycloalkylalkyl, lower alkoxy, heterocyclyl, or —O-heterocyclyl; and R⁶ is hydrogen, halo, alkyl, lower haloalkyl, or cyano.

In a more specific embodiment, compounds are provided having the structure of Formula (XXII), or a pharmaceutically acceptable isomer, racemate, hydrate, solvate, isotope, or salt thereof:

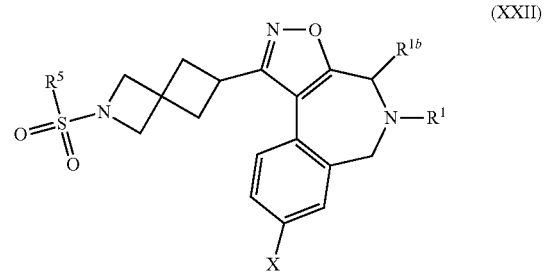

(XXII)

wherein

X is halogen, lower alkyl, lower haloalkyl, lower alkoxy, or cyano;

R¹ is hydrogen, lower alkyl-R⁶, haloalkyl, lower alkoxyalkyl, -cycloalkyl-R⁶, -alkyl-cycloalkyl-R⁶, -aryl-R⁶, -alkyl-aryl-R⁶, -heterocyclyl-R⁶, -alkyl-heterocyclyl-R⁶, lower haloalkyl, -alkyl-C(=O)R³, or —C(=O)R³;

R$^{1b}$ is hydrogen or lower alkyl;

R³ is lower alkyl, lower haloalkyl, alkoxy, lower haloalkoxy, -cycloalkyl-R⁶, —O— cycloalkyl-R⁶, or —O— heterocyclyl-R⁶;

or R$^{1b}$ and R$^1$ or R$^{1b}$ and R$^3$, together with the atoms to which they are attached, form a ring;

R$^5$ is cycloalkyl, lower alkyl, lower haloalkyl, cycloalkylalkyl, lower alkoxy, heterocyclyl, or —O-heterocyclyl; and R$^6$ is hydrogen, halo, alkyl, lower haloalkyl, or cyano.

In a more specific embodiment, compounds are provided having the structure of Formula (XXII-A), or a pharmaceutically acceptable isomer, racemate, hydrate, solvate, isotope, or salt thereof:

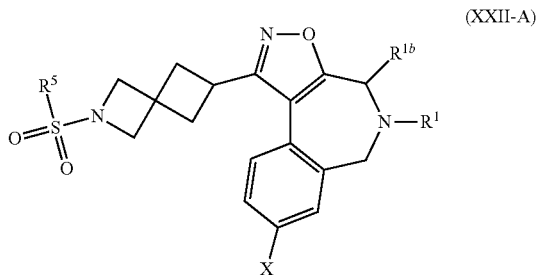

(XXII-A)

wherein

X is halogen, lower alkyl, lower haloalkyl, lower alkoxy, or cyano;

R$^1$ is hydrogen, lower alkyl-R$^6$, haloalkyl, lower alkoxyalkyl, -cycloalkyl-R$^6$, -alkyl-cycloalkyl-R$^6$, -aryl-R$^6$, -alkyl-aryl-R$^6$, -heterocyclyl-R$^6$, -alkyl-heterocyclyl-R$^6$, lower haloalkyl, or -alkyl-C(=O)R$^3$;

R$^{1b}$ is hydrogen or lower alkyl;

or R$^{1b}$ and R$^1$, together with the atoms to which they are attached, form a ring;

R$^5$ is cycloalkyl, lower alkyl, lower haloalkyl, cycloalkylalkyl, lower alkoxy, heterocyclyl, or —O— heterocyclyl;

R$^6$ is hydrogen, halo, alkyl, lower haloalkyl, or cyano.

In a more specific embodiment, compounds are provided having the structure of Formula (XXII-B), or a pharmaceutically acceptable isomer, racemate, hydrate, solvate, isotope, or salt thereof:

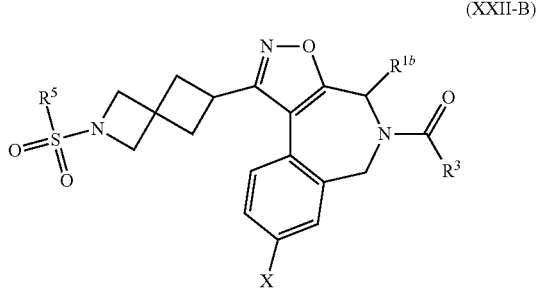

(XXII-B)

wherein

X is halogen, lower alkyl, lower haloalkyl, lower alkoxy, or cyano;

R$^{1b}$ is hydrogen or lower alkyl;

R$^3$ is lower alkyl, lower haloalkyl, lower alkoxy, lower haloalkoxy, -cycloalkyl-R$^6$, —O— cycloalkyl-R$^6$, or —O— heterocyclyl-R$^6$;

or R$^{1b}$ and R$^3$, together with the atoms to which they are attached, form a ring;

R$^5$ is cycloalkyl, lower alkyl, lower haloalkyl, cycloalkylalkyl, lower alkoxy, heterocyclyl, or —O— heterocyclyl; and R$^6$ is hydrogen, halo, alkyl, lower haloalkyl, or cyano.

In the following more specific embodiments, the various substituents (e.g., A, B, G, R$^1$, R$^{1b}$, R$^{1c}$, R$^2$ and X) are set forth in more detail with respect to the compounds of each of Formulas (I) through (XXII-B) above, as applicable to the substituents being further defined. For example, reference to R$^1$ below is intended to further limit the compounds of Formulas (I), (I-A), (II), (II-A), (III), (III-A), (IV), (IV-A), (V), (V-A), (VI), (VI-A), (VII), (VII-A), (VIII), (VIII-A), (IX), (IX-A), (X), (X-A), (XI), (XI-A), (XII), (XII-A), (XIII), (XIII-A), (XIV), (XIV-A), (XV), (XV-A), (XVI), (XVI-A), (XVII), (XVII-A), (XVIII), (XVIII-A), (XIX), (XIX-A), (XX), (XX-A), (XXI), (XXI-A), (XXII), and (XXII-A) above, but not Formulas (I-B), (II-B), (III-B), (IV-B), (V-B), (VI-B), (VII-B), (VIII-B), (IX-B), (X-B), (XI-B), (XII-B), (XIII-B), (XIV-B), (XV-B), (XVI-B), (XVII-B), (XVIII-B), (XIX-B), (XX-B), (XXI), (XXI-B), (XXII), and (XXII-B) since the R$^1$ substituent has already been further defined in the same. Thus, reference to the substituents below is intended to further modify Formulas (I) through (XXII-B) to the extent such formulas recite that particular substituent as a variable.

In further embodiments, compounds are provided having the structure of any one of Formulas (I) through (XXII-B), or a pharmaceutically acceptable isomer, racemate, hydrate, solvate, isotope, or salt thereof, wherein X is halogen. In more specific embodiments, compounds are provided having the structure of any one of Formulas (I) through (XXII-B), or a pharmaceutically acceptable isomer, racemate, hydrate, solvate, isotope, or salt thereof, wherein X is Cl, F, or Br. In more specific embodiments, compounds are provided having the structure of any one of Formulas (I) through (XXII-B), or a pharmaceutically acceptable isomer, racemate, hydrate, solvate, isotope, or salt thereof, wherein X is Cl.

In further embodiments, compounds are provided having the structure of any one of Formulas (I) through (XXII-B), or a pharmaceutically acceptable isomer, racemate, hydrate, solvate, isotope, or salt thereof, wherein X is lower alkyl. In more specific embodiments, compounds are provided having the structure of any one of Formulas (I) through (XXII-B), or a pharmaceutically acceptable isomer, racemate, hydrate, solvate, isotope, or salt thereof, wherein X is methyl, ethyl, or isopropyl.

In further embodiments, compounds are provided having the structure of any one of Formulas (I) through (XXII-B), or a pharmaceutically acceptable isomer, racemate, hydrate, solvate, isotope, or salt thereof, wherein X is lower haloalkyl. In more specific embodiments, compounds are provided having the structure of any one of Formulas (I) through (XXII-B), or a pharmaceutically acceptable isomer, racemate, hydrate, solvate, isotope, or salt thereof, wherein X is —CF$_3$.

In further embodiments, compounds are provided having the structure of any one of Formulas (I) through (XXII-B), or a pharmaceutically acceptable isomer, racemate, hydrate, solvate, isotope, or salt thereof, wherein X is lower alkoxy. In more specific embodiments, compounds are provided having the structure of any one of Formulas (I) through (XXII-B), or a pharmaceutically acceptable isomer, racemate, hydrate, solvate, isotope, or salt thereof, wherein X is methoxy, ethoxy, isopropoxy, or t-butoxy.

In further embodiments, compounds are provided having the structure of any one of Formulas (I) through (XXII-B), or a pharmaceutically acceptable isomer, racemate, hydrate, solvate, isotope, or salt thereof, wherein X is cyano.

In further embodiments, compounds are provided having the structure of any one of Formulas (I) through (XXII-B), or a pharmaceutically acceptable isomer, racemate, hydrate, solvate, isotope, or salt thereof, wherein $R^1$ is hydrogen.

In further embodiments, compounds are provided having the structure of any one of Formulas (I) through (XXII-B), or a pharmaceutically acceptable isomer, racemate, hydrate, solvate, isotope, or salt thereof, wherein $R^1$ is lower alkyl. In more specific embodiments, compounds are provided having the structure of any one of Formulas (I) through (XXII-B), or a pharmaceutically acceptable isomer, racemate, hydrate, solvate, isotope, or salt thereof, wherein $R^1$ is methyl, ethyl, or isopropyl.

In further embodiments, compounds are provided having the structure of any one of Formulas (I) through (XXII-B), or a pharmaceutically acceptable isomer, racemate, hydrate, solvate, isotope, or salt thereof, wherein $R^1$ is lower alkoxy. In more specific embodiments, compounds are provided having the structure of any one of Formulas (I) through (XXII-B), or a pharmaceutically acceptable isomer, racemate, hydrate, solvate, isotope, or salt thereof, wherein $R^1$ is methoxy, ethoxy, isopropoxy, or t-butoxy.

In further embodiments, compounds are provided having the structure of any one of Formulas (I) through (XXII-B), or a pharmaceutically acceptable isomer, racemate, hydrate, solvate, isotope, or salt thereof, wherein $R^1$ is cycloalkyl. In more specific embodiments, compounds are provided having the structure of any one of Formulas (I) through (XXII-B), or a pharmaceutically acceptable isomer, racemate, hydrate, solvate, isotope, or salt thereof, wherein $R^1$ is cyclopropyl or cyclobutyl.

In further embodiments, compounds are provided having the structure of any one of Formulas (I) through (XXII-B), or a pharmaceutically acceptable isomer, racemate, hydrate, solvate, isotope, or salt thereof, wherein $R^2$ is -Q-$(R^4)_n$. In further embodiments, n is 0. In further embodiments, n is 1, 2, or 3. In further embodiments, n is 1.

In further embodiments, compounds are provided having the structure of any one of Formulas (I) through (XXII-B) wherein $R^2$ is -Q-$(R^4)_n$ and $R^4$ is halogen. In more specific embodiments, compounds are provided wherein $R^4$ is F or Cl.

In further embodiments compounds are provided having the structure of any one of Formulas (I) through (XXII-B) wherein $R^2$ is -Q-$(R^4)_n$ and $R^4$ is lower alkyl. In more specific embodiments, compounds are provided wherein $R^4$ is methyl or ethyl.

In further embodiments compounds are provided having the structure of any one of Formulas (I) through (XXII-B) wherein $R^2$ is -Q-$(R^4)_n$ and $R^4$ is lower alkoxy. In more specific embodiments, compounds are provided wherein $R^4$ is methoxy or ethoxy.

In further embodiments compounds are provided having the structure of any one of Formulas (I) through (XXII-B) wherein $R^2$ is -Q-$(R^4)_n$ and $R^4$ is cyano.

In further embodiments compounds are provided having the structure of any one of Formulas (I) through (XXII-B) wherein $R^2$ is -Q-$(R^4)_n$ and $R^4$ is hydroxy.

In further embodiments, compounds are provided having the structure of any one of Formulas (I) through (XXII-B) wherein $R^2$ is —S(=O)$_2R^5$ or —C(=O)$R^5$ and $R^5$ is lower alkyl. In more specific embodiments, compounds are provided wherein $R^5$ is methyl, ethyl, or isopropyl.

In further embodiments, compounds are provided having the structure of any one of Formulas (I) through (XXII-B) wherein $R^2$ is —S(=O)$_2R^5$ or —C(=O)$R^5$ and $R^5$ is lower alkoxy. In more specific embodiments, compounds are provided wherein $R^5$ is t-butoxy.

In further embodiments, compounds are provided having the structure of any one of Formulas (I) through (XXII-B) wherein $R^2$ is —S(=O)$_2R^5$ or —C(=O)$R^5$ and $R^5$ is heterocyclyl or cycloalkyl. In more specific embodiments, compounds are provided wherein $R^5$ is:

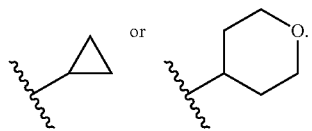

In further embodiments, compounds are provided having the structure of any one of Formulas (I) through (XXII-B) wherein $R^2$ is —S(=O)$_2R^5$ or —C(=O)$R^5$ and $R^5$ is —O-heterocyclyl. In more specific embodiments, compounds are provided wherein $R^5$ is:

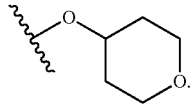

In further embodiments, compounds are provided having the structure of any one of Formulas (I) through (XXII-B) wherein $R^2$ is —S(=O)$_2R^5$ or —C(=O)$R^5$ and $R^5$ is heteroaryl. In more specific embodiments, compounds are provided wherein $R^5$ is pyridinyl.

In further embodiments, compounds are provided having the structure of any one of Formulas (I) through (XXII-B) wherein $R^2$ is —S(=O)$_2R^5$ or —C(=O)$R^5$ and $R^5$ is cycloalkylalkyl. In more specific embodiments, compounds are provided wherein $R^5$ is:

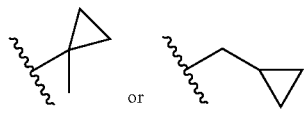

In further embodiments, compounds are provided having the structure of any one of Formulas (I) through (XXII-B) wherein $R^1$ is alkyl, cycloalkyl, lower haloalkyl; $R^4$ is H, halo, lower alkyl, lower haloalkyl, lower alkoxy, lower alkoxyalkyl, lower haloalkoxyalkyl, cyano; and X is halo or lower alkoxy. In further embodiments, $R^1$ is methyl, cyclopropyl, or $CF_3$, $R^4$ is H, F, methyl, —$CF_3$, —O—$CH_3$, or —O-isopropyl; and X is Cl or —O—$CH_3$.

In further embodiments, compounds are provided having the structure of any one of Formulas (I) through (XXII-B) wherein $R^3$ is alkyl, cycloalkyl, lower haloalkyl; $R^4$ is H, halo, lower alkyl, lower haloalkyl, lower alkoxyalkyl, lower alkoxhaloyalkyl, cyano; and X is halo, lower alkoxy. In further embodiments, $R^3$ is methyl, cyclopropyl, or CF3, $R^4$ is H, F, methyl, —$CF_3$, —O—$CH_3$, or —O-isopropyl; and X is Cl or —O—$CH_3$.

In further embodiments, compounds are provided having the structure of any one of Formulas (I) through (XXII-B) wherein $R^1$ is alkyl, haloalkyl, cycloalkyl; $R^5$ is cycloalkyl, lower alkyl, heterocyclyl and X is halo. In further embodiments, R¹ is cyclopropyl or —CH₂—CF₂-cyclopropyl. In further embodiments, compounds are provided having the structure of any one of Formulas (I) through (XXII-B) wherein R³ is alkyl, cycloalkyl, lower haloalkyl; R⁵ is cycloalkyl, lower alkyl, heterocyclyl and X is halo. In further embodiments, R³ is methyl or cyclopropyl.

In further embodiments, compounds are provided having the structure of any one of Formulas (I) through (XXII-B) wherein R¹ is

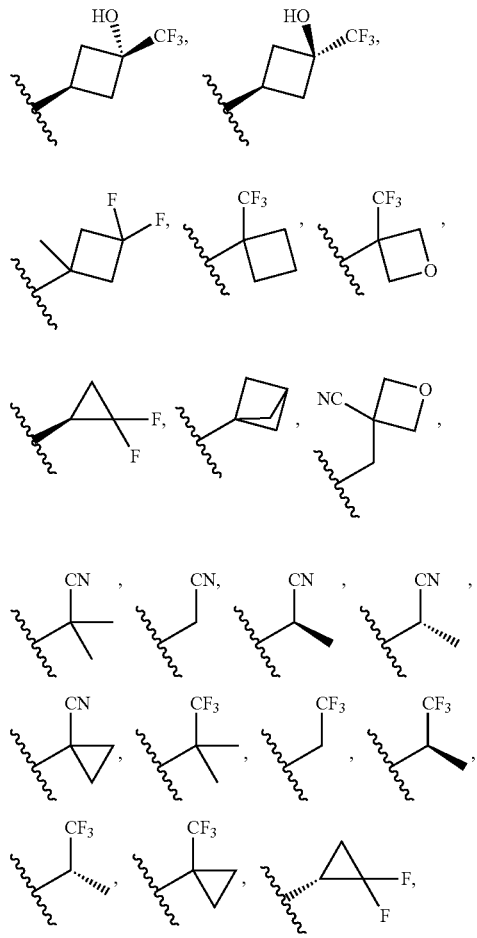

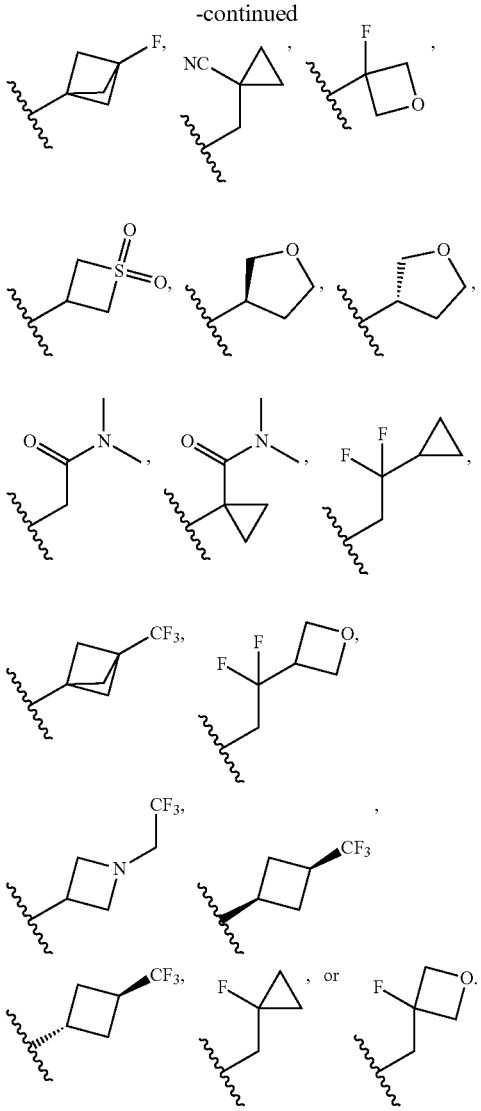

Representative compounds of Formula (I), and Formulas (II) through (XXII-B) as applicable, include the compounds listed in Table 1 below, as well as pharmaceutically acceptable isomers, racemates, hydrates, solvates, isotopes, and salts thereof.

TABLE 1

| Representative Compounds | |
|---|---|
| Cmpd. No. | Structure |
| 1 | (structure shown) |

TABLE 1-continued
Representative Compounds
| Cmpd. No. | Structure |
|---|---|
| 2 | 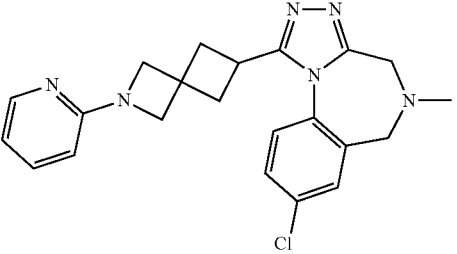 [SMILES: CN1Cc2cc(Cl)ccc2-n2c(nnc2C2CC3(C2)CN(c2ccccn2)C3)C1] |
| 3 | 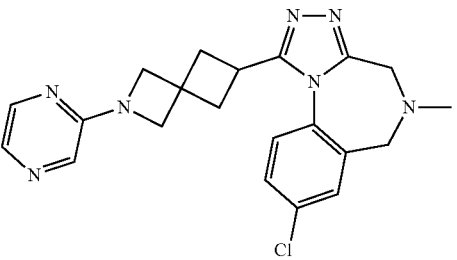 [SMILES: CN1Cc2cc(Cl)ccc2-n2c(nnc2C2CC3(C2)CN(c2cnccn2)C3)C1] |
| 4 | 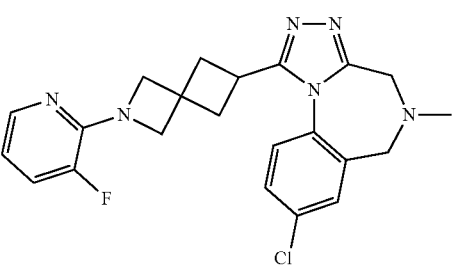 [SMILES: CN1Cc2cc(Cl)ccc2-n2c(nnc2C2CC3(C2)CN(c2ncccc2F)C3)C1] |
| 5 | 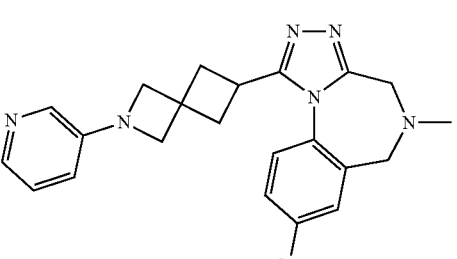 |
| 6 | 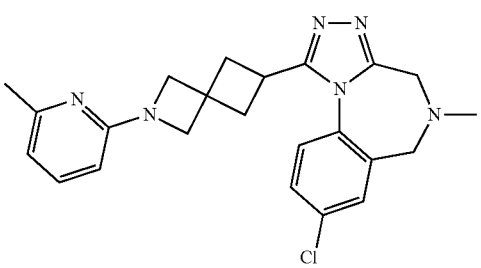 |

TABLE 1-continued
Representative Compounds
| Cmpd. No. | Structure |
|---|---|
| 7 | 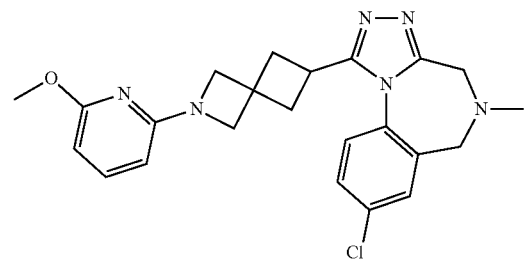 |
| 8 | 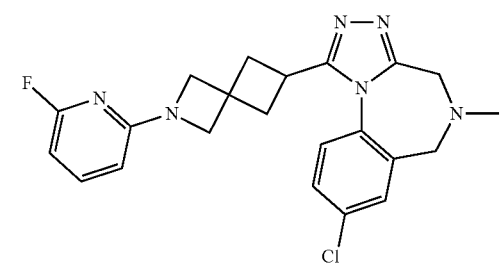 [SMILES: CN1Cc2cc(Cl)ccc2-n2c(nnc2C2CC3(C2)CN(c2cccc(F)n2)C3)C1] |
| 9 | 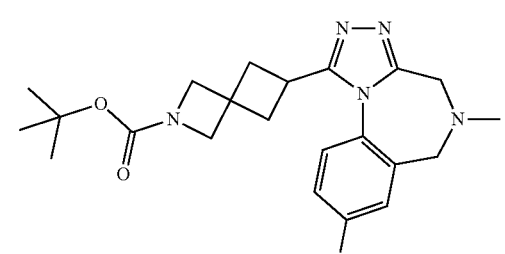 |
| 10 | 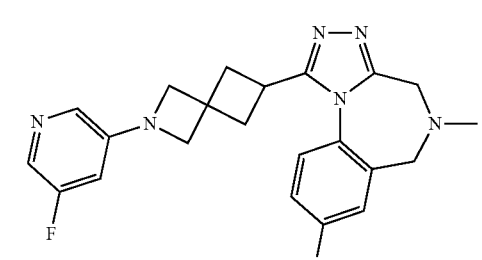 |
| 11 | 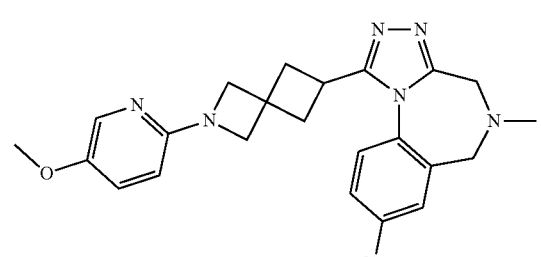 |

TABLE 1-continued

Representative Compounds

| Cmpd. No. | Structure |
|---|---|
| 12 | 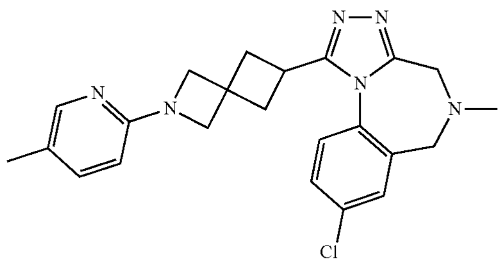 |
| 13 | 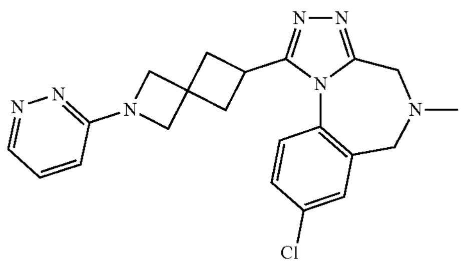 [SMILES: CN1Cc2cc(Cl)ccc2-n2c(nnc2C2CC3(C2)CN(c2cccnn2)C3)C1] |
| 14 | 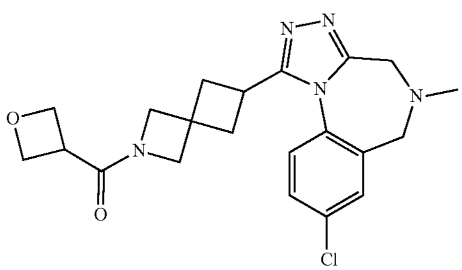 [SMILES: CN1Cc2cc(Cl)ccc2-n2c(nnc2C2CC3(C2)CN(C(=O)C2COC2)C3)C1] |
| 15 | 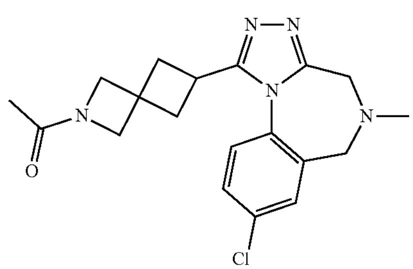 [SMILES: CC(=O)N1CC2(CC(c3nnc4n3-c3ccc(Cl)cc3CN(C)C4)C2)C1] |
| 16 | 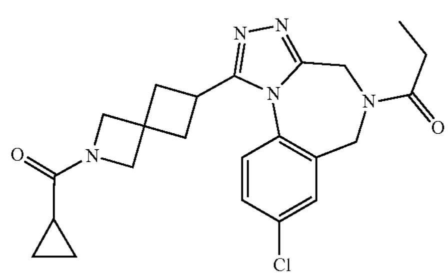 [SMILES: CCC(=O)N1Cc2cc(Cl)ccc2-n2c(nnc2C2CC3(C2)CN(C(=O)C2CC2)C3)C1] |

TABLE 1-continued

Representative Compounds

| Cmpd. No. | Structure |
|---|---|
| 17 | *structure* |
| 18 | *structure* |
| 19 | *structure* |
| 20 | *structure* |
| 21 | *structure* |

TABLE 1-continued
Representative Compounds
| Cmpd. No. | Structure |
|---|---|
| 22 | 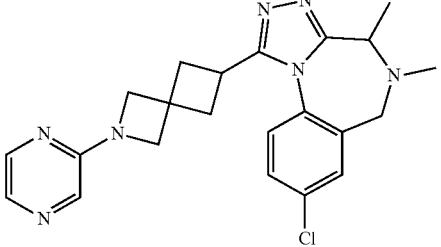 |
| 23 | 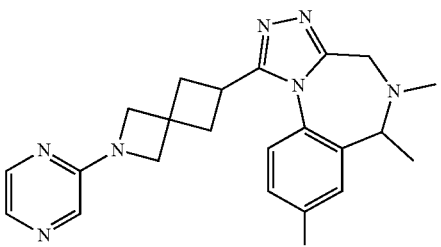 |
| 24 | 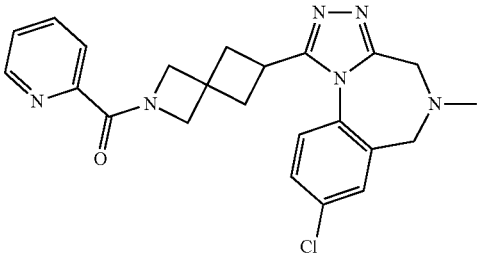 [SMILES: CN1Cc2cc(Cl)ccc2-n2c(nnc2C2CC3(C2)CN(C(=O)c2ccccn2)C3)C1] |
| 25 | 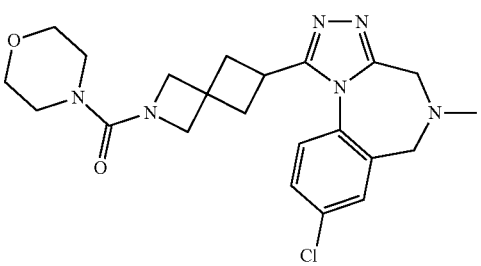 [SMILES: CN1Cc2cc(Cl)ccc2-n2c(nnc2C2CC3(C2)CN(C(=O)N2CCOCC2)C3)C1] |
| 26 | 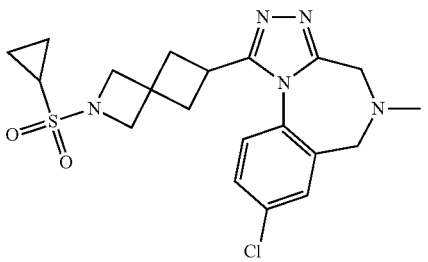 [SMILES: CN1Cc2cc(Cl)ccc2-n2c(nnc2C2CC3(C2)CN(S(=O)(=O)C2CC2)C3)C1] |

TABLE 1-continued

Representative Compounds

| Cmpd. No. | Structure |
|---|---|
| 27 | *(structure image)* |
| 28 | *(structure image)* |
| 29 | *(structure image)* |
| 30 | *(structure image)* |
| 31 | *(structure image)* |

TABLE 1-continued

Representative Compounds

| Cmpd. No. | Structure |
|---|---|
| 32 | 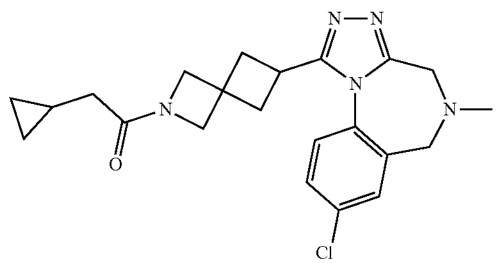 [SMILES: CN1Cc2cc(Cl)ccc2-n2c(nnc2C2CC3(C2)CN(C(=O)CC2CC2)C3)C1] |
| 33 | 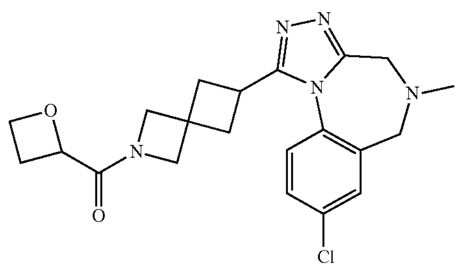 [SMILES: CN1Cc2cc(Cl)ccc2-n2c(nnc2C2CC3(C2)CN(C(=O)C2CCO2)C3)C1] |
| 34 | 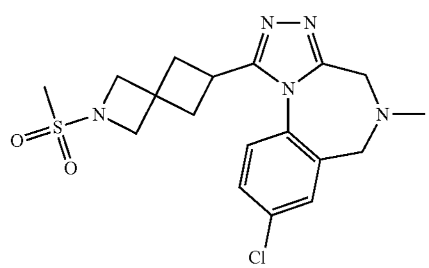 [SMILES: CN1Cc2cc(Cl)ccc2-n2c(nnc2C2CC3(C2)CN(S(C)(=O)=O)C3)C1] |
| 35 | 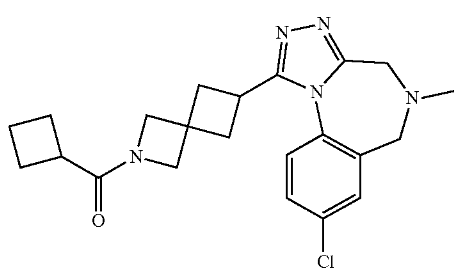 [SMILES: CN1Cc2cc(Cl)ccc2-n2c(nnc2C2CC3(C2)CN(C(=O)C2CCC2)C3)C1] |
| 36 | 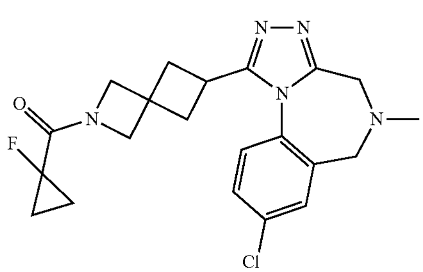 [SMILES: CN1Cc2cc(Cl)ccc2-n2c(nnc2C2CC3(C2)CN(C(=O)C2(F)CC2)C3)C1] |

TABLE 1-continued

Representative Compounds

| Cmpd. No. | Structure |
|---|---|
| 37 | 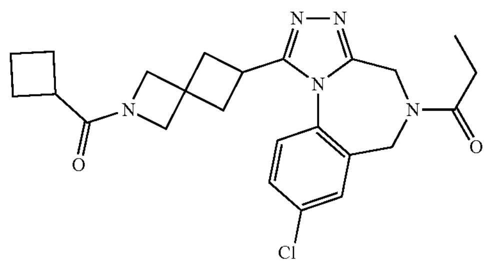 [SMILES: CCC(=O)N1Cc2cc(Cl)ccc2-n2c(nnc2C2CC3(C2)CN(C(=O)C2CCC2)C3)C1] |
| 38 | 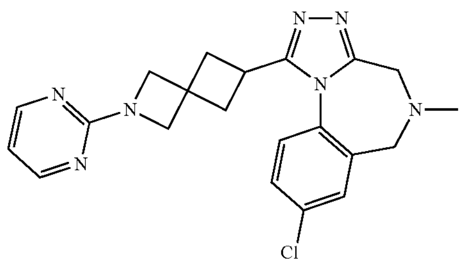 [SMILES: CN1Cc2cc(Cl)ccc2-n2c(nnc2C2CC3(C2)CN(c2ncccn2)C3)C1] |
| 39 | 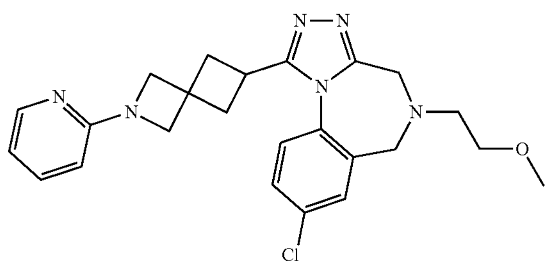 [SMILES: COCCN1Cc2cc(Cl)ccc2-n2c(nnc2C2CC3(C2)CN(c2ccccn2)C3)C1] |
| 40 | 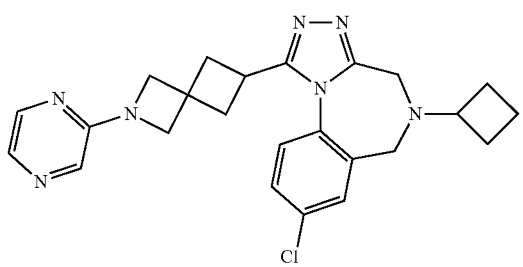 [SMILES: Clc1ccc2c(c1)CN(C1CCC1)Cc1nnc(C3CC4(C3)CN(c3cnccn3)C4)n1-2] |
| 41 | 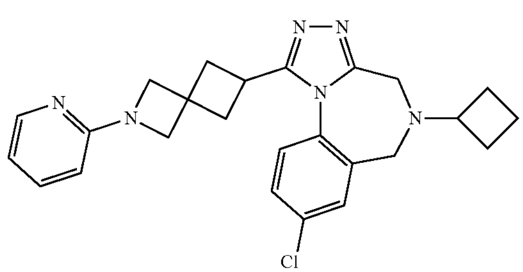 [SMILES: Clc1ccc2c(c1)CN(C1CCC1)Cc1nnc(C3CC4(C3)CN(c3ccccn3)C4)n1-2] |

TABLE 1-continued

Representative Compounds

| Cmpd. No. | Structure |
|---|---|
| 42 | 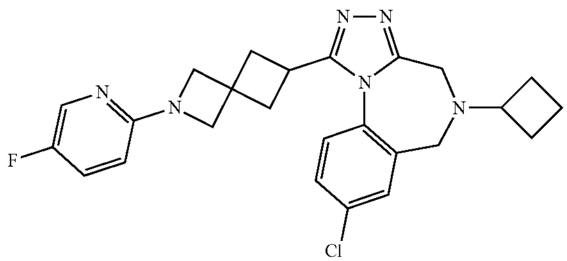 [SMILES: Fc1ccc(N2CC3(CC(c4nnc5n4-c4ccc(Cl)cc4CN(C4CCC4)C5)C3)C2)nc1] |
| 43 | 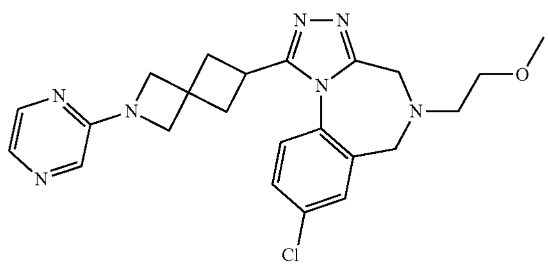 [SMILES: COCCN1Cc2cc(Cl)ccc2-n2c(nnc2C2CC3(C2)CN(c2cnccn2)C3)C1] |
| 44 | 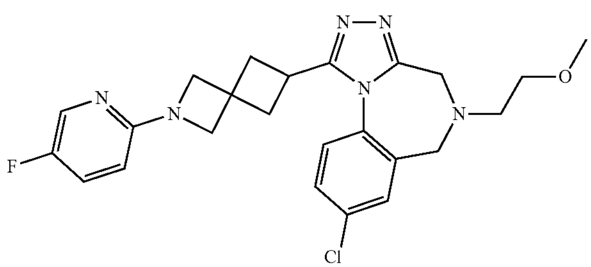 [SMILES: COCCN1Cc2cc(Cl)ccc2-n2c(nnc2C2CC3(C2)CN(c2ccc(F)cn2)C3)C1] |
| 45 | 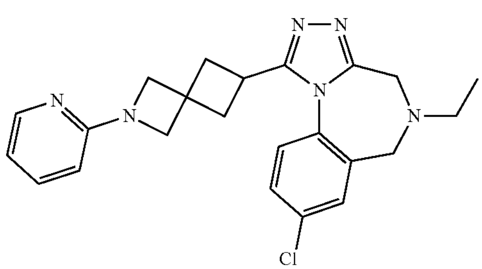 [SMILES: CCN1Cc2cc(Cl)ccc2-n2c(nnc2C2CC3(C2)CN(c2ccccn2)C3)C1] |
| 46 | 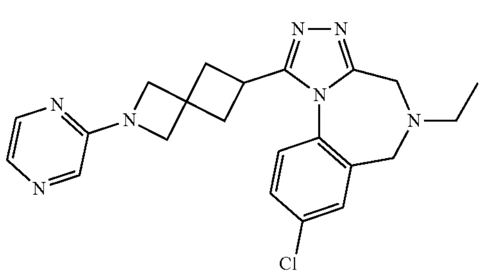 [SMILES: CCN1Cc2cc(Cl)ccc2-n2c(nnc2C2CC3(C2)CN(c2cnccn2)C3)C1] |

TABLE 1-continued

Representative Compounds

| Cmpd. No. | Structure |
|---|---|
| 47 | 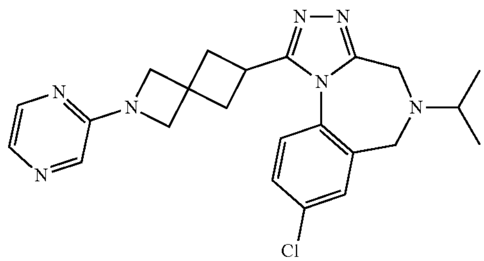 [SMILES: CC(C)N1Cc2cc(Cl)ccc2-n2c(nnc2C2CC3(C2)CN(c2cnccn2)C3)C1] |
| 48 | 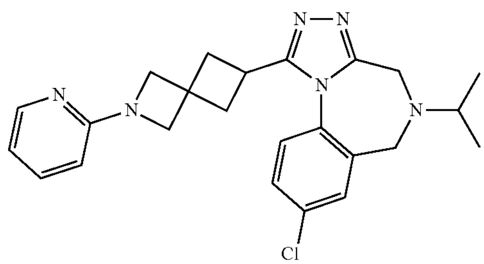 [SMILES: CC(C)N1Cc2cc(Cl)ccc2-n2c(nnc2C2CC3(C2)CN(c2ccccn2)C3)C1] |
| 49 | 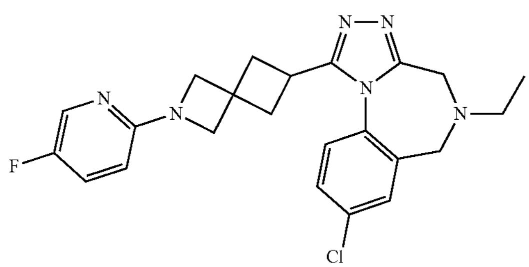 [SMILES: CCN1Cc2cc(Cl)ccc2-n2c(nnc2C2CC3(C2)CN(c2ccc(F)cn2)C3)C1] |
| 50 | 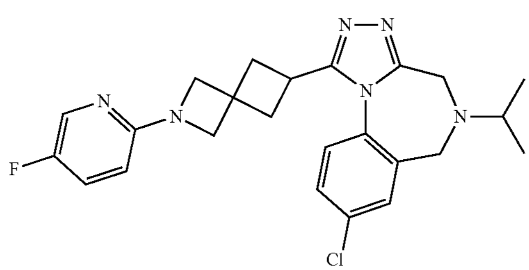 [SMILES: CC(C)N1Cc2cc(Cl)ccc2-n2c(nnc2C2CC3(C2)CN(c2ccc(F)cn2)C3)C1] |
| 51 | 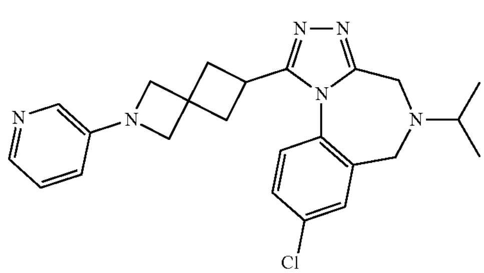 [SMILES: CC(C)N1Cc2cc(Cl)ccc2-n2c(nnc2C2CC3(C2)CN(c2cccnc2)C3)C1] |

TABLE 1-continued

Representative Compounds

| Cmpd. No. | Structure |
|---|---|
| 52 | 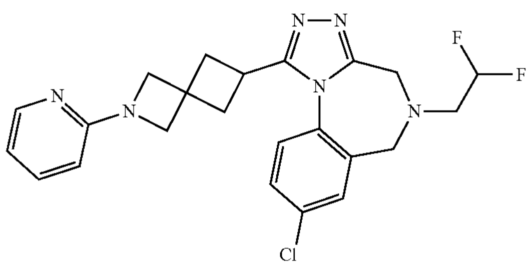 [SMILES: FC(F)CN1Cc2cc(Cl)ccc2-n2c(nnc2C2CC3(C2)CN(c2ccccn2)C3)C1] |
| 53 | 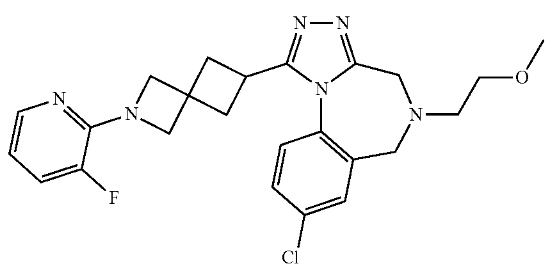 [SMILES: COCCN1Cc2cc(Cl)ccc2-n2c(nnc2C2CC3(C2)CN(c2ncccc2F)C3)C1] |
| 54 | 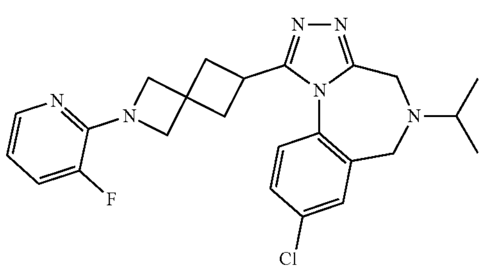 [SMILES: CC(C)N1Cc2cc(Cl)ccc2-n2c(nnc2C2CC3(C2)CN(c2ncccc2F)C3)C1] |
| 55 | 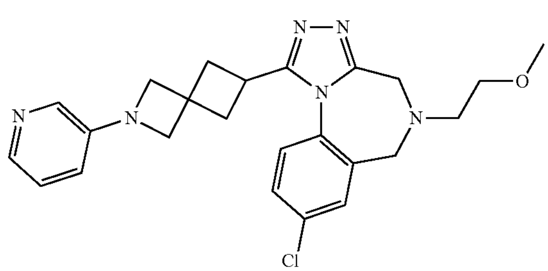 [SMILES: COCCN1Cc2cc(Cl)ccc2-n2c(nnc2C2CC3(C2)CN(c2cccnc2)C3)C1] |
| 56 | 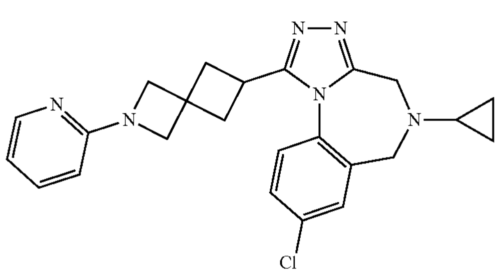 [SMILES: Clc1ccc2c(c1)CN(C1CC1)Cc1nnc(C3CC4(C3)CN(c3ccccn3)C4)n1-2] |

TABLE 1-continued

Representative Compounds

| Cmpd. No. | Structure |
|---|---|
| 57 | 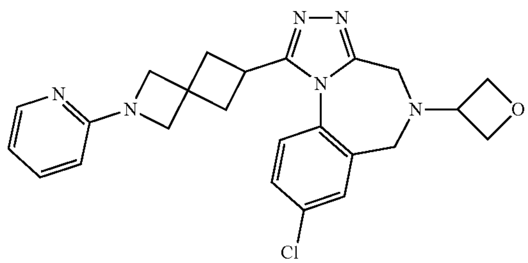 [SMILES: Clc1ccc2c(c1)CN(C1COC1)Cc1nnc(C3CC4(C3)CN(c3ccccn3)C4)n1-2] |
| 58 | 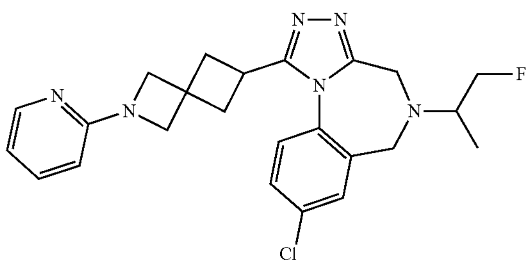 [SMILES: CC(CF)N1Cc2cc(Cl)ccc2-n2c(nnc2C2CC3(C2)CN(c2ccccn2)C3)C1] |
| 59 | 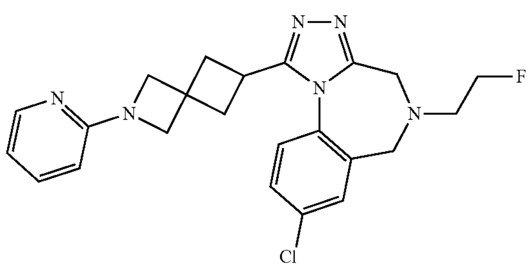 [SMILES: FCCN1Cc2cc(Cl)ccc2-n2c(nnc2C2CC3(C2)CN(c2ccccn2)C3)C1] |
| 60 | 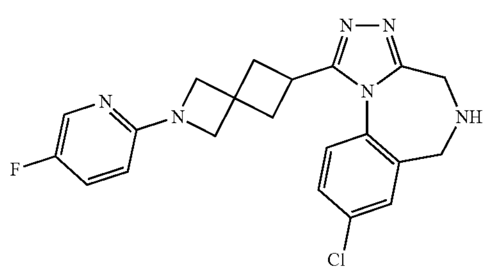 [SMILES: Fc1ccc(N2CC3(CC(c4nnc5n4-c4ccc(Cl)cc4CNC5)C3)C2)nc1] |
| 61 | 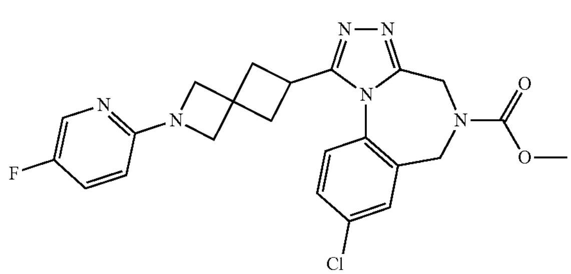 |

TABLE 1-continued

Representative Compounds

| Cmpd. No. | Structure |
|---|---|
| 62 | 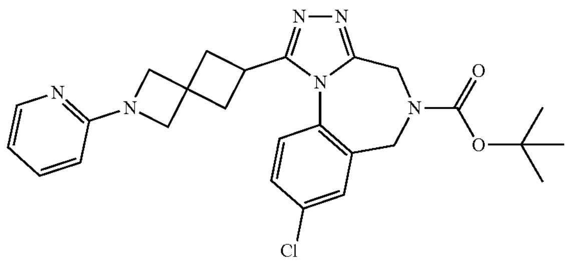 [SMILES: CC(C)(C)OC(=O)N1Cc2cc(Cl)ccc2-n2c(nnc2C2CC3(C2)CN(c2ccccn2)C3)C1] |
| 63 | 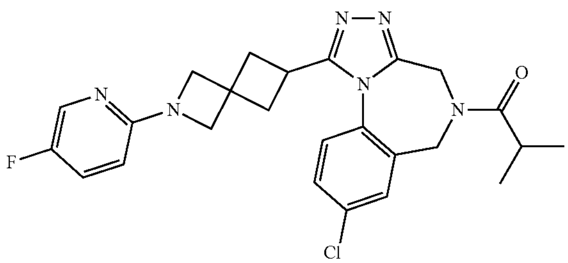 [SMILES: CC(C)C(=O)N1Cc2cc(Cl)ccc2-n2c(nnc2C2CC3(C2)CN(c2ccc(F)cn2)C3)C1] |
| 64 | 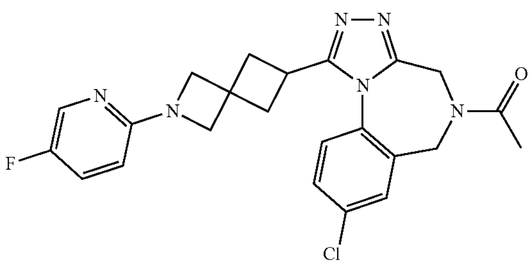 [SMILES: CC(=O)N1Cc2cc(Cl)ccc2-n2c(nnc2C2CC3(C2)CN(c2ccc(F)cn2)C3)C1] |
| 65 | 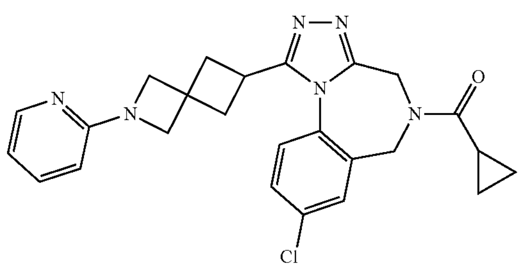 [SMILES: O=C(C1CC1)N1Cc2cc(Cl)ccc2-n2c(nnc2C2CC3(C2)CN(c2ccccn2)C3)C1] |
| 66 | 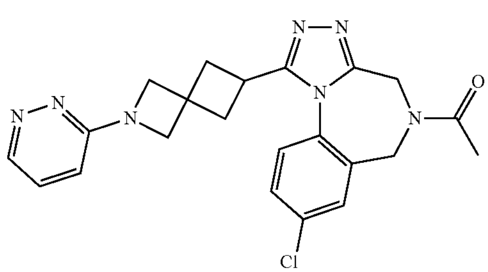 |

TABLE 1-continued

Representative Compounds

| Cmpd. No. | Structure |
|---|---|
| 67 | 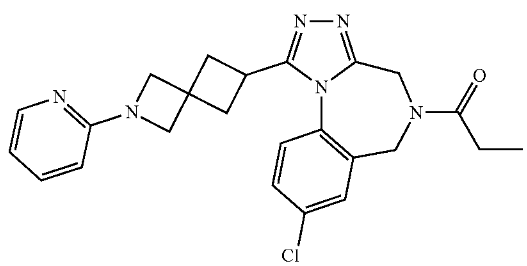 |
| 68 | 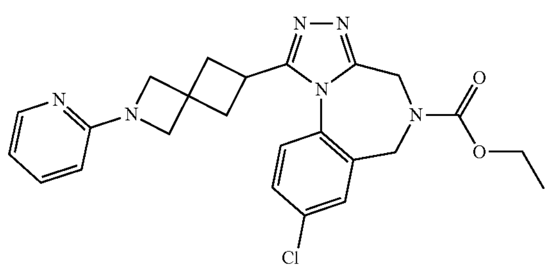 [SMILES: CCOC(=O)N1Cc2cc(Cl)ccc2-n2c(nnc2C2CC3(C2)CN(c2ccccn2)C3)C1] |
| 69 | 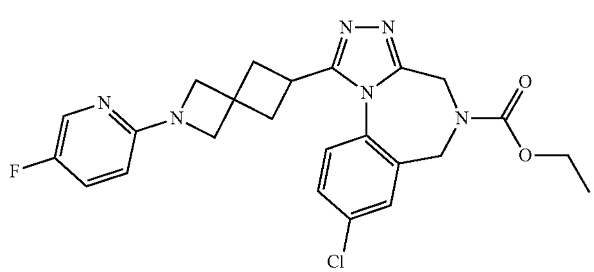 [SMILES: CCOC(=O)N1Cc2cc(Cl)ccc2-n2c(nnc2C2CC3(C2)CN(c2ccc(F)cn2)C3)C1] |
| 70 | 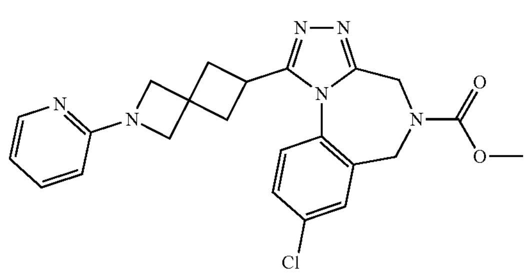 [SMILES: COC(=O)N1Cc2cc(Cl)ccc2-n2c(nnc2C2CC3(C2)CN(c2ccccn2)C3)C1] |
| 71 | 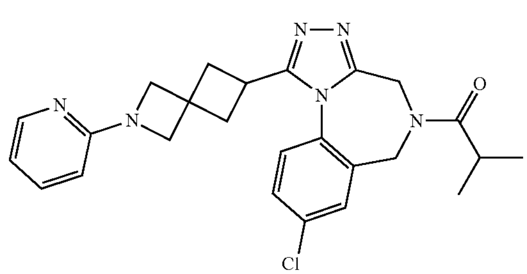 [SMILES: CC(C)C(=O)N1Cc2cc(Cl)ccc2-n2c(nnc2C2CC3(C2)CN(c2ccccn2)C3)C1] |

TABLE 1-continued

Representative Compounds

| Cmpd. No. | Structure |
|---|---|
| 72 | 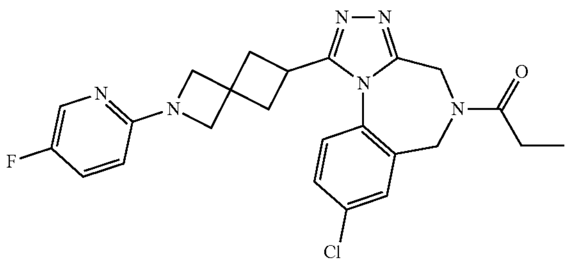 [SMILES: CCC(=O)N1Cc2cc(Cl)ccc2-n2c(nnc2C2CC3(C2)CN(c2ccc(F)cn2)C3)C1] |
| 73 | 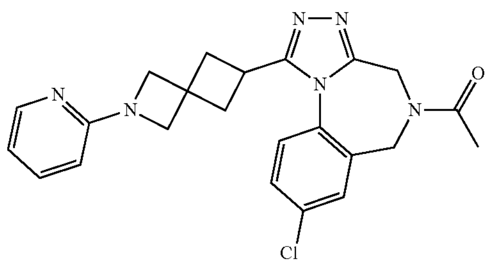 [SMILES: CC(=O)N1Cc2cc(Cl)ccc2-n2c(nnc2C2CC3(C2)CN(c2ccccn2)C3)C1] |
| 74 | 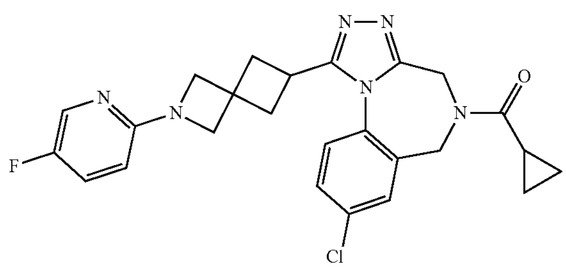 [SMILES: O=C(C1CC1)N1Cc2cc(Cl)ccc2-n2c(nnc2C2CC3(C2)CN(c2ccc(F)cn2)C3)C1] |
| 75 | 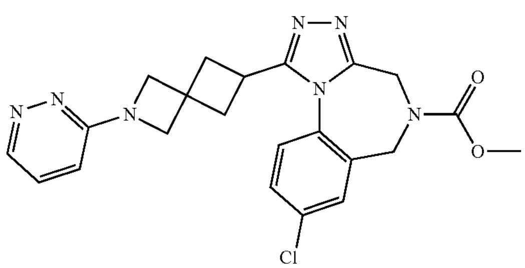 [SMILES: COC(=O)N1Cc2cc(Cl)ccc2-n2c(nnc2C2CC3(C2)CN(c2cccnn2)C3)C1] |
| 76 | 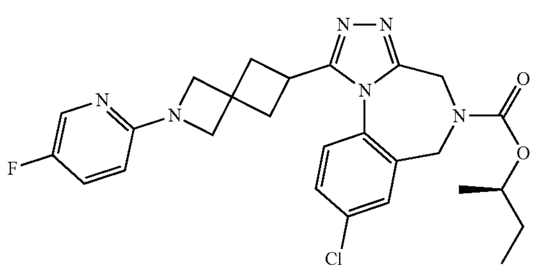 [SMILES: CC[C@@H](C)OC(=O)N1Cc2cc(Cl)ccc2-n2c(nnc2C2CC3(C2)CN(c2ccc(F)cn2)C3)C1] |

TABLE 1-continued

Representative Compounds

| Cmpd. No. | Structure |
|---|---|
| 77 | 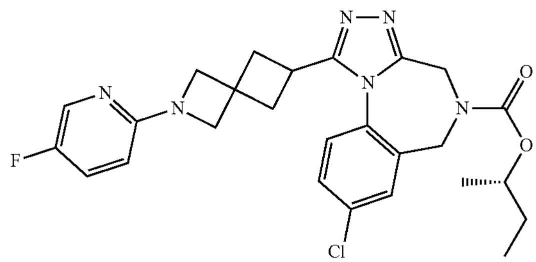 [SMILES: CC[C@H](C)OC(=O)N1Cc2cc(Cl)ccc2-n2c(nnc2C2CC3(C2)CN(c2ccc(F)cn2)C3)C1] |
| 78 | 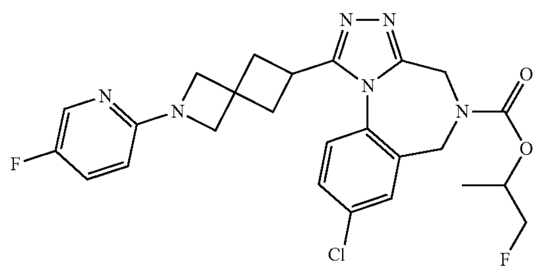 [SMILES: CC(CF)OC(=O)N1Cc2cc(Cl)ccc2-n2c(nnc2C2CC3(C2)CN(c2ccc(F)cn2)C3)C1] |
| 79 | 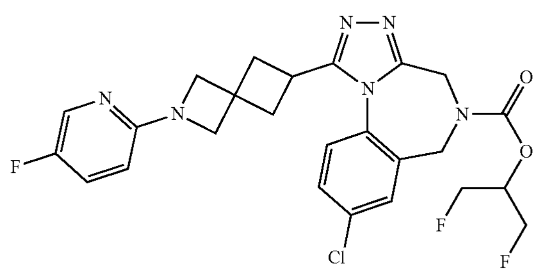 [SMILES: O=C(OC(CF)CF)N1Cc2cc(Cl)ccc2-n2c(nnc2C2CC3(C2)CN(c2ccc(F)cn2)C3)C1] |
| 80 | 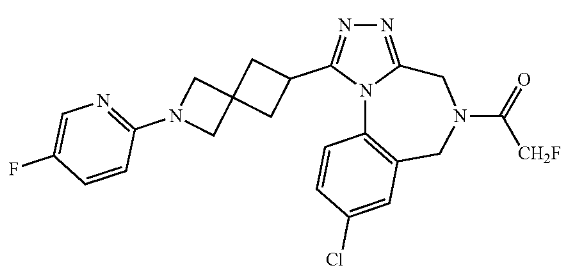 |
| 81 | 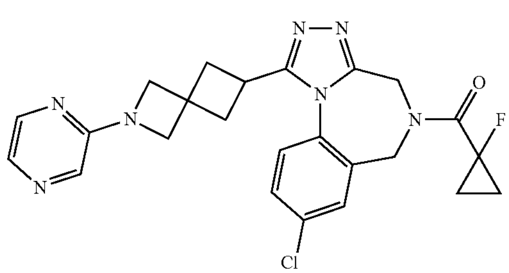 [SMILES: O=C(N1Cc2cc(Cl)ccc2-n2c(nnc2C2CC3(C2)CN(c2cnccn2)C3)C1)C1(F)CC1] |

TABLE 1-continued

Representative Compounds

| Cmpd. No. | Structure |
|---|---|
| 82 | 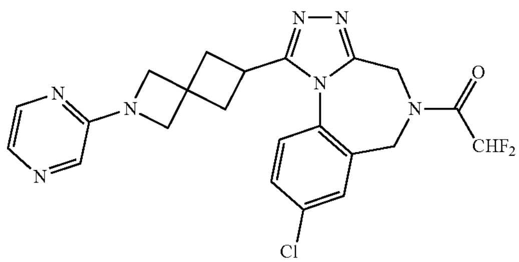 [SMILES: O=C(C(F)F)N1Cc2cc(Cl)ccc2-n2c(nnc2C2CC3(C2)CN(c2cnccn2)C3)C1] |
| 83 | 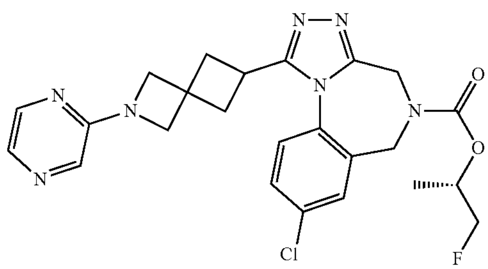 [SMILES: C[C@@H](CF)OC(=O)N1Cc2cc(Cl)ccc2-n2c(nnc2C2CC3(C2)CN(c2cnccn2)C3)C1] |
| 84 | 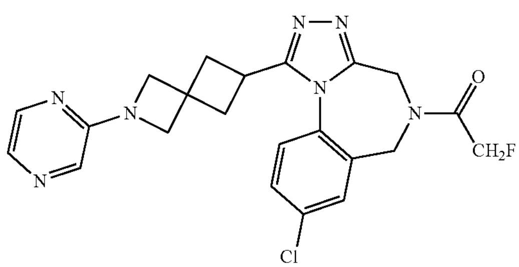 |
| 85 | 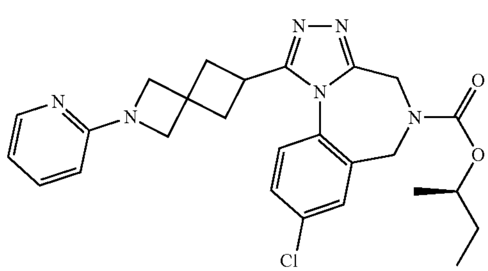 [SMILES: CC[C@@H](C)OC(=O)N1Cc2cc(Cl)ccc2-n2c(nnc2C2CC3(C2)CN(c2ccccn2)C3)C1] |
| 86 | 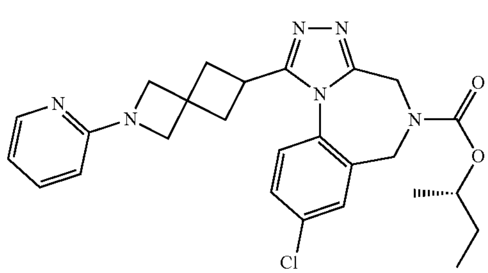 [SMILES: CC[C@H](C)OC(=O)N1Cc2cc(Cl)ccc2-n2c(nnc2C2CC3(C2)CN(c2ccccn2)C3)C1] |

TABLE 1-continued
Representative Compounds
| Cmpd. No. | Structure |
|---|---|
| 87 | 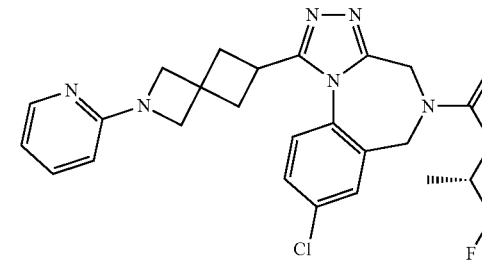 |
| 88 | 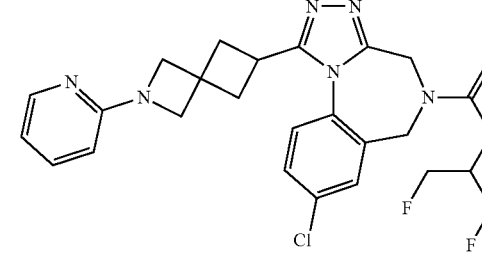 |
| 89 | 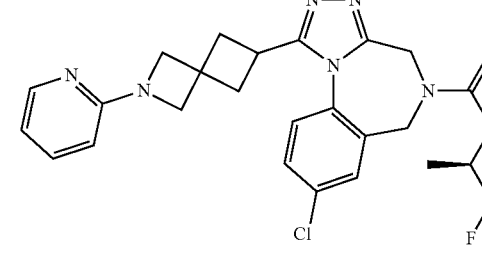 |
| 90 | 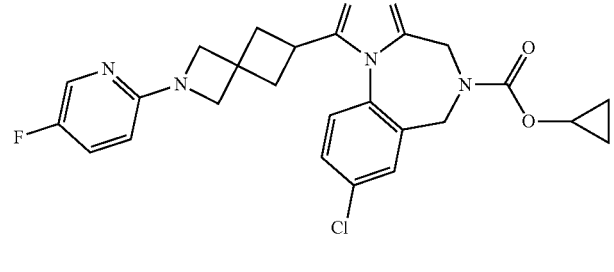 |
| 91 | 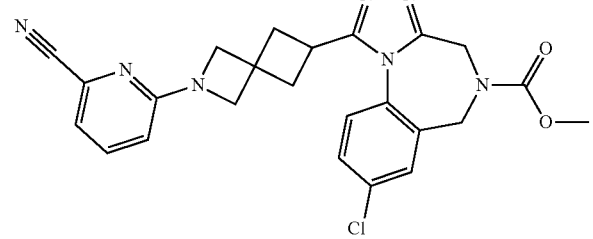 |

TABLE 1-continued

Representative Compounds

| Cmpd. No. | Structure |
|---|---|
| 92 | 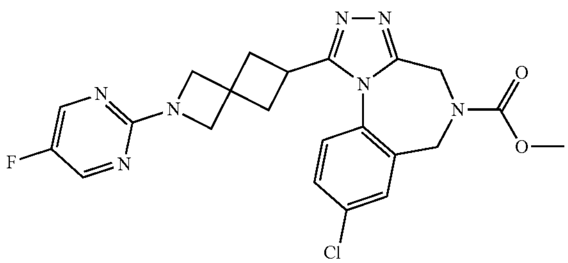 [SMILES: COC(=O)N1Cc2cc(Cl)ccc2-n2c(nnc2C2CC3(C2)CN(c2ncc(F)cn2)C3)C1] |
| 93 | 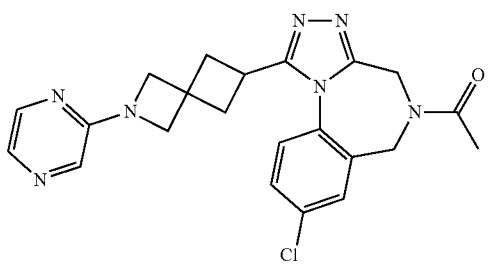 [SMILES: CC(=O)N1Cc2cc(Cl)ccc2-n2c(nnc2C2CC3(C2)CN(c2cnccn2)C3)C1] |
| 94 | 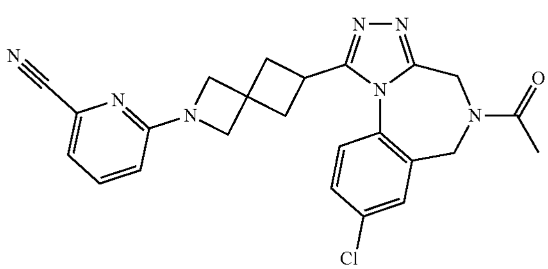 [SMILES: CC(=O)N1Cc2cc(Cl)ccc2-n2c(nnc2C2CC3(C2)CN(c2cccc(C#N)n2)C3)C1] |
| 95 | 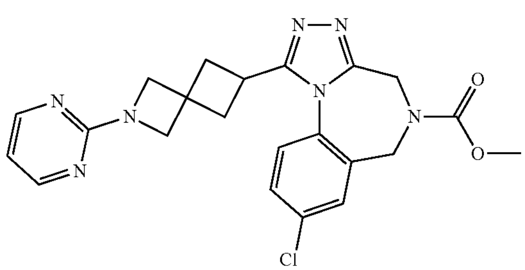 [SMILES: COC(=O)N1Cc2cc(Cl)ccc2-n2c(nnc2C2CC3(C2)CN(c2ncccn2)C3)C1] |
| 96 | 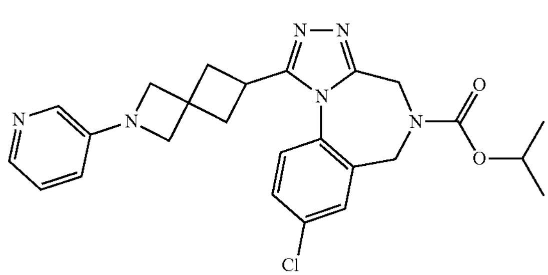 [SMILES: CC(C)OC(=O)N1Cc2cc(Cl)ccc2-n2c(nnc2C2CC3(C2)CN(c2cccnc2)C3)C1] |

TABLE 1-continued

Representative Compounds

| Cmpd. No. | Structure |
|---|---|
| 97 | 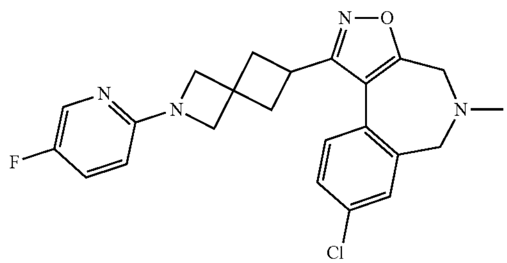 [SMILES: CN1Cc2cc(Cl)ccc2-c2c(C3CC4(C3)CN(c3ccc(F)cn3)C4)noc2C1] |
| 98 | 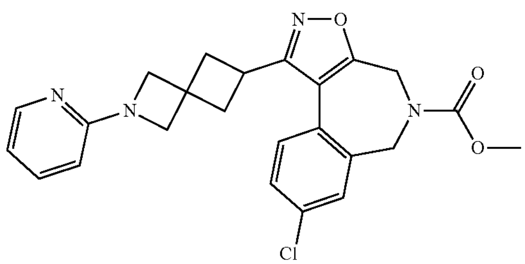 [SMILES: COC(=O)N1Cc2cc(Cl)ccc2-c2c(C3CC4(C3)CN(c3ccccn3)C4)noc2C1] |
| 99 | 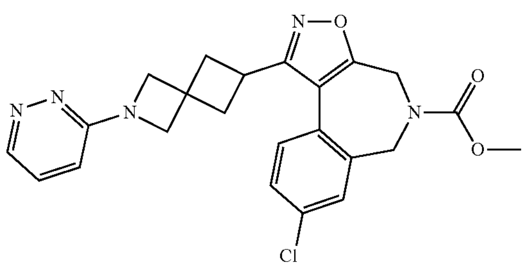 [SMILES: COC(=O)N1Cc2cc(Cl)ccc2-c2c(C3CC4(C3)CN(c3cccnn3)C4)noc2C1] |
| 100 | 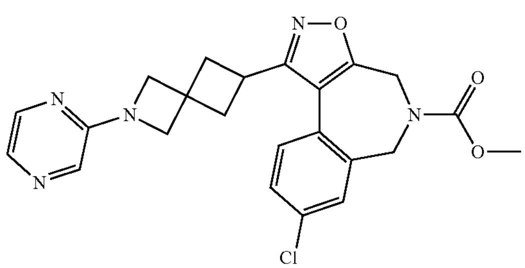 [SMILES: COC(=O)N1Cc2cc(Cl)ccc2-c2c(C3CC4(C3)CN(c3cnccn3)C4)noc2C1] |
| 101 | 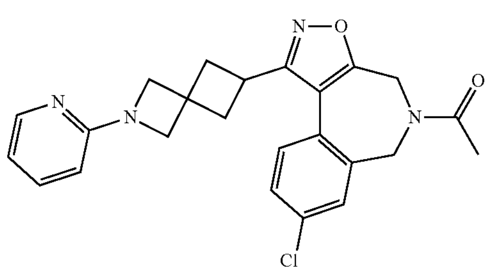 [SMILES: CC(=O)N1Cc2cc(Cl)ccc2-c2c(C3CC4(C3)CN(c3ccccn3)C4)noc2C1] |

TABLE 1-continued

Representative Compounds

| Cmpd. No. | Structure |
|---|---|
| 102 | 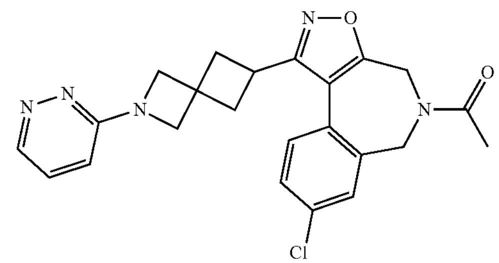 [SMILES: CC(=O)N1Cc2cc(Cl)ccc2-c2c(C3CC4(C3)CN(c3cccnn3)C4)noc2C1] |
| 103 | 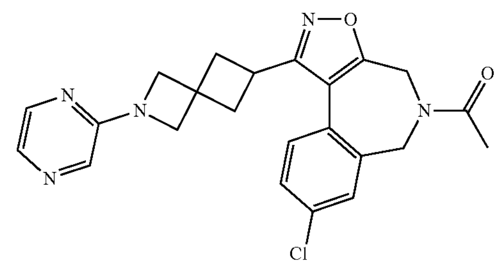 [SMILES: CC(=O)N1Cc2cc(Cl)ccc2-c2c(C3CC4(C3)CN(c3cnccn3)C4)noc2C1] |
| 104 | 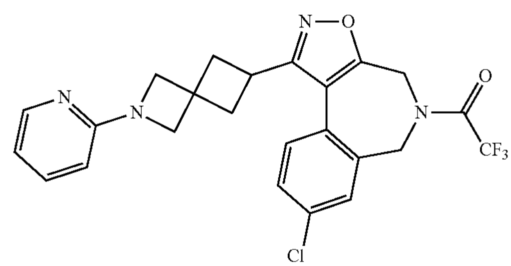 [SMILES: O=C(N1Cc2cc(Cl)ccc2-c2c(C3CC4(C3)CN(c3ccccn3)C4)noc2C1)C(F)(F)F] |
| 105 | 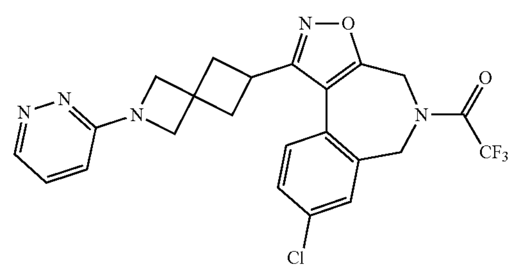 [SMILES: O=C(N1Cc2cc(Cl)ccc2-c2c(C3CC4(C3)CN(c3cccnn3)C4)noc2C1)C(F)(F)F] |
| 106 | 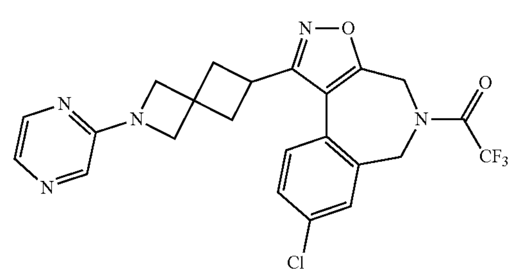 [SMILES: O=C(N1Cc2cc(Cl)ccc2-c2c(C3CC4(C3)CN(c3cnccn3)C4)noc2C1)C(F)(F)F] |

TABLE 1-continued

Representative Compounds

| Cmpd. No. | Structure |
|---|---|
| 107 | 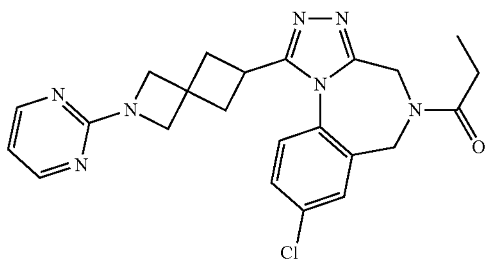 [SMILES: CCC(=O)N1Cc2cc(Cl)ccc2-n2c(nnc2C2CC3(C2)CN(c2ncccn2)C3)C1] |
| 108 | 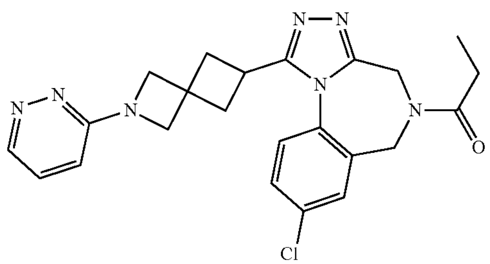 [SMILES: CCC(=O)N1Cc2cc(Cl)ccc2-n2c(nnc2C2CC3(C2)CN(c2cccnn2)C3)C1] |
| 109 | 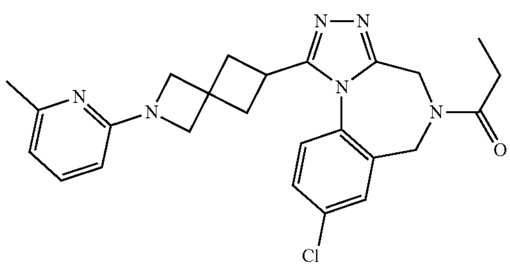 [SMILES: CCC(=O)N1Cc2cc(Cl)ccc2-n2c(nnc2C2CC3(C2)CN(c2cccc(C)n2)C3)C1] |
| 110 | 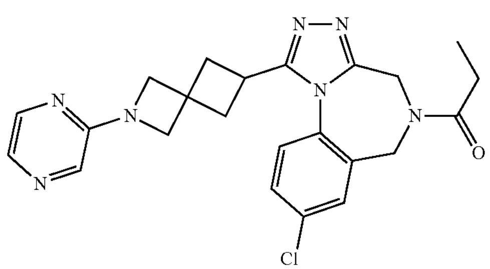 [SMILES: CCC(=O)N1Cc2cc(Cl)ccc2-n2c(nnc2C2CC3(C2)CN(c2cnccn2)C3)C1] |
| 111 | 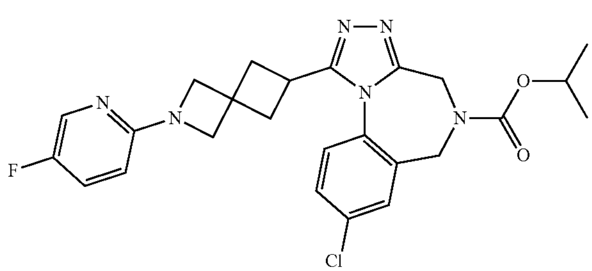 [SMILES: CC(C)OC(=O)N1Cc2cc(Cl)ccc2-n2c(nnc2C2CC3(C2)CN(c2ccc(F)cn2)C3)C1] |

TABLE 1-continued
Representative Compounds
| Cmpd. No. | Structure |
|---|---|
| 112 | 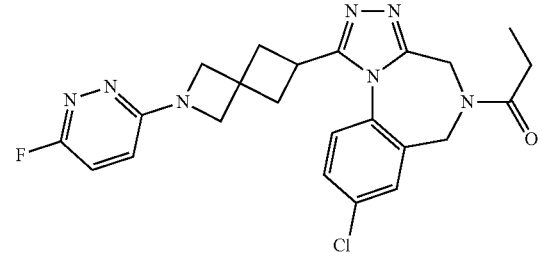 [SMILES: CCC(=O)N1Cc2cc(Cl)ccc2-n2c(nnc2C2CC3(C2)CN(c2ccc(F)nn2)C3)C1] |
| 113 | 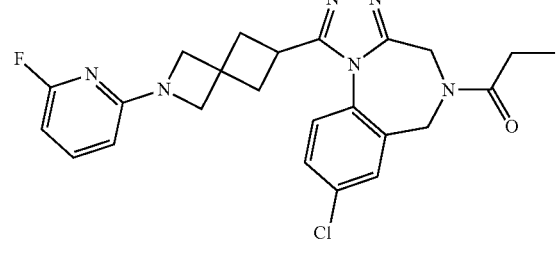 |
| 114 | 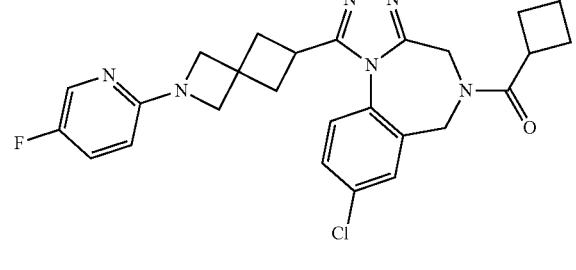 |
| 115 | 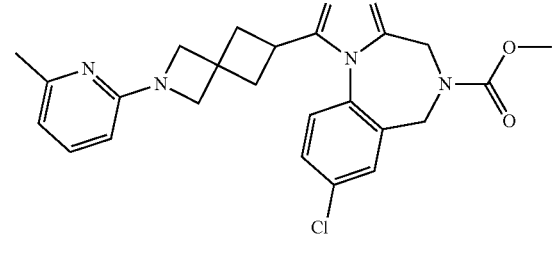 |
| 116 | 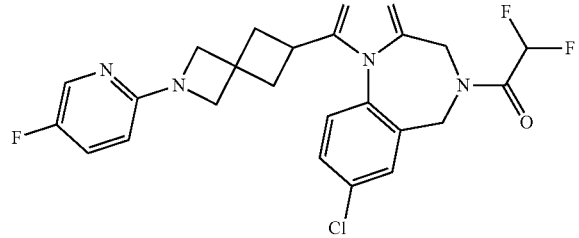 |

TABLE 1-continued

Representative Compounds

| Cmpd. No. | Structure |
|---|---|
| 117 | 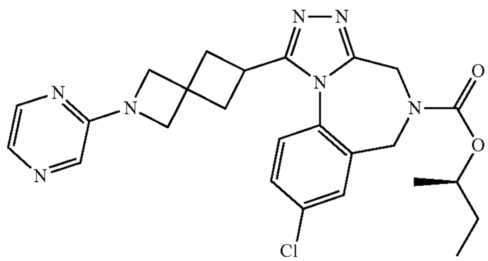 [SMILES: CC[C@@H](C)OC(=O)N1Cc2cc(Cl)ccc2-n2c(nnc2C2CC3(C2)CN(c2cnccn2)C3)C1] |
| 118 | 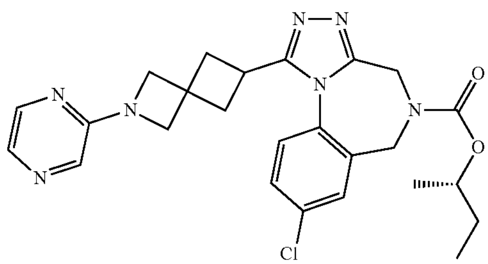 [SMILES: CC[C@H](C)OC(=O)N1Cc2cc(Cl)ccc2-n2c(nnc2C2CC3(C2)CN(c2cnccn2)C3)C1] |
| 119 | 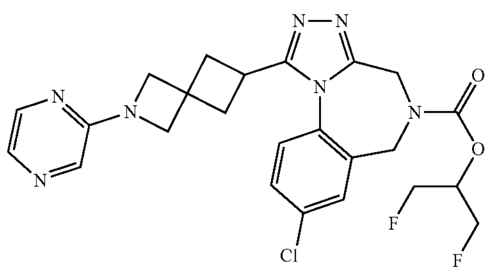 [SMILES: O=C(OC(CF)CF)N1Cc2cc(Cl)ccc2-n2c(nnc2C2CC3(C2)CN(c2cnccn2)C3)C1] |
| 120 | 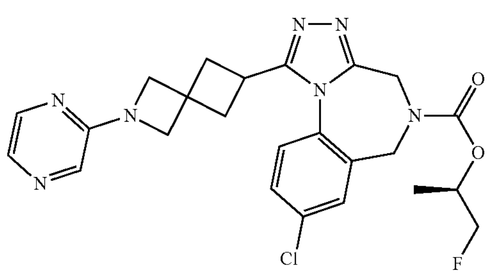 [SMILES: C[C@H](CF)OC(=O)N1Cc2cc(Cl)ccc2-n2c(nnc2C2CC3(C2)CN(c2cnccn2)C3)C1] |
| 121 | 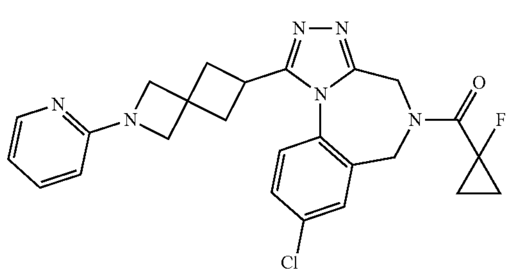 [SMILES: O=C(N1Cc2cc(Cl)ccc2-n2c(nnc2C2CC3(C2)CN(c2ccccn2)C3)C1)C1(F)CC1] |

TABLE 1-continued

Representative Compounds

| Cmpd. No. | Structure |
|---|---|
| 122 | 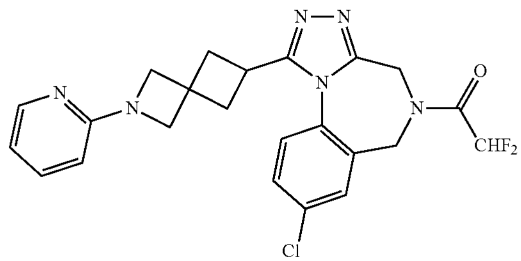 [SMILES: O=C(C(F)F)N1Cc2cc(Cl)ccc2-n2c(nnc2C2CC3(C2)CN(c2ccccn2)C3)C1] |
| 123 | 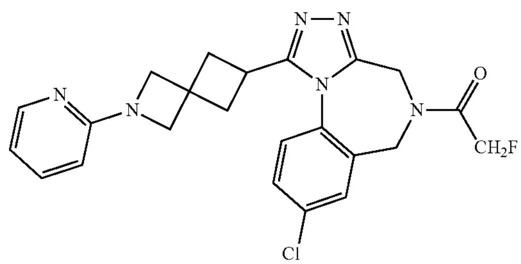 |
| 124 | 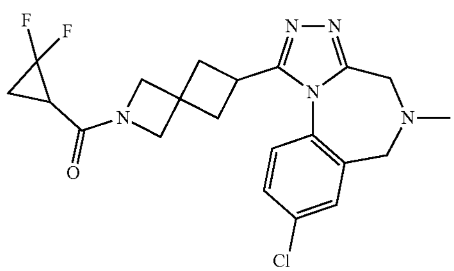 [SMILES: CN1Cc2cc(Cl)ccc2-n2c(nnc2C2CC3(C2)CN(C(=O)C2CC2(F)F)C3)C1] |
| 125 | 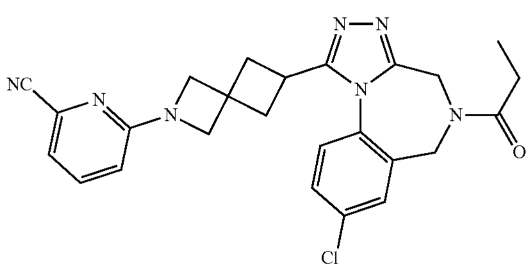 [SMILES: CCC(=O)N1Cc2cc(Cl)ccc2-n2c(nnc2C2CC3(C2)CN(c2cccc(C#N)n2)C3)C1] |
| 126 | 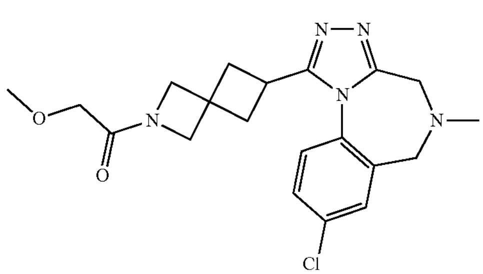 |

TABLE 1-continued

Representative Compounds

| Cmpd. No. | Structure |
|---|---|
| 127 | 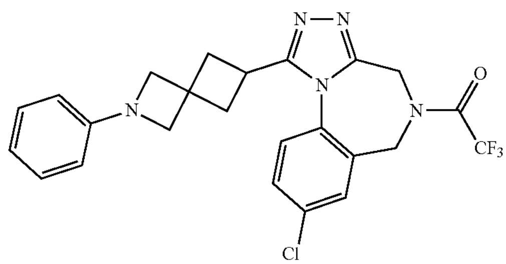 [SMILES: O=C(N1Cc2cc(Cl)ccc2-n2c(nnc2C2CC3(C2)CN(c2ccccc2)C3)C1)C(F)(F)F] |
| 128 | 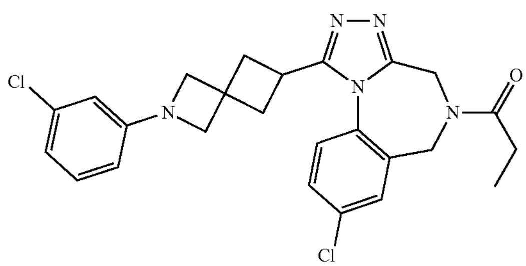 [SMILES: CCC(=O)N1Cc2cc(Cl)ccc2-n2c(nnc2C2CC3(C2)CN(c2cccc(Cl)c2)C3)C1] |
| 129 | 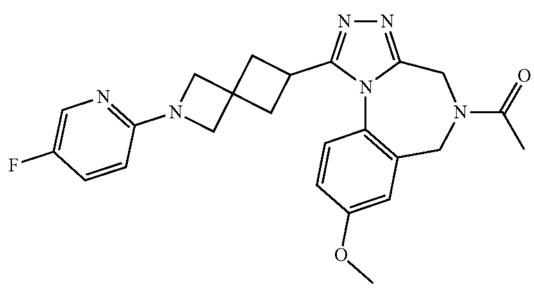 [SMILES: COc1ccc2c(c1)CN(C(C)=O)Cc1nnc(C3CC4(C3)CN(c3ccc(F)cn3)C4)n1-2] |
| 130 | 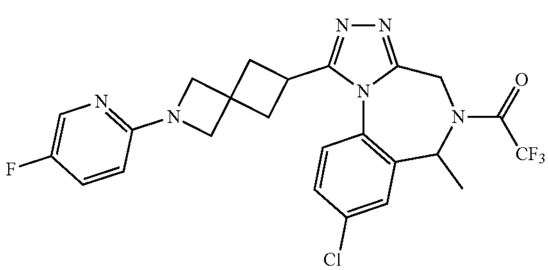 [SMILES: CC1c2cc(Cl)ccc2-n2c(nnc2C2CC3(C2)CN(c2ccc(F)cn2)C3)CN1C(=O)C(F)(F)F] |
| 131 | 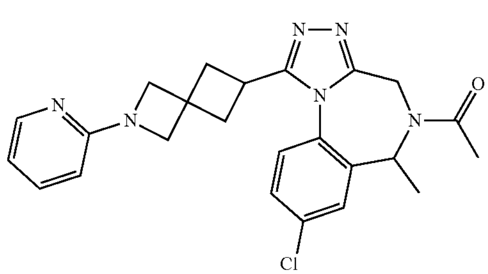 [SMILES: CC(=O)N1Cc2nnc(C3CC4(C3)CN(c3ccccn3)C4)n2-c2ccc(Cl)cc2C1C] |

TABLE 1-continued

Representative Compounds

| Cmpd. No. | Structure |
|---|---|
| 132 | 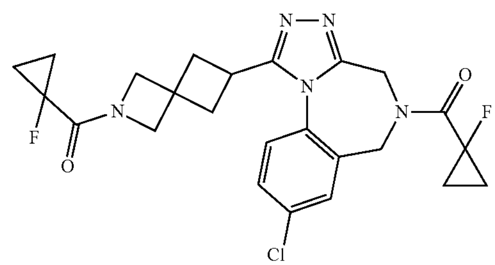 [SMILES: O=C(N1Cc2cc(Cl)ccc2-n2c(nnc2C2CC3(C2)CN(C(=O)C2(F)CC2)C3)C1)C1(F)CC1] |
| 133 | 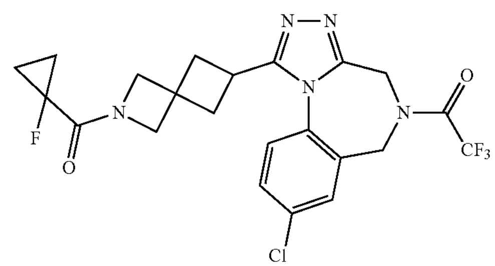 [SMILES: O=C(N1Cc2cc(Cl)ccc2-n2c(nnc2C2CC3(C2)CN(C(=O)C2(F)CC2)C3)C1)C(F)(F)F] |
| 134 | 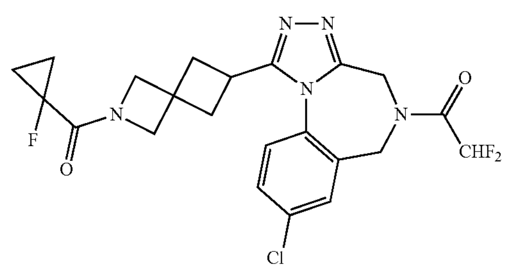 [SMILES: O=C(C(F)F)N1Cc2cc(Cl)ccc2-n2c(nnc2C2CC3(C2)CN(C(=O)C2(F)CC2)C3)C1] |
| 135 | 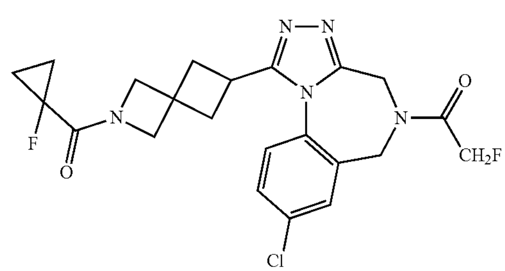 |
| 136 | 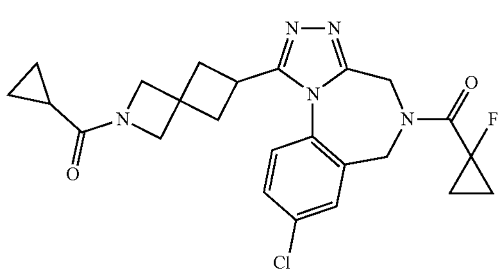 [SMILES: O=C(C1CC1)N1CC2(CC(c3nnc4n3-c3ccc(Cl)cc3CN(C(=O)C3(F)CC3)C4)C2)C1] |

TABLE 1-continued

Representative Compounds

| Cmpd. No. | Structure |
|---|---|
| 137 | 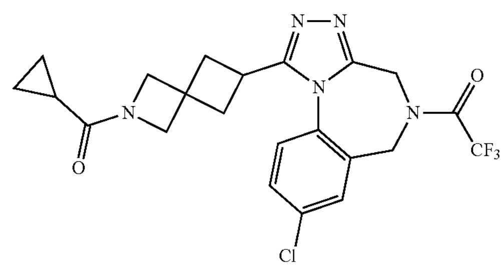 [SMILES: O=C(C1CC1)N1CC2(CC(c3nnc4n3-c3ccc(Cl)cc3CN(C(=O)C(F)(F)F)C4)C2)C1] |
| 138 | 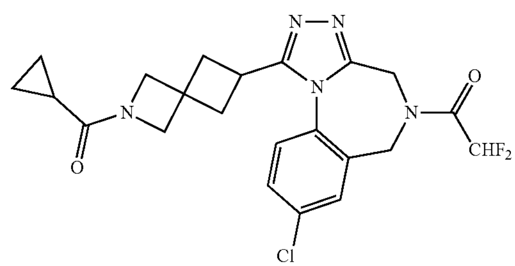 [SMILES: O=C(C(F)F)N1Cc2cc(Cl)ccc2-n2c(nnc2C2CC3(C2)CN(C(=O)C2CC2)C3)C1] |
| 139 | 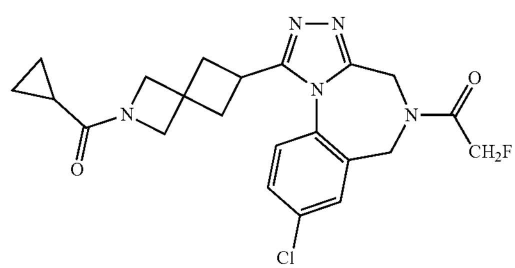 |
| 140 | 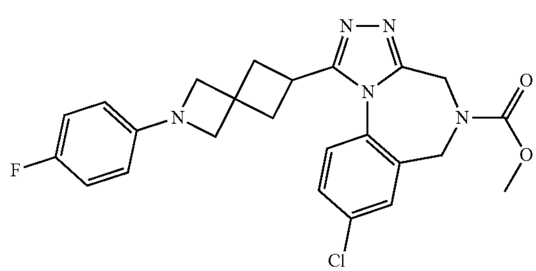 [SMILES: COC(=O)N1Cc2cc(Cl)ccc2-n2c(nnc2C2CC3(C2)CN(c2ccc(F)cc2)C3)C1] |
| 141 | 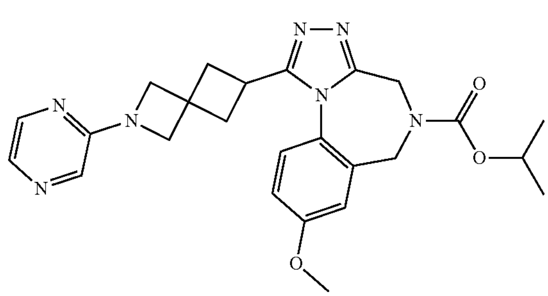 [SMILES: COc1ccc2c(c1)CN(C(=O)OC(C)C)Cc1nnc(C3CC4(C3)CN(c3cnccn3)C4)n1-2] |

103

104

TABLE 1-continued

Representative Compounds

| Cmpd. No. | Structure |
|---|---|
| 142 | 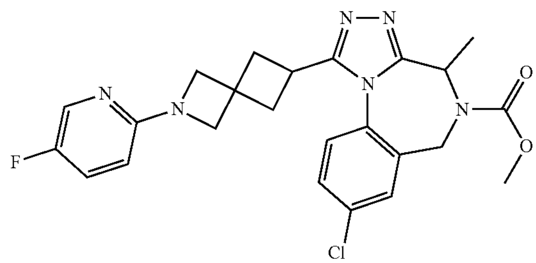 [SMILES: COC(=O)N1Cc2cc(Cl)ccc2-n2c(C3CC4(C3)CN(c3ccc(F)cn3)C4)nnc2C1C] |
| 143 | 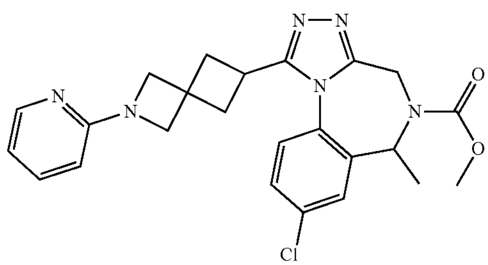 [SMILES: COC(=O)N1Cc2nnc(C3CC4(C3)CN(c3ccccn3)C4)n2-c2ccc(Cl)cc2C1C] |
| 144 | 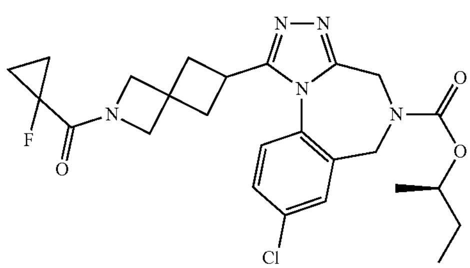 [SMILES: CC[C@@H](C)OC(=O)N1Cc2cc(Cl)ccc2-n2c(nnc2C2CC3(C2)CN(C(=O)C2(F)CC2)C3)C1] |
| 145 | 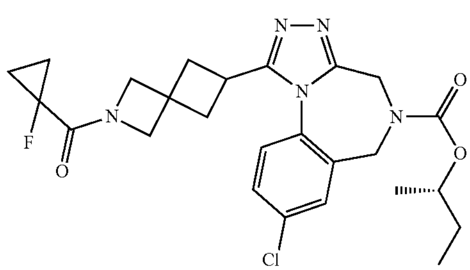 [SMILES: CC[C@H](C)OC(=O)N1Cc2cc(Cl)ccc2-n2c(nnc2C2CC3(C2)CN(C(=O)C2(F)CC2)C3)C1] |
| 146 | 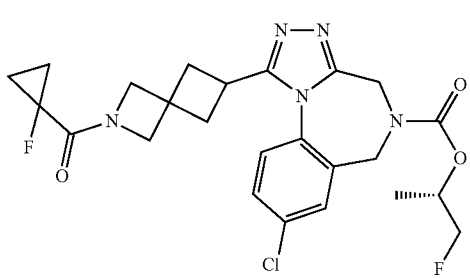 [SMILES: C[C@@H](CF)OC(=O)N1Cc2cc(Cl)ccc2-n2c(nnc2C2CC3(C2)CN(C(=O)C2(F)CC2)C3)C1] |

TABLE 1-continued
Representative Compounds
| Cmpd. No. | Structure |
|---|---|
| 147 | 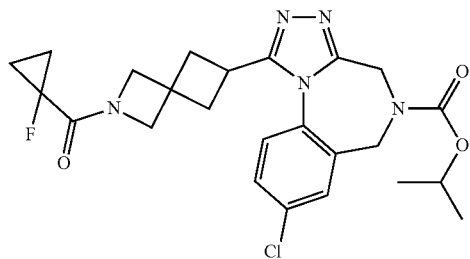 [SMILES: CC(C)OC(=O)N1Cc2cc(Cl)ccc2-n2c(nnc2C2CC3(C2)CN(C(=O)C2(F)CC2)C3)C1] |
| 148 | 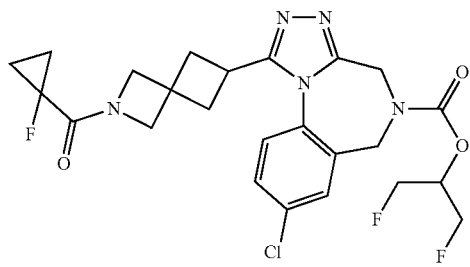 [SMILES: O=C(OC(CF)CF)N1Cc2cc(Cl)ccc2-n2c(nnc2C2CC3(C2)CN(C(=O)C2(F)CC2)C3)C1] |
| 149 | 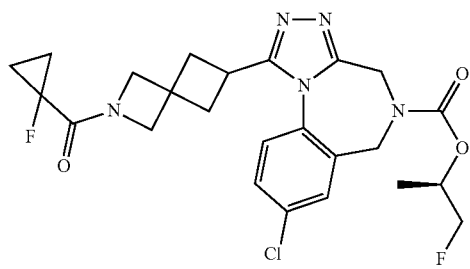 [SMILES: C[C@H](CF)OC(=O)N1Cc2cc(Cl)ccc2-n2c(nnc2C2CC3(C2)CN(C(=O)C2(F)CC2)C3)C1] |
| 150 | 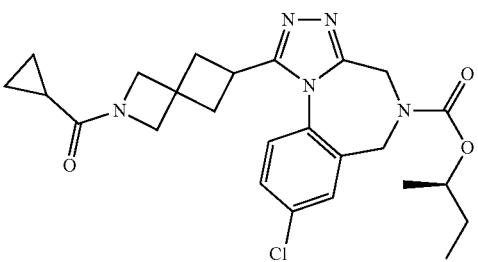 [SMILES: CC[C@@H](C)OC(=O)N1Cc2cc(Cl)ccc2-n2c(nnc2C2CC3(C2)CN(C(=O)C2CC2)C3)C1] |
| 151 | 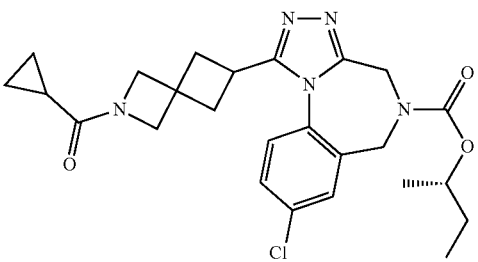 [SMILES: CC[C@H](C)OC(=O)N1Cc2cc(Cl)ccc2-n2c(nnc2C2CC3(C2)CN(C(=O)C2CC2)C3)C1] |

107
108

TABLE 1-continued

Representative Compounds

| Cmpd. No. | Structure |
|---|---|
| 152 | 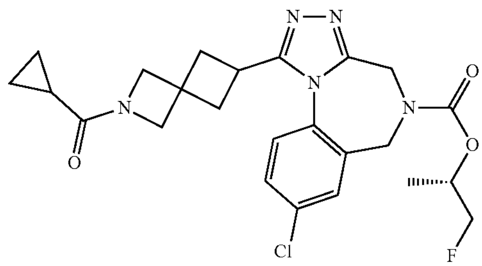 [SMILES: C[C@@H](CF)OC(=O)N1Cc2cc(Cl)ccc2-n2c(nnc2C2CC3(C2)CN(C(=O)C2CC2)C3)C1] |
| 153 | 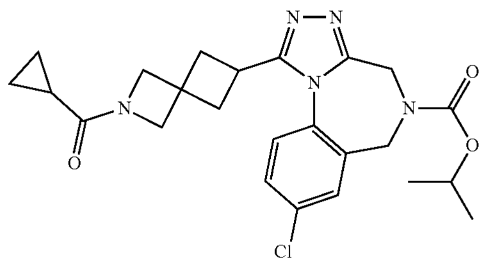 [SMILES: CC(C)OC(=O)N1Cc2cc(Cl)ccc2-n2c(nnc2C2CC3(C2)CN(C(=O)C2CC2)C3)C1] |
| 154 | 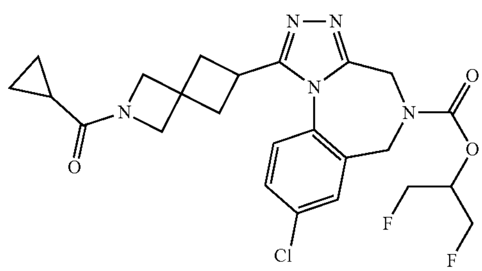 [SMILES: O=C(OC(CF)CF)N1Cc2cc(Cl)ccc2-n2c(nnc2C2CC3(C2)CN(C(=O)C2CC2)C3)C1] |
| 155 | 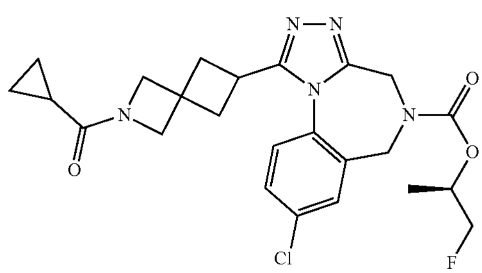 [SMILES: C[C@H](CF)OC(=O)N1Cc2cc(Cl)ccc2-n2c(nnc2C2CC3(C2)CN(C(=O)C2CC2)C3)C1] |
| 156 | 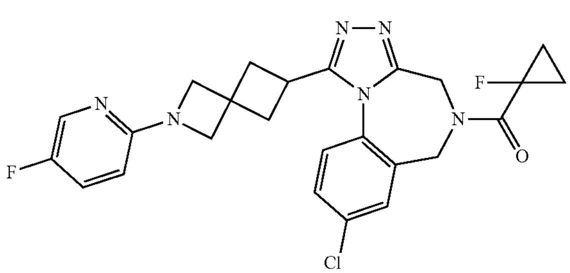 [SMILES: O=C(N1Cc2cc(Cl)ccc2-n2c(nnc2C2CC3(C2)CN(c2ccc(F)cn2)C3)C1)C1(F)CC1] |

TABLE 1-continued

Representative Compounds

| Cmpd. No. | Structure |
|---|---|
| 157 | 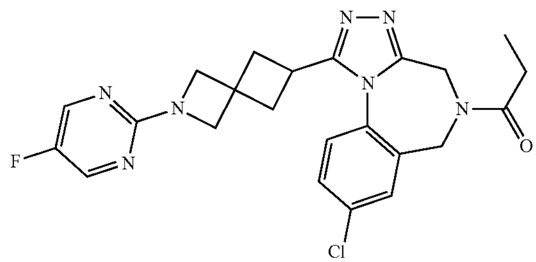 [SMILES: CCC(=O)N1Cc2cc(Cl)ccc2-n2c(nnc2C2CC3(C2)CN(c2ncc(F)cn2)C3)C1] |
| 158 | 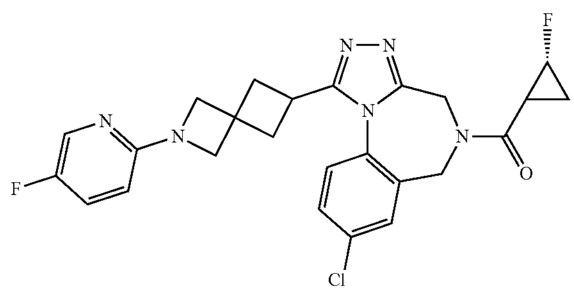 [SMILES: O=C(C1C[C@H]1F)N1Cc2cc(Cl)ccc2-n2c(nnc2C2CC3(C2)CN(c2ccc(F)cn2)C3)C1] |
| 159 | 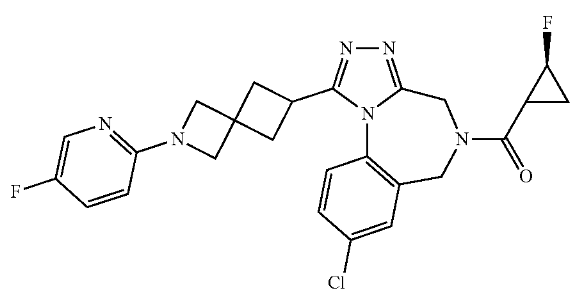 [SMILES: O=C(C1C[C@@H]1F)N1Cc2cc(Cl)ccc2-n2c(nnc2C2CC3(C2)CN(c2ccc(F)cn2)C3)C1] |
| 160 | 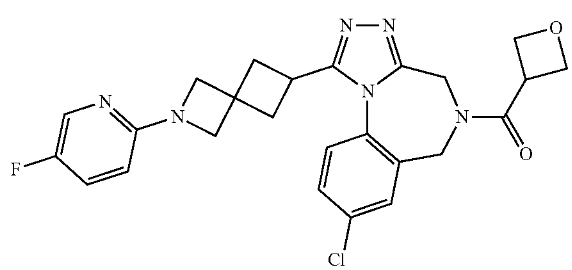 [SMILES: O=C(C1COC1)N1Cc2cc(Cl)ccc2-n2c(nnc2C2CC3(C2)CN(c2ccc(F)cn2)C3)C1] |
| 161 | 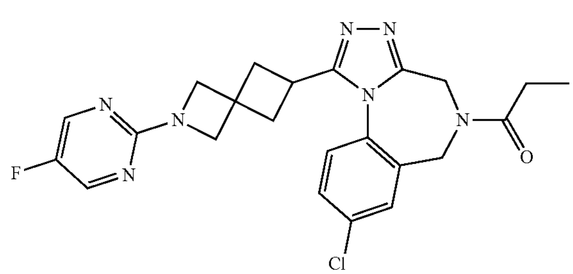 [SMILES: CCC(=O)N1Cc2cc(Cl)ccc2-n2c(nnc2C2CC3(C2)CN(c2ncc(F)cn2)C3)C1] |

TABLE 1-continued

Representative Compounds

| Cmpd. No. | Structure |
|---|---|
| 162 | 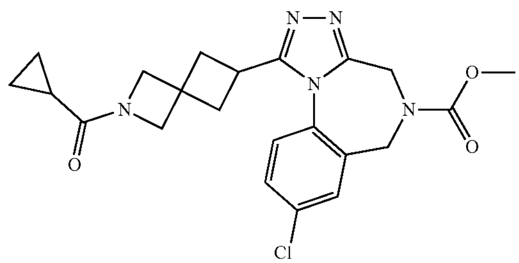 [SMILES: COC(=O)N1Cc2cc(Cl)ccc2-n2c(nnc2C2CC3(C2)CN(C(=O)C2CC2)C3)C1] |
| 163 | 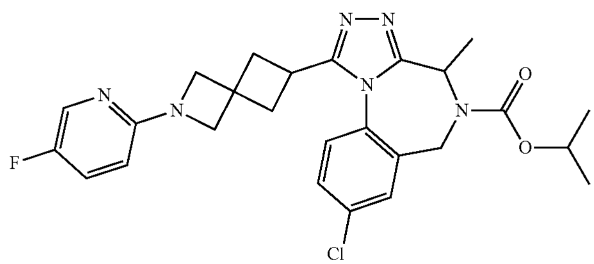 |
| 164 | 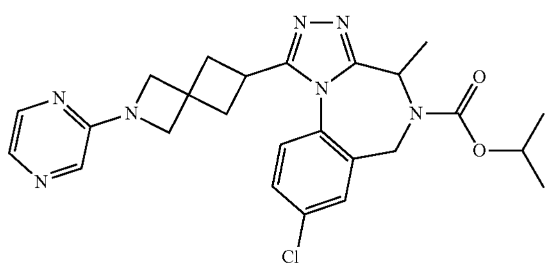 [SMILES: CC(C)OC(=O)N1Cc2cc(Cl)ccc2-n2c(C3CC4(C3)CN(c3cnccn3)C4)nnc2C1C] |
| 165 | 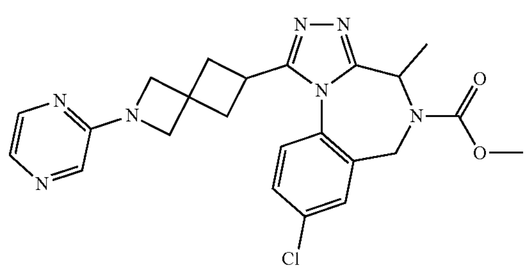 [SMILES: COC(=O)N1Cc2cc(Cl)ccc2-n2c(C3CC4(C3)CN(c3cnccn3)C4)nnc2C1C] |
| 166 | 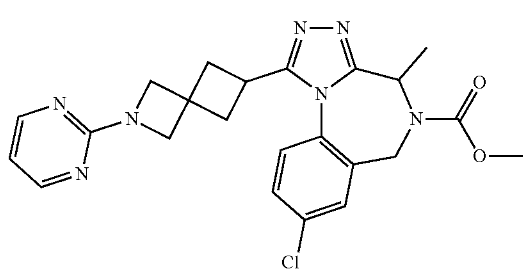 [SMILES: COC(=O)N1Cc2cc(Cl)ccc2-n2c(C3CC4(C3)CN(c3ncccn3)C4)nnc2C1C] |

TABLE 1-continued

Representative Compounds

| Cmpd. No. | Structure |
|---|---|
| 167 | 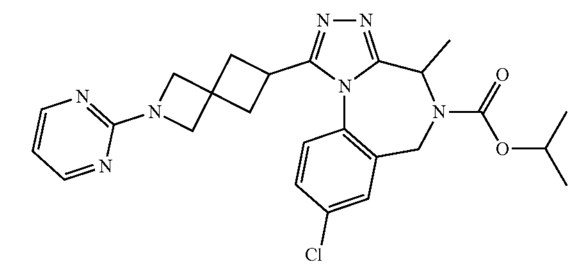 [SMILES: CC(C)OC(=O)N1Cc2cc(Cl)ccc2-n2c(C3CC4(C3)CN(c3ncccn3)C4)nnc2C1C] |
| 168 | 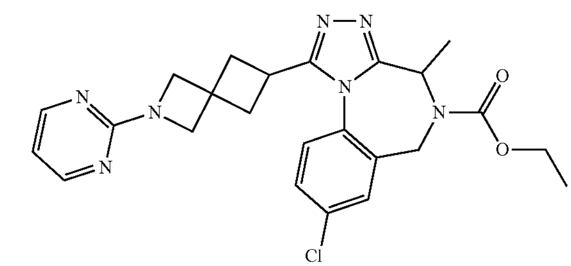 [SMILES: CCOC(=O)N1Cc2cc(Cl)ccc2-n2c(C3CC4(C3)CN(c3ncccn3)C4)nnc2C1C] |
| 169 | 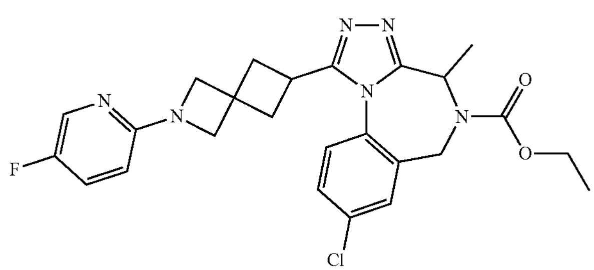 [SMILES: CCOC(=O)N1Cc2cc(Cl)ccc2-n2c(C3CC4(C3)CN(c3ccc(F)cn3)C4)nnc2C1C] |
| 170 | 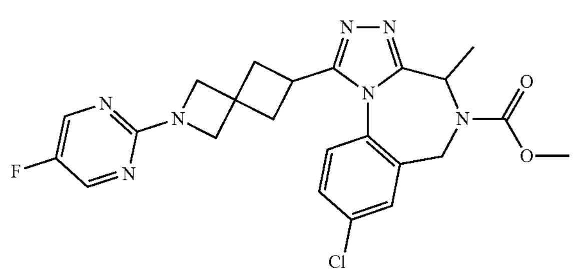 [SMILES: COC(=O)N1Cc2cc(Cl)ccc2-n2c(C3CC4(C3)CN(c3ncc(F)cn3)C4)nnc2C1C] |
| 171 | 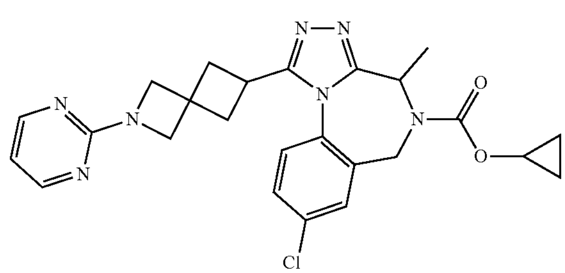 [SMILES: CC1c2nnc(C3CC4(C3)CN(c3ncccn3)C4)n2-c2ccc(Cl)cc2CN1C(=O)OC1CC1] |

TABLE 1-continued
Representative Compounds
| Cmpd. No. | Structure |
|---|---|
| 172 | 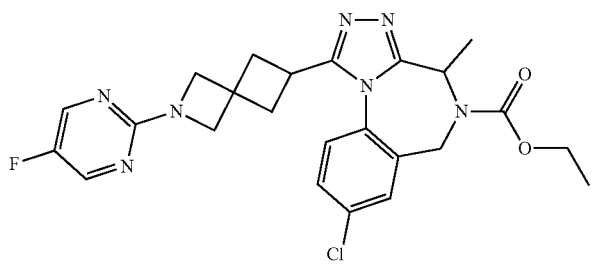 |
| 173 | 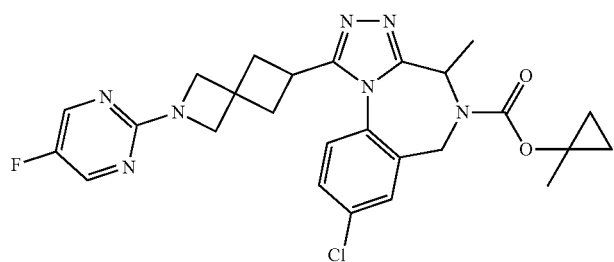 [SMILES: CC1c2nnc(C3CC4(C3)CN(c3ncc(F)cn3)C4)n2-c2ccc(Cl)cc2CN1C(=O)OC1(C)CC1] |
| 174 | 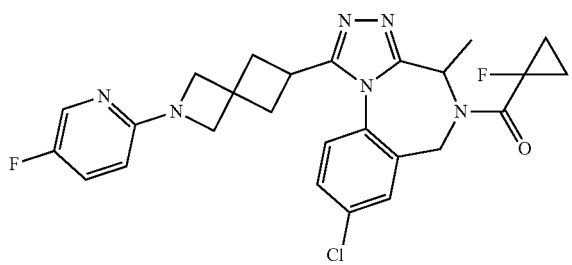 [SMILES: CC1c2nnc(C3CC4(C3)CN(c3ccc(F)cn3)C4)n2-c2ccc(Cl)cc2CN1C(=O)C1(F)CC1] |
| 175 | 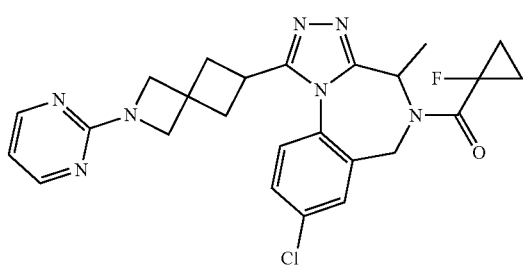 [SMILES: CC1c2nnc(C3CC4(C3)CN(c3ncccn3)C4)n2-c2ccc(Cl)cc2CN1C(=O)C1(F)CC1] |
| 176 | 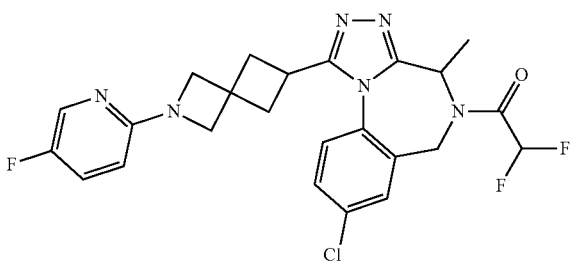 [SMILES: CC1c2nnc(C3CC4(C3)CN(c3ccc(F)cn3)C4)n2-c2ccc(Cl)cc2CN1C(=O)C(F)F] |

117
TABLE 1-continued
Representative Compounds
| Cmpd. No. | Structure |
|---|---|
| 177 | 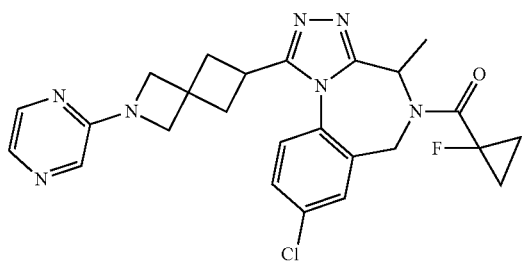 [SMILES: CC1c2nnc(C3CC4(C3)CN(c3cnccn3)C4)n2-c2ccc(Cl)cc2CN1C(=O)C1(F)CC1] |
| 178 | 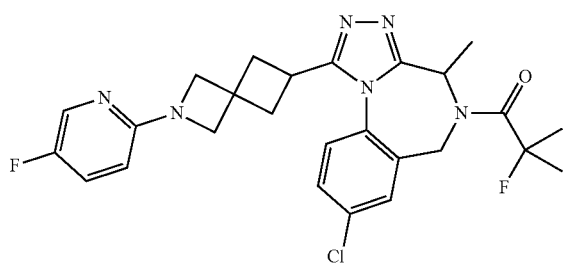 [SMILES: CC1c2nnc(C3CC4(C3)CN(c3ccc(F)cn3)C4)n2-c2ccc(Cl)cc2CN1C(=O)C(C)(C)F] |
| 179 | 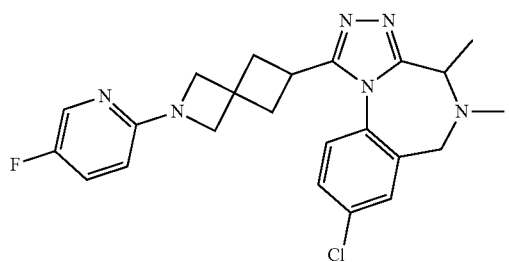 [SMILES: CC1c2nnc(C3CC4(C3)CN(c3ccc(F)cn3)C4)n2-c2ccc(Cl)cc2CN1C] |
| 180 | 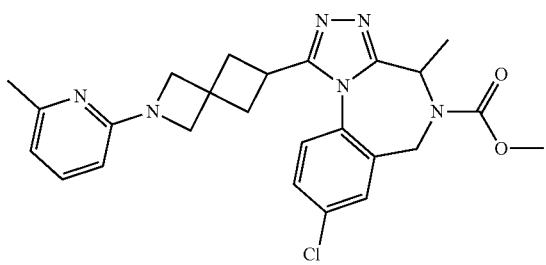 |
| 181 | 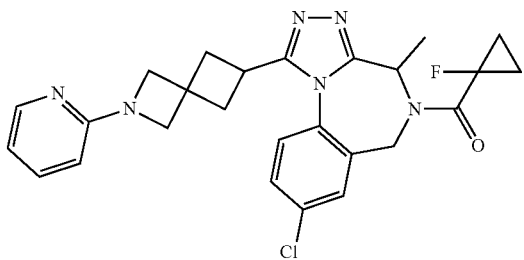 [SMILES: CC1c2nnc(C3CC4(C3)CN(c3ccccn3)C4)n2-c2ccc(Cl)cc2CN1C(=O)C1(F)CC1] |

TABLE 1-continued

Representative Compounds

| Cmpd. No. | Structure |
|---|---|
| 182 | 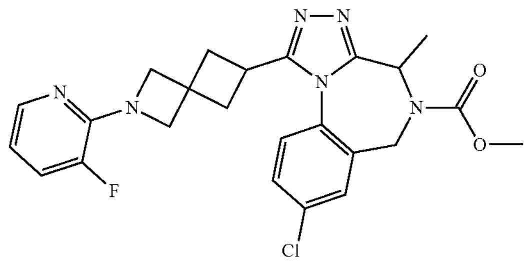 [SMILES: COC(=O)N1Cc2cc(Cl)ccc2-n2c(C3CC4(C3)CN(c3ncccc3F)C4)nnc2C1C] |
| 183 | 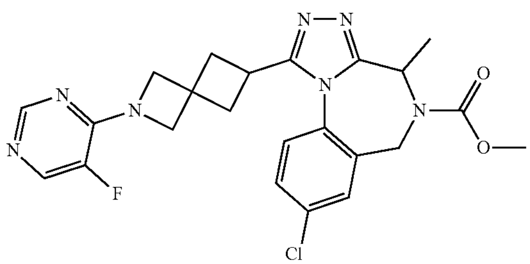 [SMILES: COC(=O)N1Cc2cc(Cl)ccc2-n2c(C3CC4(C3)CN(c3ncncc3F)C4)nnc2C1C] |
| 184 | 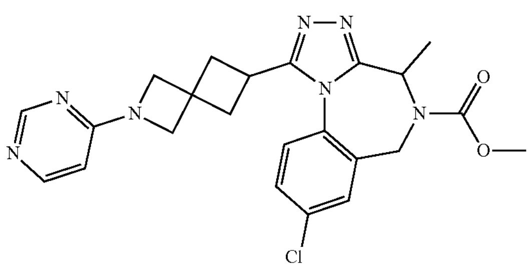 [SMILES: COC(=O)N1Cc2cc(Cl)ccc2-n2c(C3CC4(C3)CN(c3ccncn3)C4)nnc2C1C] |
| 185 | 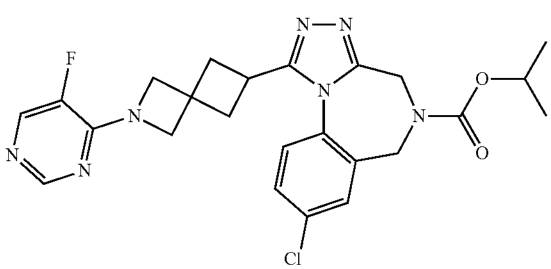 [SMILES: CC(C)OC(=O)N1Cc2cc(Cl)ccc2-n2c(nnc2C2CC3(C2)CN(c2ncncc2F)C3)C1] |
| 186 | 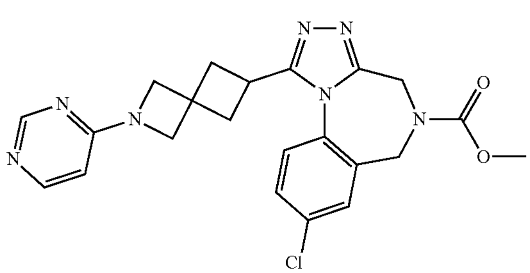 [SMILES: COC(=O)N1Cc2cc(Cl)ccc2-n2c(nnc2C2CC3(C2)CN(c2ccncn2)C3)C1] |

TABLE 1-continued

Representative Compounds

| Cmpd. No. | Structure |
|---|---|
| 187 | 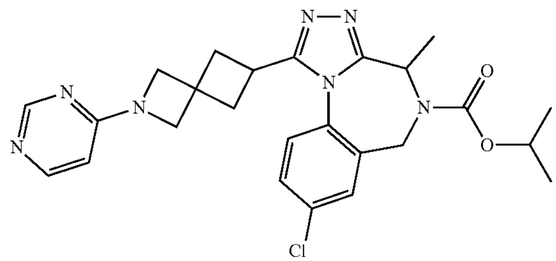 [SMILES: CC(C)OC(=O)N1Cc2cc(Cl)ccc2-n2c(C3CC4(C3)CN(c3ccncn3)C4)nnc2C1C] |
| 188 | 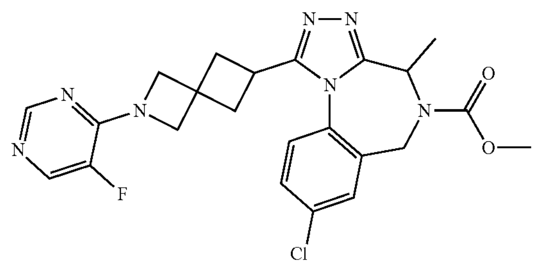 [SMILES: COC(=O)N1Cc2cc(Cl)ccc2-n2c(C3CC4(C3)CN(c3ncncc3F)C4)nnc2C1C] |
| 189 | 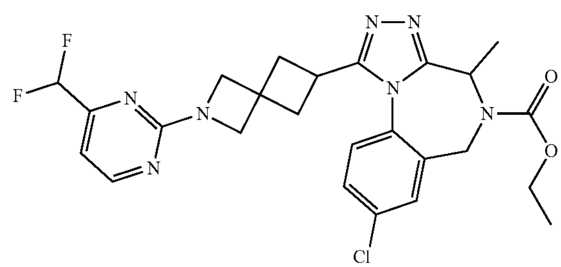 [SMILES: CCOC(=O)N1Cc2cc(Cl)ccc2-n2c(C3CC4(C3)CN(c3nccc(C(F)F)n3)C4)nnc2C1C] |
| 190 | 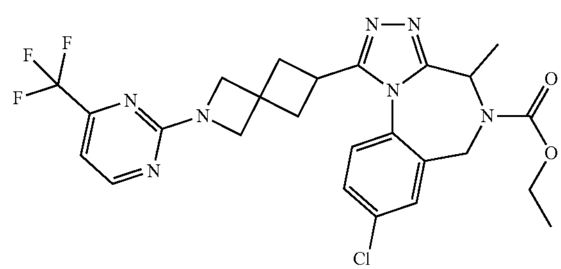 [SMILES: CCOC(=O)N1Cc2cc(Cl)ccc2-n2c(C3CC4(C3)CN(c3nccc(C(F)(F)F)n3)C4)nnc2C1C] |
| 191 | 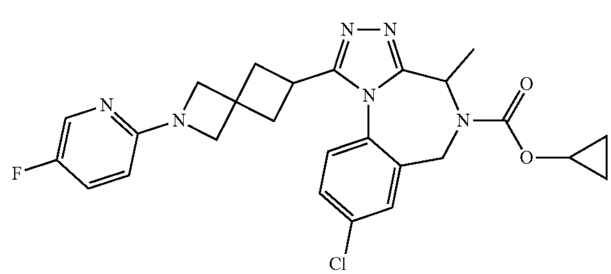 [SMILES: CC1c2nnc(C3CC4(C3)CN(c3ccc(F)cn3)C4)n2-c2ccc(Cl)cc2CN1C(=O)OC1CC1] |

123

TABLE 1-continued

Representative Compounds

| Cmpd. No. | Structure |
|---|---|
| 192 | 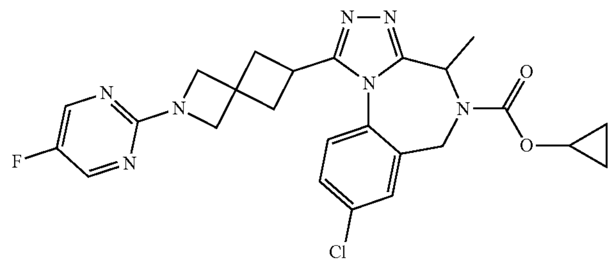 [SMILES: CC1c2nnc(C3CC4(C3)CN(c3ncc(F)cn3)C4)n2-c2ccc(Cl)cc2CN1C(=O)OC1CC1] |
| 193 | 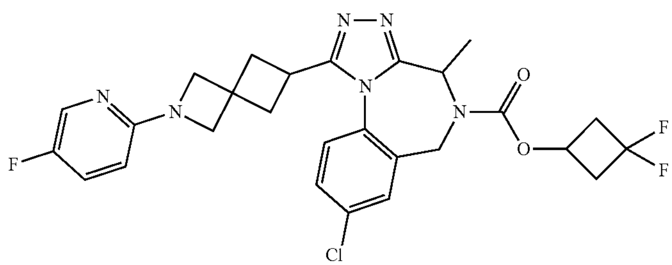 [SMILES: CC1c2nnc(C3CC4(C3)CN(c3ccc(F)cn3)C4)n2-c2ccc(Cl)cc2CN1C(=O)OC1CC(F)(F)C1] |
| 194 | 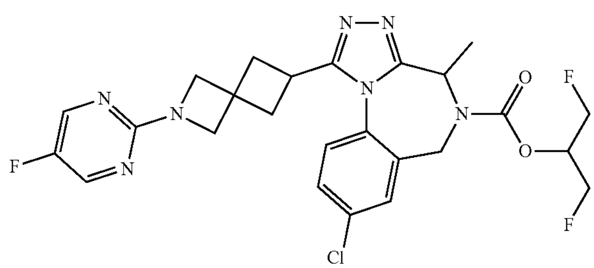 [SMILES: CC1c2nnc(C3CC4(C3)CN(c3ncc(F)cn3)C4)n2-c2ccc(Cl)cc2CN1C(=O)OC(CF)CF] |
| 195 | 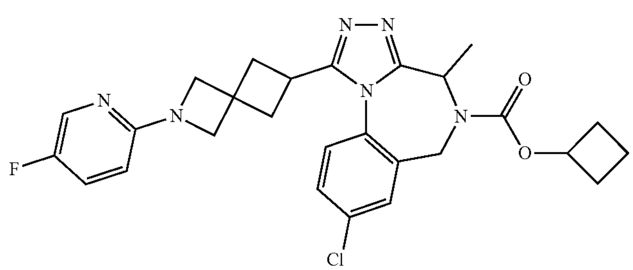 [SMILES: CC1c2nnc(C3CC4(C3)CN(c3ccc(F)cn3)C4)n2-c2ccc(Cl)cc2CN1C(=O)OC1CCC1] |
| 196 | 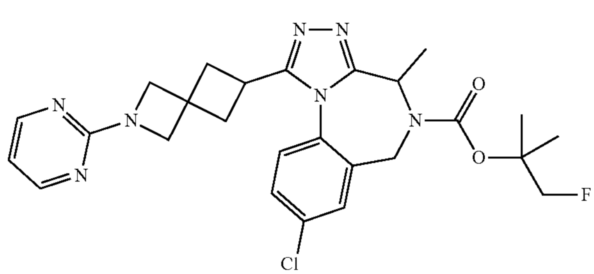 [SMILES: CC1c2nnc(C3CC4(C3)CN(c3ncccn3)C4)n2-c2ccc(Cl)cc2CN1C(=O)OC(C)(C)CF] |

124

TABLE 1-continued
Representative Compounds
| Cmpd. No. | Structure |
|---|---|
| 197 | 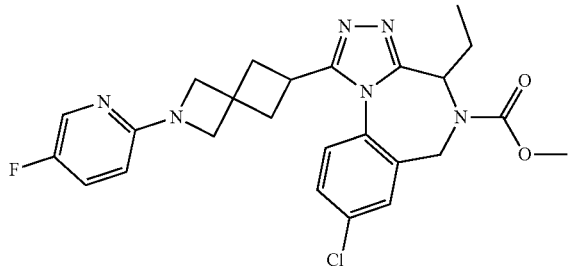 [SMILES: CCC1c2nnc(C3CC4(C3)CN(c3ccc(F)cn3)C4)n2-c2ccc(Cl)cc2CN1C(=O)OC] |
| 198 | 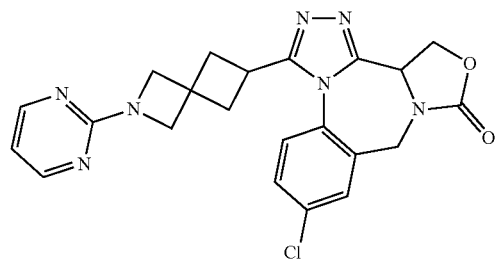 [SMILES: O=C1OCC2c3nnc(C4CC5(C4)CN(c4ncccn4)C5)n3-c3ccc(Cl)cc3CN12] |
| 199 | 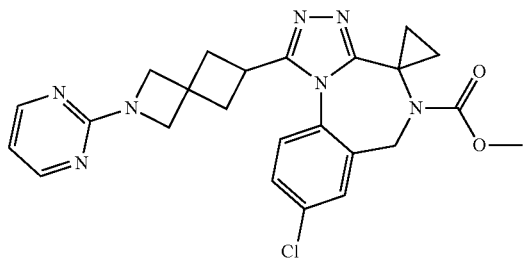 [SMILES: COC(=O)N1Cc2cc(Cl)ccc2-n2c(C3CC4(C3)CN(c3ncccn3)C4)nnc2C12CC2] |
| 200 | 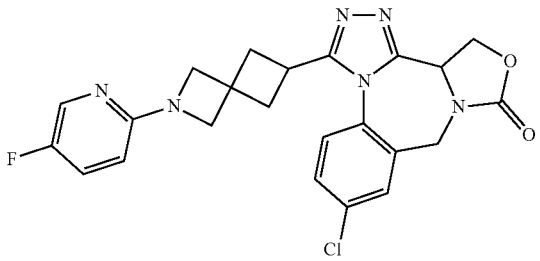 [SMILES: O=C1OCC2c3nnc(C4CC5(C4)CN(c4ccc(F)cn4)C5)n3-c3ccc(Cl)cc3CN12] |
| 201 | 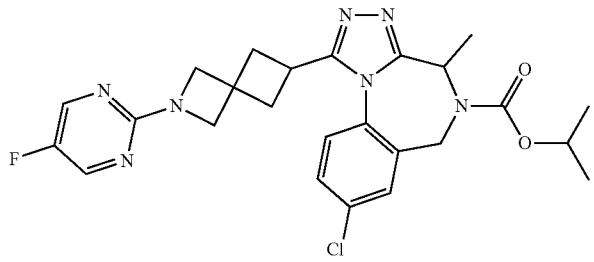 |

TABLE 1-continued

Representative Compounds

| Cmpd. No. | Structure |
|---|---|
| 202 | 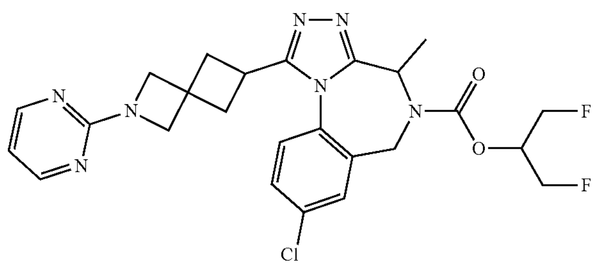 [SMILES: CC1c2nnc(C3CC4(C3)CN(c3ncccn3)C4)n2-c2ccc(Cl)cc2CN1C(=O)OC(CF)CF] |
| 203 | 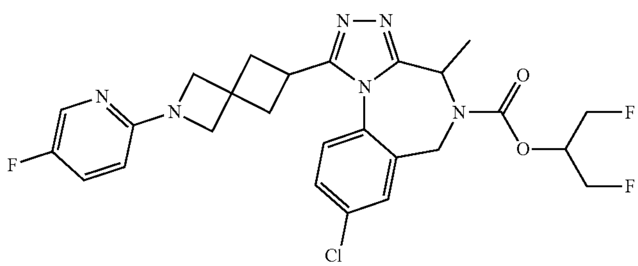 [SMILES: CC1c2nnc(C3CC4(C3)CN(c3ccc(F)cn3)C4)n2-c2ccc(Cl)cc2CN1C(=O)OC(CF)CF] |
| 204 | 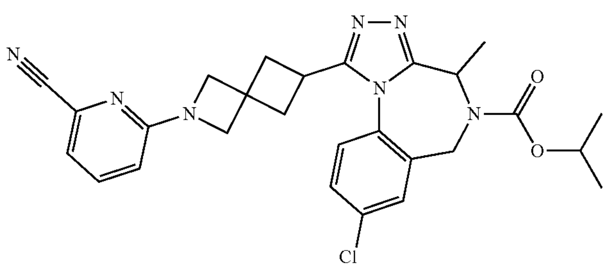 [SMILES: CC(C)OC(=O)N1Cc2cc(Cl)ccc2-n2c(C3CC4(C3)CN(c3cccc(C#N)n3)C4)nnc2C1C] |
| 205 | 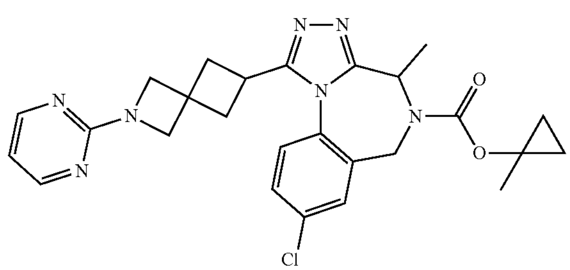 [SMILES: CC1c2nnc(C3CC4(C3)CN(c3ncccn3)C4)n2-c2ccc(Cl)cc2CN1C(=O)OC1(C)CC1] |
| 206 | 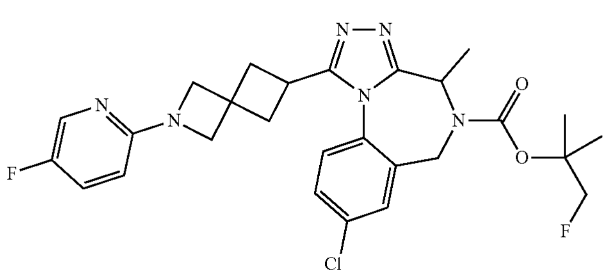 [SMILES: CC1c2nnc(C3CC4(C3)CN(c3ccc(F)cn3)C4)n2-c2ccc(Cl)cc2CN1C(=O)OC(C)(C)CF] |

TABLE 1-continued

Representative Compounds

| Cmpd. No. | Structure |
|---|---|
| 207 | 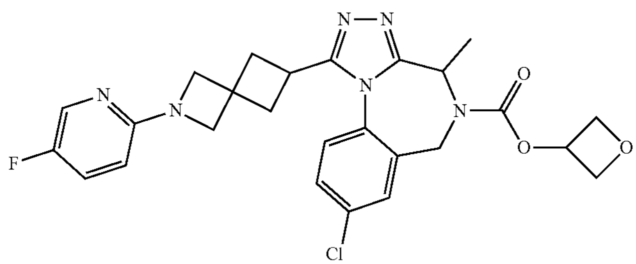 [SMILES: CC1c2nnc(C3CC4(C3)CN(c3ccc(F)cn3)C4)n2-c2ccc(Cl)cc2CN1C(=O)OC1COC1] |
| 208 | 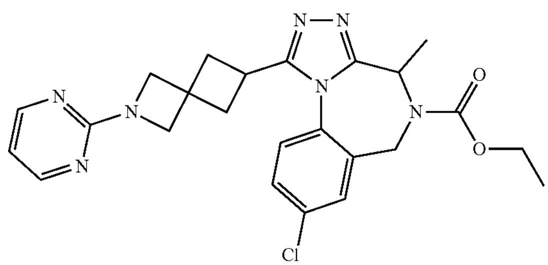 [SMILES: CCOC(=O)N1Cc2cc(Cl)ccc2-n2c(C3CC4(C3)CN(c3ncccn3)C4)nnc2C1C] |
| 209 | 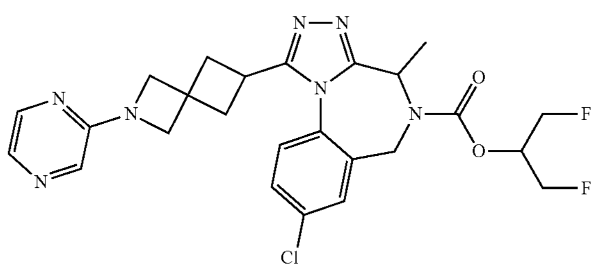 [SMILES: CC1c2nnc(C3CC4(C3)CN(c3cnccn3)C4)n2-c2ccc(Cl)cc2CN1C(=O)OC(CF)CF] |
| 210 | 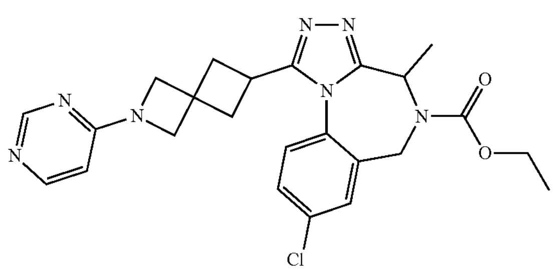 [SMILES: CCOC(=O)N1Cc2cc(Cl)ccc2-n2c(C3CC4(C3)CN(c3ccncn3)C4)nnc2C1C] |
| 211 | 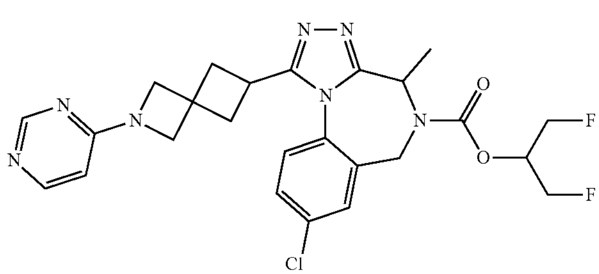 [SMILES: CC1c2nnc(C3CC4(C3)CN(c3ccncn3)C4)n2-c2ccc(Cl)cc2CN1C(=O)OC(CF)CF] |

TABLE 1-continued

Representative Compounds

| Cmpd. No. | Structure |
|---|---|
| 212 | 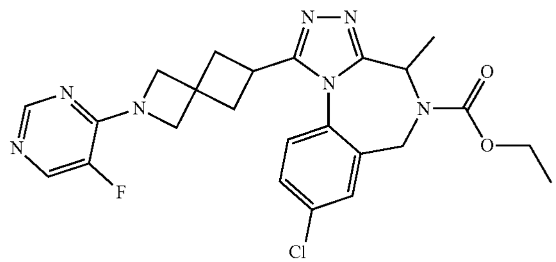 [SMILES: CCOC(=O)N1Cc2cc(Cl)ccc2-n2c(C3CC4(C3)CN(c3ncncc3F)C4)nnc2C1C] |
| 213 | 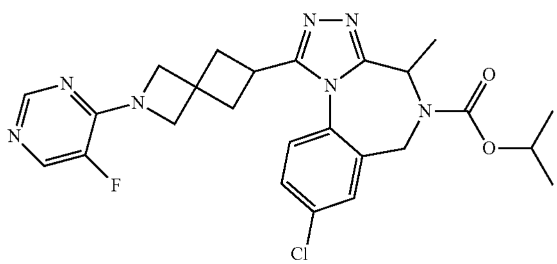 [SMILES: CC(C)OC(=O)N1Cc2cc(Cl)ccc2-n2c(C3CC4(C3)CN(c3ncncc3F)C4)nnc2C1C] |
| 214 | 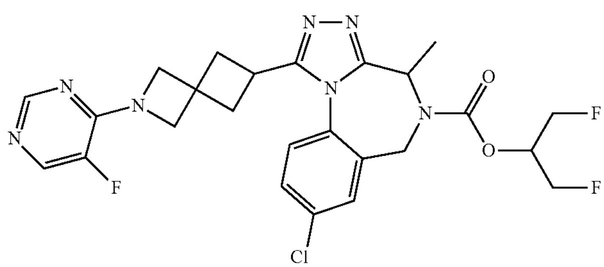 [SMILES: CC1c2nnc(C3CC4(C3)CN(c3ncncc3F)C4)n2-c2ccc(Cl)cc2CN1C(=O)OC(CF)CF] |
| 215 | 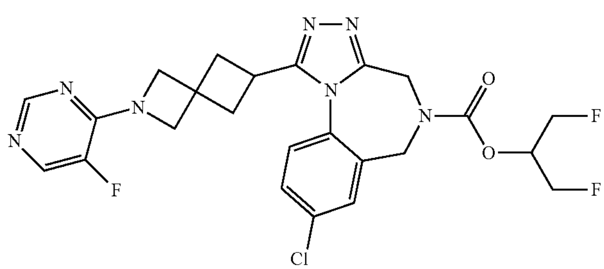 [SMILES: O=C(OC(CF)CF)N1Cc2cc(Cl)ccc2-n2c(nnc2C2CC3(C2)CN(c2ncncc2F)C3)C1] |
| 216 | 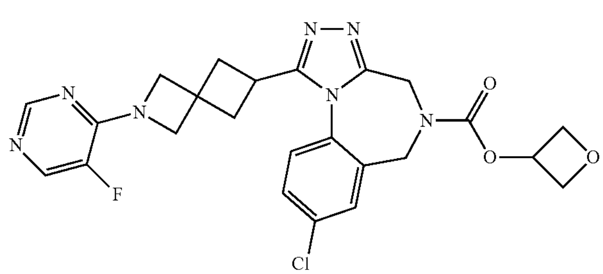 [SMILES: O=C(OC1COC1)N1Cc2cc(Cl)ccc2-n2c(nnc2C2CC3(C2)CN(c2ncncc2F)C3)C1] |

TABLE 1-continued

Representative Compounds

| Cmpd. No. | Structure |
|---|---|
| 217 | 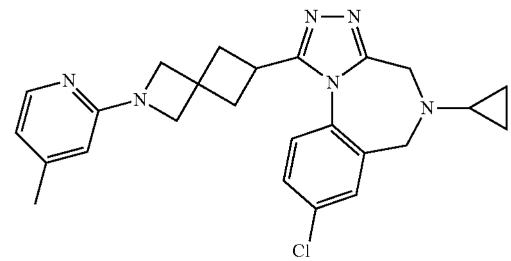 [SMILES: Cc1ccnc(N2CC3(CC(c4nnc5n4-c4ccc(Cl)cc4CN(C4CC4)C5)C3)C2)c1] |
| 218 | 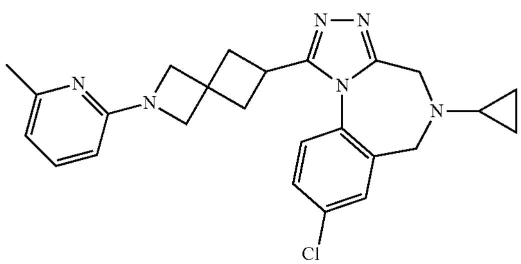 [SMILES: Cc1cccc(N2CC3(CC(c4nnc5n4-c4ccc(Cl)cc4CN(C4CC4)C5)C3)C2)n1] |
| 219 | 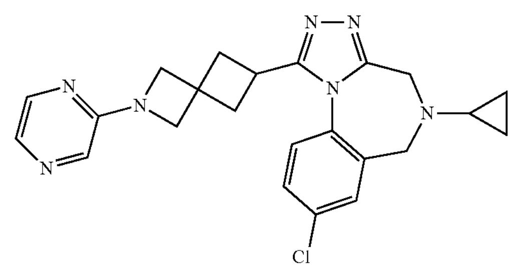 [SMILES: Clc1ccc2c(c1)CN(C1CC1)Cc1nnc(C3CC4(C3)CN(c3cnccn3)C4)n1-2] |
| 220 | 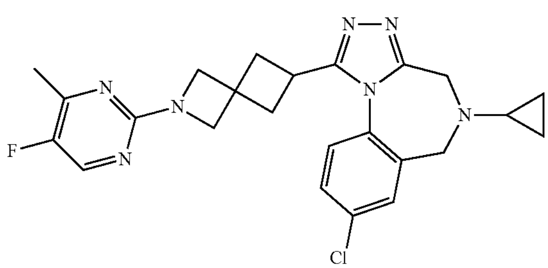 [SMILES: Cc1nc(N2CC3(CC(c4nnc5n4-c4ccc(Cl)cc4CN(C4CC4)C5)C3)C2)ncc1F] |
| 221 | 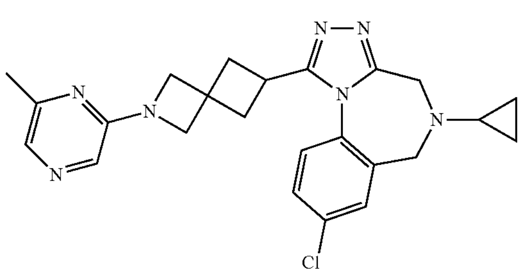 [SMILES: Cc1cncc(N2CC3(CC(c4nnc5n4-c4ccc(Cl)cc4CN(C4CC4)C5)C3)C2)n1] |

TABLE 1-continued

Representative Compounds

| Cmpd. No. | Structure |
|---|---|
| 222 | 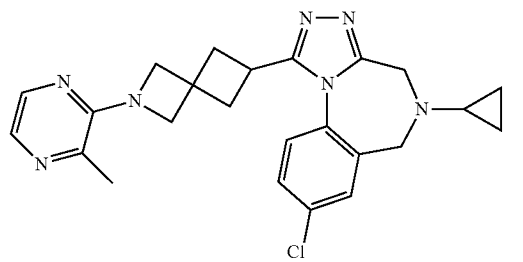 [SMILES: Cc1nccnc1N1CC2(CC(c3nnc4n3-c3ccc(Cl)cc3CN(C3CC3)C4)C2)C1] |
| 223 | 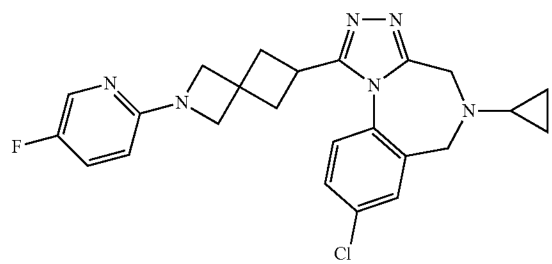 [SMILES: Fc1ccc(N2CC3(CC(c4nnc5n4-c4ccc(Cl)cc4CN(C4CC4)C5)C3)C2)nc1] |
| 224 | 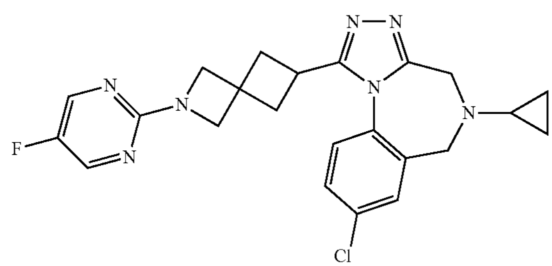 [SMILES: Fc1cnc(N2CC3(CC(c4nnc5n4-c4ccc(Cl)cc4CN(C4CC4)C5)C3)C2)nc1] |
| 225 | 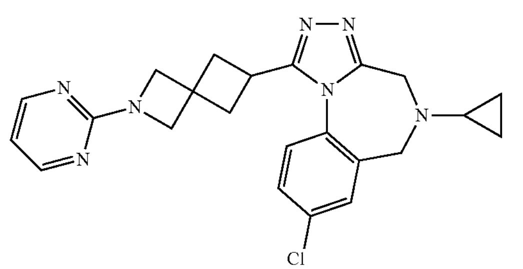 [SMILES: Clc1ccc2c(c1)CN(C1CC1)Cc1nnc(C3CC4(C3)CN(c3ncccn3)C4)n1-2] |
| 226 | 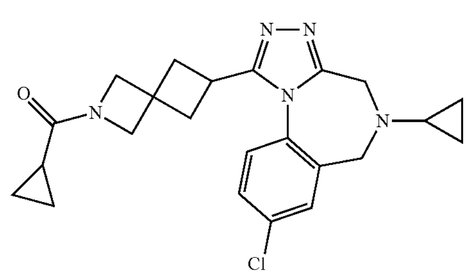 [SMILES: O=C(C1CC1)N1CC2(CC(c3nnc4n3-c3ccc(Cl)cc3CN(C3CC3)C4)C2)C1] |

TABLE 1-continued
Representative Compounds
| Cmpd. No. | Structure |
|---|---|
| 227 | 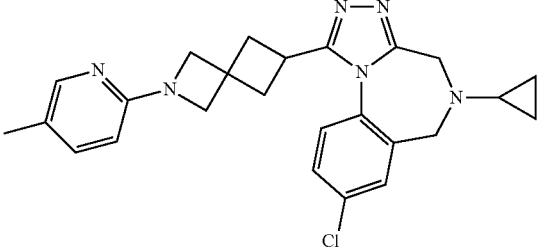 [SMILES: Cc1ccc(N2CC3(CC(c4nnc5n4-c4ccc(Cl)cc4CN(C4CC4)C5)C3)C2)nc1] |
| 228 | 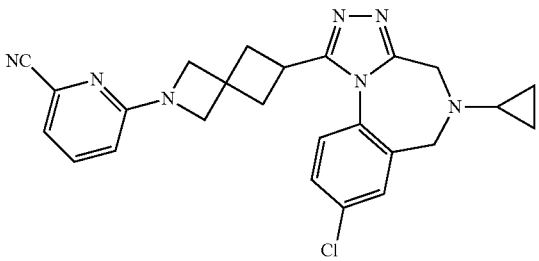 [SMILES: N#Cc1cccc(N2CC3(CC(c4nnc5n4-c4ccc(Cl)cc4CN(C4CC4)C5)C3)C2)n1] |
| 229 | 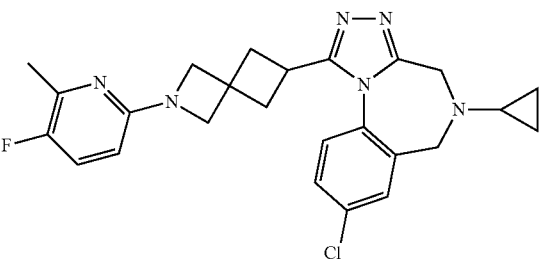 [SMILES: Cc1nc(N2CC3(CC(c4nnc5n4-c4ccc(Cl)cc4CN(C4CC4)C5)C3)C2)ccc1F] |
| 230 | 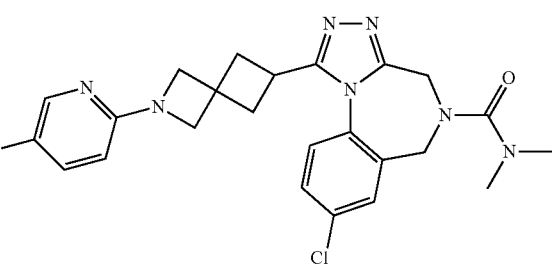 |
| 231 | 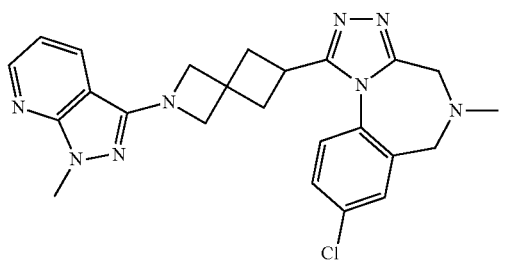 [SMILES: CN1Cc2cc(Cl)ccc2-n2c(nnc2C2CC3(C2)CN(c2nn(C)c4ncccc24)C3)C1] |

TABLE 1-continued

Representative Compounds

| Cmpd. No. | Structure |
|---|---|
| 232 | 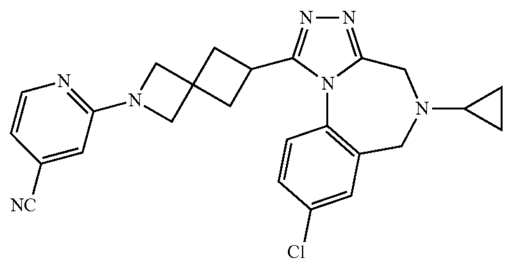 [SMILES: N#Cc1ccnc(N2CC3(CC(c4nnc5n4-c4ccc(Cl)cc4CN(C4CC4)C5)C3)C2)c1] |
| 233 | 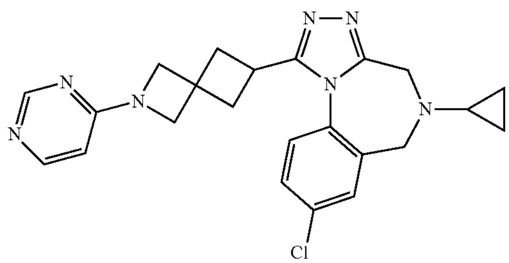 [SMILES: Clc1ccc2c(c1)CN(C1CC1)Cc1nnc(C3CC4(C3)CN(c3ccncn3)C4)n1-2] |
| 234 | 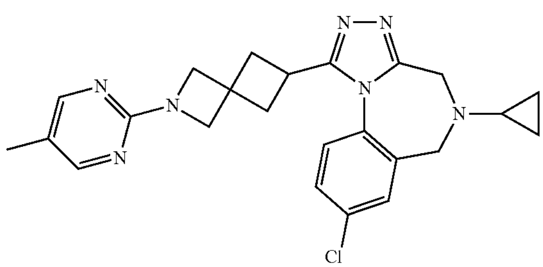 |
| 235 | 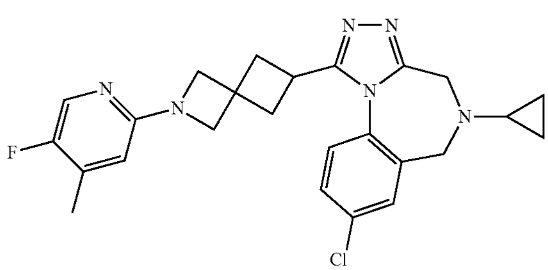 [SMILES: Cc1cc(N2CC3(CC(c4nnc5n4-c4ccc(Cl)cc4CN(C4CC4)C5)C3)C2)ncc1F] |
| 236 | 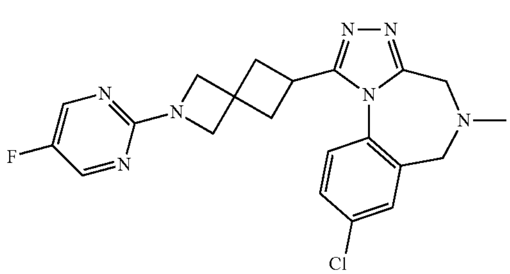 [SMILES: CN1Cc2cc(Cl)ccc2-n2c(nnc2C2CC3(C2)CN(c2ncc(F)cn2)C3)C1] |

TABLE 1-continued

Representative Compounds

| Cmpd. No. | Structure |
|---|---|
| 237 | 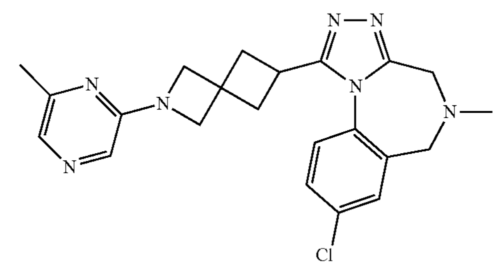 |
| 238 | 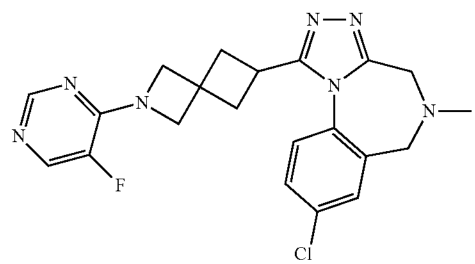 [SMILES: CN1Cc2cc(Cl)ccc2-n2c(nnc2C2CC3(C2)CN(c2ncncc2F)C3)C1] |
| 239 | 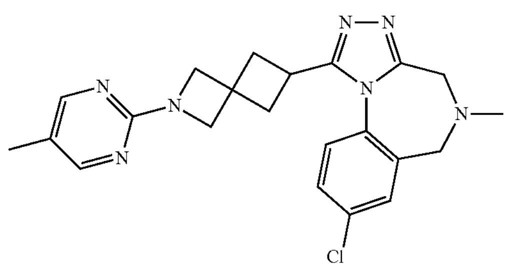 |
| 240 | 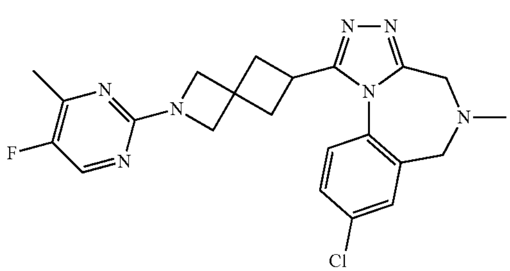 [SMILES: Cc1nc(N2CC3(CC(c4nnc5n4-c4ccc(Cl)cc4CN(C)C5)C3)C2)ncc1F] |
| 241 | 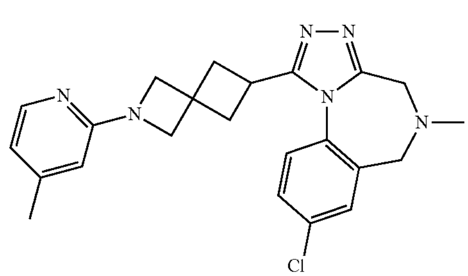 [SMILES: Cc1ccnc(N2CC3(CC(c4nnc5n4-c4ccc(Cl)cc4CN(C)C5)C3)C2)c1] |

TABLE 1-continued

Representative Compounds

| Cmpd. No. | Structure |
|---|---|
| 242 | 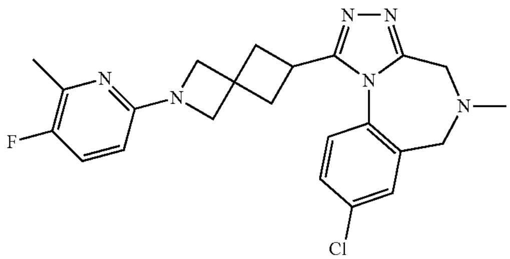 [SMILES: Cc1nc(N2CC3(CC(c4nnc5n4-c4ccc(Cl)cc4CN(C)C5)C3)C2)ccc1F] |
| 243 | 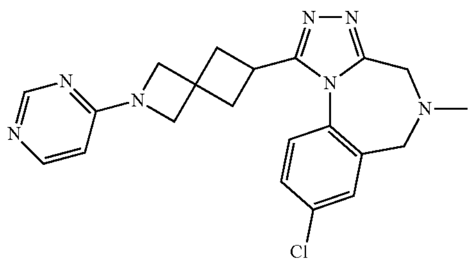 [SMILES: CN1Cc2cc(Cl)ccc2-n2c(nnc2C2CC3(C2)CN(c2ccncn2)C3)C1] |
| 244 | 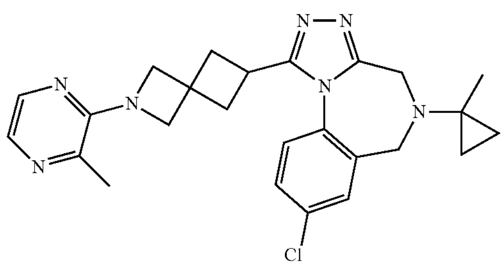 [SMILES: Cc1nccnc1N1CC2(CC(c3nnc4n3-c3ccc(Cl)cc3CN(C3(C)CC3)C4)C2)C1] |
| 245 | 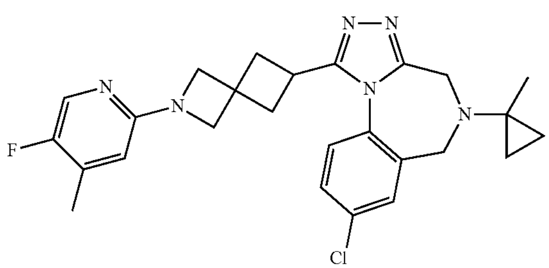 [SMILES: Cc1cc(N2CC3(CC(c4nnc5n4-c4ccc(Cl)cc4CN(C4(C)CC4)C5)C3)C2)ncc1F] |
| 246 | 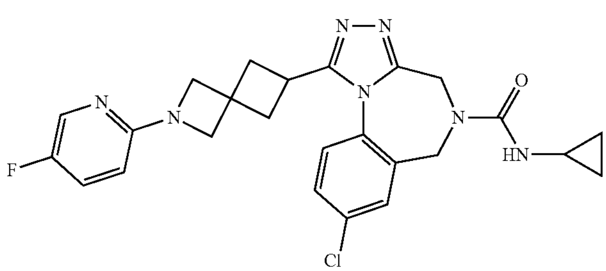 [SMILES: O=C(NC1CC1)N1Cc2cc(Cl)ccc2-n2c(nnc2C2CC3(C2)CN(c2ccc(F)cn2)C3)C1] |

US 11,186,577 B2
145                                     146
TABLE 1-continued
Representative Compounds
| Cmpd. No. | Structure |
|---|---|
| 247 | 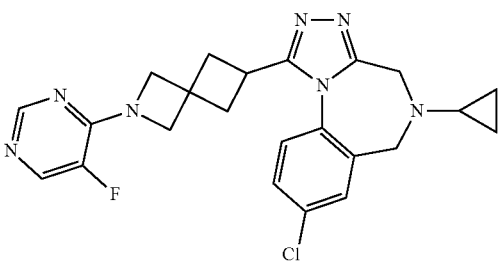 [SMILES: Fc1cncnc1N1CC2(CC(c3nnc4n3-c3ccc(Cl)cc3CN(C3CC3)C4)C2)C1] |
| 248 | 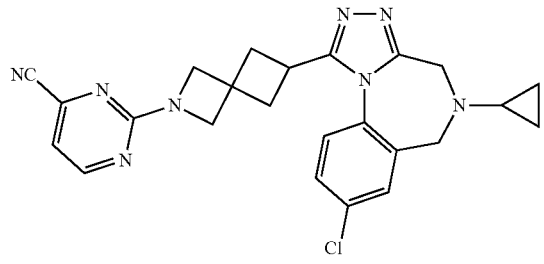 [SMILES: N#Cc1ccnc(N2CC3(CC(c4nnc5n4-c4ccc(Cl)cc4CN(C4CC4)C5)C3)C2)n1] |
| 249 | 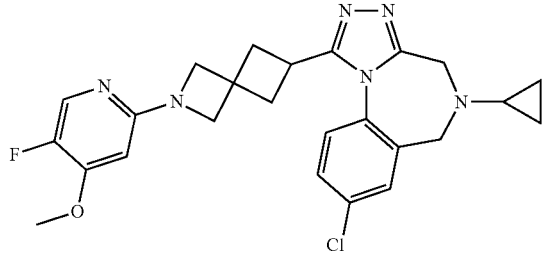 [SMILES: COc1cc(N2CC3(CC(c4nnc5n4-c4ccc(Cl)cc4CN(C4CC4)C5)C3)C2)ncc1F] |
| 250 | 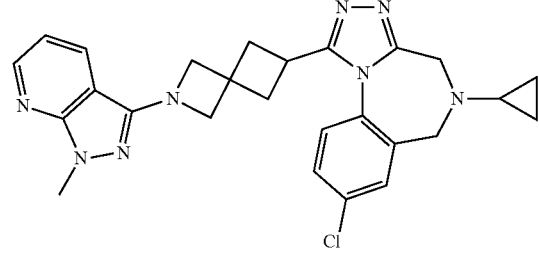 [SMILES: Cn1nc(N2CC3(CC(c4nnc5n4-c4ccc(Cl)cc4CN(C4CC4)C5)C3)C2)c2cccnc21] |
| 251 | 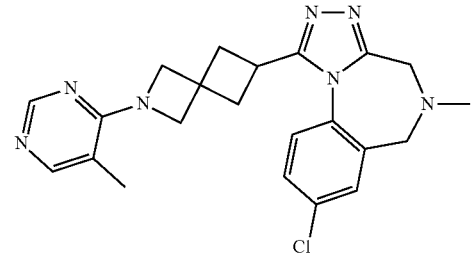 [SMILES: Cc1cncnc1N1CC2(CC(c3nnc4n3-c3ccc(Cl)cc3CN(C)C4)C2)C1] |

TABLE 1-continued
Representative Compounds
| Cmpd. No. | Structure |
|---|---|
| 252 | 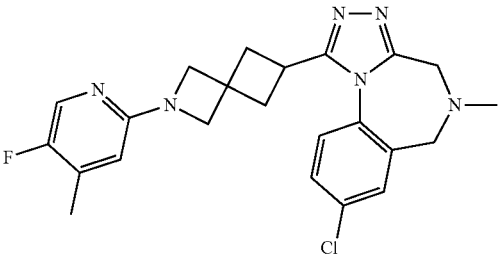 [SMILES: Cc1cc(N2CC3(CC(c4nnc5n4-c4ccc(Cl)cc4CN(C)C5)C3)C2)ncc1F] |
| 253 | 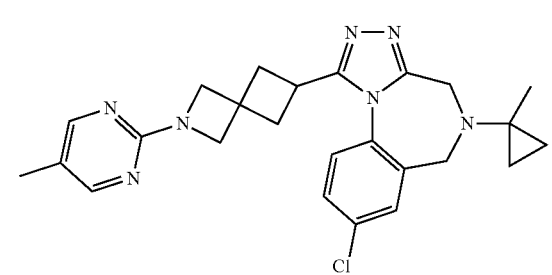 [SMILES: Cc1cnc(N2CC3(CC(c4nnc5n4-c4ccc(Cl)cc4CN(C4(C)CC4)C5)C3)C2)nc1] |
| 254 | 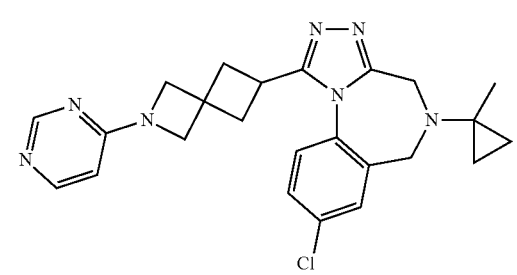 [SMILES: CC1(N2Cc3cc(Cl)ccc3-n3c(nnc3C3CC4(C3)CN(c3ccncn3)C4)C2)CC1] |
| 255 | 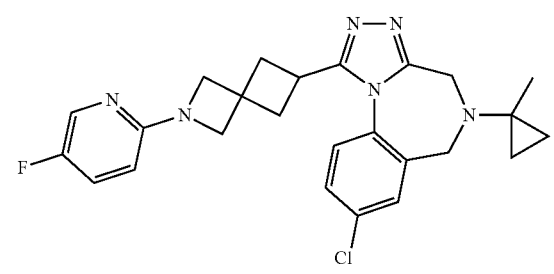 [SMILES: CC1(N2Cc3cc(Cl)ccc3-n3c(nnc3C3CC4(C3)CN(c3ccc(F)cn3)C4)C2)CC1] |
| 256 | 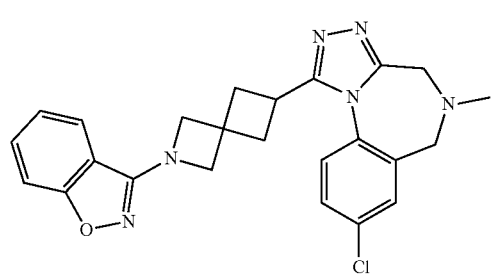 [SMILES: CN1Cc2cc(Cl)ccc2-n2c(nnc2C2CC3(C2)CN(c2noc4ccccc24)C3)C1] |

TABLE 1-continued
Representative Compounds
| Cmpd. No. | Structure |
|---|---|
| 257 | 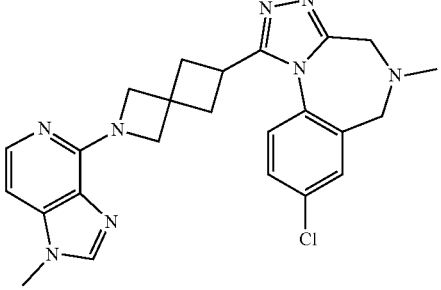 |
| 258 | 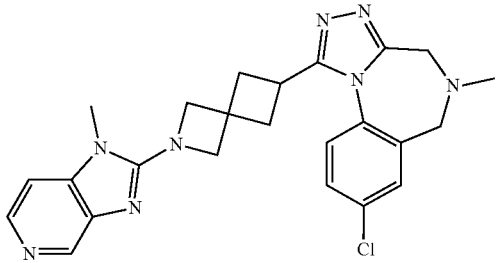 [SMILES: CN1Cc2cc(Cl)ccc2-n2c(nnc2C2CC3(C2)CN(c2nc4cnccc4n2C)C3)C1] |
| 259 | 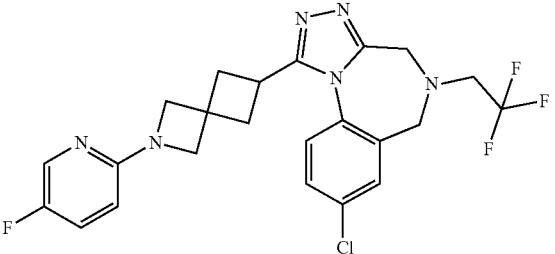 [SMILES: Fc1ccc(N2CC3(CC(c4nnc5n4-c4ccc(Cl)cc4CN(CC(F)(F)F)C5)C3)C2)nc1] |
| 260 | 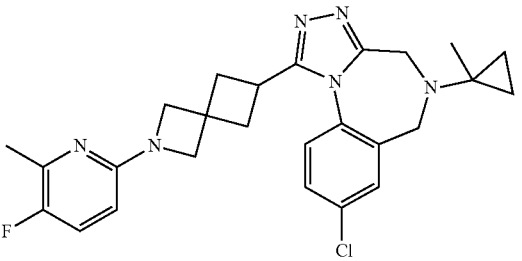 [SMILES: Cc1nc(N2CC3(CC(c4nnc5n4-c4ccc(Cl)cc4CN(C4(C)CC4)C5)C3)C2)ccc1F] |
| 261 | 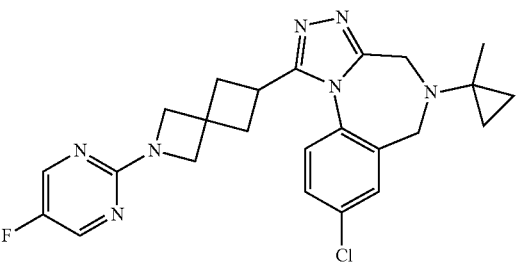 [SMILES: CC1(N2Cc3cc(Cl)ccc3-n3c(nnc3C3CC4(C3)CN(c3ncc(F)cn3)C4)C2)CC1] |

US 11,186,577 B2
TABLE 1-continued
Representative Compounds
| Cmpd. No. | Structure |
|---|---|
| 262 | 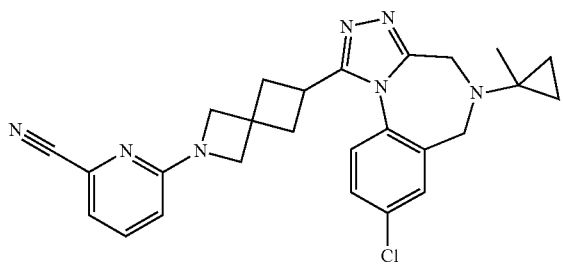 [SMILES: CC1(N2Cc3cc(Cl)ccc3-n3c(nnc3C3CC4(C3)CN(c3cccc(C#N)n3)C4)C2)CC1] |
| 263 | 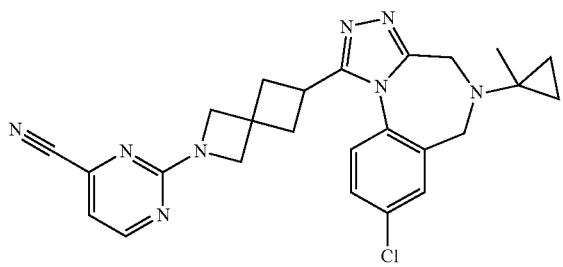 [SMILES: CC1(N2Cc3cc(Cl)ccc3-n3c(nnc3C3CC4(C3)CN(c3nccc(C#N)n3)C4)C2)CC1] |
| 264 | 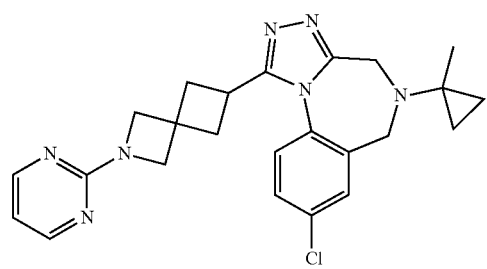 [SMILES: CC1(N2Cc3cc(Cl)ccc3-n3c(nnc3C3CC4(C3)CN(c3ncccn3)C4)C2)CC1] |
| 265 | 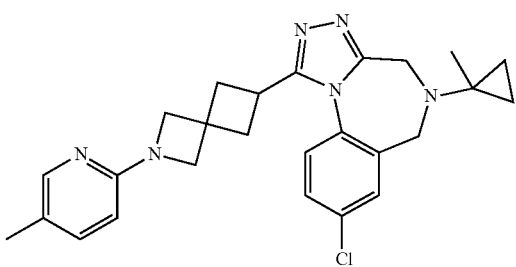 [SMILES: Cc1ccc(N2CC3(CC(c4nnc5n4-c4ccc(Cl)cc4CN(C4(C)CC4)C5)C3)C2)nc1] |
| 266 | 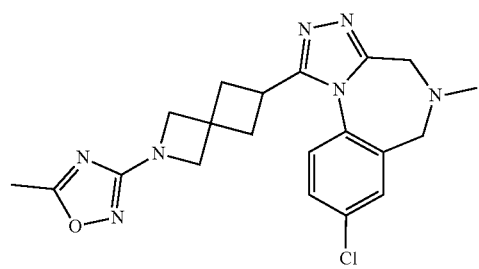 |

TABLE 1-continued

Representative Compounds

| Cmpd. No. | Structure |
|---|---|
| 267 | 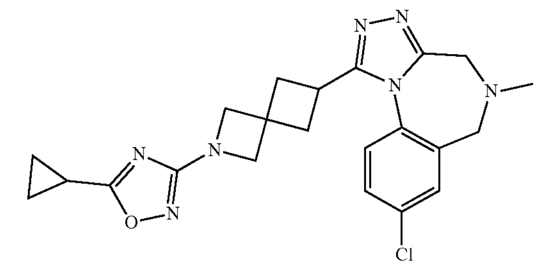 [SMILES: CN1Cc2cc(Cl)ccc2-n2c(nnc2C2CC3(C2)CN(c2noc(C4CC4)n2)C3)C1] |
| 268 | 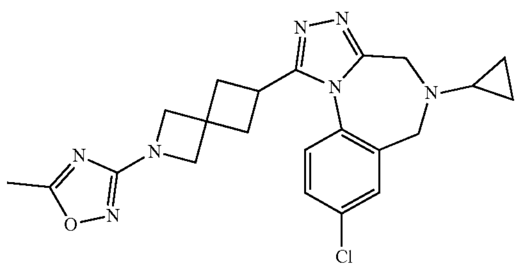 [SMILES: Cc1nc(N2CC3(CC(c4nnc5n4-c4ccc(Cl)cc4CN(C4CC4)C5)C3)C2)no1] |
| 269 | 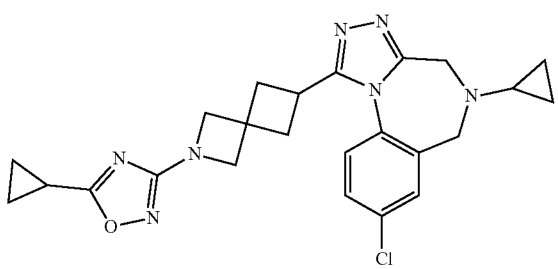 [SMILES: Clc1ccc2c(c1)CN(C1CC1)Cc1nnc(C3CC4(C3)CN(c3noc(C5CC5)n3)C4)n1-2] |
| 270 | 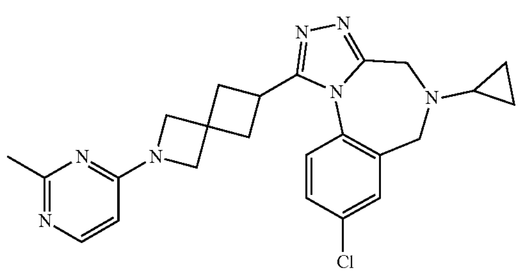 [SMILES: Cc1nccc(N2CC3(CC(c4nnc5n4-c4ccc(Cl)cc4CN(C4CC4)C5)C3)C2)n1] |
| 271 | 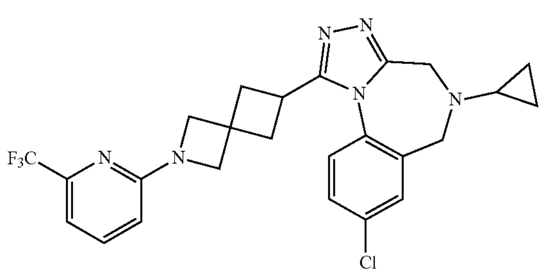 [SMILES: FC(F)(F)c1cccc(N2CC3(CC(c4nnc5n4-c4ccc(Cl)cc4CN(C4CC4)C5)C3)C2)n1] |

TABLE 1-continued
Representative Compounds
| Cmpd. No. | Structure |
|---|---|
| 272 | 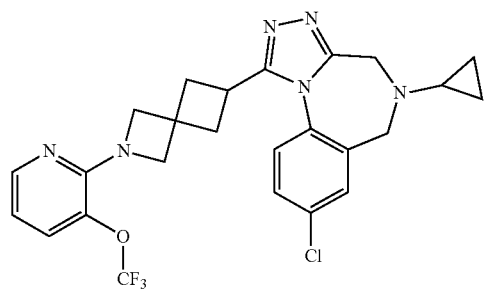 [SMILES: FC(F)(F)Oc1cccnc1N1CC2(CC(c3nnc4n3-c3ccc(Cl)cc3CN(C3CC3)C4)C2)C1] |
| 273 | 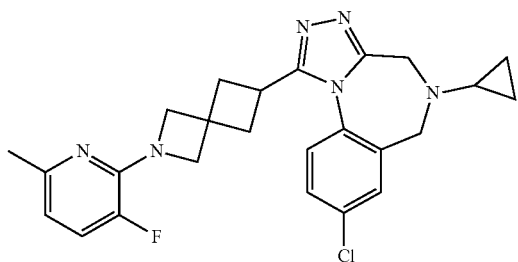 [SMILES: Cc1ccc(F)c(N2CC3(CC(c4nnc5n4-c4ccc(Cl)cc4CN(C4CC4)C5)C3)C2)n1] |
| 274 | 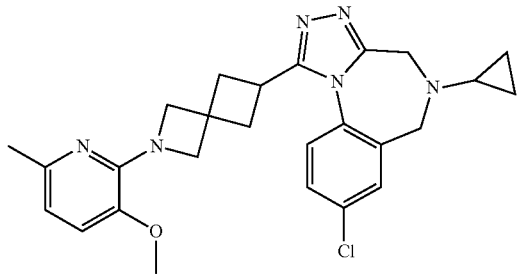 [SMILES: COc1ccc(C)nc1N1CC2(CC(c3nnc4n3-c3ccc(Cl)cc3CN(C3CC3)C4)C2)C1] |
| 275 | 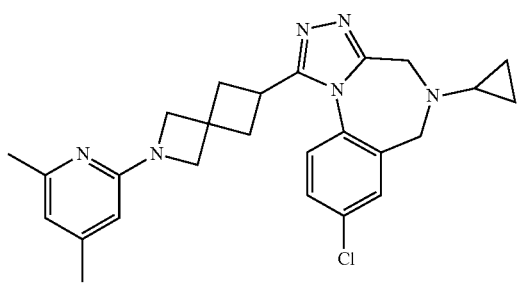 [SMILES: Cc1cc(C)nc(N2CC3(CC(c4nnc5n4-c4ccc(Cl)cc4CN(C4CC4)C5)C3)C2)c1] |
| 276 | 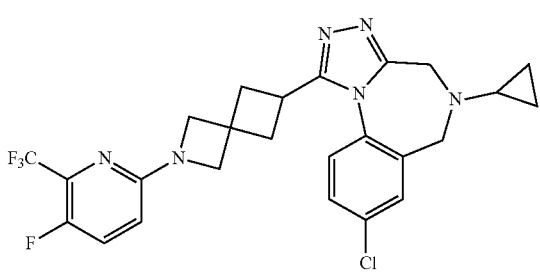 [SMILES: Fc1ccc(N2CC3(CC(c4nnc5n4-c4ccc(Cl)cc4CN(C4CC4)C5)C3)C2)nc1C(F)(F)F] |

TABLE 1-continued
Representative Compounds
| Cmpd. No. | Structure |
|---|---|
| 277 | 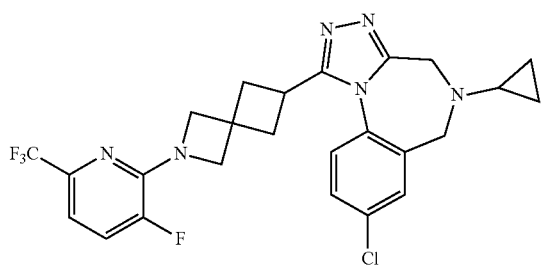 [SMILES: Fc1ccc(C(F)(F)F)nc1N1CC2(CC(c3nnc4n3-c3ccc(Cl)cc3CN(C3CC3)C4)C2)C1] |
| 278 | 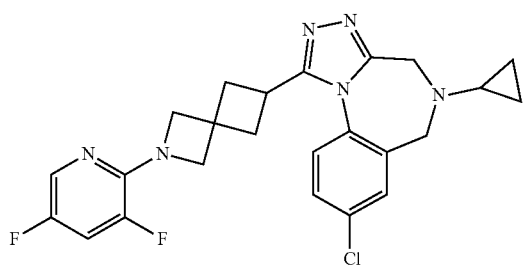 [SMILES: Fc1cnc(N2CC3(CC(c4nnc5n4-c4ccc(Cl)cc4CN(C4CC4)C5)C3)C2)c(F)c1] |
| 279 | 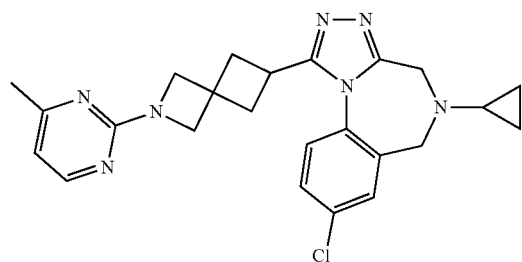 [SMILES: Cc1ccnc(N2CC3(CC(c4nnc5n4-c4ccc(Cl)cc4CN(C4CC4)C5)C3)C2)n1] |
| 280 | 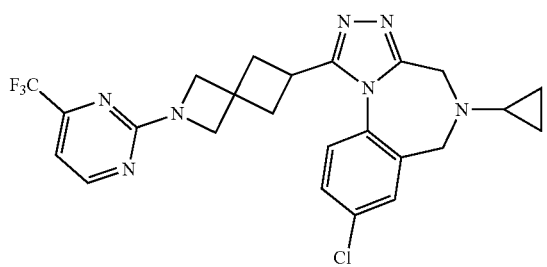 [SMILES: FC(F)(F)c1ccnc(N2CC3(CC(c4nnc5n4-c4ccc(Cl)cc4CN(C4CC4)C5)C3)C2)n1] |
| 281 | 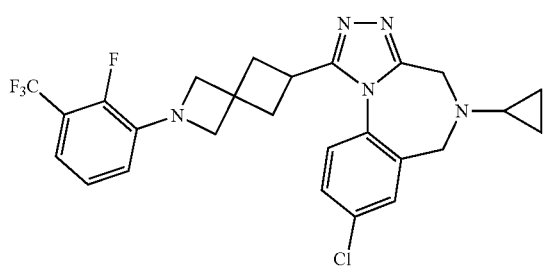 |

TABLE 1-continued
Representative Compounds
| Cmpd. No. | Structure |
|---|---|
| 282 | 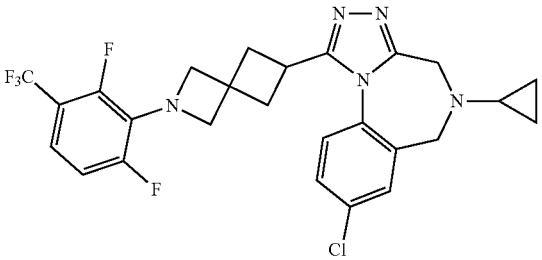 [SMILES: Fc1ccc(C(F)(F)F)c(F)c1N1CC2(CC(c3nnc4n3-c3ccc(Cl)cc3CN(C3CC3)C4)C2)C1] |
| 283 | 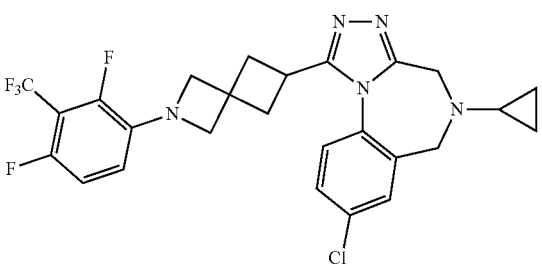 |
| 284 | 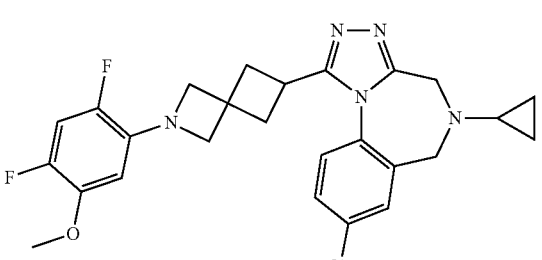 |
| 285 | 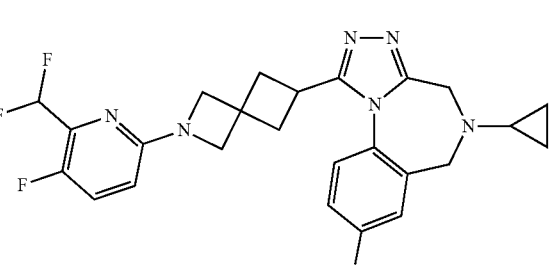 |
| 286 | 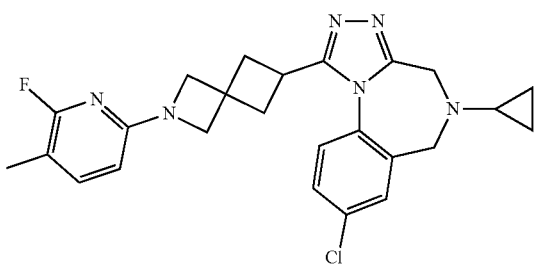 [SMILES: Cc1ccc(N2CC3(CC(c4nnc5n4-c4ccc(Cl)cc4CN(C4CC4)C5)C3)C2)nc1F] |

TABLE 1-continued

Representative Compounds

| Cmpd. No. | Structure |
|---|---|
| 287 | 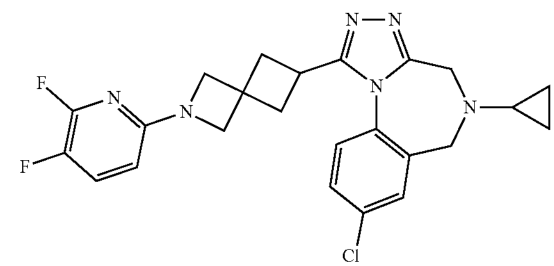 [SMILES: Fc1ccc(N2CC3(CC(c4nnc5n4-c4ccc(Cl)cc4CN(C4CC4)C5)C3)C2)nc1F] |
| 288 | 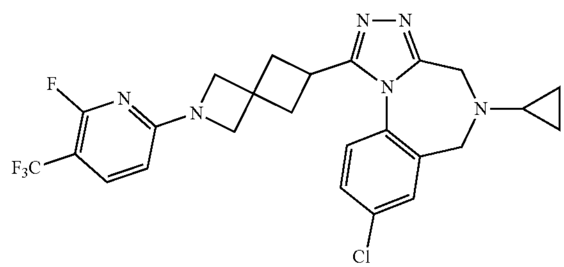 [SMILES: Fc1nc(N2CC3(CC(c4nnc5n4-c4ccc(Cl)cc4CN(C4CC4)C5)C3)C2)ccc1C(F)(F)F] |
| 289 | 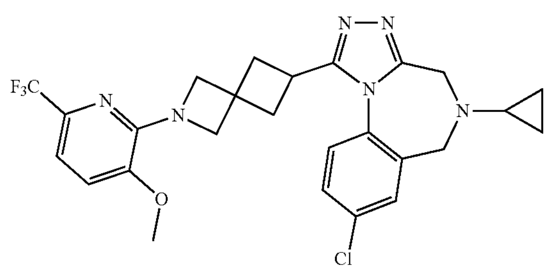 [SMILES: COc1ccc(C(F)(F)F)nc1N1CC2(CC(c3nnc4n3-c3ccc(Cl)cc3CN(C3CC3)C4)C2)C1] |
| 290 | 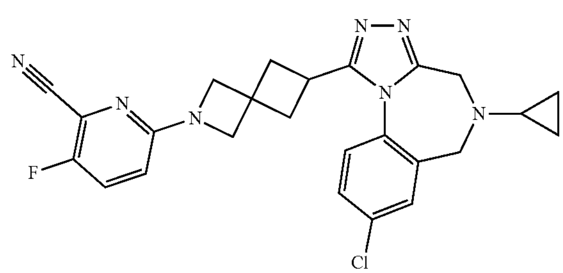 [SMILES: N#Cc1nc(N2CC3(CC(c4nnc5n4-c4ccc(Cl)cc4CN(C4CC4)C5)C3)C2)ccc1F] |
| 291 | 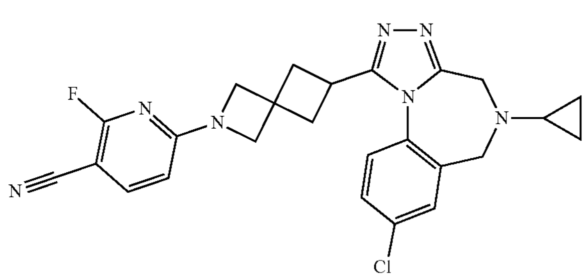 [SMILES: N#Cc1ccc(N2CC3(CC(c4nnc5n4-c4ccc(Cl)cc4CN(C4CC4)C5)C3)C2)nc1F] |

TABLE 1-continued

Representative Compounds

| Cmpd. No. | Structure |
|---|---|
| 292 | 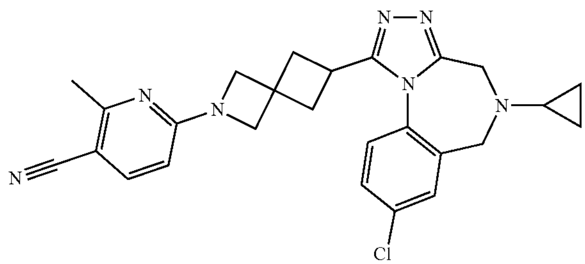 [SMILES: Cc1nc(N2CC3(CC(c4nnc5n4-c4ccc(Cl)cc4CN(C4CC4)C5)C3)C2)ccc1C#N] |
| 293 | 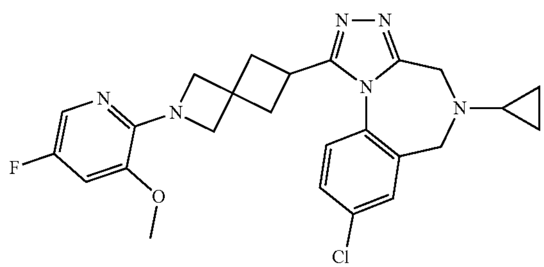 [SMILES: COc1cc(F)cnc1N1CC2(CC(c3nnc4n3-c3ccc(Cl)cc3CN(C3CC3)C4)C2)C1] |
| 294 | 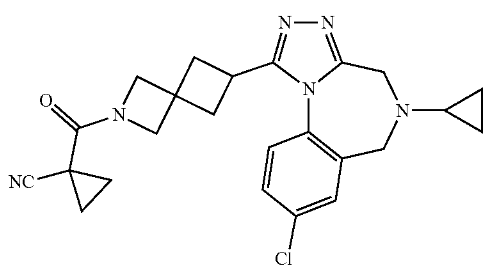 [SMILES: N#CC1(C(=O)N2CC3(CC(c4nnc5n4-c4ccc(Cl)cc4CN(C4CC4)C5)C3)C2)CC1] |
| 295 | 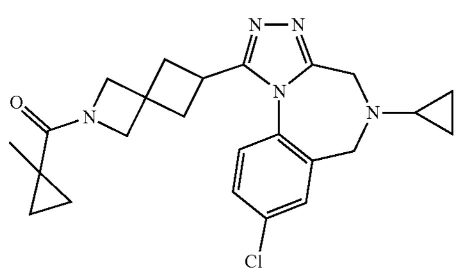 [SMILES: CC1(C(=O)N2CC3(CC(c4nnc5n4-c4ccc(Cl)cc4CN(C4CC4)C5)C3)C2)CC1] |
| 296 | 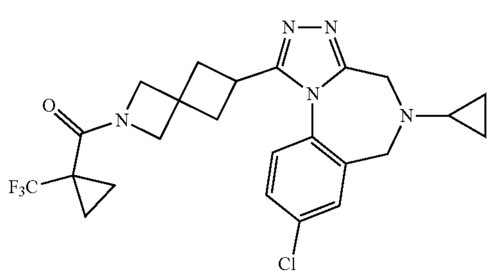 [SMILES: O=C(N1CC2(CC(c3nnc4n3-c3ccc(Cl)cc3CN(C3CC3)C4)C2)C1)C1(C(F)(F)F)CC1] |

TABLE 1-continued
Representative Compounds
| Cmpd. No. | Structure |
|---|---|
| 297 | 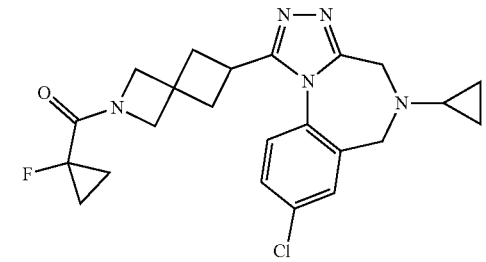 [SMILES: O=C(N1CC2(CC(c3nnc4n3-c3ccc(Cl)cc3CN(C3CC3)C4)C2)C1)C1(F)CC1] |
| 298 | 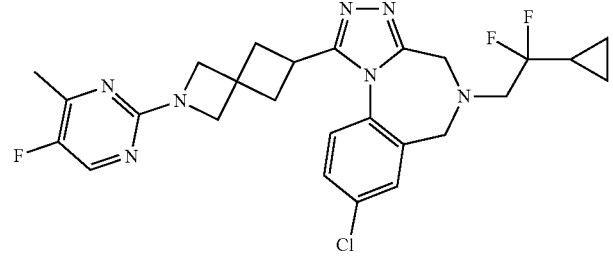 |
| 299 | 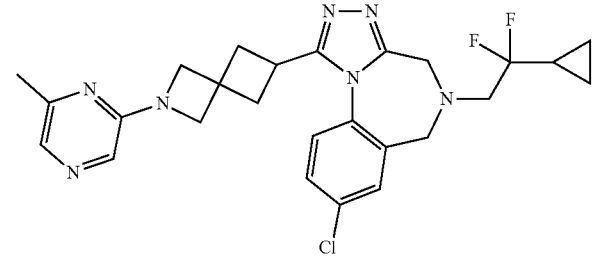 [SMILES: Cc1cncc(N2CC3(CC(c4nnc5n4-c4ccc(Cl)cc4CN(CC(F)(F)C4CC4)C5)C3)C2)n1] |
| 300 | 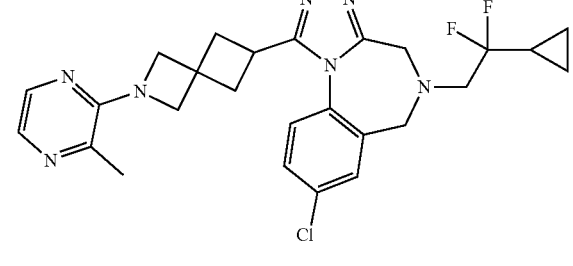 |
| 301 | 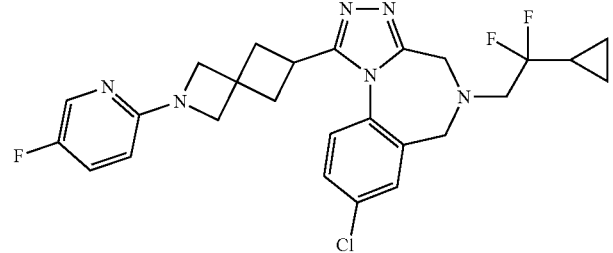 [SMILES: Fc1ccc(N2CC3(CC(c4nnc5n4-c4ccc(Cl)cc4CN(CC(F)(F)C4CC4)C5)C3)C2)nc1] |

TABLE 1-continued

Representative Compounds

| Cmpd. No. | Structure |
|---|---|
| 302 | 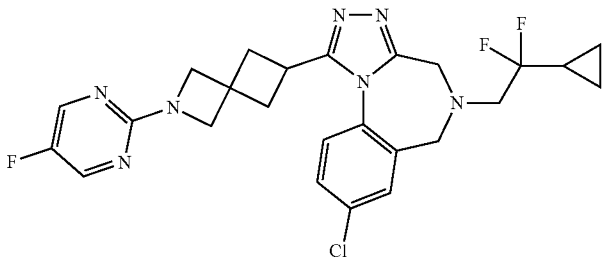 [SMILES: Fc1cnc(N2CC3(CC(c4nnc5n4-c4ccc(Cl)cc4CN(CC(F)(F)C4CC4)C5)C3)C2)nc1] |
| 303 | 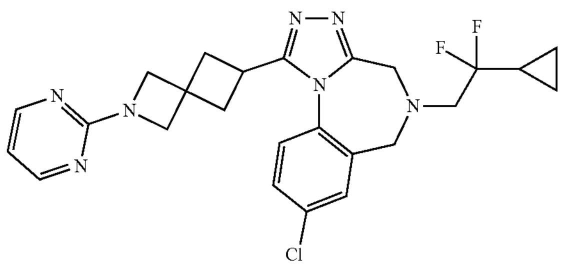 [SMILES: FC(F)(CN1Cc2cc(Cl)ccc2-n2c(nnc2C2CC3(C2)CN(c2ncccn2)C3)C1)C1CC1] |
| 304 | 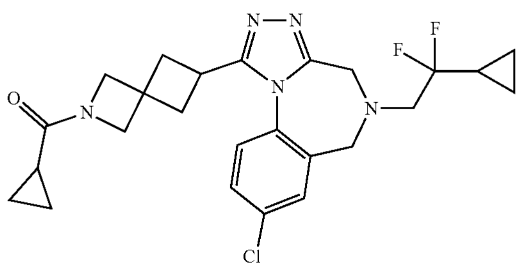 [SMILES: O=C(C1CC1)N1CC2(CC(c3nnc4n3-c3ccc(Cl)cc3CN(CC(F)(F)C3CC3)C4)C2)C1] |
| 305 | 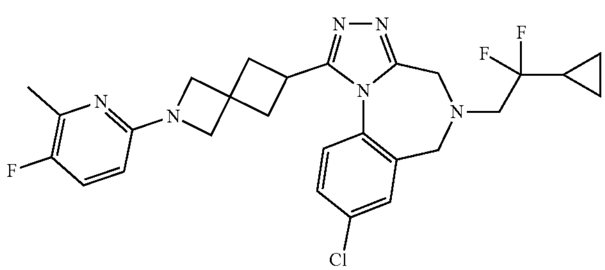 [SMILES: Cc1nc(N2CC3(CC(c4nnc5n4-c4ccc(Cl)cc4CN(CC(F)(F)C4CC4)C5)C3)C2)ccc1F] |
| 306 | 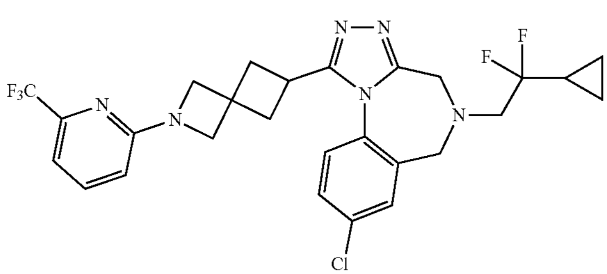 [SMILES: FC(F)(F)c1cccc(N2CC3(CC(c4nnc5n4-c4ccc(Cl)cc4CN(CC(F)(F)C4CC4)C5)C3)C2)n1] |

TABLE 1-continued

Representative Compounds

| Cmpd. No. | Structure |
|---|---|
| 307 | 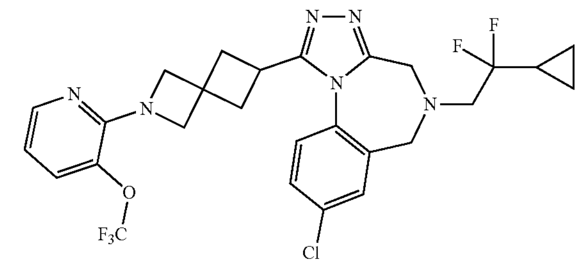 [SMILES: FC(F)(F)Oc1cccnc1N1CC2(CC(c3nnc4n3-c3ccc(Cl)cc3CN(CC(F)(F)C3CC3)C4)C2)C1] |
| 308 | 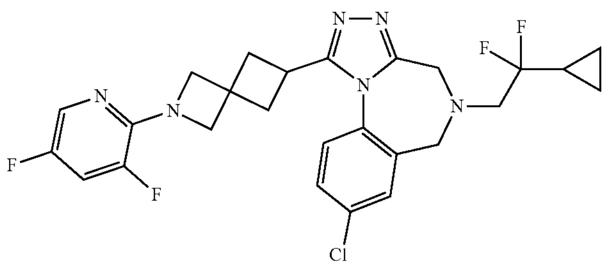 [SMILES: Fc1cnc(N2CC3(CC(c4nnc5n4-c4ccc(Cl)cc4CN(CC(F)(F)C4CC4)C5)C3)C2)c(F)c1] |
| 309 | 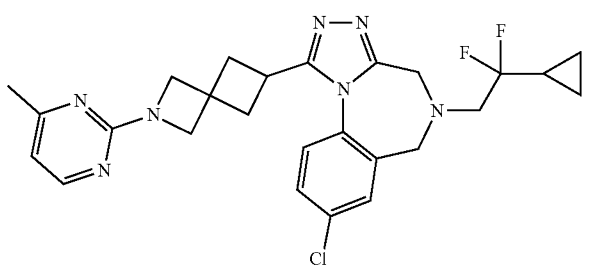 [SMILES: Cc1ccnc(N2CC3(CC(c4nnc5n4-c4ccc(Cl)cc4CN(CC(F)(F)C4CC4)C5)C3)C2)n1] |
| 310 | 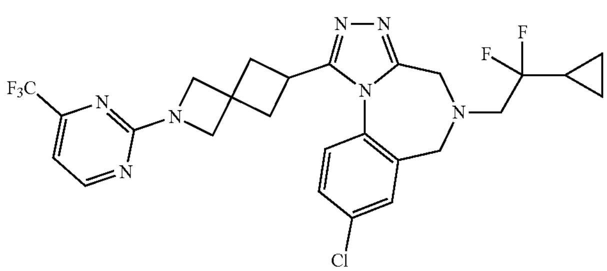 [SMILES: FC(F)(F)c1ccnc(N2CC3(CC(c4nnc5n4-c4ccc(Cl)cc4CN(CC(F)(F)C4CC4)C5)C3)C2)n1] |
| 311 | 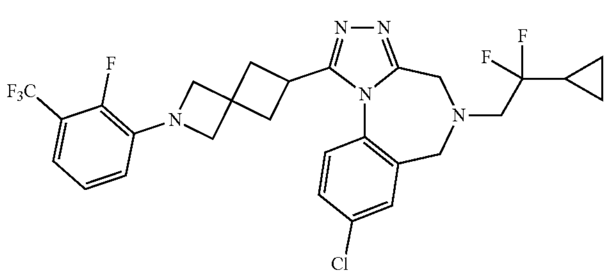 [SMILES: Fc1c(N2CC3(CC(c4nnc5n4-c4ccc(Cl)cc4CN(CC(F)(F)C4CC4)C5)C3)C2)cccc1C(F)(F)F] |

TABLE 1-continued

Representative Compounds

| Cmpd. No. | Structure |
|---|---|
| 312 | 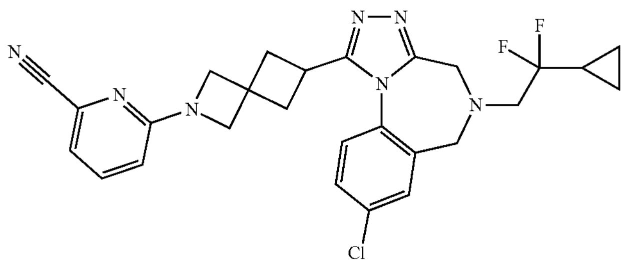 [SMILES: N#Cc1cccc(N2CC3(CC(c4nnc5n4-c4ccc(Cl)cc4CN(CC(F)(F)C4CC4)C5)C3)C2)n1] |
| 313 | 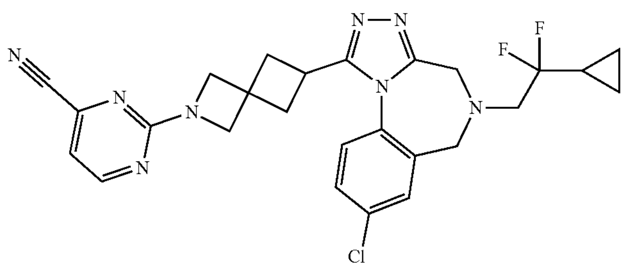 [SMILES: N#Cc1ccnc(N2CC3(CC(c4nnc5n4-c4ccc(Cl)cc4CN(CC(F)(F)C4CC4)C5)C3)C2)n1] |
| 314 | 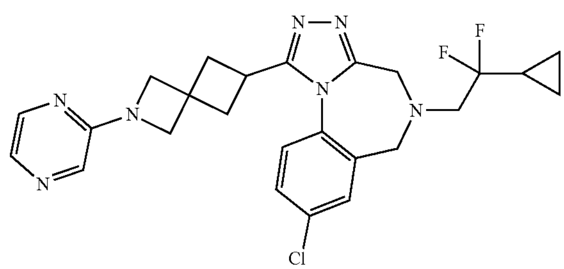 [SMILES: FC(F)(CN1Cc2cc(Cl)ccc2-n2c(nnc2C2CC3(C2)CN(c2cnccn2)C3)C1)C1CC1] |
| 315 | 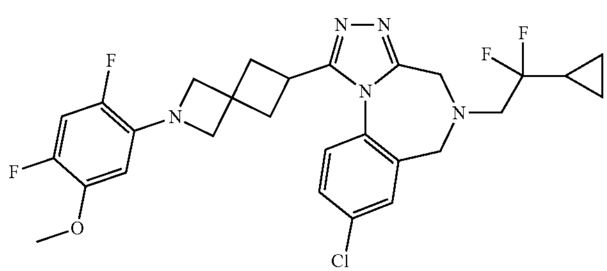 [SMILES: COc1cc(N2CC3(CC(c4nnc5n4-c4ccc(Cl)cc4CN(CC(F)(F)C4CC4)C5)C3)C2)c(F)cc1F] |
| 316 | 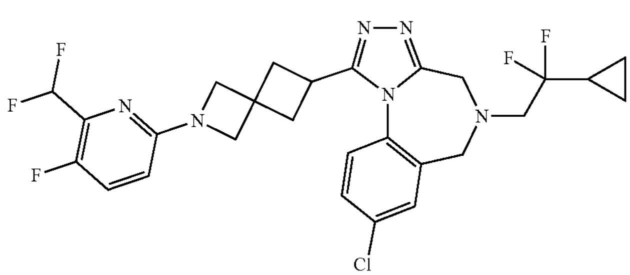 [SMILES: Fc1ccc(N2CC3(CC(c4nnc5n4-c4ccc(Cl)cc4CN(CC(F)(F)C4CC4)C5)C3)C2)nc1C(F)F] |

TABLE 1-continued

Representative Compounds

| Cmpd. No. | Structure |
|---|---|
| 317 | 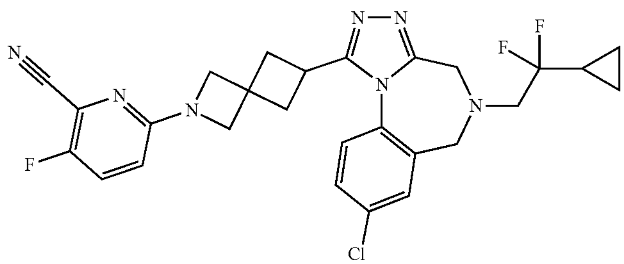 [SMILES: N#Cc1nc(N2CC3(CC(c4nnc5n4-c4ccc(Cl)cc4CN(CC(F)(F)C4CC4)C5)C3)C2)ccc1F] |
| 318 | 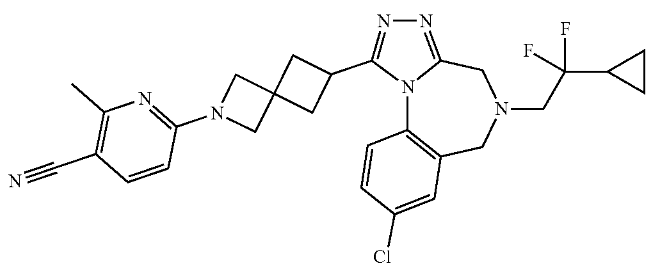 [SMILES: Cc1nc(N2CC3(CC(c4nnc5n4-c4ccc(Cl)cc4CN(CC(F)(F)C4CC4)C5)C3)C2)ccc1C#N] |
| 319 | 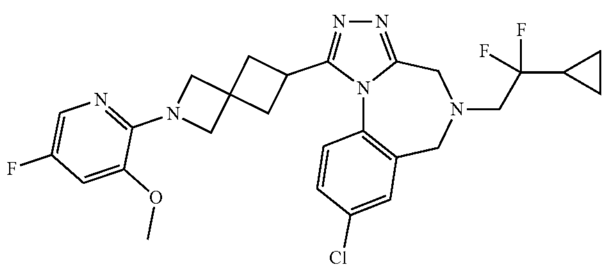 [SMILES: COc1cc(F)cnc1N1CC2(CC(c3nnc4n3-c3ccc(Cl)cc3CN(CC(F)(F)C3CC3)C4)C2)C1] |
| 320 | 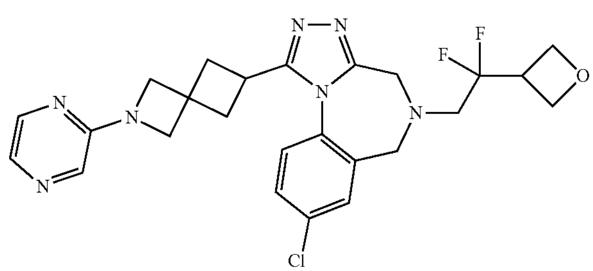 [SMILES: FC(F)(CN1Cc2cc(Cl)ccc2-n2c(nnc2C2CC3(C2)CN(c2cnccn2)C3)C1)C1COC1] |
| 321 | 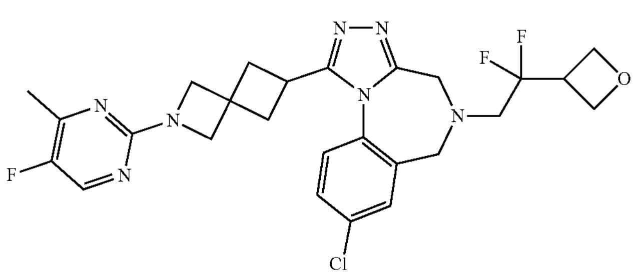 [SMILES: Cc1nc(N2CC3(CC(c4nnc5n4-c4ccc(Cl)cc4CN(CC(F)(F)C4COC4)C5)C3)C2)ncc1F] |

TABLE 1-continued
Representative Compounds
| Cmpd. No. | Structure |
|---|---|
| 322 | 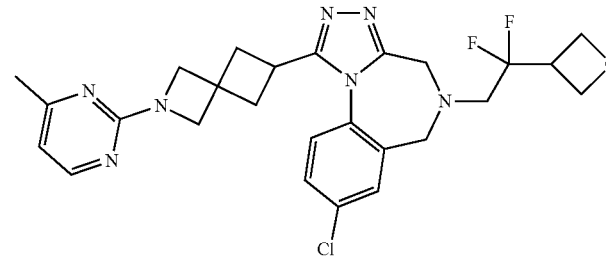 |
| 323 | 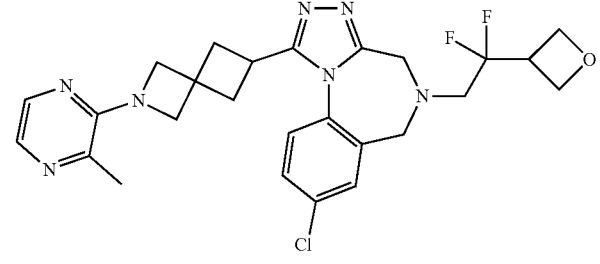 |
| 324 | 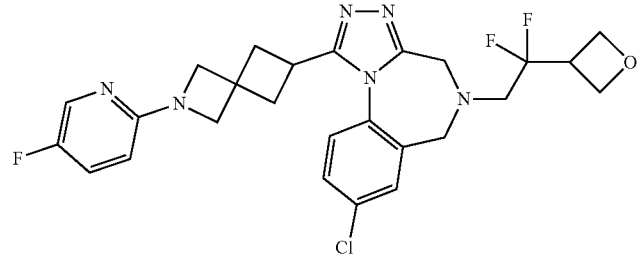 [SMILES: Fc1ccc(N2CC3(CC(c4nnc5n4-c4ccc(Cl)cc4CN(CC(F)(F)C4COC4)C5)C3)C2)nc1] |
| 325 | 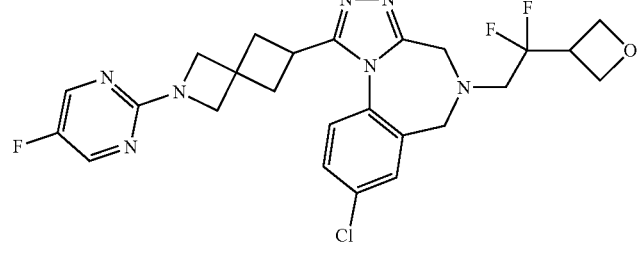 |
| 326 | 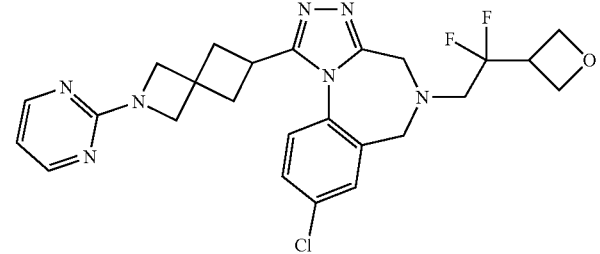 [SMILES: FC(F)(CN1Cc2cc(Cl)ccc2-n2c(nnc2C2CC3(C2)CN(c2ncccn2)C3)C1)C1COC1] |

TABLE 1-continued

Representative Compounds

| Cmpd. No. | Structure |
|---|---|
| 327 | |
| 328 | |
| 329 | |
| 330 | |
| 331 | |

TABLE 1-continued

Representative Compounds

| Cmpd. No. | Structure |
|---|---|
| 332 | 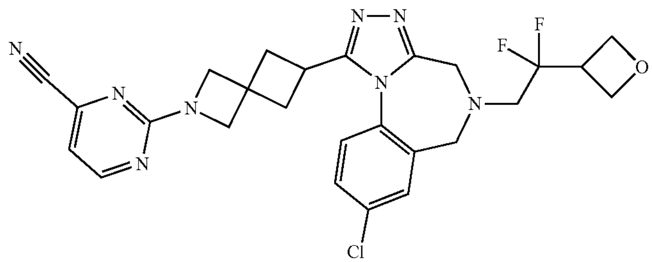 [SMILES: N#Cc1ccnc(N2CC3(CC(c4nnc5n4-c4ccc(Cl)cc4CN(CC(F)(F)C4COC4)C5)C3)C2)n1] |
| 333 | 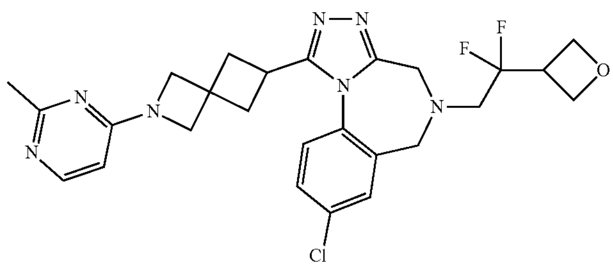 [SMILES: Cc1nccc(N2CC3(CC(c4nnc5n4-c4ccc(Cl)cc4CN(CC(F)(F)C4COC4)C5)C3)C2)n1] |
| 334 | 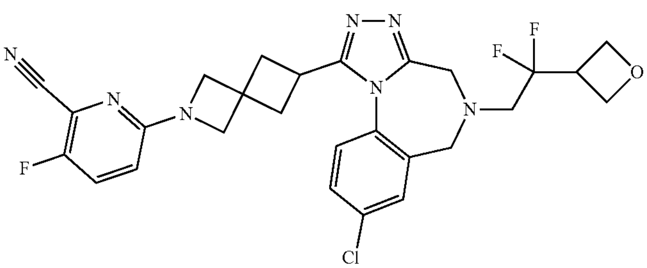 [SMILES: N#Cc1nc(N2CC3(CC(c4nnc5n4-c4ccc(Cl)cc4CN(CC(F)(F)C4COC4)C5)C3)C2)ccc1F] |
| 335 | 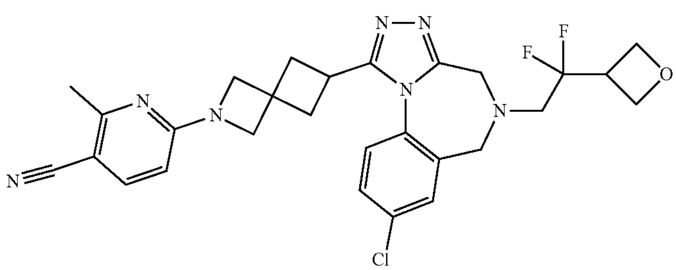 [SMILES: Cc1nc(N2CC3(CC(c4nnc5n4-c4ccc(Cl)cc4CN(CC(F)(F)C4COC4)C5)C3)C2)ccc1C#N] |
| 336 | 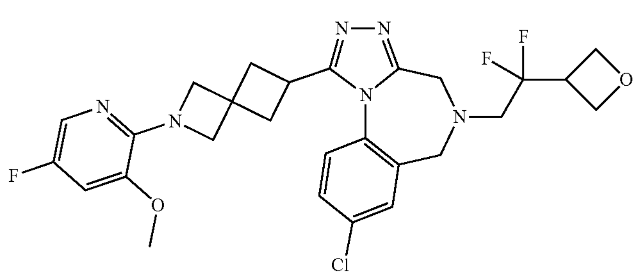 [SMILES: COc1cc(F)cnc1N1CC2(CC(c3nnc4n3-c3ccc(Cl)cc3CN(CC(F)(F)C3COC3)C4)C2)C1] |

TABLE 1-continued
Representative Compounds
| Cmpd. No. | Structure |
|---|---|
| 337 | 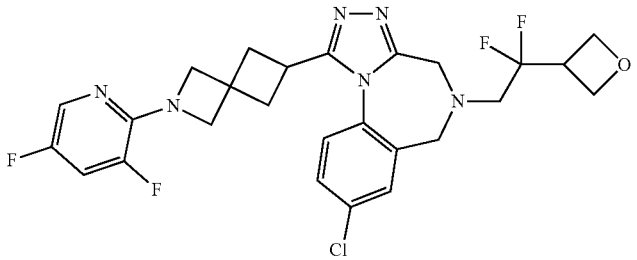 [SMILES: Fc1cnc(N2CC3(CC(c4nnc5n4-c4ccc(Cl)cc4CN(CC(F)(F)C4COC4)C5)C3)C2)c(F)c1] |
| 338 | 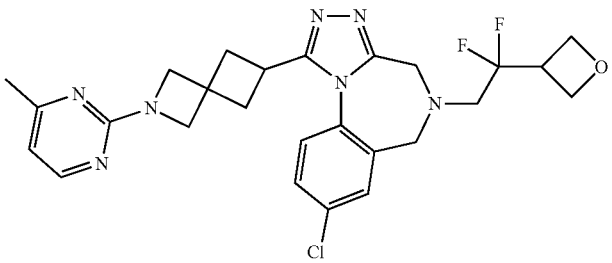 [SMILES: Cc1ccnc(N2CC3(CC(c4nnc5n4-c4ccc(Cl)cc4CN(CC(F)(F)C4COC4)C5)C3)C2)n1] |
| 339 | 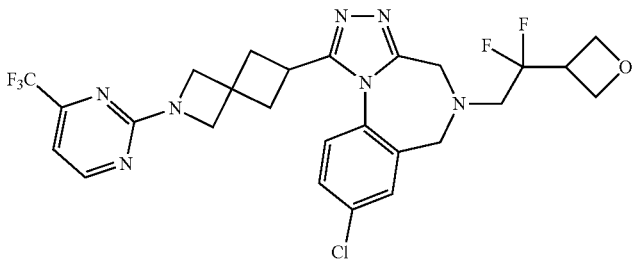 [SMILES: FC(F)(F)c1ccnc(N2CC3(CC(c4nnc5n4-c4ccc(Cl)cc4CN(CC(F)(F)C4COC4)C5)C3)C2)n1] |
| 340 | 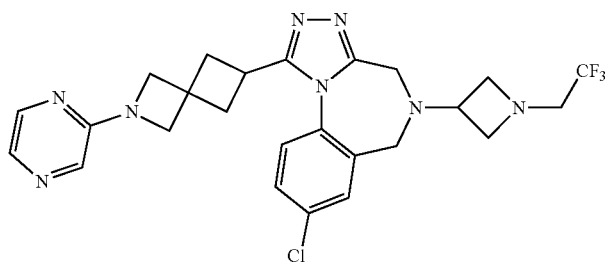 [SMILES: FC(F)(F)CN1CC(N2Cc3cc(Cl)ccc3-n3c(nnc3C3CC4(C3)CN(c3cnccn3)C4)C2)C1] |
| 341 | 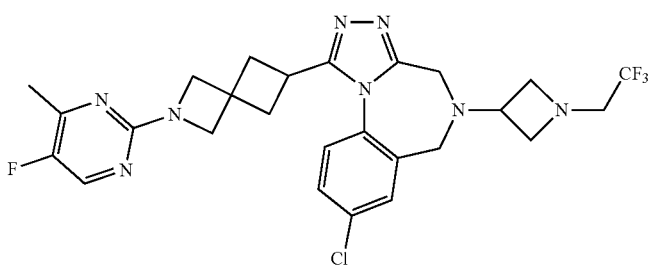 [SMILES: Cc1nc(N2CC3(CC(c4nnc5n4-c4ccc(Cl)cc4CN(C4CN(CC(F)(F)F)C4)C5)C3)C2)ncc1F] |

TABLE 1-continued
Representative Compounds
| Cmpd. No. | Structure |
|---|---|
| 342 | 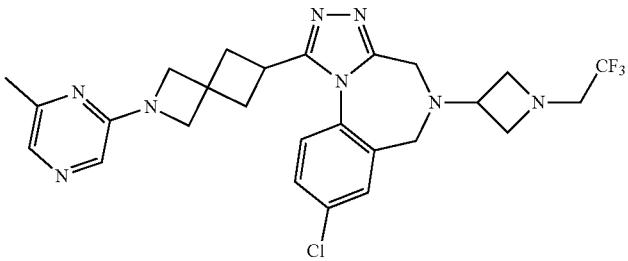 [SMILES: Cc1cncc(N2CC3(CC(c4nnc5n4-c4ccc(Cl)cc4CN(C4CN(CC(F)(F)F)C4)C5)C3)C2)n1] |
| 343 | 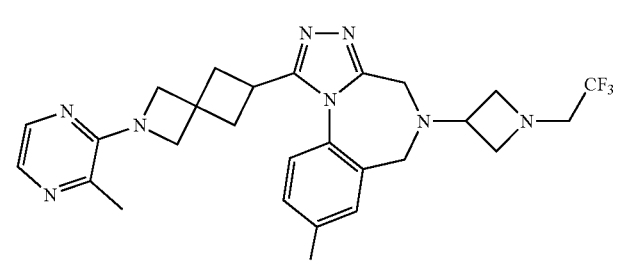 |
| 344 | 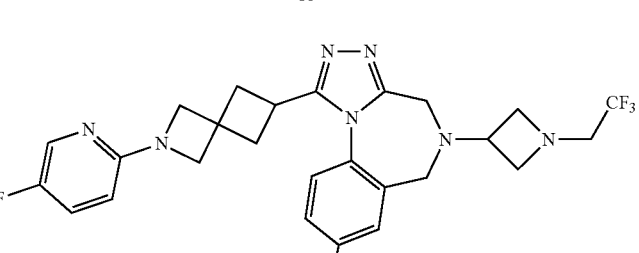 |
| 345 | 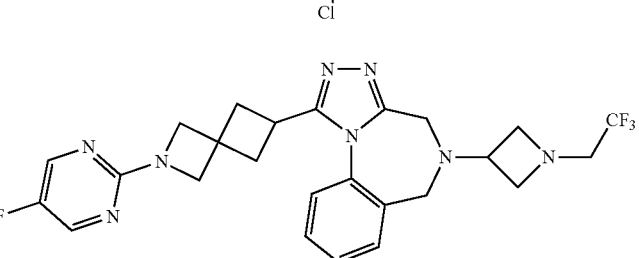 |
| 346 | 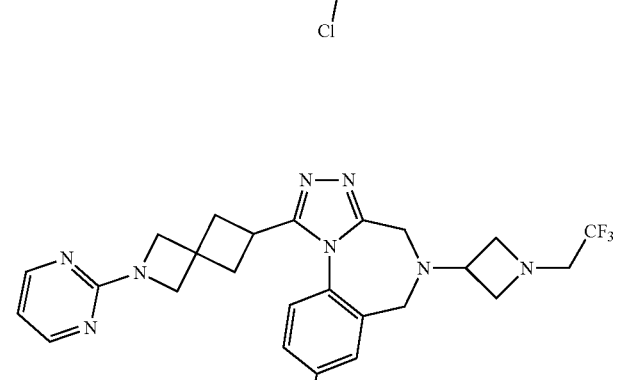 |

TABLE 1-continued
Representative Compounds
| Cmpd. No. | Structure |
|---|---|
| 347 | 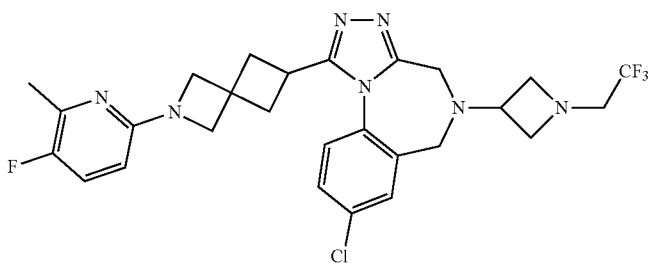 [SMILES: Cc1nc(N2CC3(CC(c4nnc5n4-c4ccc(Cl)cc4CN(C4CN(CC(F)(F)F)C4)C5)C3)C2)ccc1F] |
| 348 | 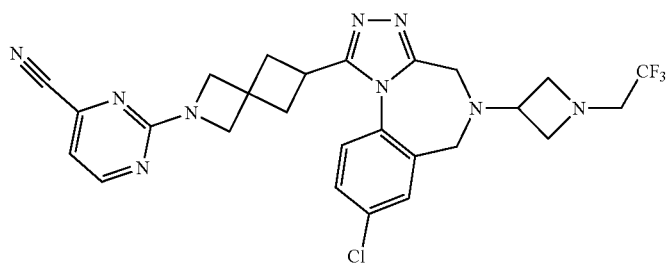 [SMILES: N#Cc1ccnc(N2CC3(CC(c4nnc5n4-c4ccc(Cl)cc4CN(C4CN(CC(F)(F)F)C4)C5)C3)C2)n1] |
| 349 | 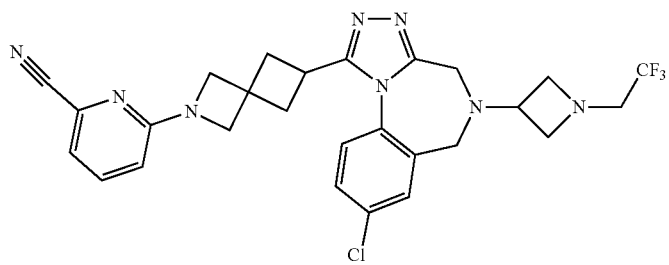 [SMILES: N#Cc1cccc(N2CC3(CC(c4nnc5n4-c4ccc(Cl)cc4CN(C4CN(CC(F)(F)F)C4)C5)C3)C2)n1] |
| 350 | 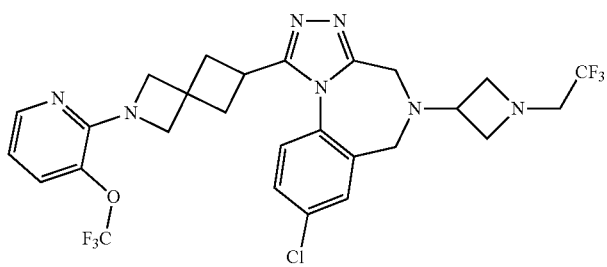 [SMILES: FC(F)(F)CN1CC(N2Cc3cc(Cl)ccc3-n3c(nnc3C3CC4(C3)CN(c3ncccc3OC(F)(F)F)C4)C2)C1] |
| 351 | 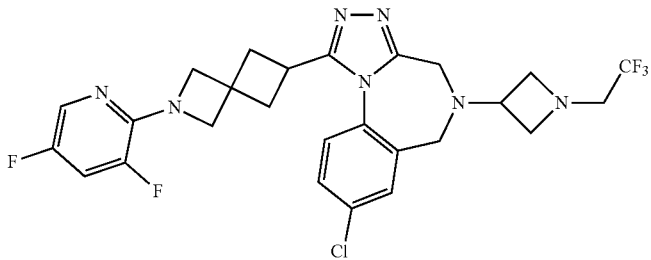 [SMILES: Fc1cnc(N2CC3(CC(c4nnc5n4-c4ccc(Cl)cc4CN(C4CN(CC(F)(F)F)C4)C5)C3)C2)c(F)c1] |

TABLE 1-continued
Representative Compounds
| Cmpd. No. | Structure |
|---|---|
| 352 | 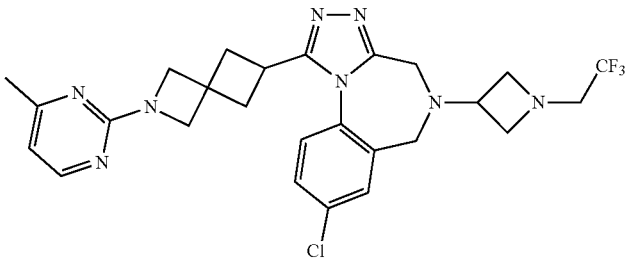 [SMILES: Cc1ccnc(N2CC3(CC(c4nnc5n4-c4ccc(Cl)cc4CN(C4CN(CC(F)(F)F)C4)C5)C3)C2)n1] |
| 353 | 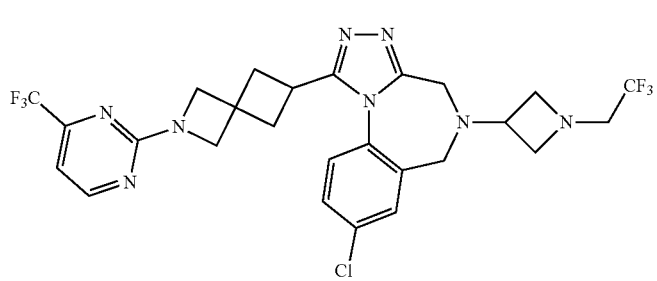 [SMILES: FC(F)(F)CN1CC(N2Cc3cc(Cl)ccc3-n3c(nnc3C3CC4(C3)CN(c3nccc(C(F)(F)F)n3)C4)C2)C1] |
| 354 | 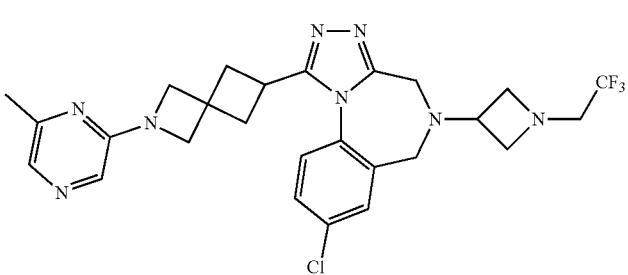 [SMILES: Cc1cncc(N2CC3(CC(c4nnc5n4-c4ccc(Cl)cc4CN(C4CN(CC(F)(F)F)C4)C5)C3)C2)n1] |
| 355 | 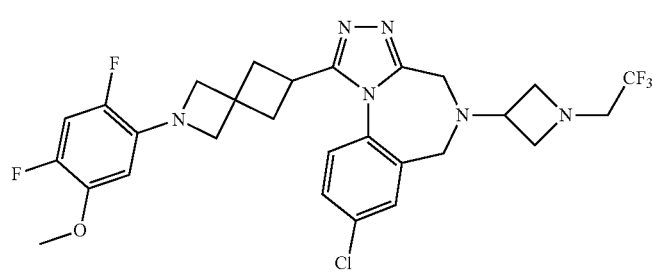 [SMILES: COc1cc(N2CC3(CC(c4nnc5n4-c4ccc(Cl)cc4CN(C4CN(CC(F)(F)F)C4)C5)C3)C2)c(F)cc1F] |
| 356 | 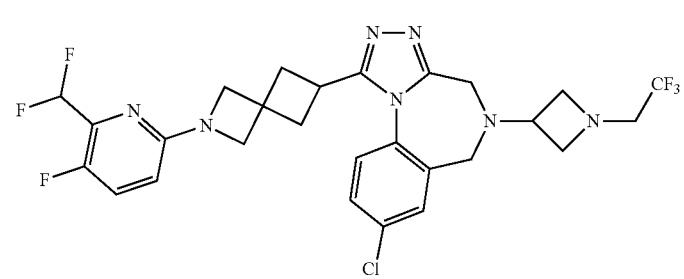 [SMILES: Fc1ccc(N2CC3(CC(c4nnc5n4-c4ccc(Cl)cc4CN(C4CN(CC(F)(F)F)C4)C5)C3)C2)nc1C(F)F] |

TABLE 1-continued

Representative Compounds

| Cmpd. No. | Structure |
|---|---|
| 357 | 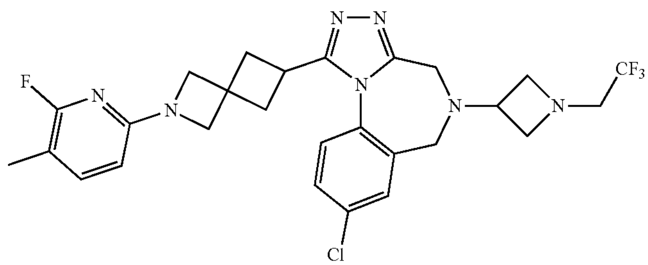 [SMILES: Cc1ccc(N2CC3(CC(c4nnc5n4-c4ccc(Cl)cc4CN(C4CN(CC(F)(F)F)C4)C5)C3)C2)nc1F] |
| 358 | 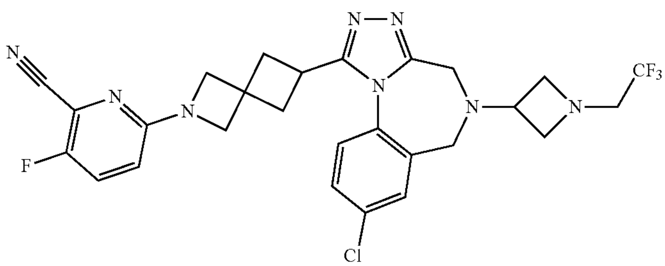 [SMILES: N#Cc1nc(N2CC3(CC(c4nnc5n4-c4ccc(Cl)cc4CN(C4CN(CC(F)(F)F)C4)C5)C3)C2)ccc1F] |
| 359 | 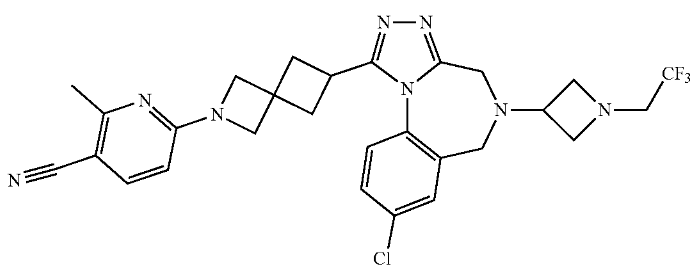 [SMILES: Cc1nc(N2CC3(CC(c4nnc5n4-c4ccc(Cl)cc4CN(C4CN(CC(F)(F)F)C4)C5)C3)C2)ccc1C#N] |
| 360 | 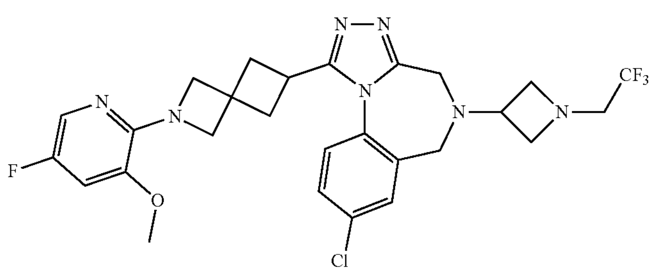 [SMILES: COc1cc(F)cnc1N1CC2(CC(c3nnc4n3-c3ccc(Cl)cc3CN(C3CN(CC(F)(F)F)C3)C4)C2)C1] |
| 361 | 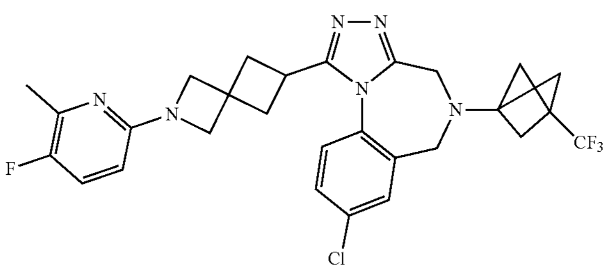 [SMILES: Cc1nc(N2CC3(CC(c4nnc5n4-c4ccc(Cl)cc4CN(C4CC(C)(C(F)(F)F)C4)C5)C3)C2)ccc1F] |

TABLE 1-continued
Representative Compounds
| Cmpd. No. | Structure |
|---|---|
| 362 | 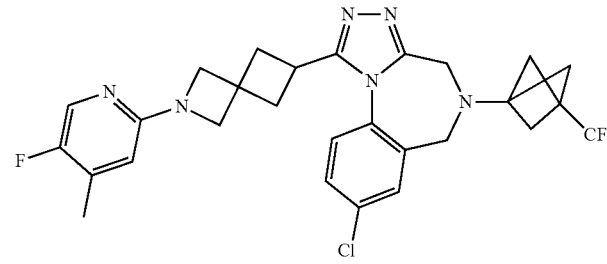 |
| 363 | 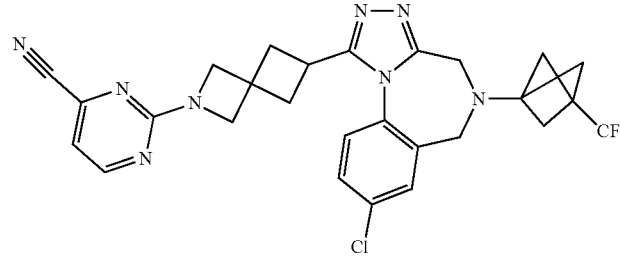 |
| 364 | 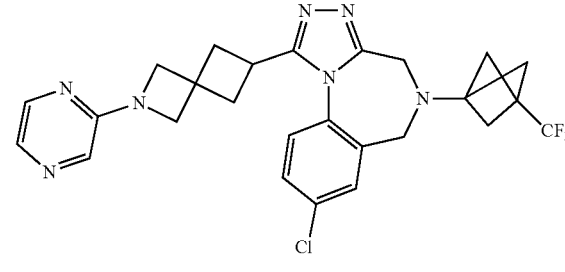 |
| 365 | 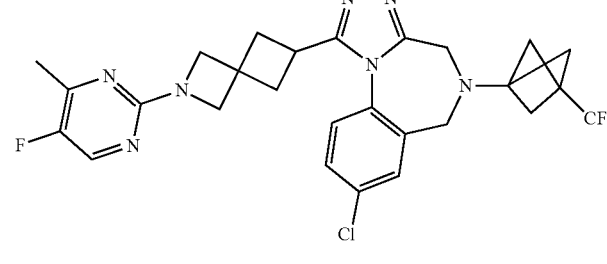 |
| 366 | 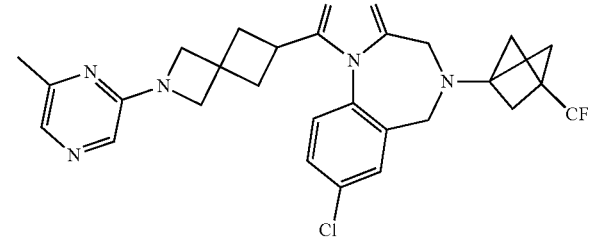 |

TABLE 1-continued

Representative Compounds

| Cmpd. No. | Structure |
|---|---|
| 367 | 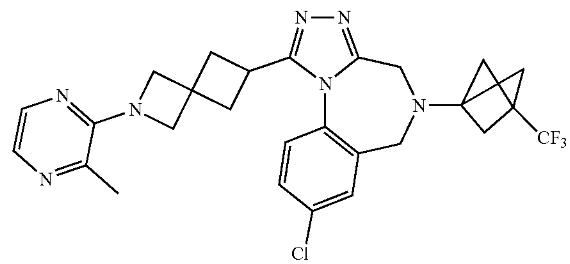 [SMILES: Cc1nccnc1N1CC2(CC(c3nnc4n3-c3ccc(Cl)cc3CN(C3CC(C)(C(F)(F)F)C3)C4)C2)C1] |
| 368 | 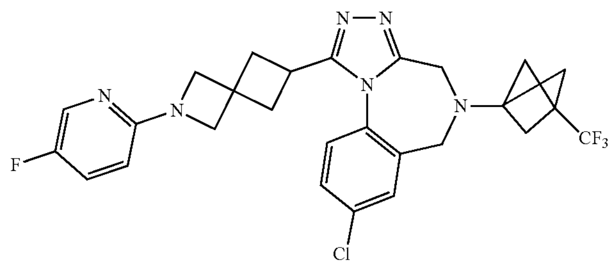 [SMILES: CC1(C(F)(F)F)CC(N2Cc3cc(Cl)ccc3-n3c(nnc3C3CC4(C3)CN(c3ccc(F)cn3)C4)C2)C1] |
| 369 | 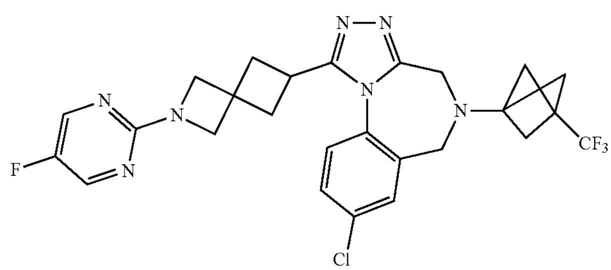 [SMILES: CC1(C(F)(F)F)CC(N2Cc3cc(Cl)ccc3-n3c(nnc3C3CC4(C3)CN(c3ncc(F)cn3)C4)C2)C1] |
| 370 | 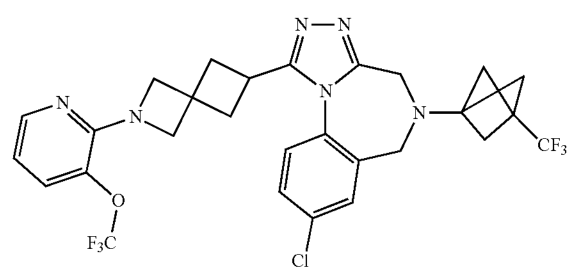 [SMILES: CC1(C(F)(F)F)CC(N2Cc3cc(Cl)ccc3-n3c(nnc3C3CC4(C3)CN(c3ncccc3OC(F)(F)F)C4)C2)C1] |
| 371 | 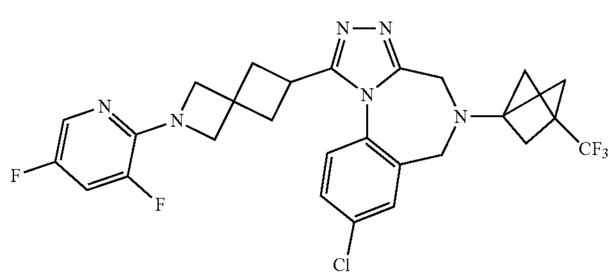 [SMILES: CC1(C(F)(F)F)CC(N2Cc3cc(Cl)ccc3-n3c(nnc3C3CC4(C3)CN(c3ncc(F)cc3F)C4)C2)C1] |

TABLE 1-continued

Representative Compounds

| Cmpd. No. | Structure |
|---|---|
| 372 | 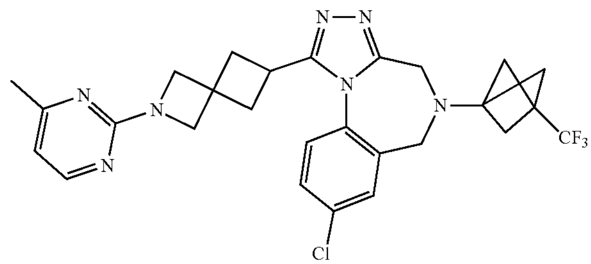 [SMILES: Cc1ccnc(N2CC3(CC(c4nnc5n4-c4ccc(Cl)cc4CN(C4CC(C)(C(F)(F)F)C4)C5)C3)C2)n1] |
| 373 | 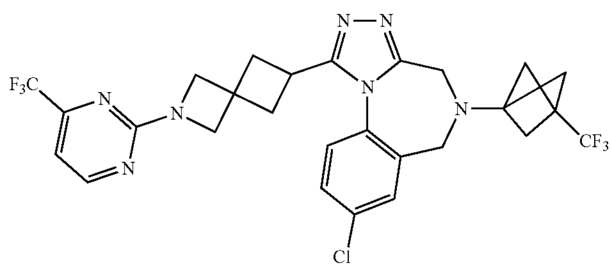 [SMILES: CC1(C(F)(F)F)CC(N2Cc3cc(Cl)ccc3-n3c(nnc3C3CC4(C3)CN(c3nccc(C(F)(F)F)n3)C4)C2)C1] |
| 374 | 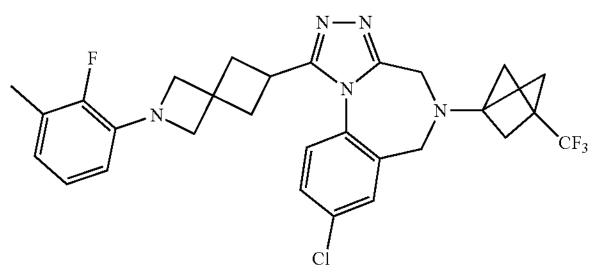 [SMILES: Cc1cccc(N2CC3(CC(c4nnc5n4-c4ccc(Cl)cc4CN(C4CC(C)(C(F)(F)F)C4)C5)C3)C2)c1F] |
| 375 | 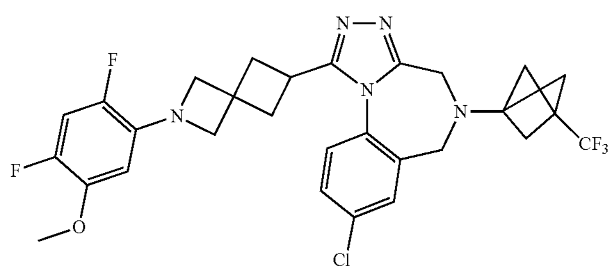 [SMILES: COc1cc(N2CC3(CC(c4nnc5n4-c4ccc(Cl)cc4CN(C4CC(C)(C(F)(F)F)C4)C5)C3)C2)c(F)cc1F] |
| 376 | 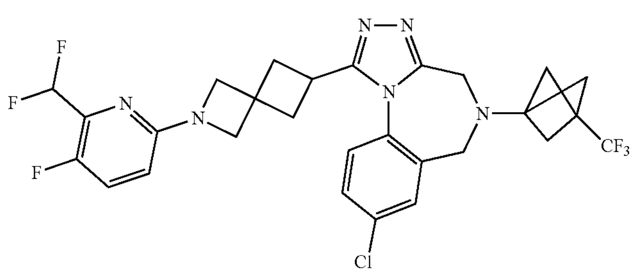 [SMILES: CC1(C(F)(F)F)CC(N2Cc3cc(Cl)ccc3-n3c(nnc3C3CC4(C3)CN(c3ccc(F)c(C(F)F)n3)C4)C2)C1] |

TABLE 1-continued

Representative Compounds

| Cmpd. No. | Structure |
|---|---|
| 377 | 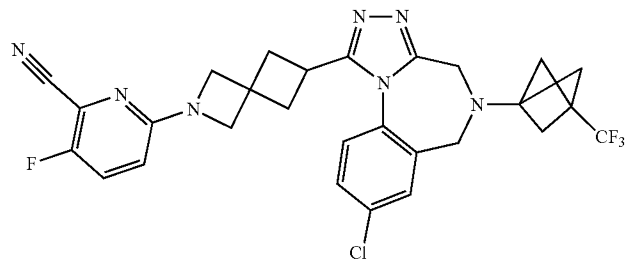 [SMILES: CC1(C(F)(F)F)CC(N2Cc3cc(Cl)ccc3-n3c(nnc3C3CC4(C3)CN(c3ccc(F)c(C#N)n3)C4)C2)C1] |
| 378 | 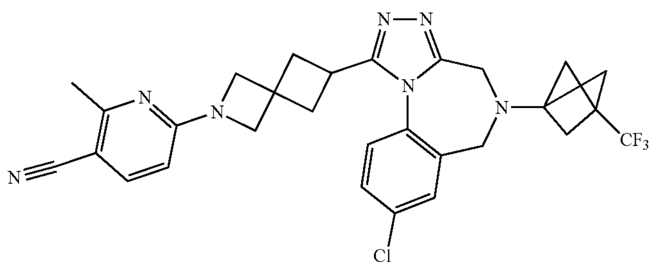 [SMILES: Cc1nc(N2CC3(CC(c4nnc5n4-c4ccc(Cl)cc4CN(C4CC(C)(C(F)(F)F)C4)C5)C3)C2)ccc1C#N] |
| 379 | 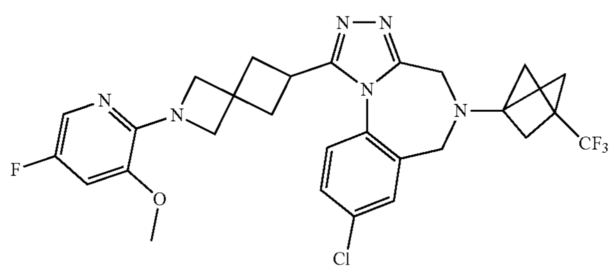 [SMILES: COc1cc(F)cnc1N1CC2(CC(c3nnc4n3-c3ccc(Cl)cc3CN(C3CC(C)(C(F)(F)F)C3)C4)C2)C1] |
| 380 | 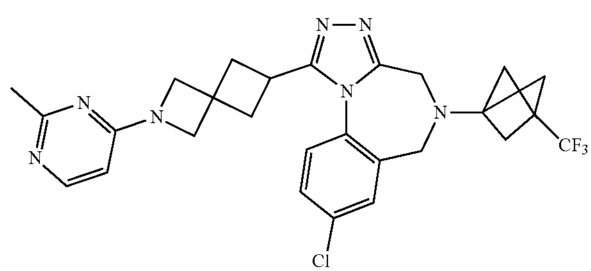 |
| 381 | 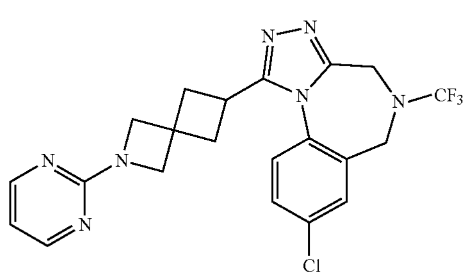 [SMILES: FC(F)(F)N1Cc2cc(Cl)ccc2-n2c(nnc2C2CC3(C2)CN(c2ncccn2)C3)C1] |

TABLE 1-continued
Representative Compounds
| Cmpd. No. | Structure |
|---|---|
| 382 | 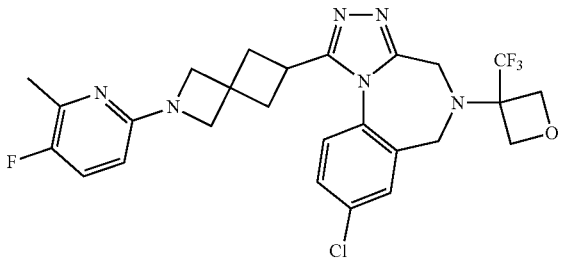 [SMILES: Cc1nc(N2CC3(CC(c4nnc5n4-c4ccc(Cl)cc4CN(C4(C(F)(F)F)COC4)C5)C3)C2)ccc1F] |
| 383 | 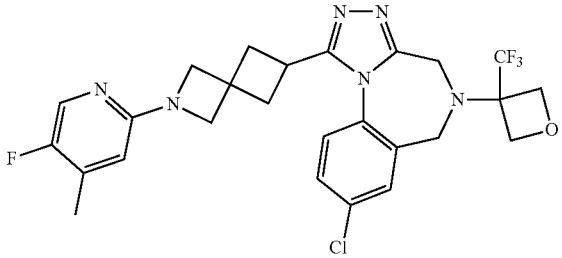 [SMILES: Cc1cc(N2CC3(CC(c4nnc5n4-c4ccc(Cl)cc4CN(C4(C(F)(F)F)COC4)C5)C3)C2)ncc1F] |
| 384 | 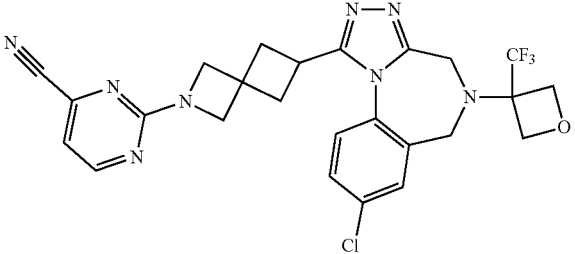 [SMILES: N#Cc1ccnc(N2CC3(CC(c4nnc5n4-c4ccc(Cl)cc4CN(C4(C(F)(F)F)COC4)C5)C3)C2)n1] |
| 385 | 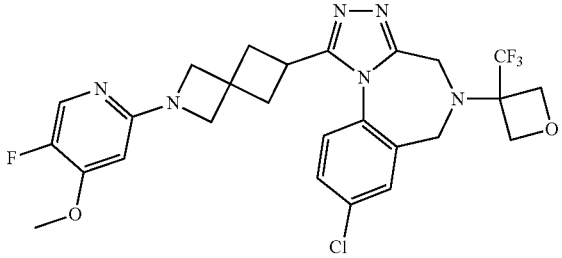 [SMILES: COc1cc(N2CC3(CC(c4nnc5n4-c4ccc(Cl)cc4CN(C4(C(F)(F)F)COC4)C5)C3)C2)ncc1F] |
| 386 | 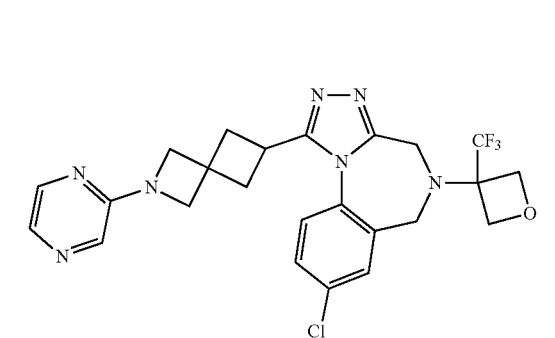 [SMILES: FC(F)(F)C1(N2Cc3cc(Cl)ccc3-n3c(nnc3C3CC4(C3)CN(c3cnccn3)C4)C2)COC1] |

TABLE 1-continued

Representative Compounds

| Cmpd. No. | Structure |
|---|---|
| 387 | 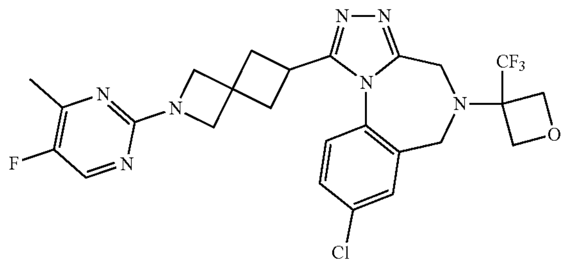 [SMILES: Cc1nc(N2CC3(CC(c4nnc5n4-c4ccc(Cl)cc4CN(C4(C(F)(F)F)COC4)C5)C3)C2)ncc1F] |
| 388 | 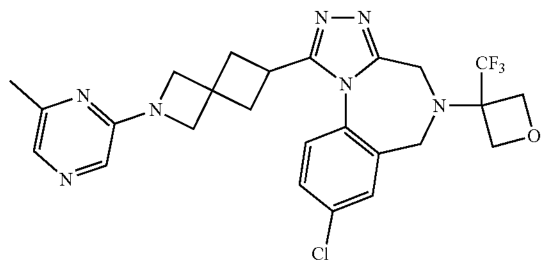 [SMILES: Cc1cncc(N2CC3(CC(c4nnc5n4-c4ccc(Cl)cc4CN(C4(C(F)(F)F)COC4)C5)C3)C2)n1] |
| 389 | 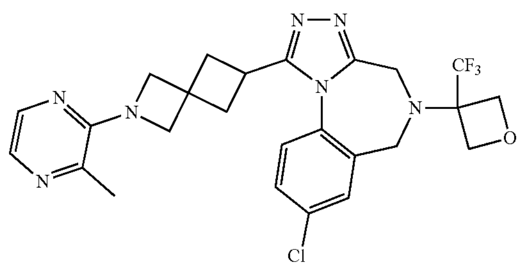 [SMILES: Cc1nccnc1N1CC2(CC(c3nnc4n3-c3ccc(Cl)cc3CN(C3(C(F)(F)F)COC3)C4)C2)C1] |
| 390 | 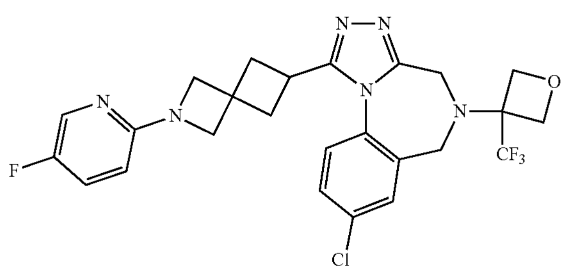 [SMILES: Fc1ccc(N2CC3(CC(c4nnc5n4-c4ccc(Cl)cc4CN(C4(C(F)(F)F)COC4)C5)C3)C2)nc1] |
| 391 | 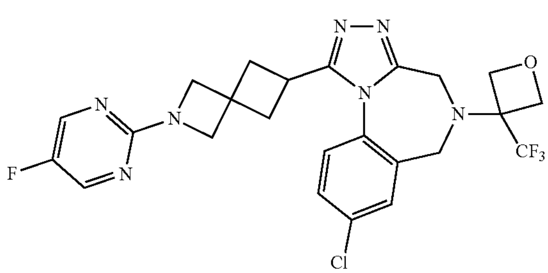 [SMILES: Fc1cnc(N2CC3(CC(c4nnc5n4-c4ccc(Cl)cc4CN(C4(C(F)(F)F)COC4)C5)C3)C2)nc1] |

TABLE 1-continued

Representative Compounds

| Cmpd. No. | Structure |
|---|---|
| 392 | 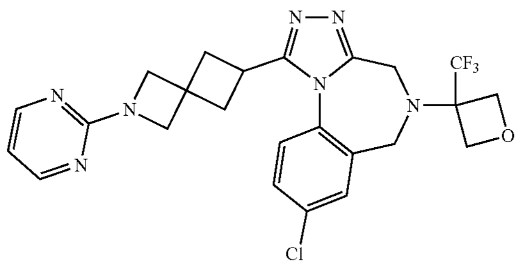 [SMILES: FC(F)(F)C1(N2Cc3cc(Cl)ccc3-n3c(nnc3C3CC4(C3)CN(c3ncccn3)C4)C2)COC1] |
| 393 | 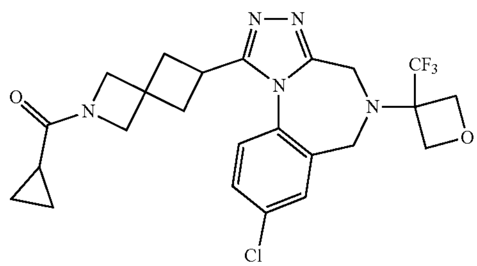 [SMILES: O=C(C1CC1)N1CC2(CC(c3nnc4n3-c3ccc(Cl)cc3CN(C3(C(F)(F)F)COC3)C4)C2)C1] |
| 394 | 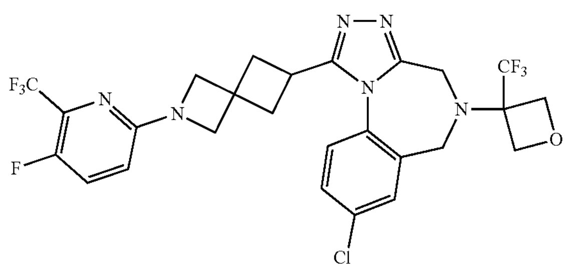 |
| 395 | 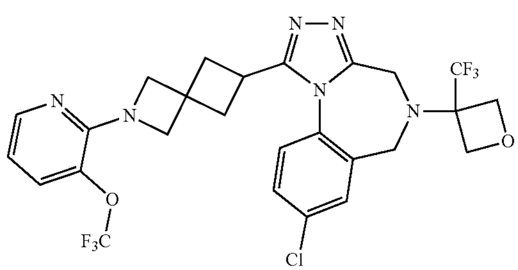 [SMILES: FC(F)(F)Oc1cccnc1N1CC2(CC(c3nnc4n3-c3ccc(Cl)cc3CN(C3(C(F)(F)F)COC3)C4)C2)C1] |
| 396 | 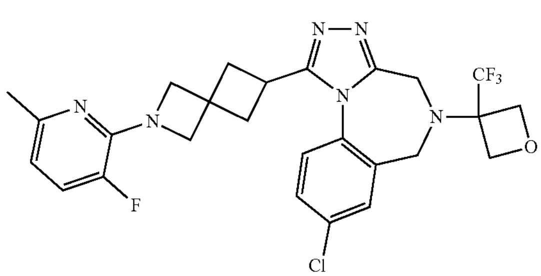 [SMILES: Cc1ccc(F)c(N2CC3(CC(c4nnc5n4-c4ccc(Cl)cc4CN(C4(C(F)(F)F)COC4)C5)C3)C2)n1] |

TABLE 1-continued
Representative Compounds
| Cmpd. No. | Structure |
|---|---|
| 397 | 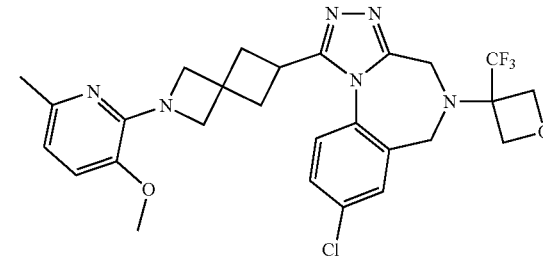 |
| 398 | 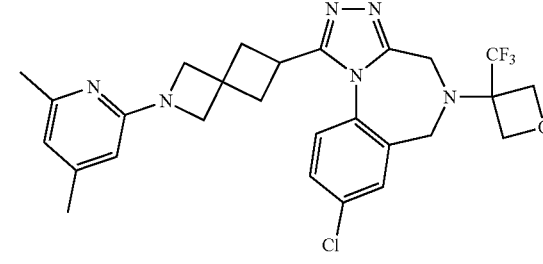 |
| 399 | 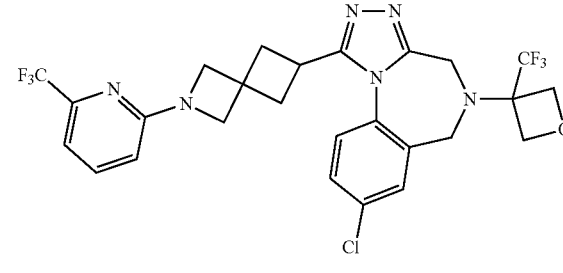 |
| 400 | 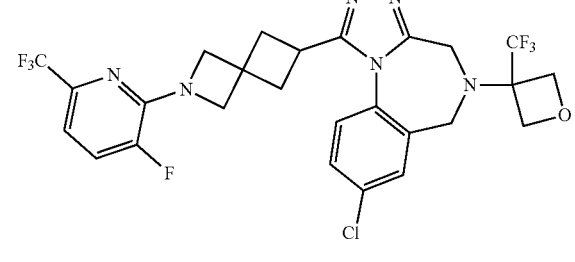 |
| 401 | 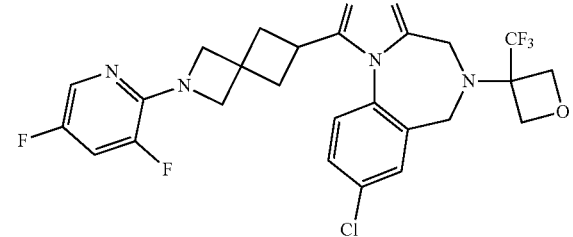 |

TABLE 1-continued

Representative Compounds

| Cmpd. No. | Structure |
|---|---|
| 402 | 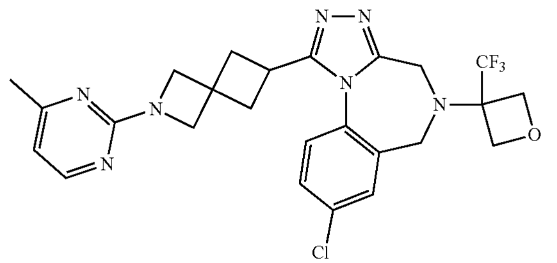 [SMILES: Cc1ccnc(N2CC3(CC(c4nnc5n4-c4ccc(Cl)cc4CN(C4(C(F)(F)F)COC4)C5)C3)C2)n1] |
| 403 | 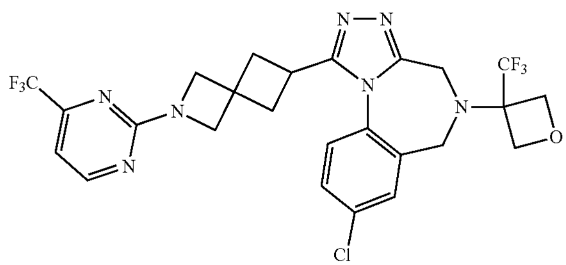 [SMILES: FC(F)(F)c1ccnc(N2CC3(CC(c4nnc5n4-c4ccc(Cl)cc4CN(C4(C(F)(F)F)COC4)C5)C3)C2)n1] |
| 404 | 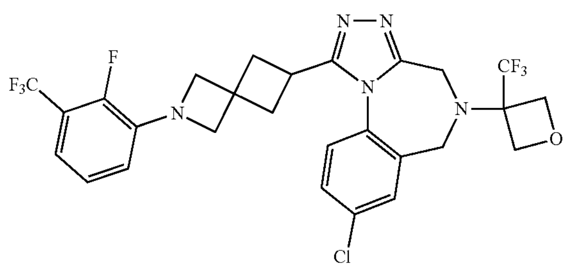 [SMILES: Fc1c(N2CC3(CC(c4nnc5n4-c4ccc(Cl)cc4CN(C4(C(F)(F)F)COC4)C5)C3)C2)cccc1C(F)(F)F] |
| 405 | 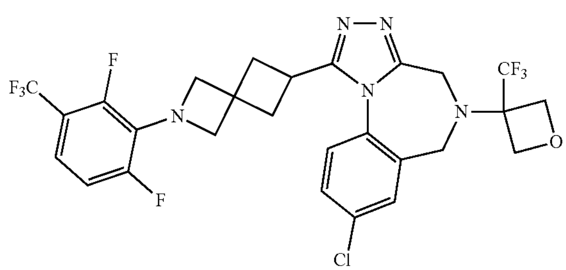 [SMILES: Fc1ccc(C(F)(F)F)c(F)c1N1CC2(CC(c3nnc4n3-c3ccc(Cl)cc3CN(C3(C(F)(F)F)COC3)C4)C2)C1] |
| 406 | 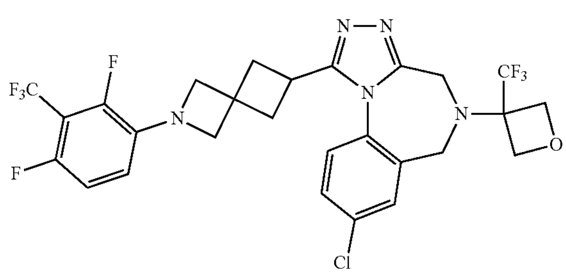 [SMILES: Fc1ccc(N2CC3(CC(c4nnc5n4-c4ccc(Cl)cc4CN(C4(C(F)(F)F)COC4)C5)C3)C2)c(F)c1C(F)(F)F] |

TABLE 1-continued
Representative Compounds
| Cmpd. No. | Structure |
|---|---|
| 407 | 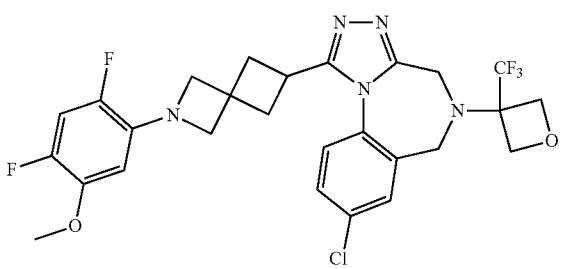 [SMILES: COc1cc(N2CC3(CC(c4nnc5n4-c4ccc(Cl)cc4CN(C4(C(F)(F)F)COC4)C5)C3)C2)c(F)cc1F] |
| 408 | 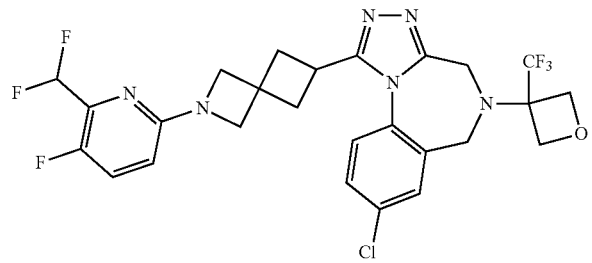 [SMILES: Fc1ccc(N2CC3(CC(c4nnc5n4-c4ccc(Cl)cc4CN(C4(C(F)(F)F)COC4)C5)C3)C2)nc1C(F)F] |
| 409 | 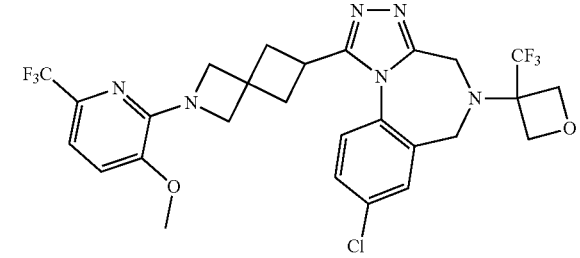 [SMILES: COc1ccc(C(F)(F)F)nc1N1CC2(CC(c3nnc4n3-c3ccc(Cl)cc3CN(C3(C(F)(F)F)COC3)C4)C2)C1] |
| 410 | 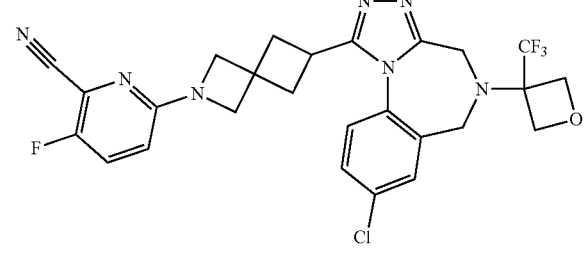 |
| 411 | 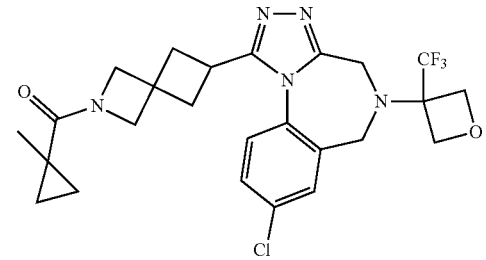 [SMILES: CC1(C(=O)N2CC3(CC(c4nnc5n4-c4ccc(Cl)cc4CN(C4(C(F)(F)F)COC4)C5)C3)C2)CC1] |

TABLE 1-continued

Representative Compounds

| Cmpd. No. | Structure |
|---|---|
| 412 | 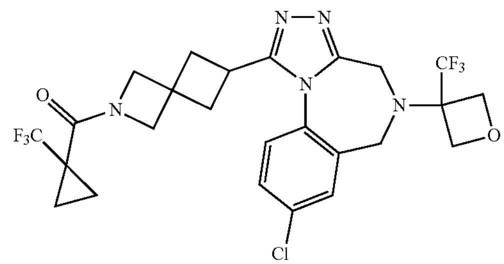 [SMILES: O=C(N1CC2(CC(c3nnc4n3-c3ccc(Cl)cc3CN(C3(C(F)(F)F)COC3)C4)C2)C1)C1(C(F)(F)F)CC1] |
| 413 | 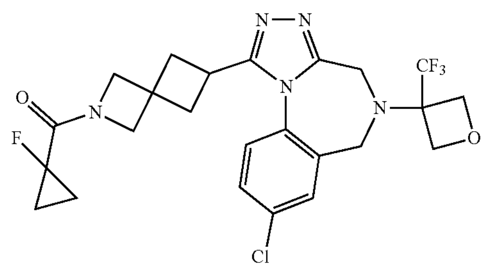 [SMILES: O=C(N1CC2(CC(c3nnc4n3-c3ccc(Cl)cc3CN(C3(C(F)(F)F)COC3)C4)C2)C1)C1(F)CC1] |
| 414 | 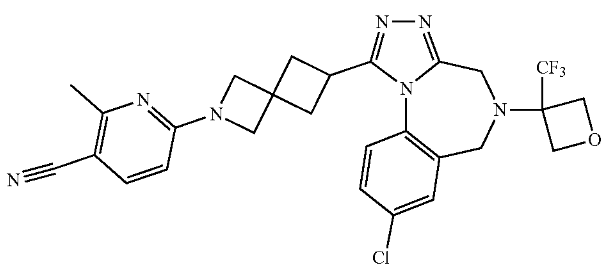 [SMILES: Cc1nc(N2CC3(CC(c4nnc5n4-c4ccc(Cl)cc4CN(C4(C(F)(F)F)COC4)C5)C3)C2)ccc1C#N] |
| 415 | 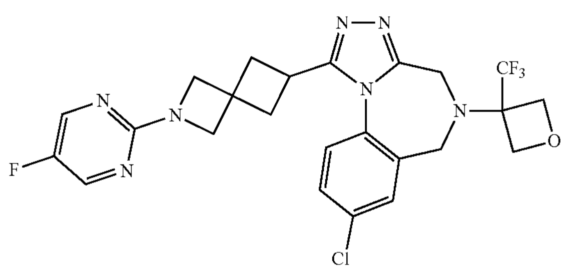 |
| 416 | 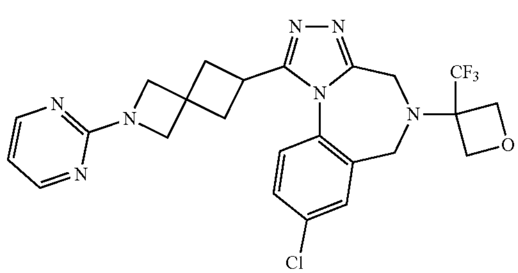 [SMILES: FC(F)(F)C1(N2Cc3cc(Cl)ccc3-n3c(nnc3C3CC4(C3)CN(c3ncccn3)C4)C2)COC1] |

TABLE 1-continued

Representative Compounds

| Cmpd. No. | Structure |
|---|---|
| 417 | 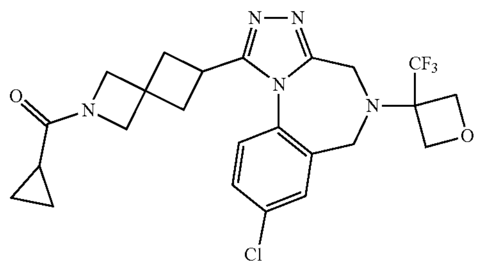 [SMILES: O=C(C1CC1)N1CC2(CC(c3nnc4n3-c3ccc(Cl)cc3CN(C3(C(F)(F)F)COC3)C4)C2)C1] |
| 418 | 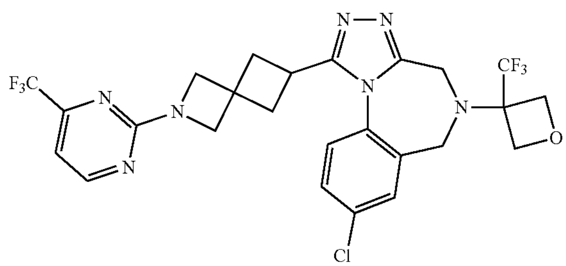 [SMILES: FC(F)(F)c1ccnc(N2CC3(CC(c4nnc5n4-c4ccc(Cl)cc4CN(C4(C(F)(F)F)COC4)C5)C3)C2)n1] |
| 419 | 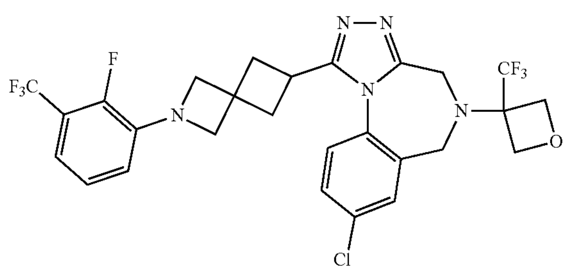 [SMILES: Fc1c(N2CC3(CC(c4nnc5n4-c4ccc(Cl)cc4CN(C4(C(F)(F)F)COC4)C5)C3)C2)cccc1C(F)(F)F] |
| 420 | 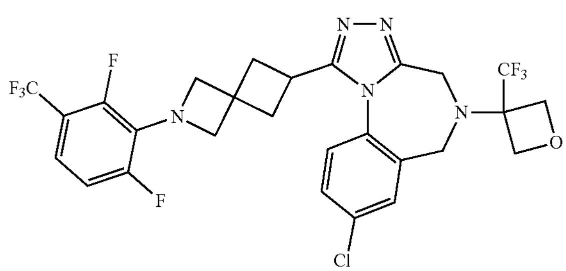 [SMILES: Fc1ccc(C(F)(F)F)c(F)c1N1CC2(CC(c3nnc4n3-c3ccc(Cl)cc3CN(C3(C(F)(F)F)COC3)C4)C2)C1] |
| 421 | 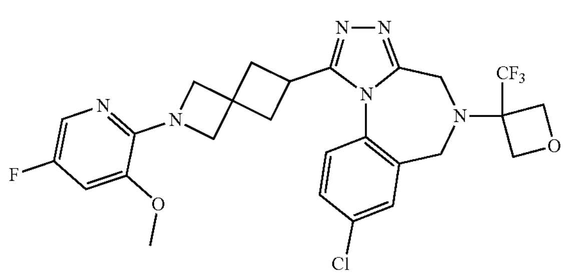 [SMILES: COc1cc(F)cnc1N1CC2(CC(c3nnc4n3-c3ccc(Cl)cc3CN(C3(C(F)(F)F)COC3)C4)C2)C1] |

TABLE 1-continued

Representative Compounds

| Cmpd. No. | Structure |
|---|---|
| 422 | 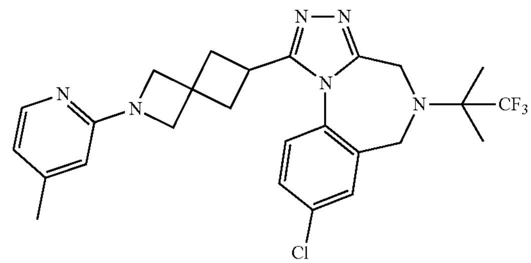 [SMILES: Cc1ccnc(N2CC3(CC(c4nnc5n4-c4ccc(Cl)cc4CN(C(C)(C)C(F)(F)F)C5)C3)C2)c1] |
| 423 | 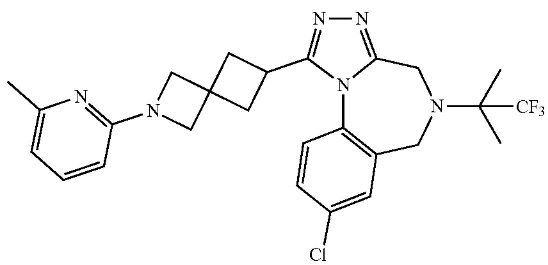 [SMILES: Cc1cccc(N2CC3(CC(c4nnc5n4-c4ccc(Cl)cc4CN(C(C)(C)C(F)(F)F)C5)C3)C2)n1] |
| 424 | 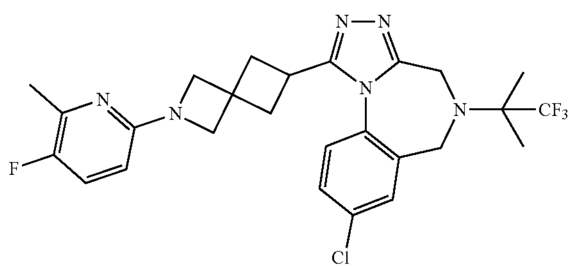 [SMILES: Cc1nc(N2CC3(CC(c4nnc5n4-c4ccc(Cl)cc4CN(C(C)(C)C(F)(F)F)C5)C3)C2)ccc1F] |
| 425 | 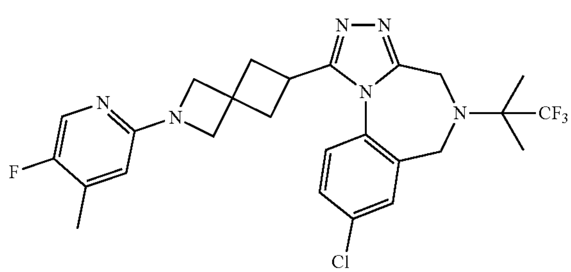 [SMILES: Cc1cc(N2CC3(CC(c4nnc5n4-c4ccc(Cl)cc4CN(C(C)(C)C(F)(F)F)C5)C3)C2)ncc1F] |
| 426 | 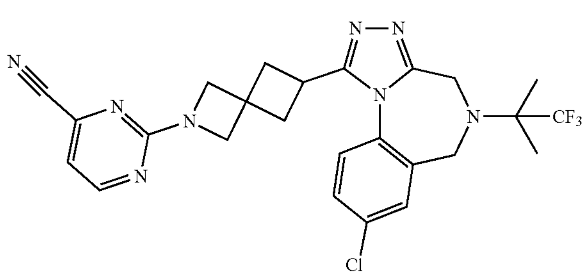 [SMILES: CC(C)(N1Cc2cc(Cl)ccc2-n2c(nnc2C2CC3(C2)CN(c2nccc(C#N)n2)C3)C1)C(F)(F)F] |

TABLE 1-continued
Representative Compounds
| Cmpd. No. | Structure |
|---|---|
| 427 | 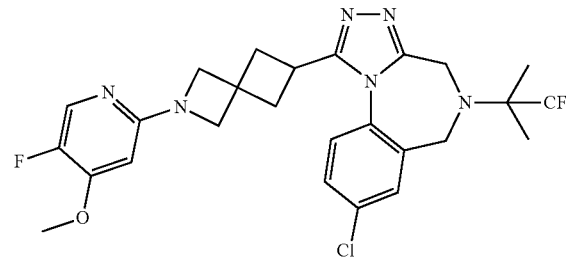 |
| 428 | 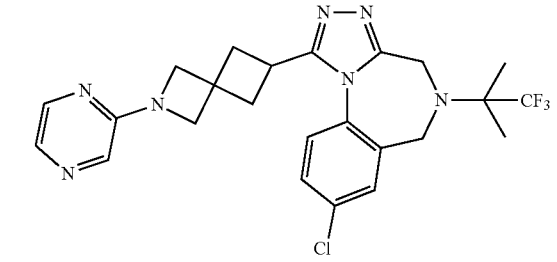 [SMILES: CC(C)(N1Cc2cc(Cl)ccc2-n2c(nnc2C2CC3(C2)CN(c2cnccn2)C3)C1)C(F)(F)F] |
| 429 | 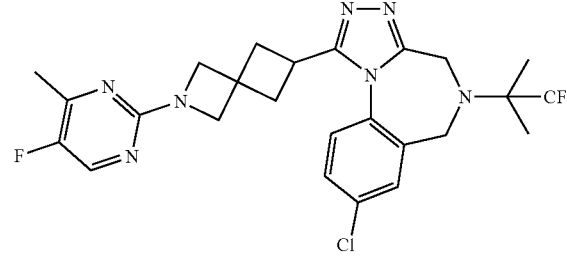 |
| 430 | 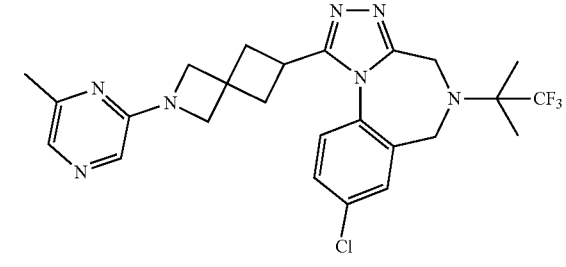 [SMILES: Cc1cncc(N2CC3(CC(c4nnc5n4-c4ccc(Cl)cc4CN(C(C)(C)C(F)(F)F)C5)C3)C2)n1] |
| 431 | 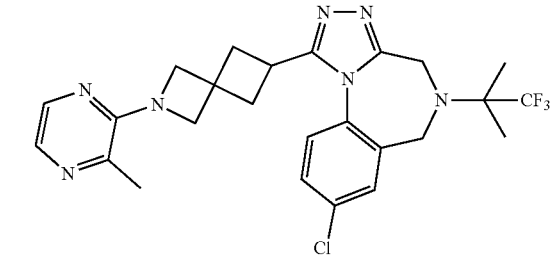 [SMILES: Cc1nccnc1N1CC2(CC(c3nnc4n3-c3ccc(Cl)cc3CN(C(C)(C)C(F)(F)F)C4)C2)C1] |

TABLE 1-continued

Representative Compounds

| Cmpd. No. | Structure |
|---|---|
| 432 | 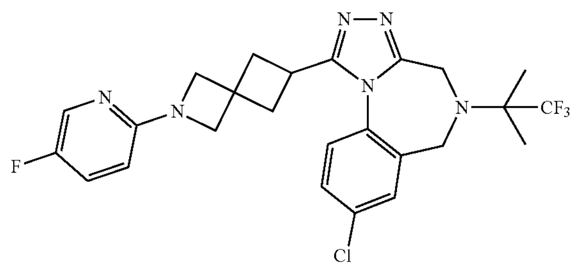 [SMILES: CC(C)(N1Cc2cc(Cl)ccc2-n2c(nnc2C2CC3(C2)CN(c2ccc(F)cn2)C3)C1)C(F)(F)F] |
| 433 | 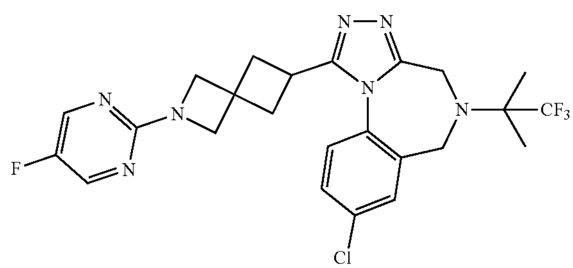 [SMILES: CC(C)(N1Cc2cc(Cl)ccc2-n2c(nnc2C2CC3(C2)CN(c2ncc(F)cn2)C3)C1)C(F)(F)F] |
| 434 | 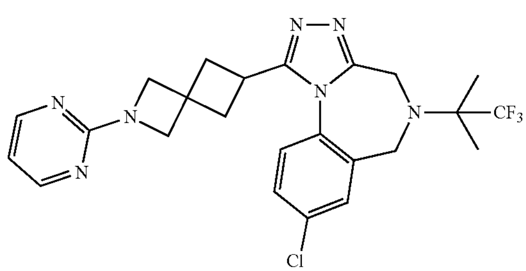 [SMILES: CC(C)(N1Cc2cc(Cl)ccc2-n2c(nnc2C2CC3(C2)CN(c2ncccn2)C3)C1)C(F)(F)F] |
| 435 | 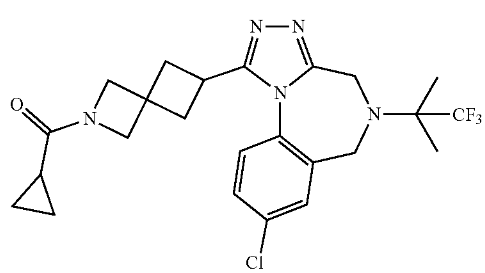 [SMILES: CC(C)(N1Cc2cc(Cl)ccc2-n2c(nnc2C2CC3(C2)CN(C(=O)C2CC2)C3)C1)C(F)(F)F] |
| 436 | 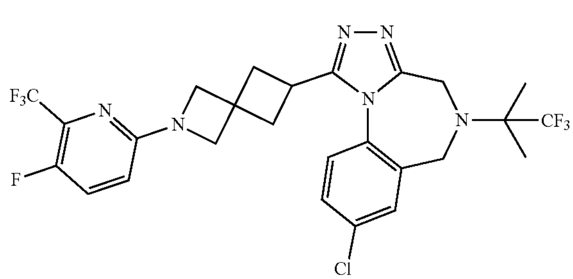 |

TABLE 1-continued

Representative Compounds

| Cmpd. No. | Structure |
|---|---|
| 437 | 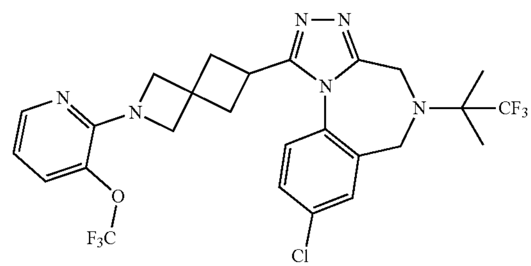 [SMILES: CC(C)(N1Cc2cc(Cl)ccc2-n2c(nnc2C2CC3(C2)CN(c2ncccc2OC(F)(F)F)C3)C1)C(F)(F)F] |
| 438 | 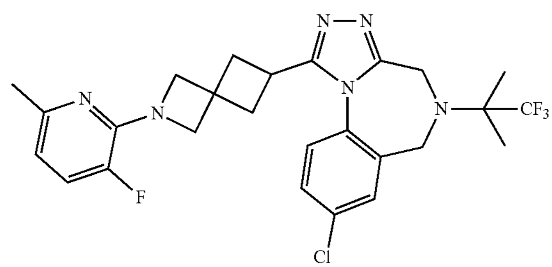 [SMILES: Cc1ccc(F)c(N2CC3(CC(c4nnc5n4-c4ccc(Cl)cc4CN(C(C)(C)C(F)(F)F)C5)C3)C2)n1] |
| 439 | 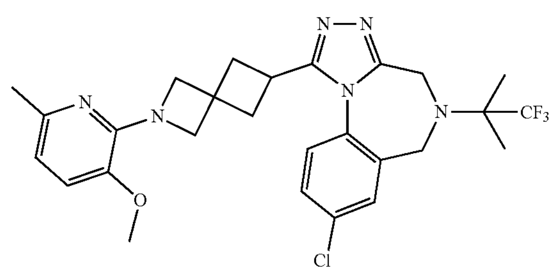 [SMILES: COc1ccc(C)nc1N1CC2(CC(c3nnc4n3-c3ccc(Cl)cc3CN(C(C)(C)C(F)(F)F)C4)C2)C1] |
| 440 | 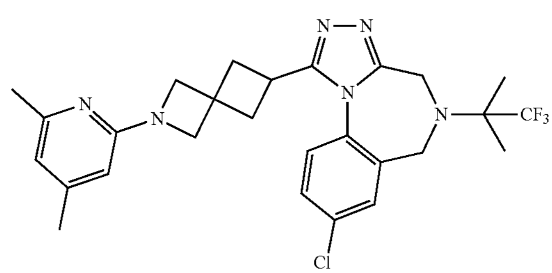 [SMILES: Cc1cc(C)nc(N2CC3(CC(c4nnc5n4-c4ccc(Cl)cc4CN(C(C)(C)C(F)(F)F)C5)C3)C2)c1] |
| 441 | 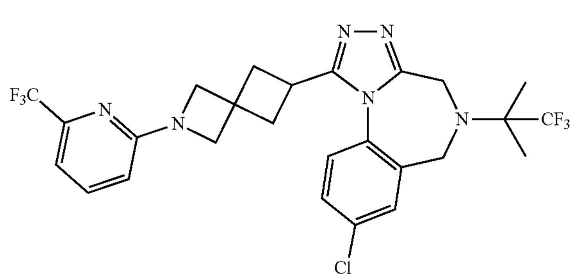 [SMILES: CC(C)(N1Cc2cc(Cl)ccc2-n2c(nnc2C2CC3(C2)CN(c2cccc(C(F)(F)F)n2)C3)C1)C(F)(F)F] |

TABLE 1-continued

Representative Compounds

| Cmpd. No. | Structure |
|---|---|
| 442 | 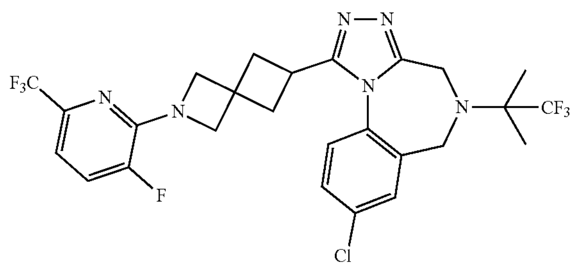 [SMILES: CC(C)(N1Cc2cc(Cl)ccc2-n2c(nnc2C2CC3(C2)CN(c2nc(C(F)(F)F)ccc2F)C3)C1)C(F)(F)F] |
| 443 | 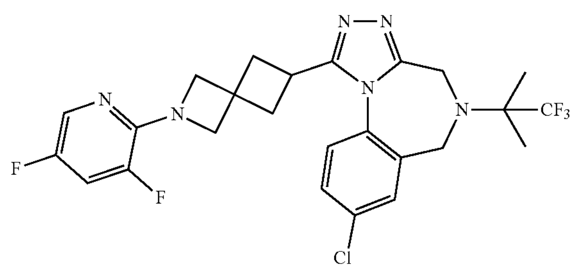 [SMILES: CC(C)(N1Cc2cc(Cl)ccc2-n2c(nnc2C2CC3(C2)CN(c2ncc(F)cc2F)C3)C1)C(F)(F)F] |
| 444 | 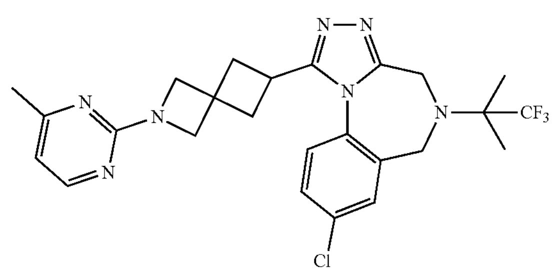 |
| 445 | 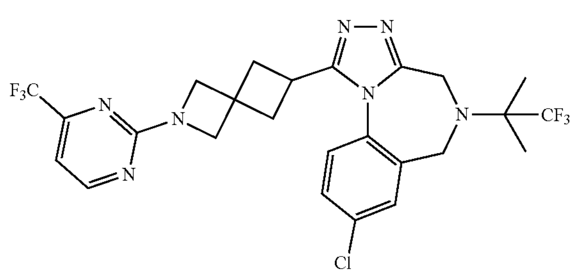 [SMILES: CC(C)(N1Cc2cc(Cl)ccc2-n2c(nnc2C2CC3(C2)CN(c2nccc(C(F)(F)F)n2)C3)C1)C(F)(F)F] |
| 446 | 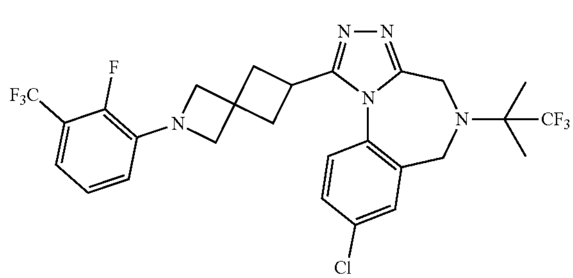 [SMILES: CC(C)(N1Cc2cc(Cl)ccc2-n2c(nnc2C2CC3(C2)CN(c2cccc(C(F)(F)F)c2F)C3)C1)C(F)(F)F] |

TABLE 1-continued

Representative Compounds

| Cmpd. No. | Structure |
|---|---|
| 447 | 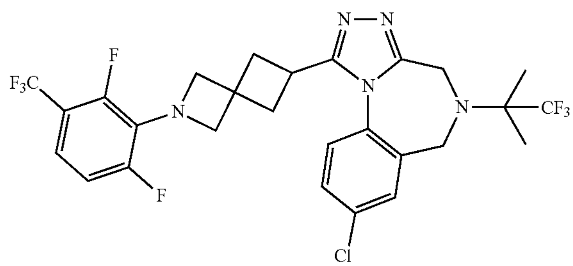 [SMILES: CC(C)(N1Cc2cc(Cl)ccc2-n2c(nnc2C2CC3(C2)CN(c2c(F)ccc(C(F)(F)F)c2F)C3)C1)C(F)(F)F] |
| 448 | 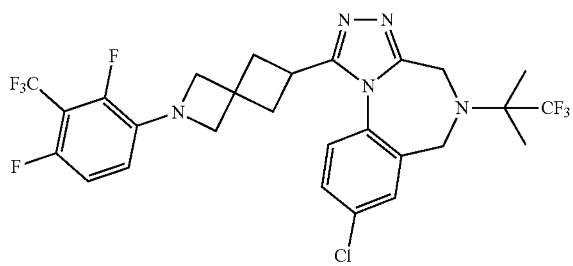 [SMILES: CC(C)(N1Cc2cc(Cl)ccc2-n2c(nnc2C2CC3(C2)CN(c2ccc(F)c(C(F)(F)F)c2F)C3)C1)C(F)(F)F] |
| 449 | 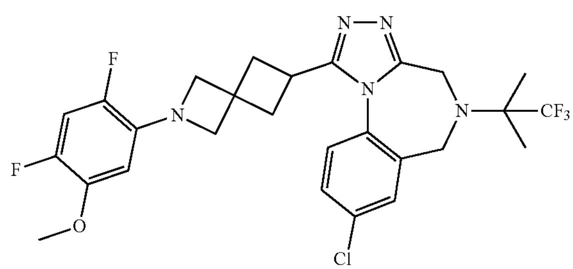 [SMILES: COc1cc(N2CC3(CC(c4nnc5n4-c4ccc(Cl)cc4CN(C(C)(C)C(F)(F)F)C5)C3)C2)c(F)cc1F] |
| 450 | 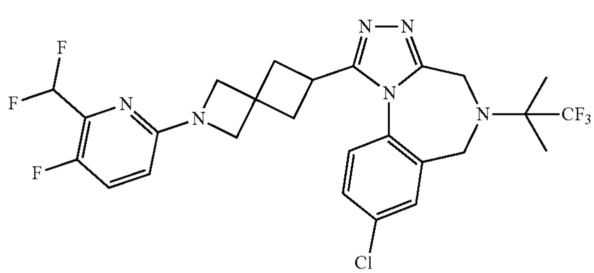 [SMILES: CC(C)(N1Cc2cc(Cl)ccc2-n2c(nnc2C2CC3(C2)CN(c2ccc(F)c(C(F)F)n2)C3)C1)C(F)(F)F] |
| 451 | 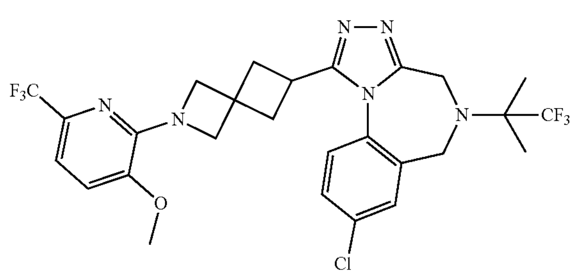 [SMILES: COc1ccc(C(F)(F)F)nc1N1CC2(CC(c3nnc4n3-c3ccc(Cl)cc3CN(C(C)(C)C(F)(F)F)C4)C2)C1] |

TABLE 1-continued

Representative Compounds

| Cmpd. No. | Structure |
|---|---|
| 452 | 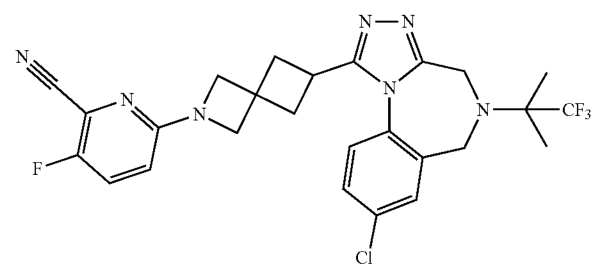 [SMILES: CC(C)(N1Cc2cc(Cl)ccc2-n2c(nnc2C2CC3(C2)CN(c2ccc(F)c(C#N)n2)C3)C1)C(F)(F)F] |
| 453 | 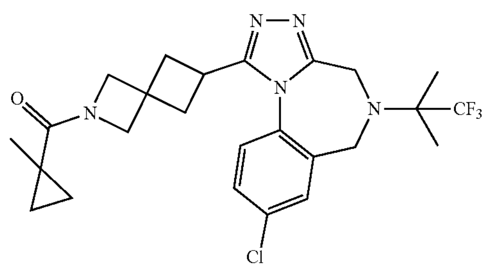 [SMILES: CC1(C(=O)N2CC3(CC(c4nnc5n4-c4ccc(Cl)cc4CN(C(C)(C)C(F)(F)F)C5)C3)C2)CC1] |
| 454 | 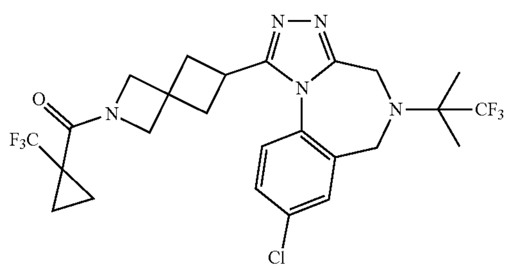 [SMILES: CC(C)(N1Cc2cc(Cl)ccc2-n2c(nnc2C2CC3(C2)CN(C(=O)C2(C(F)(F)F)CC2)C3)C1)C(F)(F)F] |
| 455 | 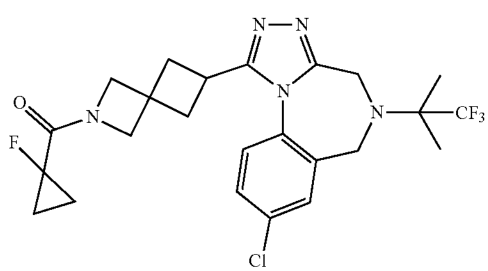 [SMILES: CC(C)(N1Cc2cc(Cl)ccc2-n2c(nnc2C2CC3(C2)CN(C(=O)C2(F)CC2)C3)C1)C(F)(F)F] |
| 456 | 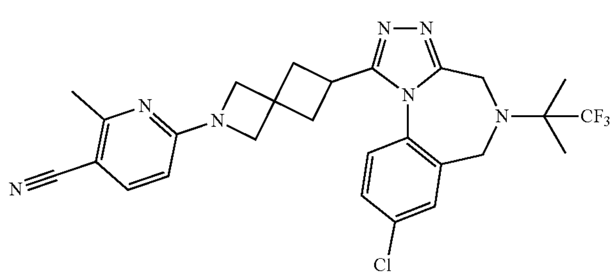 [SMILES: Cc1nc(N2CC3(CC(c4nnc5n4-c4ccc(Cl)cc4CN(C(C)(C)C(F)(F)F)C5)C3)C2)ccc1C#N] |

TABLE 1-continued

Representative Compounds

| Cmpd. No. | Structure |
|---|---|
| 457 | 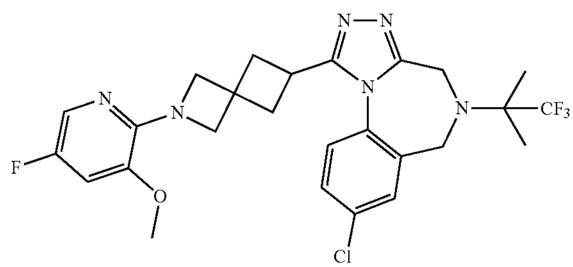 [SMILES: COc1cc(F)cnc1N1CC2(CC(c3nnc4n3-c3ccc(Cl)cc3CN(C(C)(C)C(F)(F)F)C4)C2)C1] |
| 458 | 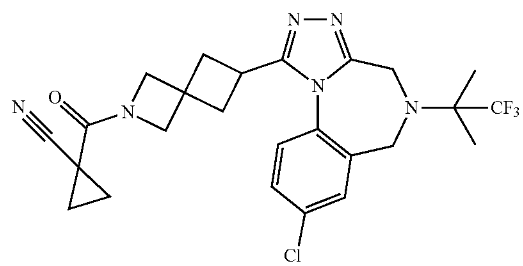 [SMILES: CC(C)(N1Cc2cc(Cl)ccc2-n2c(nnc2C2CC3(C2)CN(C(=O)C2(C#N)CC2)C3)C1)C(F)(F)F] |
| 459 | 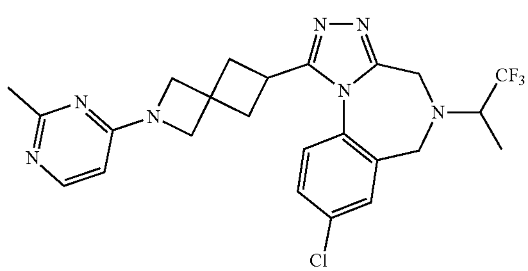 [SMILES: Cc1nccc(N2CC3(CC(c4nnc5n4-c4ccc(Cl)cc4CN(C(C)C(F)(F)F)C5)C3)C2)n1] |
| 460 | 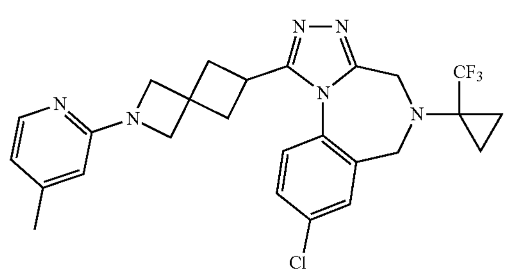 [SMILES: Cc1ccnc(N2CC3(CC(c4nnc5n4-c4ccc(Cl)cc4CN(C4(C(F)(F)F)CC4)C5)C3)C2)c1] |
| 461 | 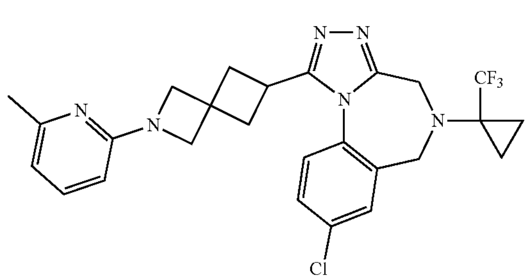 [SMILES: Cc1cccc(N2CC3(CC(c4nnc5n4-c4ccc(Cl)cc4CN(C4(C(F)(F)F)CC4)C5)C3)C2)n1] |

TABLE 1-continued
Representative Compounds
| Cmpd. No. | Structure |
|---|---|
| 462 | 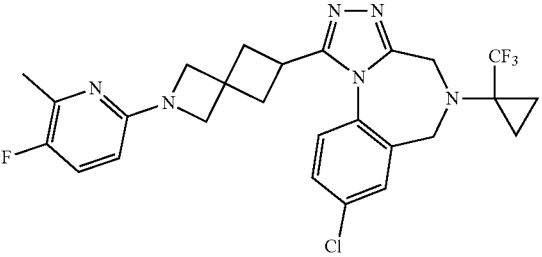 [SMILES: Cc1nc(N2CC3(CC(c4nnc5n4-c4ccc(Cl)cc4CN(C4(C(F)(F)F)CC4)C5)C3)C2)ccc1F] |
| 463 | 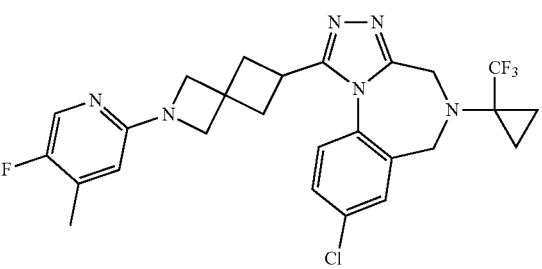 [SMILES: Cc1cc(N2CC3(CC(c4nnc5n4-c4ccc(Cl)cc4CN(C4(C(F)(F)F)CC4)C5)C3)C2)ncc1F] |
| 464 | 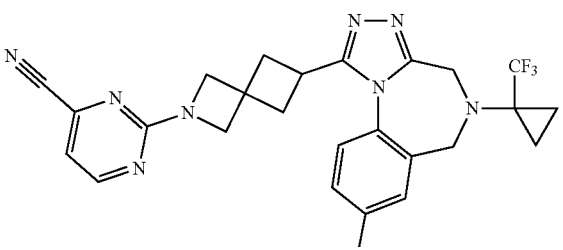 |
| 465 | 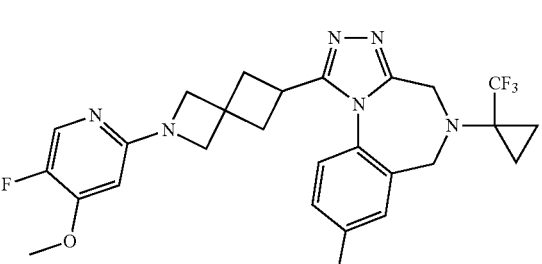 |
| 466 | 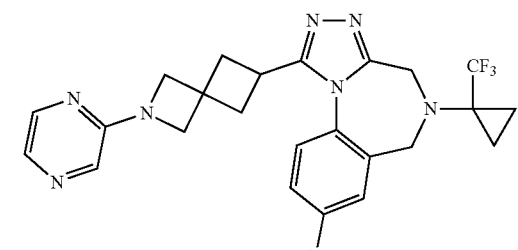 |

TABLE 1-continued

Representative Compounds

| Cmpd. No. | Structure |
|---|---|
| 467 | 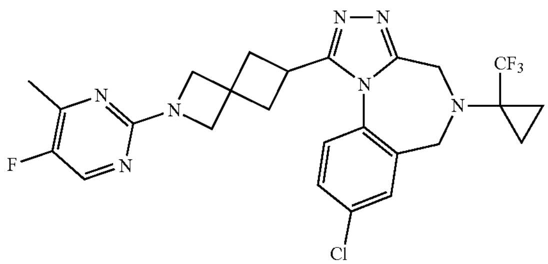 [SMILES: Cc1nc(N2CC3(CC(c4nnc5n4-c4ccc(Cl)cc4CN(C4(C(F)(F)F)CC4)C5)C3)C2)ncc1F] |
| 468 | 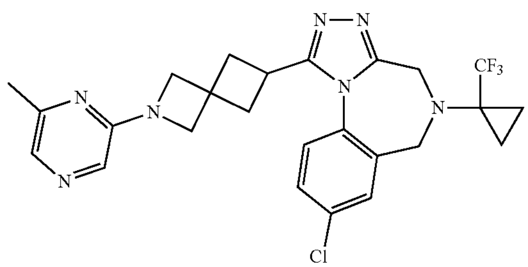 |
| 469 | 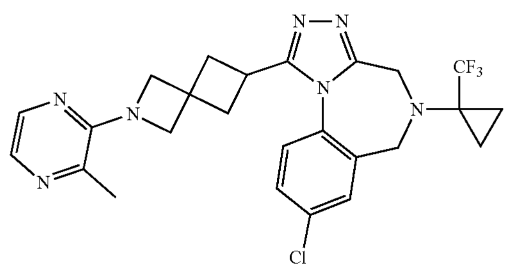 [SMILES: Cc1nccnc1N1CC2(CC(c3nnc4n3-c3ccc(Cl)cc3CN(C3(C(F)(F)F)CC3)C4)C2)C1] |
| 470 | 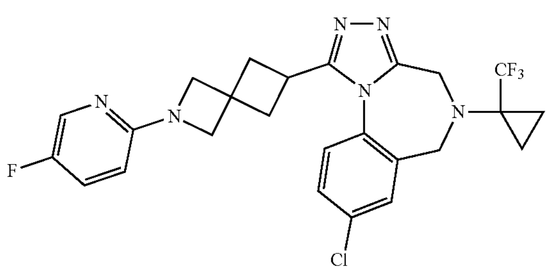 [SMILES: Fc1ccc(N2CC3(CC(c4nnc5n4-c4ccc(Cl)cc4CN(C4(C(F)(F)F)CC4)C5)C3)C2)nc1] |
| 471 | 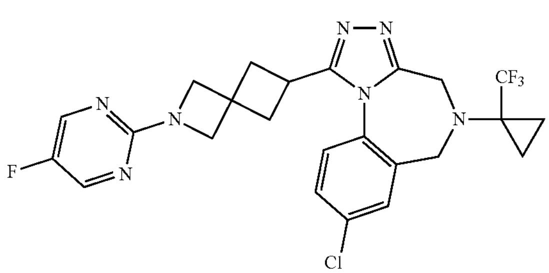 [SMILES: Fc1cnc(N2CC3(CC(c4nnc5n4-c4ccc(Cl)cc4CN(C4(C(F)(F)F)CC4)C5)C3)C2)nc1] |

TABLE 1-continued
Representative Compounds
| Cmpd. No. | Structure |
|---|---|
| 472 | 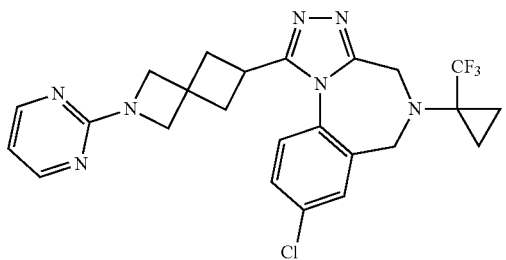 [SMILES: FC(F)(F)C1(N2Cc3cc(Cl)ccc3-n3c(nnc3C3CC4(C3)CN(c3ncccn3)C4)C2)CC1] |
| 473 | 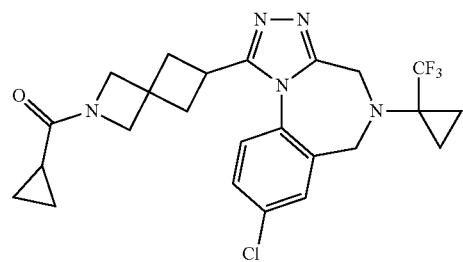 [SMILES: O=C(C1CC1)N1CC2(CC(c3nnc4n3-c3ccc(Cl)cc3CN(C3(C(F)(F)F)CC3)C4)C2)C1] |
| 474 | 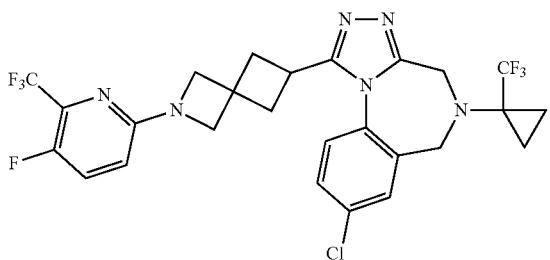 [SMILES: Fc1ccc(N2CC3(CC(c4nnc5n4-c4ccc(Cl)cc4CN(C4(C(F)(F)F)CC4)C5)C3)C2)nc1C(F)(F)F] |
| 475 | 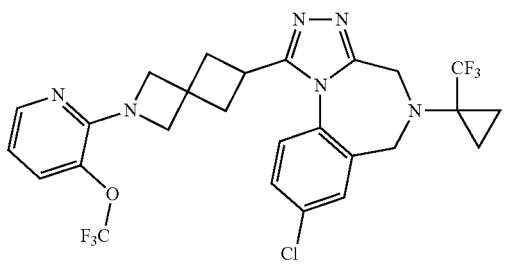 [SMILES: FC(F)(F)Oc1cccnc1N1CC2(CC(c3nnc4n3-c3ccc(Cl)cc3CN(C3(C(F)(F)F)CC3)C4)C2)C1] |
| 476 | 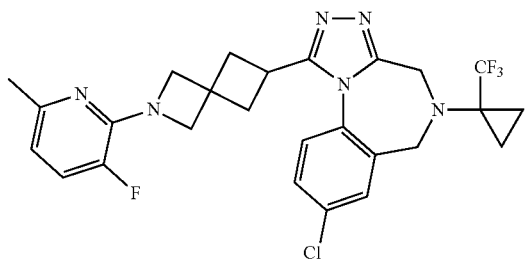 [SMILES: Cc1ccc(F)c(N2CC3(CC(c4nnc5n4-c4ccc(Cl)cc4CN(C4(C(F)(F)F)CC4)C5)C3)C2)n1] |

TABLE 1-continued

Representative Compounds

| Cmpd. No. | Structure |
|---|---|
| 477 | 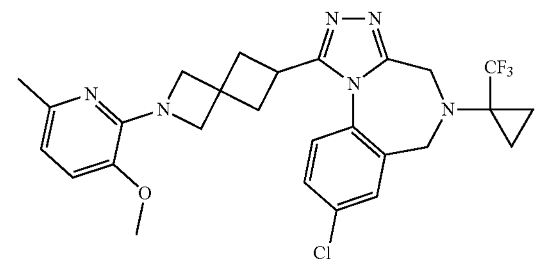 [SMILES: COc1ccc(C)nc1N1CC2(CC(c3nnc4n3-c3ccc(Cl)cc3CN(C3(C(F)(F)F)CC3)C4)C2)C1] |
| 478 | 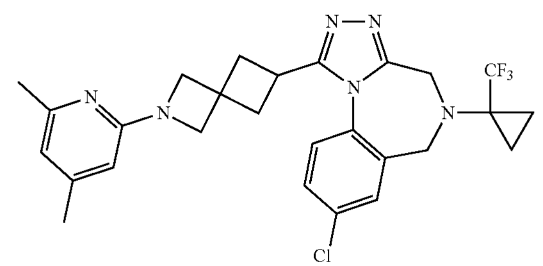 [SMILES: Cc1cc(C)nc(N2CC3(CC(c4nnc5n4-c4ccc(Cl)cc4CN(C4(C(F)(F)F)CC4)C5)C3)C2)c1] |
| 479 | 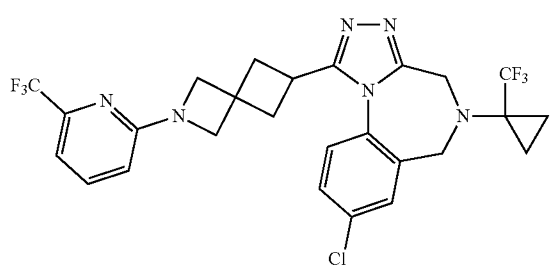 [SMILES: FC(F)(F)c1cccc(N2CC3(CC(c4nnc5n4-c4ccc(Cl)cc4CN(C4(C(F)(F)F)CC4)C5)C3)C2)n1] |
| 480 | 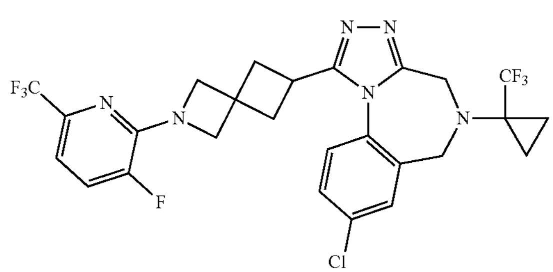 [SMILES: Fc1ccc(C(F)(F)F)nc1N1CC2(CC(c3nnc4n3-c3ccc(Cl)cc3CN(C3(C(F)(F)F)CC3)C4)C2)C1] |
| 481 | 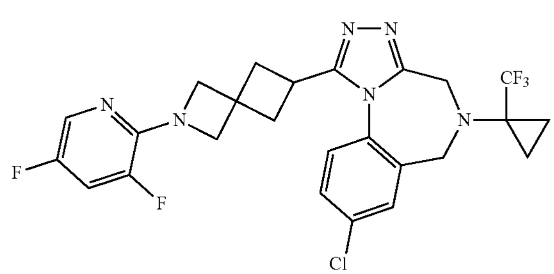 [SMILES: Fc1cnc(N2CC3(CC(c4nnc5n4-c4ccc(Cl)cc4CN(C4(C(F)(F)F)CC4)C5)C3)C2)c(F)c1] |

TABLE 1-continued

Representative Compounds

| Cmpd. No. | Structure |
|---|---|
| 482 | 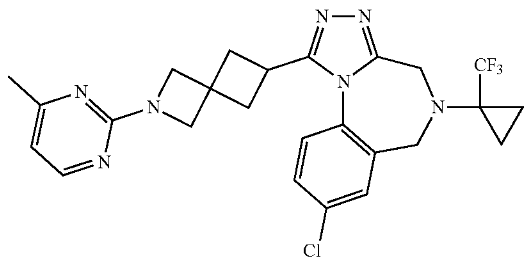 [SMILES: Cc1ccnc(N2CC3(CC(c4nnc5n4-c4ccc(Cl)cc4CN(C4(C(F)(F)F)CC4)C5)C3)C2)n1] |
| 483 | 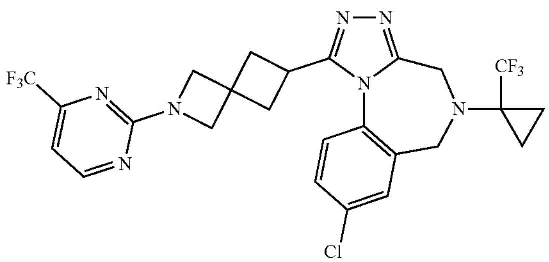 |
| 484 | 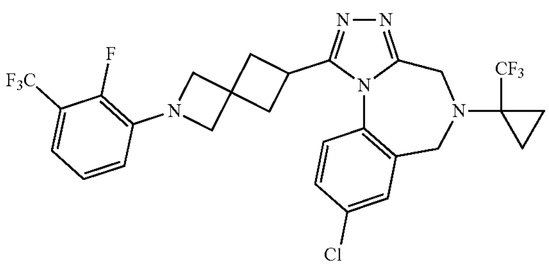 |
| 485 | 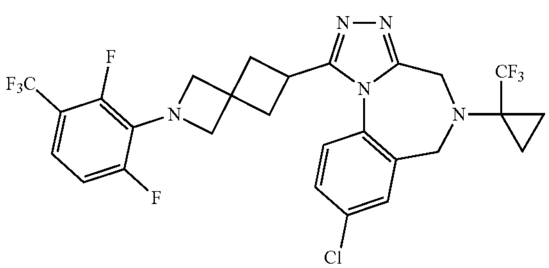 [SMILES: Fc1ccc(C(F)(F)F)c(F)c1N1CC2(CC(c3nnc4n3-c3ccc(Cl)cc3CN(C3(C(F)(F)F)CC3)C4)C2)C1] |
| 486 | 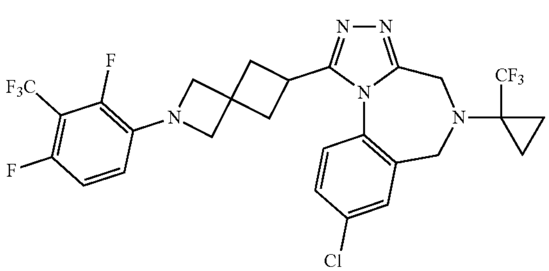 |

TABLE 1-continued

Representative Compounds

| Cmpd. No. | Structure |
|---|---|
| 487 | 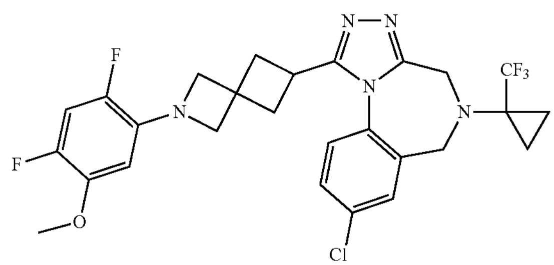 [SMILES: COc1cc(N2CC3(CC(c4nnc5n4-c4ccc(Cl)cc4CN(C4(C(F)(F)F)CC4)C5)C3)C2)c(F)cc1F] |
| 488 | 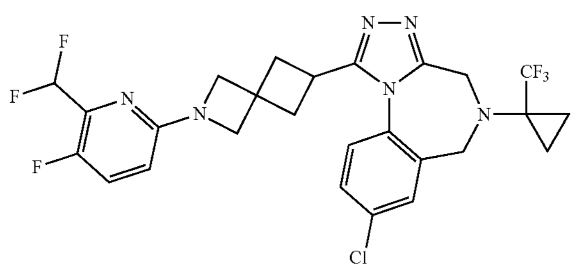 [SMILES: Fc1ccc(N2CC3(CC(c4nnc5n4-c4ccc(Cl)cc4CN(C4(C(F)(F)F)CC4)C5)C3)C2)nc1C(F)F] |
| 489 | 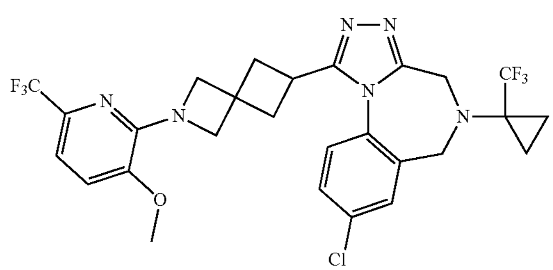 [SMILES: COc1ccc(C(F)(F)F)nc1N1CC2(CC(c3nnc4n3-c3ccc(Cl)cc3CN(C3(C(F)(F)F)CC3)C4)C2)C1] |
| 490 | 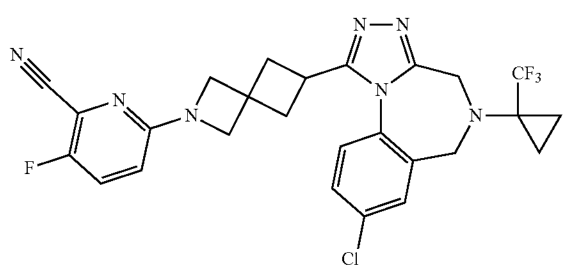 [SMILES: N#Cc1nc(N2CC3(CC(c4nnc5n4-c4ccc(Cl)cc4CN(C4(C(F)(F)F)CC4)C5)C3)C2)ccc1F] |
| 491 | 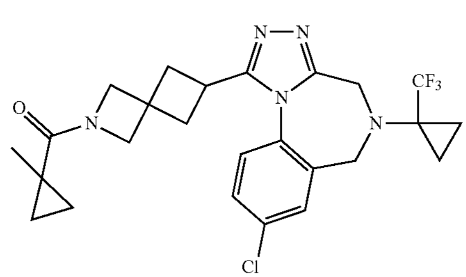 [SMILES: CC1(C(=O)N2CC3(CC(c4nnc5n4-c4ccc(Cl)cc4CN(C4(C(F)(F)F)CC4)C5)C3)C2)CC1] |

TABLE 1-continued
Representative Compounds
| Cmpd. No. | Structure |
|---|---|
| 492 | 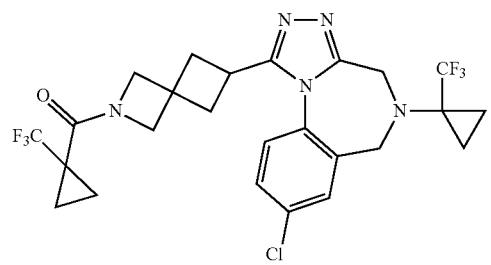 [SMILES: O=C(N1CC2(CC(c3nnc4n3-c3ccc(Cl)cc3CN(C3(C(F)(F)F)CC3)C4)C2)C1)C1(C(F)(F)F)CC1] |
| 493 | 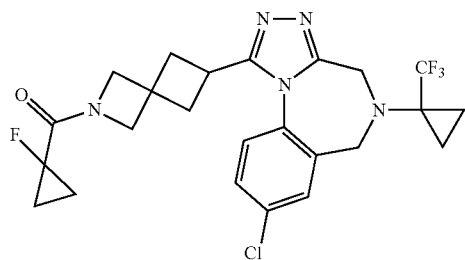 [SMILES: O=C(N1CC2(CC(c3nnc4n3-c3ccc(Cl)cc3CN(C3(C(F)(F)F)CC3)C4)C2)C1)C1(F)CC1] |
| 494 | 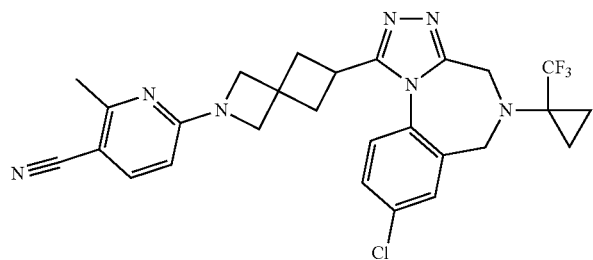 [SMILES: Cc1nc(N2CC3(CC(c4nnc5n4-c4ccc(Cl)cc4CN(C4(C(F)(F)F)CC4)C5)C3)C2)ccc1C#N] |
| 495 | 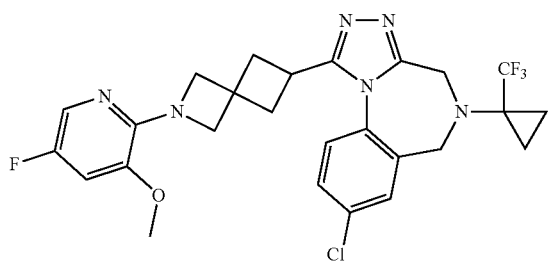 |
| 496 | 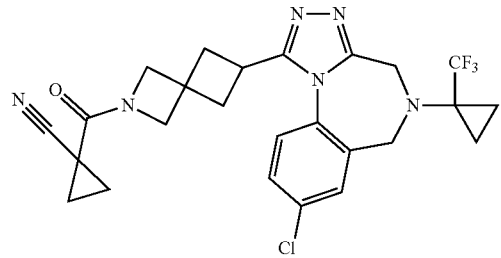 [SMILES: N#CC1(C(=O)N2CC3(CC(c4nnc5n4-c4ccc(Cl)cc4CN(C4(C(F)(F)F)CC4)C5)C3)C2)CC1] |

TABLE 1-continued

Representative Compounds

| Cmpd. No. | Structure |
|---|---|
| 497 | 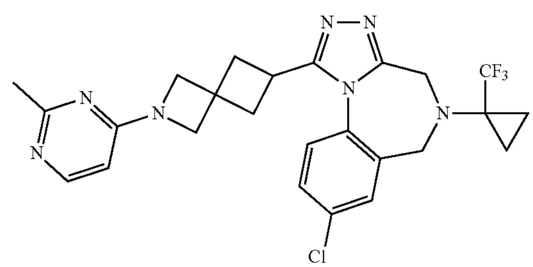 |
| 498 | 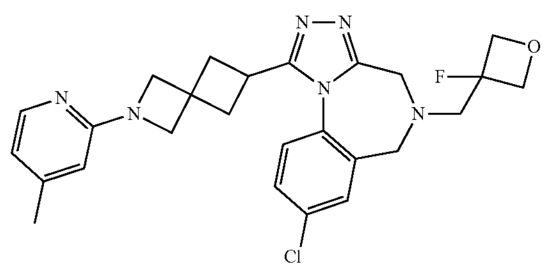 [SMILES: Cc1ccnc(N2CC3(CC(c4nnc5n4-c4ccc(Cl)cc4CN(CC4(F)COC4)C5)C3)C2)c1] |
| 499 | 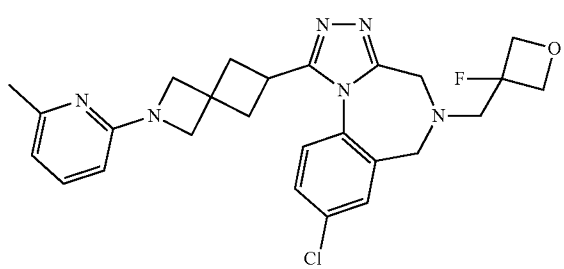 [SMILES: Cc1cccc(N2CC3(CC(c4nnc5n4-c4ccc(Cl)cc4CN(CC4(F)COC4)C5)C3)C2)n1] |
| 500 | 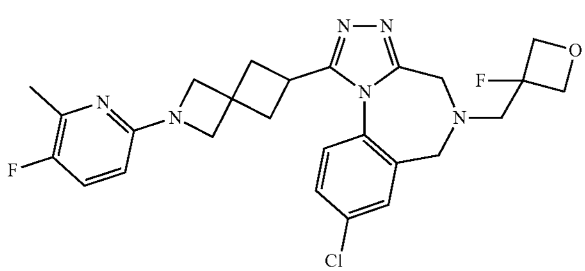 [SMILES: Cc1nc(N2CC3(CC(c4nnc5n4-c4ccc(Cl)cc4CN(CC4(F)COC4)C5)C3)C2)ccc1F] |
| 501 | 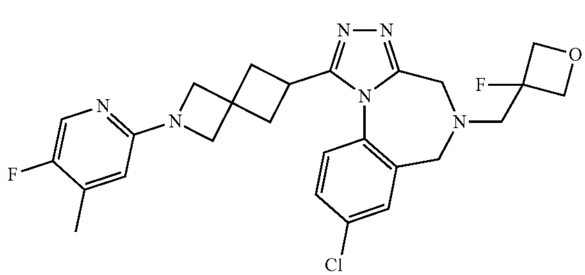 [SMILES: Cc1cc(N2CC3(CC(c4nnc5n4-c4ccc(Cl)cc4CN(CC4(F)COC4)C5)C3)C2)ncc1F] |

TABLE 1-continued
Representative Compounds
| Cmpd. No. | Structure |
|---|---|
| 502 | 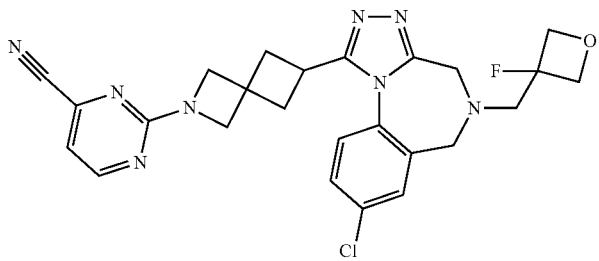 [SMILES: N#Cc1ccnc(N2CC3(CC(c4nnc5n4-c4ccc(Cl)cc4CN(CC4(F)COC4)C5)C3)C2)n1] |
| 503 | 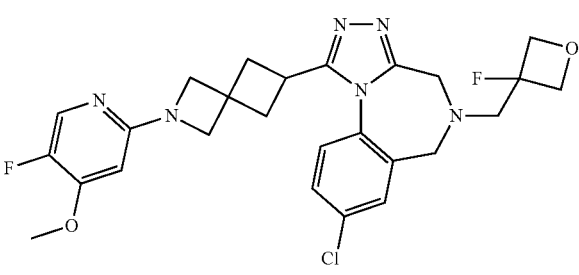 [SMILES: COc1cc(N2CC3(CC(c4nnc5n4-c4ccc(Cl)cc4CN(CC4(F)COC4)C5)C3)C2)ncc1F] |
| 504 | 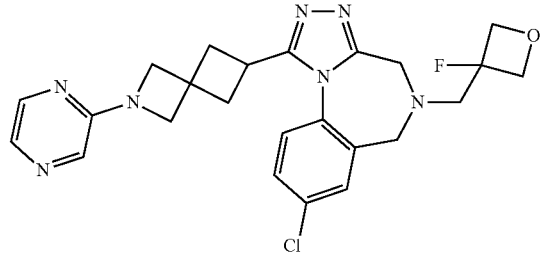 [SMILES: FC1(CN2Cc3cc(Cl)ccc3-n3c(nnc3C3CC4(C3)CN(c3cnccn3)C4)C2)COC1] |
| 505 | 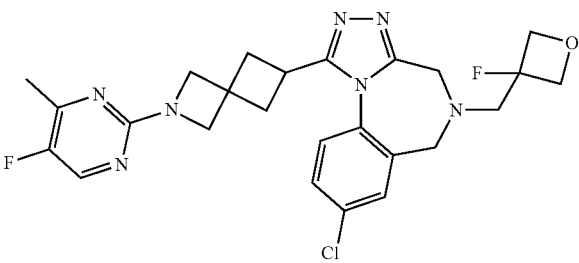 [SMILES: Cc1nc(N2CC3(CC(c4nnc5n4-c4ccc(Cl)cc4CN(CC4(F)COC4)C5)C3)C2)ncc1F] |
| 506 | 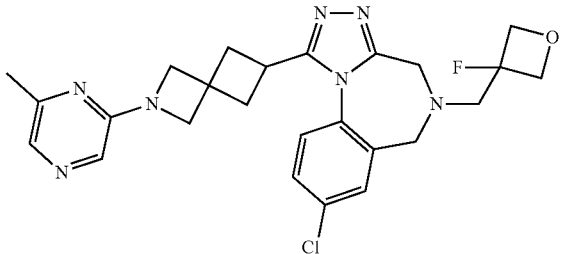 [SMILES: Cc1cncc(N2CC3(CC(c4nnc5n4-c4ccc(Cl)cc4CN(CC4(F)COC4)C5)C3)C2)n1] |

TABLE 1-continued
Representative Compounds
| Cmpd. No. | Structure |
|---|---|
| 507 | 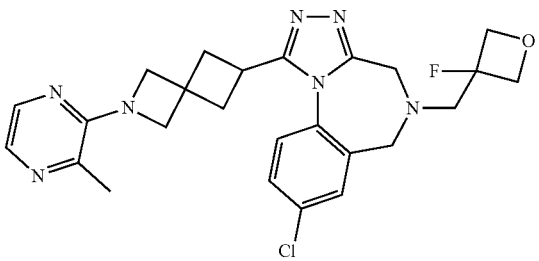 [SMILES: Cc1nccnc1N1CC2(CC(c3nnc4n3-c3ccc(Cl)cc3CN(CC3(F)COC3)C4)C2)C1] |
| 508 | 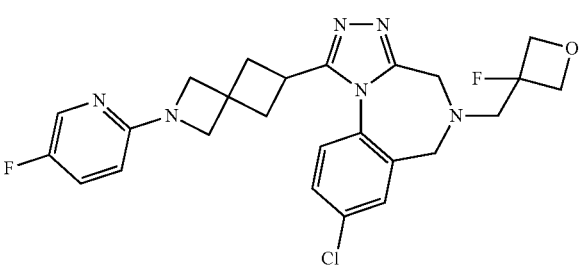 [SMILES: Fc1ccc(N2CC3(CC(c4nnc5n4-c4ccc(Cl)cc4CN(CC4(F)COC4)C5)C3)C2)nc1] |
| 509 | 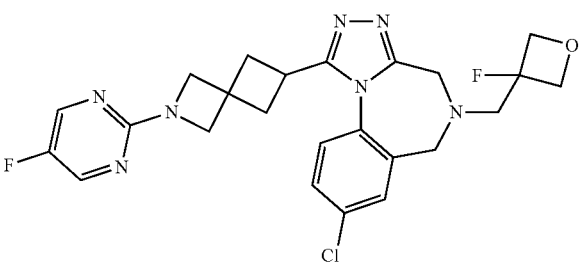 |
| 510 | 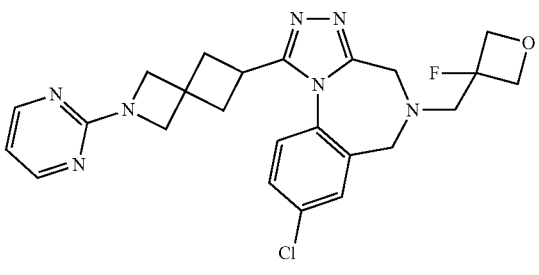 [SMILES: FC1(CN2Cc3cc(Cl)ccc3-n3c(nnc3C3CC4(C3)CN(c3ncccn3)C4)C2)COC1] |
| 511 | 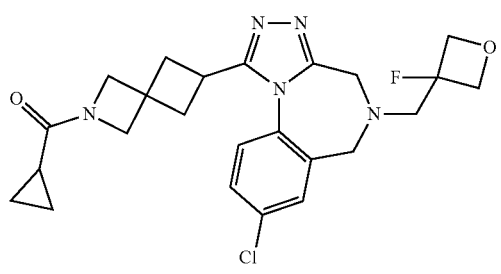 [SMILES: O=C(C1CC1)N1CC2(CC(c3nnc4n3-c3ccc(Cl)cc3CN(CC3(F)COC3)C4)C2)C1] |

251
252
TABLE 1-continued
Representative Compounds
| Cmpd. No. | Structure |
|---|---|
| 512 | 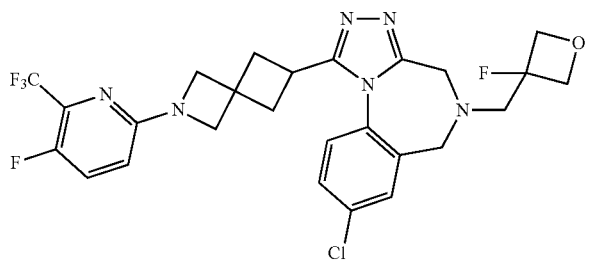 [SMILES: Fc1ccc(N2CC3(CC(c4nnc5n4-c4ccc(Cl)cc4CN(CC4(F)COC4)C5)C3)C2)nc1C(F)(F)F] |
| 513 | 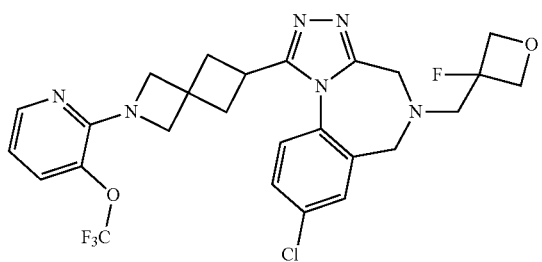 [SMILES: FC1(CN2Cc3cc(Cl)ccc3-n3c(nnc3C3CC4(C3)CN(c3ncccc3OC(F)(F)F)C4)C2)COC1] |
| 514 | 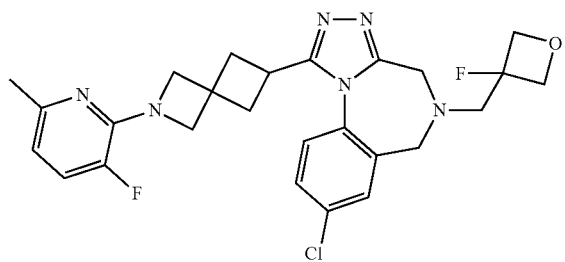 [SMILES: Cc1ccc(F)c(N2CC3(CC(c4nnc5n4-c4ccc(Cl)cc4CN(CC4(F)COC4)C5)C3)C2)n1] |
| 515 | 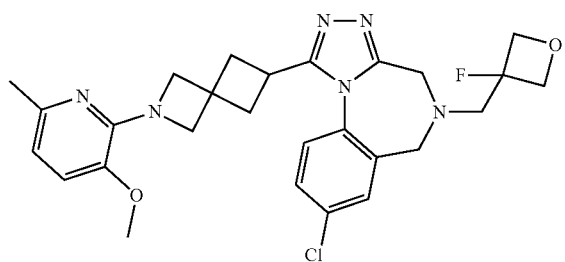 [SMILES: COc1ccc(C)nc1N1CC2(CC(c3nnc4n3-c3ccc(Cl)cc3CN(CC3(F)COC3)C4)C2)C1] |
| 516 | 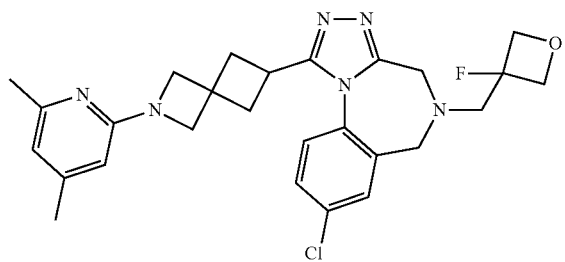 [SMILES: Cc1cc(C)nc(N2CC3(CC(c4nnc5n4-c4ccc(Cl)cc4CN(CC4(F)COC4)C5)C3)C2)c1] |

TABLE 1-continued
Representative Compounds
| Cmpd. No. | Structure |
|---|---|
| 517 | 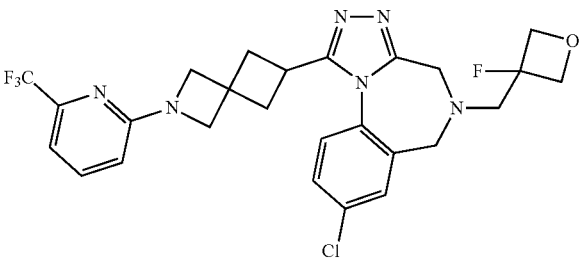 [SMILES: FC1(CN2Cc3cc(Cl)ccc3-n3c(nnc3C3CC4(C3)CN(c3cccc(C(F)(F)F)n3)C4)C2)COC1] |
| 518 | 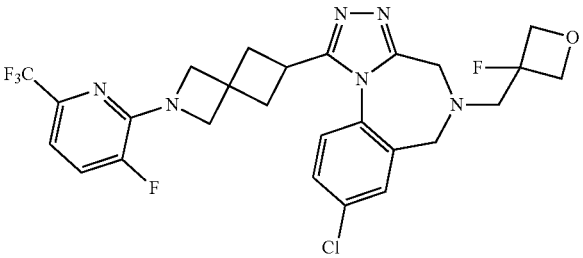 [SMILES: Fc1ccc(C(F)(F)F)nc1N1CC2(CC(c3nnc4n3-c3ccc(Cl)cc3CN(CC3(F)COC3)C4)C2)C1] |
| 519 | 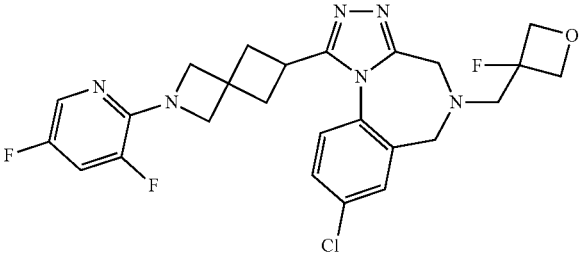 |
| 520 | 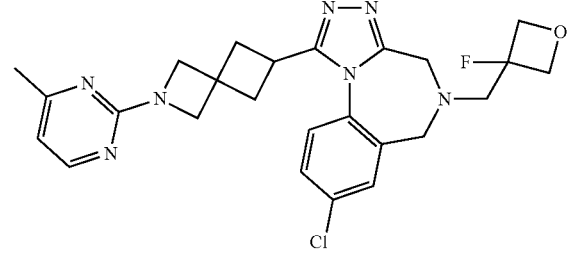 [SMILES: Cc1ccnc(N2CC3(CC(c4nnc5n4-c4ccc(Cl)cc4CN(CC4(F)COC4)C5)C3)C2)n1] |
| 521 | 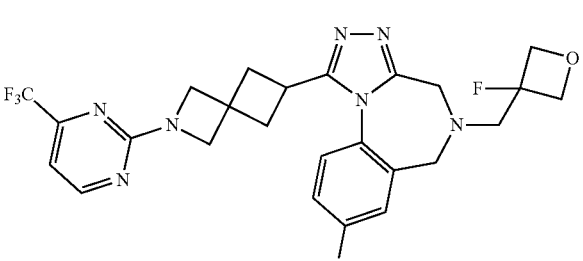 |

TABLE 1-continued

Representative Compounds

| Cmpd. No. | Structure |
|---|---|
| 522 | 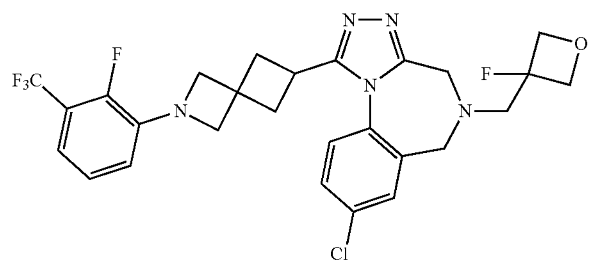 [SMILES: Fc1c(N2CC3(CC(c4nnc5n4-c4ccc(Cl)cc4CN(CC4(F)COC4)C5)C3)C2)cccc1C(F)(F)F] |
| 523 | 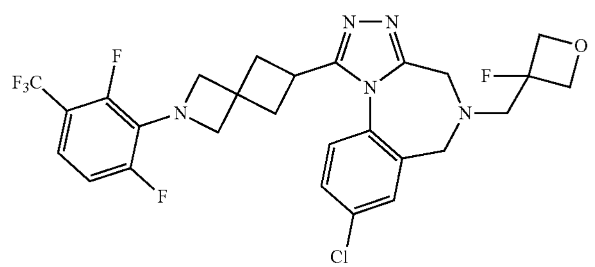 [SMILES: Fc1ccc(C(F)(F)F)c(F)c1N1CC2(CC(c3nnc4n3-c3ccc(Cl)cc3CN(CC3(F)COC3)C4)C2)C1] |
| 524 | 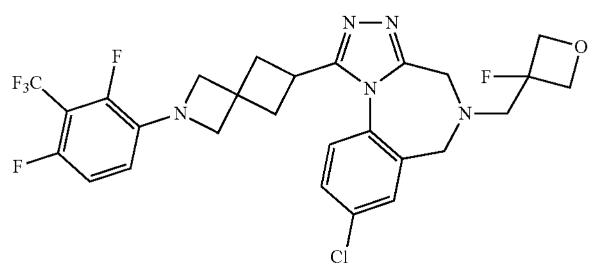 [SMILES: Fc1ccc(N2CC3(CC(c4nnc5n4-c4ccc(Cl)cc4CN(CC4(F)COC4)C5)C3)C2)c(F)c1C(F)(F)F] |
| 525 | 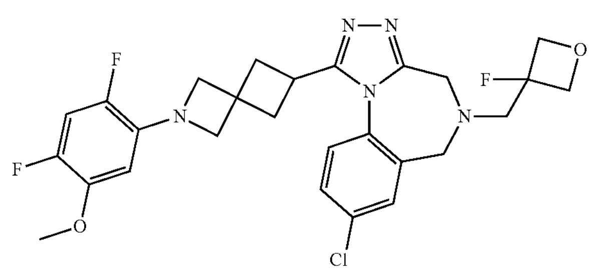 [SMILES: COc1cc(N2CC3(CC(c4nnc5n4-c4ccc(Cl)cc4CN(CC4(F)COC4)C5)C3)C2)c(F)cc1F] |
| 526 | 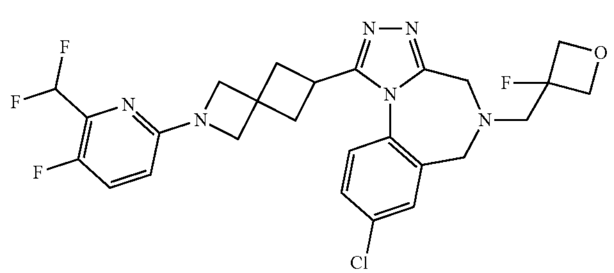 [SMILES: Fc1ccc(N2CC3(CC(c4nnc5n4-c4ccc(Cl)cc4CN(CC4(F)COC4)C5)C3)C2)nc1C(F)F] |

TABLE 1-continued
Representative Compounds
| Cmpd. No. | Structure |
|---|---|
| 527 | 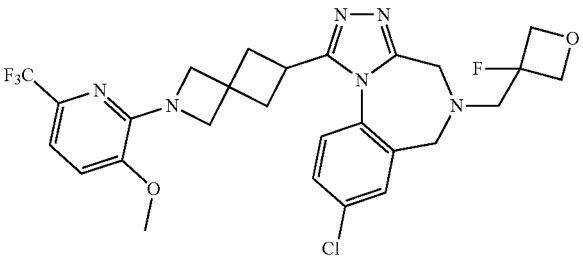 [SMILES: COc1ccc(C(F)(F)F)nc1N1CC2(CC(c3nnc4n3-c3ccc(Cl)cc3CN(CC3(F)COC3)C4)C2)C1] |
| 528 | 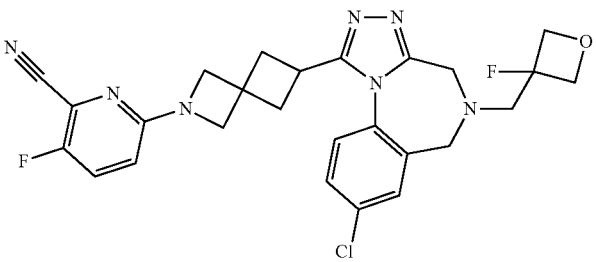 [SMILES: N#Cc1nc(N2CC3(CC(c4nnc5n4-c4ccc(Cl)cc4CN(CC4(F)COC4)C5)C3)C2)ccc1F] |
| 529 | 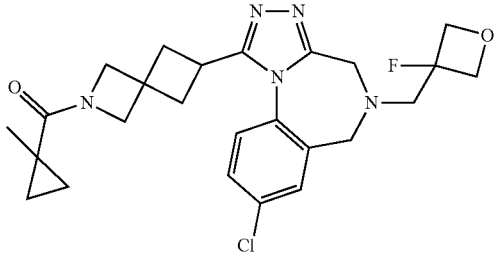 [SMILES: CC1(C(=O)N2CC3(CC(c4nnc5n4-c4ccc(Cl)cc4CN(CC4(F)COC4)C5)C3)C2)CC1] |
| 530 | 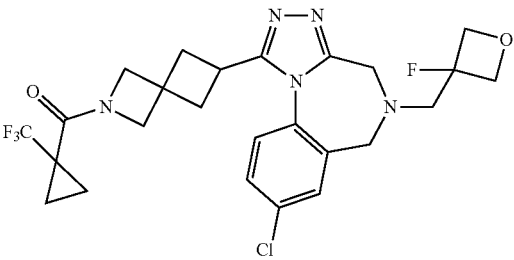 [SMILES: O=C(N1CC2(CC(c3nnc4n3-c3ccc(Cl)cc3CN(CC3(F)COC3)C4)C2)C1)C1(C(F)(F)F)CC1] |
| 531 | 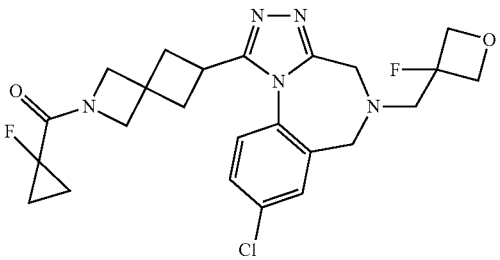 [SMILES: O=C(N1CC2(CC(c3nnc4n3-c3ccc(Cl)cc3CN(CC3(F)COC3)C4)C2)C1)C1(F)CC1] |

TABLE 1-continued
Representative Compounds
| Cmpd. No. | Structure |
|---|---|
| 532 | 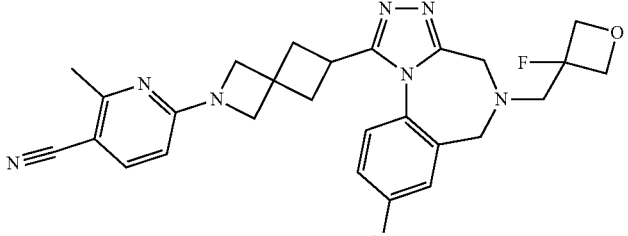 |
| 533 | 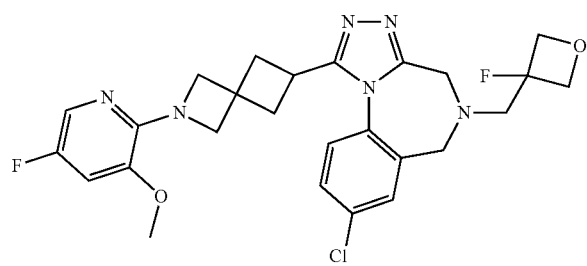 [SMILES: COc1cc(F)cnc1N1CC2(CC(c3nnc4n3-c3ccc(Cl)cc3CN(CC3(F)COC3)C4)C2)C1] |
| 534 | 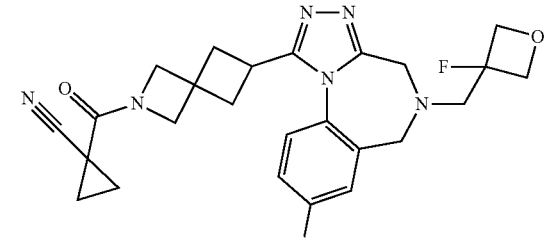 |
| 535 | 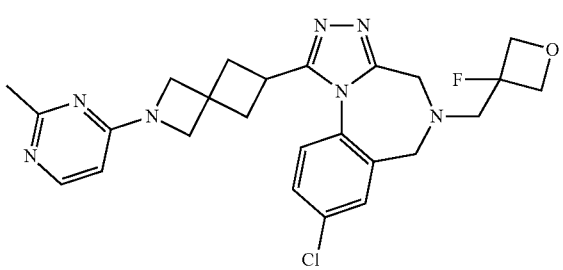 [SMILES: Cc1nccc(N2CC3(CC(c4nnc5n4-c4ccc(Cl)cc4CN(CC4(F)COC4)C5)C3)C2)n1] |
| 536 | 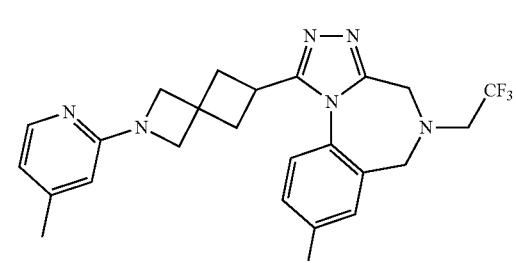 |

TABLE 1-continued

Representative Compounds

| Cmpd. No. | Structure |
|---|---|
| 537 | 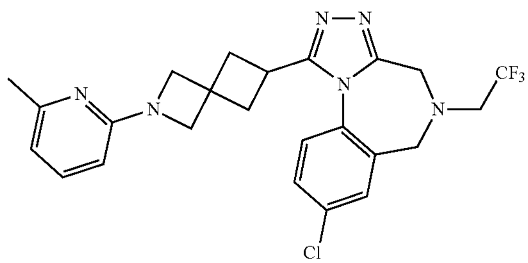 [SMILES: Cc1cccc(N2CC3(CC(c4nnc5n4-c4ccc(Cl)cc4CN(CC(F)(F)F)C5)C3)C2)n1] |
| 538 | 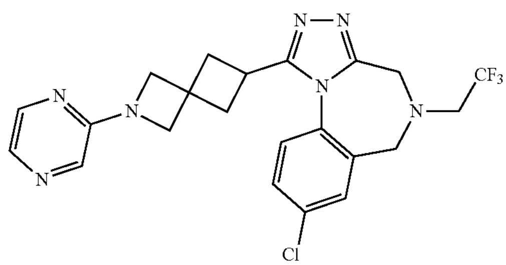 [SMILES: FC(F)(F)CN1Cc2cc(Cl)ccc2-n2c(nnc2C2CC3(C2)CN(c2cnccn2)C3)C1] |
| 539 | 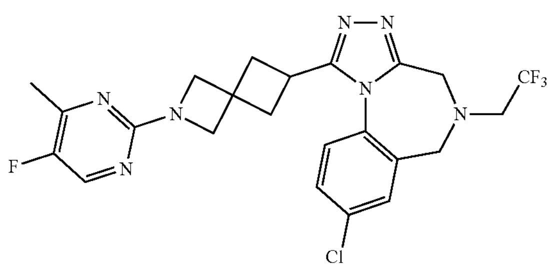 [SMILES: Cc1nc(N2CC3(CC(c4nnc5n4-c4ccc(Cl)cc4CN(CC(F)(F)F)C5)C3)C2)ncc1F] |
| 540 | 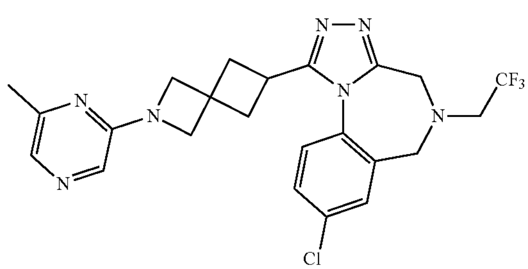 [SMILES: Cc1cncc(N2CC3(CC(c4nnc5n4-c4ccc(Cl)cc4CN(CC(F)(F)F)C5)C3)C2)n1] |
| 541 | 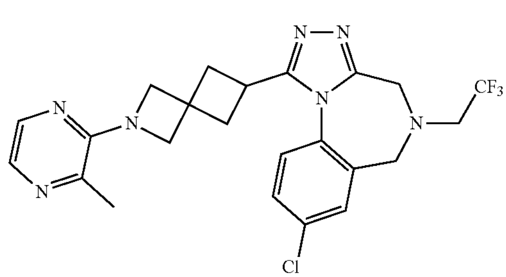 [SMILES: Cc1nccnc1N1CC2(CC(c3nnc4n3-c3ccc(Cl)cc3CN(CC(F)(F)F)C4)C2)C1] |

TABLE 1-continued

Representative Compounds

| Cmpd. No. | Structure |
|---|---|
| 542 | 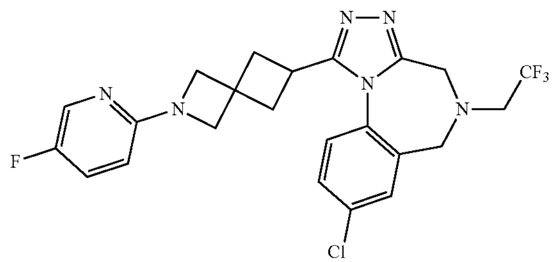 [SMILES: Fc1ccc(N2CC3(CC(c4nnc5n4-c4ccc(Cl)cc4CN(CC(F)(F)F)C5)C3)C2)nc1] |
| 543 | 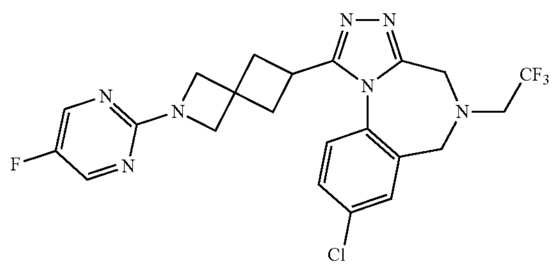 [SMILES: Fc1cnc(N2CC3(CC(c4nnc5n4-c4ccc(Cl)cc4CN(CC(F)(F)F)C5)C3)C2)nc1] |
| 544 | 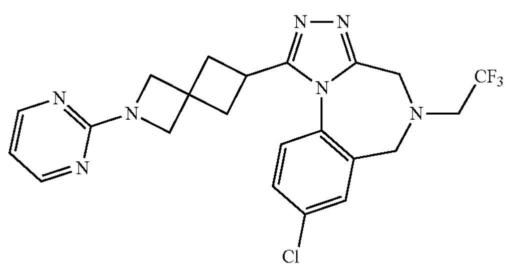 [SMILES: FC(F)(F)CN1Cc2cc(Cl)ccc2-n2c(nnc2C2CC3(C2)CN(c2ncccn2)C3)C1] |
| 545 | 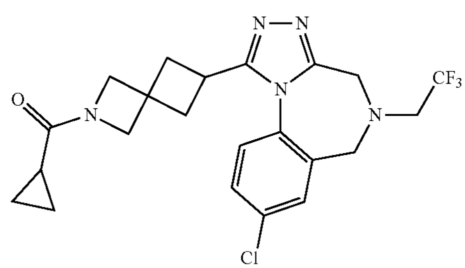 [SMILES: O=C(C1CC1)N1CC2(CC(c3nnc4n3-c3ccc(Cl)cc3CN(CC(F)(F)F)C4)C2)C1] |
| 546 | 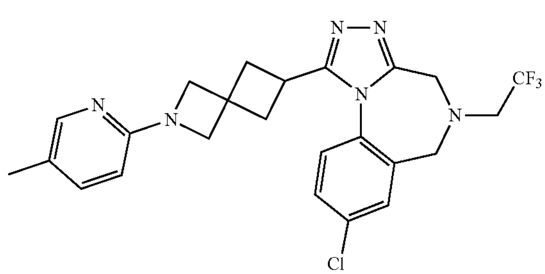 |

TABLE 1-continued

Representative Compounds

| Cmpd. No. | Structure |
|---|---|
| 547 | 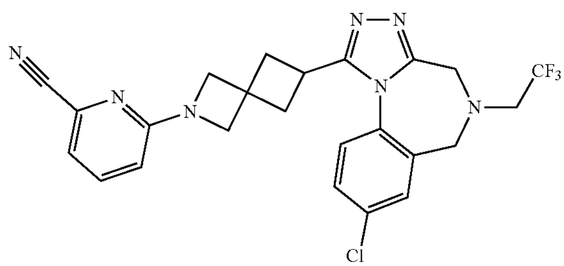 [SMILES: N#Cc1cccc(N2CC3(CC(c4nnc5n4-c4ccc(Cl)cc4CN(CC(F)(F)F)C5)C3)C2)n1] |
| 548 | 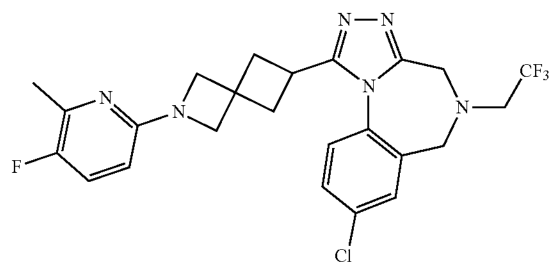 [SMILES: Cc1nc(N2CC3(CC(c4nnc5n4-c4ccc(Cl)cc4CN(CC(F)(F)F)C5)C3)C2)ccc1F] |
| 549 | 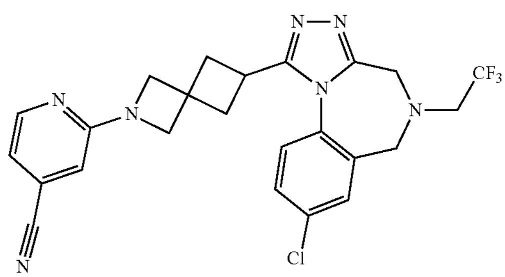 [SMILES: N#Cc1ccnc(N2CC3(CC(c4nnc5n4-c4ccc(Cl)cc4CN(CC(F)(F)F)C5)C3)C2)c1] |
| 550 | 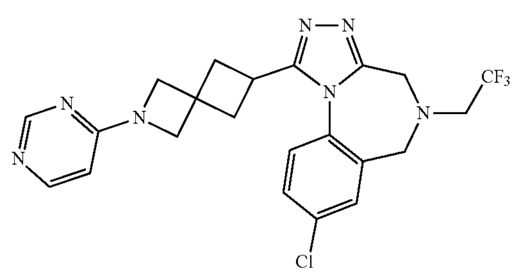 [SMILES: FC(F)(F)CN1Cc2cc(Cl)ccc2-n2c(nnc2C2CC3(C2)CN(c2ccncn2)C3)C1] |
| 552 | 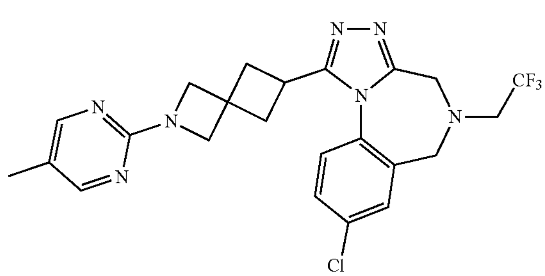 [SMILES: Cc1cnc(N2CC3(CC(c4nnc5n4-c4ccc(Cl)cc4CN(CC(F)(F)F)C5)C3)C2)nc1] |

TABLE 1-continued

Representative Compounds

| Cmpd. No. | Structure |
|---|---|
| 553 | 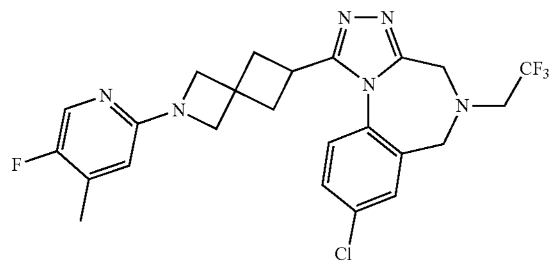 [SMILES: Cc1cc(N2CC3(CC(c4nnc5n4-c4ccc(Cl)cc4CN(CC(F)(F)F)C5)C3)C2)ncc1F] |
| 554 | 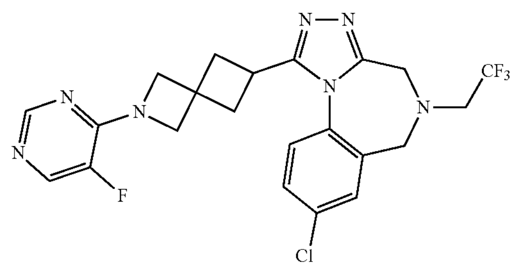 [SMILES: Fc1cncnc1N1CC2(CC(c3nnc4n3-c3ccc(Cl)cc3CN(CC(F)(F)F)C4)C2)C1] |
| 555 | 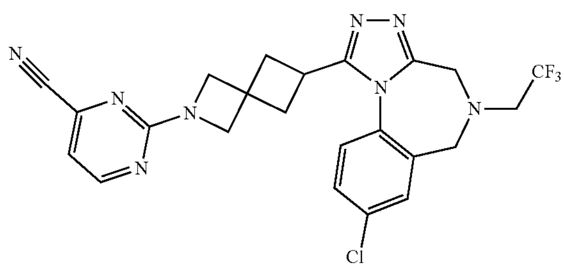 [SMILES: N#Cc1ccnc(N2CC3(CC(c4nnc5n4-c4ccc(Cl)cc4CN(CC(F)(F)F)C5)C3)C2)n1] |
| 556 | 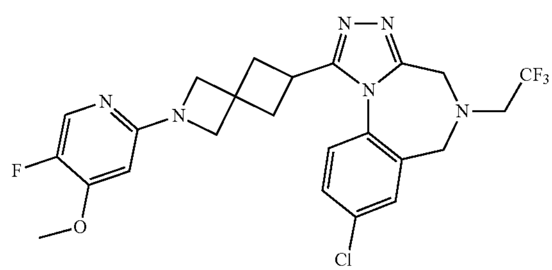 [SMILES: COc1cc(N2CC3(CC(c4nnc5n4-c4ccc(Cl)cc4CN(CC(F)(F)F)C5)C3)C2)ncc1F] |
| 557 | 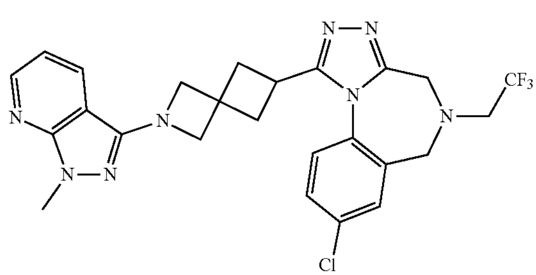 [SMILES: Cn1nc(N2CC3(CC(c4nnc5n4-c4ccc(Cl)cc4CN(CC(F)(F)F)C5)C3)C2)c2cccnc21] |

TABLE 1-continued

Representative Compounds

| Cmpd. No. | Structure |
|---|---|
| 558 | 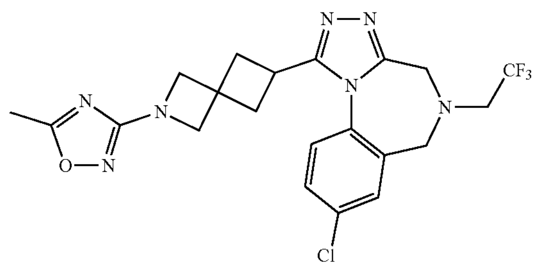 [SMILES: Cc1nc(N2CC3(CC(c4nnc5n4-c4ccc(Cl)cc4CN(CC(F)(F)F)C5)C3)C2)no1] |
| 559 | 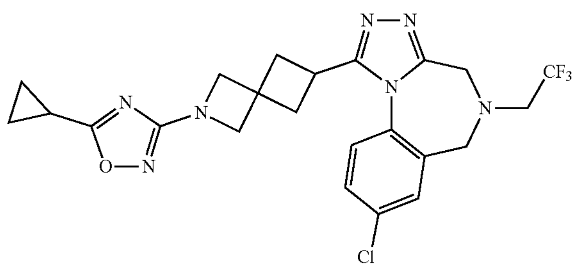 [SMILES: FC(F)(F)CN1Cc2cc(Cl)ccc2-n2c(nnc2C2CC3(C2)CN(c2noc(C4CC4)n2)C3)C1] |
| 560 | 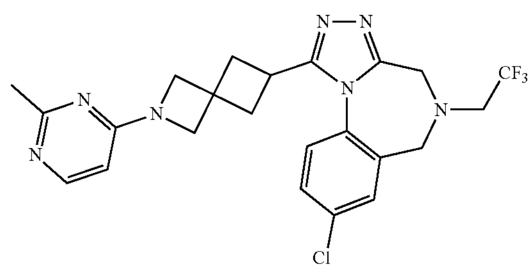 [SMILES: Cc1nccc(N2CC3(CC(c4nnc5n4-c4ccc(Cl)cc4CN(CC(F)(F)F)C5)C3)C2)n1] |
| 561 | 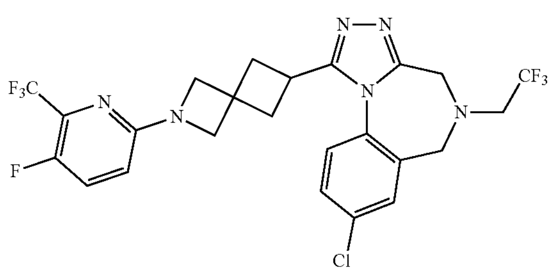 |
| 562 | 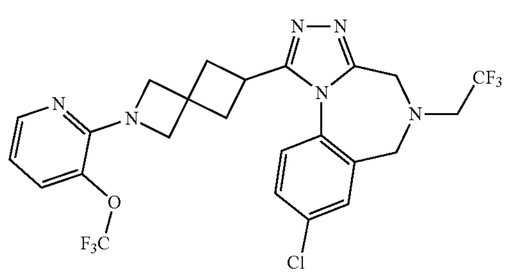 [SMILES: FC(F)(F)CN1Cc2cc(Cl)ccc2-n2c(nnc2C2CC3(C2)CN(c2ncccc2OC(F)(F)F)C3)C1] |

TABLE 1-continued
Representative Compounds
| Cmpd. No. | Structure |
|---|---|
| 563 | 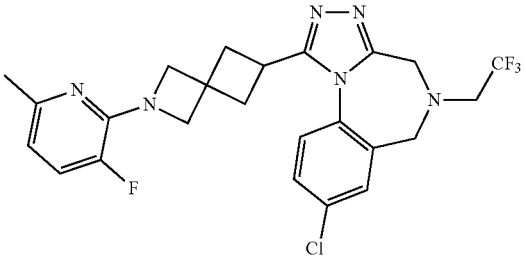 [SMILES: Cc1ccc(F)c(N2CC3(CC(c4nnc5n4-c4ccc(Cl)cc4CN(CC(F)(F)F)C5)C3)C2)n1] |
| 564 | 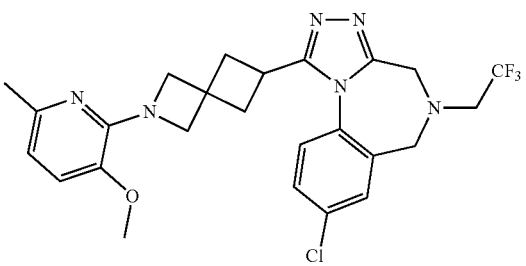 [SMILES: COc1ccc(C)nc1N1CC2(CC(c3nnc4n3-c3ccc(Cl)cc3CN(CC(F)(F)F)C4)C2)C1] |
| 565 | 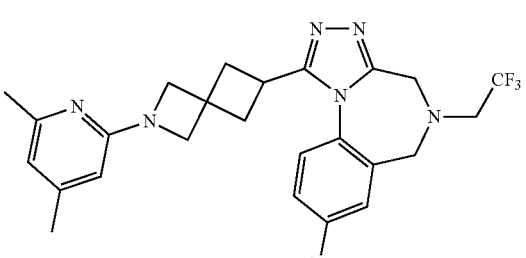 |
| 566 | 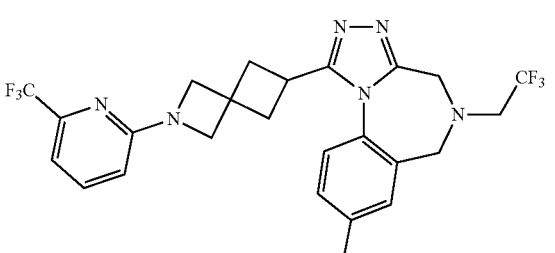 |
| 567 | 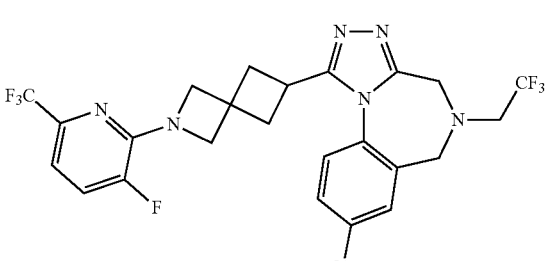 |

TABLE 1-continued

Representative Compounds

| Cmpd. No. | Structure |
|---|---|
| 568 | 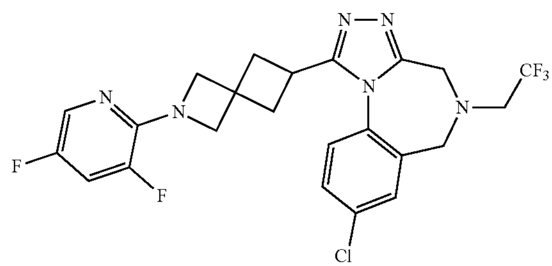 [SMILES: Fc1cnc(N2CC3(CC(c4nnc5n4-c4ccc(Cl)cc4CN(CC(F)(F)F)C5)C3)C2)c(F)c1] |
| 569 | 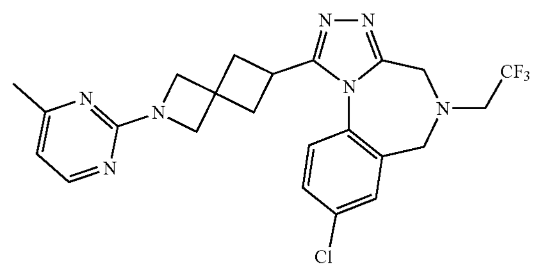 [SMILES: Cc1ccnc(N2CC3(CC(c4nnc5n4-c4ccc(Cl)cc4CN(CC(F)(F)F)C5)C3)C2)n1] |
| 570 | 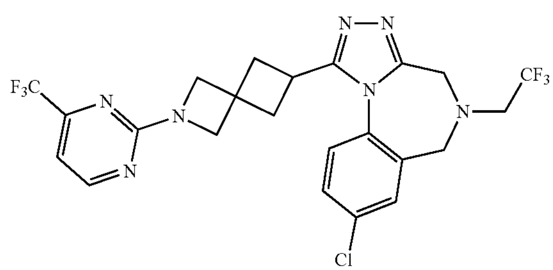 [SMILES: FC(F)(F)CN1Cc2cc(Cl)ccc2-n2c(nnc2C2CC3(C2)CN(c2nccc(C(F)(F)F)n2)C3)C1] |
| 571 | 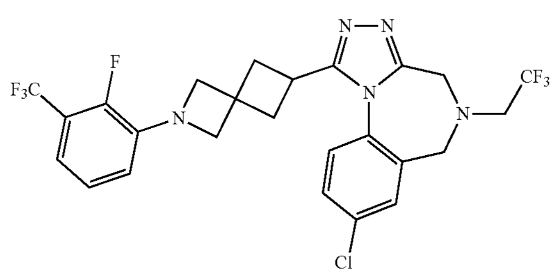 [SMILES: Fc1c(N2CC3(CC(c4nnc5n4-c4ccc(Cl)cc4CN(CC(F)(F)F)C5)C3)C2)cccc1C(F)(F)F] |
| 572 | 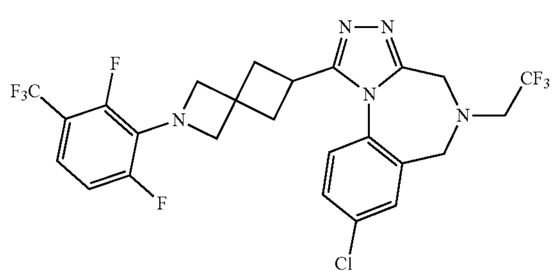 [SMILES: Fc1ccc(C(F)(F)F)c(F)c1N1CC2(CC(c3nnc4n3-c3ccc(Cl)cc3CN(CC(F)(F)F)C4)C2)C1] |

TABLE 1-continued

Representative Compounds

| Cmpd. No. | Structure |
|---|---|
| 573 | 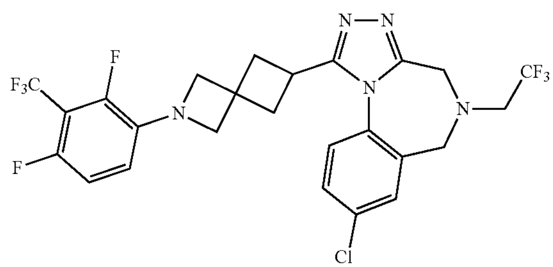 [SMILES: Fc1ccc(N2CC3(CC(c4nnc5n4-c4ccc(Cl)cc4CN(CC(F)(F)F)C5)C3)C2)c(F)c1C(F)(F)F] |
| 574 | 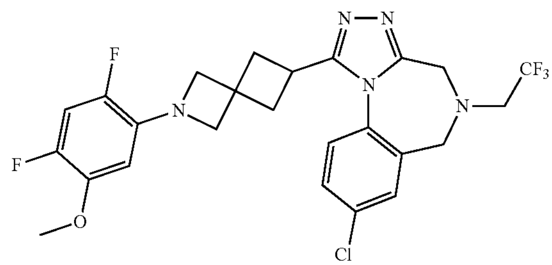 [SMILES: COc1cc(N2CC3(CC(c4nnc5n4-c4ccc(Cl)cc4CN(CC(F)(F)F)C5)C3)C2)c(F)cc1F] |
| 575 | 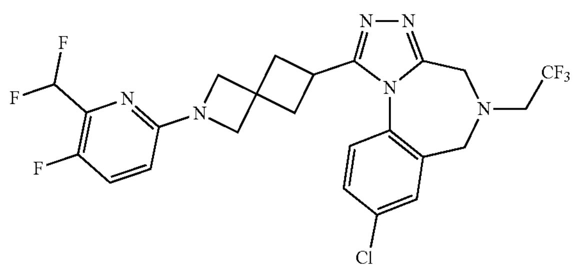 [SMILES: Fc1ccc(N2CC3(CC(c4nnc5n4-c4ccc(Cl)cc4CN(CC(F)(F)F)C5)C3)C2)nc1C(F)F] |
| 576 | 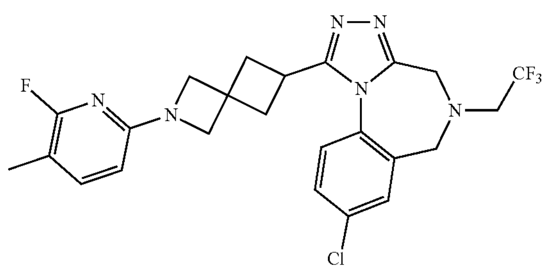 [SMILES: Cc1ccc(N2CC3(CC(c4nnc5n4-c4ccc(Cl)cc4CN(CC(F)(F)F)C5)C3)C2)nc1F] |
| 577 | 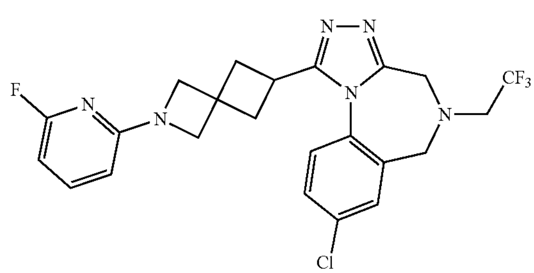 [SMILES: Fc1cccc(N2CC3(CC(c4nnc5n4-c4ccc(Cl)cc4CN(CC(F)(F)F)C5)C3)C2)n1] |

TABLE 1-continued

Representative Compounds

| Cmpd. No. | Structure |
|---|---|
| 578 | 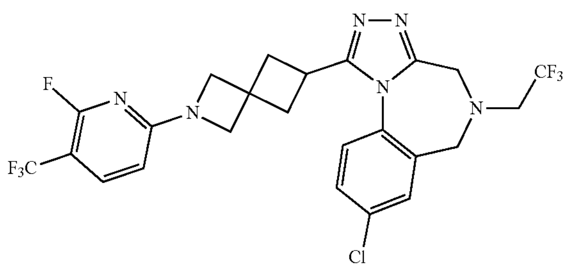 [SMILES: Fc1nc(N2CC3(CC(c4nnc5n4-c4ccc(Cl)cc4CN(CC(F)(F)F)C5)C3)C2)ccc1C(F)(F)F] |
| 579 | 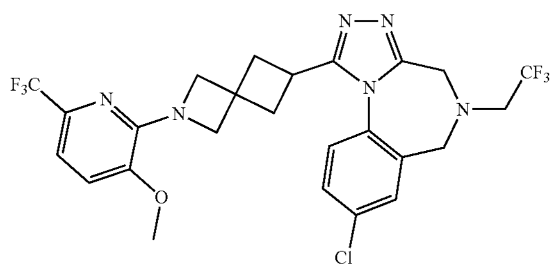 [SMILES: COc1ccc(C(F)(F)F)nc1N1CC2(CC(c3nnc4n3-c3ccc(Cl)cc3CN(CC(F)(F)F)C4)C2)C1] |
| 580 | 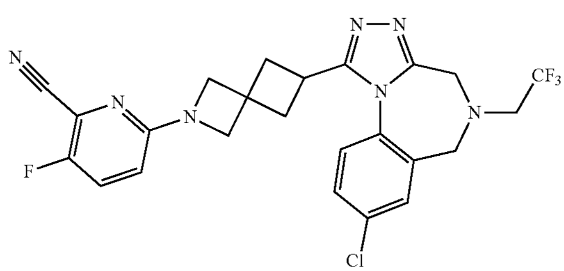 [SMILES: N#Cc1nc(N2CC3(CC(c4nnc5n4-c4ccc(Cl)cc4CN(CC(F)(F)F)C5)C3)C2)ccc1F] |
| 581 | 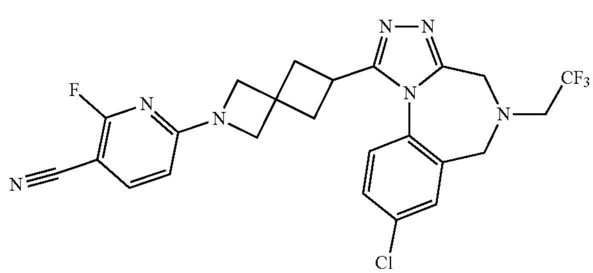 [SMILES: N#Cc1ccc(N2CC3(CC(c4nnc5n4-c4ccc(Cl)cc4CN(CC(F)(F)F)C5)C3)C2)nc1F] |
| 582 | 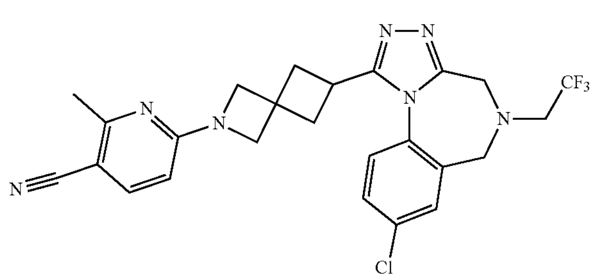 [SMILES: Cc1nc(N2CC3(CC(c4nnc5n4-c4ccc(Cl)cc4CN(CC(F)(F)F)C5)C3)C2)ccc1C#N] |

TABLE 1-continued

Representative Compounds

| Cmpd. No. | Structure |
|---|---|
| 583 | 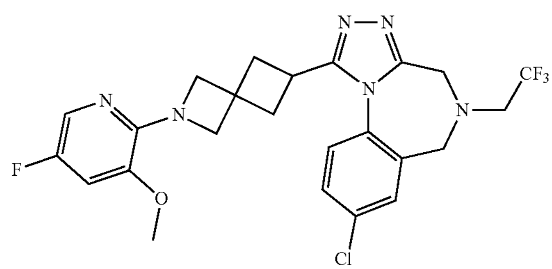 [SMILES: COc1cc(F)cnc1N1CC2(CC(c3nnc4n3-c3ccc(Cl)cc3CN(CC(F)(F)F)C4)C2)C1] |
| 584 | 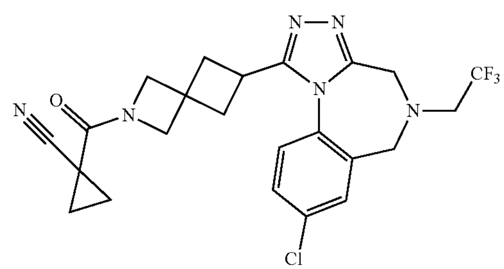 [SMILES: N#CC1(C(=O)N2CC3(CC(c4nnc5n4-c4ccc(Cl)cc4CN(CC(F)(F)F)C5)C3)C2)CC1] |
| 585 | 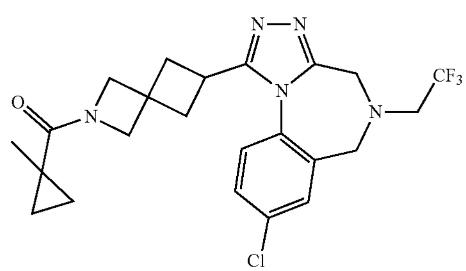 [SMILES: CC1(C(=O)N2CC3(CC(c4nnc5n4-c4ccc(Cl)cc4CN(CC(F)(F)F)C5)C3)C2)CC1] |
| 586 | 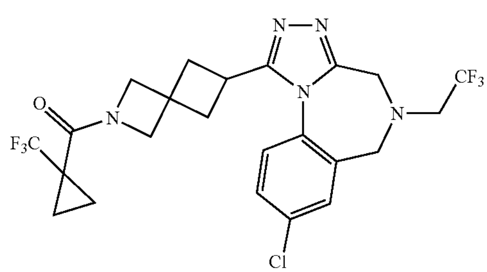 [SMILES: O=C(N1CC2(CC(c3nnc4n3-c3ccc(Cl)cc3CN(CC(F)(F)F)C4)C2)C1)C1(C(F)(F)F)CC1] |
| 587 | 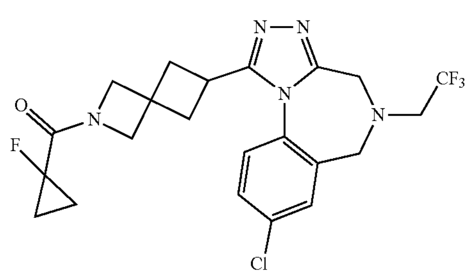 [SMILES: O=C(N1CC2(CC(c3nnc4n3-c3ccc(Cl)cc3CN(CC(F)(F)F)C4)C2)C1)C1(F)CC1] |

TABLE 1-continued
Representative Compounds
| Cmpd. No. | Structure |
|---|---|
| 588 | 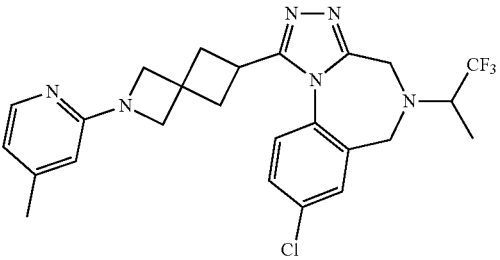 [SMILES: Cc1ccnc(N2CC3(CC(c4nnc5n4-c4ccc(Cl)cc4CN(C(C)C(F)(F)F)C5)C3)C2)c1] |
| 589 | 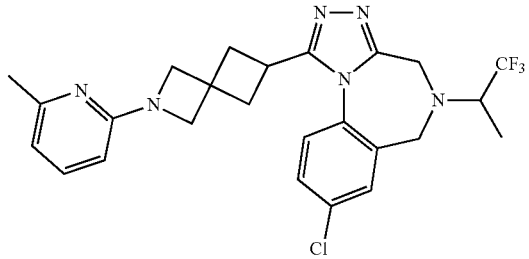 [SMILES: Cc1cccc(N2CC3(CC(c4nnc5n4-c4ccc(Cl)cc4CN(C(C)C(F)(F)F)C5)C3)C2)n1] |
| 590 | 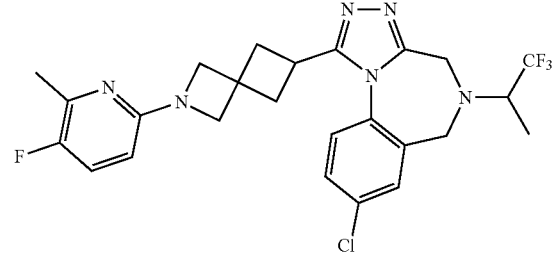 |
| 591 | 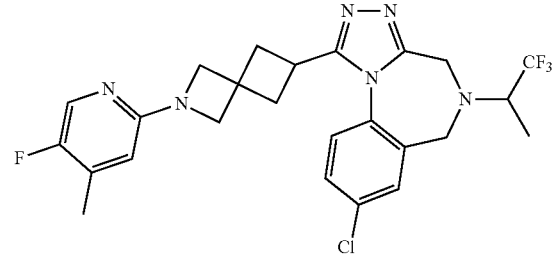 [SMILES: Cc1cc(N2CC3(CC(c4nnc5n4-c4ccc(Cl)cc4CN(C(C)C(F)(F)F)C5)C3)C2)ncc1F] |
| 592 | 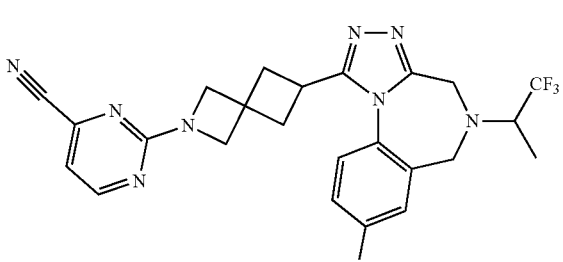 |

TABLE 1-continued
Representative Compounds
| Cmpd. No. | Structure |
|---|---|
| 593 | 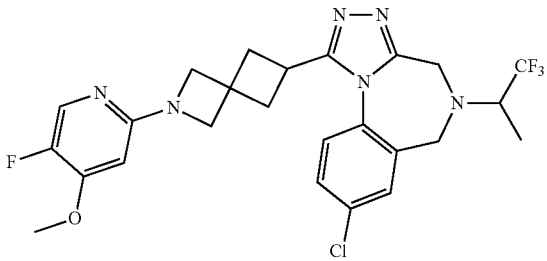 [SMILES: COc1cc(N2CC3(CC(c4nnc5n4-c4ccc(Cl)cc4CN(C(C)C(F)(F)F)C5)C3)C2)ncc1F] |
| 594 | 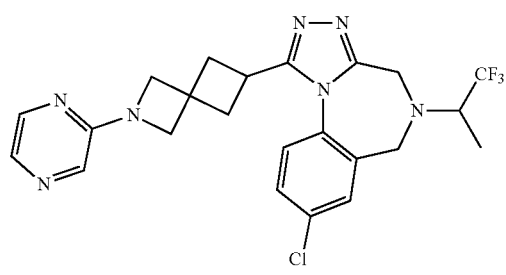 [SMILES: CC(N1Cc2cc(Cl)ccc2-n2c(nnc2C2CC3(C2)CN(c2cnccn2)C3)C1)C(F)(F)F] |
| 595 | 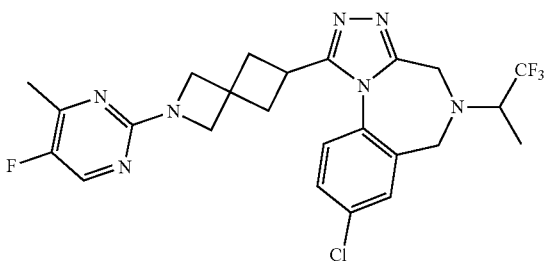 [SMILES: Cc1nc(N2CC3(CC(c4nnc5n4-c4ccc(Cl)cc4CN(C(C)C(F)(F)F)C5)C3)C2)ncc1F] |
| 596 | 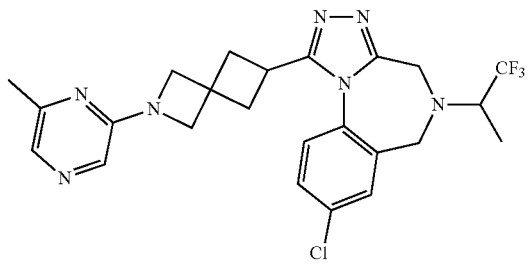 [SMILES: Cc1cncc(N2CC3(CC(c4nnc5n4-c4ccc(Cl)cc4CN(C(C)C(F)(F)F)C5)C3)C2)n1] |
| 597 | 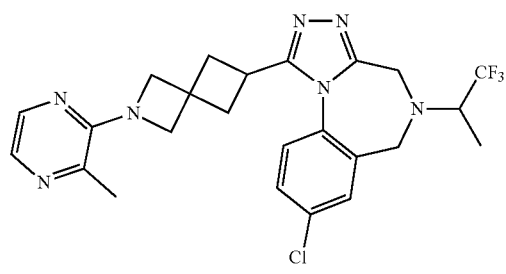 [SMILES: Cc1nccnc1N1CC2(CC(c3nnc4n3-c3ccc(Cl)cc3CN(C(C)C(F)(F)F)C4)C2)C1] |

TABLE 1-continued

Representative Compounds

| Cmpd. No. | Structure |
|---|---|
| 598 | 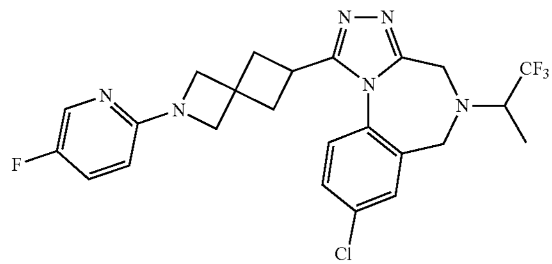 [SMILES: CC(N1Cc2cc(Cl)ccc2-n2c(nnc2C2CC3(C2)CN(c2ccc(F)cn2)C3)C1)C(F)(F)F] |
| 599 | 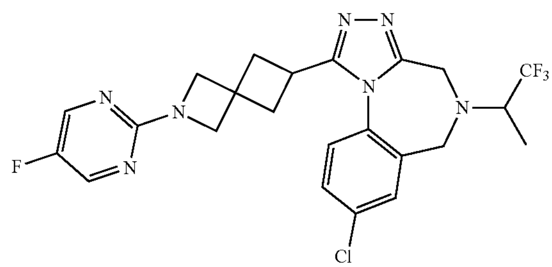 [SMILES: CC(N1Cc2cc(Cl)ccc2-n2c(nnc2C2CC3(C2)CN(c2ncc(F)cn2)C3)C1)C(F)(F)F] |
| 600 | 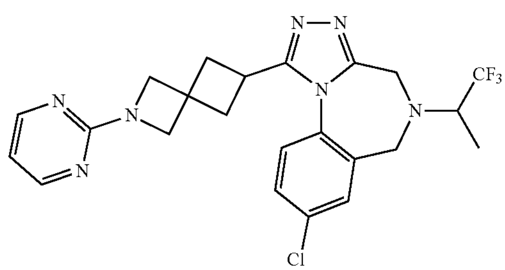 [SMILES: CC(N1Cc2cc(Cl)ccc2-n2c(nnc2C2CC3(C2)CN(c2ncccn2)C3)C1)C(F)(F)F] |
| 601 | 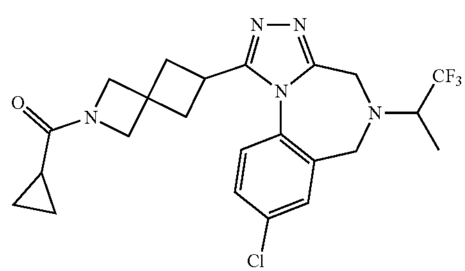 [SMILES: CC(N1Cc2cc(Cl)ccc2-n2c(nnc2C2CC3(C2)CN(C(=O)C2CC2)C3)C1)C(F)(F)F] |
| 602 | 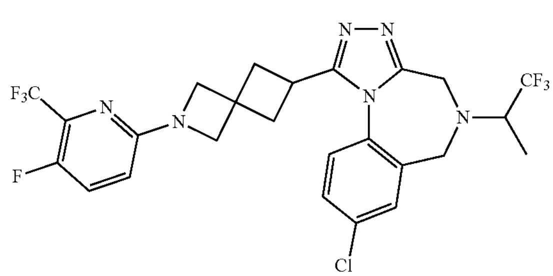 [SMILES: CC(N1Cc2cc(Cl)ccc2-n2c(nnc2C2CC3(C2)CN(c2ccc(F)c(C(F)(F)F)n2)C3)C1)C(F)(F)F] |

TABLE 1-continued

Representative Compounds

| Cmpd. No. | Structure |
|---|---|
| 603 | 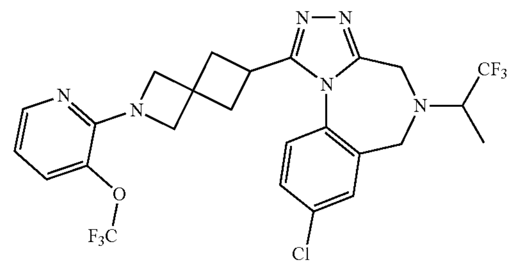 [SMILES: CC(N1Cc2cc(Cl)ccc2-n2c(nnc2C2CC3(C2)CN(c2ncccc2OC(F)(F)F)C3)C1)C(F)(F)F] |
| 604 | 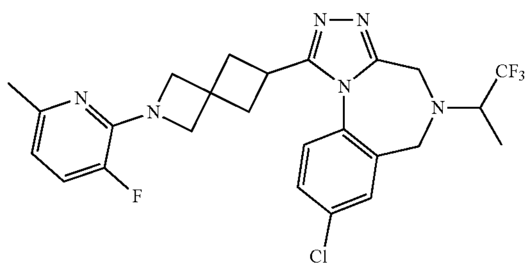 [SMILES: Cc1ccc(F)c(N2CC3(CC(c4nnc5n4-c4ccc(Cl)cc4CN(C(C)C(F)(F)F)C5)C3)C2)n1] |
| 605 | 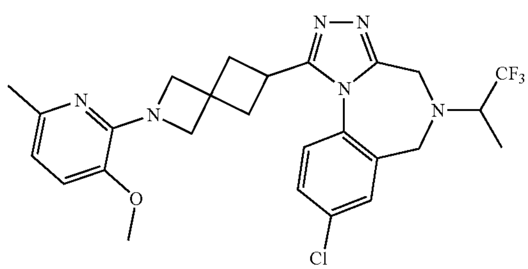 [SMILES: COc1ccc(C)nc1N1CC2(CC(c3nnc4n3-c3ccc(Cl)cc3CN(C(C)C(F)(F)F)C4)C2)C1] |
| 606 | 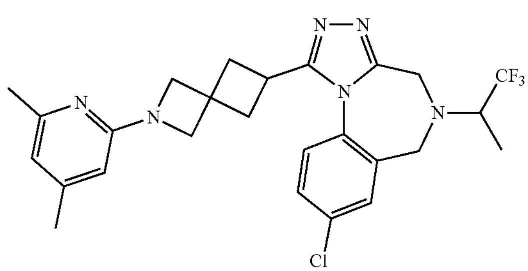 [SMILES: Cc1cc(C)nc(N2CC3(CC(c4nnc5n4-c4ccc(Cl)cc4CN(C(C)C(F)(F)F)C5)C3)C2)c1] |
| 607 | 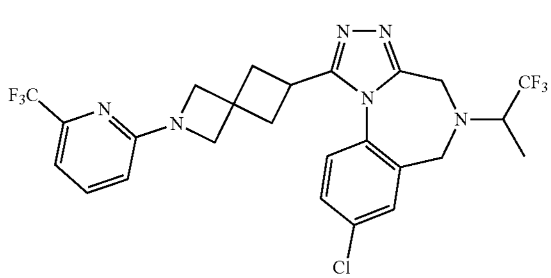 [SMILES: CC(N1Cc2cc(Cl)ccc2-n2c(nnc2C2CC3(C2)CN(c2cccc(C(F)(F)F)n2)C3)C1)C(F)(F)F] |

TABLE 1-continued

Representative Compounds

| Cmpd. No. | Structure |
|---|---|
| 608 | 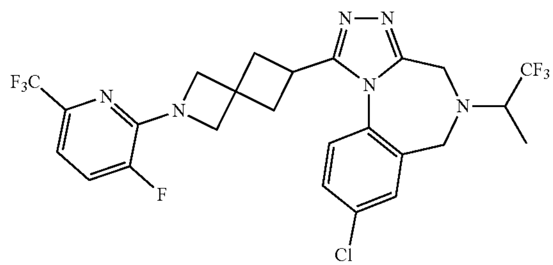 [SMILES: CC(N1Cc2cc(Cl)ccc2-n2c(nnc2C2CC3(C2)CN(c2nc(C(F)(F)F)ccc2F)C3)C1)C(F)(F)F] |
| 609 | 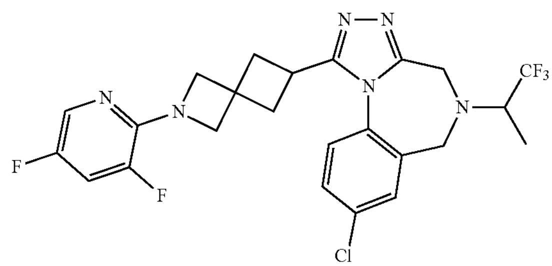 [SMILES: CC(N1Cc2cc(Cl)ccc2-n2c(nnc2C2CC3(C2)CN(c2ncc(F)cc2F)C3)C1)C(F)(F)F] |
| 610 | 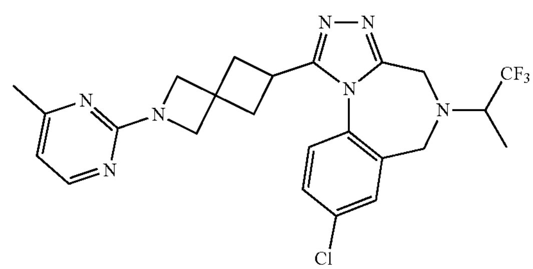 [SMILES: Cc1ccnc(N2CC3(CC(c4nnc5n4-c4ccc(Cl)cc4CN(C(C)C(F)(F)F)C5)C3)C2)n1] |
| 611 | 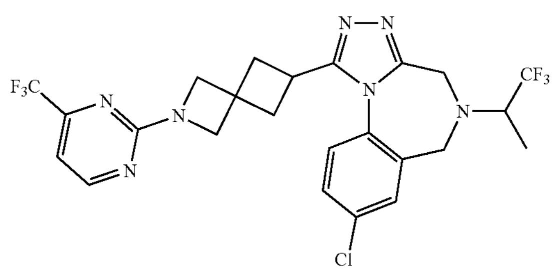 [SMILES: CC(N1Cc2cc(Cl)ccc2-n2c(nnc2C2CC3(C2)CN(c2nccc(C(F)(F)F)n2)C3)C1)C(F)(F)F] |
| 612 | 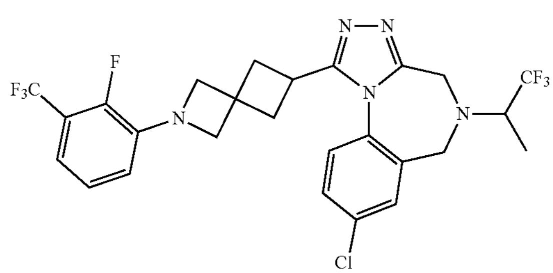 [SMILES: CC(N1Cc2cc(Cl)ccc2-n2c(nnc2C2CC3(C2)CN(c2cccc(C(F)(F)F)c2F)C3)C1)C(F)(F)F] |

TABLE 1-continued

Representative Compounds

| Cmpd. No. | Structure |
|---|---|
| 613 | 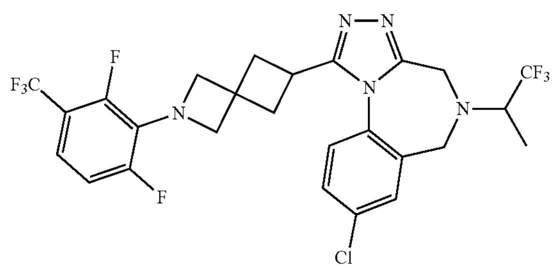 [SMILES: CC(N1Cc2cc(Cl)ccc2-n2c(nnc2C2CC3(C2)CN(c2c(F)ccc(C(F)(F)F)c2F)C3)C1)C(F)(F)F] |
| 614 | 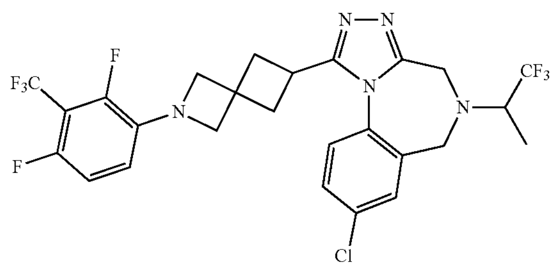 [SMILES: CC(N1Cc2cc(Cl)ccc2-n2c(nnc2C2CC3(C2)CN(c2ccc(F)c(C(F)(F)F)c2F)C3)C1)C(F)(F)F] |
| 615 | 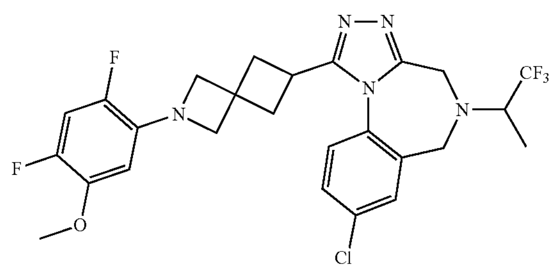 [SMILES: COc1cc(N2CC3(CC(c4nnc5n4-c4ccc(Cl)cc4CN(C(C)C(F)(F)F)C5)C3)C2)c(F)cc1F] |
| 616 | 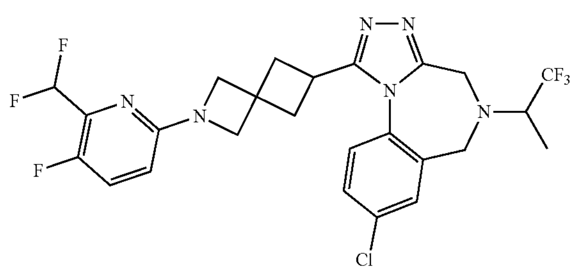 [SMILES: CC(N1Cc2cc(Cl)ccc2-n2c(nnc2C2CC3(C2)CN(c2ccc(F)c(C(F)F)n2)C3)C1)C(F)(F)F] |
| 617 | 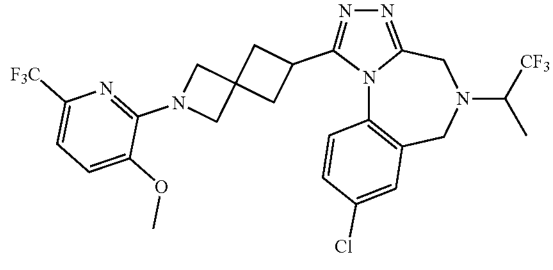 [SMILES: COc1ccc(C(F)(F)F)nc1N1CC2(CC(c3nnc4n3-c3ccc(Cl)cc3CN(C(C)C(F)(F)F)C4)C2)C1] |

TABLE 1-continued

Representative Compounds

| Cmpd. No. | Structure |
|---|---|
| 618 | 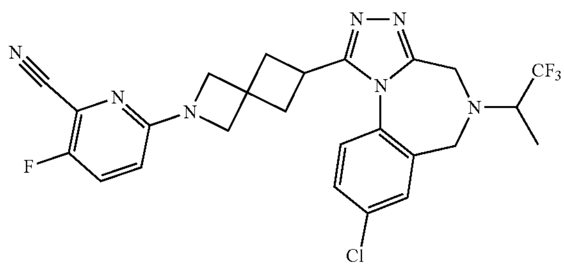 [SMILES: CC(N1Cc2cc(Cl)ccc2-n2c(nnc2C2CC3(C2)CN(c2ccc(F)c(C#N)n2)C3)C1)C(F)(F)F] |
| 619 | 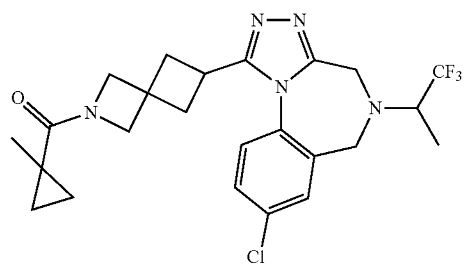 [SMILES: CC(N1Cc2cc(Cl)ccc2-n2c(nnc2C2CC3(C2)CN(C(=O)C2(C)CC2)C3)C1)C(F)(F)F] |
| 620 | 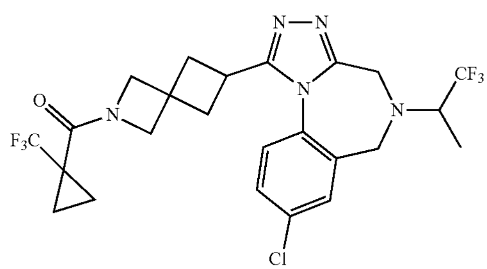 [SMILES: CC(N1Cc2cc(Cl)ccc2-n2c(nnc2C2CC3(C2)CN(C(=O)C2(C(F)(F)F)CC2)C3)C1)C(F)(F)F] |
| 621 | 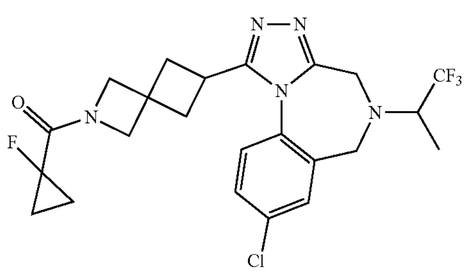 [SMILES: CC(N1Cc2cc(Cl)ccc2-n2c(nnc2C2CC3(C2)CN(C(=O)C2(F)CC2)C3)C1)C(F)(F)F] |
| 622 | 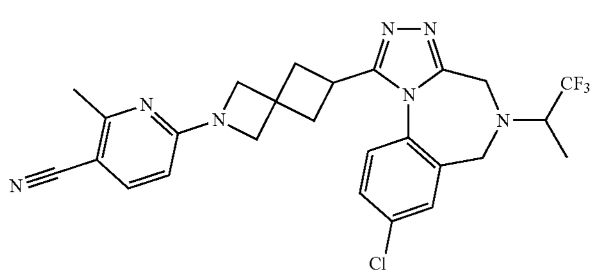 [SMILES: Cc1nc(N2CC3(CC(c4nnc5n4-c4ccc(Cl)cc4CN(C(C)C(F)(F)F)C5)C3)C2)ccc1C#N] |

TABLE 1-continued

Representative Compounds

| Cmpd. No. | Structure |
|---|---|
| 623 | 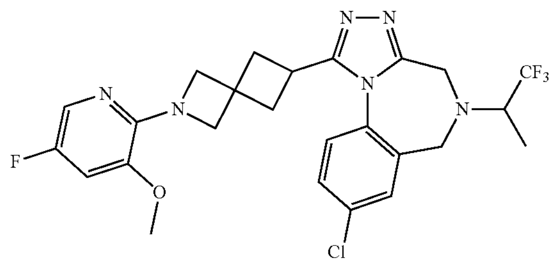 [SMILES: COc1cc(F)cnc1N1CC2(CC(c3nnc4n3-c3ccc(Cl)cc3CN(C(C)C(F)(F)F)C4)C2)C1] |
| 624 | 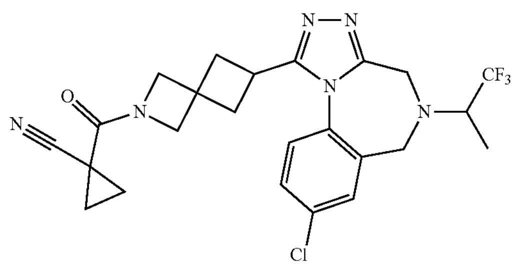 [SMILES: CC(N1Cc2cc(Cl)ccc2-n2c(nnc2C2CC3(C2)CN(C(=O)C2(C#N)CC2)C3)C1)C(F)(F)F] |
| 625 | 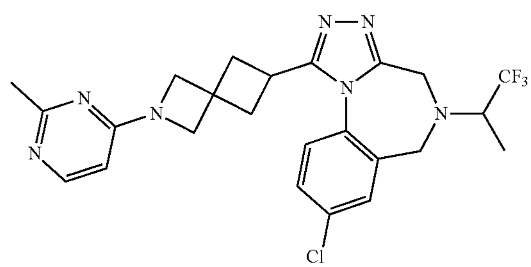 [SMILES: Cc1nccc(N2CC3(CC(c4nnc5n4-c4ccc(Cl)cc4CN(C(C)C(F)(F)F)C5)C3)C2)n1] |
| 626 | 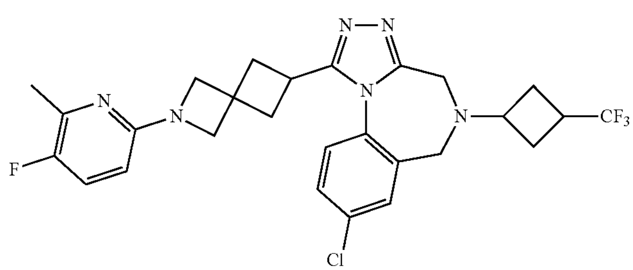 [SMILES: Cc1nc(N2CC3(CC(c4nnc5n4-c4ccc(Cl)cc4CN(C4CC(C(F)(F)F)C4)C5)C3)C2)ccc1F] |
| 627 | 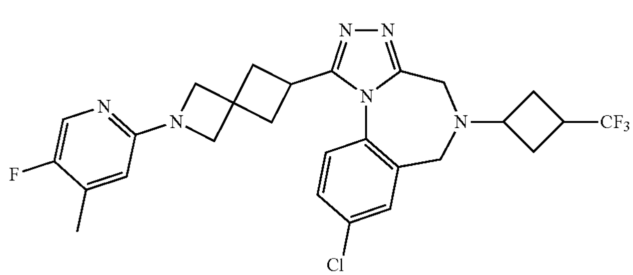 [SMILES: Cc1cc(N2CC3(CC(c4nnc5n4-c4ccc(Cl)cc4CN(C4CC(C(F)(F)F)C4)C5)C3)C2)ncc1F] |

TABLE 1-continued

Representative Compounds

| Cmpd. No. | Structure |
|---|---|
| 628 | 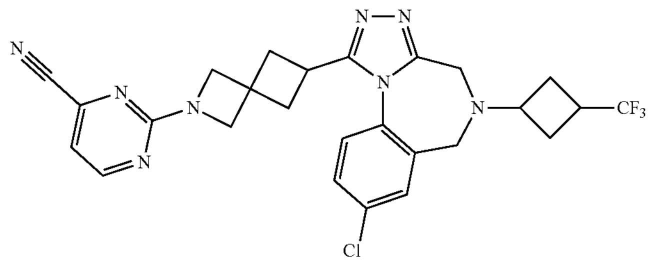 [SMILES: N#Cc1ccnc(N2CC3(CC(c4nnc5n4-c4ccc(Cl)cc4CN(C4CC(C(F)(F)F)C4)C5)C3)C2)n1] |
| 629 | 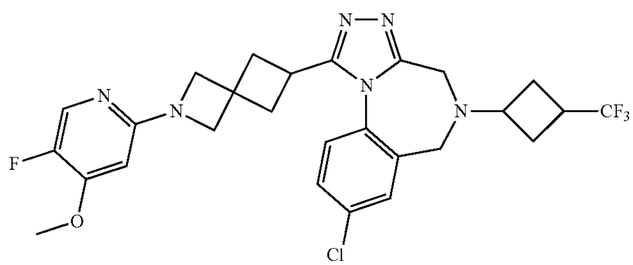 [SMILES: COc1cc(N2CC3(CC(c4nnc5n4-c4ccc(Cl)cc4CN(C4CC(C(F)(F)F)C4)C5)C3)C2)ncc1F] |
| 630 | 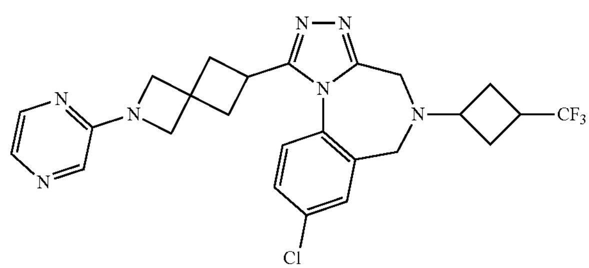 [SMILES: FC(F)(F)C1CC(N2Cc3cc(Cl)ccc3-n3c(nnc3C3CC4(C3)CN(c3cnccn3)C4)C2)C1] |
| 631 | 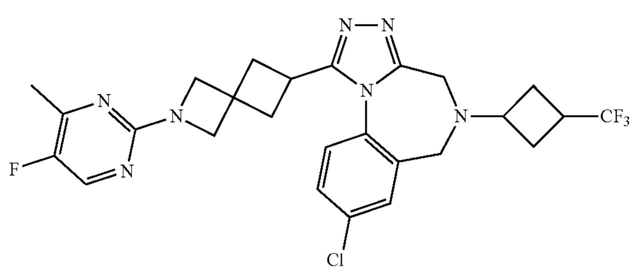 [SMILES: Cc1nc(N2CC3(CC(c4nnc5n4-c4ccc(Cl)cc4CN(C4CC(C(F)(F)F)C4)C5)C3)C2)ncc1F] |
| 632 | 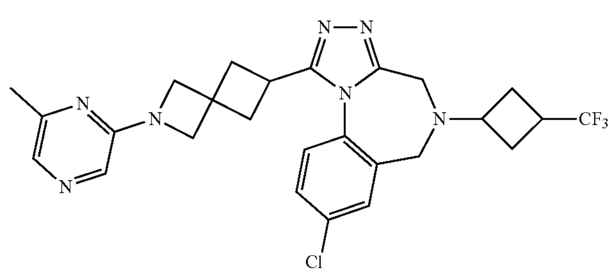 [SMILES: Cc1cncc(N2CC3(CC(c4nnc5n4-c4ccc(Cl)cc4CN(C4CC(C(F)(F)F)C4)C5)C3)C2)n1] |

TABLE 1-continued

Representative Compounds

| Cmpd. No. | Structure |
|---|---|
| 633 | 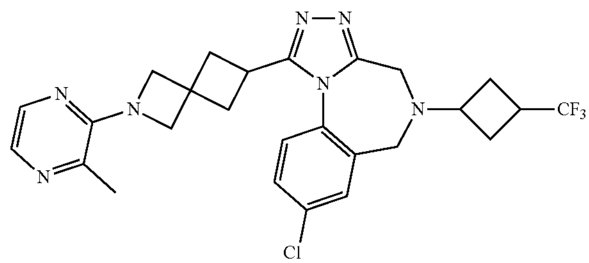 [SMILES: Cc1nccnc1N1CC2(CC(c3nnc4n3-c3ccc(Cl)cc3CN(C3CC(C(F)(F)F)C3)C4)C2)C1] |
| 634 | 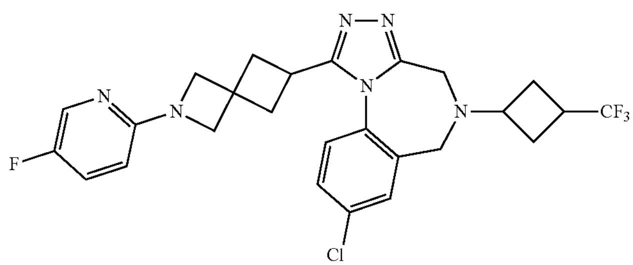 [SMILES: Fc1ccc(N2CC3(CC(c4nnc5n4-c4ccc(Cl)cc4CN(C4CC(C(F)(F)F)C4)C5)C3)C2)nc1] |
| 635 | 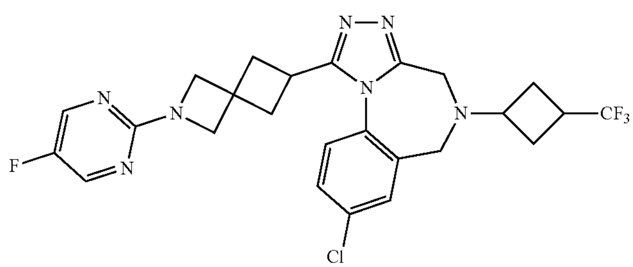 [SMILES: Fc1cnc(N2CC3(CC(c4nnc5n4-c4ccc(Cl)cc4CN(C4CC(C(F)(F)F)C4)C5)C3)C2)nc1] |
| 636 | 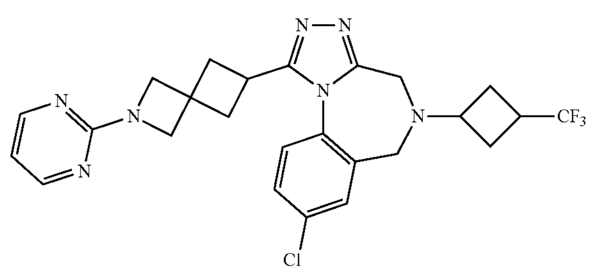 [SMILES: FC(F)(F)C1CC(N2Cc3cc(Cl)ccc3-n3c(nnc3C3CC4(C3)CN(c3ncccn3)C4)C2)C1] |
| 637 | 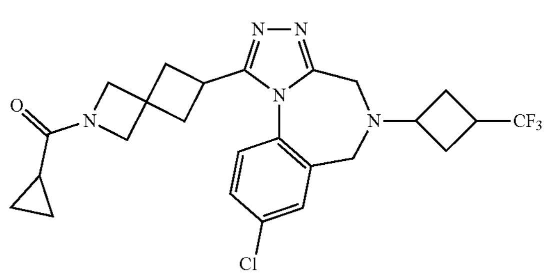 [SMILES: O=C(C1CC1)N1CC2(CC(c3nnc4n3-c3ccc(Cl)cc3CN(C3CC(C(F)(F)F)C3)C4)C2)C1] |

TABLE 1-continued

Representative Compounds

| Cmpd. No. | Structure |
|---|---|
| 638 | 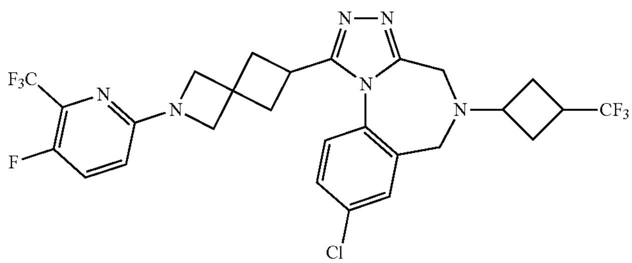 [SMILES: Fc1ccc(N2CC3(CC(c4nnc5n4-c4ccc(Cl)cc4CN(C4CC(C(F)(F)F)C4)C5)C3)C2)nc1C(F)(F)F] |
| 639 | 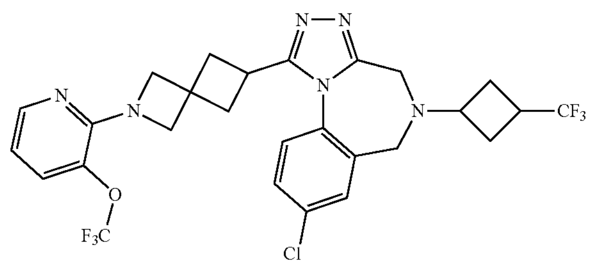 [SMILES: FC(F)(F)Oc1cccnc1N1CC2(CC(c3nnc4n3-c3ccc(Cl)cc3CN(C3CC(C(F)(F)F)C3)C4)C2)C1] |
| 640 | 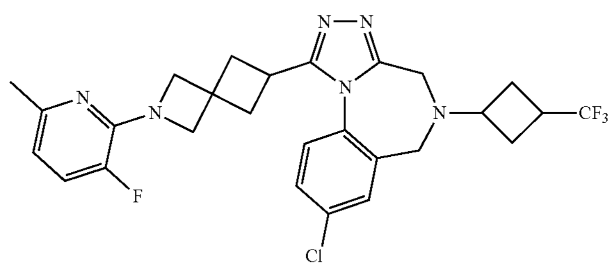 [SMILES: Cc1ccc(F)c(N2CC3(CC(c4nnc5n4-c4ccc(Cl)cc4CN(C4CC(C(F)(F)F)C4)C5)C3)C2)n1] |
| 641 | 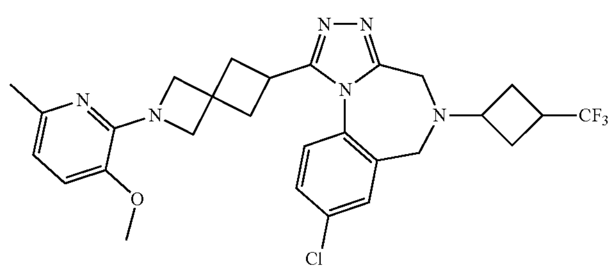 [SMILES: COc1ccc(C)nc1N1CC2(CC(c3nnc4n3-c3ccc(Cl)cc3CN(C3CC(C(F)(F)F)C3)C4)C2)C1] |
| 642 | 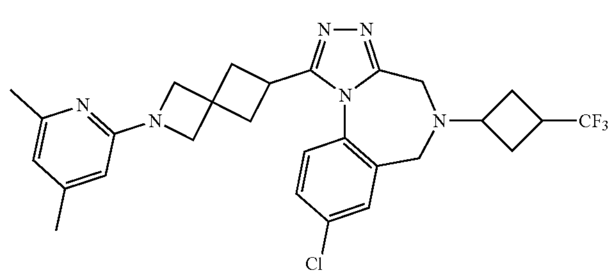 [SMILES: Cc1cc(C)nc(N2CC3(CC(c4nnc5n4-c4ccc(Cl)cc4CN(C4CC(C(F)(F)F)C4)C5)C3)C2)c1] |

TABLE 1-continued

Representative Compounds

| Cmpd. No. | Structure |
|---|---|
| 643 | 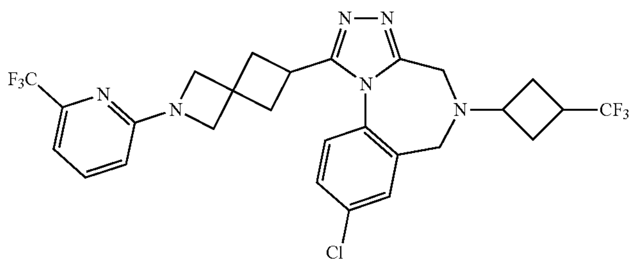 |
| 644 | 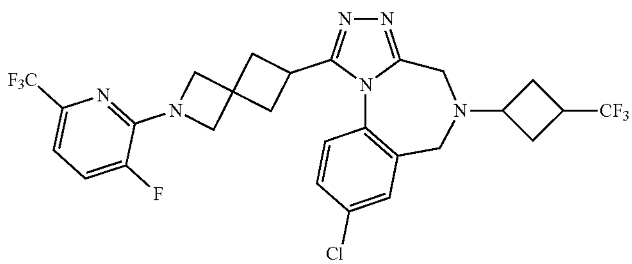 [SMILES: Fc1ccc(C(F)(F)F)nc1N1CC2(CC(c3nnc4n3-c3ccc(Cl)cc3CN(C3CC(C(F)(F)F)C3)C4)C2)C1] |
| 645 | 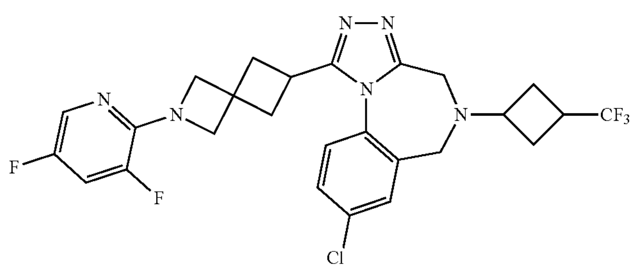 |
| 646 | 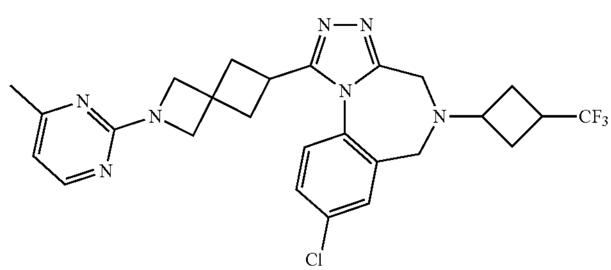 [SMILES: Cc1ccnc(N2CC3(CC(c4nnc5n4-c4ccc(Cl)cc4CN(C4CC(C(F)(F)F)C4)C5)C3)C2)n1] |
| 647 | 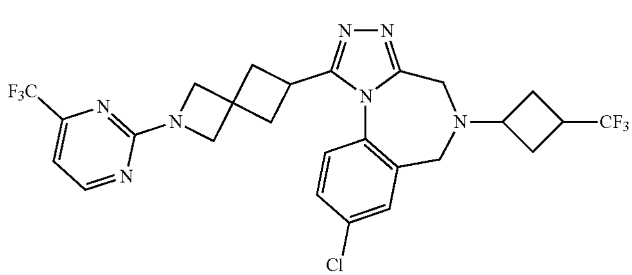 |

TABLE 1-continued
Representative Compounds
| Cmpd. No. | Structure |
|---|---|
| 648 | 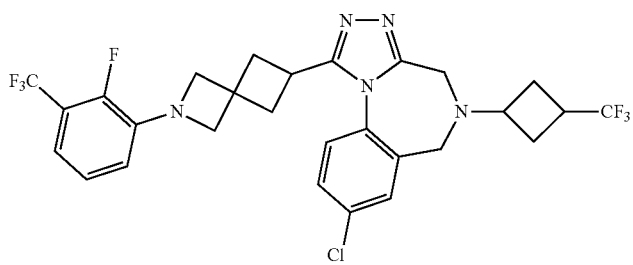 [SMILES: Fc1c(N2CC3(CC(c4nnc5n4-c4ccc(Cl)cc4CN(C4CC(C(F)(F)F)C4)C5)C3)C2)cccc1C(F)(F)F] |
| 649 | 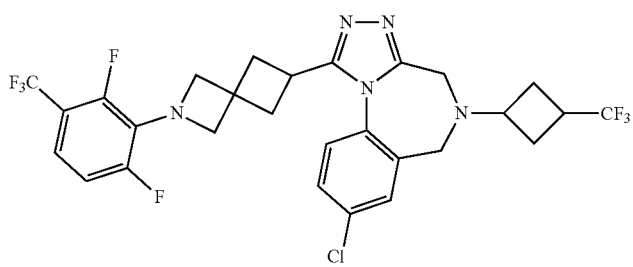 [SMILES: Fc1ccc(C(F)(F)F)c(F)c1N1CC2(CC(c3nnc4n3-c3ccc(Cl)cc3CN(C3CC(C(F)(F)F)C3)C4)C2)C1] |
| 650 | 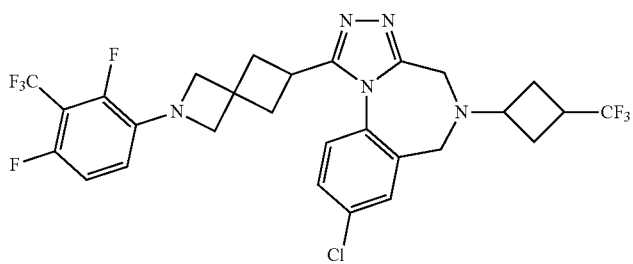 [SMILES: Fc1ccc(N2CC3(CC(c4nnc5n4-c4ccc(Cl)cc4CN(C4CC(C(F)(F)F)C4)C5)C3)C2)c(F)c1C(F)(F)F] |
| 651 | 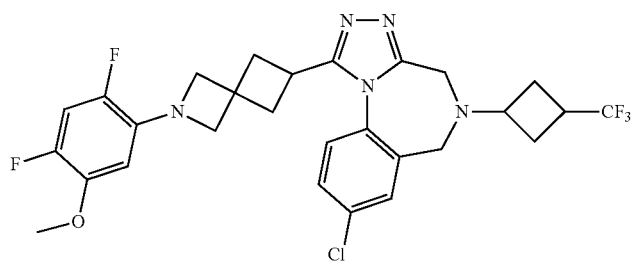 [SMILES: COc1cc(N2CC3(CC(c4nnc5n4-c4ccc(Cl)cc4CN(C4CC(C(F)(F)F)C4)C5)C3)C2)c(F)cc1F] |
| 652 | 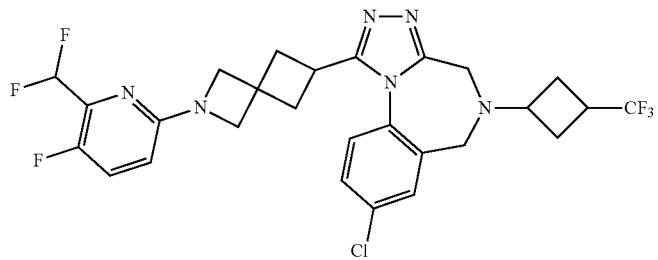 [SMILES: Fc1ccc(N2CC3(CC(c4nnc5n4-c4ccc(Cl)cc4CN(C4CC(C(F)(F)F)C4)C5)C3)C2)nc1C(F)F] |

TABLE 1-continued

Representative Compounds

| Cmpd. No. | Structure |
|---|---|
| 653 | 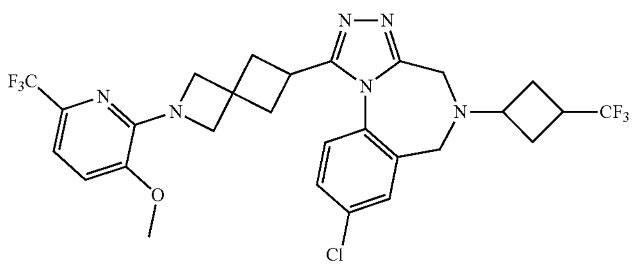 [SMILES: COc1ccc(C(F)(F)F)nc1N1CC2(CC(c3nnc4n3-c3ccc(Cl)cc3CN(C3CC(C(F)(F)F)C3)C4)C2)C1] |
| 654 | 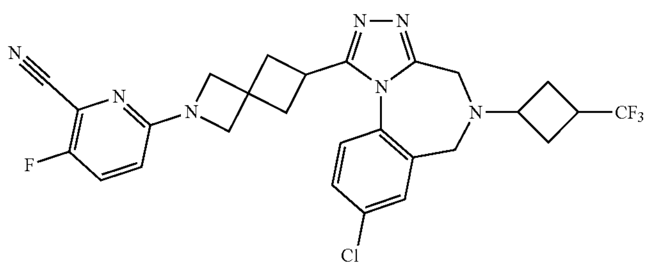 [SMILES: N#Cc1nc(N2CC3(CC(c4nnc5n4-c4ccc(Cl)cc4CN(C4CC(C(F)(F)F)C4)C5)C3)C2)ccc1F] |
| 655 | 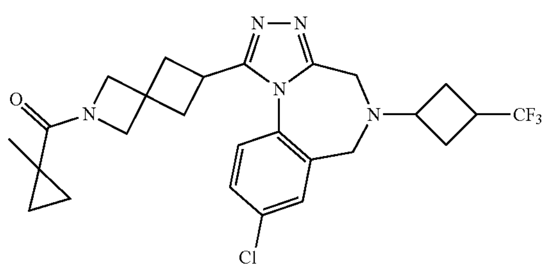 [SMILES: CC1(C(=O)N2CC3(CC(c4nnc5n4-c4ccc(Cl)cc4CN(C4CC(C(F)(F)F)C4)C5)C3)C2)CC1] |
| 656 | 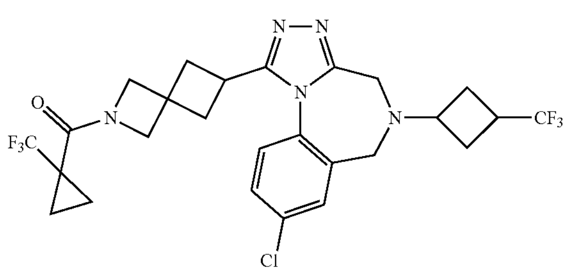 [SMILES: O=C(N1CC2(CC(c3nnc4n3-c3ccc(Cl)cc3CN(C3CC(C(F)(F)F)C3)C4)C2)C1)C1(C(F)(F)F)CC1] |
| 657 | 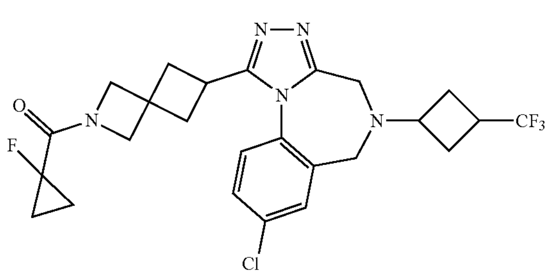 [SMILES: O=C(N1CC2(CC(c3nnc4n3-c3ccc(Cl)cc3CN(C3CC(C(F)(F)F)C3)C4)C2)C1)C1(F)CC1] |

TABLE 1-continued

Representative Compounds

| Cmpd. No. | Structure |
|---|---|
| 658 | 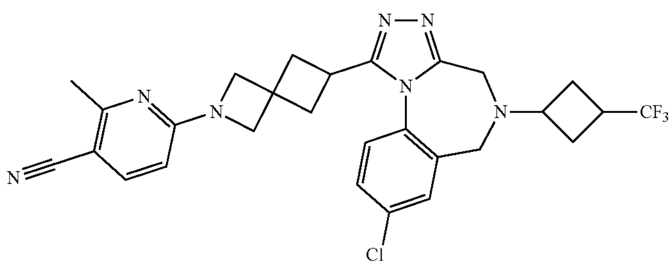 [SMILES: Cc1nc(N2CC3(CC(c4nnc5n4-c4ccc(Cl)cc4CN(C4CC(C(F)(F)F)C4)C5)C3)C2)ccc1C#N] |
| 659 | 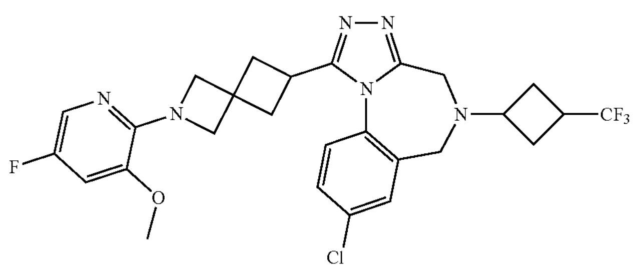 [SMILES: COc1cc(F)cnc1N1CC2(CC(c3nnc4n3-c3ccc(Cl)cc3CN(C3CC(C(F)(F)F)C3)C4)C2)C1] |
| 660 | 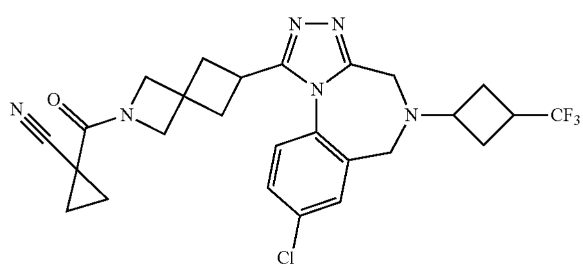 [SMILES: N#CC1(C(=O)N2CC3(CC(c4nnc5n4-c4ccc(Cl)cc4CN(C4CC(C(F)(F)F)C4)C5)C3)C2)CC1] |
| 661 | 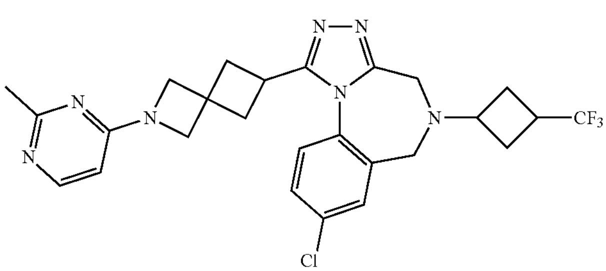 [SMILES: Cc1nccc(N2CC3(CC(c4nnc5n4-c4ccc(Cl)cc4CN(C4CC(C(F)(F)F)C4)C5)C3)C2)n1] |
| 662 | 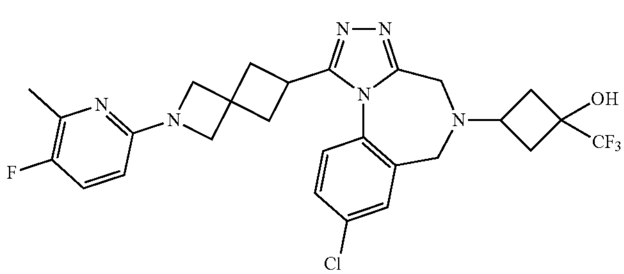 |

TABLE 1-continued

Representative Compounds

| Cmpd. No. | Structure |
|---|---|
| 663 | 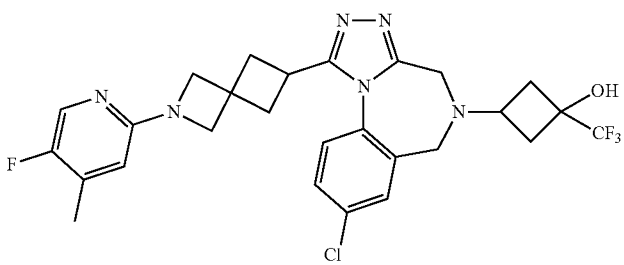 [SMILES: Cc1cc(N2CC3(CC(c4nnc5n4-c4ccc(Cl)cc4CN(C4CC(O)(C(F)(F)F)C4)C5)C3)C2)ncc1F] |
| 664 | 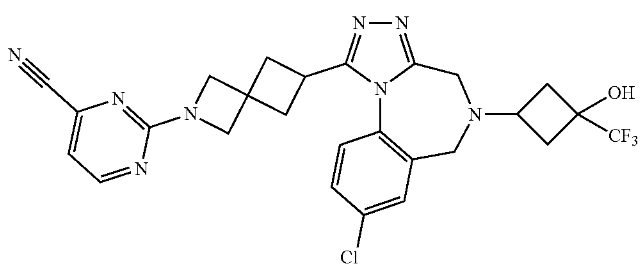 [SMILES: N#Cc1ccnc(N2CC3(CC(c4nnc5n4-c4ccc(Cl)cc4CN(C4CC(O)(C(F)(F)F)C4)C5)C3)C2)n1] |
| 665 | 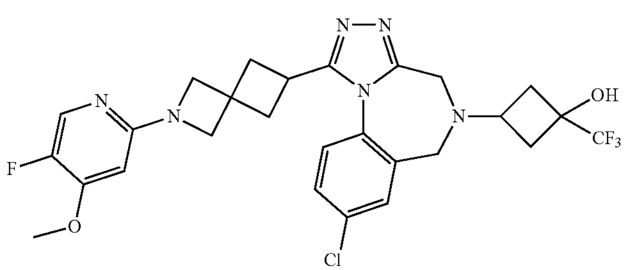 [SMILES: COc1cc(N2CC3(CC(c4nnc5n4-c4ccc(Cl)cc4CN(C4CC(O)(C(F)(F)F)C4)C5)C3)C2)ncc1F] |
| 667 | 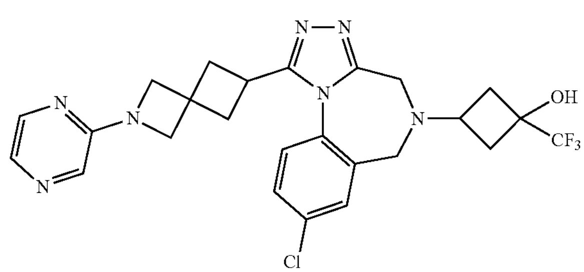 [SMILES: OC1(C(F)(F)F)CC(N2Cc3cc(Cl)ccc3-n3c(nnc3C3CC4(C3)CN(c3cnccn3)C4)C2)C1] |
| 668 | 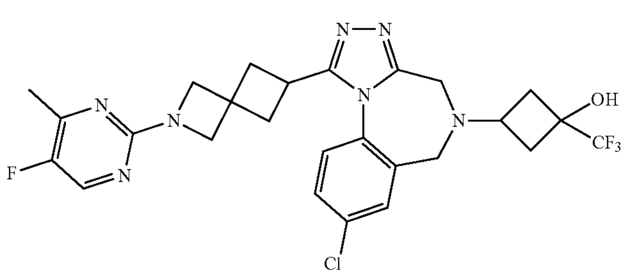 [SMILES: Cc1nc(N2CC3(CC(c4nnc5n4-c4ccc(Cl)cc4CN(C4CC(O)(C(F)(F)F)C4)C5)C3)C2)ncc1F] |

TABLE 1-continued

Representative Compounds

| Cmpd. No. | Structure |
|---|---|
| 669 | 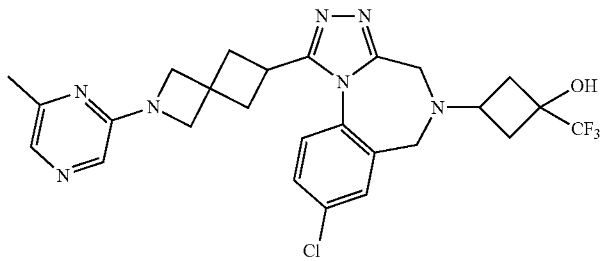 [SMILES: Cc1cncc(N2CC3(CC(c4nnc5n4-c4ccc(Cl)cc4CN(C4CC(O)(C(F)(F)F)C4)C5)C3)C2)n1] |
| 670 | 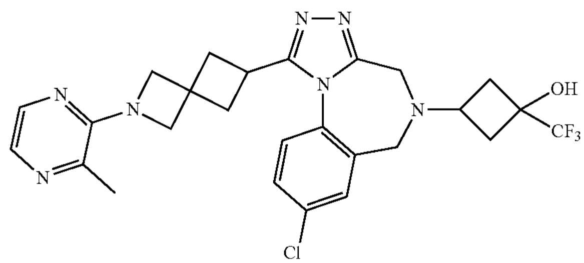 [SMILES: Cc1nccnc1N1CC2(CC(c3nnc4n3-c3ccc(Cl)cc3CN(C3CC(O)(C(F)(F)F)C3)C4)C2)C1] |
| 671 | 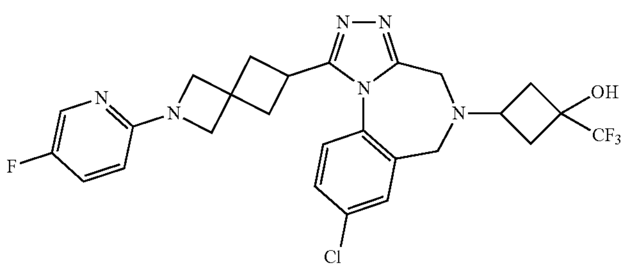 |
| 672 | 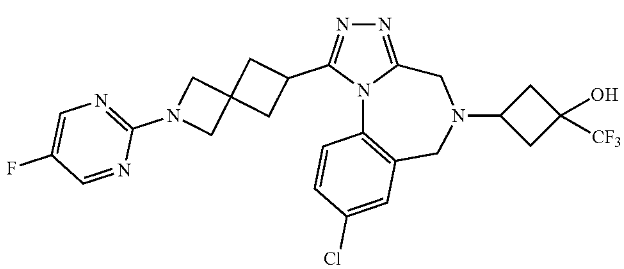 [SMILES: OC1(C(F)(F)F)CC(N2Cc3cc(Cl)ccc3-n3c(nnc3C3CC4(C3)CN(c3ncc(F)cn3)C4)C2)C1] |
| 673 | 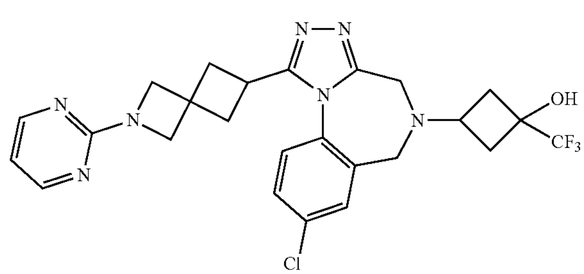 [SMILES: OC1(C(F)(F)F)CC(N2Cc3cc(Cl)ccc3-n3c(nnc3C3CC4(C3)CN(c3ncccn3)C4)C2)C1] |

TABLE 1-continued
Representative Compounds
| Cmpd. No. | Structure |
|---|---|
| 674 | 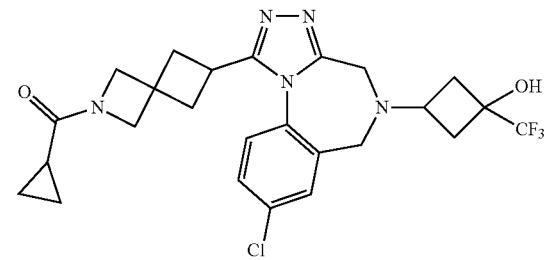 [SMILES: O=C(C1CC1)N1CC2(CC(c3nnc4n3-c3ccc(Cl)cc3CN(C3CC(O)(C(F)(F)F)C3)C4)C2)C1] |
| 675 | 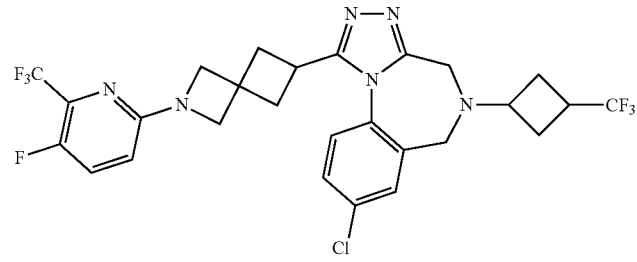 |
| 676 | 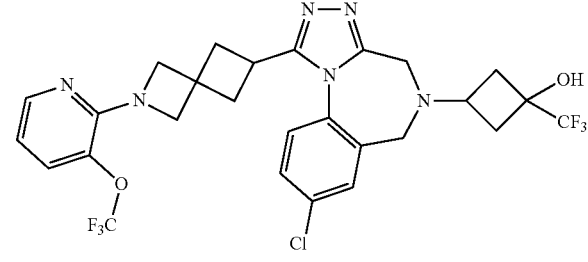 [SMILES: OC1(C(F)(F)F)CC(N2Cc3cc(Cl)ccc3-n3c(nnc3C3CC4(C3)CN(c3ncccc3OC(F)(F)F)C4)C2)C1] |
| 677 | 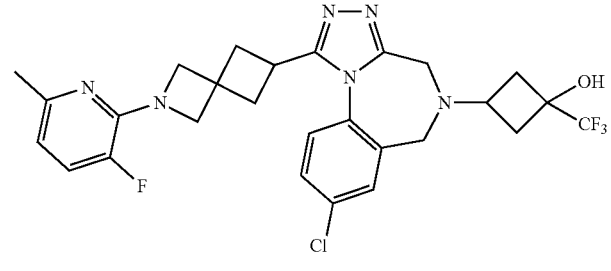 [SMILES: Cc1ccc(F)c(N2CC3(CC(c4nnc5n4-c4ccc(Cl)cc4CN(C4CC(O)(C(F)(F)F)C4)C5)C3)C2)n1] |
| 678 | 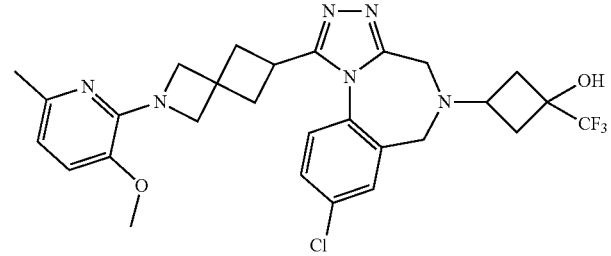 [SMILES: COc1ccc(C)nc1N1CC2(CC(c3nnc4n3-c3ccc(Cl)cc3CN(C3CC(O)(C(F)(F)F)C3)C4)C2)C1] |

TABLE 1-continued

Representative Compounds

| Cmpd. No. | Structure |
|---|---|
| 679 | 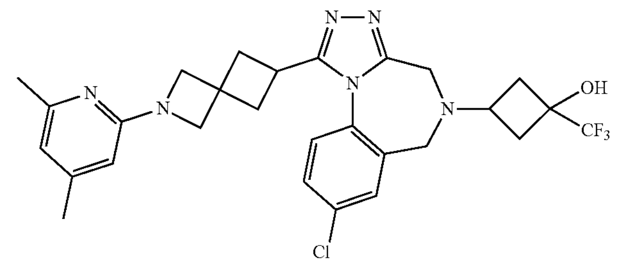 [SMILES: Cc1cc(C)nc(N2CC3(CC(c4nnc5n4-c4ccc(Cl)cc4CN(C4CC(O)(C(F)(F)F)C4)C5)C3)C2)c1] |
| 680 | 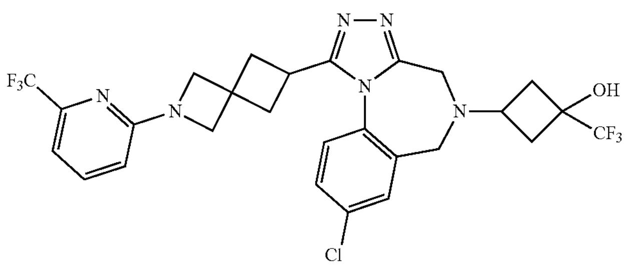 [SMILES: OC1(C(F)(F)F)CC(N2Cc3cc(Cl)ccc3-n3c(nnc3C3CC4(C3)CN(c3cccc(C(F)(F)F)n3)C4)C2)C1] |
| 681 | 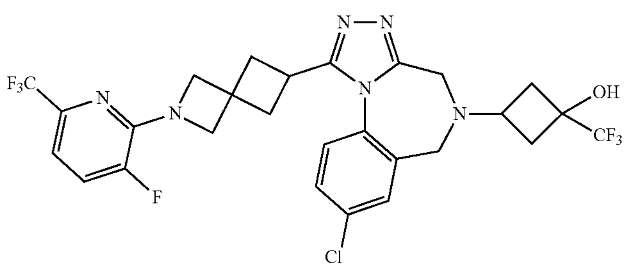 [SMILES: OC1(C(F)(F)F)CC(N2Cc3cc(Cl)ccc3-n3c(nnc3C3CC4(C3)CN(c3nc(C(F)(F)F)ccc3F)C4)C2)C1] |
| 682 | 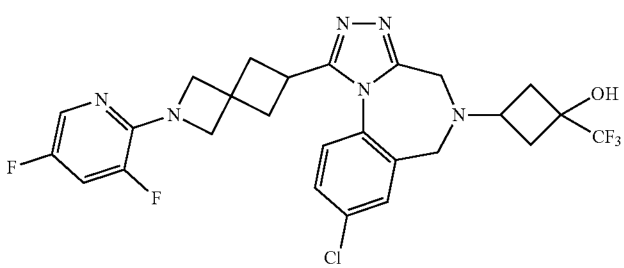 |
| 683 | 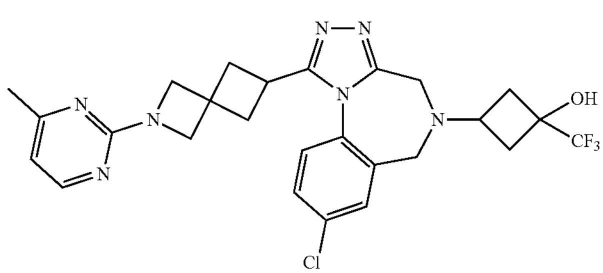 [SMILES: Cc1ccnc(N2CC3(CC(c4nnc5n4-c4ccc(Cl)cc4CN(C4CC(O)(C(F)(F)F)C4)C5)C3)C2)n1] |

TABLE 1-continued

Representative Compounds

| Cmpd. No. | Structure |
|---|---|
| 684 | 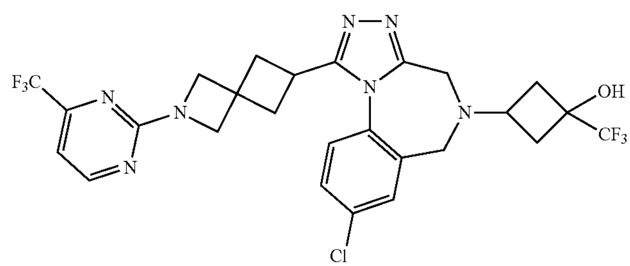 [SMILES: OC1(C(F)(F)F)CC(N2Cc3cc(Cl)ccc3-n3c(nnc3C3CC4(C3)CN(c3nccc(C(F)(F)F)n3)C4)C2)C1] |
| 685 | 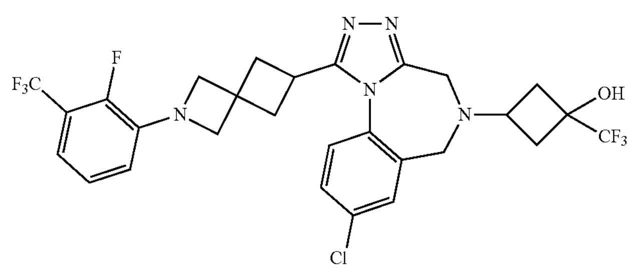 [SMILES: OC1(C(F)(F)F)CC(N2Cc3cc(Cl)ccc3-n3c(nnc3C3CC4(C3)CN(c3cccc(C(F)(F)F)c3F)C4)C2)C1] |
| 686 | 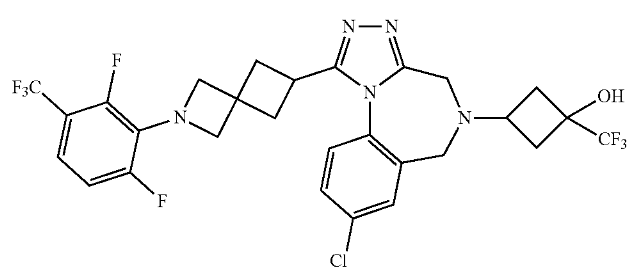 [SMILES: OC1(C(F)(F)F)CC(N2Cc3cc(Cl)ccc3-n3c(nnc3C3CC4(C3)CN(c3c(F)ccc(C(F)(F)F)c3F)C4)C2)C1] |
| 687 | 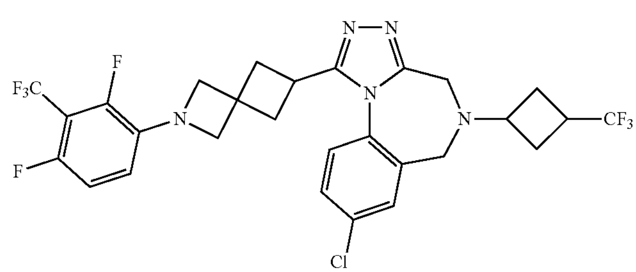 [SMILES: Fc1ccc(N2CC3(CC(c4nnc5n4-c4ccc(Cl)cc4CN(C4CC(C(F)(F)F)C4)C5)C3)C2)c(F)c1C(F)(F)F] |
| 688 | 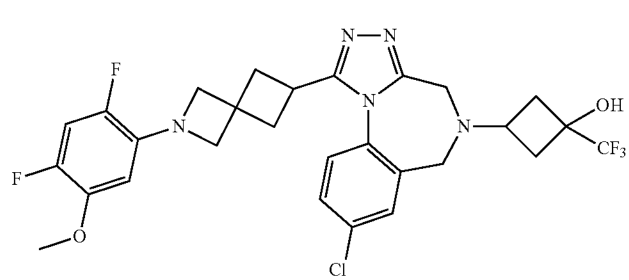 [SMILES: COc1cc(N2CC3(CC(c4nnc5n4-c4ccc(Cl)cc4CN(C4CC(O)(C(F)(F)F)C4)C5)C3)C2)c(F)cc1F] |

TABLE 1-continued

Representative Compounds

| Cmpd. No. | Structure |
|---|---|
| 689 | 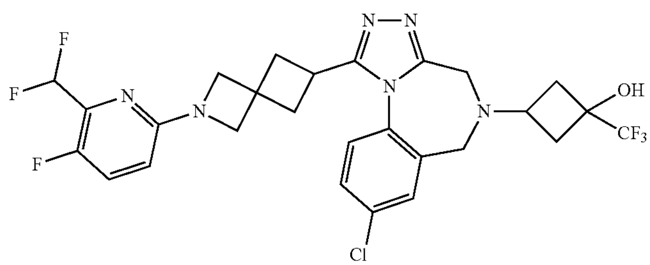 [SMILES: OC1(C(F)(F)F)CC(N2Cc3cc(Cl)ccc3-n3c(nnc3C3CC4(C3)CN(c3ccc(F)c(C(F)F)n3)C4)C2)C1] |
| 690 | 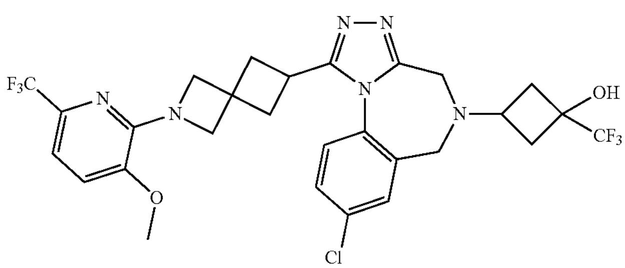 [SMILES: COc1ccc(C(F)(F)F)nc1N1CC2(CC(c3nnc4n3-c3ccc(Cl)cc3CN(C3CC(O)(C(F)(F)F)C3)C4)C2)C1] |
| 691 | 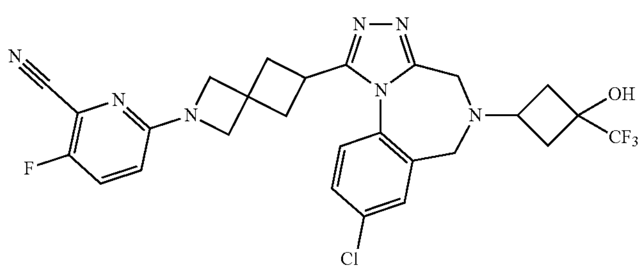 [SMILES: N#Cc1nc(N2CC3(CC(c4nnc5n4-c4ccc(Cl)cc4CN(C4CC(O)(C(F)(F)F)C4)C5)C3)C2)ccc1F] |
| 692 | 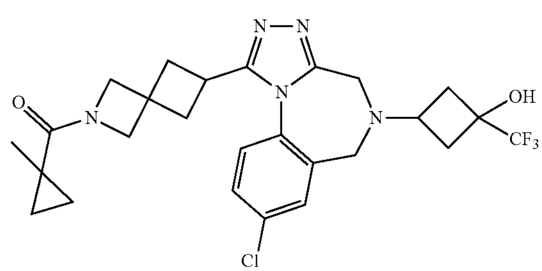 [SMILES: CC1(C(=O)N2CC3(CC(c4nnc5n4-c4ccc(Cl)cc4CN(C4CC(O)(C(F)(F)F)C4)C5)C3)C2)CC1] |
| 693 | 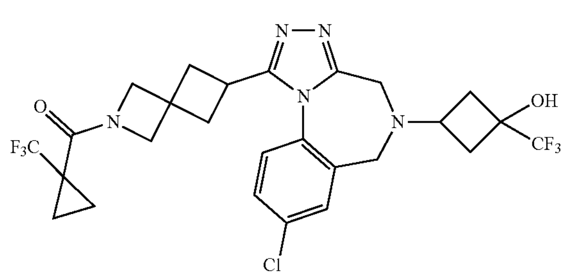 [SMILES: O=C(N1CC2(CC(c3nnc4n3-c3ccc(Cl)cc3CN(C3CC(O)(C(F)(F)F)C3)C4)C2)C1)C1(C(F)(F)F)CC1] |

TABLE 1-continued

Representative Compounds

| Cmpd. No. | Structure |
|---|---|
| 694 | 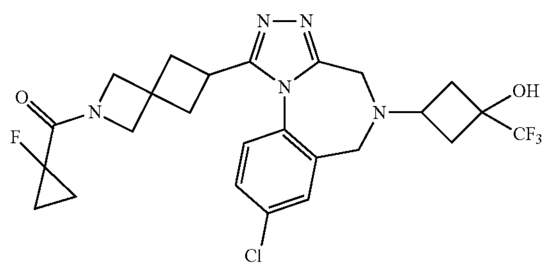 [SMILES: O=C(N1CC2(CC(c3nnc4n3-c3ccc(Cl)cc3CN(C3CC(O)(C(F)(F)F)C3)C4)C2)C1)C1(F)CC1] |
| 695 | 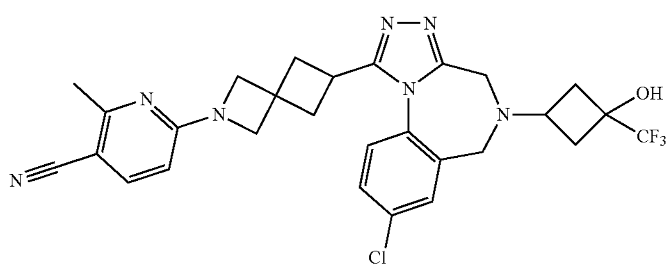 [SMILES: Cc1nc(N2CC3(CC(c4nnc5n4-c4ccc(Cl)cc4CN(C4CC(O)(C(F)(F)F)C4)C5)C3)C2)ccc1C#N] |
| 696 | 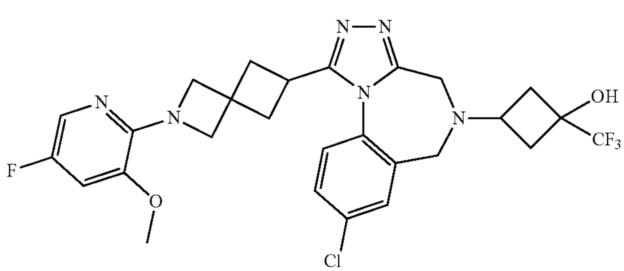 [SMILES: COc1cc(F)cnc1N1CC2(CC(c3nnc4n3-c3ccc(Cl)cc3CN(C3CC(O)(C(F)(F)F)C3)C4)C2)C1] |
| 697 | 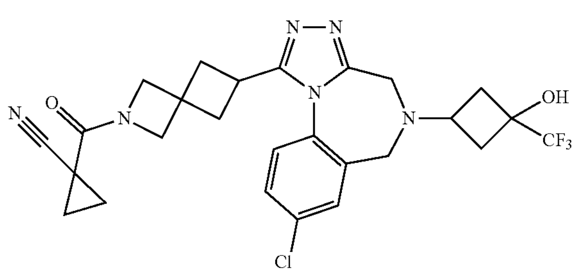 [SMILES: N#CC1(C(=O)N2CC3(CC(c4nnc5n4-c4ccc(Cl)cc4CN(C4CC(O)(C(F)(F)F)C4)C5)C3)C2)CC1] |
| 698 | 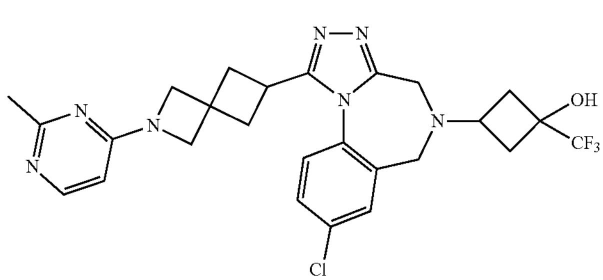 [SMILES: Cc1nccc(N2CC3(CC(c4nnc5n4-c4ccc(Cl)cc4CN(C4CC(O)(C(F)(F)F)C4)C5)C3)C2)n1] |

TABLE 1-continued

Representative Compounds

| Cmpd. No. | Structure |
|---|---|
| 699 | 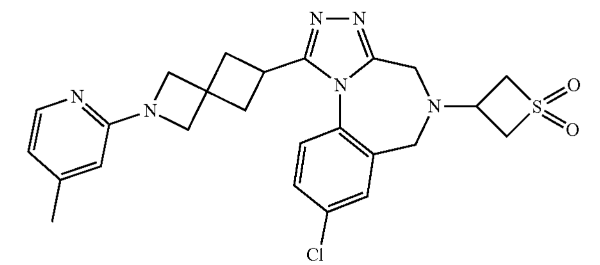 [SMILES: Cc1ccnc(N2CC3(CC(c4nnc5n4-c4ccc(Cl)cc4CN(C4CS(=O)(=O)C4)C5)C3)C2)c1] |
| 700 | 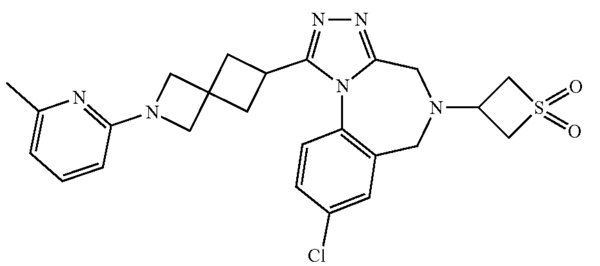 [SMILES: Cc1cccc(N2CC3(CC(c4nnc5n4-c4ccc(Cl)cc4CN(C4CS(=O)(=O)C4)C5)C3)C2)n1] |
| 701 | 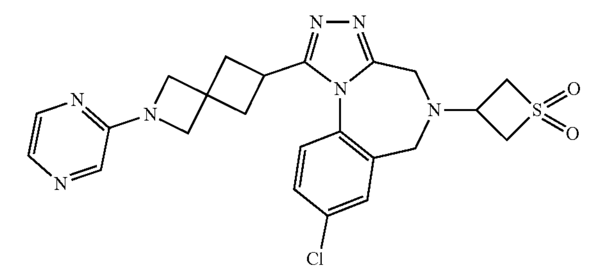 [SMILES: O=S1(=O)CC(N2Cc3cc(Cl)ccc3-n3c(nnc3C3CC4(C3)CN(c3cnccn3)C4)C2)C1] |
| 702 | 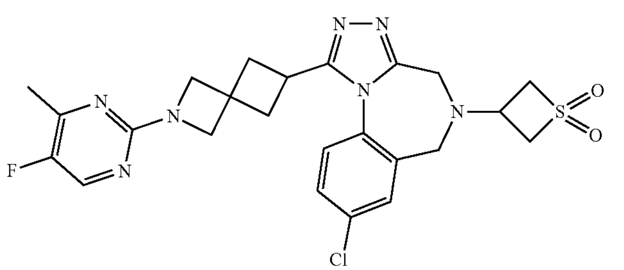 [SMILES: Cc1nc(N2CC3(CC(c4nnc5n4-c4ccc(Cl)cc4CN(C4CS(=O)(=O)C4)C5)C3)C2)ncc1F] |
| 703 | 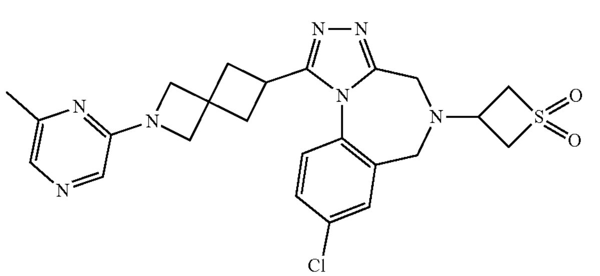 [SMILES: Cc1cncc(N2CC3(CC(c4nnc5n4-c4ccc(Cl)cc4CN(C4CS(=O)(=O)C4)C5)C3)C2)n1] |

TABLE 1-continued

Representative Compounds

| Cmpd. No. | Structure |
|---|---|
| 704 | 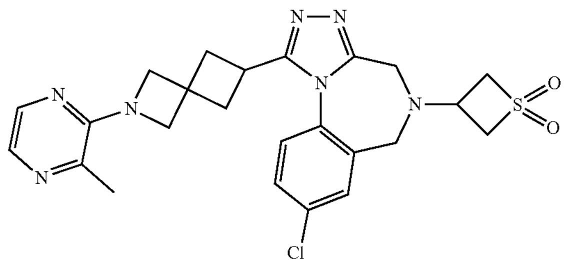 [SMILES: Cc1nccnc1N1CC2(CC(c3nnc4n3-c3ccc(Cl)cc3CN(C3CS(=O)(=O)C3)C4)C2)C1] |
| 705 | 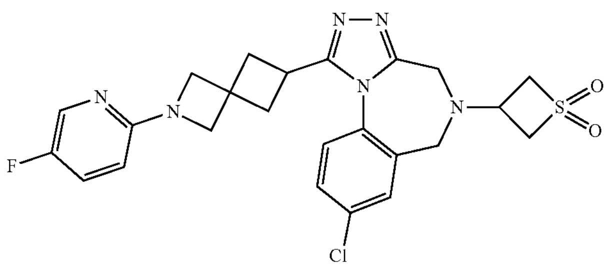 [SMILES: O=S1(=O)CC(N2Cc3cc(Cl)ccc3-n3c(nnc3C3CC4(C3)CN(c3ccc(F)cn3)C4)C2)C1] |
| 706 | 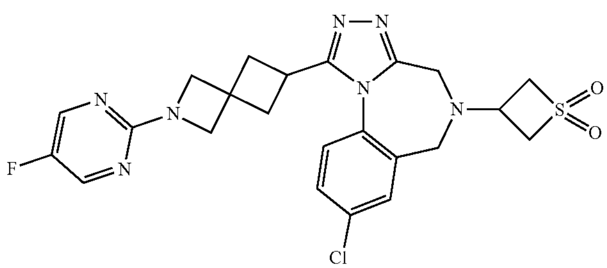 [SMILES: O=S1(=O)CC(N2Cc3cc(Cl)ccc3-n3c(nnc3C3CC4(C3)CN(c3ncc(F)cn3)C4)C2)C1] |
| 707 | 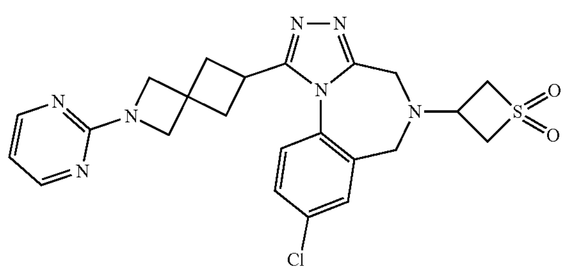 [SMILES: O=S1(=O)CC(N2Cc3cc(Cl)ccc3-n3c(nnc3C3CC4(C3)CN(c3ncccn3)C4)C2)C1] |
| 708 | 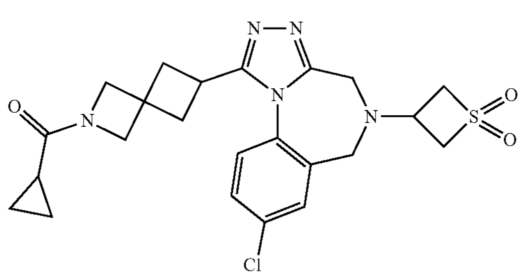 [SMILES: O=C(C1CC1)N1CC2(CC(c3nnc4n3-c3ccc(Cl)cc3CN(C3CS(=O)(=O)C3)C4)C2)C1] |

TABLE 1-continued

Representative Compounds

| Cmpd. No. | Structure |
|---|---|
| 709 | 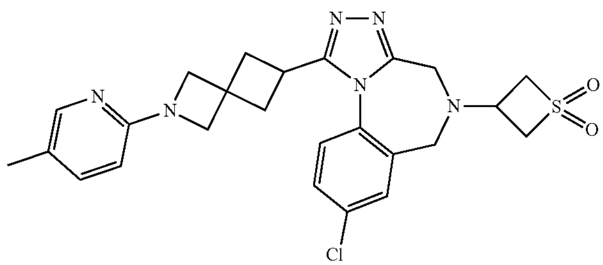 [SMILES: Cc1ccc(N2CC3(CC(c4nnc5n4-c4ccc(Cl)cc4CN(C4CS(=O)(=O)C4)C5)C3)C2)nc1] |
| 710 | 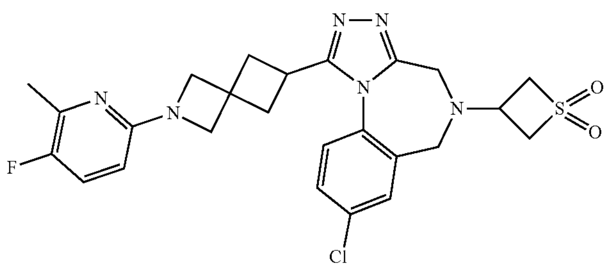 [SMILES: Cc1nc(N2CC3(CC(c4nnc5n4-c4ccc(Cl)cc4CN(C4CS(=O)(=O)C4)C5)C3)C2)ccc1F] |
| 711 | 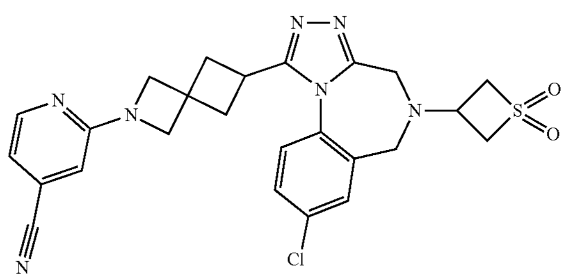 [SMILES: N#Cc1ccnc(N2CC3(CC(c4nnc5n4-c4ccc(Cl)cc4CN(C4CS(=O)(=O)C4)C5)C3)C2)c1] |
| 712 | 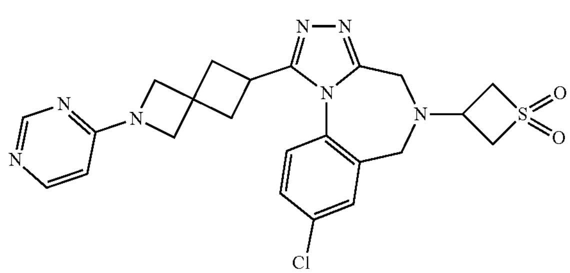 [SMILES: O=S1(=O)CC(N2Cc3cc(Cl)ccc3-n3c(nnc3C3CC4(C3)CN(c3ccncn3)C4)C2)C1] |
| 713 | 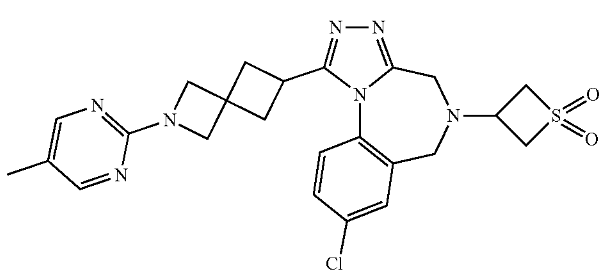 [SMILES: Cc1cnc(N2CC3(CC(c4nnc5n4-c4ccc(Cl)cc4CN(C4CS(=O)(=O)C4)C5)C3)C2)nc1] |

TABLE 1-continued

Representative Compounds

| Cmpd. No. | Structure |
|---|---|
| 714 | 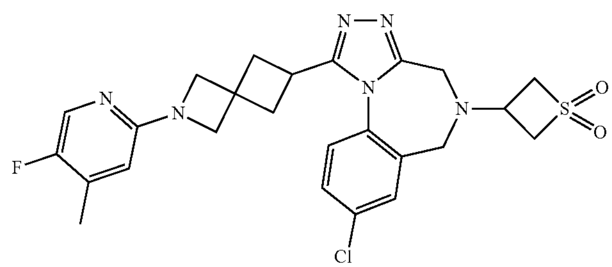 [SMILES: Cc1cc(N2CC3(CC(c4nnc5n4-c4ccc(Cl)cc4CN(C4CS(=O)(=O)C4)C5)C3)C2)ncc1F] |
| 715 | 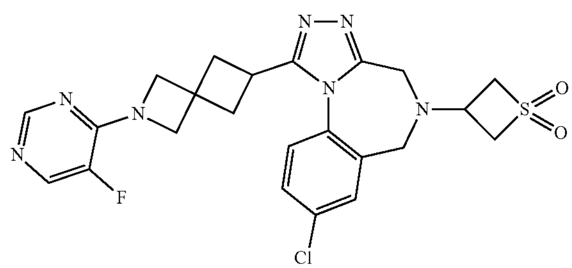 [SMILES: O=S1(=O)CC(N2Cc3cc(Cl)ccc3-n3c(nnc3C3CC4(C3)CN(c3ncncc3F)C4)C2)C1] |
| 716 | 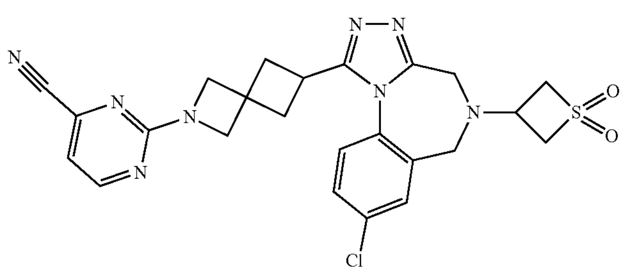 [SMILES: N#Cc1ccnc(N2CC3(CC(c4nnc5n4-c4ccc(Cl)cc4CN(C4CS(=O)(=O)C4)C5)C3)C2)n1] |
| 717 | 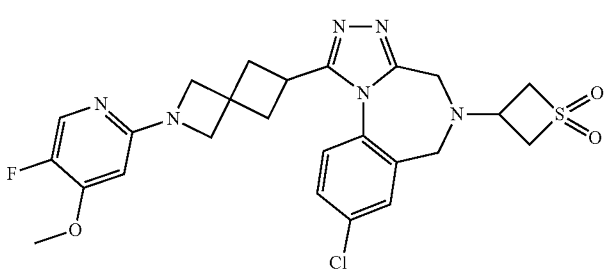 [SMILES: COc1cc(N2CC3(CC(c4nnc5n4-c4ccc(Cl)cc4CN(C4CS(=O)(=O)C4)C5)C3)C2)ncc1F] |
| 718 | 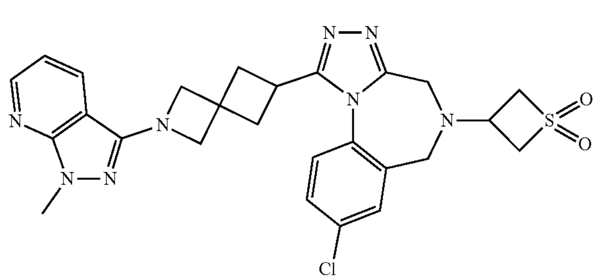 [SMILES: Cn1nc(N2CC3(CC(c4nnc5n4-c4ccc(Cl)cc4CN(C4CS(=O)(=O)C4)C5)C3)C2)c2cccnc21] |

TABLE 1-continued

Representative Compounds

| Cmpd. No. | Structure |
|---|---|
| 719 | 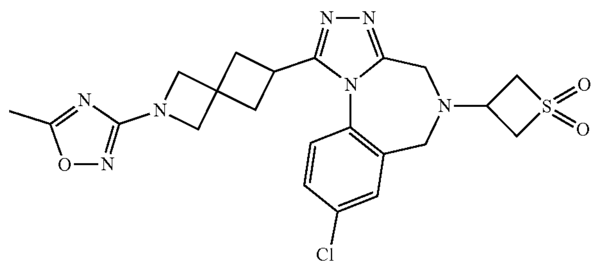 [SMILES: Cc1nc(N2CC3(CC(c4nnc5n4-c4ccc(Cl)cc4CN(C4CS(=O)(=O)C4)C5)C3)C2)no1] |
| 720 | 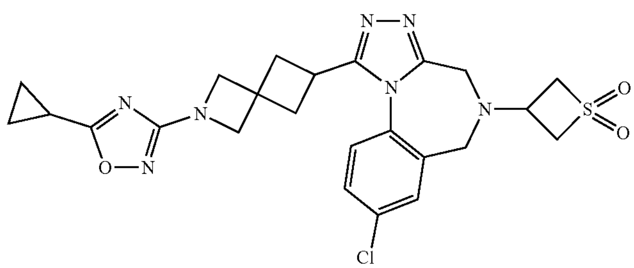 [SMILES: O=S1(=O)CC(N2Cc3cc(Cl)ccc3-n3c(nnc3C3CC4(C3)CN(c3noc(C5CC5)n3)C4)C2)C1] |
| 721 | 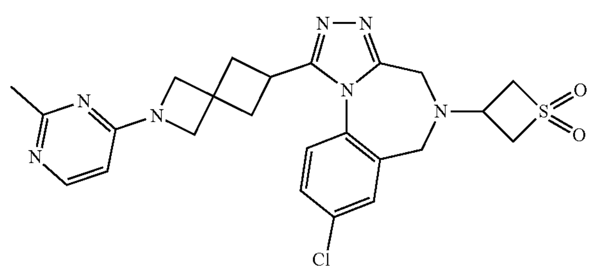 [SMILES: Cc1nccc(N2CC3(CC(c4nnc5n4-c4ccc(Cl)cc4CN(C4CS(=O)(=O)C4)C5)C3)C2)n1] |
| 722 | 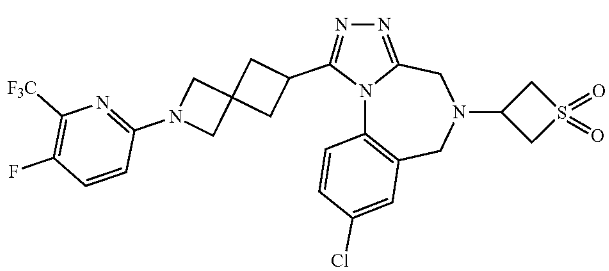 |
| 723 | 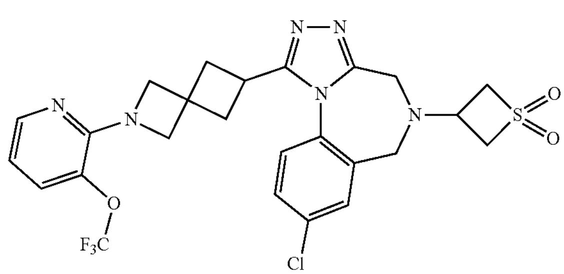 [SMILES: O=S1(=O)CC(N2Cc3cc(Cl)ccc3-n3c(nnc3C3CC4(C3)CN(c3ncccc3OC(F)(F)F)C4)C2)C1] |

TABLE 1-continued

Representative Compounds

| Cmpd. No. | Structure |
|---|---|
| 724 | 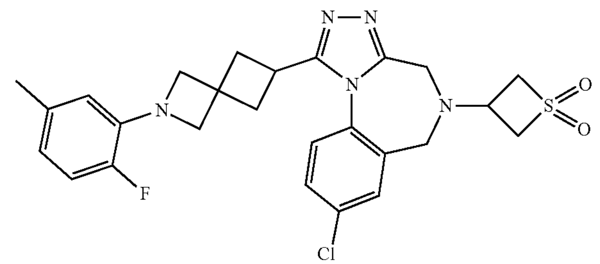 [SMILES: Cc1ccc(F)c(N2CC3(CC(c4nnc5n4-c4ccc(Cl)cc4CN(C4CS(=O)(=O)C4)C5)C3)C2)c1] |
| 725 | 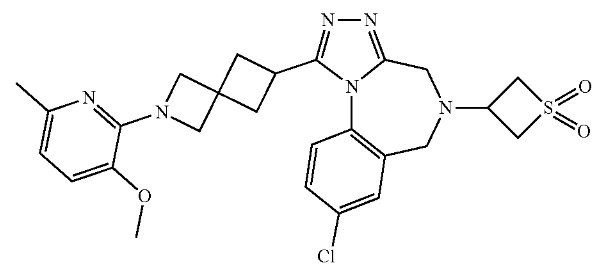 [SMILES: COc1ccc(C)nc1N1CC2(CC(c3nnc4n3-c3ccc(Cl)cc3CN(C3CS(=O)(=O)C3)C4)C2)C1] |
| 726 | 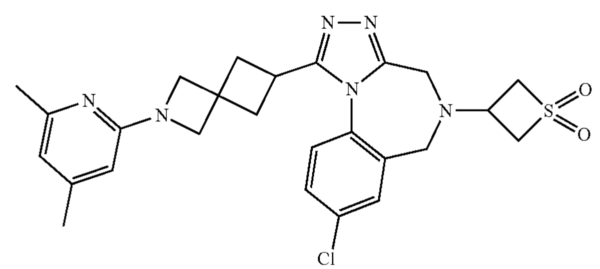 [SMILES: Cc1cc(C)nc(N2CC3(CC(c4nnc5n4-c4ccc(Cl)cc4CN(C4CS(=O)(=O)C4)C5)C3)C2)c1] |
| 727 | 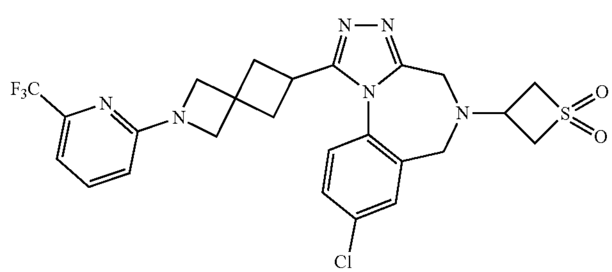 [SMILES: O=S1(=O)CC(N2Cc3cc(Cl)ccc3-n3c(nnc3C3CC4(C3)CN(c3cccc(C(F)(F)F)n3)C4)C2)C1] |
| 728 | 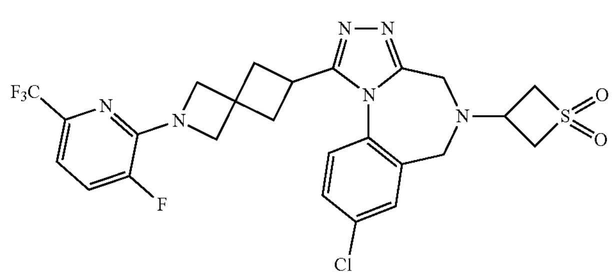 [SMILES: O=S1(=O)CC(N2Cc3cc(Cl)ccc3-n3c(nnc3C3CC4(C3)CN(c3nc(C(F)(F)F)ccc3F)C4)C2)C1] |

TABLE 1-continued

Representative Compounds

| Cmpd. No. | Structure |
|---|---|
| 729 | 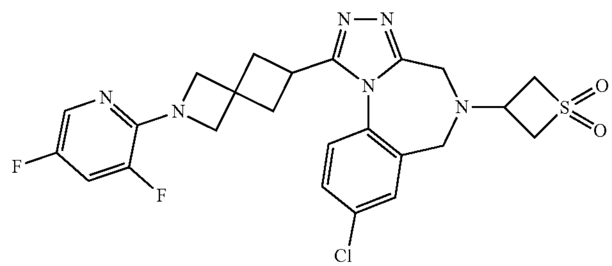 [SMILES: O=S1(=O)CC(N2Cc3cc(Cl)ccc3-n3c(nnc3C3CC4(C3)CN(c3ncc(F)cc3F)C4)C2)C1] |
| 730 | 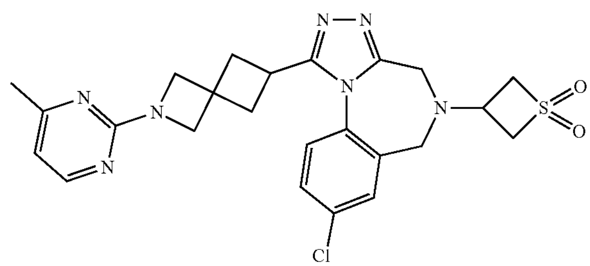 [SMILES: Cc1ccnc(N2CC3(CC(c4nnc5n4-c4ccc(Cl)cc4CN(C4CS(=O)(=O)C4)C5)C3)C2)n1] |
| 731 | 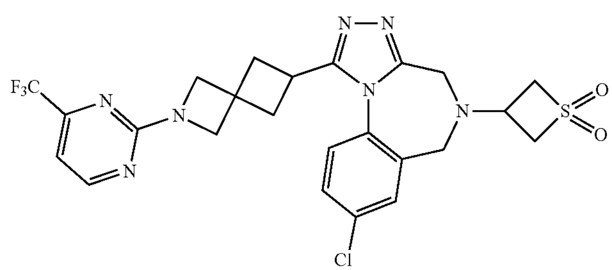 [SMILES: O=S1(=O)CC(N2Cc3cc(Cl)ccc3-n3c(nnc3C3CC4(C3)CN(c3nccc(C(F)(F)F)n3)C4)C2)C1] |
| 732 | 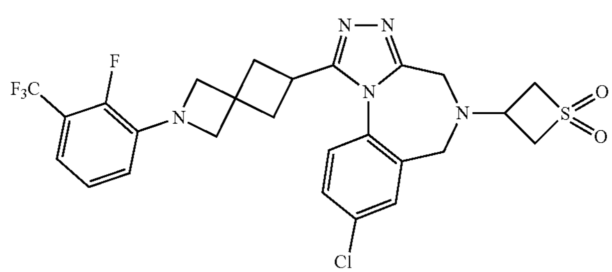 [SMILES: O=S1(=O)CC(N2Cc3cc(Cl)ccc3-n3c(nnc3C3CC4(C3)CN(c3cccc(C(F)(F)F)c3F)C4)C2)C1] |
| 733 | 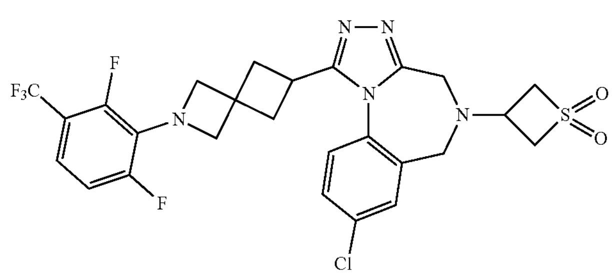 [SMILES: O=S1(=O)CC(N2Cc3cc(Cl)ccc3-n3c(nnc3C3CC4(C3)CN(c3c(F)ccc(C(F)(F)F)c3F)C4)C2)C1] |

TABLE 1-continued

Representative Compounds

| Cmpd. No. | Structure |
|---|---|
| 734 | 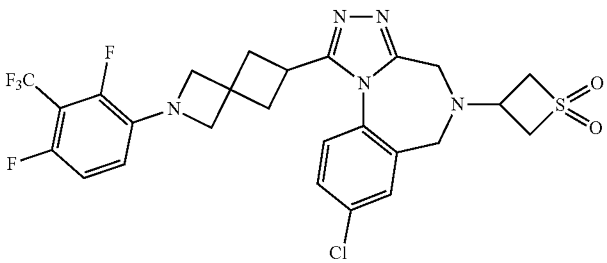 |
| 735 | 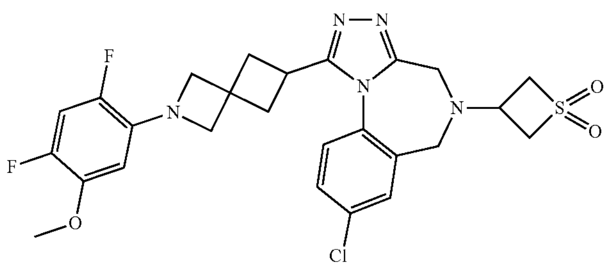 [SMILES: COc1cc(N2CC3(CC(c4nnc5n4-c4ccc(Cl)cc4CN(C4CS(=O)(=O)C4)C5)C3)C2)c(F)cc1F] |
| 736 | 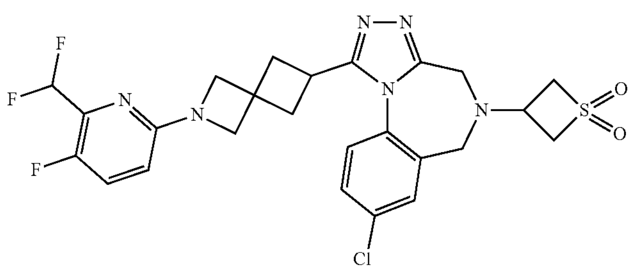 [SMILES: O=S1(=O)CC(N2Cc3cc(Cl)ccc3-n3c(nnc3C3CC4(C3)CN(c3ccc(F)c(C(F)F)n3)C4)C2)C1] |
| 737 | 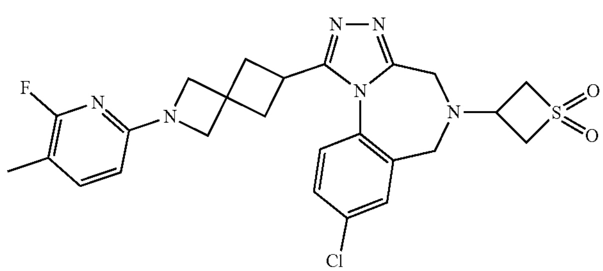 [SMILES: Cc1ccc(N2CC3(CC(c4nnc5n4-c4ccc(Cl)cc4CN(C4CS(=O)(=O)C4)C5)C3)C2)nc1F] |
| 738 | 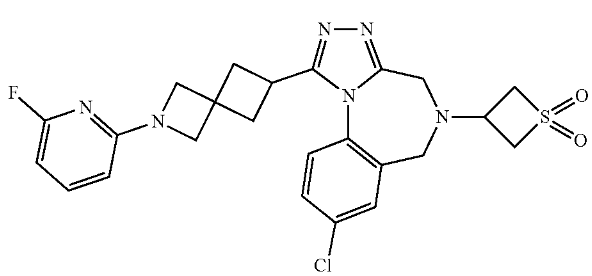 [SMILES: O=S1(=O)CC(N2Cc3cc(Cl)ccc3-n3c(nnc3C3CC4(C3)CN(c3cccc(F)n3)C4)C2)C1] |

TABLE 1-continued

Representative Compounds

| Cmpd. No. | Structure |
|---|---|
| 739 | 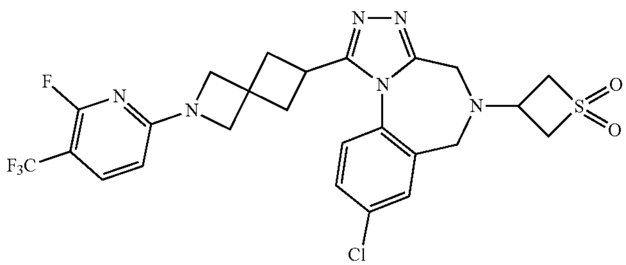 [SMILES: O=S1(=O)CC(N2Cc3cc(Cl)ccc3-n3c(nnc3C3CC4(C3)CN(c3ccc(C(F)(F)F)c(F)n3)C4)C2)C1] |
| 740 | 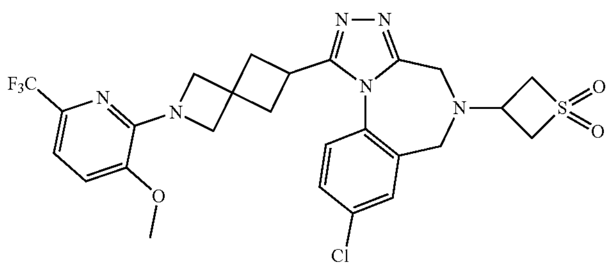 [SMILES: COc1ccc(C(F)(F)F)nc1N1CC2(CC(c3nnc4n3-c3ccc(Cl)cc3CN(C3CS(=O)(=O)C3)C4)C2)C1] |
| 741 | 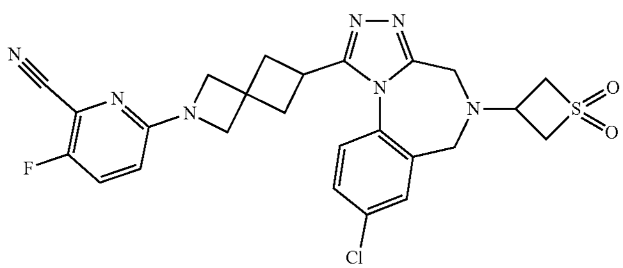 [SMILES: N#Cc1nc(N2CC3(CC(c4nnc5n4-c4ccc(Cl)cc4CN(C4CS(=O)(=O)C4)C5)C3)C2)ccc1F] |
| 742 | 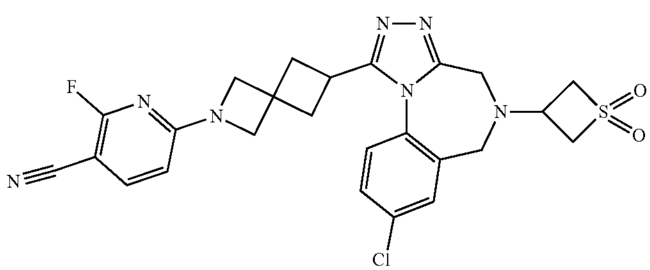 [SMILES: N#Cc1ccc(N2CC3(CC(c4nnc5n4-c4ccc(Cl)cc4CN(C4CS(=O)(=O)C4)C5)C3)C2)nc1F] |
| 743 | 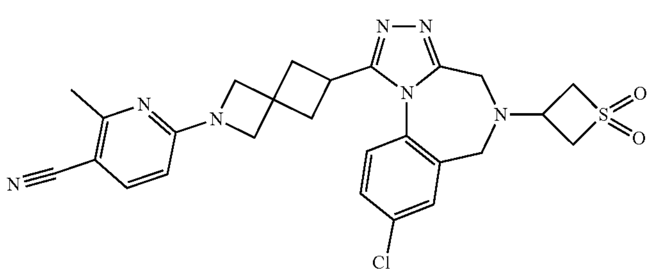 [SMILES: Cc1nc(N2CC3(CC(c4nnc5n4-c4ccc(Cl)cc4CN(C4CS(=O)(=O)C4)C5)C3)C2)ccc1C#N] |

TABLE 1-continued

Representative Compounds

| Cmpd. No. | Structure |
|---|---|
| 744 | 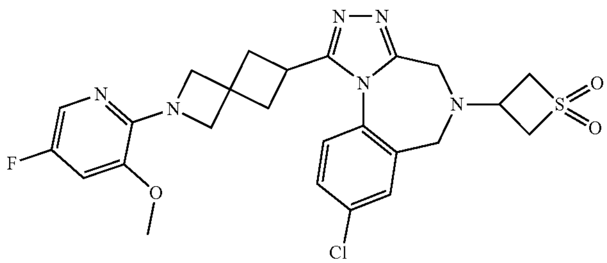 [SMILES: COc1cc(F)cnc1N1CC2(CC(c3nnc4n3-c3ccc(Cl)cc3CN(C3CS(=O)(=O)C3)C4)C2)C1] |
| 745 | 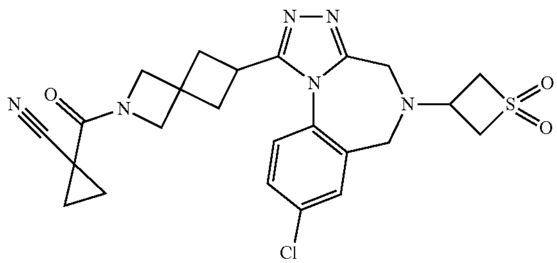 [SMILES: N#CC1(C(=O)N2CC3(CC(c4nnc5n4-c4ccc(Cl)cc4CN(C4CS(=O)(=O)C4)C5)C3)C2)CC1] |
| 746 | 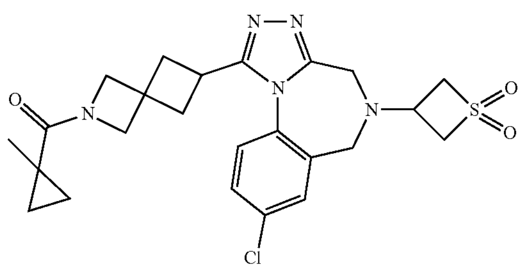 [SMILES: CC1(C(=O)N2CC3(CC(c4nnc5n4-c4ccc(Cl)cc4CN(C4CS(=O)(=O)C4)C5)C3)C2)CC1] |
| 747 | 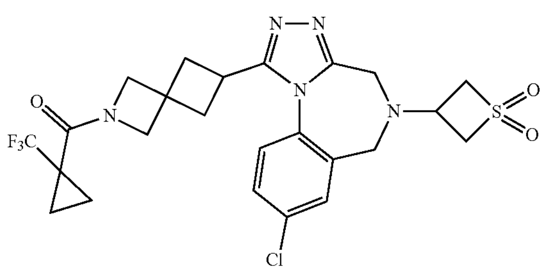 [SMILES: O=C(N1CC2(CC(c3nnc4n3-c3ccc(Cl)cc3CN(C3CS(=O)(=O)C3)C4)C2)C1)C1(C(F)(F)F)CC1] |
| 748 | 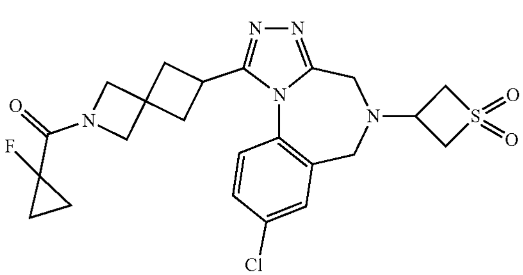 [SMILES: O=C(N1CC2(CC(c3nnc4n3-c3ccc(Cl)cc3CN(C3CS(=O)(=O)C3)C4)C2)C1)C1(F)CC1] |

TABLE 1-continued
Representative Compounds
| Cmpd. No. | Structure |
|---|---|
| 749 | 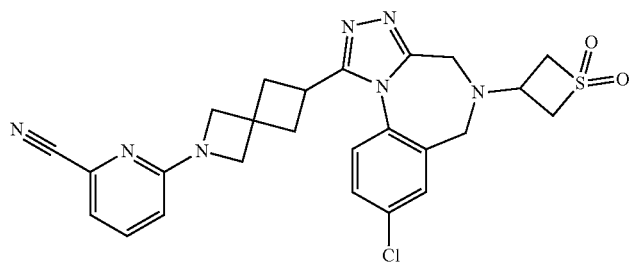 [SMILES: N#Cc1cccc(N2CC3(CC(c4nnc5n4-c4ccc(Cl)cc4CN(C4CS(=O)(=O)C4)C5)C3)C2)n1] |
| 750 | 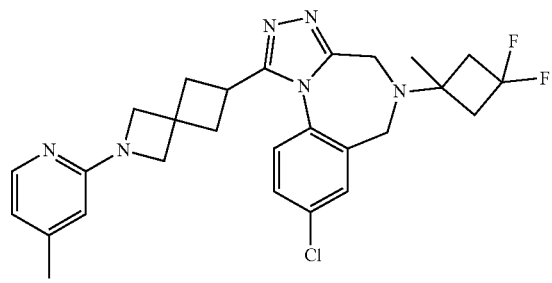 [SMILES: Cc1ccnc(N2CC3(CC(c4nnc5n4-c4ccc(Cl)cc4CN(C4(C)CC(F)(F)C4)C5)C3)C2)c1] |
| 751 | 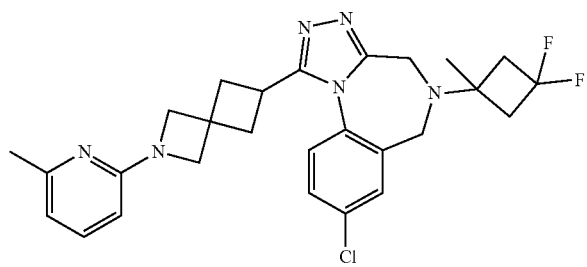 |
| 752 | 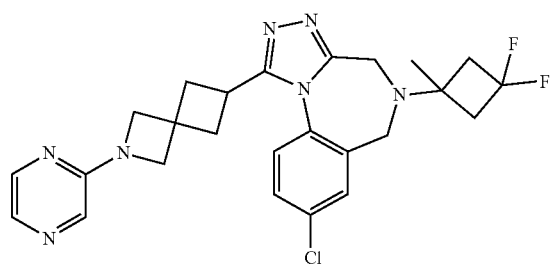 |
| 753 | 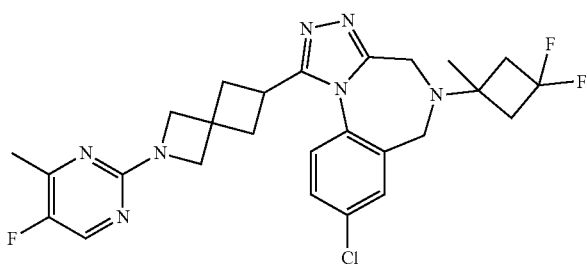 [SMILES: Cc1nc(N2CC3(CC(c4nnc5n4-c4ccc(Cl)cc4CN(C4(C)CC(F)(F)C4)C5)C3)C2)ncc1F] |

TABLE 1-continued

Representative Compounds

| Cmpd. No. | Structure |
|---|---|
| 754 | 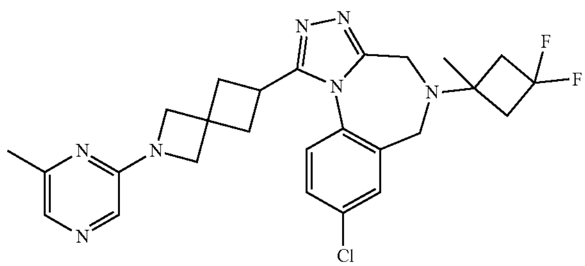 [SMILES: Cc1cncc(N2CC3(CC(c4nnc5n4-c4ccc(Cl)cc4CN(C4(C)CC(F)(F)C4)C5)C3)C2)n1] |
| 755 | 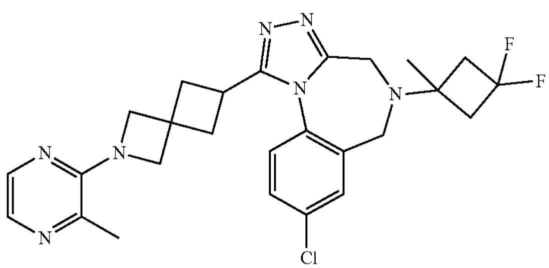 [SMILES: Cc1nccnc1N1CC2(CC(c3nnc4n3-c3ccc(Cl)cc3CN(C3(C)CC(F)(F)C3)C4)C2)C1] |
| 756 | 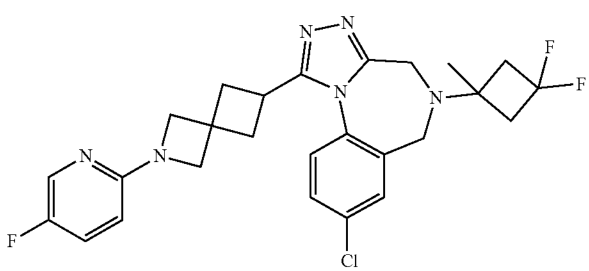 [SMILES: CC1(N2Cc3cc(Cl)ccc3-n3c(nnc3C3CC4(C3)CN(c3ccc(F)cn3)C4)C2)CC(F)(F)C1] |
| 757 | 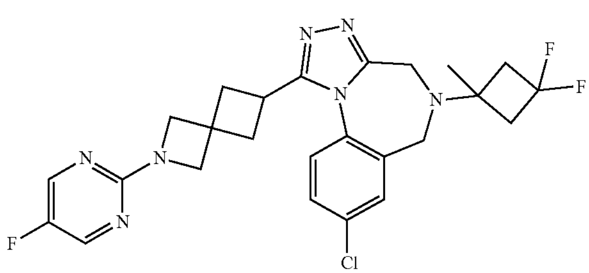 [SMILES: CC1(N2Cc3cc(Cl)ccc3-n3c(nnc3C3CC4(C3)CN(c3ncc(F)cn3)C4)C2)CC(F)(F)C1] |
| 758 | 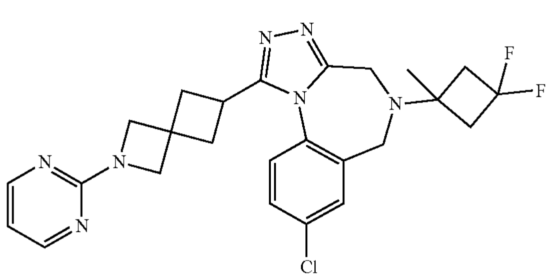 [SMILES: CC1(N2Cc3cc(Cl)ccc3-n3c(nnc3C3CC4(C3)CN(c3ncccn3)C4)C2)CC(F)(F)C1] |

TABLE 1-continued

Representative Compounds

| Cmpd. No. | Structure |
|---|---|
| 759 | 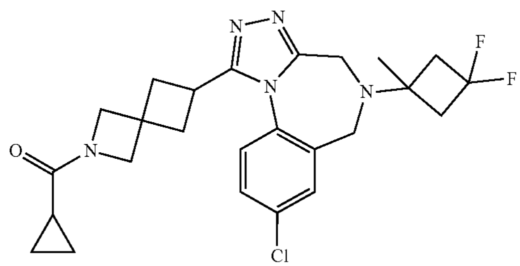 [SMILES: CC1(N2Cc3cc(Cl)ccc3-n3c(nnc3C3CC4(C3)CN(C(=O)C3CC3)C4)C2)CC(F)(F)C1] |
| 760 | 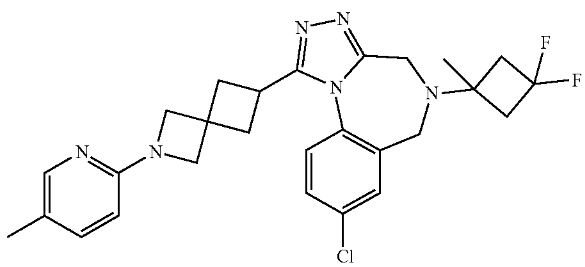 [SMILES: Cc1ccc(N2CC3(CC(c4nnc5n4-c4ccc(Cl)cc4CN(C4(C)CC(F)(F)C4)C5)C3)C2)nc1] |
| 761 | 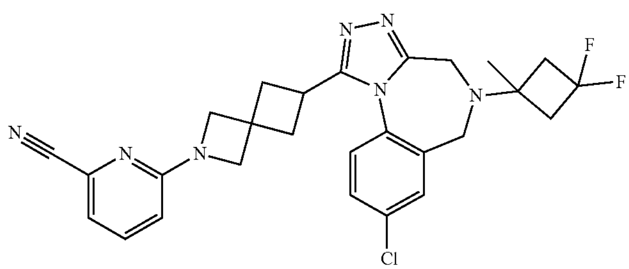 [SMILES: CC1(N2Cc3cc(Cl)ccc3-n3c(nnc3C3CC4(C3)CN(c3cccc(C#N)n3)C4)C2)CC(F)(F)C1] |
| 762 | 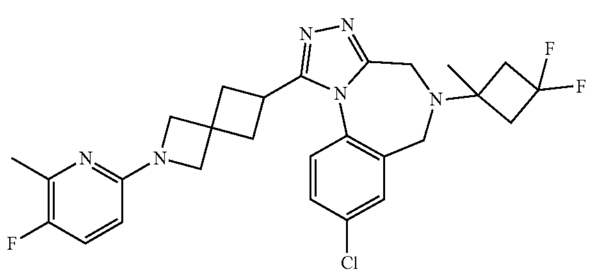 [SMILES: Cc1nc(N2CC3(CC(c4nnc5n4-c4ccc(Cl)cc4CN(C4(C)CC(F)(F)C4)C5)C3)C2)ccc1F] |
| 763 | 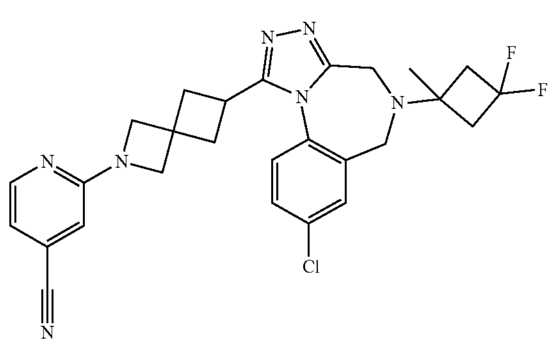 [SMILES: CC1(N2Cc3cc(Cl)ccc3-n3c(nnc3C3CC4(C3)CN(c3cc(C#N)ccn3)C4)C2)CC(F)(F)C1] |

TABLE 1-continued

Representative Compounds

| Cmpd. No. | Structure |
|---|---|
| 764 | 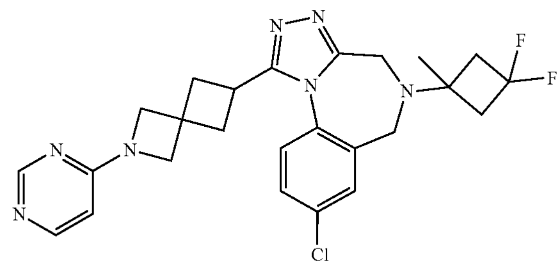 [SMILES: CC1(N2Cc3cc(Cl)ccc3-n3c(nnc3C3CC4(C3)CN(c3ccncn3)C4)C2)CC(F)(F)C1] |
| 765 | 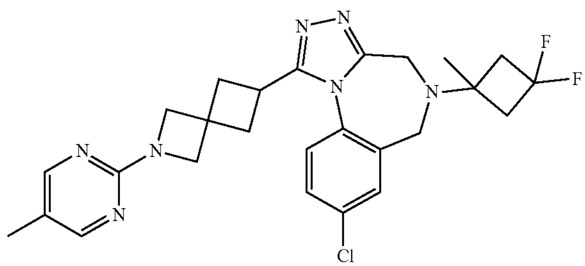 [SMILES: Cc1cnc(N2CC3(CC(c4nnc5n4-c4ccc(Cl)cc4CN(C4(C)CC(F)(F)C4)C5)C3)C2)nc1] |
| 766 | 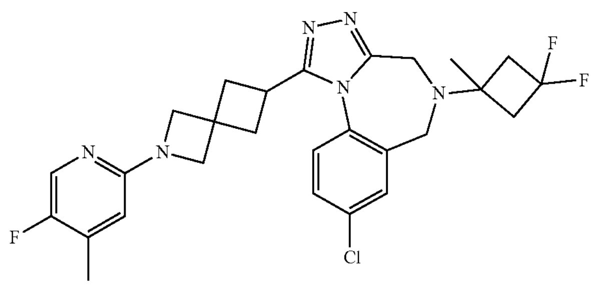 [SMILES: Cc1cc(N2CC3(CC(c4nnc5n4-c4ccc(Cl)cc4CN(C4(C)CC(F)(F)C4)C5)C3)C2)ncc1F] |
| 767 | 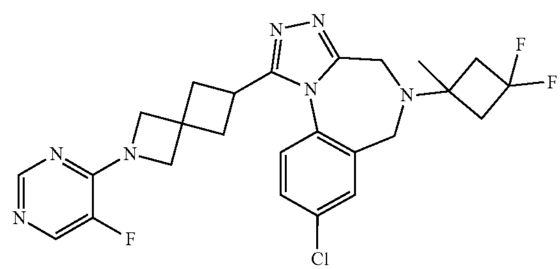 [SMILES: CC1(N2Cc3cc(Cl)ccc3-n3c(nnc3C3CC4(C3)CN(c3ncncc3F)C4)C2)CC(F)(F)C1] |
| 768 | 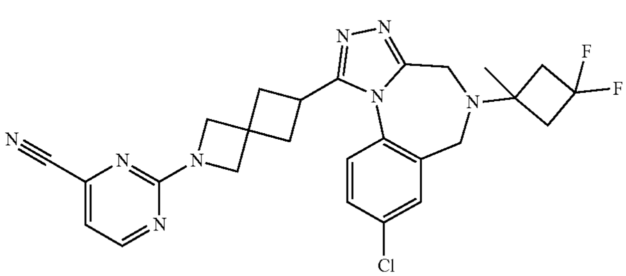 [SMILES: CC1(N2Cc3cc(Cl)ccc3-n3c(nnc3C3CC4(C3)CN(c3nccc(C#N)n3)C4)C2)CC(F)(F)C1] |

TABLE 1-continued

Representative Compounds

| Cmpd. No. | Structure |
|---|---|
| 769 | 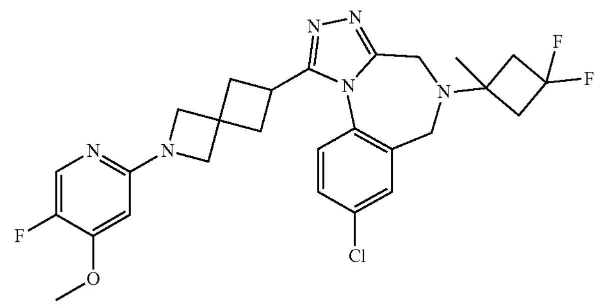 [SMILES: COc1cc(N2CC3(CC(c4nnc5n4-c4ccc(Cl)cc4CN(C4(C)CC(F)(F)C4)C5)C3)C2)ncc1F] |
| 770 | 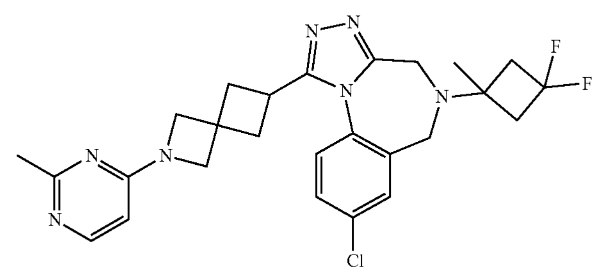 [SMILES: Cc1nccc(N2CC3(CC(c4nnc5n4-c4ccc(Cl)cc4CN(C4(C)CC(F)(F)C4)C5)C3)C2)n1] |
| 771 | 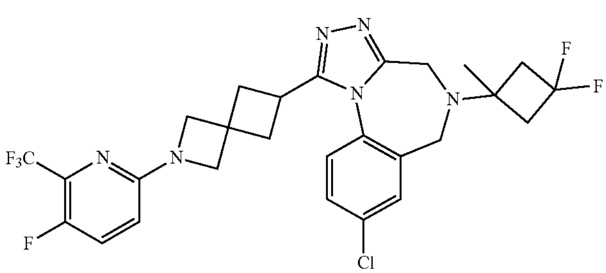 [SMILES: CC1(N2Cc3cc(Cl)ccc3-n3c(nnc3C3CC4(C3)CN(c3ccc(F)c(C(F)(F)F)n3)C4)C2)CC(F)(F)C1] |
| 772 | 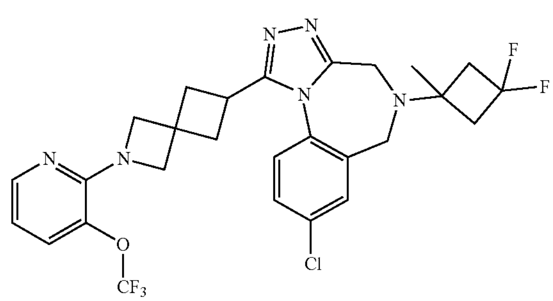 [SMILES: CC1(N2Cc3cc(Cl)ccc3-n3c(nnc3C3CC4(C3)CN(c3ncccc3OC(F)(F)F)C4)C2)CC(F)(F)C1] |
| 773 | 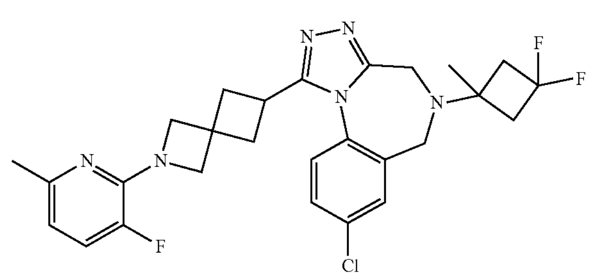 [SMILES: Cc1ccc(F)c(N2CC3(CC(c4nnc5n4-c4ccc(Cl)cc4CN(C4(C)CC(F)(F)C4)C5)C3)C2)n1] |

TABLE 1-continued
Representative Compounds
| Cmpd. No. | Structure |
|---|---|
| 774 | 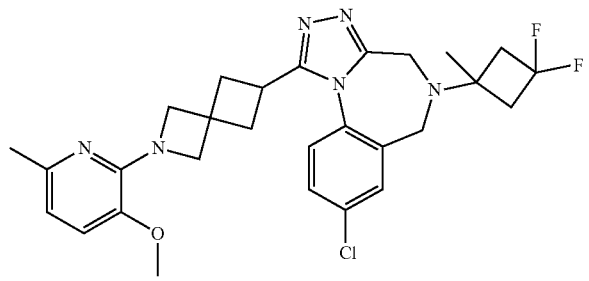 [SMILES: COc1ccc(C)nc1N1CC2(CC(c3nnc4n3-c3ccc(Cl)cc3CN(C3(C)CC(F)(F)C3)C4)C2)C1] |
| 775 | 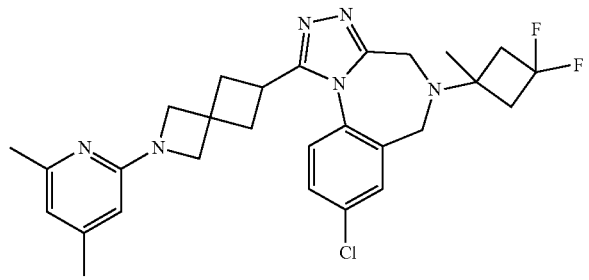 [SMILES: Cc1cc(C)nc(N2CC3(CC(c4nnc5n4-c4ccc(Cl)cc4CN(C4(C)CC(F)(F)C4)C5)C3)C2)c1] |
| 776 | 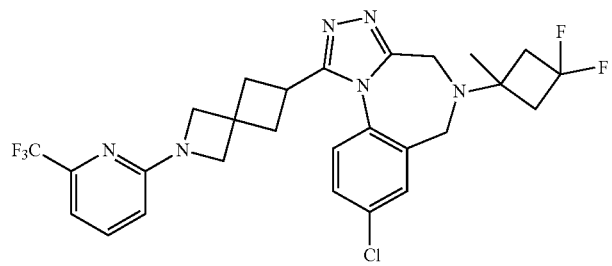 [SMILES: CC1(N2Cc3cc(Cl)ccc3-n3c(nnc3C3CC4(C3)CN(c3cccc(C(F)(F)F)n3)C4)C2)CC(F)(F)C1] |
| 777 | 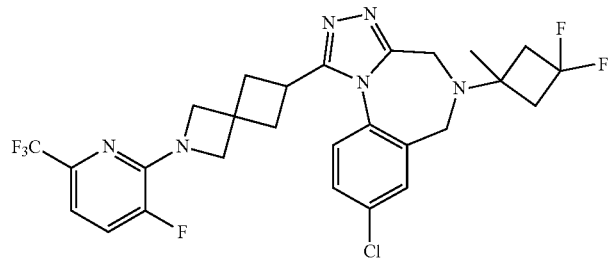 [SMILES: CC1(N2Cc3cc(Cl)ccc3-n3c(nnc3C3CC4(C3)CN(c3nc(C(F)(F)F)ccc3F)C4)C2)CC(F)(F)C1] |
| 778 | 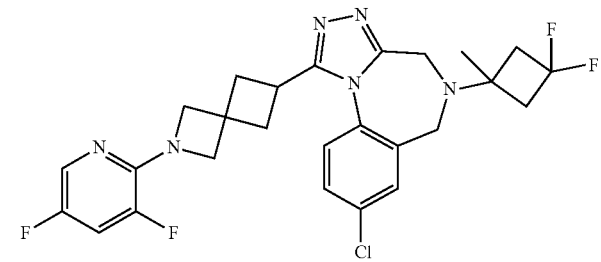 [SMILES: CC1(N2Cc3cc(Cl)ccc3-n3c(nnc3C3CC4(C3)CN(c3ncc(F)cc3F)C4)C2)CC(F)(F)C1] |

TABLE 1-continued

Representative Compounds

| Cmpd. No. | Structure |
|---|---|
| 779 | 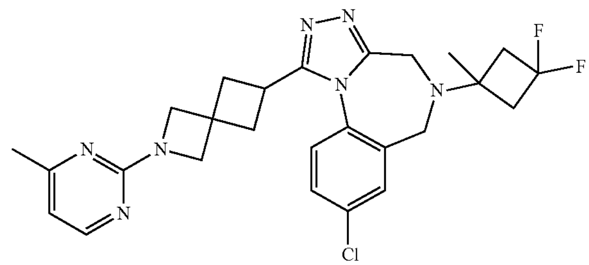 [SMILES: Cc1ccnc(N2CC3(CC(c4nnc5n4-c4ccc(Cl)cc4CN(C4(C)CC(F)(F)C4)C5)C3)C2)n1] |
| 780 | 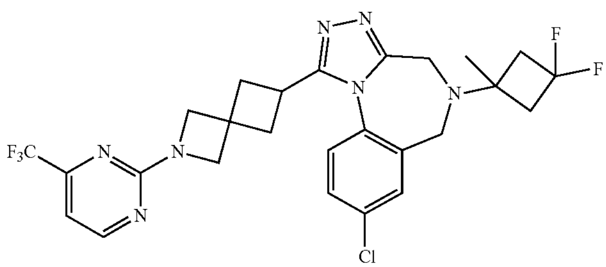 [SMILES: CC1(N2Cc3cc(Cl)ccc3-n3c(nnc3C3CC4(C3)CN(c3nccc(C(F)(F)F)n3)C4)C2)CC(F)(F)C1] |
| 781 | 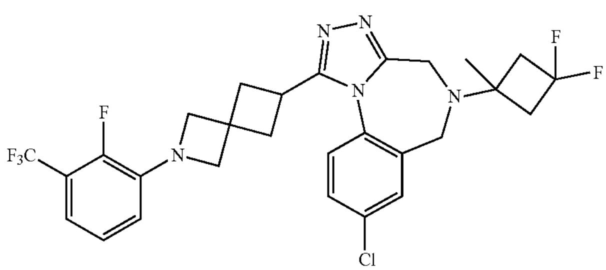 [SMILES: CC1(N2Cc3cc(Cl)ccc3-n3c(nnc3C3CC4(C3)CN(c3cccc(C(F)(F)F)c3F)C4)C2)CC(F)(F)C1] |
| 782 | 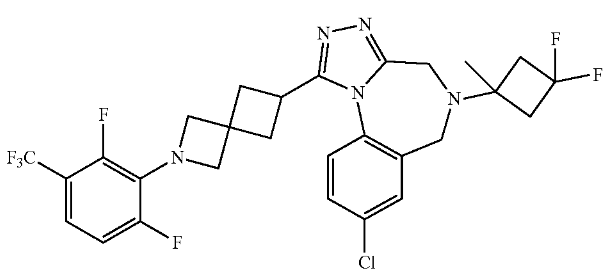 [SMILES: CC1(N2Cc3cc(Cl)ccc3-n3c(nnc3C3CC4(C3)CN(c3c(F)ccc(C(F)(F)F)c3F)C4)C2)CC(F)(F)C1] |
| 783 | 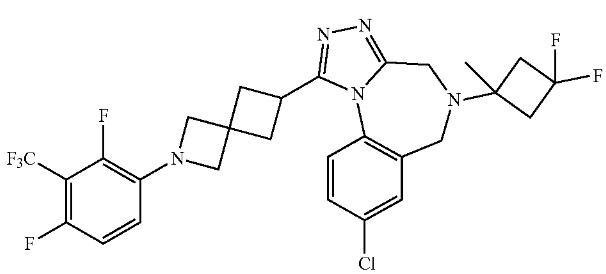 [SMILES: CC1(N2Cc3cc(Cl)ccc3-n3c(nnc3C3CC4(C3)CN(c3ccc(F)c(C(F)(F)F)c3F)C4)C2)CC(F)(F)C1] |

TABLE 1-continued

Representative Compounds

| Cmpd. No. | Structure |
|---|---|
| 784 | 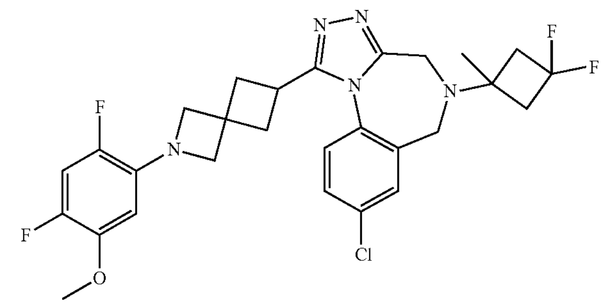 [SMILES: COc1cc(N2CC3(CC(c4nnc5n4-c4ccc(Cl)cc4CN(C4(C)CC(F)(F)C4)C5)C3)C2)c(F)cc1F] |
| 785 | 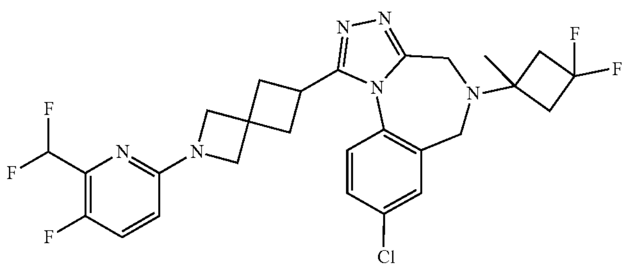 [SMILES: CC1(N2Cc3cc(Cl)ccc3-n3c(nnc3C3CC4(C3)CN(c3ccc(F)c(C(F)F)n3)C4)C2)CC(F)(F)C1] |
| 786 | 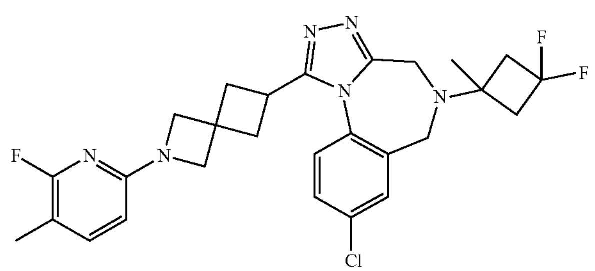 [SMILES: Cc1ccc(N2CC3(CC(c4nnc5n4-c4ccc(Cl)cc4CN(C4(C)CC(F)(F)C4)C5)C3)C2)nc1F] |
| 787 | 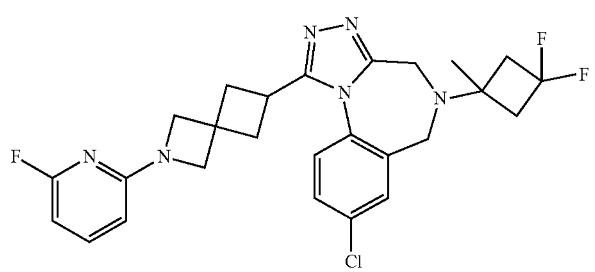 [SMILES: CC1(N2Cc3cc(Cl)ccc3-n3c(nnc3C3CC4(C3)CN(c3cccc(F)n3)C4)C2)CC(F)(F)C1] |
| 788 | 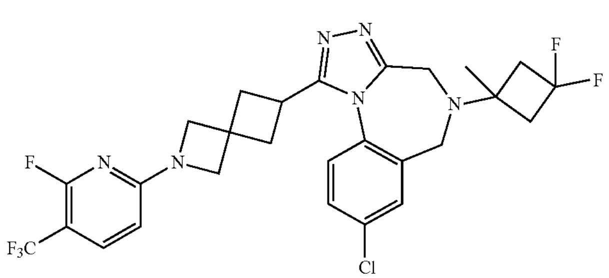 [SMILES: CC1(N2Cc3cc(Cl)ccc3-n3c(nnc3C3CC4(C3)CN(c3ccc(C(F)(F)F)c(F)n3)C4)C2)CC(F)(F)C1] |

TABLE 1-continued

Representative Compounds

| Cmpd. No. | Structure |
|---|---|
| 789 | 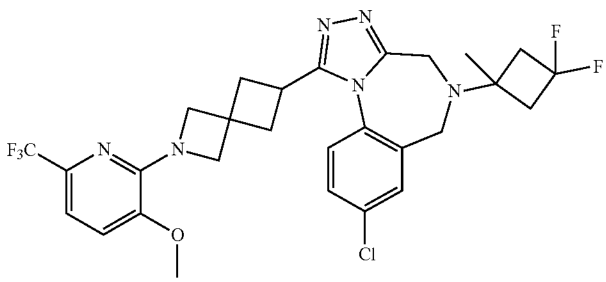 [SMILES: COc1ccc(C(F)(F)F)nc1N1CC2(CC(c3nnc4n3-c3ccc(Cl)cc3CN(C3(C)CC(F)(F)C3)C4)C2)C1] |
| 790 | 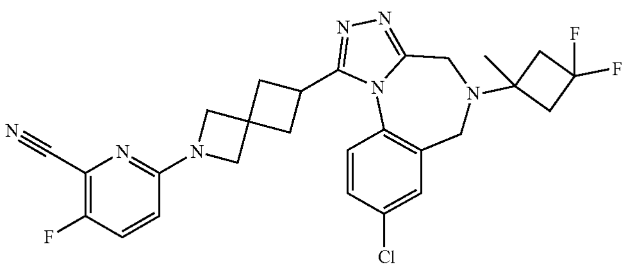 [SMILES: CC1(N2Cc3cc(Cl)ccc3-n3c(nnc3C3CC4(C3)CN(c3ccc(F)c(C#N)n3)C4)C2)CC(F)(F)C1] |
| 791 | 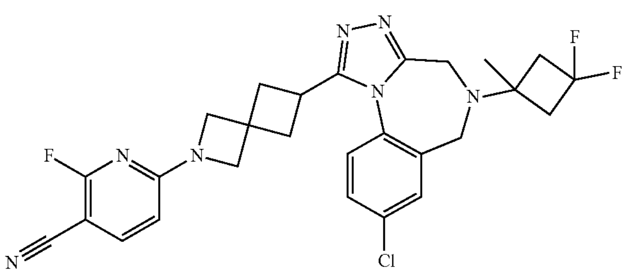 [SMILES: CC1(N2Cc3cc(Cl)ccc3-n3c(nnc3C3CC4(C3)CN(c3ccc(C#N)c(F)n3)C4)C2)CC(F)(F)C1] |
| 792 | 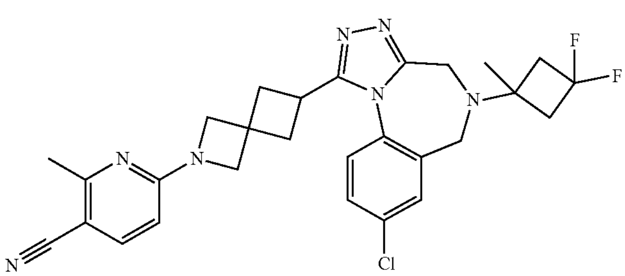 [SMILES: Cc1nc(N2CC3(CC(c4nnc5n4-c4ccc(Cl)cc4CN(C4(C)CC(F)(F)C4)C5)C3)C2)ccc1C#N] |
| 793 | 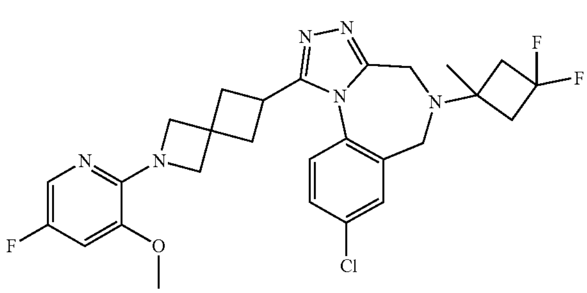 [SMILES: COc1cc(F)cnc1N1CC2(CC(c3nnc4n3-c3ccc(Cl)cc3CN(C3(C)CC(F)(F)C3)C4)C2)C1] |

TABLE 1-continued

Representative Compounds

| Cmpd. No. | Structure |
|---|---|
| 794 | 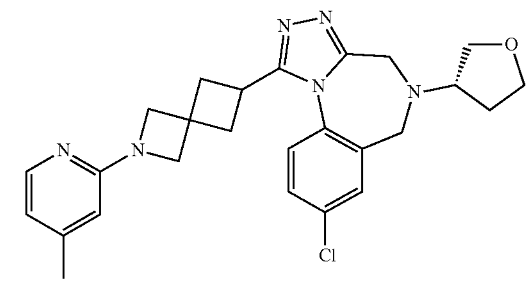 [SMILES: Cc1ccnc(N2CC3(CC(c4nnc5n4-c4ccc(Cl)cc4CN([C@H]4CCOC4)C5)C3)C2)c1] |
| 795 | 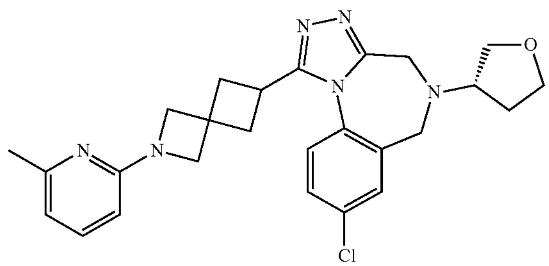 [SMILES: Cc1cccc(N2CC3(CC(c4nnc5n4-c4ccc(Cl)cc4CN([C@H]4CCOC4)C5)C3)C2)n1] |
| 796 | 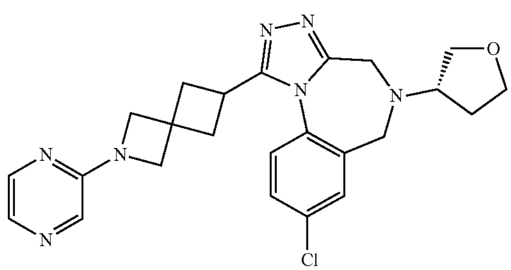 [SMILES: Clc1ccc2c(c1)CN([C@H]1CCOC1)Cc1nnc(C3CC4(C3)CN(c3cnccn3)C4)n1-2] |
| 797 | 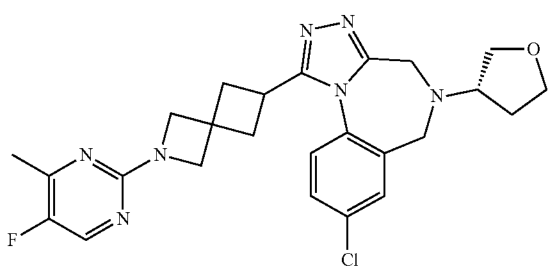 [SMILES: Cc1nc(N2CC3(CC(c4nnc5n4-c4ccc(Cl)cc4CN([C@H]4CCOC4)C5)C3)C2)ncc1F] |
| 798 | 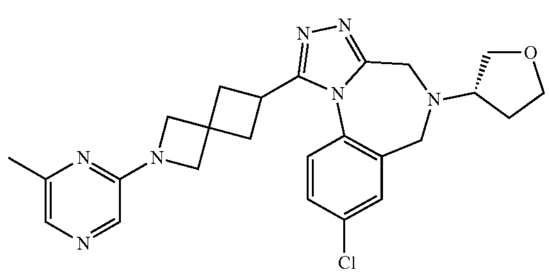 [SMILES: Cc1cncc(N2CC3(CC(c4nnc5n4-c4ccc(Cl)cc4CN([C@H]4CCOC4)C5)C3)C2)n1] |

TABLE 1-continued
Representative Compounds
| Cmpd. No. | Structure |
|---|---|
| 799 | 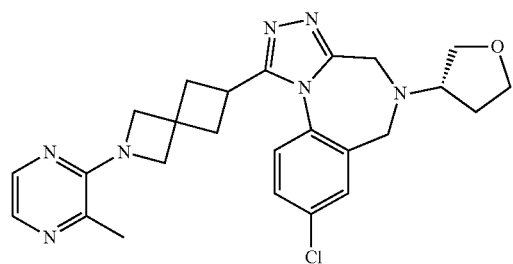 [SMILES: Cc1nccnc1N1CC2(CC(c3nnc4n3-c3ccc(Cl)cc3CN([C@H]3CCOC3)C4)C2)C1] |
| 800 | 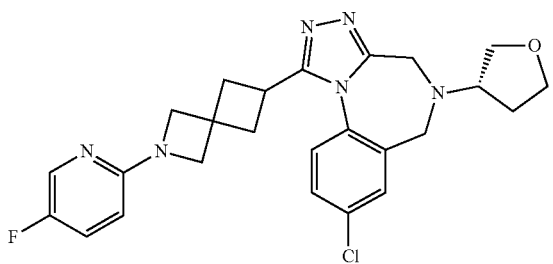 [SMILES: Fc1ccc(N2CC3(CC(c4nnc5n4-c4ccc(Cl)cc4CN([C@H]4CCOC4)C5)C3)C2)nc1] |
| 801 | 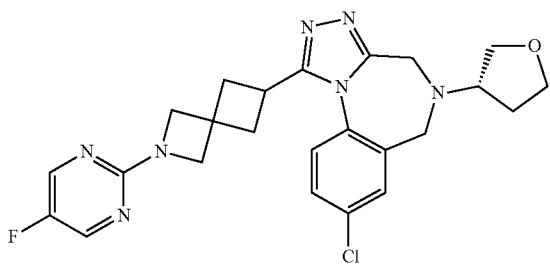 [SMILES: Fc1cnc(N2CC3(CC(c4nnc5n4-c4ccc(Cl)cc4CN([C@H]4CCOC4)C5)C3)C2)nc1] |
| 802 | 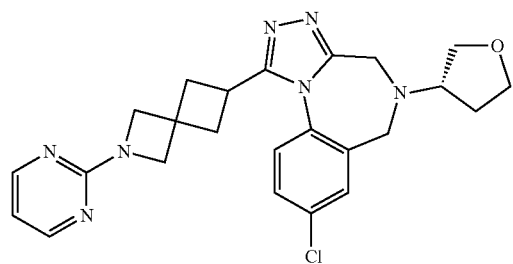 [SMILES: Clc1ccc2c(c1)CN([C@H]1CCOC1)Cc1nnc(C3CC4(C3)CN(c3ncccn3)C4)n1-2] |
| 803 | 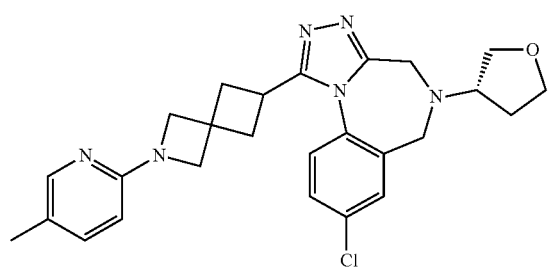 |

TABLE 1-continued

Representative Compounds

| Cmpd. No. | Structure |
|---|---|
| 804 | 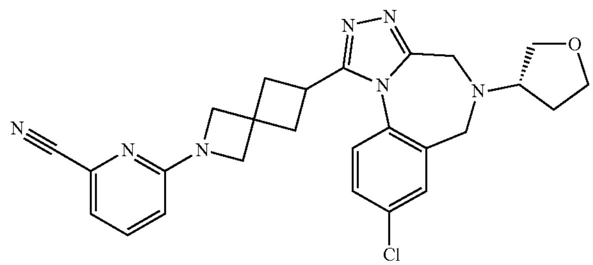 [SMILES: N#Cc1cccc(N2CC3(CC(c4nnc5n4-c4ccc(Cl)cc4CN([C@H]4CCOC4)C5)C3)C2)n1] |
| 805 | 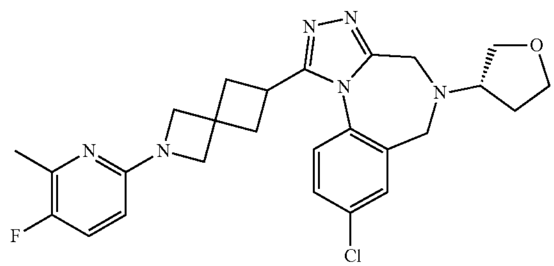 [SMILES: Cc1nc(N2CC3(CC(c4nnc5n4-c4ccc(Cl)cc4CN([C@H]4CCOC4)C5)C3)C2)ccc1F] |
| 806 | 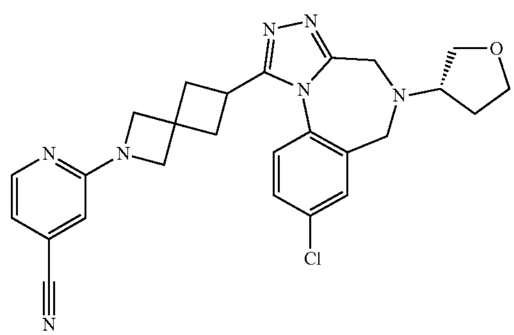 [SMILES: N#Cc1ccnc(N2CC3(CC(c4nnc5n4-c4ccc(Cl)cc4CN([C@H]4CCOC4)C5)C3)C2)c1] |
| 807 | 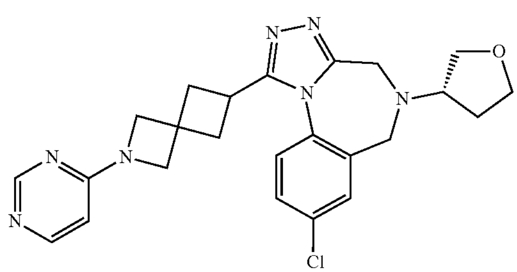 [SMILES: Clc1ccc2c(c1)CN([C@H]1CCOC1)Cc1nnc(C3CC4(C3)CN(c3ccncn3)C4)n1-2] |
| 808 | 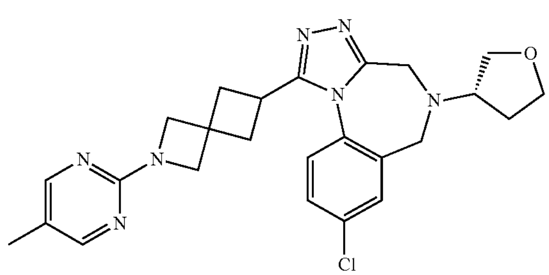 [SMILES: Cc1cnc(N2CC3(CC(c4nnc5n4-c4ccc(Cl)cc4CN([C@H]4CCOC4)C5)C3)C2)nc1] |

TABLE 1-continued

Representative Compounds

| Cmpd. No. | Structure |
|---|---|
| 809 | 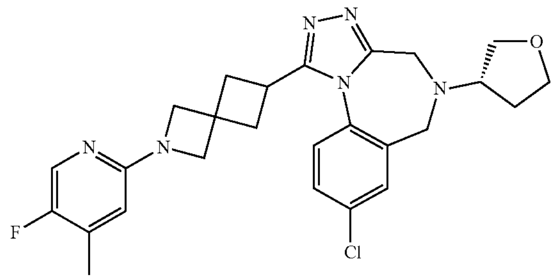 [SMILES: Cc1cc(N2CC3(CC(c4nnc5n4-c4ccc(Cl)cc4CN([C@H]4CCOC4)C5)C3)C2)ncc1F] |
| 810 | 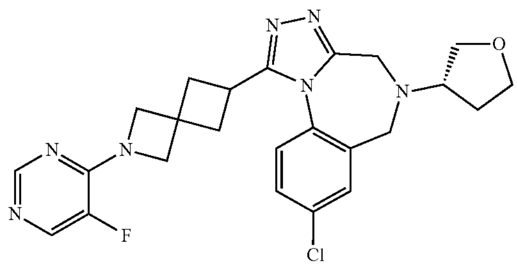 [SMILES: Fc1cncnc1N1CC2(CC(c3nnc4n3-c3ccc(Cl)cc3CN([C@H]3CCOC3)C4)C2)C1] |
| 811 | 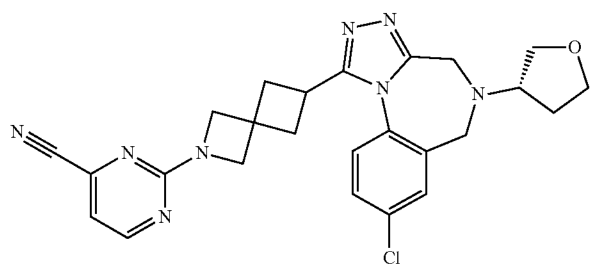 [SMILES: N#Cc1ccnc(N2CC3(CC(c4nnc5n4-c4ccc(Cl)cc4CN([C@H]4CCOC4)C5)C3)C2)n1] |
| 812 | 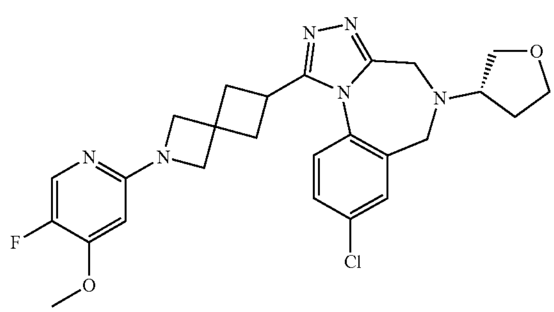 [SMILES: COc1cc(N2CC3(CC(c4nnc5n4-c4ccc(Cl)cc4CN([C@H]4CCOC4)C5)C3)C2)ncc1F] |
| 813 | 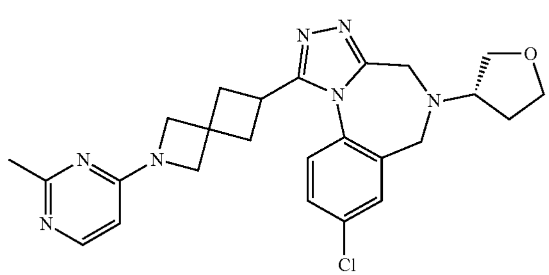 |

TABLE 1-continued

Representative Compounds

| Cmpd. No. | Structure |
|---|---|
| 814 | 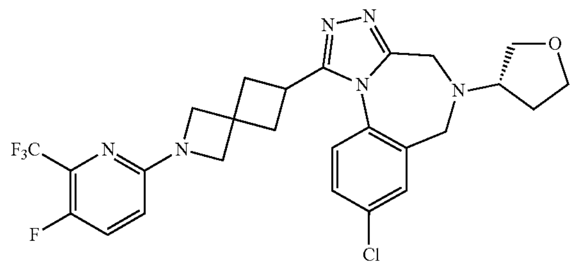 [SMILES: Fc1ccc(N2CC3(CC(c4nnc5n4-c4ccc(Cl)cc4CN([C@H]4CCOC4)C5)C3)C2)nc1C(F)(F)F] |
| 815 | 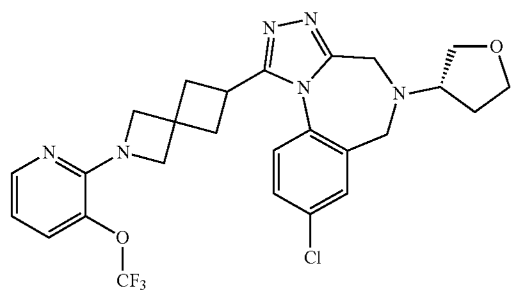 [SMILES: FC(F)(F)Oc1cccnc1N1CC2(CC(c3nnc4n3-c3ccc(Cl)cc3CN([C@H]3CCOC3)C4)C2)C1] |
| 816 | 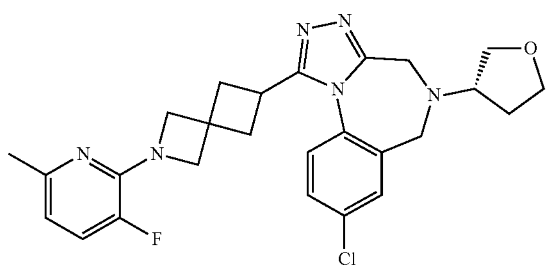 [SMILES: Cc1ccc(F)c(N2CC3(CC(c4nnc5n4-c4ccc(Cl)cc4CN([C@H]4CCOC4)C5)C3)C2)n1] |
| 817 | 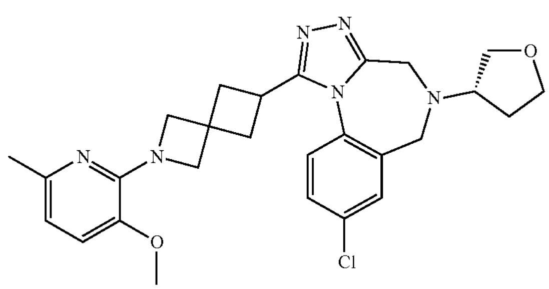 [SMILES: COc1ccc(C)nc1N1CC2(CC(c3nnc4n3-c3ccc(Cl)cc3CN([C@H]3CCOC3)C4)C2)C1] |
| 818 | 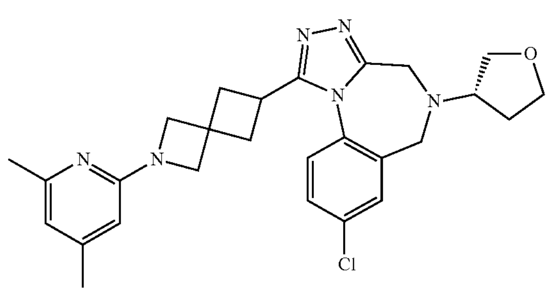 [SMILES: Cc1cc(C)nc(N2CC3(CC(c4nnc5n4-c4ccc(Cl)cc4CN([C@H]4CCOC4)C5)C3)C2)c1] |

TABLE 1-continued

Representative Compounds

| Cmpd. No. | Structure |
|---|---|
| 819 | 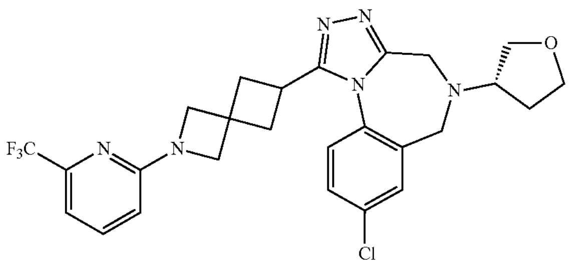 [SMILES: FC(F)(F)c1cccc(N2CC3(CC(c4nnc5n4-c4ccc(Cl)cc4CN([C@H]4CCOC4)C5)C3)C2)n1] |
| 820 | 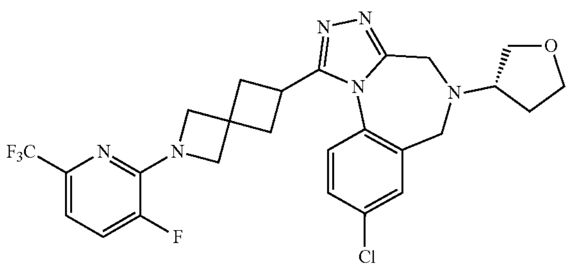 [SMILES: Fc1ccc(C(F)(F)F)nc1N1CC2(CC(c3nnc4n3-c3ccc(Cl)cc3CN([C@H]3CCOC3)C4)C2)C1] |
| 821 | 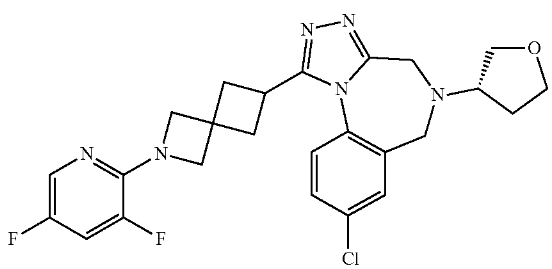 [SMILES: Fc1cnc(N2CC3(CC(c4nnc5n4-c4ccc(Cl)cc4CN([C@H]4CCOC4)C5)C3)C2)c(F)c1] |
| 822 | 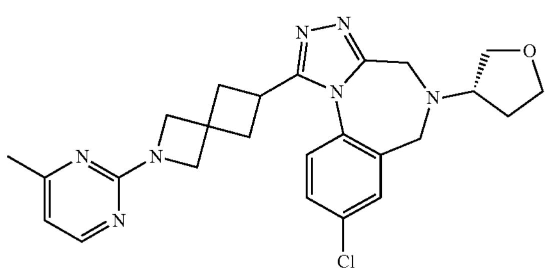 |
| 823 | 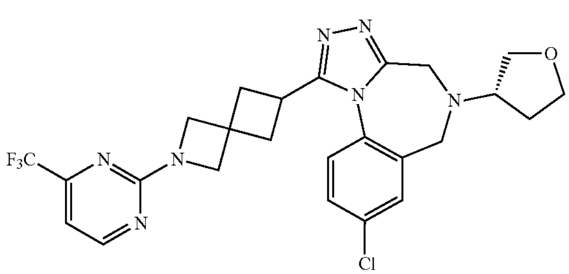 [SMILES: FC(F)(F)c1ccnc(N2CC3(CC(c4nnc5n4-c4ccc(Cl)cc4CN([C@H]4CCOC4)C5)C3)C2)n1] |

TABLE 1-continued

Representative Compounds

| Cmpd. No. | Structure |
|---|---|
| 824 | 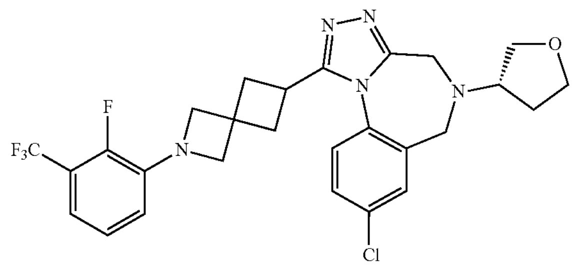 [SMILES: Fc1c(N2CC3(CC(c4nnc5n4-c4ccc(Cl)cc4CN([C@H]4CCOC4)C5)C3)C2)cccc1C(F)(F)F] |
| 825 | 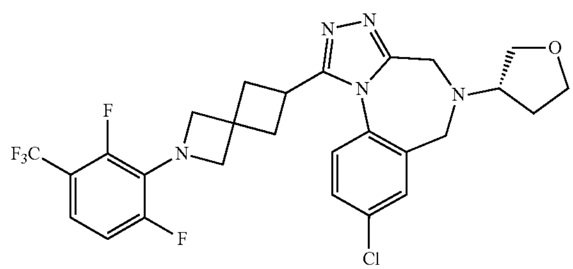 [SMILES: Fc1ccc(C(F)(F)F)c(F)c1N1CC2(CC(c3nnc4n3-c3ccc(Cl)cc3CN([C@H]3CCOC3)C4)C2)C1] |
| 826 | 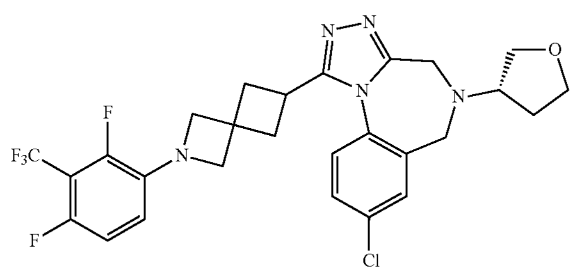 [SMILES: Fc1ccc(N2CC3(CC(c4nnc5n4-c4ccc(Cl)cc4CN([C@H]4CCOC4)C5)C3)C2)c(F)c1C(F)(F)F] |
| 827 | 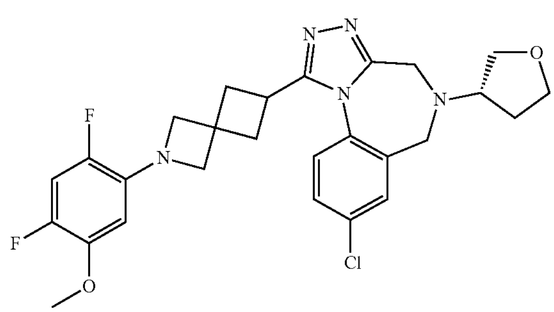 [SMILES: COc1cc(N2CC3(CC(c4nnc5n4-c4ccc(Cl)cc4CN([C@H]4CCOC4)C5)C3)C2)c(F)cc1F] |
| 828 | 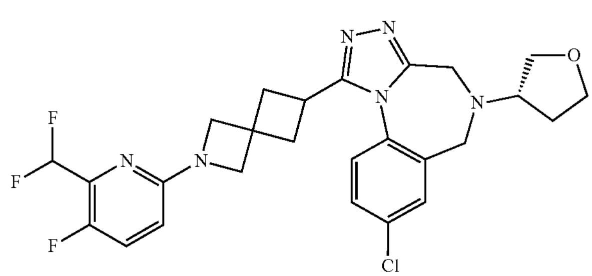 [SMILES: Fc1ccc(N2CC3(CC(c4nnc5n4-c4ccc(Cl)cc4CN([C@H]4CCOC4)C5)C3)C2)nc1C(F)F] |

TABLE 1-continued

Representative Compounds

| Cmpd. No. | Structure |
|---|---|
| 829 | 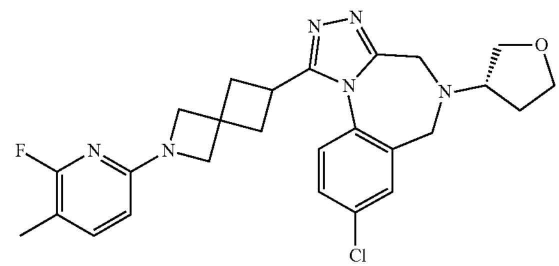 [SMILES: Cc1ccc(N2CC3(CC(c4nnc5n4-c4ccc(Cl)cc4CN([C@H]4CCOC4)C5)C3)C2)nc1F] |
| 830 | 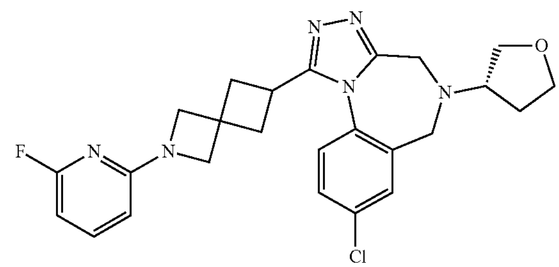 [SMILES: Fc1cccc(N2CC3(CC(c4nnc5n4-c4ccc(Cl)cc4CN([C@H]4CCOC4)C5)C3)C2)n1] |
| 831 | 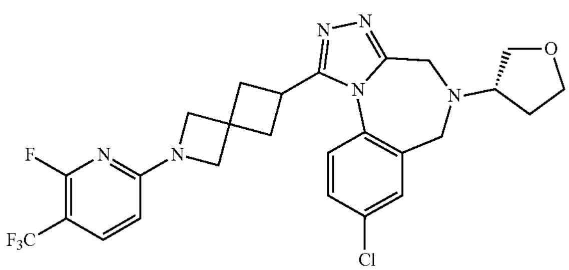 [SMILES: Fc1nc(N2CC3(CC(c4nnc5n4-c4ccc(Cl)cc4CN([C@H]4CCOC4)C5)C3)C2)ccc1C(F)(F)F] |
| 832 | 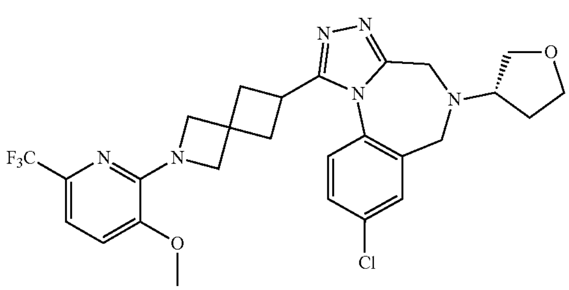 [SMILES: COc1ccc(C(F)(F)F)nc1N1CC2(CC(c3nnc4n3-c3ccc(Cl)cc3CN([C@H]3CCOC3)C4)C2)C1] |
| 833 | 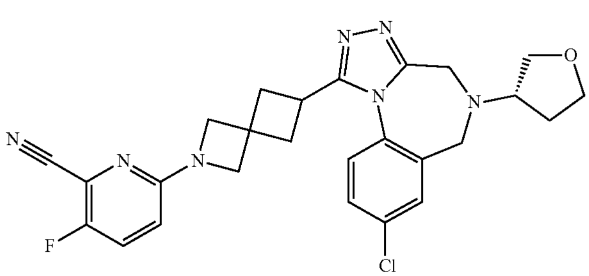 [SMILES: N#Cc1nc(N2CC3(CC(c4nnc5n4-c4ccc(Cl)cc4CN([C@H]4CCOC4)C5)C3)C2)ccc1F] |

TABLE 1-continued

Representative Compounds

| Cmpd. No. | Structure |
|---|---|
| 834 | 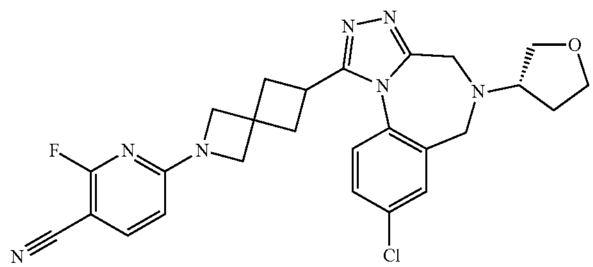 [SMILES: N#Cc1ccc(N2CC3(CC(c4nnc5n4-c4ccc(Cl)cc4CN([C@H]4CCOC4)C5)C3)C2)nc1F] |
| 835 | 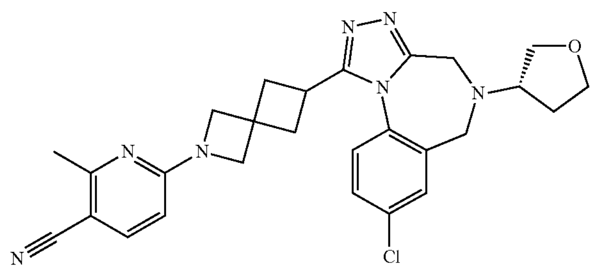 [SMILES: Cc1nc(N2CC3(CC(c4nnc5n4-c4ccc(Cl)cc4CN([C@H]4CCOC4)C5)C3)C2)ccc1C#N] |
| 836 | 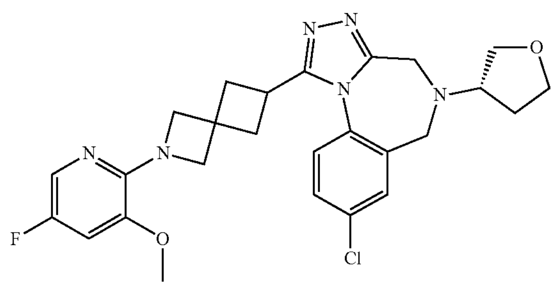 [SMILES: COc1cc(F)cnc1N1CC2(CC(c3nnc4n3-c3ccc(Cl)cc3CN([C@H]3CCOC3)C4)C2)C1] |
| 837 | 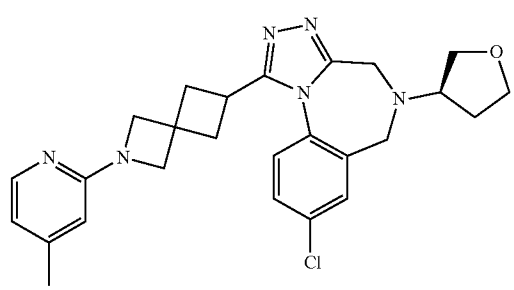 [SMILES: Cc1ccnc(N2CC3(CC(c4nnc5n4-c4ccc(Cl)cc4CN([C@@H]4CCOC4)C5)C3)C2)c1] |
| 838 | 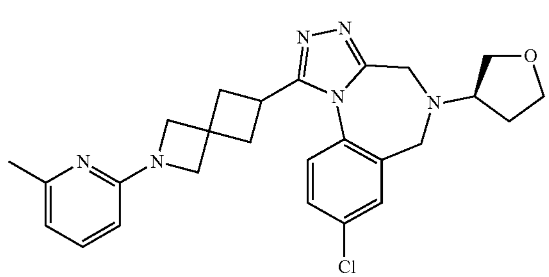 [SMILES: Cc1cccc(N2CC3(CC(c4nnc5n4-c4ccc(Cl)cc4CN([C@@H]4CCOC4)C5)C3)C2)n1] |

TABLE 1-continued
Representative Compounds
| Cmpd. No. | Structure |
|---|---|
| 839 | 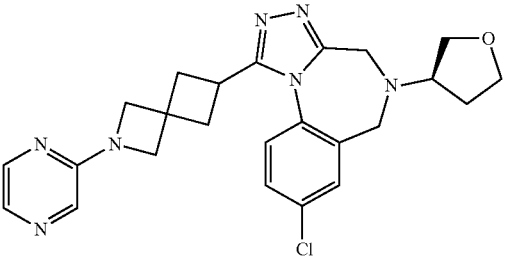 [SMILES: Clc1ccc2c(c1)CN([C@@H]1CCOC1)Cc1nnc(C3CC4(C3)CN(c3cnccn3)C4)n1-2] |
| 840 | 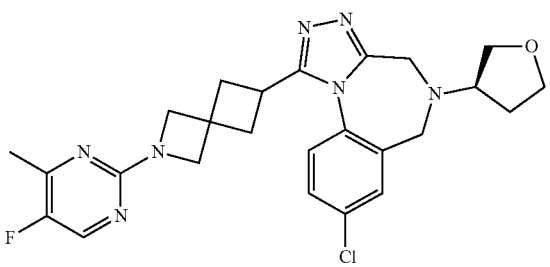 |
| 841 | 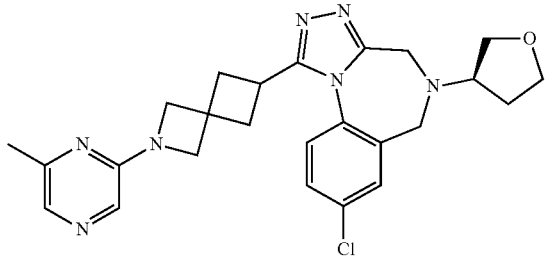 |
| 842 | 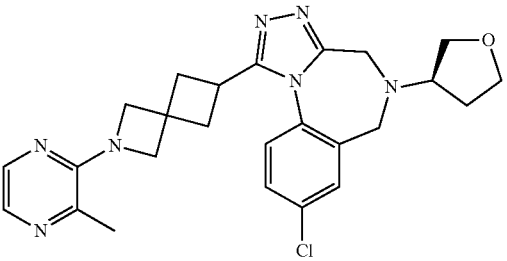 |
| 843 | 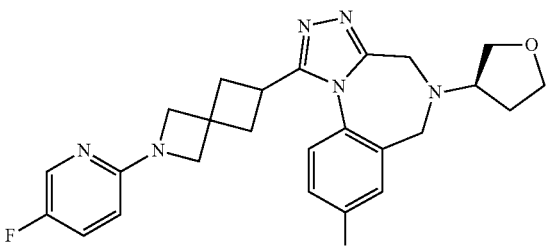 |

383
TABLE 1-continued
Representative Compounds
| Cmpd. No. | Structure |
|---|---|
| 844 | 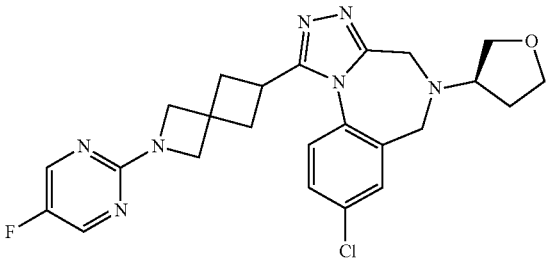 [SMILES: Cc1nc(N2CC3(CC(c4nnc5n4-c4ccc(Cl)cc4CN([C@@H]4CCOC4)C5)C3)C2)ncc1F] |
| 845 | 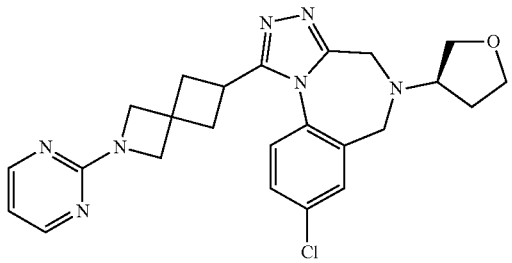 |
| 846 | 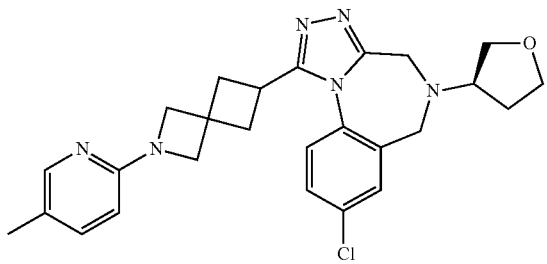 [SMILES: Cc1ccc(N2CC3(CC(c4nnc5n4-c4ccc(Cl)cc4CN([C@@H]4CCOC4)C5)C3)C2)nc1] |
| 847 | 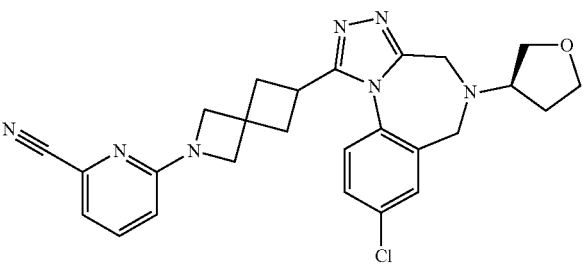 [SMILES: N#Cc1cccc(N2CC3(CC(c4nnc5n4-c4ccc(Cl)cc4CN([C@@H]4CCOC4)C5)C3)C2)n1] |
| 848 | 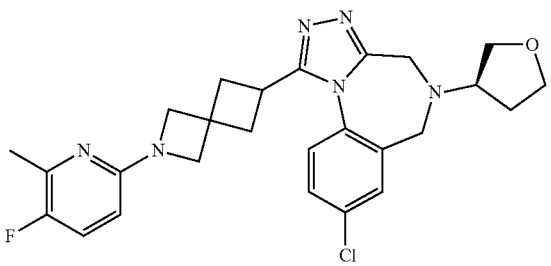 [SMILES: Cc1nc(N2CC3(CC(c4nnc5n4-c4ccc(Cl)cc4CN([C@@H]4CCOC4)C5)C3)C2)ccc1F] |

TABLE 1-continued

Representative Compounds

| Cmpd. No. | Structure |
|---|---|
| 849 | 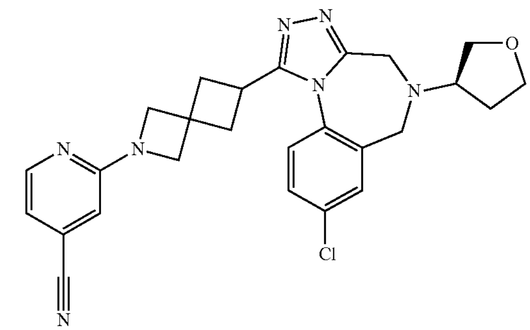 [SMILES: N#Cc1ccnc(N2CC3(CC(c4nnc5n4-c4ccc(Cl)cc4CN([C@@H]4CCOC4)C5)C3)C2)c1] |
| 850 | 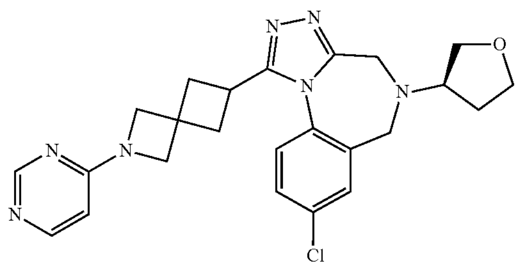 [SMILES: Clc1ccc2c(c1)CN([C@@H]1CCOC1)Cc1nnc(C3CC4(C3)CN(c3ccncn3)C4)n1-2] |
| 851 | 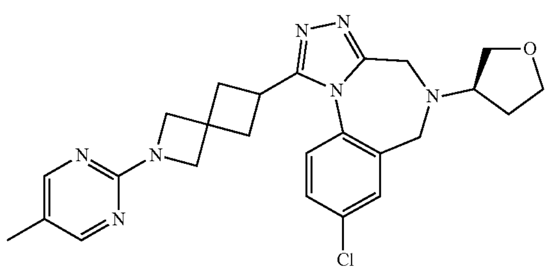 [SMILES: Cc1cnc(N2CC3(CC(c4nnc5n4-c4ccc(Cl)cc4CN([C@@H]4CCOC4)C5)C3)C2)nc1] |
| 852 | 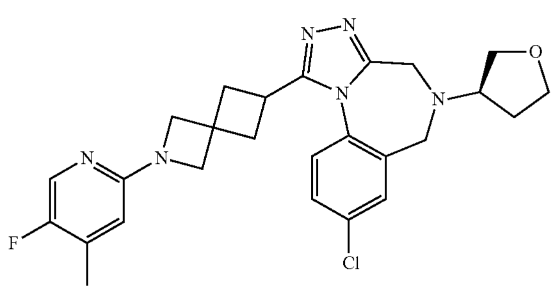 [SMILES: Cc1cc(N2CC3(CC(c4nnc5n4-c4ccc(Cl)cc4CN([C@@H]4CCOC4)C5)C3)C2)ncc1F] |
| 853 | 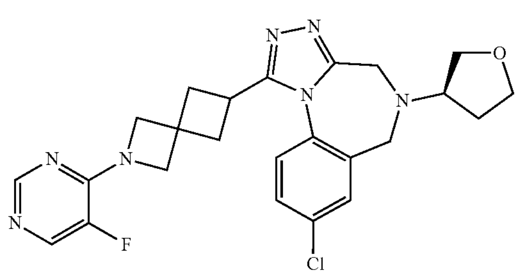 [SMILES: Fc1cncnc1N1CC2(CC(c3nnc4n3-c3ccc(Cl)cc3CN([C@@H]3CCOC3)C4)C2)C1] |

TABLE 1-continued

Representative Compounds

| Cmpd. No. | Structure |
|---|---|
| 854 | 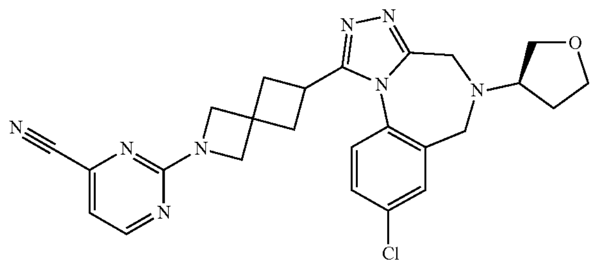 [SMILES: N#Cc1ccnc(N2CC3(CC(c4nnc5n4-c4ccc(Cl)cc4CN([C@@H]4CCOC4)C5)C3)C2)n1] |
| 855 | 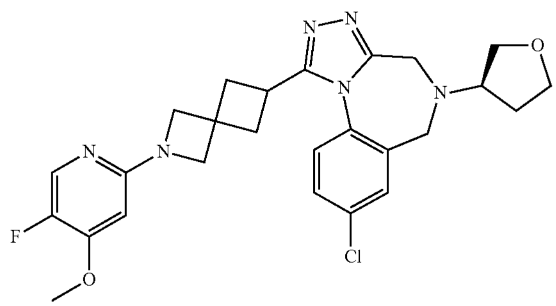 [SMILES: COc1cc(N2CC3(CC(c4nnc5n4-c4ccc(Cl)cc4CN([C@@H]4CCOC4)C5)C3)C2)ncc1F] |
| 856 | 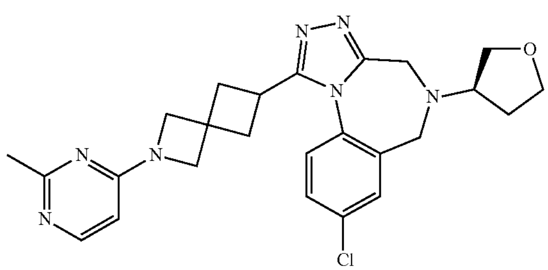 [SMILES: Cc1nccc(N2CC3(CC(c4nnc5n4-c4ccc(Cl)cc4CN([C@@H]4CCOC4)C5)C3)C2)n1] |
| 857 | 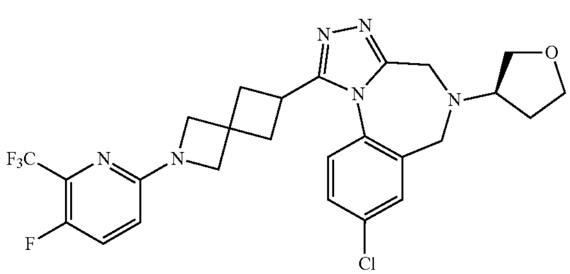 [SMILES: Fc1ccc(N2CC3(CC(c4nnc5n4-c4ccc(Cl)cc4CN([C@@H]4CCOC4)C5)C3)C2)nc1C(F)(F)F] |
| 858 | 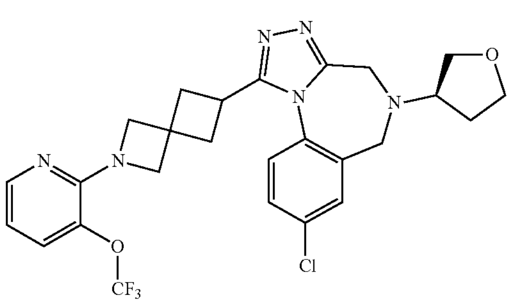 [SMILES: FC(F)(F)Oc1cccnc1N1CC2(CC(c3nnc4n3-c3ccc(Cl)cc3CN([C@@H]3CCOC3)C4)C2)C1] |

TABLE 1-continued

Representative Compounds

| Cmpd. No. | Structure |
|---|---|
| 859 | 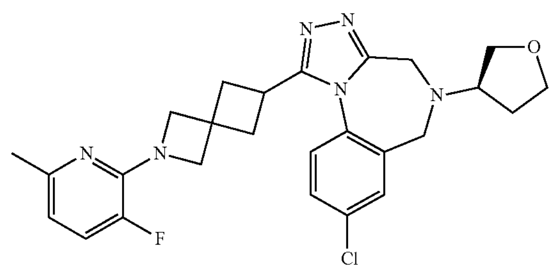 [SMILES: Cc1ccc(F)c(N2CC3(CC(c4nnc5n4-c4ccc(Cl)cc4CN([C@@H]4CCOC4)C5)C3)C2)n1] |
| 860 | 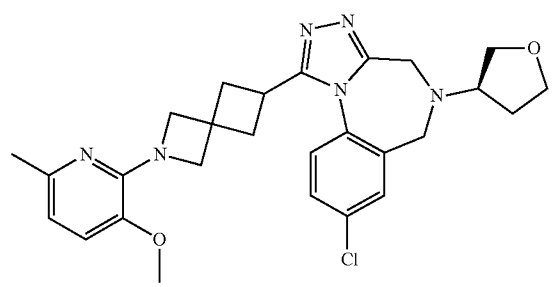 [SMILES: COc1ccc(C)nc1N1CC2(CC(c3nnc4n3-c3ccc(Cl)cc3CN([C@@H]3CCOC3)C4)C2)C1] |
| 861 | 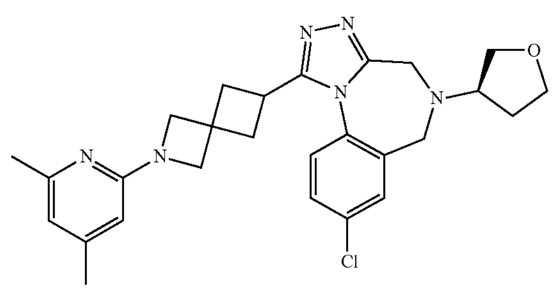 [SMILES: Cc1cc(C)nc(N2CC3(CC(c4nnc5n4-c4ccc(Cl)cc4CN([C@@H]4CCOC4)C5)C3)C2)c1] |
| 862 | 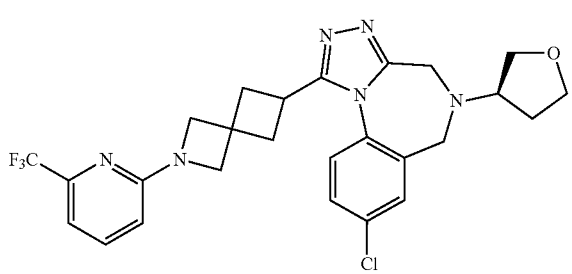 [SMILES: FC(F)(F)c1cccc(N2CC3(CC(c4nnc5n4-c4ccc(Cl)cc4CN([C@@H]4CCOC4)C5)C3)C2)n1] |
| 863 | 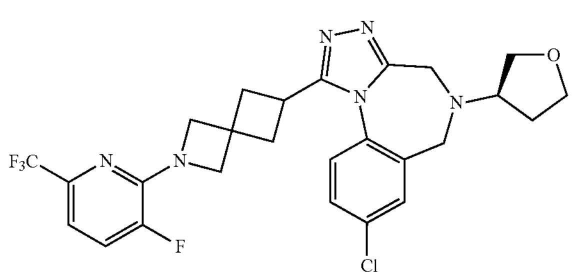 [SMILES: Fc1ccc(C(F)(F)F)nc1N1CC2(CC(c3nnc4n3-c3ccc(Cl)cc3CN([C@@H]3CCOC3)C4)C2)C1] |

TABLE 1-continued
Representative Compounds
| Cmpd. No. | Structure |
|---|---|
| 864 | 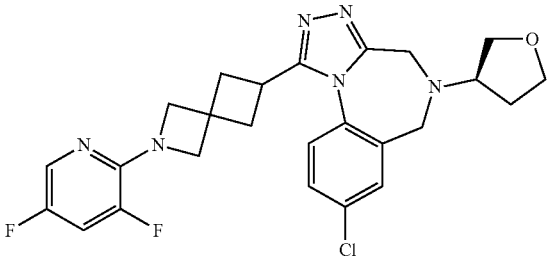 [SMILES: Fc1cnc(N2CC3(CC(c4nnc5n4-c4ccc(Cl)cc4CN([C@@H]4CCOC4)C5)C3)C2)c(F)c1] |
| 865 | 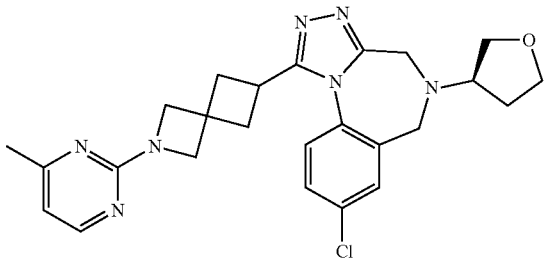 [SMILES: Cc1ccnc(N2CC3(CC(c4nnc5n4-c4ccc(Cl)cc4CN([C@@H]4CCOC4)C5)C3)C2)n1] |
| 866 | 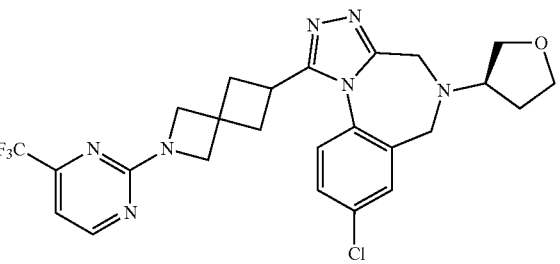 |
| 867 | 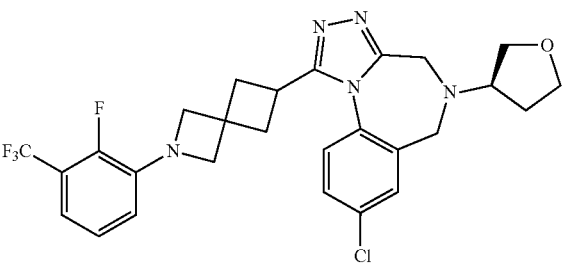 [SMILES: Fc1c(N2CC3(CC(c4nnc5n4-c4ccc(Cl)cc4CN([C@@H]4CCOC4)C5)C3)C2)cccc1C(F)(F)F] |
| 868 | 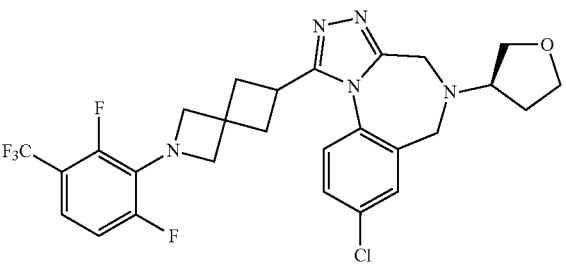 [SMILES: Fc1ccc(C(F)(F)F)c(F)c1N1CC2(CC(c3nnc4n3-c3ccc(Cl)cc3CN([C@@H]3CCOC3)C4)C2)C1] |

TABLE 1-continued

Representative Compounds

| Cmpd. No. | Structure |
|---|---|
| 869 | 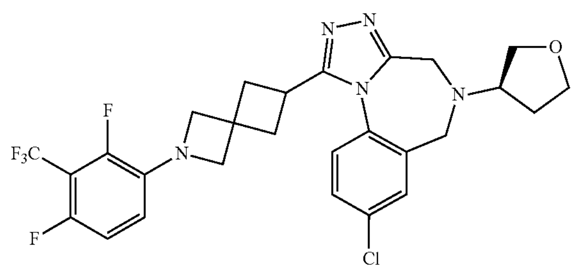 [SMILES: Fc1ccc(N2CC3(CC(c4nnc5n4-c4ccc(Cl)cc4CN([C@@H]4CCOC4)C5)C3)C2)c(F)c1C(F)(F)F] |
| 870 | 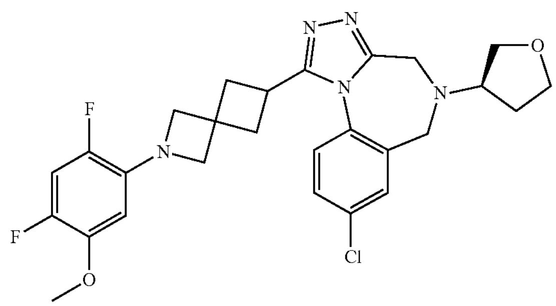 [SMILES: COc1cc(N2CC3(CC(c4nnc5n4-c4ccc(Cl)cc4CN([C@@H]4CCOC4)C5)C3)C2)c(F)cc1F] |
| 871 | 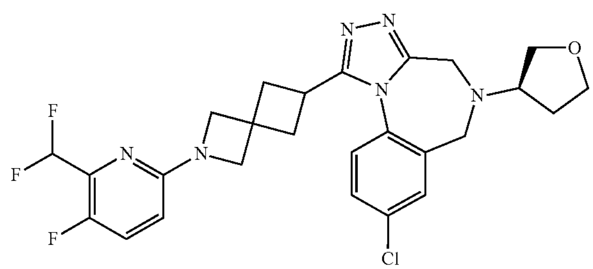 [SMILES: Fc1ccc(N2CC3(CC(c4nnc5n4-c4ccc(Cl)cc4CN([C@@H]4CCOC4)C5)C3)C2)nc1C(F)F] |
| 872 | 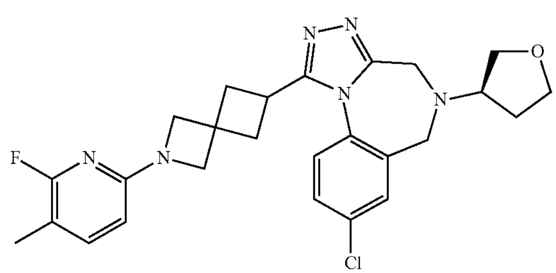 [SMILES: Cc1ccc(N2CC3(CC(c4nnc5n4-c4ccc(Cl)cc4CN([C@@H]4CCOC4)C5)C3)C2)nc1F] |
| 873 | 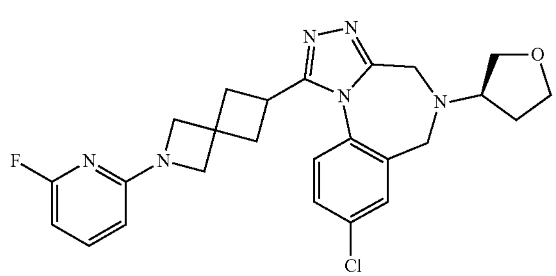 [SMILES: Fc1cccc(N2CC3(CC(c4nnc5n4-c4ccc(Cl)cc4CN([C@@H]4CCOC4)C5)C3)C2)n1] |

TABLE 1-continued

Representative Compounds

| Cmpd. No. | Structure |
|---|---|
| 874 | 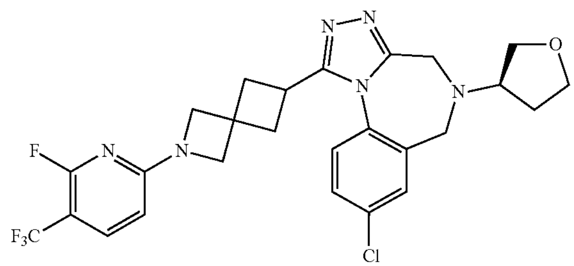 [SMILES: Fc1nc(N2CC3(CC(c4nnc5n4-c4ccc(Cl)cc4CN([C@@H]4CCOC4)C5)C3)C2)ccc1C(F)(F)F] |
| 875 | 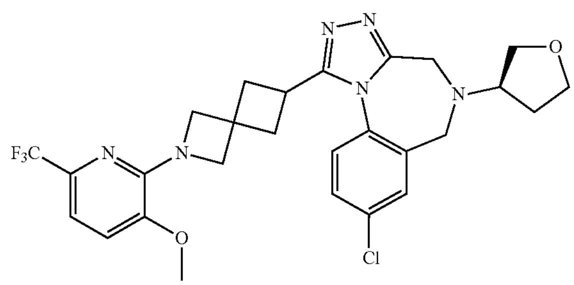 [SMILES: COc1ccc(C(F)(F)F)nc1N1CC2(CC(c3nnc4n3-c3ccc(Cl)cc3CN([C@@H]3CCOC3)C4)C2)C1] |
| 876 | 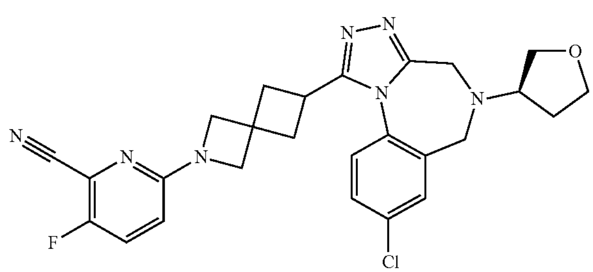 [SMILES: N#Cc1nc(N2CC3(CC(c4nnc5n4-c4ccc(Cl)cc4CN([C@@H]4CCOC4)C5)C3)C2)ccc1F] |
| 877 | 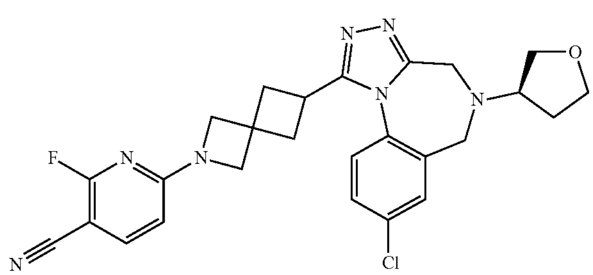 [SMILES: N#Cc1ccc(N2CC3(CC(c4nnc5n4-c4ccc(Cl)cc4CN([C@@H]4CCOC4)C5)C3)C2)nc1F] |
| 878 | 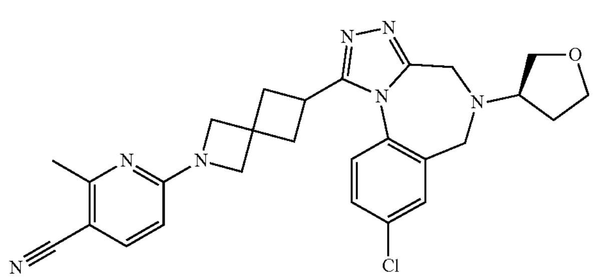 [SMILES: Cc1nc(N2CC3(CC(c4nnc5n4-c4ccc(Cl)cc4CN([C@@H]4CCOC4)C5)C3)C2)ccc1C#N] |

TABLE 1-continued

Representative Compounds

| Cmpd. No. | Structure |
|---|---|
| 879 | 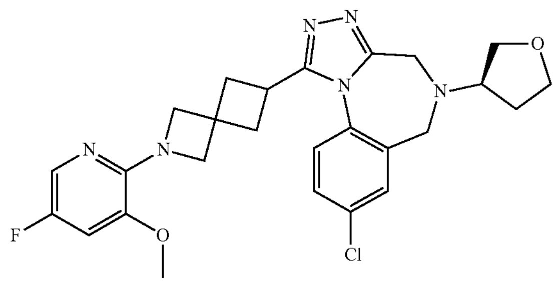 [SMILES: COc1cc(F)cnc1N1CC2(CC(c3nnc4n3-c3ccc(Cl)cc3CN([C@@H]3CCOC3)C4)C2)C1] |
| 880 | 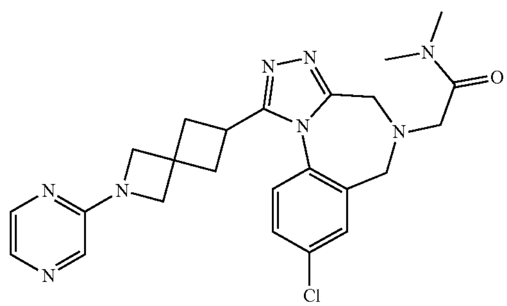 [SMILES: CN(C)C(=O)CN1Cc2cc(Cl)ccc2-n2c(nnc2C2CC3(C2)CN(c2cnccn2)C3)C1] |
| 881 | 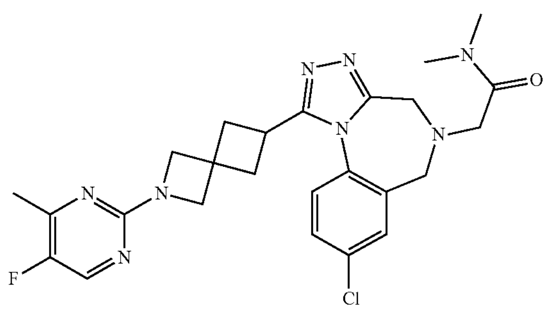 [SMILES: Cc1nc(N2CC3(CC(c4nnc5n4-c4ccc(Cl)cc4CN(CC(=O)N(C)C)C5)C3)C2)ncc1F] |
| 882 | 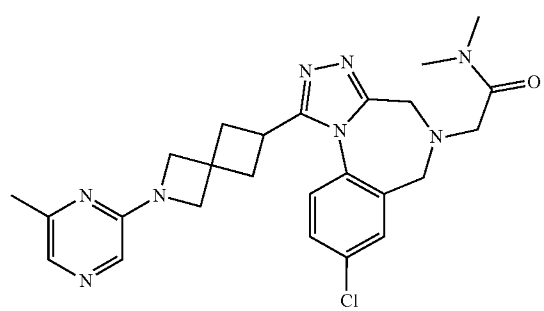 |
| 883 | 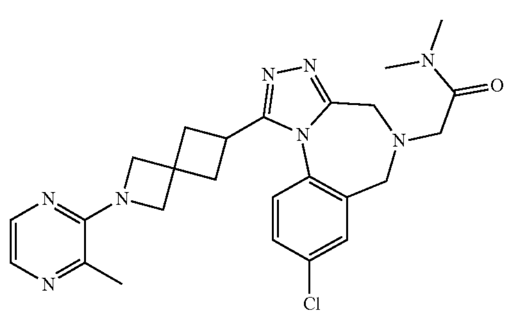 [SMILES: Cc1nccnc1N1CC2(CC(c3nnc4n3-c3ccc(Cl)cc3CN(CC(=O)N(C)C)C4)C2)C1] |

TABLE 1-continued

Representative Compounds

| Cmpd. No. | Structure |
|---|---|
| 884 | 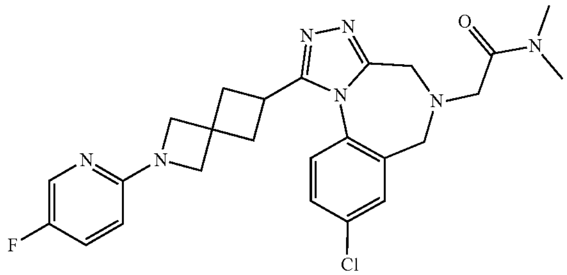 [SMILES: CN(C)C(=O)CN1Cc2cc(Cl)ccc2-n2c(nnc2C2CC3(C2)CN(c2ccc(F)cn2)C3)C1] |
| 885 | 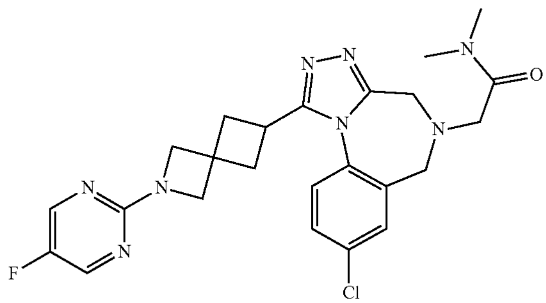 [SMILES: CN(C)C(=O)CN1Cc2cc(Cl)ccc2-n2c(nnc2C2CC3(C2)CN(c2ncc(F)cn2)C3)C1] |
| 886 | 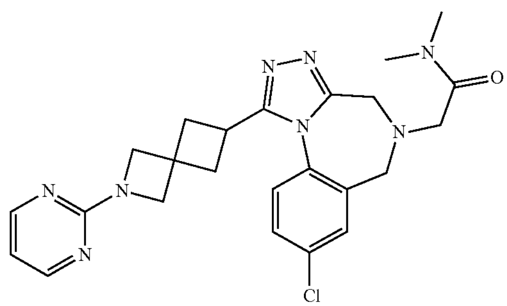 [SMILES: CN(C)C(=O)CN1Cc2cc(Cl)ccc2-n2c(nnc2C2CC3(C2)CN(c2ncccn2)C3)C1] |
| 887 | 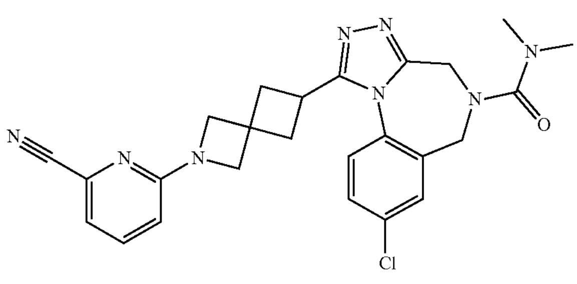 [SMILES: CN(C)C(=O)N1Cc2cc(Cl)ccc2-n2c(nnc2C2CC3(C2)CN(c2cccc(C#N)n2)C3)C1] |
| 888 | 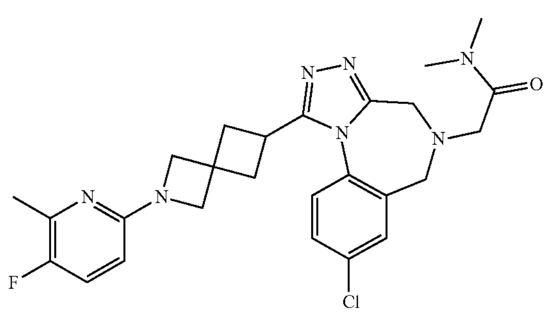 [SMILES: Cc1nc(N2CC3(CC(c4nnc5n4-c4ccc(Cl)cc4CN(CC(=O)N(C)C)C5)C3)C2)ccc1F] |

TABLE 1-continued

Representative Compounds

| Cmpd. No. | Structure |
|---|---|
| 889 | 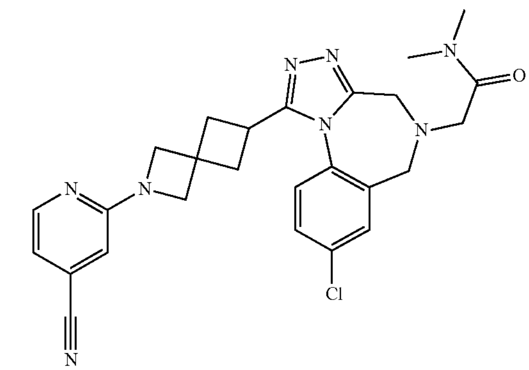 [SMILES: CN(C)C(=O)CN1Cc2cc(Cl)ccc2-n2c(nnc2C2CC3(C2)CN(c2cc(C#N)ccn2)C3)C1] |
| 890 | 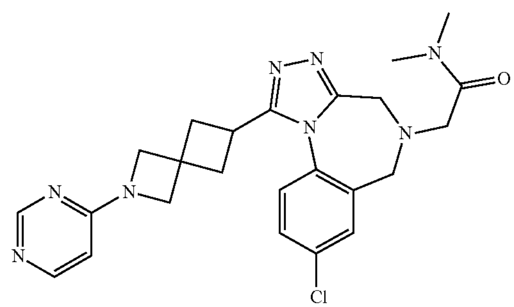 [SMILES: CN(C)C(=O)CN1Cc2cc(Cl)ccc2-n2c(nnc2C2CC3(C2)CN(c2ccncn2)C3)C1] |
| 891 | 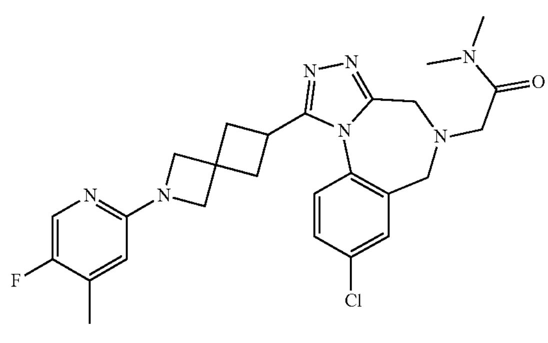 [SMILES: Cc1cc(N2CC3(CC(c4nnc5n4-c4ccc(Cl)cc4CN(CC(=O)N(C)C)C5)C3)C2)ncc1F] |
| 892 | 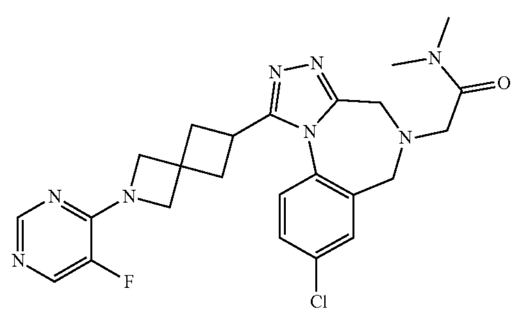 [SMILES: CN(C)C(=O)CN1Cc2cc(Cl)ccc2-n2c(nnc2C2CC3(C2)CN(c2ncncc2F)C3)C1] |

TABLE 1-continued

Representative Compounds

| Cmpd. No. | Structure |
|---|---|
| 893 | 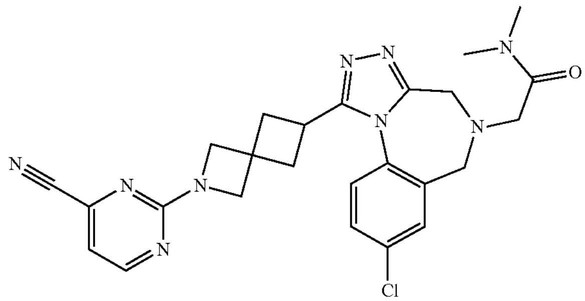 [SMILES: CN(C)C(=O)CN1Cc2cc(Cl)ccc2-n2c(nnc2C2CC3(C2)CN(c2nccc(C#N)n2)C3)C1] |
| 894 | 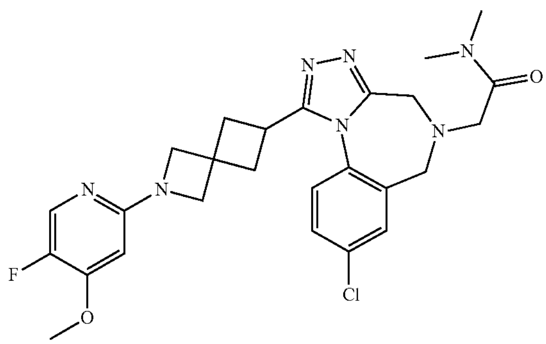 [SMILES: COc1cc(N2CC3(CC(c4nnc5n4-c4ccc(Cl)cc4CN(CC(=O)N(C)C)C5)C3)C2)ncc1F] |
| 895 | 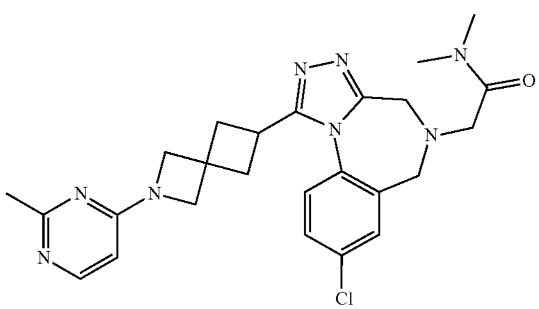 [SMILES: Cc1nccc(N2CC3(CC(c4nnc5n4-c4ccc(Cl)cc4CN(CC(=O)N(C)C)C5)C3)C2)n1] |
| 896 | 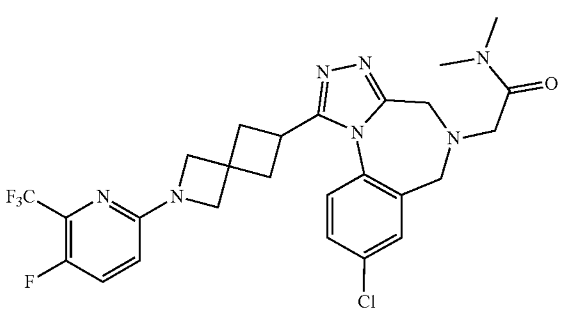 [SMILES: CN(C)C(=O)CN1Cc2cc(Cl)ccc2-n2c(nnc2C2CC3(C2)CN(c2ccc(F)c(C(F)(F)F)n2)C3)C1] |

TABLE 1-continued

Representative Compounds

| Cmpd. No. | Structure |
|---|---|
| 897 | 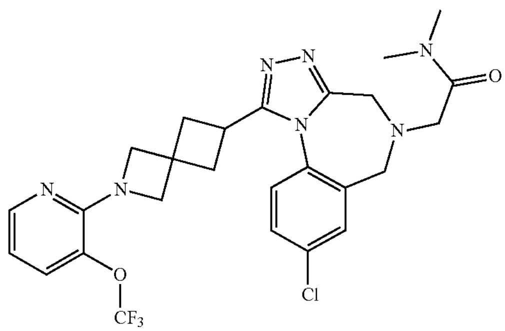 [SMILES: CN(C)C(=O)CN1Cc2cc(Cl)ccc2-n2c(nnc2C2CC3(C2)CN(c2ncccc2OC(F)(F)F)C3)C1] |
| 898 | 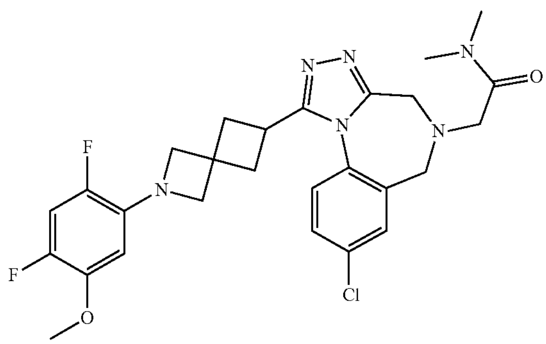 [SMILES: COc1cc(N2CC3(CC(c4nnc5n4-c4ccc(Cl)cc4CN(CC(=O)N(C)C)C5)C3)C2)c(F)cc1F] |
| 899 | 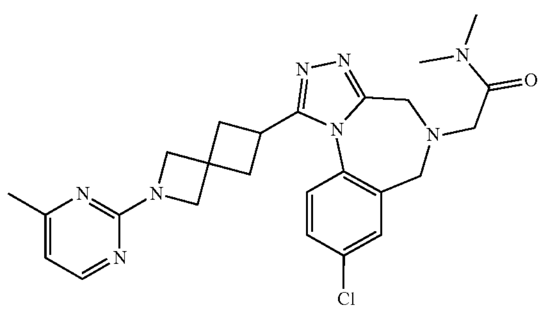 [SMILES: Cc1ccnc(N2CC3(CC(c4nnc5n4-c4ccc(Cl)cc4CN(CC(=O)N(C)C)C5)C3)C2)n1] |
| 900 | 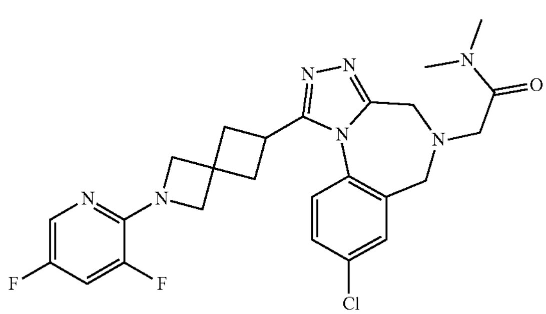 [SMILES: CN(C)C(=O)CN1Cc2cc(Cl)ccc2-n2c(nnc2C2CC3(C2)CN(c2ncc(F)cc2F)C3)C1] |

TABLE 1-continued

Representative Compounds

| Cmpd. No. | Structure |
|---|---|
| 901 | 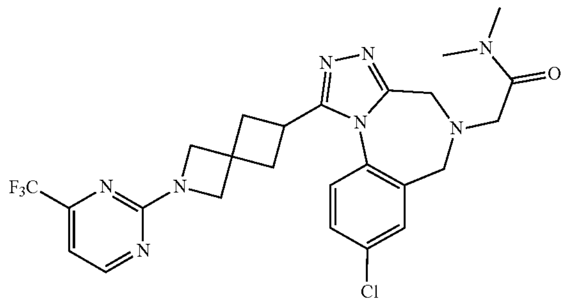 [SMILES: CN(C)C(=O)CN1Cc2cc(Cl)ccc2-n2c(nnc2C2CC3(C2)CN(c2nccc(C(F)(F)F)n2)C3)C1] |
| 902 | 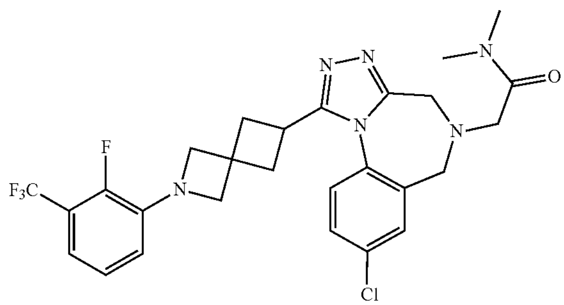 [SMILES: CN(C)C(=O)CN1Cc2cc(Cl)ccc2-n2c(nnc2C2CC3(C2)CN(c2cccc(C(F)(F)F)c2F)C3)C1] |
| 903 | 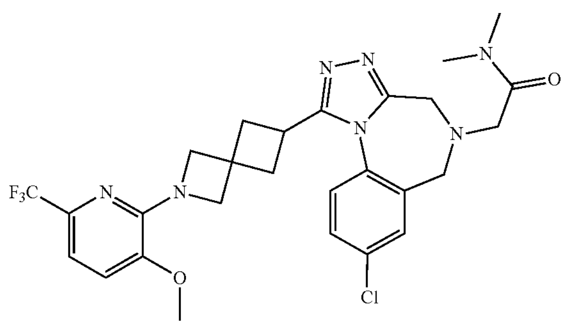 [SMILES: COc1ccc(C(F)(F)F)nc1N1CC2(CC(c3nnc4n3-c3ccc(Cl)cc3CN(CC(=O)N(C)C)C4)C2)C1] |
| 904 | 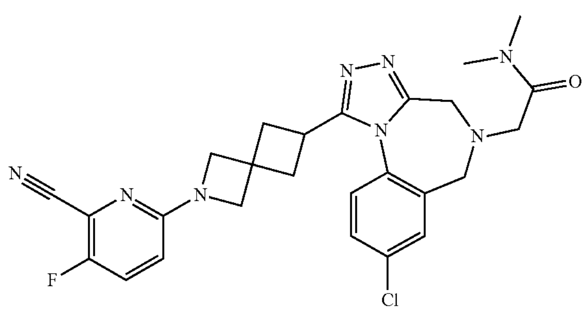 [SMILES: CN(C)C(=O)CN1Cc2cc(Cl)ccc2-n2c(nnc2C2CC3(C2)CN(c2ccc(F)c(C#N)n2)C3)C1] |
| 905 | 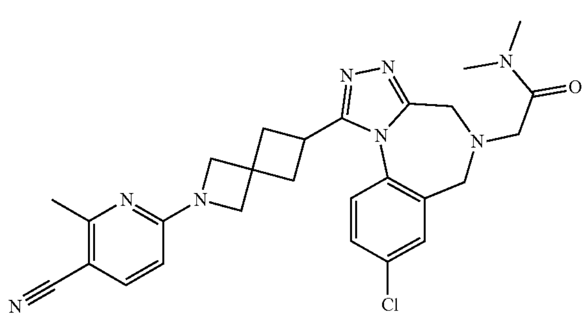 [SMILES: Cc1nc(N2CC3(CC(c4nnc5n4-c4ccc(Cl)cc4CN(CC(=O)N(C)C)C5)C3)C2)ccc1C#N] |

TABLE 1-continued
Representative Compounds
| Cmpd. No. | Structure |
|---|---|
| 906 | 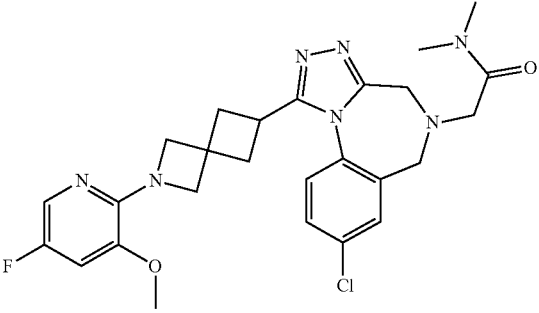 [SMILES: COc1cc(F)cnc1N1CC2(CC(c3nnc4n3-c3ccc(Cl)cc3CN(CC(=O)N(C)C)C4)C2)C1] |
| 907 | 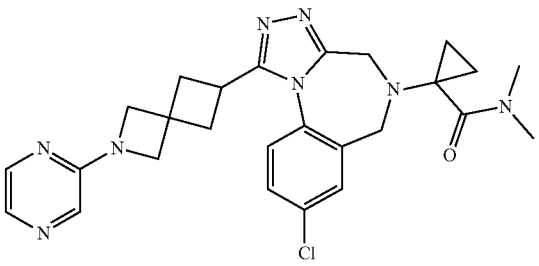 [SMILES: CN(C)C(=O)C1(N2Cc3cc(Cl)ccc3-n3c(nnc3C3CC4(C3)CN(c3cnccn3)C4)C2)CC1] |
| 908 | 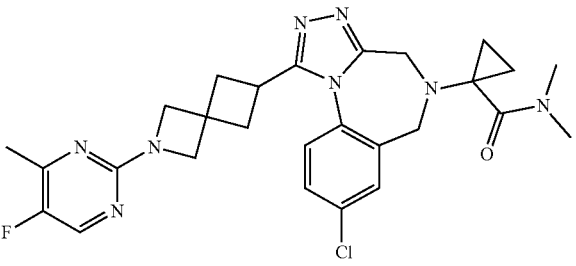 |
| 909 | 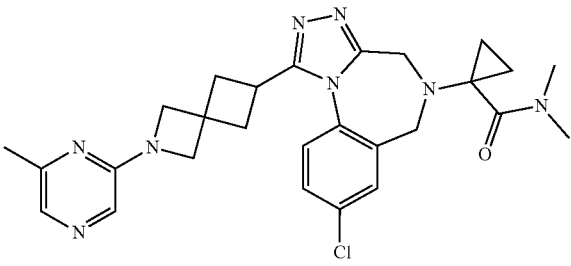 |
| 910 | 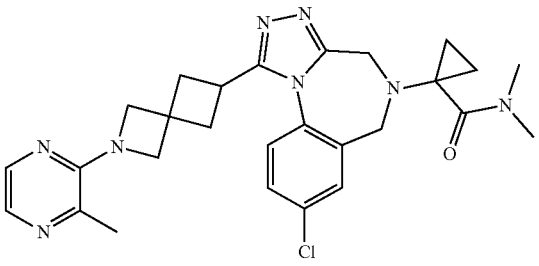 [SMILES: Cc1nccnc1N1CC2(CC(c3nnc4n3-c3ccc(Cl)cc3CN(C3(C(=O)N(C)C)CC3)C4)C2)C1] |

TABLE 1-continued

Representative Compounds

| Cmpd. No. | Structure |
|---|---|
| 911 | 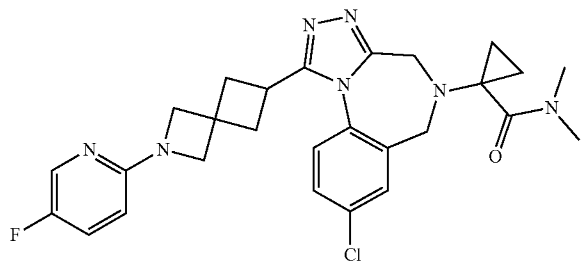 [SMILES: CN(C)C(=O)C1(N2Cc3cc(Cl)ccc3-n3c(nnc3C3CC4(C3)CN(c3ccc(F)cn3)C4)C2)CC1] |
| 912 | 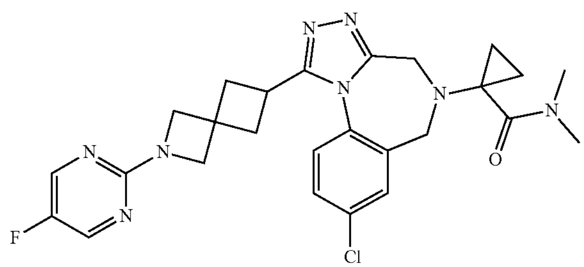 [SMILES: CN(C)C(=O)C1(N2Cc3cc(Cl)ccc3-n3c(nnc3C3CC4(C3)CN(c3ncc(F)cn3)C4)C2)CC1] |
| 913 | 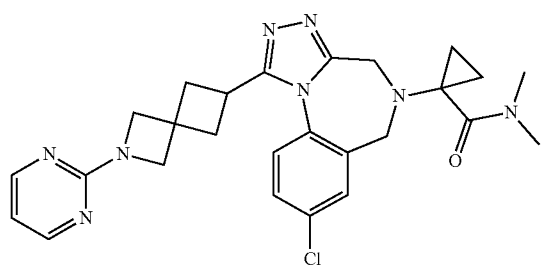 [SMILES: CN(C)C(=O)C1(N2Cc3cc(Cl)ccc3-n3c(nnc3C3CC4(C3)CN(c3ncccn3)C4)C2)CC1] |
| 914 | 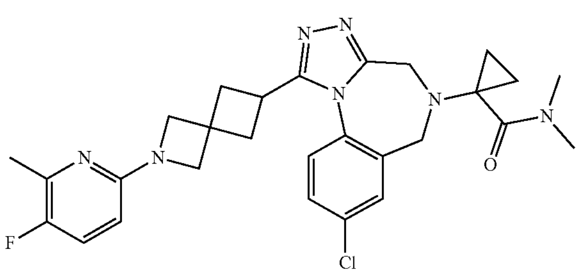 [SMILES: Cc1nc(N2CC3(CC(c4nnc5n4-c4ccc(Cl)cc4CN(C4(C(=O)N(C)C)CC4)C5)C3)C2)ccc1F] |
| 915 | 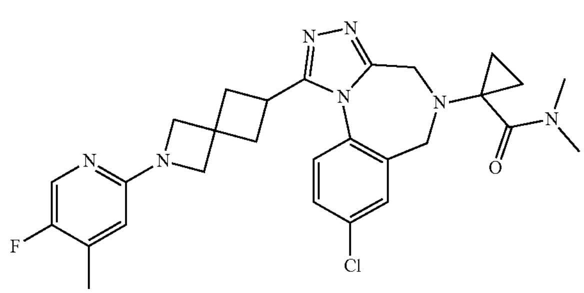 [SMILES: Cc1cc(N2CC3(CC(c4nnc5n4-c4ccc(Cl)cc4CN(C4(C(=O)N(C)C)CC4)C5)C3)C2)ncc1F] |

TABLE 1-continued

Representative Compounds

| Cmpd. No. | Structure |
|---|---|
| 916 | 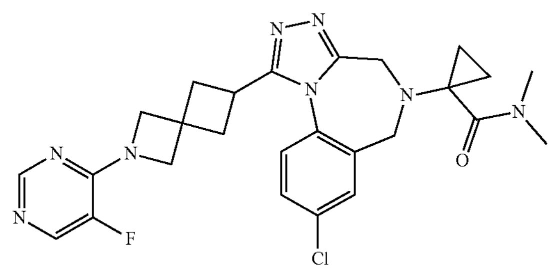 [SMILES: CN(C)C(=O)C1(N2Cc3cc(Cl)ccc3-n3c(nnc3C3CC4(C3)CN(c3ncncc3F)C4)C2)CC1] |
| 917 | 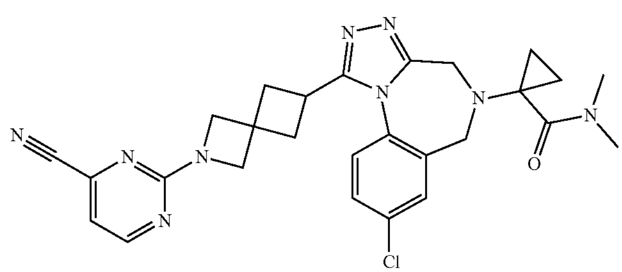 [SMILES: CN(C)C(=O)C1(N2Cc3cc(Cl)ccc3-n3c(nnc3C3CC4(C3)CN(c3nccc(C#N)n3)C4)C2)CC1] |
| 918 | 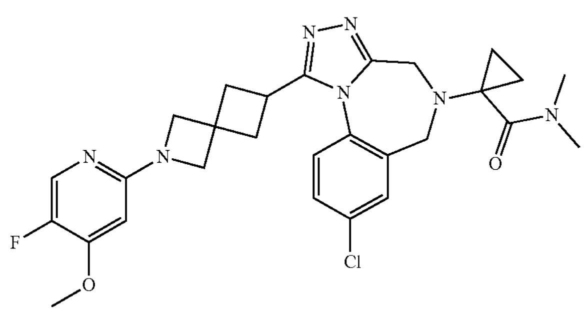 [SMILES: COc1cc(N2CC3(CC(c4nnc5n4-c4ccc(Cl)cc4CN(C4(C(=O)N(C)C)CC4)C5)C3)C2)ncc1F] |
| 919 | 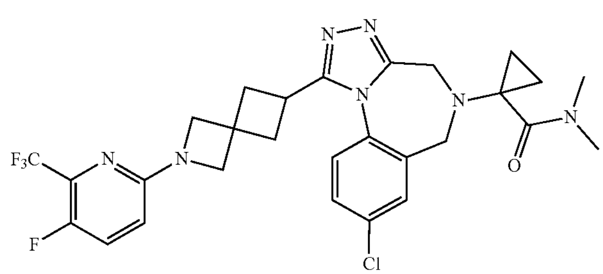 [SMILES: CN(C)C(=O)C1(N2Cc3cc(Cl)ccc3-n3c(nnc3C3CC4(C3)CN(c3ccc(F)c(C(F)(F)F)n3)C4)C2)CC1] |
| 920 | 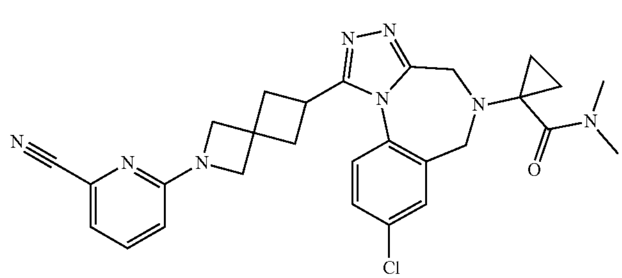 [SMILES: CN(C)C(=O)C1(N2Cc3cc(Cl)ccc3-n3c(nnc3C3CC4(C3)CN(c3cccc(C#N)n3)C4)C2)CC1] |

TABLE 1-continued

Representative Compounds

| Cmpd. No. | Structure |
|---|---|
| 921 | 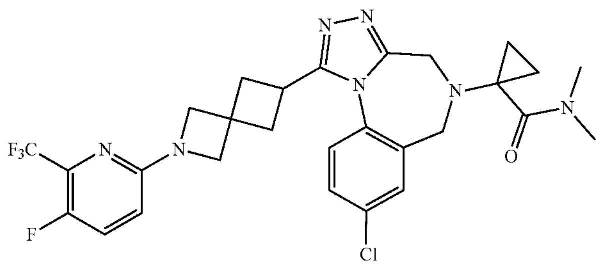 [SMILES: CN(C)C(=O)C1(N2Cc3cc(Cl)ccc3-n3c(nnc3C3CC4(C3)CN(c3ccc(F)c(C(F)(F)F)n3)C4)C2)CC1] |
| 922 | 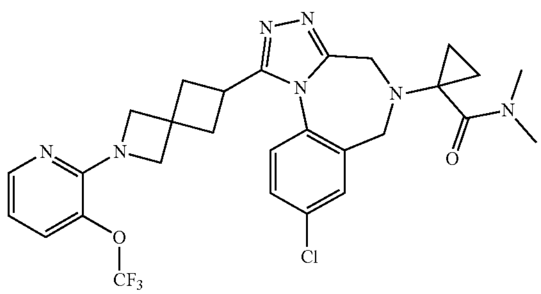 [SMILES: CN(C)C(=O)C1(N2Cc3cc(Cl)ccc3-n3c(nnc3C3CC4(C3)CN(c3ncccc3OC(F)(F)F)C4)C2)CC1] |
| 923 | 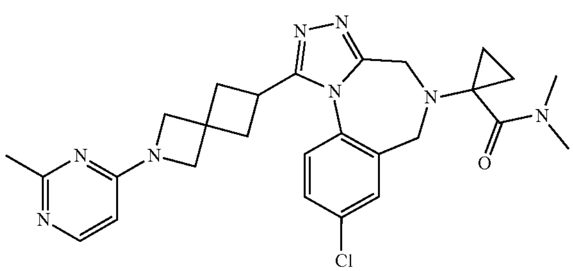 |
| 924 | 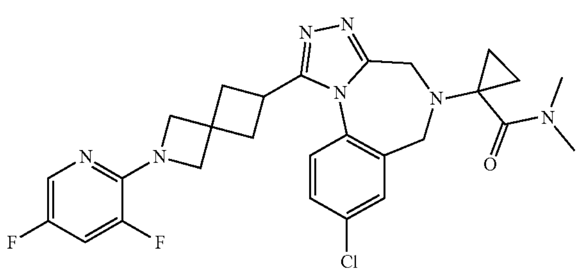 [SMILES: CN(C)C(=O)C1(N2Cc3cc(Cl)ccc3-n3c(nnc3C3CC4(C3)CN(c3ncc(F)cc3F)C4)C2)CC1] |
| 925 | 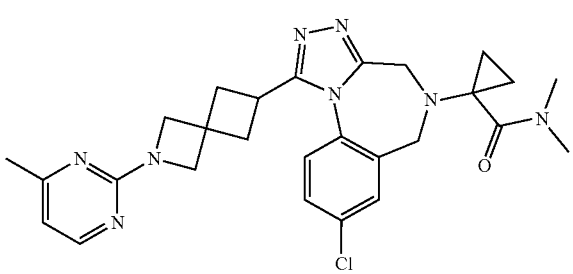 |

TABLE 1-continued

Representative Compounds

| Cmpd. No. | Structure |
|---|---|
| 926 | 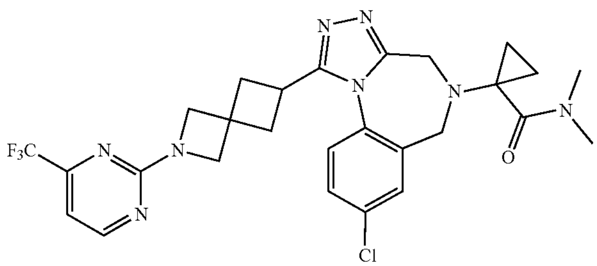 [SMILES: CN(C)C(=O)C1(N2Cc3cc(Cl)ccc3-n3c(nnc3C3CC4(C3)CN(c3nccc(C(F)(F)F)n3)C4)C2)CC1] |
| 927 | 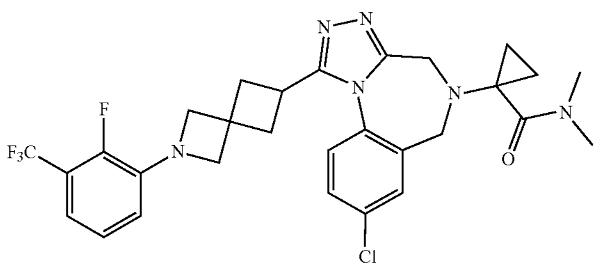 [SMILES: CN(C)C(=O)C1(N2Cc3cc(Cl)ccc3-n3c(nnc3C3CC4(C3)CN(c3cccc(C(F)(F)F)c3F)C4)C2)CC1] |
| 928 | 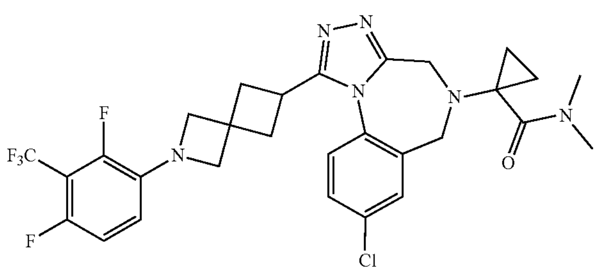 [SMILES: CN(C)C(=O)C1(N2Cc3cc(Cl)ccc3-n3c(nnc3C3CC4(C3)CN(c3ccc(F)c(C(F)(F)F)c3F)C4)C2)CC1] |
| 929 | 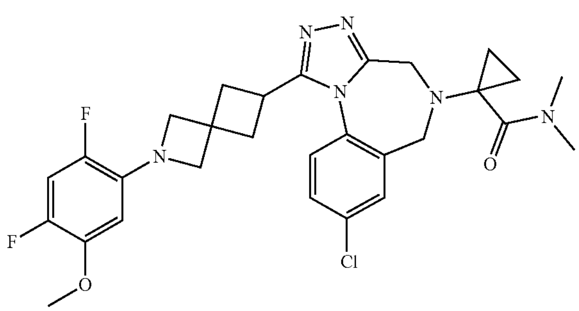 |
| 930 | 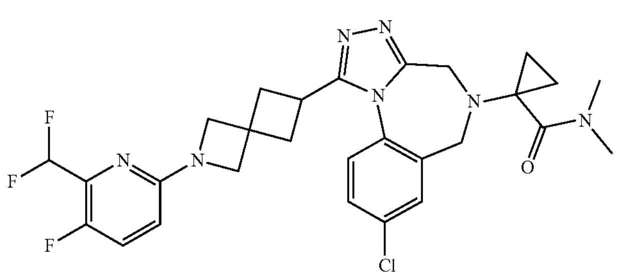 [SMILES: CN(C)C(=O)C1(N2Cc3cc(Cl)ccc3-n3c(nnc3C3CC4(C3)CN(c3ccc(F)c(C(F)F)n3)C4)C2)CC1] |

TABLE 1-continued

Representative Compounds

| Cmpd. No. | Structure |
|---|---|
| 931 | 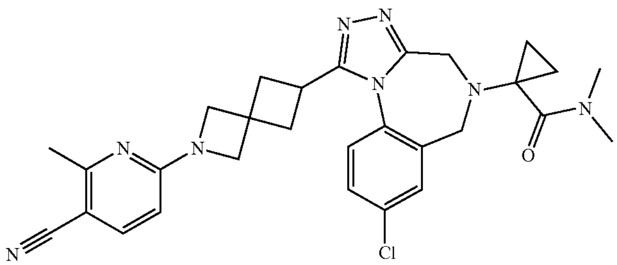 [SMILES: Cc1nc(N2CC3(CC(c4nnc5n4-c4ccc(Cl)cc4CN(C4(C(=O)N(C)C)CC4)C5)C3)C2)ccc1C#N] |
| 932 | 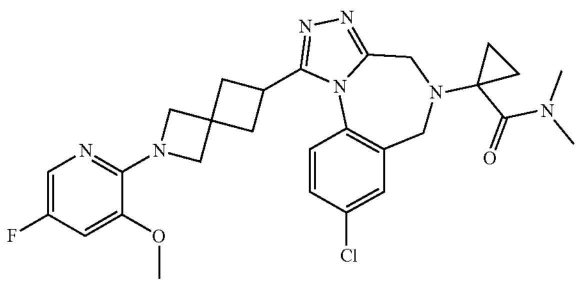 [SMILES: COc1cc(F)cnc1N1CC2(CC(c3nnc4n3-c3ccc(Cl)cc3CN(C3(C(=O)N(C)C)CC3)C4)C2)C1] |
| 933 | 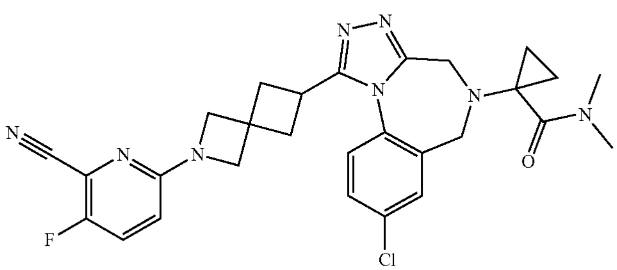 [SMILES: CN(C)C(=O)C1(N2Cc3cc(Cl)ccc3-n3c(nnc3C3CC4(C3)CN(c3ccc(F)c(C#N)n3)C4)C2)CC1] |
| 934 | 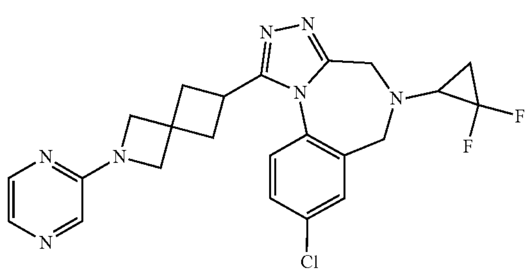 [SMILES: FC1(F)CC1N1Cc2cc(Cl)ccc2-n2c(nnc2C2CC3(C2)CN(c2cnccn2)C3)C1] |
| 935 | 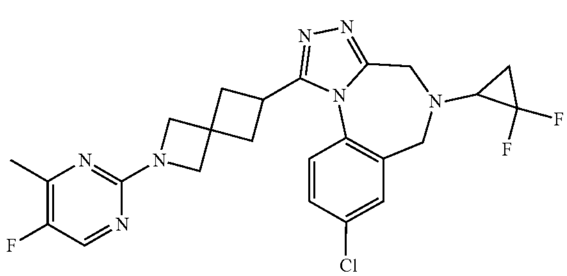 [SMILES: Cc1nc(N2CC3(CC(c4nnc5n4-c4ccc(Cl)cc4CN(C4CC4(F)F)C5)C3)C2)ncc1F] |

TABLE 1-continued

Representative Compounds

| Cmpd. No. | Structure |
|---|---|
| 936 | 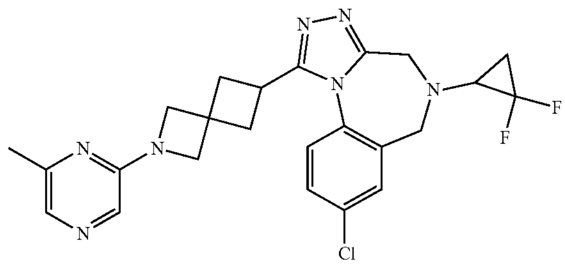 [SMILES: Cc1cncc(N2CC3(CC(c4nnc5n4-c4ccc(Cl)cc4CN(C4CC4(F)F)C5)C3)C2)n1] |
| 937 | 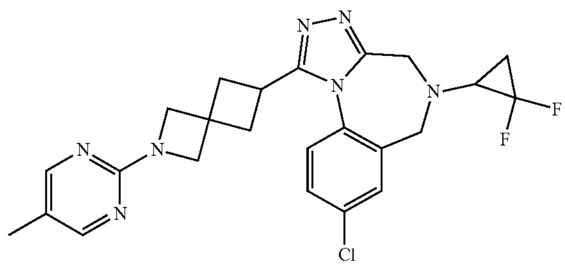 [SMILES: Cc1cnc(N2CC3(CC(c4nnc5n4-c4ccc(Cl)cc4CN(C4CC4(F)F)C5)C3)C2)nc1] |
| 938 | 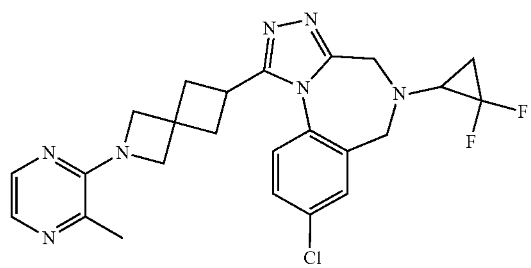 [SMILES: Cc1nccnc1N1CC2(CC(c3nnc4n3-c3ccc(Cl)cc3CN(C3CC3(F)F)C4)C2)C1] |
| 939 | 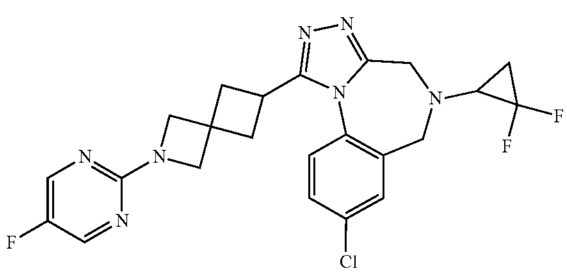 [SMILES: Fc1cnc(N2CC3(CC(c4nnc5n4-c4ccc(Cl)cc4CN(C4CC4(F)F)C5)C3)C2)nc1] |
| 940 | 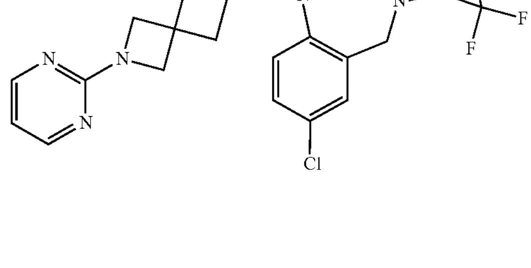 |

TABLE 1-continued

Representative Compounds

| Cmpd. No. | Structure |
|---|---|
| 941 | 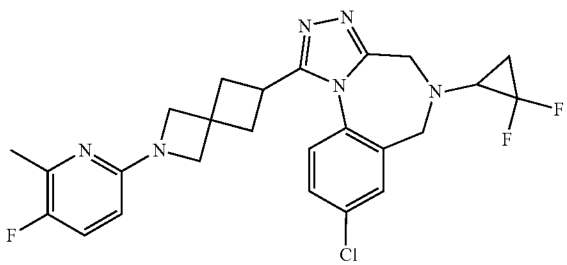 [SMILES: Cc1nc(N2CC3(CC(c4nnc5n4-c4ccc(Cl)cc4CN(C4CC4(F)F)C5)C3)C2)ccc1F] |
| 942 | 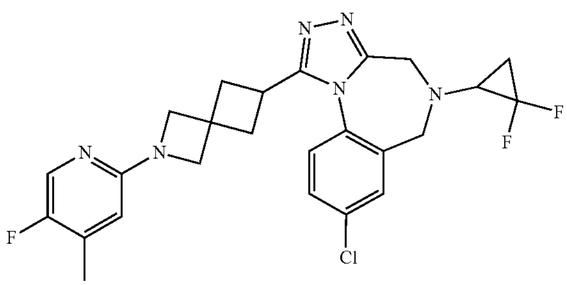 [SMILES: Cc1cc(N2CC3(CC(c4nnc5n4-c4ccc(Cl)cc4CN(C4CC4(F)F)C5)C3)C2)ncc1F] |
| 943 | 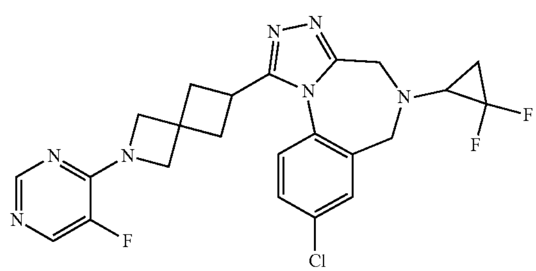 [SMILES: Fc1cncnc1N1CC2(CC(c3nnc4n3-c3ccc(Cl)cc3CN(C3CC3(F)F)C4)C2)C1] |
| 944 | 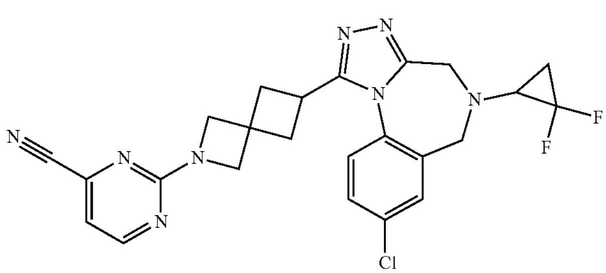 [SMILES: N#Cc1ccnc(N2CC3(CC(c4nnc5n4-c4ccc(Cl)cc4CN(C4CC4(F)F)C5)C3)C2)n1] |
| 945 | 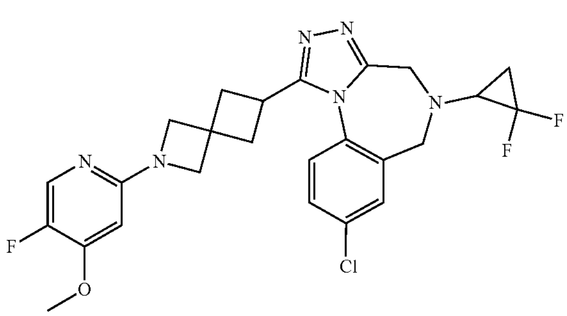 [SMILES: COc1cc(N2CC3(CC(c4nnc5n4-c4ccc(Cl)cc4CN(C4CC4(F)F)C5)C3)C2)ncc1F] |

TABLE 1-continued

Representative Compounds

| Cmpd. No. | Structure |
|---|---|
| 946 | 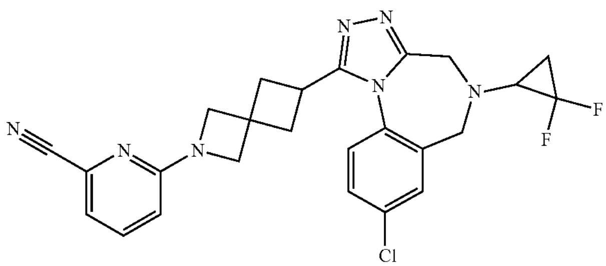 [SMILES: N#Cc1cccc(N2CC3(CC(c4nnc5n4-c4ccc(Cl)cc4CN(C4CC4(F)F)C5)C3)C2)n1] |
| 947 | 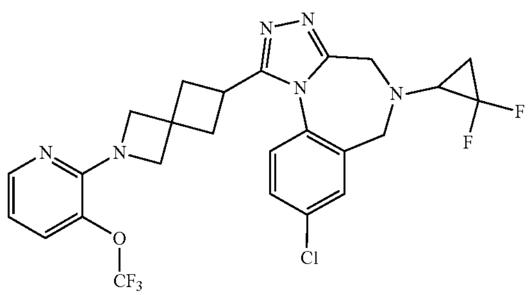 [SMILES: FC(F)(F)Oc1cccnc1N1CC2(CC(c3nnc4n3-c3ccc(Cl)cc3CN(C3CC3(F)F)C4)C2)C1] |
| 948 | 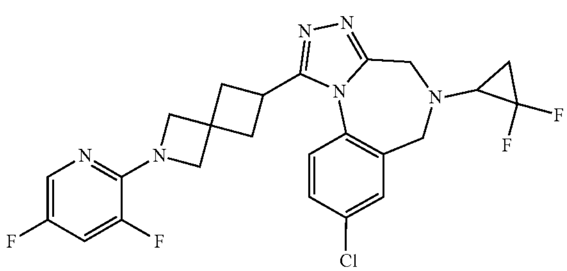 [SMILES: Fc1cnc(N2CC3(CC(c4nnc5n4-c4ccc(Cl)cc4CN(C4CC4(F)F)C5)C3)C2)c(F)c1] |
| 949 | 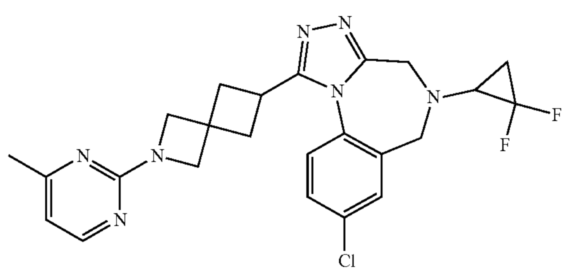 [SMILES: Cc1ccnc(N2CC3(CC(c4nnc5n4-c4ccc(Cl)cc4CN(C4CC4(F)F)C5)C3)C2)n1] |
| 950 | 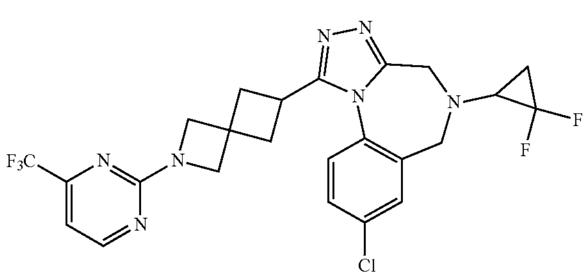 [SMILES: FC(F)(F)c1ccnc(N2CC3(CC(c4nnc5n4-c4ccc(Cl)cc4CN(C4CC4(F)F)C5)C3)C2)n1] |

TABLE 1-continued

Representative Compounds

| Cmpd. No. | Structure |
|---|---|
| 951 | 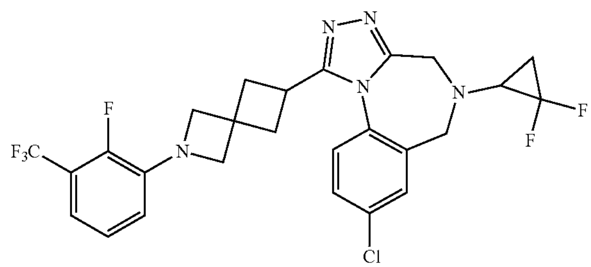 [SMILES: Fc1c(N2CC3(CC(c4nnc5n4-c4ccc(Cl)cc4CN(C4CC4(F)F)C5)C3)C2)cccc1C(F)(F)F] |
| 952 | 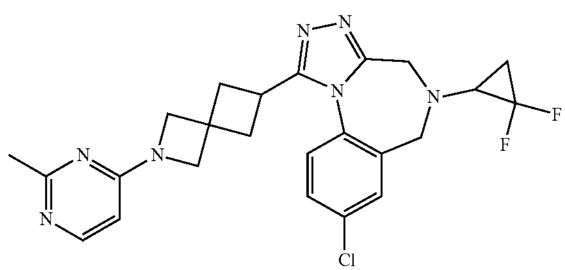 [SMILES: Cc1nccc(N2CC3(CC(c4nnc5n4-c4ccc(Cl)cc4CN(C4CC4(F)F)C5)C3)C2)n1] |
| 953 | 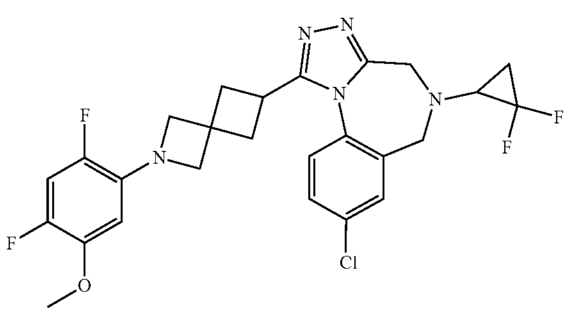 [SMILES: COc1cc(N2CC3(CC(c4nnc5n4-c4ccc(Cl)cc4CN(C4CC4(F)F)C5)C3)C2)c(F)cc1F] |
| 954 | 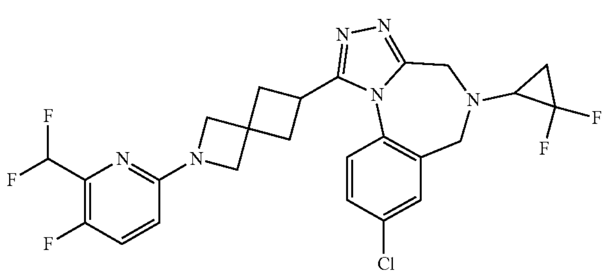 [SMILES: Fc1ccc(N2CC3(CC(c4nnc5n4-c4ccc(Cl)cc4CN(C4CC4(F)F)C5)C3)C2)nc1C(F)F] |
| 955 | 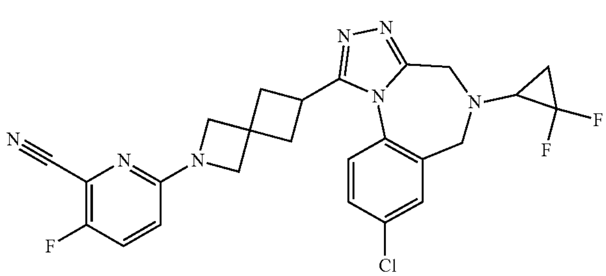 [SMILES: N#Cc1nc(N2CC3(CC(c4nnc5n4-c4ccc(Cl)cc4CN(C4CC4(F)F)C5)C3)C2)ccc1F] |

TABLE 1-continued

Representative Compounds

| Cmpd. No. | Structure |
|---|---|
| 956 | 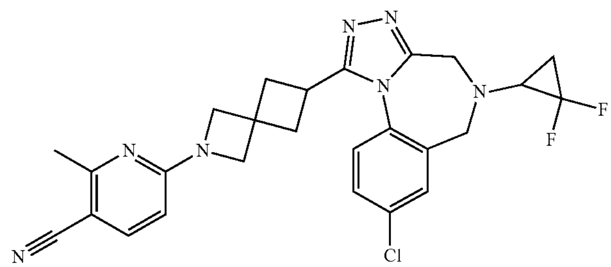 [SMILES: Cc1nc(N2CC3(CC(c4nnc5n4-c4ccc(Cl)cc4CN(C4CC4(F)F)C5)C3)C2)ccc1C#N] |
| 957 | 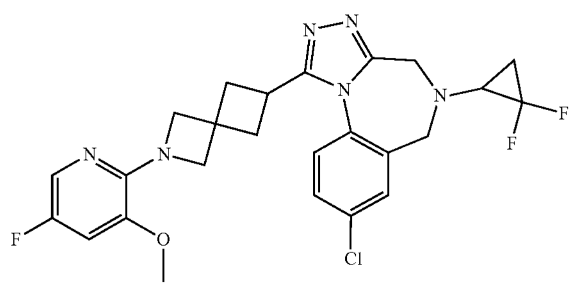 [SMILES: COc1cc(F)cnc1N1CC2(CC(c3nnc4n3-c3ccc(Cl)cc3CN(C3CC3(F)F)C4)C2)C1] |
| 958 | 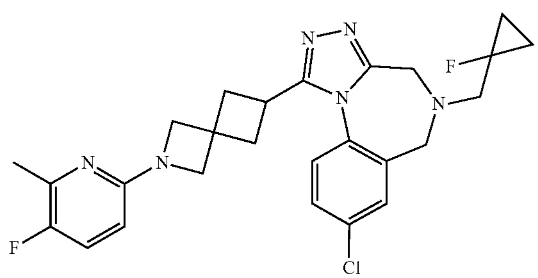 [SMILES: Cc1nc(N2CC3(CC(c4nnc5n4-c4ccc(Cl)cc4CN(CC4(F)CC4)C5)C3)C2)ccc1F] |
| 959 | 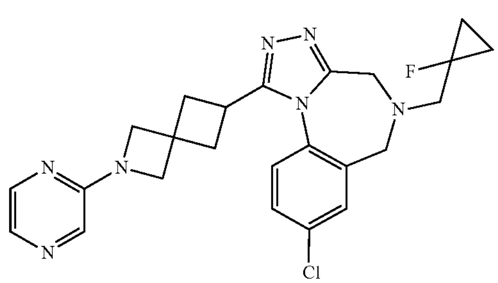 [SMILES: FC1(CN2Cc3cc(Cl)ccc3-n3c(nnc3C3CC4(C3)CN(c3cnccn3)C4)C2)CC1] |
| 960 | 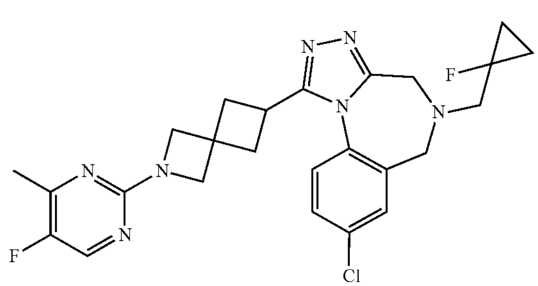 [SMILES: Cc1nc(N2CC3(CC(c4nnc5n4-c4ccc(Cl)cc4CN(CC4(F)CC4)C5)C3)C2)ncc1F] |

TABLE 1-continued
Representative Compounds
| Cmpd. No. | Structure |
|---|---|
| 961 | 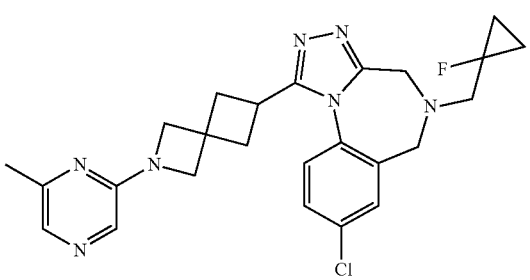 [SMILES: Cc1cncc(N2CC3(CC(c4nnc5n4-c4ccc(Cl)cc4CN(CC4(F)CC4)C5)C3)C2)n1] |
| 962 | 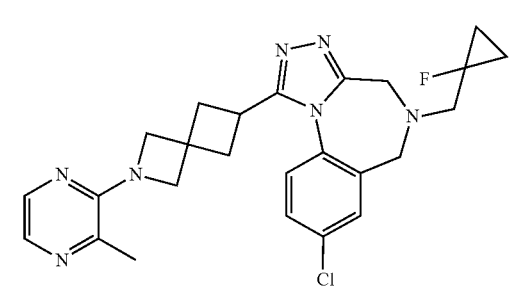 [SMILES: Cc1nccnc1N1CC2(CC(c3nnc4n3-c3ccc(Cl)cc3CN(CC3(F)CC3)C4)C2)C1] |
| 963 | 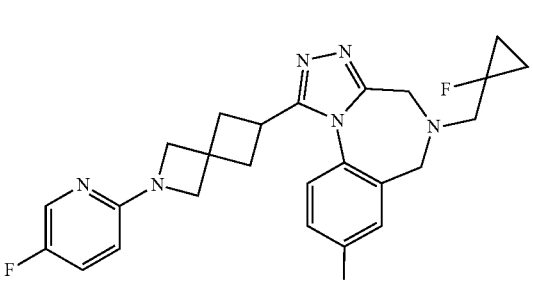 |
| 964 | 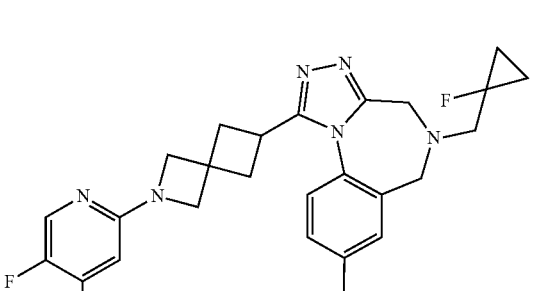 |
| 965 | 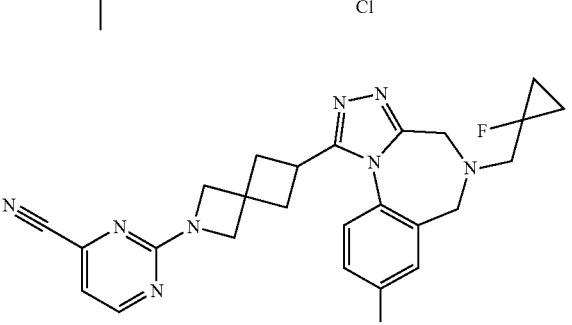 |

TABLE 1-continued
Representative Compounds
| Cmpd. No. | Structure |
|---|---|
| 966 | 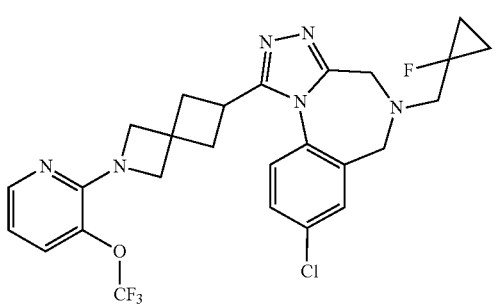 [SMILES: FC1(CN2Cc3cc(Cl)ccc3-n3c(nnc3C3CC4(C3)CN(c3ncccc3OC(F)(F)F)C4)C2)CC1] |
| 967 | 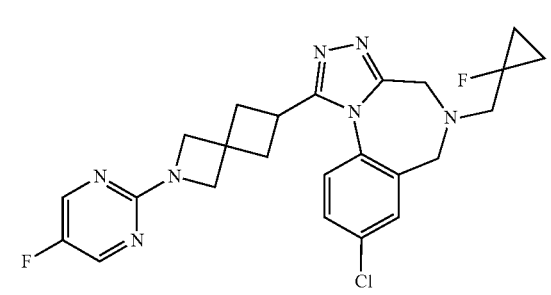 [SMILES: Fc1cnc(N2CC3(CC(c4nnc5n4-c4ccc(Cl)cc4CN(CC4(F)CC4)C5)C3)C2)nc1] |
| 968 | 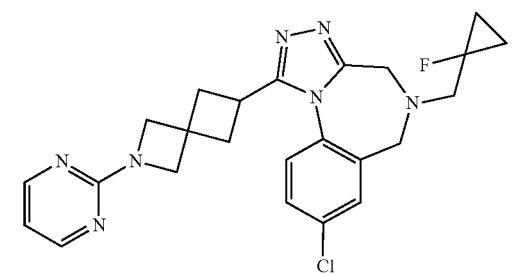 [SMILES: FC1(CN2Cc3cc(Cl)ccc3-n3c(nnc3C3CC4(C3)CN(c3ncccn3)C4)C2)CC1] |
| 969 | 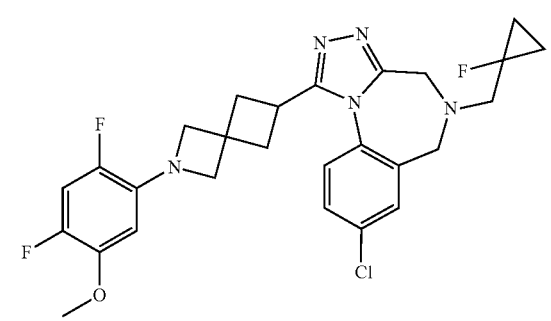 [SMILES: COc1cc(N2CC3(CC(c4nnc5n4-c4ccc(Cl)cc4CN(CC4(F)CC4)C5)C3)C2)c(F)cc1F] |
| 970 | 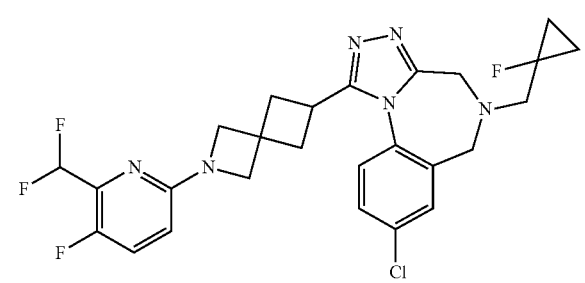 [SMILES: Fc1ccc(N2CC3(CC(c4nnc5n4-c4ccc(Cl)cc4CN(CC4(F)CC4)C5)C3)C2)nc1C(F)F] |

TABLE 1-continued

Representative Compounds

| Cmpd. No. | Structure |
|---|---|
| 971 | 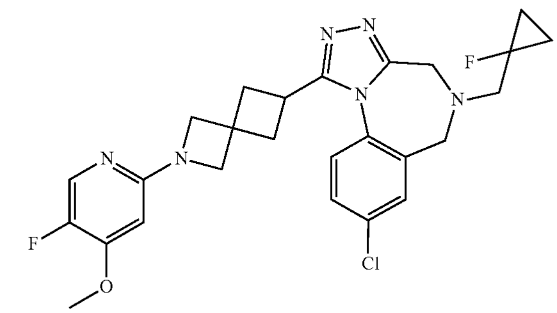 [SMILES: COc1cc(N2CC3(CC(c4nnc5n4-c4ccc(Cl)cc4CN(CC4(F)CC4)C5)C3)C2)ncc1F] |
| 972 | 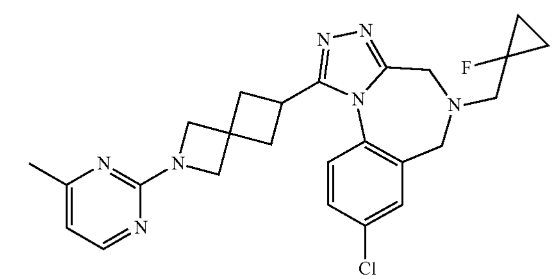 [SMILES: Cc1ccnc(N2CC3(CC(c4nnc5n4-c4ccc(Cl)cc4CN(CC4(F)CC4)C5)C3)C2)n1] |
| 973 | 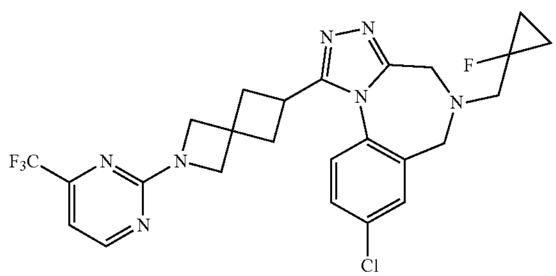 [SMILES: FC1(CN2Cc3cc(Cl)ccc3-n3c(nnc3C3CC4(C3)CN(c3nccc(C(F)(F)F)n3)C4)C2)CC1] |
| 974 | 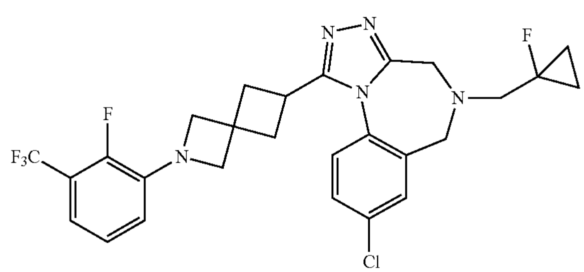 [SMILES: Fc1c(N2CC3(CC(c4nnc5n4-c4ccc(Cl)cc4CN(CC4(F)CC4)C5)C3)C2)cccc1C(F)(F)F] |
| 975 | 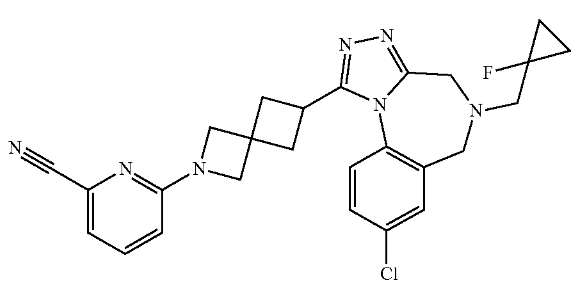 [SMILES: N#Cc1cccc(N2CC3(CC(c4nnc5n4-c4ccc(Cl)cc4CN(CC4(F)CC4)C5)C3)C2)n1] |

TABLE 1-continued
Representative Compounds
| Cmpd. No. | Structure |
|---|---|
| 976 | 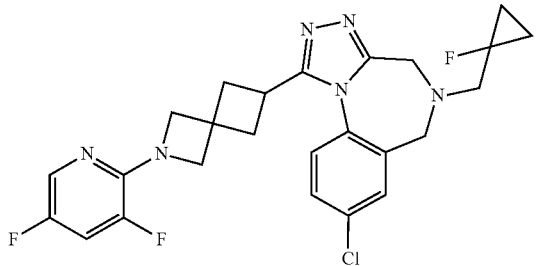 [SMILES: Fc1cnc(N2CC3(CC(c4nnc5n4-c4ccc(Cl)cc4CN(CC4(F)CC4)C5)C3)C2)c(F)c1] |
| 977 | 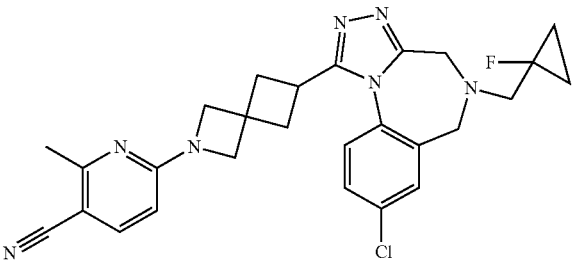 [SMILES: Cc1nc(N2CC3(CC(c4nnc5n4-c4ccc(Cl)cc4CN(CC4(F)CC4)C5)C3)C2)ccc1C#N] |
| 978 | 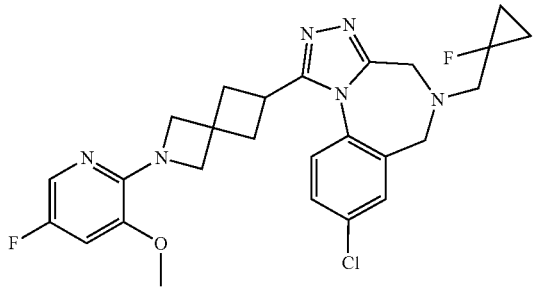 [SMILES: COc1cc(F)cnc1N1CC2(CC(c3nnc4n3-c3ccc(Cl)cc3CN(CC3(F)CC3)C4)C2)C1] |
| 979 | 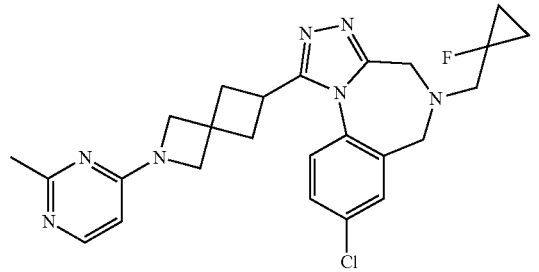 [SMILES: Cc1nccc(N2CC3(CC(c4nnc5n4-c4ccc(Cl)cc4CN(CC4(F)CC4)C5)C3)C2)n1] |
| 980 | 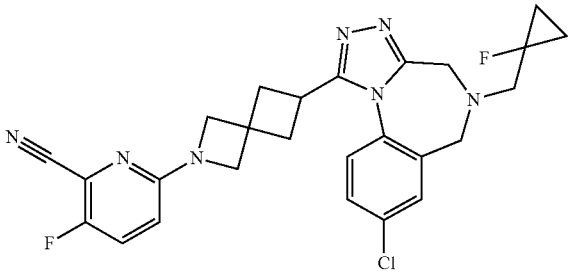 [SMILES: N#Cc1nc(N2CC3(CC(c4nnc5n4-c4ccc(Cl)cc4CN(CC4(F)CC4)C5)C3)C2)ccc1F] |

TABLE 1-continued

Representative Compounds

| Cmpd. No. | Structure |
|---|---|
| 981 | 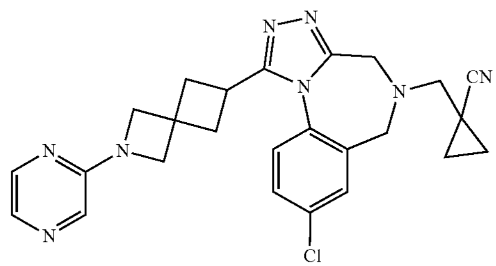 [SMILES: N#CC1(CN2Cc3cc(Cl)ccc3-n3c(nnc3C3CC4(C3)CN(c3cnccn3)C4)C2)CC1] |
| 982 | 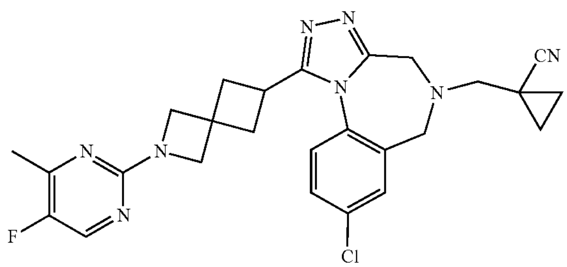 [SMILES: Cc1nc(N2CC3(CC(c4nnc5n4-c4ccc(Cl)cc4CN(CC4(C#N)CC4)C5)C3)C2)ncc1F] |
| 983 | 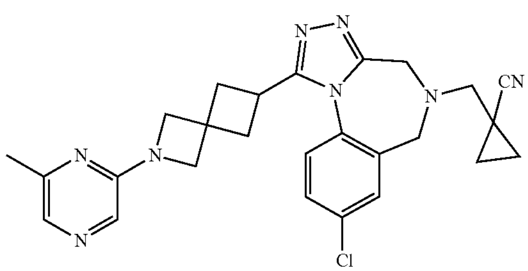 [SMILES: Cc1cncc(N2CC3(CC(c4nnc5n4-c4ccc(Cl)cc4CN(CC4(C#N)CC4)C5)C3)C2)n1] |
| 984 | 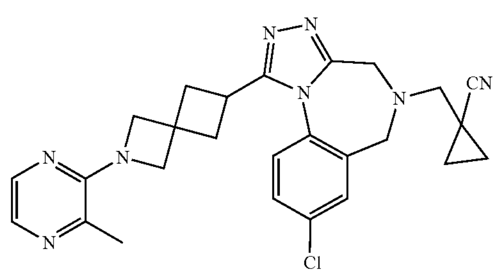 [SMILES: Cc1nccnc1N1CC2(CC(c3nnc4n3-c3ccc(Cl)cc3CN(CC3(C#N)CC3)C4)C2)C1] |
| 985 | 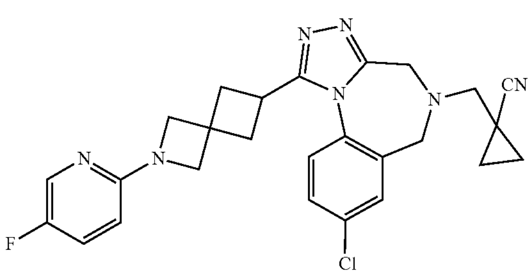 [SMILES: N#CC1(CN2Cc3cc(Cl)ccc3-n3c(nnc3C3CC4(C3)CN(c3ccc(F)cn3)C4)C2)CC1] |

TABLE 1-continued

Representative Compounds

| Cmpd. No. | Structure |
|---|---|
| 986 | 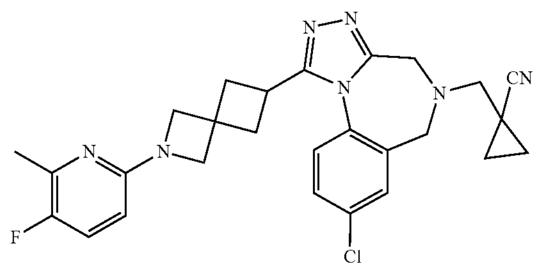 [SMILES: Cc1nc(N2CC3(CC(c4nnc5n4-c4ccc(Cl)cc4CN(CC4(C#N)CC4)C5)C3)C2)ccc1F] |
| 987 | 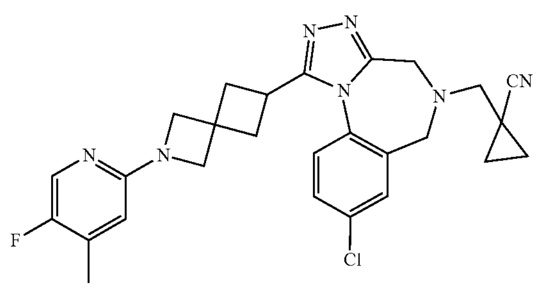 [SMILES: Cc1cc(N2CC3(CC(c4nnc5n4-c4ccc(Cl)cc4CN(CC4(C#N)CC4)C5)C3)C2)ncc1F] |
| 988 | 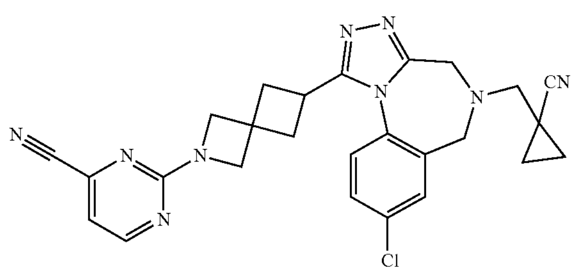 [SMILES: N#Cc1ccnc(N2CC3(CC(c4nnc5n4-c4ccc(Cl)cc4CN(CC4(C#N)CC4)C5)C3)C2)n1] |
| 989 | 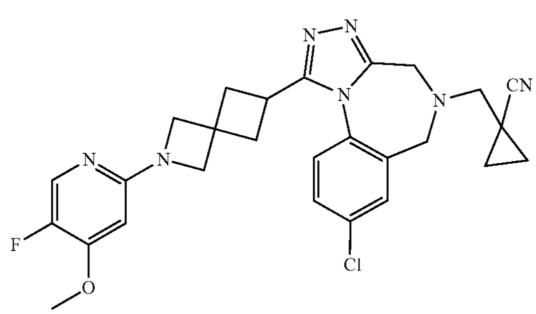 [SMILES: COc1cc(N2CC3(CC(c4nnc5n4-c4ccc(Cl)cc4CN(CC4(C#N)CC4)C5)C3)C2)ncc1F] |
| 990 | 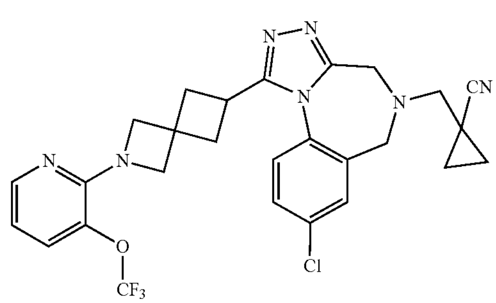 [SMILES: N#CC1(CN2Cc3cc(Cl)ccc3-n3c(nnc3C3CC4(C3)CN(c3ncccc3OC(F)(F)F)C4)C2)CC1] |

TABLE 1-continued

Representative Compounds

| Cmpd. No. | Structure |
|---|---|
| 991 | 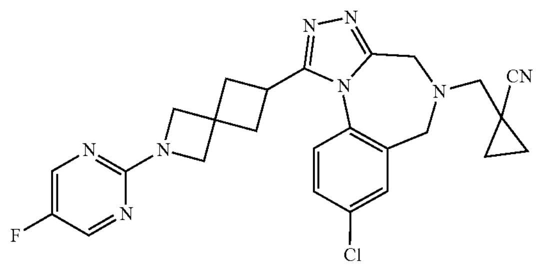 [SMILES: N#CC1(CN2Cc3cc(Cl)ccc3-n3c(nnc3C3CC4(C3)CN(c3ncc(F)cn3)C4)C2)CC1] |
| 992 | 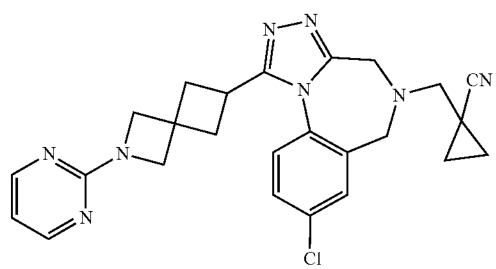 [SMILES: N#CC1(CN2Cc3cc(Cl)ccc3-n3c(nnc3C3CC4(C3)CN(c3ncccn3)C4)C2)CC1] |
| 993 | 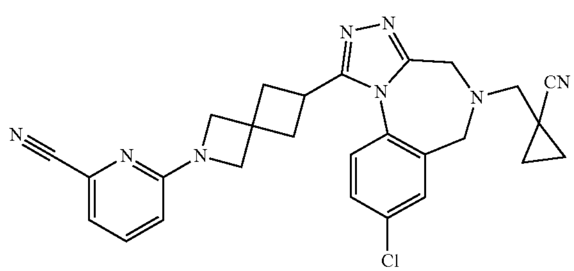 [SMILES: N#Cc1cccc(N2CC3(CC(c4nnc5n4-c4ccc(Cl)cc4CN(CC4(C#N)CC4)C5)C3)C2)n1] |
| 994 | 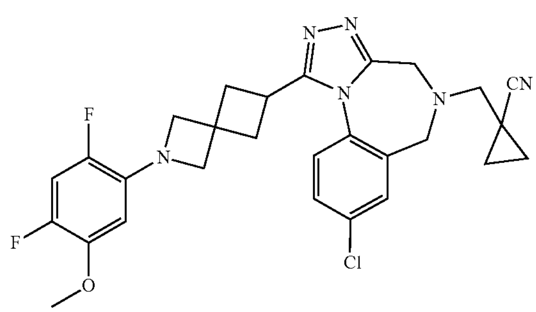 [SMILES: COc1cc(N2CC3(CC(c4nnc5n4-c4ccc(Cl)cc4CN(CC4(C#N)CC4)C5)C3)C2)c(F)cc1F] |
| 995 | 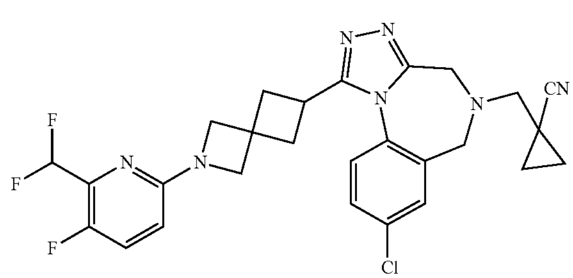 [SMILES: N#CC1(CN2Cc3cc(Cl)ccc3-n3c(nnc3C3CC4(C3)CN(c3ccc(F)c(C(F)F)n3)C4)C2)CC1] |

TABLE 1-continued
Representative Compounds
| Cmpd. No. | Structure |
|---|---|
| 996 | 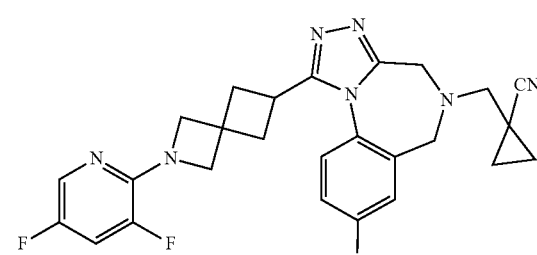 |
| 997 | 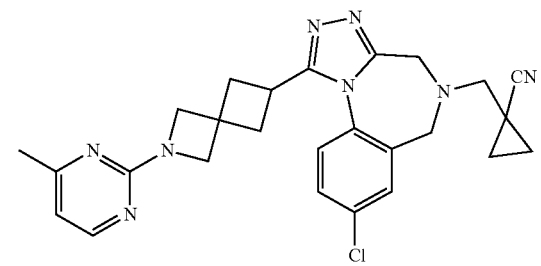 [SMILES: Cc1ccnc(N2CC3(CC(c4nnc5n4-c4ccc(Cl)cc4CN(CC4(C#N)CC4)C5)C3)C2)n1] |
| 998 | 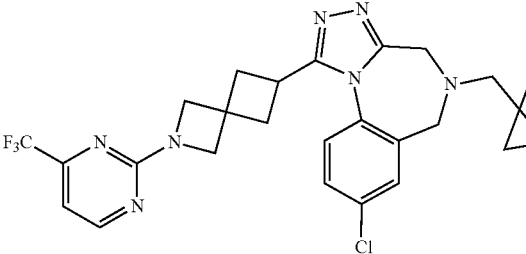 |
| 999 | 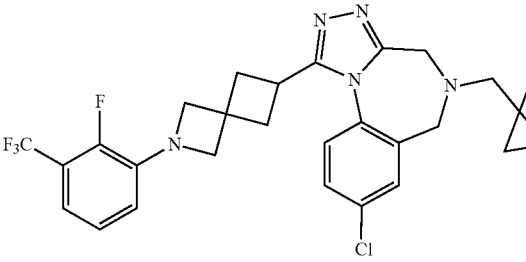 |
| 1000 | 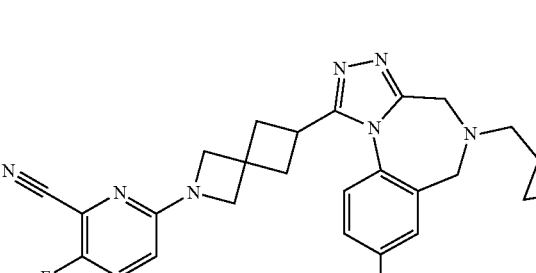 |

TABLE 1-continued
Representative Compounds
| Cmpd. No. | Structure |
|---|---|
| 1001 | 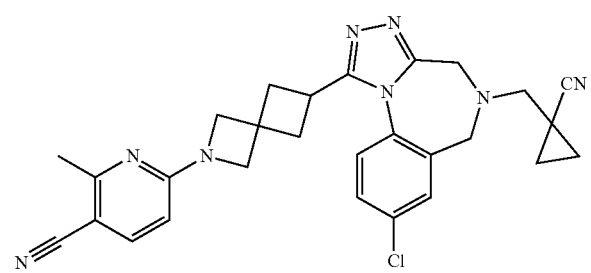 [SMILES: Cc1nc(N2CC3(CC(c4nnc5n4-c4ccc(Cl)cc4CN(CC4(C#N)CC4)C5)C3)C2)ccc1C#N] |
| 1002 | 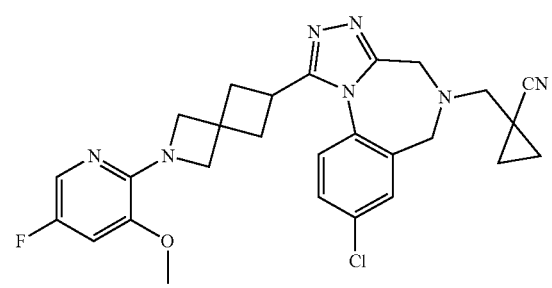 [SMILES: COc1cc(F)cnc1N1CC2(CC(c3nnc4n3-c3ccc(Cl)cc3CN(CC3(C#N)CC3)C4)C2)C1] |
| 1003 | 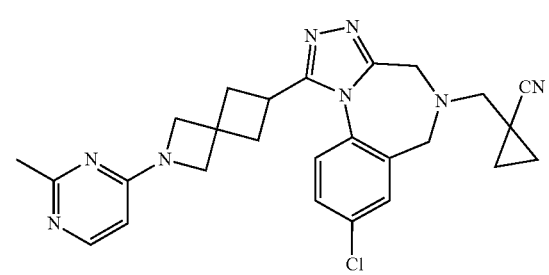 [SMILES: Cc1nccc(N2CC3(CC(c4nnc5n4-c4ccc(Cl)cc4CN(CC4(C#N)CC4)C5)C3)C2)n1] |
| 1004 | 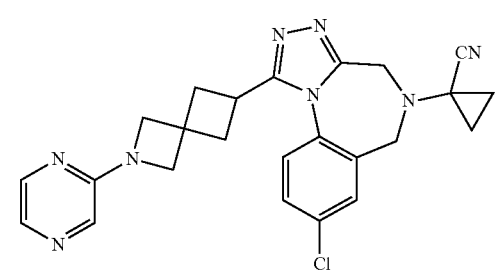 [SMILES: N#CC1(N2Cc3cc(Cl)ccc3-n3c(nnc3C3CC4(C3)CN(c3cnccn3)C4)C2)CC1] |
| 1005 | 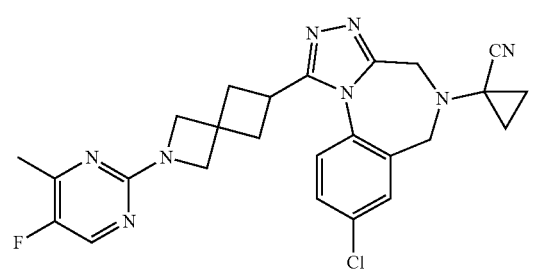 [SMILES: Cc1nc(N2CC3(CC(c4nnc5n4-c4ccc(Cl)cc4CN(C4(C#N)CC4)C5)C3)C2)ncc1F] |

TABLE 1-continued

Representative Compounds

| Cmpd. No. | Structure |
|---|---|
| 1006 | 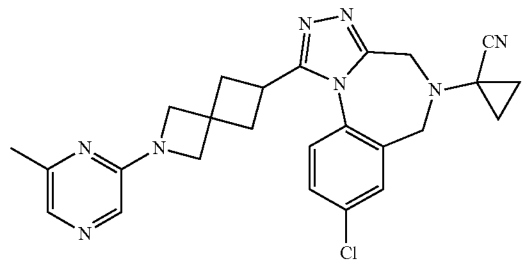 [SMILES: Cc1cncc(N2CC3(CC(c4nnc5n4-c4ccc(Cl)cc4CN(C4(C#N)CC4)C5)C3)C2)n1] |
| 1007 | 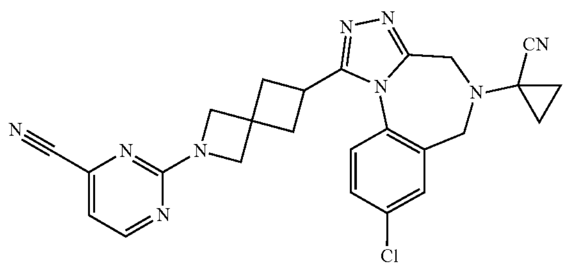 [SMILES: N#Cc1ccnc(N2CC3(CC(c4nnc5n4-c4ccc(Cl)cc4CN(C4(C#N)CC4)C5)C3)C2)n1] |
| 1008 | 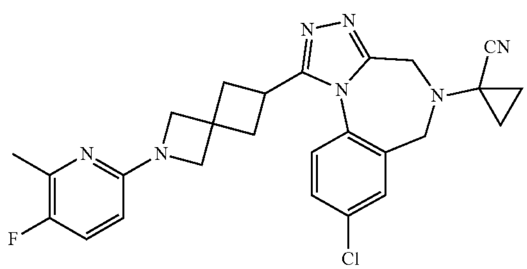 [SMILES: Cc1nc(N2CC3(CC(c4nnc5n4-c4ccc(Cl)cc4CN(C4(C#N)CC4)C5)C3)C2)ccc1F] |
| 1009 | 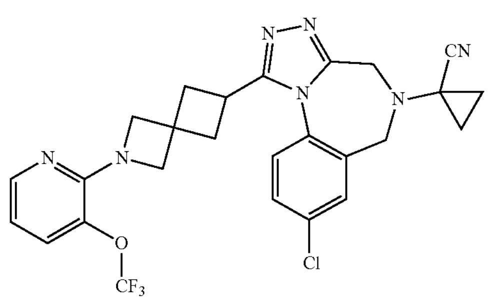 [SMILES: N#CC1(N2Cc3cc(Cl)ccc3-n3c(nnc3C3CC4(C3)CN(c3ncccc3OC(F)(F)F)C4)C2)CC1] |
| 1010 | 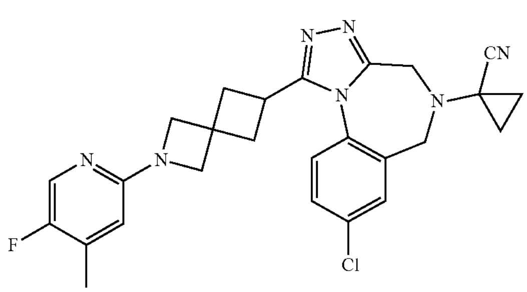 [SMILES: Cc1cc(N2CC3(CC(c4nnc5n4-c4ccc(Cl)cc4CN(C4(C#N)CC4)C5)C3)C2)ncc1F] |

TABLE 1-continued

Representative Compounds

| Cmpd. No. | Structure |
|---|---|
| 1011 | 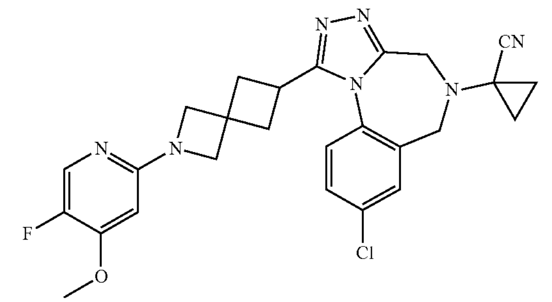 [SMILES: COc1cc(N2CC3(CC(c4nnc5n4-c4ccc(Cl)cc4CN(C4(C#N)CC4)C5)C3)C2)ncc1F] |
| 1012 | 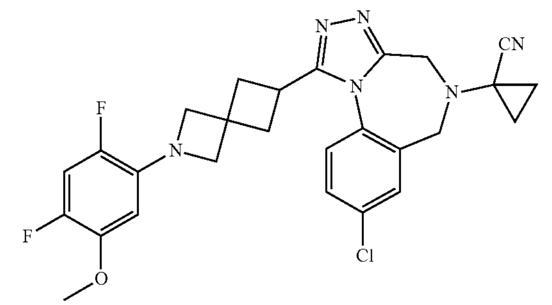 [SMILES: COc1cc(N2CC3(CC(c4nnc5n4-c4ccc(Cl)cc4CN(C4(C#N)CC4)C5)C3)C2)c(F)cc1F] |
| 1013 | 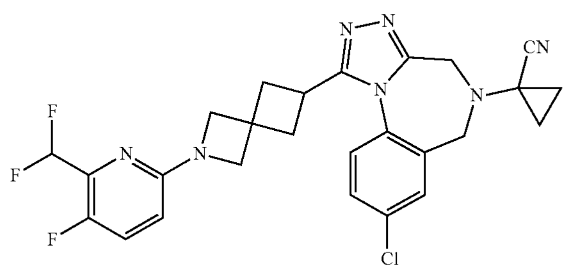 [SMILES: N#CC1(N2Cc3cc(Cl)ccc3-n3c(nnc3C3CC4(C3)CN(c3ccc(F)c(C(F)F)n3)C4)C2)CC1] |
| 1014 | 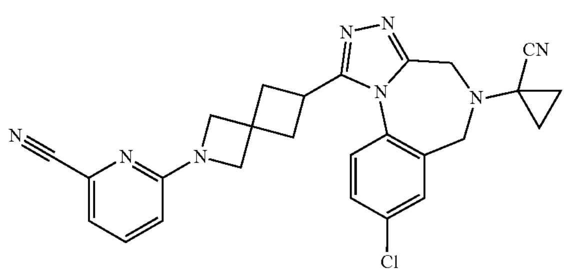 |
| 1015 | 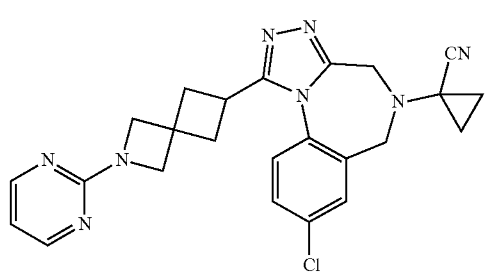 [SMILES: N#CC1(N2Cc3cc(Cl)ccc3-n3c(nnc3C3CC4(C3)CN(c3ncccn3)C4)C2)CC1] |

TABLE 1-continued

Representative Compounds

| Cmpd. No. | Structure |
|---|---|
| 1016 | 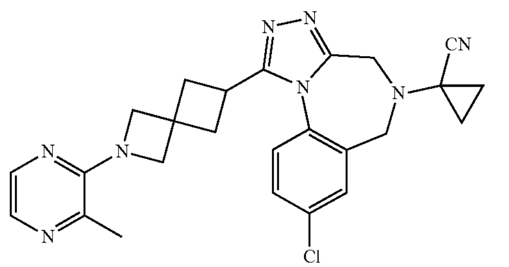 [SMILES: Cc1nccnc1N1CC2(CC(c3nnc4n3-c3ccc(Cl)cc3CN(C3(C#N)CC3)C4)C2)C1] |
| 1017 | 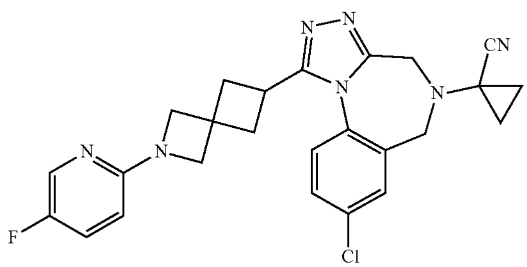 [SMILES: N#CC1(N2Cc3cc(Cl)ccc3-n3c(nnc3C3CC4(C3)CN(c3ccc(F)cn3)C4)C2)CC1] |
| 1018 | 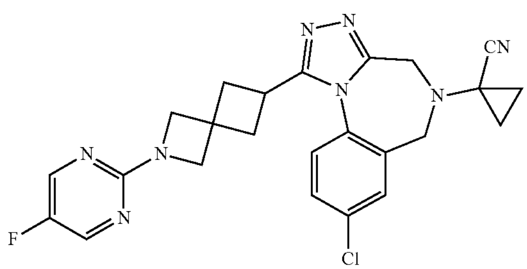 |
| 1019 | 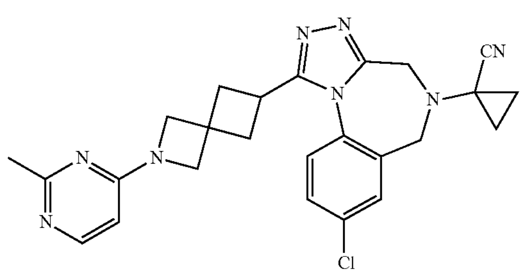 |
| 1020 | 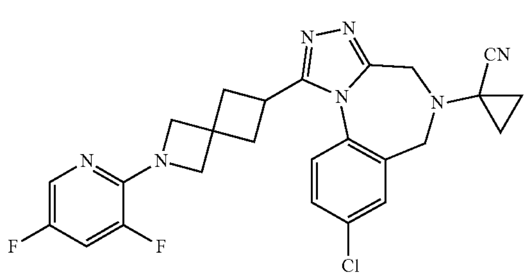 [SMILES: N#CC1(N2Cc3cc(Cl)ccc3-n3c(nnc3C3CC4(C3)CN(c3ncc(F)cc3F)C4)C2)CC1] |

TABLE 1-continued

Representative Compounds

| Cmpd. No. | Structure |
|---|---|
| 1021 | 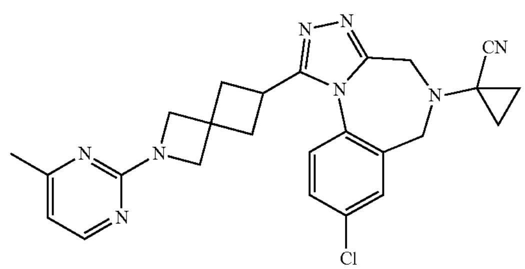 [SMILES: Cc1ccnc(N2CC3(CC(c4nnc5n4-c4ccc(Cl)cc4CN(C4(C#N)CC4)C5)C3)C2)n1] |
| 1022 | 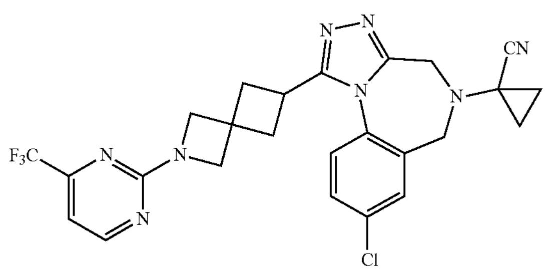 [SMILES: N#CC1(N2Cc3cc(Cl)ccc3-n3c(nnc3C3CC4(C3)CN(c3nccc(C(F)(F)F)n3)C4)C2)CC1] |
| 1023 | 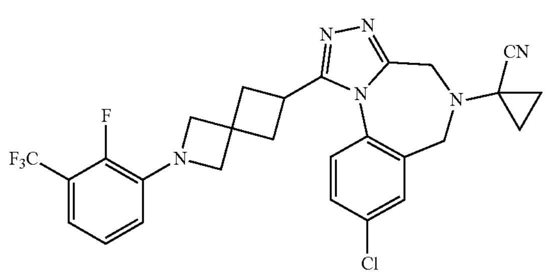 [SMILES: N#CC1(N2Cc3cc(Cl)ccc3-n3c(nnc3C3CC4(C3)CN(c3cccc(C(F)(F)F)c3F)C4)C2)CC1] |
| 1024 | 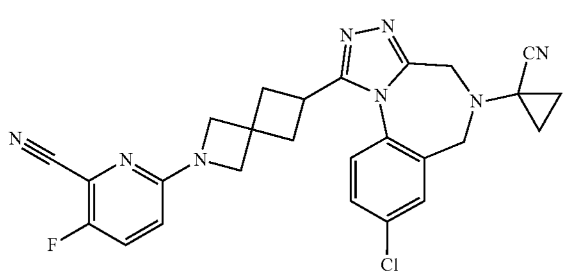 [SMILES: N#Cc1nc(N2CC3(CC(c4nnc5n4-c4ccc(Cl)cc4CN(C4(C#N)CC4)C5)C3)C2)ccc1F] |
| 1025 | 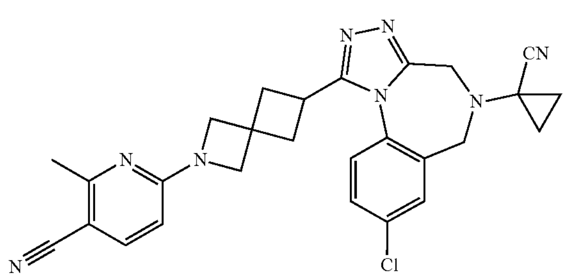 [SMILES: Cc1nc(N2CC3(CC(c4nnc5n4-c4ccc(Cl)cc4CN(C4(C#N)CC4)C5)C3)C2)ccc1C#N] |

TABLE 1-continued

Representative Compounds

| Cmpd. No. | Structure |
|---|---|
| 1026 | 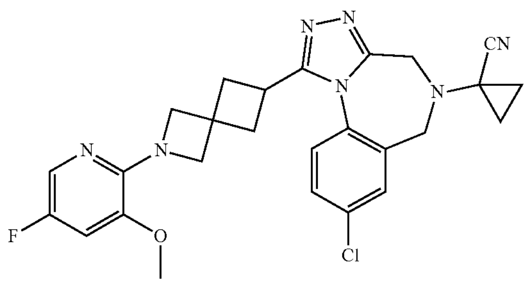 [SMILES: COc1cc(F)cnc1N1CC2(CC(c3nnc4n3-c3ccc(Cl)cc3CN(C3(C#N)CC3)C4)C2)C1] |
| 1027 | 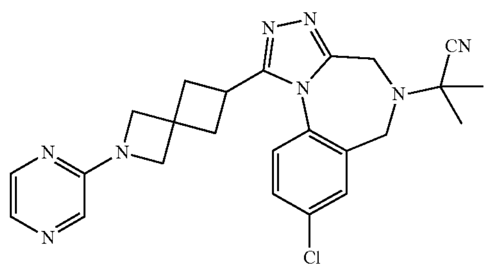 [SMILES: CC(C)(C#N)N1Cc2cc(Cl)ccc2-n2c(nnc2C2CC3(C2)CN(c2cnccn2)C3)C1] |
| 1028 | 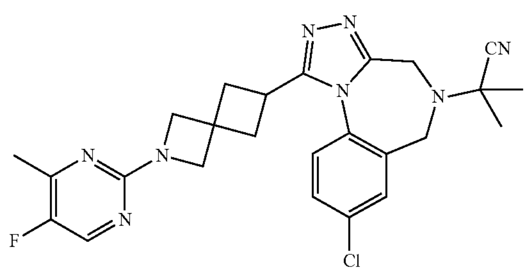 [SMILES: Cc1nc(N2CC3(CC(c4nnc5n4-c4ccc(Cl)cc4CN(C(C)(C)C#N)C5)C3)C2)ncc1F] |
| 1029 | 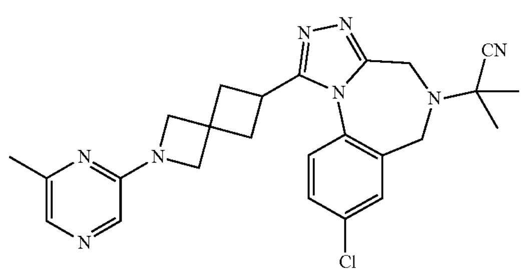 [SMILES: Cc1cncc(N2CC3(CC(c4nnc5n4-c4ccc(Cl)cc4CN(C(C)(C)C#N)C5)C3)C2)n1] |
| 1030 | 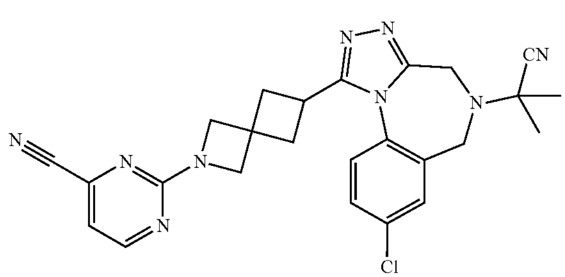 [SMILES: CC(C)(C#N)N1Cc2cc(Cl)ccc2-n2c(nnc2C2CC3(C2)CN(c2nccc(C#N)n2)C3)C1] |

TABLE 1-continued

Representative Compounds

| Cmpd. No. | Structure |
|---|---|
| 1031 | 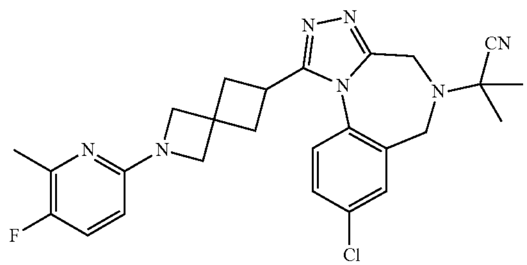 [SMILES: Cc1nc(N2CC3(CC(c4nnc5n4-c4ccc(Cl)cc4CN(C(C)(C)C#N)C5)C3)C2)ccc1F] |
| 1032 | 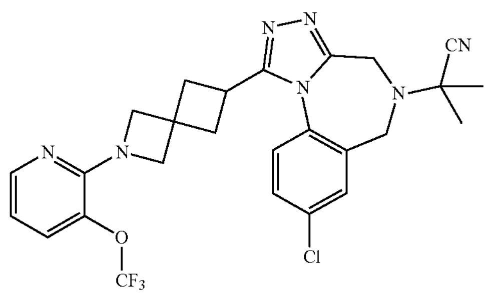 [SMILES: CC(C)(C#N)N1Cc2cc(Cl)ccc2-n2c(nnc2C2CC3(C2)CN(c2ncccc2OC(F)(F)F)C3)C1] |
| 1033 | 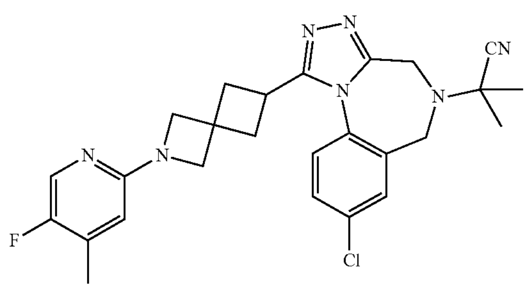 [SMILES: Cc1cc(N2CC3(CC(c4nnc5n4-c4ccc(Cl)cc4CN(C(C)(C)C#N)C5)C3)C2)ncc1F] |
| 1034 | 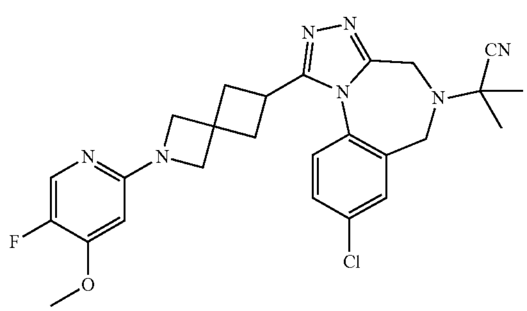 [SMILES: COc1cc(N2CC3(CC(c4nnc5n4-c4ccc(Cl)cc4CN(C(C)(C)C#N)C5)C3)C2)ncc1F] |
| 1035 | 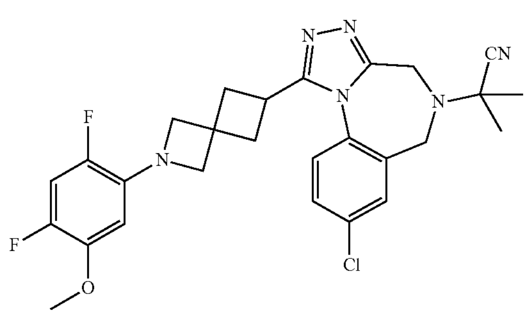 [SMILES: COc1cc(N2CC3(CC(c4nnc5n4-c4ccc(Cl)cc4CN(C(C)(C)C#N)C5)C3)C2)c(F)cc1F] |

TABLE 1-continued
Representative Compounds
| Cmpd. No. | Structure |
|---|---|
| 1036 | 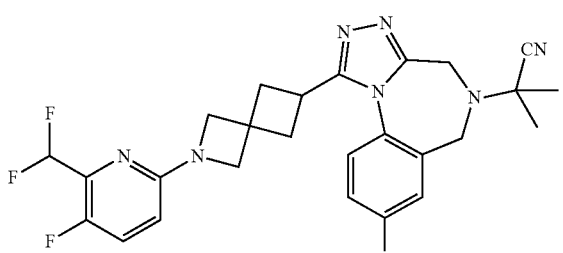 |
| 1037 | 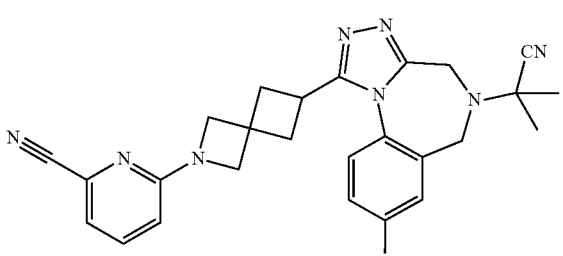 |
| 1038 | 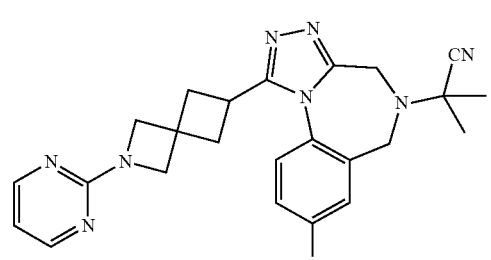 |
| 1039 | 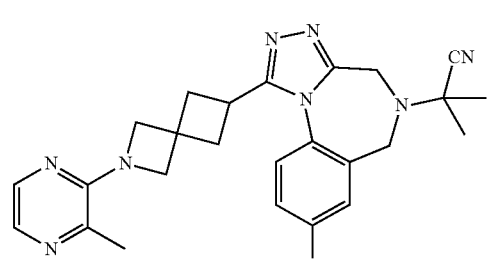 |
| 1040 | 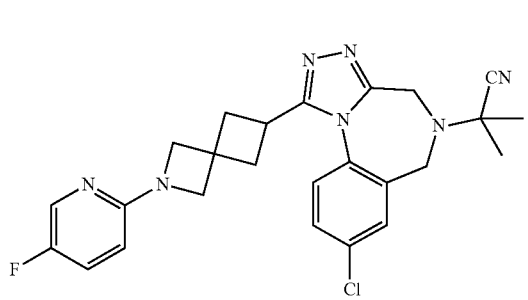 [SMILES: CC(C)(C#N)N1Cc2cc(Cl)ccc2-n2c(nnc2C2CC3(C2)CN(c2ccc(F)cn2)C3)C1] |

TABLE 1-continued

Representative Compounds

| Cmpd. No. | Structure |
|---|---|
| 1041 | 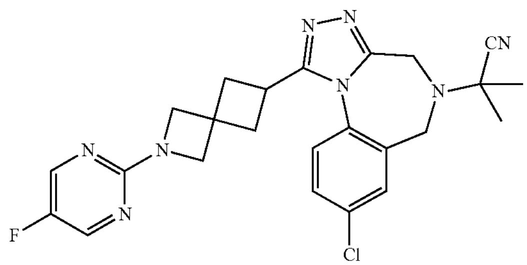 [SMILES: CC(C)(C#N)N1Cc2cc(Cl)ccc2-n2c(nnc2C2CC3(C2)CN(c2ncc(F)cn2)C3)C1] |
| 1042 | 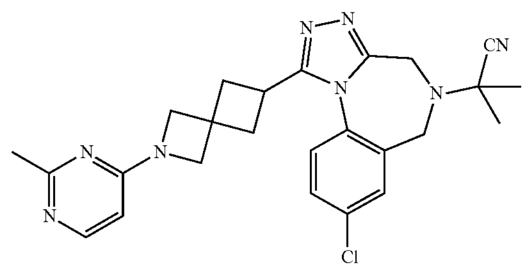 [SMILES: Cc1nccc(N2CC3(CC(c4nnc5n4-c4ccc(Cl)cc4CN(C(C)(C)C#N)C5)C3)C2)n1] |
| 1043 | 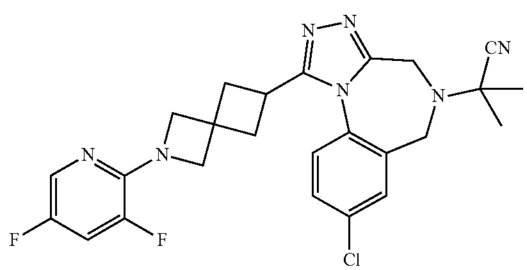 [SMILES: CC(C)(C#N)N1Cc2cc(Cl)ccc2-n2c(nnc2C2CC3(C2)CN(c2ncc(F)cc2F)C3)C1] |
| 1044 | 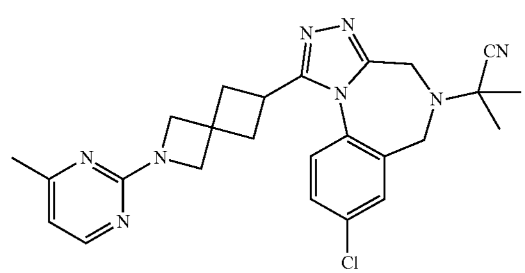 [SMILES: Cc1ccnc(N2CC3(CC(c4nnc5n4-c4ccc(Cl)cc4CN(C(C)(C)C#N)C5)C3)C2)n1] |
| 1045 | 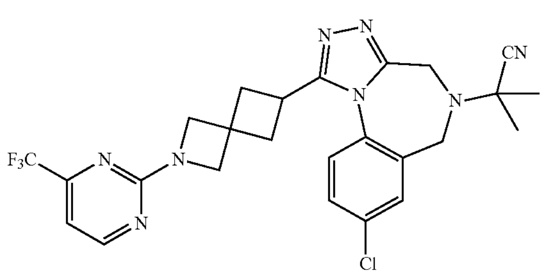 [SMILES: CC(C)(C#N)N1Cc2cc(Cl)ccc2-n2c(nnc2C2CC3(C2)CN(c2nccc(C(F)(F)F)n2)C3)C1] |

TABLE 1-continued

Representative Compounds

| Cmpd. No. | Structure |
|---|---|
| 1046 | 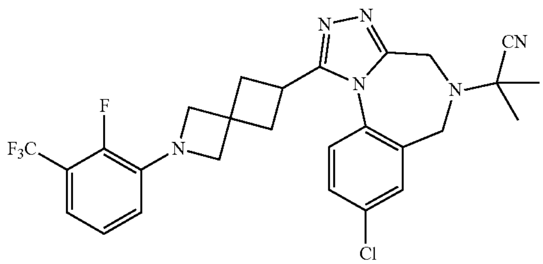 [SMILES: CC(C)(C#N)N1Cc2cc(Cl)ccc2-n2c(nnc2C2CC3(C2)CN(c2cccc(C(F)(F)F)c2F)C3)C1] |
| 1047 | 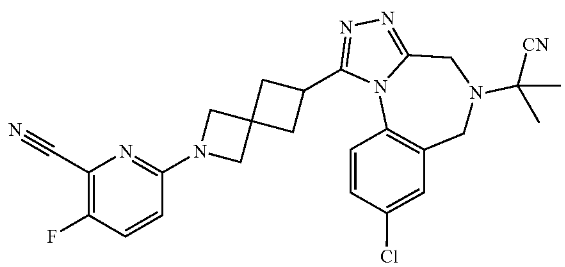 [SMILES: CC(C)(C#N)N1Cc2cc(Cl)ccc2-n2c(nnc2C2CC3(C2)CN(c2ccc(F)c(C#N)n2)C3)C1] |
| 1048 | 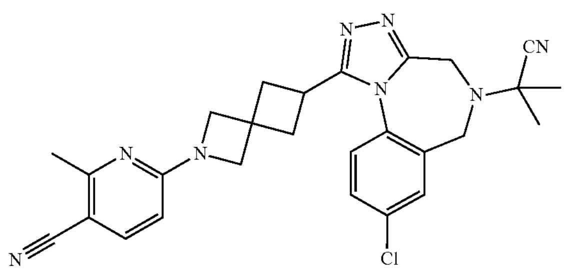 [SMILES: Cc1nc(N2CC3(CC(c4nnc5n4-c4ccc(Cl)cc4CN(C(C)(C)C#N)C5)C3)C2)ccc1C#N] |
| 1049 | 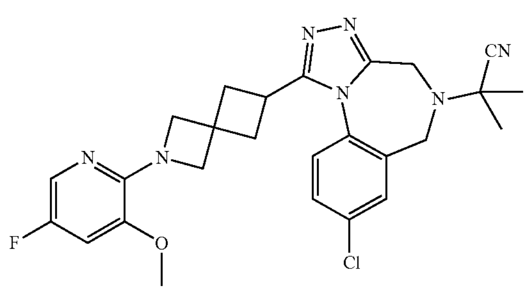 [SMILES: COc1cc(F)cnc1N1CC2(CC(c3nnc4n3-c3ccc(Cl)cc3CN(C(C)(C)C#N)C4)C2)C1] |
| 1050 | 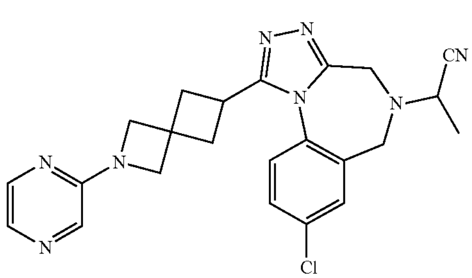 [SMILES: CC(C#N)N1Cc2cc(Cl)ccc2-n2c(nnc2C2CC3(C2)CN(c2cnccn2)C3)C1] |

467
468

TABLE 1-continued

Representative Compounds

| Cmpd. No. | Structure |
|---|---|
| 1051 | 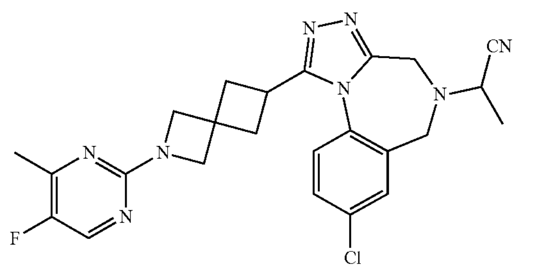 [SMILES: Cc1nc(N2CC3(CC(c4nnc5n4-c4ccc(Cl)cc4CN(C(C)C#N)C5)C3)C2)ncc1F] |
| 1052 | 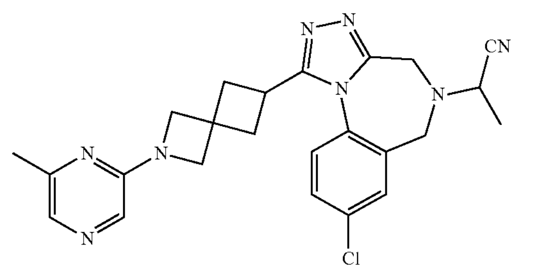 [SMILES: Cc1cncc(N2CC3(CC(c4nnc5n4-c4ccc(Cl)cc4CN(C(C)C#N)C5)C3)C2)n1] |
| 1053 | 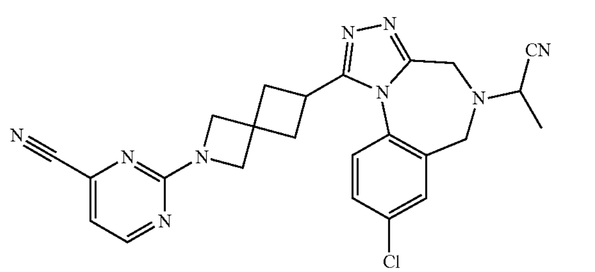 [SMILES: CC(C#N)N1Cc2cc(Cl)ccc2-n2c(nnc2C2CC3(C2)CN(c2nccc(C#N)n2)C3)C1] |
| 1054 | 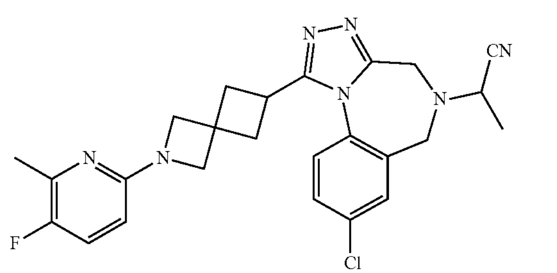 [SMILES: Cc1nc(N2CC3(CC(c4nnc5n4-c4ccc(Cl)cc4CN(C(C)C#N)C5)C3)C2)ccc1F] |
| 1055 | 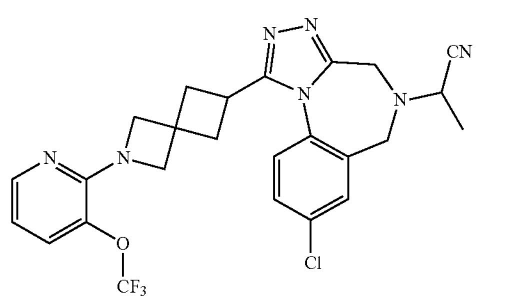 [SMILES: CC(C#N)N1Cc2cc(Cl)ccc2-n2c(nnc2C2CC3(C2)CN(c2ncccc2OC(F)(F)F)C3)C1] |

TABLE 1-continued

Representative Compounds

| Cmpd. No. | Structure |
|---|---|
| 1056 | 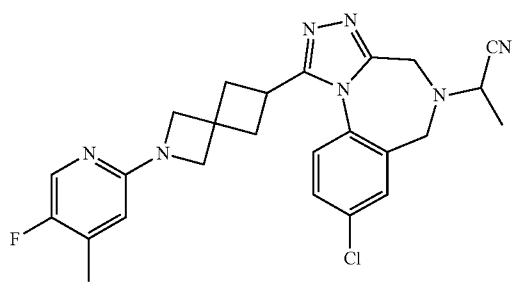 [SMILES: Cc1cc(N2CC3(CC(c4nnc5n4-c4ccc(Cl)cc4CN(C(C)C#N)C5)C3)C2)ncc1F] |
| 1057 | 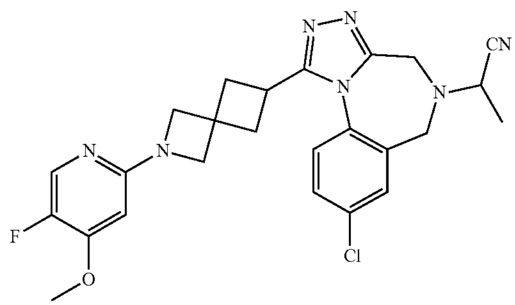 [SMILES: COc1cc(N2CC3(CC(c4nnc5n4-c4ccc(Cl)cc4CN(C(C)C#N)C5)C3)C2)ncc1F] |
| 1058 | 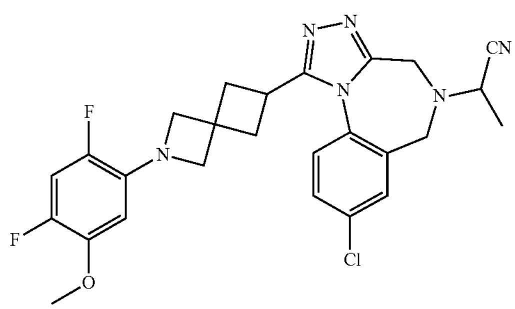 [SMILES: COc1cc(N2CC3(CC(c4nnc5n4-c4ccc(Cl)cc4CN(C(C)C#N)C5)C3)C2)c(F)cc1F] |
| 1059 | 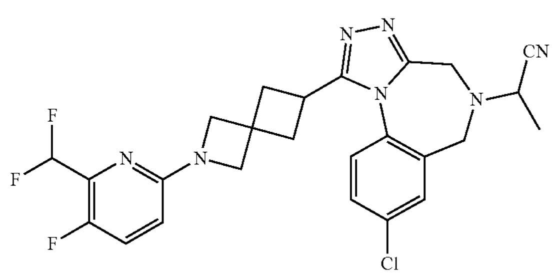 [SMILES: CC(C#N)N1Cc2cc(Cl)ccc2-n2c(nnc2C2CC3(C2)CN(c2ccc(F)c(C(F)F)n2)C3)C1] |
| 1060 | 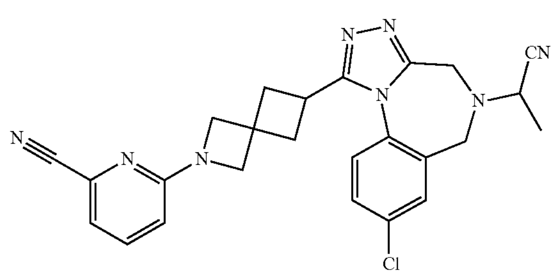 [SMILES: CC(C#N)N1Cc2cc(Cl)ccc2-n2c(nnc2C2CC3(C2)CN(c2cccc(C#N)n2)C3)C1] |

TABLE 1-continued
Representative Compounds
| Cmpd. No. | Structure |
|---|---|
| 1061 | 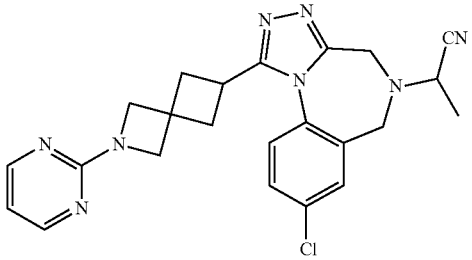 |
| 1062 | 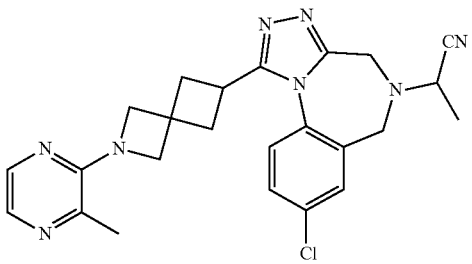 [SMILES: Cc1nccnc1N1CC2(CC(c3nnc4n3-c3ccc(Cl)cc3CN(C(C)C#N)C4)C2)C1] |
| 1063 | 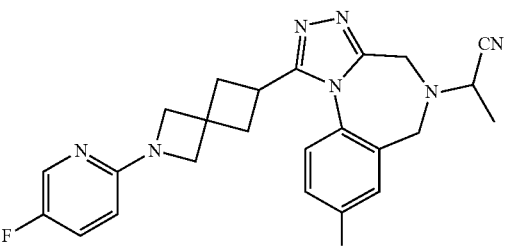 |
| 1064 | 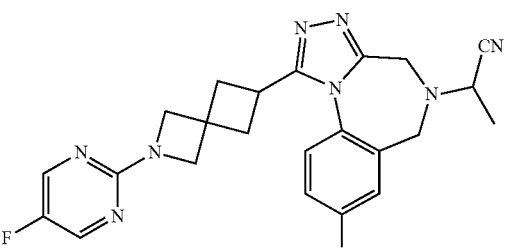 |
| 1065 | 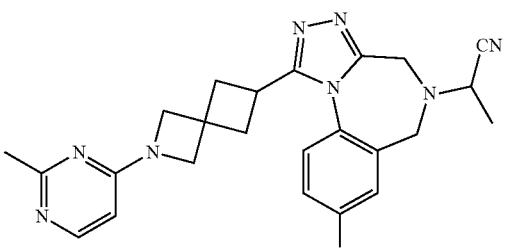 |

TABLE 1-continued

Representative Compounds

| Cmpd. No. | Structure |
|---|---|
| 1066 | 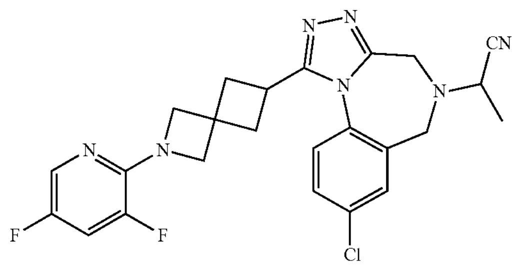 [SMILES: CC(C#N)N1Cc2cc(Cl)ccc2-n2c(nnc2C2CC3(C2)CN(c2ncc(F)cc2F)C3)C1] |
| 1067 | 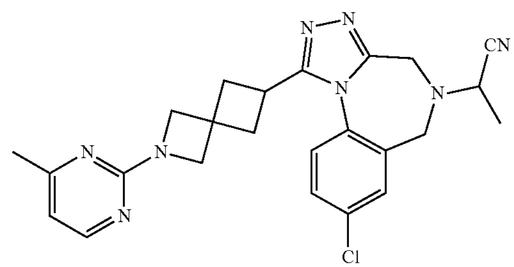 [SMILES: Cc1ccnc(N2CC3(CC(c4nnc5n4-c4ccc(Cl)cc4CN(C(C)C#N)C5)C3)C2)n1] |
| 1068 | 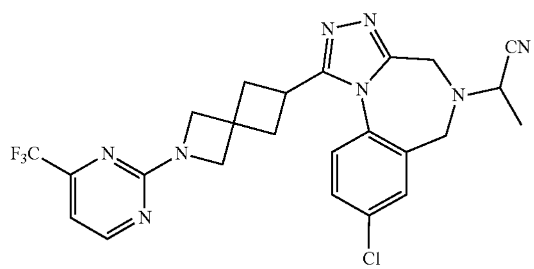 [SMILES: CC(C#N)N1Cc2cc(Cl)ccc2-n2c(nnc2C2CC3(C2)CN(c2nccc(C(F)(F)F)n2)C3)C1] |
| 1069 | 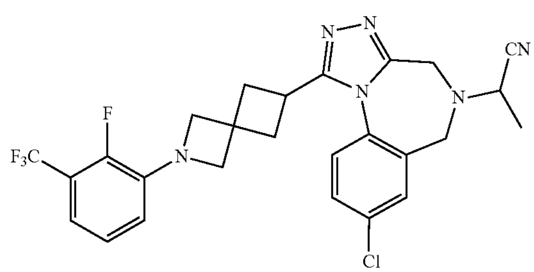 [SMILES: CC(C#N)N1Cc2cc(Cl)ccc2-n2c(nnc2C2CC3(C2)CN(c2cccc(C(F)(F)F)c2F)C3)C1] |
| 1070 | 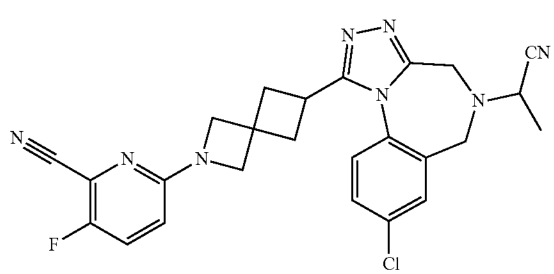 [SMILES: CC(C#N)N1Cc2cc(Cl)ccc2-n2c(nnc2C2CC3(C2)CN(c2ccc(F)c(C#N)n2)C3)C1] |

TABLE 1-continued

Representative Compounds

| Cmpd. No. | Structure |
|---|---|
| 1071 | 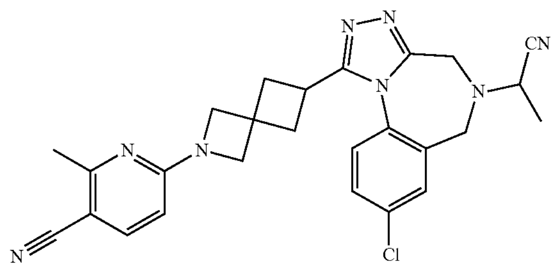 [SMILES: Cc1nc(N2CC3(CC(c4nnc5n4-c4ccc(Cl)cc4CN(C(C)C#N)C5)C3)C2)ccc1C#N] |
| 1072 | 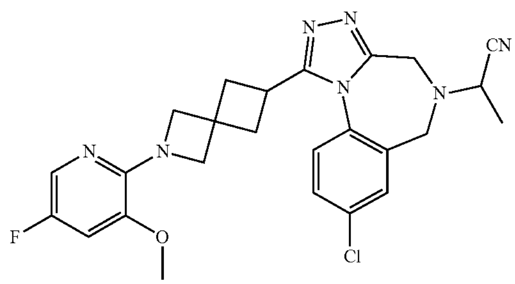 [SMILES: COc1cc(F)cnc1N1CC2(CC(c3nnc4n3-c3ccc(Cl)cc3CN(C(C)C#N)C4)C2)C1] |

In certain embodiments, the invention provides a pharmaceutical composition comprising a compound of the invention together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semisolid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, e.g., rectal, depot, subcutaneous, intravenous, intraurethral, intramuscular, intranasal, ophthalmic solution, or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents, and the like can be employed.

For topical administration, the compounds of the present invention can be formulated using bland, moisturizing bases such as ointments or creams.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule, or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di-, or tri-glycerides.

For injection, the formulation can also be a powder suitable for reconstitution with an appropriate solution as described above. Examples of these include, but are not limited to, freeze dried, rotary dried, or spray dried powders, amorphous powders, granules, precipitates, or particulates. For injection, the formulations can optionally contain stabilizers, pH modifiers, surfactants, bioavailability modifiers, and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the Physicians' Desk Reference, incorporated herein by reference.

When used to prevent the onset of a malcondition, the compounds provided herein will be administered to a subject at risk for developing the same, typically on the advice and under the supervision of a physician, at the dosage levels described above. Subjects at risk for developing a particular malcondition generally include those that have a family history of the same, or those who have been identified by genetic testing or screening to be particularly susceptible to developing the malcondition.

Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method is provided for antagonizing the V1a receptor, the method comprising contacting the receptor with an effective amount of a compound having the structure of Formula (I) through (XX-B), or a pharmaceutically acceptable isomer, racemate, hydrate, solvate, isotope, or salt thereof, or a pharmaceutical composition comprising the same.

The term "antagonism" is used herein to encompass molecules that interact in some way with a receptor and thereby function as an antagonist, either by binding to the receptor at the binding site of its natural ligand or at locations other than the binding site. The phrase to "V1a antagonism" is used herein to encompass molecules that interact in some way with the V1a receptor and thereby function as an antagonist, either by binding to the V1a receptor at the binding site of its natural ligand, or at a location other than the binding site (i.e., allosteric binding).

In an embodiment, a method is provided for treatment of a malcondition in a subject for which antagonism of the V1a receptor is medically indicated. Such method comprises administering to the subject an effective amount of a compound having the structure of Formula (I) through (XX-B), or a pharmaceutically acceptable isomer, racemate, hydrate, solvate, isotope, or salt thereof, or a pharmaceutical composition comprising the same, at a frequency and for duration sufficient to provide a beneficial effect to the subject.

As used herein, a "subject" means both mammals and non-mammals. Mammals include, for example: humans; non-human primates (e.g., apes and monkeys); cattle; horses; sheep; and goats. Non-mammals include, for example, fish and birds.

"Treating" or "treatment" within the meaning herein refers to an alleviation of symptoms associated with a malcondition, or inhibition of further progression or worsening of those symptoms, or prevention or prophylaxis of the malcondition in certain instances.

The expression "effective amount", when used to describe use of a compound for treating a subject suffering from a malcondition for which antagonism of the V1a receptor is medically indicated, refers to an the amount of the compound sufficient to produce a beneficial therapeutic effect for the subject.

The phrase "malcondition" is intended to broadly encompass any and all diseases, disorders, syndromes and/or symptoms wherein the V1a receptor plays a role in the same, such that a therapeutically beneficial effect can be achieved by antagonism of the V1a receptor.

In certain embodiments, the present invention provides a method for antagonizing the V1a receptor with a compound of Formula (I) through (XX-B), or a pharmaceutically acceptable isomer, racemate, hydrate, solvate, isotope, or salt thereof, by contacting the receptor with a suitable amount of the compound to antagonize the receptor. Such contacting can take place in vitro, for example in carrying out an assay to determine the V1a inhibition activity of a compound undergoing experimentation related to a submission for regulatory approval.

In certain embodiments, the method for antagonizing the V1a receptor can also be carried out in vivo, that is, within the living body of the subject. The compound of Formula (I) through (XX-B), or a pharmaceutically acceptable isomer, racemate, hydrate, solvate, isotope, or salt thereof, can be supplied to the living organism via one of the routes as described above (e.g., orally) or can be provided locally within the body tissues. In the presence of the inventive compound, inhibition of the receptor takes place, and the effect thereof can be studied.

In another embodiment, a compound of Formula (I) through (XX-B) is an imaging agent, wherein the compound contains an isotope, such as isotopes of F, O, N and C. In certain embodiments, the isotope is a fluorine isotope. The compounds may be used for therapeutic purposes, or to diagnose or assess the progression of a malcondition (a vasopressin-dependent condition) in a subject for which antagonism of the V1a receptor is medically indicated.

In some embodiments, imaging and/or diagnostic methods are provided comprising administering to a subject in need thereof the imaging agent described herein and detecting the compound comprised in the imaging agent in the subject. In some aspects, the amount of the compound in the subject is quantified. In further aspects, a vasopressin-dependent condition in the subject is detected via a detection of the compound in the subject. In certain embodiments, the imaging is effected by a radiodiagnostic method. The radiodiagnostic method may be performed by any instrument capable of detecting radiation by the compounds. Exemplary radiodiagnostic methods include, but not limited to, Positron Emission Tomography (PET), PET-Time-Activity Curve (TAC) or PET-Magnetic Resonance Imaging (MM). In particular aspect, the radiodiagnostic method is PET. In one embodiment, methods of treatment are provided comprising administering a compound of Formula (I) through (XX-B), or a pharmaceutically acceptable isomer, racemate, hydrate, solvate, isotope, or salt thereof, alone or in combination with another pharmacologically active agent or second medicament, to a subject having a malcondition for which antagonizing the V1a receptor is medically indicated.

As mentioned above, V1a receptor antagonists provide significant promise for the treatment of malconditions which benefit from antagonism of the V1a receptor. As summarized in the review article by Szczepanska-Sadowaska et al., *Current Drug Metabolism* 18:306-345, 2017 (incorporated by reference herein in its entirety), vasopressin has been associated with a wide range of regulatory functions in numerous organs and/or tissues and implicated in or with: (1) the cardiovascular system, (2) renal effects, (3) circadian rhythm, (4) food intake and metabolic and endocrine regulation, (5) uterus, (6) endotoxemia, and (7) stress, depression and psychiatric disorders. AVP is also involved in the regulation of several functions, such as, hepatic, pancreatic, and platelet-aggregating effects, and effects on the central and peripheral nervous system. The effects of the AVP receptors depends on where they are located.

In the cardiovascular system, vasopressin is associated with: (a) peripheral effects (e.g., it acts as a potent vasoconstrictor and plays a role in the regulation of carioca muscle differentiation, growth and contractility); (b) central cardiovascular control (e.g., buffering excessive increases and decreases in blood pressure); (c) regulation of cardiovascular reflexes (e.g., in the regulation of the baroreceptor reflex); (d) interaction with other factors (e.g., factors regulating blood pressure such as Ang II); (e) adaption to hemorrhage; and (f) cardiovascular diseases (e.g., hypertension and heart failure, intracranial hemorrhage and stroke).

As for renal effects, vasopressin has antidiuretic action, and interacts with AngII in the regulation of urine excretion. Vasopressin also exerts a diposgenic action, manifested by reduction of the osmotic thirst threshold.

In the context of circadian rhythm, vasopressin neurons in the suprachiasmatic nuclei (SCN) of the hypothalamus manifest a distinct circadian rhythmicity, and studies have shown distinct circadian rhythmicity of vasopressin concentration in the cerebrospinal fluid (CSF). It has been suggested that SCN vasopressin neurons belong to the group of autonomous pacemakers and play a role in the regulation of the circadian rhythm, and studies have shown that circadian rhythmicity of vasopressin release has repercussions in the diurnal rhythmicity of other functions, such as corticosterone release, locomotor activity and body temperature.

With regard to food intake and metabolic and endocrine regulation, vasopressin has been associated with regulation of food intake and glucose homeostasis, and animal studies with V1a receptor knockout mice consuming high fat diet show that vasopressin acting on V1a receptor improves glucose tolerance and protects from the development of obesity. Studies have also shown that vasopressin plays a direct role in the regulation of glucagon and insulin release from the pancreatic cells. In the adrenal gland, vasopressin causes hypertrophy and hyperplasia of the adrenal cortex and stimulates secretion of aldosterone and glucocorticoids through stimulation of V1a receptors. Stimulation of the V1a receptor by vasopressin also influences release of luteinizing hormone releasing hormone (LHRL) and is believed to play a role in initiating the preovulatory LH surge.

The presence of V1a receptors has also been reported in the uterus, with the density of such receptors higher in the myometrium than in the endometrium, and they react with oxytocin (OT) receptors.

Endotoxemia is associated with the increased expression of the vasopressin gene in the hypothalamic nuclei and elevated concentration of vasopressin in the blood. Vasopressin exerts various effects on the cardiovascular system during endotoxemia, including reducing renal medullary blood flow where aortic contractility is reduced. There is also evidence that vasopressin plays a role in the regulation of immunologic processes, and that it may play a role in the regeneration of the liver.

With regard to stress, depression and psychiatric disorders, the role of vasopressin in the regulation of behavior has been studied for many decades, with early studies showing that it facilitates conditioned avoidance responses in rats. Experimental studies have shown that vasopressin has long-lasting effects on learning and new memory acquisition as well as emotional and social behaviors, and clinical observations have shown that depression and other psychiatric disorders are associated with significant changes in vasopressin secretion. Neurogenic stress has also been shown to stimulate vasopressin release in the blood and CSF. A strong association has been shown between chronic stress, inappropriate activation of the vasopressinergic system and depression. Studies in humans have shown that patients with major depression manifested an elevated plasma vasopressin level, and in patients with unipolar depression there was a significant positive correlation between peripheral plasma vasopressin and hypercortisolemia. There is also evidence that vasopressin is an anxiogenic agent, and direct administration of V1a receptor antagonist into the paraventricular nucleus (PVN) of rats attenuated anxiety and depression behavior. Aggression has also been associated with an increased release of vasopression into the CSF. Vasopressin plays a role in the regulation of pain, and its antinociceptive action has been shown in a number of studies. Inappropriate secretion of vasopressin has also been suggested in the disordered processing of psychosomatic stress which occurs in schizophrenia.

Due to its wide and pivotal role for maintaining body homeostatic under a variety of conditions, vasopressin and its receptors, including V1a, have been recognized as an important target for diagnostic and therapeutic applications. To this end, vasopressin antagonists have shown efficacy in easing congestion symptoms and edema and increasing plasma sodium ion concentration in clinical trials. In addition, the compounds of the present invention have utility across a broad spectrum of malconditions, including the following: heart failure; hepatic cirrhosis, psychiatric disorders (e.g., major depressive disorder or generalized anxiety disorder), brain injury, circadian rhythm disorders (e.g., associated with shift work or jet lag, resulting in sleep drifting later each day, abnormal night sleep patterns, and/or difficulty staying awake during the day), bone growth, diabetes mellitus, ovarian function, septic shock (e.g., maintaining haemodynamic parameters and preventing organ damage), and cancer and metatisis (e.g., decreasing dissemination of tumor cells and the spread of metasteses by improving haemostasis and slowing of proliferation of carcinoma cells).

The compounds of the present invention selectively block the effects of V1a receptors, are orally bioavailable/effective, and demonstrate central nervous system (CNS)-penetrating effects. These compounds, (when acting peripherally and/or centrally) are useful in the treatment of vasopressin-dependent conditions or in the conditions related to inappropriate secretion of vasopressin, particularly in the response to chronic stress and in circuits that are dysregulated in affective disorders. These compounds reduce measures of stress, fear, aggression, depression, and anxiety.

In an embodiment, a method is provided for treatment or prevention of vasopressin-dependent conditions or in the conditions related to inappropriate secretion of vasopressin, comprising administering to a subject in need thereof an effective amount of a compound having the structure of Formulas (I) through (XX-B), or a pharmaceutically acceptable isomer, racemate, hydrate, solvate, isotope or salt thereof, or a pharmaceutical composition comprising the same, at a frequency and for a duration sufficient to provide a beneficial effect to the subject.

In an embodiment, a method is provided for treatment of a vasopressin-dependent condition, whether organic, stress-induced or iatrogenic.

As used herein a "vasopressin-dependent condition" is defined as conditions related to inappropriate secretion of vasopressin, particularly in the response to chronic stress and in circuits that are dysregulated in affective disorders, such as disorders of stress, mood, and behavioral disorders, including stress-related affective disorders. Vasopressin-dependent conditions, include conditions such as cardiovascular conditions, for example hypertension, pulmonary hypertension, cardiac insufficiency, myocardial infarction or coronary vasospasm, in particular in smokers, Raynaud's syndrome, unstable angina and PTCA (percutaneous transluminal coronary angioplasty), cardiac ischemia, hemostasis disturbances or thrombosis; conditions of the central nervous system, such as migraine, cerebral vasospasm, cerebral hemorrhage, trauma and cerebral edema, depression, anxiety, stress, emotional disorders, obsessive-compulsive disorder, panic attacks, psychotic states, aggression, memory or sleep disorders, or cognitive disorders, for example disorders associated with impaired social cognition (e.g., schizophrenia, autism spectrum disorder); conditions of the renal system, such as renal vasospasm, necrosis of the renal cortex, nephrogenic diabetes insipidus or diabetic nephropathy; or conditions of the gastric system, such as gastric vasospasm, cirrhosis of the liver, ulcers or the pathology of vomiting, for example nausea, including nausea due to chemotherapy, or travel sickness; circadian rhythm-related disorders such as phase shift sleep disorders, jet-lag, sleep disorders and other chronobiological disorders. Additional examples of vasopressin-dependent conditions include but are not limited to neuropsychiatric disorders, neuropsychiatric symptoms in neurodegenerative diseases, PTSD, inappropriate aggression, anxiety, depressive disorders, major depression, obsessive compulsive disorder, autistic spectrum disorders, schizophrenia, and aggressive behavior, and other affective disorders.

In an embodiment, a method is provided for treatment of an autism spectrum disorder, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject.

Autism spectrum disorder (ASD), also referred to herein as autistic spectrum disorders, is a blanket term describing a complex developmental disorder that affects the brain's normal development of social and communication skills. Core symptoms of ASD include impaired social interactions such as social interaction difficulties, communication challenges including impaired verbal and nonverbal communication, problems processing information from the senses, and a tendency to engage in restricted and repetitive patterns of behavior. In one embodiment, the core symptoms of the autism spectrum disorder are impaired social interactions and communication challenges. In one embodiment, the core symptom of the autism spectrum disorder is impaired social interactions. In one embodiment, the core symptom of the autism spectrum disorder is impaired communication challenges. In one embodiment, the core symptom of the autism spectrum disorder is the tendency to engage in restricted and repetitive patterns of behavior.

In an embodiment, a method is provided for treatment of an anxiety disorder, comprising administering to a subject in need thereof an effective amount of a compound having the structure of Formulas (I) through (XX-B), or a pharmaceutically acceptable isomer, racemate, hydrate, solvate, isotope or salt thereof, or a pharmaceutical composition comprising the same, at a frequency and for a duration sufficient to provide a beneficial effect to the subject.

Anxiety disorder is a blanket term covering several different forms of abnormal and pathological fear and anxiety. Current psychiatric diagnostic criteria recognize a wide variety of anxiety disorders, including generalized anxiety disorder, panic disorder, stress-related disorders, obsessive compulsive disorder, phobia, social anxiety disorder, separation anxiety disorder and post-traumatic stress disorder (PTSD). In one embodiment, the anxiety disorder is a social anxiety disorder. In one embodiment, the anxiety disorder is phobia. In one embodiment, the anxiety disorder is a stress-related disorder. In one embodiment, the anxiety related disorder is PTSD.

Generalized anxiety disorder is a common chronic disorder characterized by long-lasting anxiety that is not focused on any one object or situation. A person suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attack's potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from social phobia, specific phobia, agoraphobia, phobia of an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

In an embodiment, a method is provided for treatment of a depressive disorder, depression, or depressive illness, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for duration sufficient to provide a beneficial effect to the subject. Examples of such disorders include major depression, MDD, drug-resistant depression, dysthymia and bipolar disorder.

In an embodiment, a method is provided for treatment of a mood disorder, or an affective disorder comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for duration sufficient to provide a beneficial effect to the subject.

Examples of a mood disorder or a affective disorder include major depressive disorder (MDD); bipolar disorder; anhedonia; dysthymia; major depression, Psychotic major depression (PMD), or psychotic depression; postpartum depression; seasonal affective disorder (SAD); and catatonic depression is a rare and severe form of major depression involving disturbances of motor behavior and other symptoms.

The terms "anhedonia" and "anhedonic symptom" are used interchangeably and is defined as the inability to experience pleasure from activities usually found enjoyable, e.g. exercise, hobbies, music, sexual activities or social interactions. The terms "anhedonia" and "anhedonic symptom" are closely related to criterion of "depressive disorder with melancholic features" which is defined in DSM-5 as melancholic depression characterized by a loss of pleasure in most or all activities, a failure of reactivity to pleasurable stimuli, a quality of depressed mood more pronounced than that of grief or loss, a worsening of symptoms in the morning hours, early morning waking, psychomotor retardation, excessive weight loss, or excessive guilt. The term "treatment of depressive disorder with melancholic features" comprises treatment of both the depressive disorder and melancholic features associated herewith. In one embodiment, the mood disorder is anhedonia. In one embodiment, the mood disorder is major depression. In one embodiment, the mood disorder is seasonal affective disorder (SAD).

In an embodiment, a method is provided for treatment of an affective disorder, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject. Affective disorders such as disorders of stress, mood, and behavioral disorders, including stress-related affective disorders, obsessive compulsive disorder, autistic spectrum disorders, Personality disorders, ADHD, panic attacks and the like. As used herein, "autistic spectrum disorders" and "Autism spectrum disorders" are used interchangeably and refer to autism, monogenetic causes of autism such as synaptophathies, e.g., Rett syndrome, Fragile X syndrome, Angelman syndrome and the like.

In an embodiment, a method is provided for treatment of Anger, Aggression or Aggressive Disorder, or Impulse Control Disorders comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject. Examples of Anger, Aggression or Aggressive Disorder, or Impulse Control Disorders include, but are not limited to, inappropriate aggression, aggressive behavior, aggression related to social isolation, for treatment of interpersonal violence co-occurring with such illness as ADHD, autism, bipolar disorder, emotional disorders, disorders of memory and/or cognition and cognitive disorders (such as Alzheimer's disease, Parkinson's disease, Huntington's disease and the like), and addictive disorder/substance abuse.

In an embodiment, a method is provided for treatment of Intermittent Explosive Disorder (sometimes abbreviated as IED) comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for a duration sufficient to provide a beneficial effect to the subject. Intermittent explosive disorder is a behavioral disorder characterized by explosive outbursts of anger and violence, often to the point of rage, that are disproportionate to the situation at hand (e.g., impulsive screaming triggered by relatively inconsequential events). Impulsive aggression is unpremeditated, and is defined by a disproportionate reaction to any provocation, real or perceived. Some individuals have reported affective changes prior to an outburst (e.g., tension, mood changes, energy changes, etc.). The disorder is currently categorized in the *Diagnostic and Statistical Manual of Mental Disorders* (DSM-5) under the "Disruptive, Impulse-Control, and Conduct Disorders" category. The disorder itself is not easily characterized and often exhibits comorbidity with other mood disorders, particularly bipolar disorder. Individuals diagnosed with IED report their outbursts as being brief (lasting less than an hour), with a variety of bodily symptoms (sweating, stuttering, chest tightness, twitching, palpitations) reported by a third of one sample. Aggressive acts are frequently reported accompanied by a sensation of relief and in some cases pleasure, but often followed by later remorse.

In other embodiments, a method is provided for treatment of a Schizophrenia spectrum disorders, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for duration sufficient to provide a beneficial effect to the subject. Examples of Schizophrenia spectrum disorders include schizophrenia, schizoaffective disorder, psychotic states and memory disorders.

In other embodiments, a method is provided for treatment of a circadian rhythm related disorders, comprising administering to a subject in need thereof an effective amount of a compound having the structure of Formulas (I) through (XXII-B), or a pharmaceutically acceptable isomer, racemate, hydrate, solvate, isotope or salt thereof, or a pharmaceutical composition comprising the same, at a frequency and for duration sufficient to provide a beneficial effect to the subject. Circadian rhythm sleep disorders are caused by desynchronization or misalignment between internal sleep-wake rhythms (body clock) and the external light-darkness cycle. Circadian rhythm disorders (sometimes also referred to as phase shift disorders) include sleep disorders associated with jet lag, shift work, or altered sleep phase types, resulting in sleep drifting later each day, abnormal nigh sleep patterns, and/or difficulty staying awake during the day. The cause may be internal (e.g., delayed or advanced sleep phase syndrome, or Non-24-h sleep-wake syndrome) or external (e.g., jet lag, shift work). If the cause is external, other circadian body rhythms, including temperature and hormone secretion, can become out of sync with the light-darkness cycle (external desynchronization) and with one another (internal desynchronization); in addition to insomnia and excessive sleepiness, these alterations may cause nausea, malaise, irritability, and depression. Risk of cardiovascular and metabolic disorders may also be increased. Compounds of the invention are useful for treating circadian rhythm-related disorders, such as depression, jet-lag, work-shift syndrome, sleep disorders, glaucoma, reproduction, cancer, premenstrual syndrome, immune disorders, inflammatory articular diseases and neuroendocrine disorders, Non-24 Hour Disorder.

The compounds according to the invention may also be used in the treatment or prevention of Neuropsychiatric Disorders such as anorexia nervosa, bulimia, mood disorders, depression, anxiety, sleeping disorders, addictive disorders, panic attacks, phobias, obsession, pain-perception disorders (fibromyalgia), dependency on a substance, hemorrhagic stress, muscular spasms and hypoglycemia. Addictive disorder, including disorders related to substance abuse or addiction, and compulsive behavior.

The compounds according to the invention may also be used in the treatment or prevention of chronic stress states such as immunodepression, fertility disorders and dysfunctions of the hypothalamopituitaryadrenal axis.

The compounds according to the invention can also be used in the treatment of disorders such as primary or secondary dysmenorrhea, premature labor or endometriosis, male or female sexual dysfunction, hypertension, chronic heart failure, inappropriate secretion of vasopressin, liver cirrhosis and nephrotic syndrome.

The compounds according to the invention can also be used in the treatment or prevention of any pathology resulting from stress, such as fatigue and its syndromes, ACTH-dependent disorders, cardiac disorders, pain, modifications in gastric emptying, in fecal excretion (colitis, irritable bowel syndrome or Crohn's disease) or in acid secretion, hyperglycemia, immunosuppression, inflammatory processes (rheumatoid arthritis and osteoarthritis), multiple infections, septic shock, cancers, asthma, psoriasis and allergies.

The compounds according to the invention may also be used as psychostimulants, bringing about an increase in consciousness/alertness and/or in emotional reactivity towards the environment and making adaptation easier.

The compounds according to the present invention can be used in healing, in analgesia, in anxiolysis, in the prevention of pain, in the prevention of anxiety, depression, schizophrenia, autism or obsessive-compulsive syndrome, in maternal behavior (facilitation of recognition and acceptance of the mother by the child) and social behavior, memory; regulation of food and drink intake, dependence on drugs, withdrawal and sexual motivation; hypertension, hyponatremia, cardiac insufficiency, atherosclerosis, angiogenesis, the proliferation of tumors, Kaposi's sarcoma, to regulate the storage of fat by the adipocyte, to control hyperlipidemia, triglyceridemia and metabolic syndrome.

The compounds according to the invention can also be used in the treatment of cancers, such as small cell lung cancers or breast cancers; hyponatremic encephalopathy; pulmonary syndrome; Meniere's disease; ocular hypertension; glaucoma; cataracts; obesity; type-I and type-II diabetes; atherosclerosis; metabolic syndrome; hyperlipidemia; insulin resistance; or hypertriglyceridemia; in post-operative treatments, in particular after abdominal surgery; autism; hypercortisolemia; hyperaldosteronemia; pheochromocytoma; Cushing's syndrome; preeclampsia; disorders of micturition; or premature ejaculation.

Compounds having the structure of Formula (I), as well as the sub-structures for Formulas (II) through (XXII-B), can be synthesized using standard synthetic techniques known to those of skill in the art. For examples, compounds of the present invention can be synthesized using the general synthetic procedures set forth in Schemes 1 and 2.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

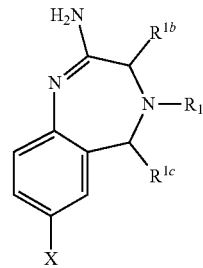

Reagents and conditions: i) iPrOH; ii) TFA, iii) MP-carbonate, MeOH; iv) R²Br, RuPhos, Pd(OAc)₂, Cs₂CO₃ dioxane; v) R²Cl, Cs₂CO₃, DMF.

Scheme 1

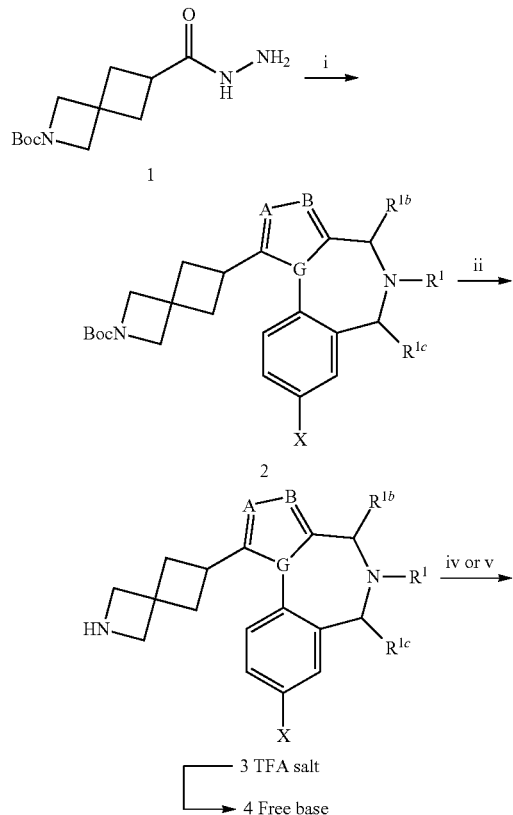

Scheme 2

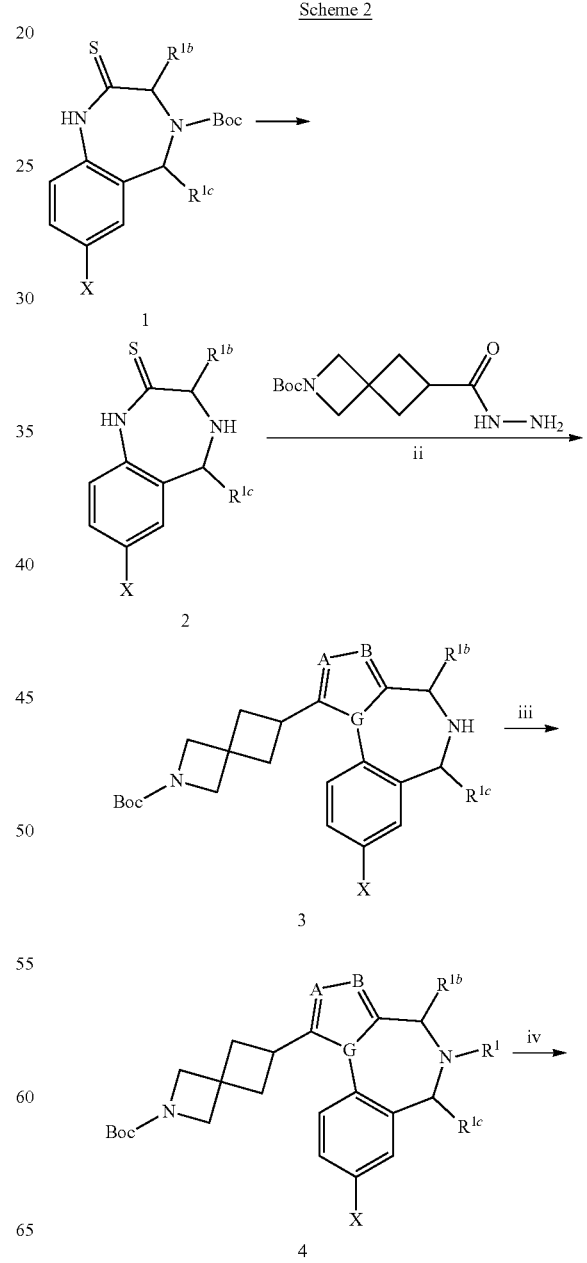

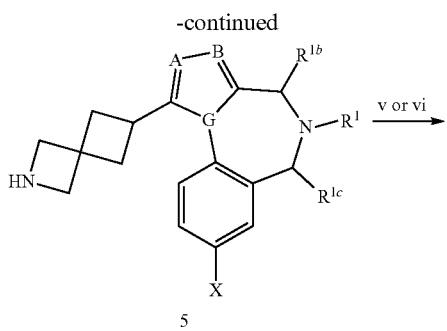
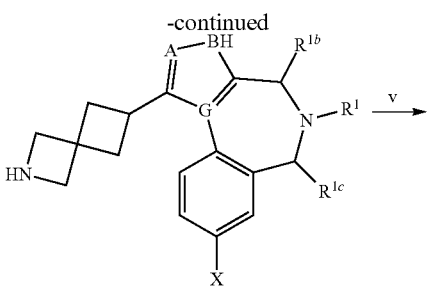

Reagents and conditions: i) TFA, DCM; ii) dioxane; iii) R₁Cl; iv) TFA, DCM; v) R²Br, RuPhos, Pd(OAc)₂, Cs₂CO₃ dioxane; vi) R²Cl, Cs₂CO₃, DMF.

Regents and conditions: i) NH₂OH·HCl, Na₂CO₃, MeOH then N-chlorosuccinimide, DMF; ii) NEt₃, DCM; iii) K₂CO₃, THF, iv) Pd(OAc)₂, pivalic acid, K₂CO₃, DMA; v) TFA, DCM; vi) R²Br, RuPhos, Pd(OAc)₂, Cs₂CO₃, dioxane.

Scheme 3

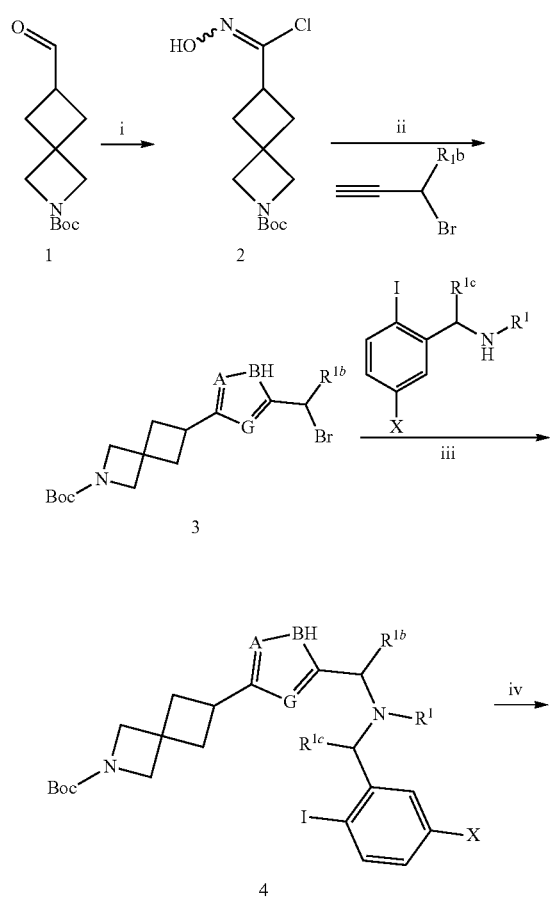

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

General Methods

All the starting materials and reagents are commercially available and were used as is. ¹H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad. Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector. The columns used for the preparative purification of the compounds were a Waters Sunfire OBD Phenomenex Luna Phenyl Hexyl (10 µm 21.2×150 mm, 10 µm) or Waters Xbridge Phenyl (10 µm 19×150 mm, 5 µm). Appropriate focused gradients were selected based on acetonitrile and methanol solvent systems under either acidic or basic conditions. The modifiers used under acidic/basic conditions were formic acid (0.1% V/V) and ammonium bicarbonate (10 mM) respectively. The purification was controlled by Waters Fractionlynx software through monitoring at 210-400 nm, and triggered a threshold collection value at 260 nm and, when using the Fractionlynx, the presence of target molecular ion as observed under APi conditions. Collected fractions were analysed by LCMS (Waters Acquity systems with Waters SQD). Normal phase flash column chromatography was performed utilizing a Biotage Isolera system. The silica gel columns were purchased from either Interchim or Biotage. The mobile phase was either ethyl acetate in hexanes or methanol in dichloromethane with various ratios, and the fraction collection was triggered by UV absorbance at 254 nm. Analytical high-performance liquid chromatography-mass spectrometry (HPLC-MS) was performed utilizing HP or Waters DAD+Micromass ZQ, single quadrapole LC-MS or Quattro Micro LC-MS-MS. Method 1: The RP-HPLC column was Phenomenex Luna 5 µm C18 (2), (100×4.6 mm). Mobile phase 5-95% acetonitrile in water (0.1% formic acid) gradient, flow rate 2.0 mL/min, and 6.5 min run time; Method 2: The RP-HPLC column was Waters Xterra MS 5 µm C18, 100×4.6 mm. Mobile phase 5-95% acetonitrile in water (10 mM ammonium bicarbonate (ammonium hydrogen carbonate); Method 3: method 1 with mobile phase 50-100% acetonitrile in water (0.1% formic acid) gradient, and 5 min run time; Method 4: method 1 with mobile phase 10-100% acetonitrile in water (0.1% formic acid) gradient, and 10 min run time; Method 5: method 1 with 20 min run time.

Abbreviations

The following abbreviations are used in the examples:
Aq. Aqueous solution
BrettPhos: 2-(dicyclohexylphosphino)3,6-dimethoxy-2',4',6'-triisopropyl-1,1'-biphenyl
$CDCl_3$: deuterochloroform
DMSO: dimethyl sulfoxide
DMA: N,N-Dimethylacetamide
ESI: electrospray Ionisation
eq.: equivalent
g: gram
HATU: (1-[bis(dimethylamino)methylene]-1H-1,2,3-triazolo[4,5-b]pyridinium-3-oxidhexafluoro-phosphate
HPLC: high performance liquid chromatography
M: molar
mg: milligram
MHz: megahertz
Ml: milliliter
Mmol: millimole
MP: macroporous
MS: mass spectrometry
NMP: N-methyl-2-pyrrolidone
NMR: nuclear magnetic resonance
RuPhos: 2-dicyclohexylphosphino-2',6'-diisopropoxybiphenyl
SFC: supercritical fluid chromatography
THF: tetrahydrofuran
µL: microliters
DCM: dichloromethane
EtOAc: ethyl acetate
$NaHCO_3$: sodium hydrogencarbonate
LiCl: lithium chloride
$NEt_3$: triethylamine
DMF: dimethylformamide
MeOH: methanol Example 1

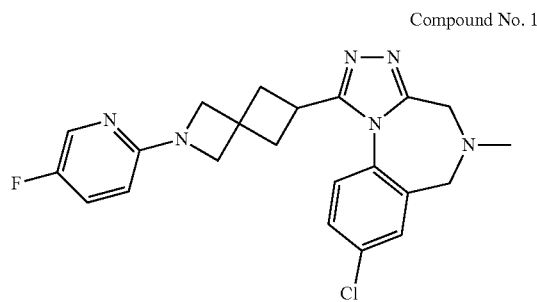 [SMILES: CN1Cc2cc(Cl)ccc2-n2c(nnc2C2CC3(C2)CN(c2ccc(F)cn2)C3)C1]

Compound No. 1

Step 1: Synthesis of tert-butyl 6-(hydrazinecarbonyl)-2-azaspiro[3.3]heptane-2-carboxylate

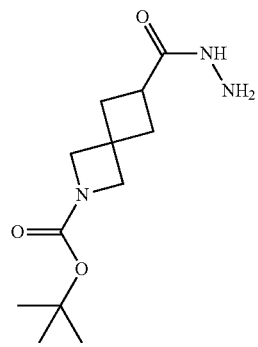 [SMILES: CC(C)(C)OC(=O)N1CC2(CC(C(=O)NN)C2)C1]

To a stirred solution of 2-(tert-butoxycarbonyl)-2-azaspiro[3.3]heptane-6-carboxylic acid (0.26 g, 1 mmol, 1 eq.) in THF (5 mL) was added 1-1'-Carbonyldiimidazole (0.19 g, 1.2 mmol, 1.2 eq.) and the mixture was stirred at RT overnight. The resulting mixture was added to a solution of hydrazine monohydrate (0.07 mL, 1.4 mmol, 1.4 eq.) in THF (10 mL) and stirred at RT overnight. The mixture was diluted with brine and extracted with ethyl acetate. The organic phase was separated, washed with brine, dried ($MgSO_4$), filtered and concentrated in vacuo to afford the title compound as a white solid (0.29 g, 100% yield). This material was used without further purification. $^1$H NMR (400 MHz, $CDCl_3$) δ 6.61-6.59 (m, 1H), 3.91-3.80 (m, 6H), 2.81-2.73 (m, 1H), 2.48-2.43 (m, 2H), 2.35-2.30 (m, 2H), 1.40 (s, 9H).

Step 2: Synthesis of terttert-butyl 6-(8-chloro-5-methyl-5,6-dihydro-4H-benzo[f][1,2,4]triazolo[4,3-a][1,4]diazepin-1-yl)-2-azaspiro[3.3]heptane-2-carboxylate

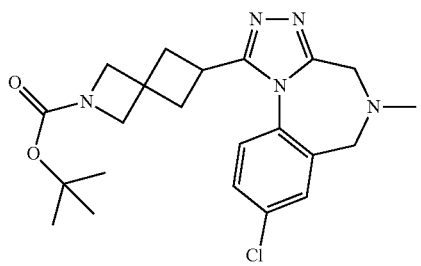 [SMILES: CN1Cc2cc(Cl)ccc2-n2c(nnc2C2CC3(C2)CN(C(=O)OC(C)(C)C)C3)C1]

To a solution of tert-butyl 6-(hydrazinecarbonyl)-2-azaspiro[3.3]heptane-2-carboxylate (0.27 g, 1.06 mmol, 1 eq.) in 2-propanol (20 mL) was added 7-chloro-4-methyl-1,3,4,5-tetrahydro-2H-benzo[e][1,4]diazepin-2-imine (0.22 g, 1.06 mmol, 1 eq.) and the mixture was stirred at 80° C. over the weekend. The reaction mixture was concentrated under reduced pressure to afford an orange solid. Sat. aq. NaHCO$_3$ (20 mL) was added to the orange solid and the mixture was extracted with DCM (×2). The organic phases were combined, washed with brine, passed through a hydrophobic phase separator and concentrated in vacuo to give an orange solid. The crude material was purified by silica gel chromatography eluting with 0-10% methanol in DCM to afford the title compound as a yellow solid (0.257 g, 56% yield). $^1$H NMR (400 MHz, CDCl$_3$) δ 7.50 (d, J=7.3 Hz, 2H), 7.12 (d, J=8.9 Hz, 1H), 4.00 (s, 2H), 3.93 (s, 2H), 3.67 (s, 2H), 3.49-3.42 (m, 1H), 3.34 (s, 2H), 2.78 (dd, J=8.3, 12.7 Hz, 2H), 2.63-2.54 (m, 2H), 2.48 (s, 3H), 1.43 (s, 9H).

Step 3: Synthesis of 8-chloro-5-methyl-1-(2-azaspiro[3.3]heptan-6-yl)-5,6-dihydro-4H-benzo[f][1,2,4]triazolo[4,3-a][1,4]diazepine bis(2,2,2-trifluoroacetate)

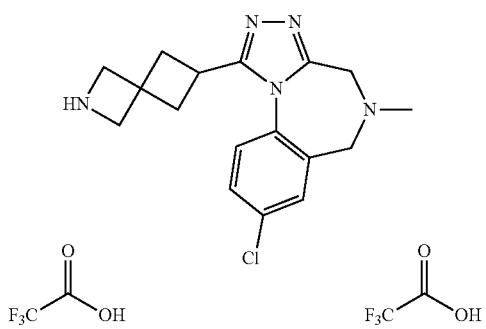 [SMILES: O=C(O)C(F)(F)F ; CN1Cc2cc(Cl)ccc2-n2c(nnc2C2CC3(CNC3)C2)C1 ; O=C(O)C(F)(F)F]

TFA (0.33 mL, 4.32 mmol, 74.4 eq.) was added dropwise to a solution of tert-butyl 6-(8-chloro-5-methyl-5,6-dihydro-4H-benzo[f][1,2,4]triazolo[4,3-a][1,4]diazepin-1-yl)-2-azaspiro[3.3]heptane-2-carboxylate (0.025 g, 0.058 mmol, 1.0 eq.) in DCM (1 mL) at RT and mixture was stirred at RT for 20 min. The mixture was concentrated in vacuo to give a yellow residue which was used without further purification (5.3 mg, 26% yield). $^1$H NMR (400 MHz, DMSO) δ 8.80-8.75 (m, 2H), 7.90-7.86 (m, 2H), 7.60-7.58 (d, J=8.7 Hz, 1H), 4.61-4.15 (m, 4H), 4.11-4.08 (m, 2H), 4.01-3.98 (m, 2H), 3.74-3.68 (m, 1H), 2.96 (s, 3H), 2.71-2.53 (m, 4H).

Step 4: Synthesis of 8-chloro-1-(2-(5-fluoropyridin-2-yl)-2-azaspiro[3.3]heptan-6-yl)-5-methyl-5,6-dihydro-4H-benzo[f][1,2,4]triazolo[4,3-a][1,4]diazepine (Compound No. 1)

A mixture of 8-chloro-5-methyl-1-(2-azaspiro[3.3]heptan-6-yl)-5,6-dihydro-4H-benzo[f][1,2,4]triazolo[4,3-a][1,4]diazepine bis(2,2,2-trifluoroacetate) (0.045 g, 0.08 mmol, 1 eq.), 2-bromo-5-fluoropyridine (0.029 g, 0.16 mmol, 2.04 eq.), RuPhos (0.013 g, 0.03 mmol, 0.345 eq.), palladium acetate (0.003 g, 0.01 mmol, 0.165 eq.), cesium carbonate (0.133 g, 0.41 mmol, 5.06 eq.) in NMP (1 mL) was degassed using N$_2$, for 10 minutes and then heated to 80° C. for 20 minutes. The reaction was allowed to cool and allowed to stand at RT over the weekend. The mixture was diluted with EtOAc, 4% aq. sol. of LiCl and filtered through a layer of celite. The organic phase was separated, washed with aq. sol. of LiCl, dried (MgSO$_4$), filtered and concentrated in vacuo to give a yellow oil. The crude material was purified by column chromatography on a Biotage® KP-NH cartridge eluting with 0-100% EtOAc in isohexane followed by 0-5% methanol in ethyl acetate to give a colourless glass. This was lyophilized to afford the title compound as a white solid (11.5 mg, 21% yield). $^1$H NMR (400 MHz, CDCl$_3$) δ 8.00 (d, J=2.9 Hz, 1H), 7.53-7.49 (m, 2H), 7.25-7.19 (m, 1H), 7.14 (d, J=8.3 Hz, 1H), 6.24 (dd, J=3.3, 8.8 Hz, 1H), 4.08 (s, 2H), 3.99 (s, 2H), 3.68 (s, 2H), 3.57-3.47 (m, 1H), 3.35 (s, 2H), 2.86 (dd, J=8.2, 12.9 Hz, 2H), 2.71-2.62 (m, 2H), 2.48 (s, 3H). m/z 425 (M+H)$^+$.

Compound Nos. 2 to 13 and 17 to 21

Compound Nos. 2 to 13 were prepared according to the methods set forth in Example 1. For example, Compound No. 2 of Table 2 lists the method of "Example 1", indicating that this compound was prepared according to the procedure of Example 1 using appropriately substituted intermediates. Analytical data (NMR, mass spectrum) is also presented in Table 2.

Compound Nos. 17 to 21 are prepared according to the procedure of Example 1 using appropriately substituted intermediates.

TABLE 2

| Compound Nos. 2 to 13 | | |
|---|---|---|
| Compound No. | Analytical Data | Synthesis Method |
| 2 | $^1$H NMR (400 MHz, CDCl$_3$) δ 8.14 (dd, J = 1.0, 5.1 Hz, 1H), 7.53-7.48 (m, 2H), 7.46-7.41 (m, 1H), 7.15 (d, J = 8.1 Hz, 1H), 6.61-6.58 (m, 1H), 6.27 (d, J = 8.3 Hz, 1H), 4.12 (s, 2H), 4.02 (s, 2H), 3.68 (s, 2H), 3.57-3.47 (m, 1H), 3.35 (s, 2H), 2.87 (dd, J = 8.2, 12.8 Hz, 2H), 2.71-2.63 (m, 2H), 2.49 (s, 3H). m/z 407 (M + H)$^+$. | Example 1 |
| 3 | $^1$H NMR (400 MHz, CDCl$_3$) δ 8.01 (dd, J = 1.5, 2.8 Hz, 1H), 7.84 (d, J = 2.5 Hz, 1H), 7.77 (d, J = 1.3 Hz, 1H), 7.51 (d, J = 7.8 Hz, 2H), 7.14 (d, J = 8.6 Hz, 1H), 4.18 (s, 2H), 4.12 (s, 2H), 3.68 (s, 2H), 3.58-3.48 (m, 1H), 3.35 (s, 2H), 2.89 (dd, J = 8.1, 12.9 Hz, 2H), 2.74-2.65 (m, 2H), 2.49 (s, 3H). m/z 408 (M + H)$^+$. | Example 1 |
| 4 | $^1$H NMR (400 MHz, CDCl$_3$) δ 7.92-7.89 (m, 1H), 7.53-7.48 (m, 2H), 7.17-7.09 (m, 1H), 6.60-6.55 (m, 1H), 4.23 (d, J = 1.8 Hz, 2H), 4.15 (d, J = 2.0 Hz, 2H), 3.68 (s, 2H), 3.56-3.46 (m, 1H), 3.35 (s, 2H), 2.86 (dd, J = 8.5, 12.8 Hz, 2H), 2.70-2.62 (m, 2H), 2.48 (s, 3H). m/z 425 (M + H)$^+$. | Example 1 |

TABLE 2-continued

Compound Nos. 2 to 13

| Compound No. | Analytical Data | Synthesis Method |
|---|---|---|
| 5 | $^1$H NMR (400 MHz, CDCl$_3$) δ 8.01 (dd, J = 1.3, 4.5 Hz, 1H), 7.85 (d, J = 2.8 Hz, 1H), 7.50 (d, J = 7.8 Hz, 2H), 7.16-7.07 (m, 2H), 6.73-6.69 (m, 1H), 4.00 (s, 2H), 3.94 (s, 2H), 3.68 (s, 2H), 3.57-3.47 (m, 1H), 3.35 (s, 2H), 2.87 (dd, J = 8.0, 12.8 Hz, 2H), 2.72-2.64 (m, 2H), 2.49 (s, 3H). m/z 425 (M + H)$^+$. | Example 1 |
| 6 | $^1$H NMR (400 MHz, CDCl$_3$) δ 7.50 (d, J = 7.8 Hz, 2H), 7.33 (dd, J = 7.7, 7.7 Hz, 1H), 7.15 (d, J = 8.6 Hz, 1H), 6.46 (d, J = 7.3 Hz, 1H), 6.08 (d, J = 8.1 Hz, 1H), 4.10 (s, 2H), 3.99 (s, 2H), 3.67 (s, 2H), 3.56-3.46 (m, 1H), 3.35 (s, 2H), 2.84 (dd, J = 8.3, 12.6 Hz, 2H), 2.69-2.60 (m, 2H), 2.48 (s, 3H), 2.39 (s, 3H). m/z 421 (M + H)$^+$. | Example 1 |
| 7 | $^1$H NMR (400 MHz, CDCl$_3$) δ 7.51 (d, J = 7.9 Hz, 2H), 7.36 (dd, J = 7.8, 7.8 Hz, 1H), 7.15 (d, J = 8.3 Hz, 1H), 6.04 (d, J = 7.9 Hz, 1H), 5.83 (d, J = 7.8 Hz, 1H), 4.08 (s, 2H), 3.99 (s, 2H), 3.85 (s, 3H), 3.68 (s, 2H), 3.55-3.46 (m, 1H), 3.35 (s, 2H), 2.85 (dd, J = 8.2, 12.7 Hz, 2H), 2.69-2.61 (m, 2H), 2.49(s, 3H). m/z 437 (M + H)$^+$. | Example 1 |
| 8 | $^1$H NMR (400 MHz, CDCl$_3$) δ 7.53-7.47 (m, 3H), 7.14 (d, J = 8.3 Hz, 1H), 6.15 (dd, J = 1.9, 7.7 Hz, 1H), 6.05 (dd, J = 2.0, 8.0 Hz, 1H), 4.11 (s, 2H), 4.02 (s, 2H), 3.68 (s, 2H), 3.56-3.47 (m, 1H), 3.35 (s, 2H), 2.86 (dd, J = 8.2, 12.8 Hz, 2H), 2.71-2.61 (m, 2H), 2.49 (s, 3H). m/z 425 (M + H)$^+$. | Example 1 |
| 9 | $^1$H NMR (400 MHz, CDCl$_3$) d 7.49 (d, J = 7.4 Hz, 2H), 7.12 (d, J = 8.8 Hz, 1H), 4.00 (s, 2H), 3.93 (s, 2H), 3.66 (s, 2H), 3.49-3.39 (m, 1H), 3.34 (s, 2H), 2.78 (dd, J = 8.3, 12.7 Hz, 2H), 2.58 (dd, J = 10.6, 10.6 Hz, 2H), 2.48 (s, 3H), 1.43 (s, 9H). m/z 430 (M + H)$^+$. | Exam, ple 1; Product of Step 2 |
| 10 | $^1$H NMR (400 MHz, CDCl$_3$) δ 7.85 (d, J = 2.3 Hz, 1H), 7.64 (dd, J = 1.9, 1.9 Hz, 1H), 7.51 (d, J = 7.3 Hz, 2H), 7.15-7.12 (m, 1H), 6.42 -6.37 (m, 1H), 3.99 (d, J = 18.2 Hz, 4H), 3.68 (s, 2H), 3.56-3.47 (m, 1H), 3.35 (s, 2H), 2.88 (dd, J = 8.1, 12.9 Hz, 2H), 2.73-2.65 (m, 2H), 2.49 (s, 3H). m/z 425 (M + H)$^+$. | Example 1 |
| 11 | $^1$H NMR (400 MHz, CDCl$_3$) δ 7.87 (d, J = 2.8 Hz, 1H), 7.53-7.48 (m, 2H), 7.17 -7.11 (m, 2H), 6.28 (d, J = 9.1 Hz, 1H), 4.05 (s, 2H), 3.95 (s, 2H), 3.77 (s, 3H), 3.67 (s, 2H), 3.56-3.46 (m, 1H), 3.35 (s, 2H), 2.85 (dd, J = 8.3, 12.6 Hz, 2H), 2.69-2.61 (m, 2H), 2.48 (s, 3H). m/z 437 (M + H)$^+$. | Example 1 |
| 12 | $^1$H NMR (400 MHz, CDCl$_3$) δ7.96 (d, J = 2.3 Hz, 1H), 7.53-7.48 (m, 2H), 7.29 (d, J = 3.4 Hz, 1H), 7.15 (d, J = 8.1 Hz, 1H), 6.23 (d, J = 8.3 Hz, 1H), 4.07 (s, 2H), 3.97 (s, 2H), 3.67 (s, 2H), 3.56-3.47 (m, 1H), 3.35 (s, 2H), 2.85 (dd, J = 8.2, 12.8 Hz, 2H), 2.69-2.61 (m, 2H), 2.48 (s, 3H), 2.18 (s, 3H). m/z 421 (M + H)$^+$. | Example 1 |
| 13 | $^1$H NMR (400 MHz, CDCl$_3$) δ 8.57 (dd, J = 1.3, 4.5 Hz, 1H), 7.54-7.49 (m, 2H), 7.19-7.13 (m, 2H), 6.52 (dd, J = 1.4, 9.0 Hz, 1H), 4.26 (s, 2H), 4.13 (s, 2H), 3.68 (s, 2H), 3.59-3.49 (m, 1H), 3.35 (s, 2H), 2.89 (dd, J = 8.0, 12.8 Hz, 2H), 2.75-2.67 (m, 2H), 2.49 (s, 3H). m/z 408 (M + H)$^+$. | Example 1 |

Example 2

Compound No. 15

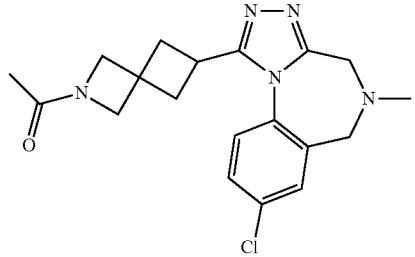

Step 1: Synthesis of 1-(6-(8-chloro-5-methyl-5,6-dihydro-4H-benzo[f][1,2,4]triazolo[4,3-a][1,4]diazepin-1-yl)-2-azaspiro[3.3]heptan-2-yl)-2,2,2-trifluoroethan-1-one

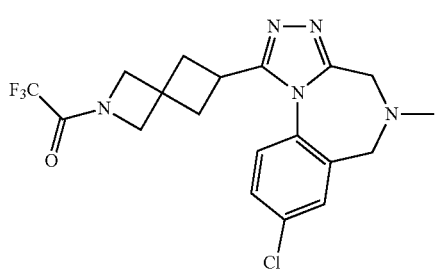 [SMILES: CN1Cc2cc(Cl)ccc2-n2c(nnc2C2CC3(C2)CN(C(=O)C(F)(F)F)C3)C1]

To a solution of 8-chloro-5-methyl-1-(2-azaspiro[3.3]heptan-6-yl)-5,6-dihydro-4H-benzo[f][1,2,4]triazolo[4,3-a][1,4]diazepine bis(2,2,2-trifluoroacetate) from Example 1 step 3 (0.055 g, 0.1 mmol, 1 eq.), NEt$_3$ (69 µL, 0.49 mmol, 5.0 eq.) in DCM (2 mL) was added trifluoroacetic anhydride (21 µL, 0.15 mmol, 1.5 eq.) and the mixture was stirred at RT for 1 hour. The mixture was diluted with DCM/water and the organic layer was separated by passing through a hydrophobic phase separator. The organic phase was concentrated in vacuo to give the title compound as a yellow oil. This material was used without further purification (32 mg).

Step 2: Synthesis of 1-(6-(8-chloro-5,6-dihydro-4H-benzo[f][1,2,4]triazolo[4,3-a][1,4]diazepin-1-yl)-2-azaspiro[3.3]heptan-2-yl)ethan-1-one (Compound No. 15)

A suspension of 1-(6-(8-chloro-5,6-dihydro-4H-benzo[f][1,2,4]triazolo[4,3-a][1,4]diazepin-1-yl)-2-azaspiro[3.3]heptan-2-yl)-2,2,2-trifluoroethan-1-one (0.43 g, 0.1 mmol, 1 eq.) from step 1, K$_2$CO$_3$ (0.056 g, 0.4 mmol, 4.0 eq.) and MeOH (2 mL) was stirred at RT for 1 hour. The mixture was concentrated under reduced pressure and the residue was treated with 20% MeOH in DCM, filtered and the filtrate was concentrated under reduced pressure to give a yellow gum. To a solution of the yellow gum in DCM (2 mL) was added NEt$_3$ (21.11 µL, 1.50 eq.), AcCl (10.81 µL, 0.15 mmol, 1.50 eq.) and the mixture was stirred at RT for 45 minutes. The mixture was concentrated under reduced pressure and the residue was treated with EtAc, sat. sol. of NaHCO$_3$. The organic phase was separated, the aqueous phase was extracted with EtOAc. The organic phases were combined, dried (MgSO₄), filtered and concentrated in vacuo to give a yellow residue. This was purified using reverse phase column chromatography on a C18 cartridge, eluting with 5-50% MeCN/H₂O/0.1% formic acid. After lyophilisation this give the title compound as a white solid (4.5 mg, 10% yield) ¹H NMR (400 MHz, CDCl₃) δ 7.53-7.49 (m, 2H), 7.14-7.09 (m, 1H), 4.19 (d, J=12.4 Hz, 2H), 4.06 (s, 1H), 3.99 (s, 1H), 3.67 (s, 2H), 3.53-3.43 (m, 1H), 3.34 (s, 2H), 2.87-2.78 (m, 2H), 2.69-2.57 (m, 2H), 2.48 (s, 3H), 1.85 (s, 3H). m/z 372 (M+H)⁺.

Compound 16

Compound No. 16 was prepared according to the methods set forth in Example 2. using appropriately substituted intermediates. Analytical data (NMR, mass spectrum): ¹H NMR (400 MHz, DMSO) δ 7.76-7.75 (m, 1H), 7.65 (dd, J=2.4, 8.5 Hz, 1H), 7.50 (d, J=8.5 Hz, 1H), 4.59 (s, 2H), 4.42 (s, 2H), 4.10-4.08 (m, 4H), 3.70-3.62 (m, 1H), 2.61 (d, J=8.2 Hz, 4H), 2.56-2.53 (m, 2H), 1.52-1.45 (m, 1H), 1.10 (t, J=7.3 Hz, 3H), 0.71-0.68 (m, 4H). m/z 440 (M+H)⁺.

Example 3

Compound No. 24

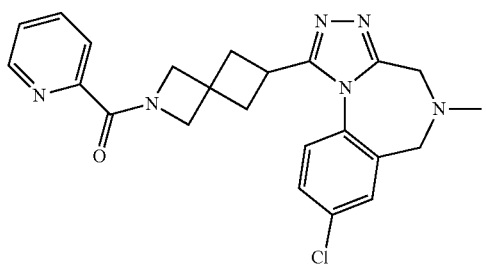

To a solution of 8-chloro-5-methyl-1-(2-azaspiro[3.3]heptan-6-yl)-5,6-dihydro-4H-benzo[f][1,2,4]triazolo[4,3-a][1,4]diazepine bis(2,2,2-trifluoroacetate) from Example 1 Step 3 (0.202 g, 0.47 mmol, 1 eq.) in MeOH (10 mL) was added MP-carbonate (2.43 g, 7.05 mmol, 15.0 eq.) and the mixture was stirred at RT for 2 hours. The mixture was filtered and concentrated in vacuo to give a yellow oil. To a solution of the yellow oil (0.03 g, 0.09 mmol, 1.0 eq.) in DCM (1 mL) was added DIPEA (40 μL, 0.23 mmol, 2.5 eq.), picolinoyl chloride hydrochloride (0.19 g, 0.11 mmol, 1.2 eq.) and the mixture was stirred at RT for 15 minutes. The mixture was diluted with DCM, passed through a hydrophobic phase separator and concentrated in vacuo to give a residue. The residue was purified by preparative HPLC to give the title compound (23.7 mg, 60% yield). ¹H NMR (400 MHz, CDCl₃) δ 8.56 (dd, J=4.5, 9.6 Hz, 1H), 8.09 (dd, J=8.0, 16.8 Hz, 1H), 7.83-7.76 (m, 1H), 7.54-7.48 (m, 2H), 7.37-7.33 (m, 1H), 7.13 (d, J=8.3 Hz, 1H), 4.81 (s, 1H), 4.72 (s, 1H), 4.30 (s, 1H), 4.22 (s, 1H), 3.67 (s, 2H), 3.53-3.44 (m, 1H), 3.35 (s, 2H), 2.90-2.81 (m, 2H), 2.71-2.61 (m, 2H), 2.48 (s, 3H). m/z 435 (M+H)⁺.

Compounds 14 and 25 to 33

Compound Nos. 14 and 25 to 33 were prepared according to the methods set forth in Example 3. For example, Compound No. 14 of Table 3 lists the method of "Example 3", indicating that this compound was prepared according to the procedure of Example 3 using appropriately substituted intermediates. Analytical data (NMR, mass spectrum) is also presented in Table 3.

TABLE 3

Compound Nos. 14 and 25 to 33

| Compound No. | Analytical Data | Synthesis Method |
|---|---|---|
| 14 | ¹H NMR (400 MHz, CDCl₃) δ 7.52-7.48 (m, 2H), 7.12-7.07 (m, 1H), 4.92-4.86 (m, 2H), 4.76-4.69 (m, 2H), 4.10-4.03 (m, 4H), 3.83-3.74 (m, 1H), 3.69 (s, 2H), 3.52-3.43 (m, 1H), 3.36 (s, 2H), 2.87-2.76 (m, 2H), 2.70-2.57 (m, 2H), 2.49 (s, 3H). m/z 414 (M + H)⁺. | Example 3 (using oxetane-3-carbonyl chloride) |
| 25 | ¹H NMR (400 MHz, CDCl₃) δ 7.50 (d, J = 7.2 Hz, 2H), 7.12-7.09 (m, 1H), 4.04 (d, J = 14.3 Hz, 4H), 3.69-3.62 (m, 6H), 3.49-3.39 (m, 1H), 3.33 (dd, J = 4.8, 9.7 Hz, 6H), 2.78 (dd, J = 7.8, 12.8 Hz, 2H), 2.66-2.58 (m, 2H), 2.48 (s, 3H). m/z 443 (M + H)⁺. | Example 3 (using 4-morpholine-carbonyl chloride) |
| 26 | ¹H NMR (400 MHz, CDCl₃) δ 7.51-7.49 (m, 2H), 7.12-7.09 (m, 1H), 4.00 (d, J = 18.6 Hz, 4H), 3.67 (s, 2H), 3.51-3.42 (m, 1H), 3.34 (s, 2H), 2.81 (dd, J = 8.0, 13.0 Hz, 2H), 2.68-2.60 (m, 2H), 2.48 (s, 3H), 2.35-2.27 (m, 1H), 1.17-1.12 (m, 2H), 1.01-0.97 (m, 2H). m/z 434 (M + H)⁺. | Example 3 (using cyclopropyl-sulfonyl chloride) |
| 27 | ¹H NMR (400 MHz, DMSO) δ 7.71 (d, J = 2.4 Hz, 1H), 7.66-7.63 (m, 1H), 7.48 (dd, J = 2.3, 8.5 Hz, 1H), 4.24-4.20 (m, 2H), 4.05 (s, 1H), 3.90-3.80 (m, 3H), 3.76 (s, 2H), 3.51-3.36 (m, 3H), 3.35 (s, 2H), 2.85-2.79 (m, 2H), 2.72-2.63 (m, 2H), 2.48 (s, 3H), 2.41-2.35 (m, 1H), 1.89-1.75 (m, 2H), 1.53-1.46 (m, 2H). m/z 442 (M + H)⁺. | Example 3 (using tetrahydro-2H-pyran-4-carbonyl chloride) |
| 28 | ¹H NMR (400 MHz, DMSO) δ 7.71 (d, J = 2.5 Hz, 1H), 7.64 (dd, J = 2.4, 8.5 Hz, 1H), 7.49 (dd, J = 3.0, 8.5 Hz, 1H), 4.30 (s, 1H), 4.18 (s, 1H), 3.91 (s, 1H), 3.77 (s, 1H), 3.68-3.61 (m, 1H), 3.48 (s, 2H), 3.37 (s, 2H), 2.56-2.53 (m, 4H), 2.33 (s, 3H), 1.51-1.43 (m, 1H), 0.70-0.64 (m, 4H). m/z 398 (M + H)⁺. | Example 3 (using cyclopropyl-carbonyl chloride) |
| 29 | ¹H NMR (400 MHz, CDCl₃) δ 7.52-7.49 (m, 2H), 7.13-7.10 (m, 1H), 4.85-4.77 (m, 1H), 4.06 (s, 2H), 4.00 (s, 2H), 3.92-3.85 (m, 2H), 3.68 (s, 2H), 3.56-3.43 (m, 3H), 3.35 (s, 2H), 2.80 (dd, J = 8.2, 12.7 Hz, 2H), 2.65-2.58 (m, 2H), 2.49 (s, 3H), 1.93-1.84 (m, 2H), 1.69-1.59 (m, 2H). m/z 458 (M + H)⁺. | Example 3 (using tetrahydro-2H-pyran-carbono-chloridate) |
| 30 | ¹H NMR (400 MHz, CDCl₃) δ 7.54-7.47 (m, 2H), 7.12 (dd, J = 8.1, 8.1 Hz, 1H), 4.20 (d, J = 13.9 Hz, 2H), 4.05 (s, 1H), 3.98 (s, 1H), 3.67 (s, 2H), 3.51-3.43 (m, 1H), 3.35 (s, 2H), 2.87-2.76 (m, 2H), 2.70-2.59 (m, 2H), 2.48 (s, 4H), 1.08 (d, J = 6.6 Hz, 6H). m/z 400 (M + H)⁺. | Example 3 (using isobutyryl chloride) |
| 31 | ¹H NMR (400 MHz, DMSO) δ 7.65-7.59 (m, 2H), 7.45 (d, J = 8.4 Hz, 1H), 4.13 (s, 2H), 4.04 (s, 2H), 3.67-3.58 (m, 1H), 3.53 (s, 2H), 3.40 (s, 2H), 2.60-2.54 (m, 4H), 2.38 (s, 3H), 1.24 (s, 3H), 0.92-0.89 (m, 2H), 0.48-0.44 (m, 2H). m/z 412 (M + H)⁺. | Example 3 (using 1-methylcyclo-propane-1-carbonyl chloride) |
| 32 | ¹H NMR (400 MHz, CDCl₃) δ 7.54-7.47 (m, 2H), 7.14-7.08 (m, 1H), 4.16 (d, J = 12.6 Hz, 2H), 4.09-4.05 (m, 2H), 4.00 (s, 1H), 3.67 (s, 2H), 3.48 (dd, J = 7.8, 7.8 Hz, 1H), 3.34 (s, 2H), 2.86-2.76 (m, 2H), 2.69-2.60 (m, 2H), 2.47 (s, 3H), 2.01 (d, J = 6.6 Hz, 2H), 1.03 (d, J = 1.5 Hz, 1H), 0.54 (d, J = 6.3 Hz, 2H), 0.17-0.14 (m, 2H). m/z 412 (M + H)⁺. | Example 3 (using 2-cyclopropyl-acetyl chloride) |
| 33 | ¹H NMR (400 MHz, CDCl₃) δ 7.53-7.48 (m, 2H), 7.11 (d, J = 8.7 Hz, 1H), 5.21-5.15 (m, 1H), 4.71-4.57 (m, 2H), 4.42-4.25 (m, 2H), 4.15 (s, 1H), 4.08 (s, 1H), 3.67 (s, 2H), 3.51-3.42 (m, 1H), 3.34 (s, 2H), 2.94-2.77 (m, 4H), 2.69-2.59 (m, 2H), 2.48 (s, 3H). m/z 414 (M + H)⁺. | Example 3 |

Example 4

Compound No. 34

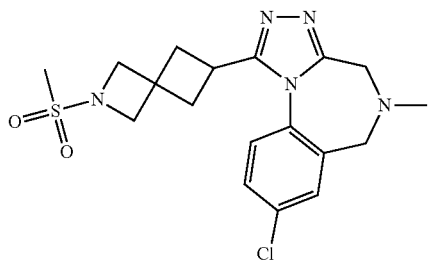

Step 1: Synthesis of 8-chloro-5-methyl-1-(2-azaspiro[3.3]heptan-6-yl)-5,6-dihydro-4H-benzo[f][1,2,4]triazolo[4,3-a][1,4]diazepine

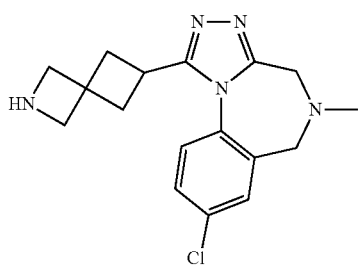 [SMILES: CN1Cc2cc(Cl)ccc2-n2c(nnc2C2CC3(CNC3)C2)C1]

To a solution of tert-butyl 6-(8-chloro-5-methyl-5,6-dihydro-4H-benzo[f][1,2,4]triazolo[4,3-a][1,4]diazepin-1-yl)-2-azaspiro[3.3]heptane-2-carboxylate form Example 1 Step 2 (415 mg, 0.965 mmol, 1 eq.) in DCM (17 mL) was added TFA (6 mL) dropwise at RT. Mixture was stirred at RT for 15 minutes and concentrated in vacuo to give an off white solid. MeOH was added and the mixture was passed through an SCX (10 g, cartridge) eluting with MeOH followed by 2.3M ammonia solution in MeOH to give the title compound as an off white solid. (300 mg, 94% yield). $^1$H NMR (400 MHz, CDCl$_3$) δ 7.52-7.48 (m, 2H), 7.14 (d, J=8.4 Hz, 1H), 3.72 (s, 2H), 3.65 (d, J=11.9 Hz, 4H), 3.46-3.38 (s, 1H), 3.33 (s, 2H), 2.73 (dd, J=8.4, 12.5 Hz, 2H), 2.63-2.54 (m, 2H), 2.47 (s, 3H).

Step 2: Synthesis of 8-chloro-5-methyl-1-(2-(methylsulfonyl)-2-azaspiro[3.3]heptan-6-yl)-5,6-dihydro-4H-benzo[f][1,2,4]triazolo[4,3-a][1,4]diazepine (Compound No. 34)

To a solution of 8-chloro-5-methyl-1-(2-azaspiro[3.3]heptan-6-yl)-5,6-dihydro-4H-benzo[f][1,2,4]triazolo[4,3-a][1,4]diazepine 30 mg, 0.091 mmol, 1 eq.), DIPEA (19 µL, 0.109 mmol, 1.2 eq.) in DCM 91 mL) was added methanesulfonyl chloride (8 µL, 0.10 mmol, 1.1 eq.) and the mixture was stirred at RT for 15 minutes. The mixture was diluted with DCM/H$_2$O and passed through a phase separator. The organics were concentrated in vacuo and the residue purified by preparative HPLC to give the title compound as an off white solid. (4.4 mg, 12% yield). $^1$H NMR (400 MHz, CDCl$_3$) δ 7.51-7.49 (m, 2H), 7.11-7.08 (m, 1H), 3.99 (s, 2H), 3.95 (s, 2H), 3.67 (s, 2H), 3.52-3.43 (m, 1H), 3.34 (s, 2H), 2.84 (s, 3H), 2.83-2.79 (m, 2H), 2.68-2.60 (m, 2H), 2.48 (s, 3H). m/z 408 (M+H)$^+$.

Compounds 35 to 37

Compound Nos. 35 to 37 were prepared according to the methods set forth in Example 4, using appropriately substituted intermediates. Analytical data (NMR, mass spectrum) is also presented in Table 4.

TABLE 4

Compound Nos. 35 to 37

| Compound No. | Analytical Data | Synthesis Method |
|---|---|---|
| 35 | $^1$H NMR (400 MHz, DMSO) δ 7.65-7.59 (m, 2H), 7.44 (d, J = 8.4 Hz, 1H), 3.99-3.97 (s, 2H), 3.92-3.89 (s, 2H), 3.66-3.62 (m, 1H), 3.52 (s, 2H), 3.38 (s, 2H), 3.10-3.01 (m, 1H), 2.58-2.55 (m, 4H), 2.34 (s, 3H), 2.19-2.05 (m, 4H), 1.98-1.79 (m, 2H). m/z 412 (M + H)$^+$. | Example 4 |
| 36 | $^1$H NMR (400 MHz, CDCl$_3$) δ 7.52-7.49 (m, 2H), 7.12 (d, J = 7.9 Hz, 1H), 4.52 (d, J = 3.8 Hz, 1H), 4.46 (d, J = 3.9 Hz, 1H), 4.15 (s, 1H), 4.07 (s, 1H), 3.67 (s, 2H), 3.53-3.44 (m, 1H), 3.34 (s, 2H), 2.84 (dd, J = 8.2, 12.9 Hz, 2H), 2.67-2.61 (m, 2H), 2.48 (s, 3H), 1.36-1.30 (m, 2H), 1.26-1.16 (m, 2H). m/z 416 (M + H)$^+$. | Example 4 |
| 37 | $^1$H NMR (400 MHz, DMSO) d 7.74 (s, 1H), 7.64 (dd, J = 2.4, 8.5 Hz, 1H), 7.49 (d, J = 8.5 Hz, 1H), 4.59 (s, 2H), 4.41 (s, 2H), 3.99 (s, 2H), 3.90-3.87 (m, 2H), 3.68-3.60 (m, 1H), 3.10-3.01 (m, 1H), 2.60 (d, J = 7.3 Hz, 4H) 2.56-2.54 (m, 2H), 2.17-2.05 (m, 4H), 1.98-1.78 (m, 2H), 1.10 (t, J = 7.4 Hz, 3H). m/z 454 (M + H)$^+$. | Example 4 |

Example 5

Compound No. 38

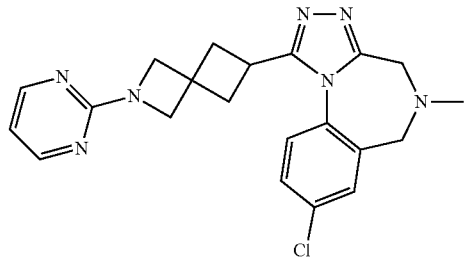

To a solution of 8-chloro-5-methyl-1-(2-azaspiro[3.3]heptan-6-yl)-5,6-dihydro-4H-benzo[f][1,2,4]triazolo[4,3-a][1,4]diazepine from ex4 step 1 (30 mg, 0.091 mmol, 1 eq.) in DMF (1 mL) was added Cs$_2$CO$_3$ (36 mg, 0.19 mmol, 1.2 eq.), 2-chloropyrimidine (10 mg, 0.091 mmol, 1 eq.) and the mixture was heated to 80° C. overnight. The mixture was diluted with water and extracted with EtOAc (3×). The organic fractions were combined, washed with brine, dried (MgSO4), filtered, concentrated in vacuo to give a yellow film and purified using preparative HPLC to give the title compound as an off white solid. (11 mg, 29% yield). $^1$H NMR (400 MHz, DMSO) δ 8.32 (d, J=4.8 Hz, 2H), 7.71 (d, J=2.4 Hz, 1H), 7.65 (dd, J=2.4, 8.5 Hz, 1H), 7.50 (d, J=8.4 Hz, 1H), 6.65 (dd, J=4.8, 4.8 Hz, 1H), 4.10 (s, 2H), 3.96 (s, 2H), 3.74-3.64 (m, 1H), 3.49 (s, 2H), 3.37 (s, 2H), 2.61-2.54 (m, 4H), 2.33 (s, 3H). m/z 408 (M+H)$^+$.

Example 6

Compound No. 39

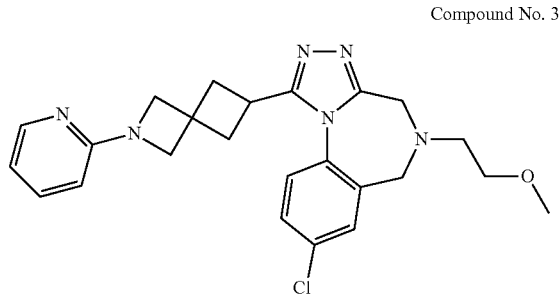

Step 1: Synthesis of tert-butyl (4-chloro-2-(((2-methoxyethyl)amino)methyl)phenyl)carbamate

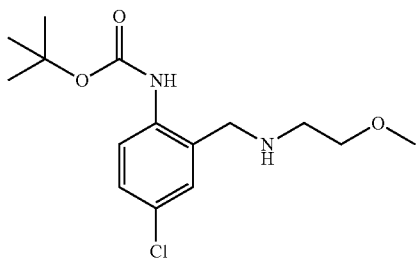 [SMILES: COCCNCc1cc(Cl)ccc1NC(=O)OC(C)(C)C]

To a solution of tert-butyl (4-chloro-2-formylphenyl)carbamate (0.4 g, 1.56 mmol, 1.0 eq.) in MeOH (10 mL) was added 2-methoxyethylamine (273 µL, 3.13 mmol, 2.0 eq.) and the mixture was heated to 65° C. for 45 minutes. The mixture was cooled in ice and sodium borohydride (0.12 g, 3.13 mmol, 2.0 eq.) was added portionwise. An additional amount of sodium borohydride (0.06 g, 1.56 mmol, 1 eq.) was added after 1 hour at RT. The mixture was stirred at RT for 16 hours, diluted with EtOAc/sat. NaHCO₃ and the organic layer separated. The aqueous phase was extracted with fresh EtOAc (×2), the organic phases were combined, washed with brine, dried (MgSO4) filtered and concentrated in vacuo to give the title compound as a colourless oil. (0.429 g, 98% yield). ¹H NMR (400 MHz, CDCl₃) δ 9.70 (s, 1H), 7.95 (d, J=8.5 Hz, 1H), 7.20 (dd, J=2.5, 8.8 Hz, 1H), 7.06 (d, J=2.5 Hz, 1H), 3.82 (s, 2H), 3.50 (t, J=5.0 Hz, 2H), 3.37 (s, 3H), 2.75 (t, J=5.0 Hz, 2H), 1.53 (s, 9H).

Step 2: Synthesis of tert-butyl (4-chloro-2-(((cyanomethyl)(2-methoxyethyl)amino)methyl)phenyl)carbamate

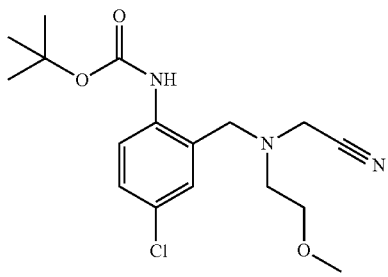 [SMILES: COCCN(CC#N)Cc1cc(Cl)ccc1NC(=O)OC(C)(C)C]

A mixture of tert-butyl (4-chloro-2-(((2-methoxyethyl)amino)methyl)phenyl) carbamate (0.49 g, 1.56 mmol, 1 eq.), sodium bicarbonate (0.14 g, 1.72 mmol, 1.10 eq.), potassium iodide (0.05 g, 0.31 mmol, 0.20 eq.), chloroacetonitrile (0.109 mL, 1.72 mmol, 1.10 eq.) in EtOAc (5 mL) was heated to 75° C. overnight. The mixture was allowed to cool, diluted with EtOAc/NaHCO₃ (1:1) and the organic layer was separated, washed with brine, dried (MgSO₄), filtered and concentrated in vacuo to give a yellow oil. The residue was triturated with MeOH to give the title compound as an off white solid. (0.320 g, 58% yield) ¹H NMR (400 MHz, CDCl₃) δ 8.47 (s, 1H), 7.97 (d, J=8.8 Hz, 1H), 7.29-7.27 (m, 1H), 7.16 (d, J=2.5 Hz, 1H), 3.74 (s, 2H), 3.62-3.58 (m, 4H), 3.40 (s, 3H), 2.86 (t, J=5.1 Hz, 2H), 1.52 (s, 9H).

Step 3: Synthesis of 7-chloro-4-(2-methoxyethyl)-4,5-dihydro-3H-benzo[e][1,4]diazepin-2-amine

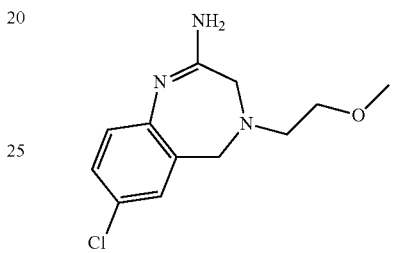

Acetyl chloride (1.21 mL, 16.96 mmol, 20.0 eq.) was added to 2-propanol (7 mL) at RT over 20 minutes (reaction is exothermic) to give a suspension. This suspension was added to a solution of tert-butyl (4-chloro-2-(((cyanomethyl)(2-methoxyethyl)amino)methyl)phenyl) carbamate (0.30 g, 0.85 mmol, 1.0 eq.) in 2-propanol (8 mL) and the mixture was heated to 40° C. overnight. The mixture was allowed to cool, concentrated in vacuo, EtOAc/NaHCO₃ was added and the organic phase was separated. The aqueous layer was extracted with further EtOAc (×2), the organics were combined, washed with brine and concentrated in vacuo to give a yellow oil. This was purified using flash column chromatography (Biotage® KP-NH) eluting with 0-100% EtOAc in isohexane followed by 0-10% methanol in ethyl acetate to give a yellow glass. (0.196 g, 91% yield). ¹H NMR (400 MHz, CDCl₃) δ 7.24-7.19 (m, 2H), 6.92 (d, J=6.9 Hz, 1H), 3.61-3.57 (m, 2H), 3.45 (s, 2H), 3.39 (s, 3H), 3.23 (s, 2H), 2.88-2.84 (m, 2H).

Step 4: Synthesis of methyl 2-(pyridin-2-yl)-2-azaspiro[3.3]heptane-6-carboxylate

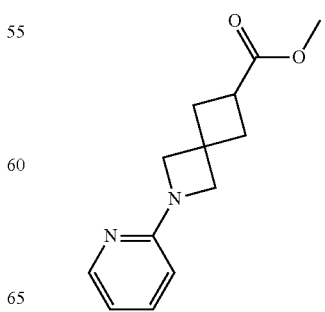

To a solution of 2-(tert-butyl) 6-methyl 2-azaspiro[3.3]heptane-2,6-dicarboxylate (1.10 g, 4.31 mmol, 1.0 eq.) in DCM (15 mL) was added TFA (5 mL) and the mixture was stirred at RT for 1 hour. Toluene was added and the mixture was concentrated in vacuo to give a yellow oil. A mixture of the yellow oil (0.58 g, 2.15 mmol, 1.0 eq.), 2-bromopyridine (247 μL, 2.59 mmol, 1.2 eq.), RuPhos (0.201 g, 0.43 mmol, 0.20 eq.), palladium acetate (0.048 g, 0.22 mmol, 0.1 eq.), cesium carbonate (2.106 g, 6.46 mmol, 3.0 eq.) in dioxane (10 mL) was de-gassed using nitrogen for 10 minutes and heated to 80° C. overnight. The mixture was diluted with EtOAc, filtered through a layer of celite and the filtrate was concentrated in vacuo. The residue was purified by flash column chromatography (Biotage® KP-NH) eluting with 0-50% EtOAc in Isohexane to give the title compound as a pale yellow oil. (0.40 g, 80% yield). $^1$H NMR (400 MHz, CDCl$_3$) δ 8.13 (dd, J=1.0, 5.1 Hz, 1H), 7.45-7.40 (m, 1H), 6.58 (dd, J=5.2, 6.2 Hz, 1H), 6.26 (d, J=8.6 Hz, 1H), 4.04 (s, 2H), 3.97 (s, 2H), 3.70 (s, 3H), 3.09-3.02 (m, 1H), 2.53-2.47 (m, 4H).

Step 5: Synthesis of 2-(pyridin-2-yl)-2-azaspiro[3.3]heptane-6-carbohydrazide

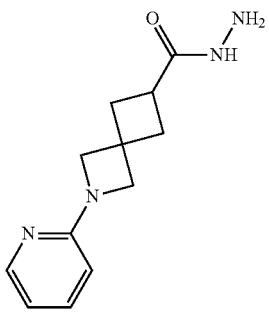 [SMILES: NNC(=O)C1CC2(C1)CN(c1ccccn1)C2]

To a solution of methyl 2-(pyridin-2-yl)-2-azaspiro[3.3]heptane-6-carboxylate 0.4 g, 1.72 mmol, 1.0 eq.) in MeOH (5 mL) was added hydrazine hydrate (501 μL, 10.33 mmol, 6.0 eq.) over 3 minutes. The mixture was stirred at RT overnight. The mixture was diluted with EtOAc, filtered through a layer of celite, the filtrate was washed with brine and the organic layer was separated. The aqueous phase was father extracted with fresh EtOAc (×2), DCM (×2), the organic phases were combine and concentrated in vacuo to give the title compound as a colourless oil. (0.324 g, 81% yield). $^1$H NMR (400 MHz, CDCl$_3$) δ 8.13 (dd, J=1.0, 5.1 Hz, 1H), 7.46-7.40 (m, 1H), 6.63 (s, 1H), 6.61-6.57 (m, 1H), 6.27 (d, J=8.3 Hz, 1H), 4.06 (s, 2H), 3.97 (s, 2H), 3.92-3.86 (m, 2H), 2.90-2.81 (m, 1H), 2.59-2.52 (m, 2H), 2.46-2.39 (m, 2H).

Step 6: Synthesis of 8-chloro-5-(2-methoxyethyl)-1-(2-(pyridin-2-yl)-2-azaspiro[3.3]heptan-6-yl)-5,6-dihydro-4H-benzo[f][1,2,4]triazolo[4,3-a][1,4]diazepine (Compound No. 39)

A mixture of 7-chloro-4-(2-methoxyethyl)-4,5-dihydro-3H-benzo[e][1,4]diazepin-2-amine from step 3 (0.036 g, 0.14 mmol, 1.0 eq.), 2-(pyridin-2-yl)-2-azaspiro[3.3]heptane-6-carbohydrazide from step 4 (0.035 g, 0.15 mmol, 1.05 eq.), AcOH (2 drops) in 2-propanol (1 mL) was heated to 80° C. for 90 minutes. The mixture was concentrated in vacuo, diluted with DCM/NaHCO$_3$ and passed through a through a phase separator and concentrated in vacuo. The residue was purified using preparative HPLC to give the title compound. (0.031 g, 48% yield). $^1$H NMR (400 MHz, CDCl$_3$) δ 8.14-8.13 (m, 1H), 7.56-7.51 (m, 2H), 7.45-7.41 (m, 1H), 7.16 (d, J=8.6 Hz, 1H), 6.61-6.58 (m, 1H), 6.27 (d, J=8.3 Hz, 1H), 4.1 (s, 2H), 4.03 (s, 2H), 3.76-3.70 (m, 2H), 3.60-3.57 (m, 2H), 3.57-3.47 (m, 3H), 3.39 (s, 3H), 2.89-2.81 (m, 4H), 2.69-2.64 (m, 2H). m/z 451 (M+H)$^+$.

Compounds 40 to 56

Compound Nos. 40 to 56 were prepared according to the methods set forth in Example 6 using appropriately substituted intermediates. Analytical data (NMR, mass spectrum) is also presented in Table 5.

TABLE 5

Compound Nos. 40 to 56

| Compound No. | Analytical Data | Synthesis Method |
|---|---|---|
| 40 | $^1$H NMR (400 MHz, CDCl$_3$) δ 8.01 (dd, J = 1.5, 2.5 Hz, 1H), 7.84 (d, J = 2.8 Hz, 1H), 7.77 (d, J = 1.5 Hz, 1H), 7.51-7.46 (m, 2H), 7.13 (d, J = 8.3 Hz, 1H), 4.17 (s, 2H), 4.11 (s, 2H), 3.63-3.47 (m, 3H), 3.28 (s, 2H), 3.18-3.09 (m, 1H), 2.88 (dd, J = 8.1, 12.9 Hz, 2H), 2.73-2.65 (m, 2H), 2.19-2.13 (m, 2H), 2.01-1.90 (m, 2H). m/z 448 (M + H)$^+$. | Example 6 |
| 41 | $^1$H NMR (400 MHz, CDCl$_3$) δ 8.13 (dd, J = 1.0, 5.1 Hz, 1H), 7.51-7.41 (m, 3H), 7.14 (d, J = 8.3 Hz, 1H), 6.59 (dd, J = 5.2, 6.2 Hz, 1H), 6.27 (d, J = 8.3 Hz, 1H), 4.11 (s, 2H), 4.01 (s, 2H), 3.60-3.48 (m, 3H), 3.28 (s, 2H), 3.18-3.09 (m, 1H), 2.86 (dd, J = 8.2, 12.8 Hz, 2H), 2.70-2.61 (m, 2H), 2.19-2.11 (m, 2H), 2.01-1.89 (m, 2H), 1.82-1.65 (m, 2H). m/z 447 (M + H)$^+$. | Example 6 |
| 42 | $^1$H NMR (400 MHz, CDCl$_3$) δ 8.00 (d, J = 2.8 Hz, 1H), 7.51-7.45 (m, 2H), 7.25-7.19 (m, 1H), 7.13 (d, J = 8.3 Hz, 1H), 6.23 (dd, J = 3.3, 9.1 Hz, 1H), 4.07 (s, 2H), 3.98 (s, 2H), 3.63-3.48 (m, 3H), 3.27 (s, 2H), 3.18-3.08 (m, 1H), 2.85 (dd, J = 8.1, 12.6 Hz, 2H), 2.69-2.61 (m, 2H), 2.20-2.12 (m, 2H), 2.01-1.88 (m, 2H), 1.82-1.65 (m, 2H). m/z 464 (M + H)$^+$. | Example 6 |
| 43 | $^1$H NMR (400 MHz, CDCl$_3$) 8.01 (1H, dd, J = 1.5, 2.8 Hz), 7.84 (1H, d, J = 2.8 Hz), 7.77 (1H, d, J = 1.5 Hz), 7.53-7.48 (2H, m), 7.13 (1H, d, J = 8.3 Hz), 4.18 (2H, s), 4.12 (2H, s), 3.76 (2H, s), 3.60-3.47 (5H, m), 3.40 (3H, s), 2.92-2.80 (4H, m), 2.73-2.65 (2H, m). m/z 452 (M + H)$^+$. | Example 6 |
| 44 | $^1$H NMR (400 MHz, CDCl$_3$) δ 8.00 (d, J = 3.0 Hz, 1H), 7.53-7.48 (m, 2H), 7.22 (ddd, J = 2.9, 8.0, 9.0 Hz, 1H), 7.14 (d, J = 8.3 Hz, 1H), 6.23 (dd, J = 3.5, 9.1 Hz, 1H), 4.08 (s, 2H), 3.98 (s, 2H), 3.76 (s, 2H), 3.60-3.46 (m, 5H), 3.39 (s, 3H), 2.89-2.80 (m, 4H), 2.70-2.62 (m, 2H). m/z 469 (M + H)$^+$. | Example 6 |
| 45 | $^1$H NMR (400 MHz, CDCl$_3$) δ 8.14 (dd, J = 1.0, 5.1 Hz, 1H), 7.50 (d, J = 7.3 Hz, 2H), 7.46-7.41 (m, 1H), 7.17-7.13 (m, 1H), 6.59 (dd, J = 5.1, 6.3 Hz, 1H), 6.27 (d, J = 8.3 Hz, 1H), 4.11 (s, 2H), 4.01 (s, 2H), 3.70 (s, 2H), 3.57-3.47 (m, 1H), 3.40 (s, 2H), 2.87 (dd, J = 8.2, 12.8 Hz, 2H), 2.71-2.62 (m, 4H), 1.19 (dd, J = 7.2, 7.2 Hz, 3H). m/z 421 (M + H)$^+$. | Example 6 |
| 46 | $^1$H NMR (400 MHz, CDCl$_3$) δ 8.01 (1H, dd, J = 1.5, 2.8 Hz), 7.84 (1H, d, J = 2.8 Hz), 7.77 (1H, d, J = 1.3 Hz), 7.52-7.49 (2H, m), 7.15-7.12 (1H, m), 4.18 (2H, s), 4.12 (2H, s), 3.70 (2H, s), 3.58-3.48 (1H, m), 3.40 (2H, s), 2.89 (2H, dd, J = 8.1, 12.9 Hz), 2.73-2.62 (4H, m), 1.19 (3H, dd, J = 7.2, 7.2 Hz). m/z 422 (M + H)$^+$. | Example 6 |
| 47 | $^1$H NMR (400 MHz, CDCl$_3$) δ 8.01 (dd, J = 1.5, 2.8 Hz, 1H), 7.84 (d, J = 2.8 Hz, 1H), 7.77 (d, J = 1.5 Hz, 1H), 7.53-7.47 (m, 2H), 7.12 (d, J = 8.3 Hz, 1H), 4.18 (s, 2H), 4.12 (s, 2H), 3.81 (s, 2H), 3.56-3.49 (m, 3H), 2.99- | Example 6 |

TABLE 5-continued

Compound Nos. 40 to 56

| Compound No. | Analytical Data | Synthesis Method |
|---|---|---|
| | 2.86 (m, 3H), 2.73-2.66 (m, 2H), 1.19 (d, J = 6.6 Hz, 6H). m/z 436 (M + H)⁺. | |
| 48 | ¹H NMR (400 MHz, CDCl₃) δ 8.14 (1H, dd, J = 1.0, 5.1 Hz), 7.52-7.41 (3H, m), 7.13 (1H, d, J = 8.6 Hz), 6.59 (1H, dd, J = 5.2, 6.2 Hz), 6.27 (1H, d, J = 8.3 Hz), 4.11 (2H, s), 4.02 (2H, s), 3.81 (2H, s), 3.51 (3H, d, J = 9.1 Hz), 2.98-2.83 (3H, m), 2.70-2.63 (2H, m), 1.19 (6H, d, J = 6.3 Hz). m/z 435 (M + H)⁺. | Example 6 |
| 49 | ¹H NMR (400 MHz, CDCl₃) δ 8.00 (d, J = 2.9 Hz, 1H), 7.51-7.49 (m, 2H), 7.25-7.19 (m, 1H), 7.16-7.13 (m, 1H), 6.24 (dd, J = 3.5, 9.0 Hz, 1H), 4.08 (s, 2H), 3.99 (s, 2H), 3.70 (s, 2H), 3.55-3.47 (m, 1H), 3.40 (s, 2H), 2.86 (dd, J = 8.2, 12.8 Hz, 2H), 2.70-2.62 (m, 4H), 1.19 (dd, J = 7.2, 7.2 Hz, 3H). m/z 439 (M + H)⁺. | Example 6 |
| 50 | ¹H NMR (400 MHz, CDCl₃) δ 8.00 (d, J = 3.0 Hz, 1H), 7.52-7.46 (m, 2H), 7.25-7.19 (m, 1H), 7.12 (d, J = 8.4 Hz, 1H), 6.24 (dd, J = 3.5, 9.0 Hz, 1H), 4.08 (s, 2H), 3.99 (s, 2H), 3.81 (s, 2H), 3.51 (d, J = 8.0 Hz, 3H), 3.00-2.83 (m, 3H), 2.70-2.61 (m, 2H), 1.19 (d, J = 6.5 Hz, 6H). m/z 453 (M + H)⁺. | Example 6 |
| 51 | ¹H NMR (400 MHz, CDCl₃) δ 8.01 (dd, J = 1.1, 4.7 Hz, 1H), 7.85 (d, J = 2.8 Hz, 1H), 7.53-7.46 (m, 2H), 7.13-7.07 (m, 2H), 6.73-6.69 (m, 1H), 4.00 (s, 2H), 3.94 (s, 2H), 3.81 (s, 2H), 3.51 (d, J = 5.8 Hz, 3H), 2.99-2.83 (m, 3H), 2.72-2.64 (m, 2H), 1.19 (d, J = 6.6 Hz, 6H). m/z 435 (M + H)⁺. | Example 6 |
| 52 | ¹H NMR (400 MHz, CDCl₃) δ 8.14 (dd, J = 1.0, 5.3 Hz, 1H), 7.56-7.50 (m, 2H), 7.49-7.43 (m, 1H), 7.17 (d, J = 8.3 Hz, 1H), 6.61 (dd, J = 5.2, 6.2 Hz, 1H), 6.28 (d, J = 8.3 Hz, 1H), 5.95 (tt, J = 4.1, 40 Hz, 1H), 4.14 (s, 2H), 4.04 (s, 2H), 3.82 (s, 2H), 3.56-3.49 (m, 3H), 3.07-2.95 (m, 2H), 2.87 (dd, J = 8.3, 12.9 Hz, 2H), 2.72-2.64 (m, 2H). m/z 457 (M + H)⁺. | Example 6 |
| 53 | ¹H NMR (400 MHz, CDCl₃) δ 7.92-7.89 (m, 1H), 7.53-7.48 (m, 2H), 7.16-7.09 (m, 2H), 6.60-6.55 (m, 1H), 4.23 (d, J = 1.5 Hz, 2H), 4.15 (d, J = 2.0 Hz, 2H), 3.74 (s, 2H), 3.60-3.46 (m, 5H), 3.39 (s, 3H), 2.89-2.80 (m, 4H), 2.70-2.62 (m, 2H). m/z 469 (M + H)⁺. | Example 6 |
| 54 | ¹H NMR (400 MHz, CDCl₃) δ 7.91 (d, J = 4.9 Hz, 1H), 7.52-7.47 (m, 2H), 7.16-7.10 (m, 2H), 6.60-6.55 (m, 1H), 4.23 (d, J = 1.6 Hz, 2H), 4.15 (d, J = 2.0 Hz, 2H), 3.81 (s, 2H), 3.54-3.48 (m, 3H), 3.00-2.83 (m, 3H), 2.70-2.63 (m, 2H), 1.19 (d, J = 6.4 Hz, 6H). m/z 453 (M + H)⁺. | Example 6 |
| 55 | ¹H NMR (400 MHz, CDCl₃) δ 8.01 (dd, J = 1.3, 4.8 Hz, 1H), 7.85 (d, J = 2.5 Hz, 1H), 7.53-7.47 (m, 2H), 7.15-7.07 (m, 2H), 6.73-6.69 (m, 1H), 4.00 (s, 2H), 3.94 (s, 2H), 3.75 (s, 2H), 3.60-3.48 (m, 5H), 3.39 (s, 3H), 2.90-2.80 (m, 4H), 2.72-2.63 (m, 2H). m/z 451 (M + H)⁺. | Example 6 |
| 56 | ¹H NMR (400 MHz, CDCl₃) δ 8.14 (dd, J = 1.0, 5.1 Hz, 1H), 7.52-7.48 (m, 2H), 7.46-7.41 (m, 1H), 7.17-7.14 (m, 1H), 6.59 (dd, J = 5.4, 6.7 Hz, 1H), 6.27 (d, J = 8.3 Hz, 1H), 4.12 (s, 2H), 4.02 (s, 2H), 3.82 (s, 2H), 3.56-3.49 (m, 3H), 2.87 (dd, J = 8.2, 12.8 Hz, 2H), 2.71-2.62 (m, 2H), 2.09-2.00 (m, 1H), 0.62-0.56 (m, 4H). m/z 433 (M + H)⁺. | Example 6 |

Example 7

Compound No. 57

Step 1: Synthesis of tert-butyl 8-chloro-1-(2-(pyridin-2-yl)-2-azaspiro[3.3]heptan-6-yl)-4H-benzo[f][1,2,4]triazolo[4,3-a][1,4]diazepine-5(6H)-carboxylate To a solution of tert-butyl 7-chloro-2-thioxo-1,2,3,5-tetrahydro-4H-benzo[e][1,4]diazepine-4-carboxylate (0.4 g, 1.28 mmol, 1.0 eq.), was added 2-(pyridin-2-yl)-2-azaspiro[3.3]heptane-6-carbohydrazide from Ex6 step 4 (0.320 g, 1.28 mmol, 1.0 eq.) in dioxane (10 mL) and the mixture was heated to 90° C. for 36 hours. The mixture was allowed to cool, saturated with nitrogen gas and was concentrated in vacuo. The residue was purified by flash column chromatography eluting with 50-100 EtOAc in isohexane then 0-10% MeOH in DCM to give the title product as an off white foam. (0.50 g, 81% yield). m/z 493 (M+H)⁺.

Step 2: Synthesis of 8-chloro-1-(2-(pyridin-2-yl)-2-azaspiro[3.3]heptan-6-yl)-5,6-dihydro-4H-benzo[f][1,2,4]triazolo[4,3-a][1,4]diazepine hydrochloride To a solution of tert-butyl 8-chloro-1-(2-(pyridin-2-yl)-2-azaspiro[3.3]heptan-6-yl)-4H-benzo[f][1,2,4]triazolo[4,3-a][1,4]diazepine-5(6H)-carboxylate (0.10 g, 0.20 mmol, 1.0 eq.) in MeOH was added 4N HCl solution in dioxane (0.5 mL, 2.03 mmol, 10.0 eq.) and the mixture was stirred at RT for 6 hours. The mixture was concentrated in vacuo, EtOAc was added and the solution was washed with Sat. NaHCO$_3$, the aqueous layer was re-extracted with EtOAc (×2). The organic phases were combined, dried (MgSO4), filtered and concentrated in vacuo to give the title compound as a colourless glass. (0.075 g, 93% yield). $^1$H NMR (400 MHz, CDCl$_3$) δ 8.14-8.13 (m, 1H), 7.52-7.41 (m, 3H), 7.15 (d, J=9.0 Hz, 1H), 6.61-6.53 (m, 1H), 6.27 (d, J=8.4 Hz, 1H), 4.11 (s, 2H), 4.01 (s, 2H), 3.71 (s, 2H), 3.57-3.50 (m, 1H), 3.50 (s, 2H), 2.85 (dd, J=8.2, 12.8 Hz, 2H), 2.70-2.61 (m, 2H)

Step 3: Synthesis of 8-chloro-5-(oxetan-3-yl)-1-(2-(pyridin-2-yl)-2-azaspiro[3.3]heptan-6-yl)-5,6-dihydro-4H-benzo[f][1,2,4]triazolo[4,3-a][1,4]diazepine (Compound No. 57)

A solution of 8-chloro-1-(2-(pyridin-2-yl)-2-azaspiro[3.3]heptan-6-yl)-5,6-dihydro-4H-benzo[f][1,2,4]triazolo[4,3-a][1,4]diazepine (0.025 g, 0.06 mmol, 1.0 eq.), 3-oxetanone (35 μL, 0.51 mmol, 8.0 eq.) in MeOH (0.5 mL) was heated to 70° C. for 6 hours. The mixture was cooled to 0° C. and sodium cyanoborohydride (0.012 g, 0.19 mmol, 3.0 eq.) was added and the mixture stirred at RT overnight. The mixture was concentrated in vacuo, diluted with DCM, passed through a phase separator and concentrated in vacuo. The residue was purified by preparative HPLC. (0.005 g, 17% yield). $^1$H NMR (400 MHz, CDCl$_3$) δ 8.16-8.11 (m, 2H), 7.56-7.51 (m, 1H), 7.50-7.45 (m, 1H), 7.16 (d, J=8.6 Hz, 1H), 6.64-6.60 (m, 1H), 6.29 (d, J=8.3 Hz, 1H), 4.77-4.65 (m, 4H), 4.16 (s, 2H), 4.04 (s, 2H), 3.97-3.90 (m, 1H), 3.63 (s, 2H), 3.57-3.47 (m, 1H), 3.36-3.24 (m, 2H), 2.86 (dd, J=8.3, 12.6 Hz, 2H), 2.71-2.62 (m, 2H). m/z 449 (M+H)$^+$.

Example 8

Compound No. 58

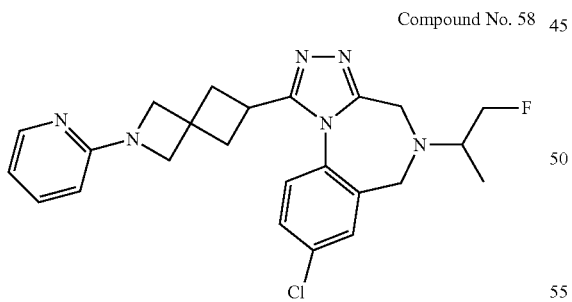

A mixture of 8-chloro-1-(2-(pyridin-2-yl)-2-azaspiro[3.3]heptan-6-yl)-5,6-dihydro-4H-benzo[f][1,2,4]triazolo[4,3-a][1,4]diazepine dihydrochloride (0.050 g, 0.11 mmol, 1.0 eq.), Et$_3$N (30 μL, 0.21 mmol, 2.0 eq.), fluoroacetone (62 μL, 0.86 mmol, 8.0 eq.) in MeOH (1 mL) was heated to 70° C. for 2.5 hours. Mixture was cooled to 0° C. and sodium borohydride (0.02 g, 0.32 mmol, 3 eq.) was added, mixture was stirred at RT for 2 hours. Additional sodium borohydride (0.02 g, 0.32 mmol, 3 eq.), Et$_3$N (30 μL, 0.21 mmol, 2.0 eq.), fluoroacetone (62 μL, 0.86 mmol, 8.0 eq.) were added and the mixture was stirred at RT for 3 days. The mixture was concentrated in vacuo, diluted with DCM, passed through a phase separator and concentrated in vacuo. The residue was purified by preparative HPLC. To give the title compound (0.0147 g, 30% yield). $^1$H NMR (400 MHz, CDCl$_3$) δ 8.13 (dd, J=1.0, 5.1 Hz, 1H), 7.54 (d, J=2.3 Hz, 1H), 7.49 (dd, J=2.4, 8.5 Hz, 1H), 7.46-7.41 (m, 1H), 7.14 (d, J=8.6 Hz, 1H), 6.60 (dd, J=5.4, 6.7 Hz, 1H), 6.27 (d, J=8.3 Hz, 1H), 4.62-4.41 (m, 2H), 4.12 (s, 2H), 4.02 (s, 2H), 3.87 (s, 2H), 3.62 (s, 2H), 3.57-3.48 (m, 1H), 3.22-3.11 (m, 1H), 2.87 (dd, J=8.2, 12.8 Hz, 2H), 2.71-2.63 (m, 2H), 1.22 (dd, J=1.5, 6.8 Hz, 3H). m/z 453 (M+H)$^+$.

Example 9

Compound No. 59

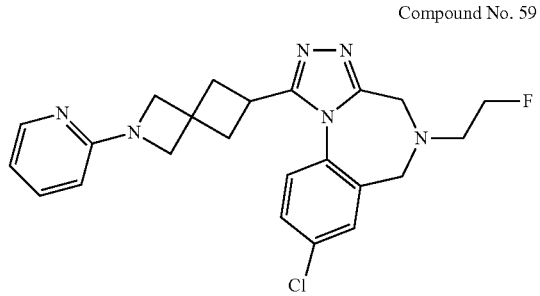 [SMILES: FCCN1Cc2cc(Cl)ccc2-n2c(nnc2C2CC3(C2)CN(c2ccccn2)C3)C1]

A mixture of 8-chloro-1-(2-(pyridin-2-yl)-2-azaspiro[3.3]heptan-6-yl)-5,6-dihydro-4H-benzo[f][1,2,4]triazolo[4,3-a][1,4]diazepine in MeCN (1 mL) was added K$_2$CO$_3$ (0.018 g, 0.13 mmol, 2.0 eq.) followed by fluoro-2-iodoethane (6 μL, 0.08 mmol, 2.0 eq.) and stirred at RT for 2 hours. Mixture was then heated to 80° C. overnight. Mixture was diluted with NaHCO$_3$/DCM, passed through a phase separator and concentrated in vacuo. The residue was purified by preparative HPLC. to give the title compound as white solid (0.0124 g, 44% yield). $^1$H NMR (400 MHz, CDCl$_3$) δ 8.14 (dd, J=1.0, 5.1 Hz, 1H), 7.53-7.49 (m, 2H), 7.46-7.41 (m, 1H), 7.18-7.14 (m, 1H), 6.59 (dd, J=5.1, 6.3 Hz, 1H), 6.27 (d, J=8.6 Hz, 1H), 4.70 (dd, J=4.7, 4.7 Hz, 1H), 4.58 (dd, J=4.8, 4.8 Hz, 1H), 4.12 (s, 2H), 4.02 (s, 2H), 3.77 (s, 2H), 3.56-3.51 (m, 3H), 3.00-2.83 (m, 4H), 2.71-2.63 (m, 2H). m/z 439 (M+H)$^+$.

Example 10

Compound No. 60

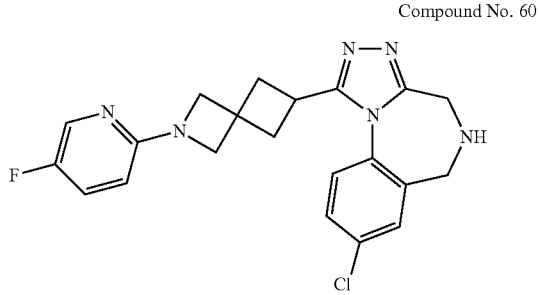 [SMILES: Fc1ccc(N2CC3(CC(c4nnc5n4-c4ccc(Cl)cc4CNC5)C3)C2)nc1]

Step 1: Synthesis of 2-(4-fluoropyridin-2-yl)-2-azaspiro[3.3]heptane-6-carbohydrazide

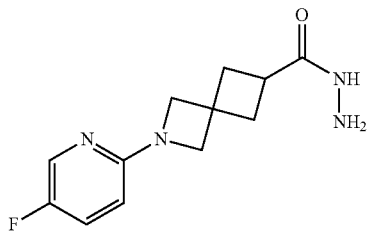 [SMILES: NNC(=O)C1CC2(C1)CN(c1ccc(F)cn1)C2]

A solution of methyl 2-(4-fluoropyridin-2-yl)-2-azaspiro[3.3]heptane-6-carboxylate [prepared in a similar manner as Ex6 step 4 using 2-bromo-5-fluoropyridine instead of 2-bromopyridine] (510 mg, 2.11 mmol, 1.0 eq.) in EtOH (10 mL) was added dropwise to a mixture of hydrazine monohydrate (0.62 mL, 12.7 mmol, 6.0 eq.) in EtOH. Mixture was heated to 50° C. for 1 hours, diluted with EtOAc, washed with brine and concentrated in vacuo. To give the title compound as a pink solid. (365 mg, 69% yield). $^1$H NMR (400 MHz, CDCl$_3$) δ 7.97 (d, J=3.0 Hz, 1H), 7.93 (s, 1H), 7.25-7.18 (m, 1H), 6.23 (dd, J=3.5, 9.1 Hz, 1H), 4.00 (s, 2H), 3.94 (s, 2H), 3.85-3.76 (m, 2H), 2.96-2.86 (m, 1H), 2.57-2.50 (m, 2H), 2.44-2.37 (m, 2H).

Step 2: Synthesis of tert-butyl 8-chloro-1-(2-(5-fluoropyridin-2-yl)-2-azaspiro[3.3]heptan-6-yl)-4H-benzo[f][1,2,4]triazolo[4,3-a][1,4]diazepine-5(6H)-carboxylate

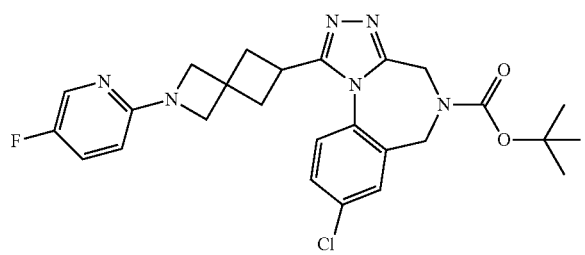 [SMILES: CC(C)(C)OC(=O)N1Cc2cc(Cl)ccc2-n2c(nnc2C2CC3(C2)CN(c2ccc(F)cn2)C3)C1]

The title compound was prepared in the manner of Example 7 step 1 (189 mg, 67% yield). $^1$H NMR (400 MHz, CDCl$_3$) δ 8.00-7.99 (m, 1H), 7.58-7.45 (m, 2H), 7.26-7.17 (m, 2H), 6.23 (dd, J=5, 6.3 Hz, 1H), 4.66-4.20 (m, 4H), 4.02 (s, 2H), 3.98 (s, 2H), 3.52-3.48 (m, 1H), 2.88-2.85 (m, 2H), 2.66-2.55 (m, 2H), 1.62 (s, 9H).

Step 3: Synthesis of 8-chloro-1-(2-(5-fluoropyridin-2-yl)-2-azaspiro[3.3]heptan-6-yl)-5,6-dihydro-4H-benzo[f][1,2,4]triazolo[4,3-a][1,4]diazepine (Compound No. 60)

The title compound was prepared in the manner of Example 7 step 2 (5.2 mg, 97% yield). $^1$H NMR (400 MHz, DMSO) δ 8.08 (dd, J=1.0, 5.0 Hz, 1H), 7.71 (s, 1H), 7.65 (dd, J=2.2, 8.1 Hz, 1H), 7.55-7.50 (m, 2H), 6.43 (dd, J=5.0, 6.1 Hz, 1H), 4.02 (s, 2H), 3.89 (s, 2H), 3.76 (s, 2H), 3.73-3.67 (m, 1H), 3.58 (s, 2H), 2.65-2.56 (m, 4H). m/z 411 (M+H)$^+$.

Example 11

Compound No. 61

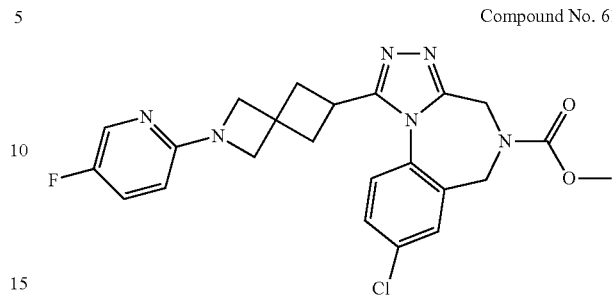

To a cooled suspension of 8-chloro-1-(2-(5-fluoropyridin-2-yl)-2-azaspiro[3.3]heptan-6-yl)-4,5-dihydro-6H-benzo[f][1,2,4]triazolo[4,3-a][1,4]diazepin-6-one (prepared as in Example 7, step 2) (77 mg, 0.19 mmol, 1.0 eq.), Et$_3$N (0.091 mL, 0.65 mmol, 3.5 eq.), at 0° C. in THF (5 mL) was added methyl chloroformate (0.022 mL, 0.28 mMol, 1.5 eq.) dropwise. The resulting thick suspension was stirred at RT for 1 hour, diluted with EtOAc, washed with an aq. sol. of sat. NaHCO$_3$, dried, concentrated in vacuo. and the residue was purified by preparative HPLC to give the title compound (20.48 mg, 23% yield). $^1$H NMR (400 MHz, DMSO) δ 8.03 (d, J=3.0 Hz, 1H), 7.69 (dd, J=2.5, 8.5 Hz, 2H), 7.54 (d, J=8.5 Hz, 1H), 7.50-7.44 (m, 1H), 6.39 (dd, J=3.3, 9.1 Hz, 1H), 4.50 (s, 2H), 4.33 (s, 2H), 3.98 (s, 2H), 3.85 (s, 2H), 3.71-3.67 (m, 4H), 2.58 (d, J=8.2 Hz, 4H). m/z 469 (M+H)$^+$.

Compounds 62 to 91

Compound Nos. 62 to 75, 78, 79, 81, 82, and 90 were prepared according to the methods set forth in Example 11 using appropriately substituted intermediates. Analytical data (NMR, mass spectrum) is also presented in Table 6. Compound Nos. 76, 77, 80, and 83 to 89 are prepared according to the procedure of Example 11 using appropriately substituted intermediates.

TABLE 6

Compound Nos. 62 to 75, 78, 79, 81, 82, and 90

| Compound No. | Analytical Data | Synthesis Method |
|---|---|---|
| 62 | $^1$H NMR (400 MHz, DMSO) δ 8.03-8.01 (m, 1H), 7.64-7.61 (m, 2H), 7.50-7.41 (m, 2H), 6.56 (dd, J = 5.3, 6.8 Hz, 1H), 6.30 (d, J = 8.4 Hz, 1H), 4.45 (s, 2H), 4.28 (s, 2H), 3.99 (s, 2H), 3.88 (s, 2H), 3.67-3.63 (m, 1H), 2.60 (d, J = 8.0 Hz, 4H), 1.47 (s, 9H). m/z 493 (M + H)$^+$. | Example 11 |
| 63 | $^1$H NMR (400 MHz, DMSO) δ 8.00 (d, J = 3.0 Hz, 1H), 7.76-7.76 (m, 1H), 7.66 (dd, J = 2.4, 8.5 Hz, 1H), 7.52 (d, J = 8.5 Hz, 1H), 7.43-7.37 (m, 1H), 6.37 (dd, J = 3.5, 9.0 Hz, 1H), 4.61 (s, 2H), 4.45 (s, 2H), 4.01 (s, 2H), 3.90 (s, 2H), 3.71-3.70 (m, 1H), 3.10 (dd, J = 6.5, 6.5 Hz, 1H), 2.64 (d, J = 8.0 Hz, 4H), 1.12 (d, J = 6.8 Hz, 6H). m/z 481 (M + H)$^+$. | Example 11 |
| 64 | $^1$H NMR (400 MHz, CDCl$_3$) δ 8.00 (1H, d, J = 3.0 Hz), 7.60-7.51 (2H, m), 7.25-7.18 (2H, m), 6.24 (1H, dd, J = 3.4, 9.0 Hz), 4.70-4.61 (4H, m), 4.08 (2H, s), 4.00 (2H, s), 3.55-3.46 (1H, m), 2.87 (2H, dd, J = 8.1, 12.6 Hz), 2.71-2.66 (2H, m), 2.28 (1H, s), 2.20 (2H, s). m/z 453 (M + H)$^+$. | Example 11 |

TABLE 6-continued

Compound Nos. 62 to 75, 78, 79, 81, 82, and 90

| Compound No. | Analytical Data | Synthesis Method |
|---|---|---|
| 65 | $^1$H NMR (400 MHz, DMSO) δ 8.04-8.02 (m, 1H), 7.71 (s, 1H), 7.64 (dd, J = 2.4, 8.5 Hz, 1H), 7.51 (d, J = 8.5 Hz, 1H), 7.46-7.42 (m, 1H), 6.56 (dd, J = 5.0, 6.8 Hz, 1H), 6.30 (d, J = 8.3 Hz, 1H), 4.68 (s, 2H), 4.53 (s, 2H), 4.00 (s, 2H), 3.89 (s, 2H), 2.62 (d, J = 8.2 Hz, 4H), 2.54 (dd, J = 1.8, 1.8 Hz, 1H), 2.11-2.07 (m, 1H), 0.84-0.82 (m, 4H). m/z 461 (M + H)$^+$. | Example 11 |
| 66 | $^1$H NMR (400 MHz, DMSO) δ 8.57 (d, J = 3.3 Hz, 1H), 8.14 (dd, J = 2.9, 92.1 Hz, 1H), 7.77-7.70 (m, 1H), 7.63-7.58 (m, 1H), 7.39 (dd, J = 4.4, 9.0 Hz, 1H), 6.80 (dd, J = 1.3, 9.1 Hz, 1H), 4.72 (s, 1H), 4.52-4.47 (m, 3H), 4.17 (s, 2H), 4.04 (s, 2H), 3.81-3.71 (m, 1H), 2.67 (d, J = 7.8 Hz, 4H), 2.28 (s, 2H), 2.17 (s, 1H). m/z 436 (M + H)$^+$. | Example 11 |
| 67 | $^1$H NMR (400 MHz, DMSO) δ 8.03-8.02 (m, 1H), 7.73 (s, 1H), 7.63 (dd, J = 2.4, 8.5 Hz, 1H), 7.51-7.41 (m, 2H), 6.56 (dd, J = 5.3, 7.1 Hz, 1H), 6.30 (d, J = 8.3 Hz, 1H), 4.57 (s, 2H), 4.40 (s, 2H), 3.99 (s, 2H), 3.89 (s, 2H), 2.61 (d, J = 8.2 Hz, 4H), 2.45 (d, J = 1.6 Hz, 1H), 1.09-1.06 (m, 3H). m/z 489 (M + H)$^+$. | Example 11 |
| 68 | $^1$H NMR (400 MHz, DMSO) δ 8.09 (dd, J = 1.0, 5.1 Hz, 1H), 7.80 (s, 1H), 7.74 (dd, J = 2.4, 8.5 Hz, 1H), 7.60-7.50 (m, 2H), 6.65 (dd, J = 4.9, 6.2 Hz, 1H), 6.39 (d, J = 8.3 Hz, 1H), 4.54 (s, 2H), 4.43-4.40 (m, 2H), 4.18 (q, J = 7.1 Hz, 2H), 4.04 (s, 2H), 3.91 (s, 2H), 3.78-3.69 (m, 1H), 2.67-2.59 (m, 4H), 1.32-1.29 (m, 3H). m/z 465 (M + H)$^+$. | Example 11 |
| 69 | $^1$H NMR (400 MHz, DMSO) δ 8.00 (d, J = 3.0 Hz, 1H), 7.67-7.64 (m, 2H), 7.52-7.49 (m, 1H), 7.43-7.37 (m, 1H), 6.37 (dd, J = 3.5, 9.0 Hz, 1H), 4.53 (s, 2H), 4.36 (s, 2H), 4.18 (q, J = 7.0 Hz, 2H), 4.00 (s, 2H), 3.90 (s, 2H), 3.04 (s, 1H), 2.63 (d, J = 8.0 Hz, 4H), 1.29 (dd, J = 7.0, 7.0 Hz, 3H). m/z 483 (M + H)$^+$. | Example 11 |
| 70 | $^1$H NMR (400 MHz, DMSO) δ 8.03-8.02 (m, 1H), 7.65-7.62 (m, 1H), 7.50-7.41 (m, 2H), 6.56 (dd, J = 5.1, 6.9 Hz, 1H), 6.30 (d, J = 8.3 Hz, 1H), 4.50 (s, 2H), 4.33 (s, 2H), 3.99 (s, 2H), 3.88 (s, 2H), 3.76 (s, 3H), 3.70-3.62 (m, 1H), 2.60 (d, J = 8.2 Hz, 4H). m/z 451 (M + H)$^+$. | Example 11 |
| 71 | $^1$H NMR (400 MHz, DMSO) δ 8.04 (d, J = 4.8 Hz, 1H), 7.78-7.75 (m, 1H), 7.66 (dd, J = 2.3, 8.5 Hz, 1H), 7.52 (d, J = 8.8 Hz, 1H), 7.49-7.44 (m, 1H), 6.61-6.56 (m, 1H), 6.32 (d, J = 8.3 Hz, 1H), 4.60 (s, 2H), 4.44 (s, 2H), 4.02 (s, 2H), 3.91 (s, 2H), 3.73-3.69 (m, 1H), 3.09 (dd, J = 6.5, 6.5 Hz, 1H), 2.66-2.61 (m, 4H), 1.12 (d, J = 6.7 Hz, 6H). m/z 463 (M + H)$^+$. | Example 11 |
| 72 | $^1$H NMR (400 MHz, DMSO) δ 8.00 (1H, d, J = 2.5 Hz), 7.76 (1H, s), 7.65 (1H, dd, J = 2.3, 8.6 Hz), 7.51 (1H, d, J = 8.5 Hz), 7.43-7.37 (1H, m), 6.36 (1H, dd, J = 3.5, 9.0 Hz), 4.59 (2H, s), 4.42 (2H, s), 4.00 (2H, s), 3.90 (2H, s), 3.72-3.67 (1H, m), 2.62 (4H, d, J = 8.0 Hz), 2.51-2.49 (m, 2H), 1.10 (3H, dd, J = 7.3, 7.3 Hz). m/z 467 (M + H)$^+$. | Example 11 |
| 73 | $^1$H NMR (400 MHz, DMSO) δ 8.03-8.02 (m, 1H), 7.74-7.74 (m, 1H), 7.63 (dd, J = 2.4, 8.5 Hz, 1H), 7.51-7.41 (m, 2H), 6.56 (dd, J = 5.1, 6.9 Hz, 1H), 6.30 (d, J = 8.3 Hz, 1H), 4.57 (s, 2H), 4.40 (s, 2H), 3.99 (s, 2H), 3.89 (s, 2H), 3.68-3.67 (m, 1H), 2.61 (d, J = 8.2 Hz, 4H), 2.16 (s, 3H).). m/z 435 (M + H)$^+$. | Example 11 |
| 74 | $^1$H NMR (400 MHz, DMSO) δ 8.00 (d, J = 2.9 Hz, 1H), 7.73 (s, 1H), 7.66 (dd, J = 2.3, 8.5 Hz, 1H), 7.53 (d, J = 8.5 Hz, 1H), 7.43-7.37 (m, 1H), 6.37 (dd, J = 3.6, 9.0 Hz, 1H), 4.70 (s, 2H), 4.55 (s, 2H), 4.01 (s, 2H), 3.91 (s, 2H), 3.70-3.62 (m, 1H), 2.64 (d, J = 8.0 Hz, 4H), 2.11 (dd, J = 6.1, 6.1 Hz, 1H), 0.86 (d, J = 5.8 Hz, 4H). m/z 479 (M + H)$^+$. | Example 11 |
| 75 | $^1$H NMR (400 MHz, DMSO) δ 8.57 (dd, J = 1.5, 4.5 Hz, 1H), 7.82-7.77 (m, 1H), 7.74 (dd, J = 2.5, 8.6 Hz, 1H), 7.59 (d, J = 8.6 Hz, 1H), 7.39 (dd, J = 4.4, 9.0 Hz, 1H), 6.79 (dd, J = 1.4, 9.0 Hz, 1H), 4.55 (s, 2H), 4.41 (s, 2H), 4.16 (s, 2H), 4.03 (s, 2H), 3.37 (d, J = 1.3 Hz, 3H), 2.66 (d, J = 8.1 Hz, 4H), 2.13 (s, 1H). m/z 452 (M + H)$^+$. | Example 11 |
| 78 | $^1$H NMR (400 MHz, DMSO) d 8.04 (d, J = 3.0 Hz, 1H), 7.77-7.74 (m, 1H), 7.70 (dd, J = 2.4, 8.5 Hz, 1H), 7.55 (d, J = 8.4 Hz, 1H), 7.51-7.45 (m, 1H), 6.40 (dd, J = 3.5, 9.0 Hz, 1H), 5.06-4.95 (m, 1H), 4.64-4.47 (m, 6H), 3.99 (s, 2H), 3.86 (s, 2H), 3.74-3.64 (m, 1H), 2.60-2.55 (m, 4H), 1.25 (d, J = 6.1 Hz, 3H). m/z 516 (M + H)$^+$. | Example 11 |
| 79 | $^1$H NMR (400 MHz, CDCl$_3$) d 8.00 (d, J = 2.9 Hz, 1H), 7.58-7.54 (m, 2H), 7.25-7.19 (m, 2H), 6.24 (dd, J = 3.1, 9.0 Hz, 1H), 5.24-5.10 (m, 1H), 4.76-4.68 (m, 4H), 4.64-4.56 (m, 4H), 4.08 (s, 2H), 4.00 (s, 2H), 3.55-3.46 (m, 1H), 2.87 (d, J = 8.1, 12.4 Hz, 2H), 2.68 (s, 2H). m/z 534 (M + H)$^+$. | Example 11 |
| 81 | $^1$H NMR (400 MHz, DMSO) d 8.03 (dd, J = 1.5, 2.8 Hz, 1H), 7.86-7.82 (m, 2H), 7.79 (s, 1H), 7.73 (dd, J = 2.4, 8.6 Hz, 1H), 7.58 (d, J = 8.5 Hz, 1H), 4.61 -4.58 (m, 4H), 4.12 (s, 2H), 4.00 (s, 2H), 3.78-3.69 (m, 1H), 2.63 (d, J = 7.9 Hz, 4H), 1.46 (d, J = 19.8 Hz, 2H), 1.32-1.25 (m, 2H). m/z 480 (M + H)$^+$. | Example 11 |
| 82 | $^1$H NMR (400 MHz, DMSO) d 8.03 (dd, J = 1.5, 2.6 Hz, 1H), 7.87-7.82 (m, 3H), 7.73 (ddd, J = 2.4, 4.2, 8.6 Hz, 1H), 7.58 (d, J = 8.5 Hz, 1H), 7.21-6.82 (m, 1H), 4.56-4.55 (m, 4H), 4.12 (s, 2H), 4.00 (s, 2H), 3.76-3.69 (m, 1H), 2.63 (d, J = 7.5 Hz, 4H). m/z 472 (M + H)$^+$. | Example 11 |
| 90 | $^1$H NMR (400 MHz, DMSO) d 7.95 (d, J = 2.8 Hz, 1H), 7.67 (d, J = 1.8 Hz, 1H), 7.61 (dd, J = 2.4, 8.5 Hz, 1H), 7.47-7.36 (m, 2H), 6.31 (dd, J = 3.5, 9.1 Hz, 1H), 4.48-4.21 (m, 4H), 4.00 (d, J = 2.8 Hz, 1H), 3.89 (s, 2H), 3.79 (s, 2H), 3.64-3.55 (m, 1H), 2.43 (dd, J = 1.8, 1.8 Hz, 4H), 0.62-0.61 (m, 4H). m/z 495 (M + H)$^+$. | Example 11 |

Example 12

Compound No. 91

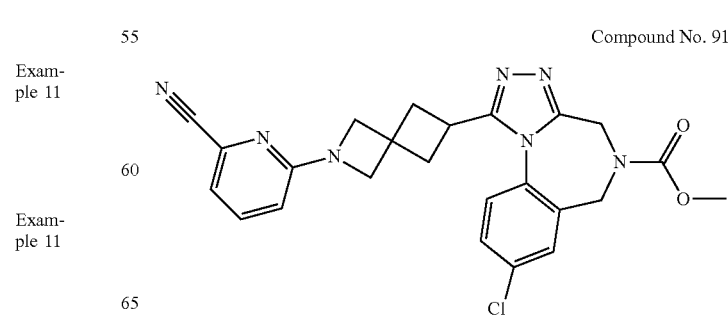

Step 1: Synthesis of tert-butyl (2-amino-5-chlorobenzyl)glycinate

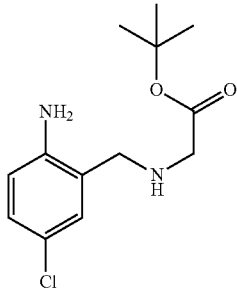 [SMILES: CC(C)(C)OC(=O)CNCc1cc(Cl)ccc1N]

To a solution of 2-amino-5-chlorobenzylamine (3.0 g, 19.16 mmol, 1.0 eq.), tert-butylbromoacetate (2.97 mL, 20.11 mmol, 1.05 eq.) in THF (60 mL) was added Et$_3$N (3.20 mL, 22.99 mmol, 1.2 eq.) and the mixture was stirred at room temperature overnight. The mixture was diluted with EtOAc, water and the layers separated. The aq. phase was extracted with EtOAc, the organic phases were combined, dried (MgSO$_4$), filtered and concentrated in vacuo to afford the title compound as a yellow solid (5.09 g, 98% yield). $^1$H NMR (400 MHz, CDCl$_3$) δ 7.06-7.01 (m, 1H), 6.99 (d, J=2.4 Hz, 1H), 6.57 (d, J=8.4 Hz, 1H), 3.73 (s, 2H), 3.27 (s, 2H), 1.48 (s, 9H).

Step 2: Synthesis of 7-chloro-1,3,4,5-tetrahydro-2H-benzo[e][1,4]diazepin-2-one

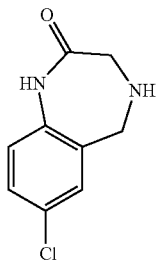 [SMILES: O=C1CNCc2cc(Cl)ccc2N1]

To a solution of tert-butyl (2-amino-5-chlorobenzyl)glycinate in THF (90 mL) was slowly added a solution of KOtBu (2.53 g, 22.56 mmol, 1.2 eq.) in THF (60 mL). The mixture was stirred at RT for 90 minutes, diluted with sat. sol. of NH$_4$Cl and extracted with EtOAc (×3). The organic phases were combined, dried (MgSO$_4$), filtered and concentrated in vacuo to afford the title compound as a yellow powder (3.11 g, 84% yield). $^1$H NMR (400 MHz, CDCl$_3$) δ 7.57 (s, 1H), 7.23-7.17 (m, 2H), 6.83 (d, J=8.4 Hz, 1H), 4.00 (s, 2H), 3.73 (s, 2H).

Step 3: Synthesis of tert-butyl 7-chloro-2-oxo-1,2,3,5-tetrahydro-4H-benzo[e][1,4]diazepine-4-carboxylate

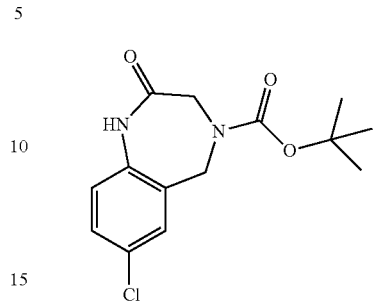

To a cooled suspension of 7-chloro-1,3,4,5-tetrahydro-2H-benzo[e][1,4]diazepin-2-one (3.11 g, 15.82 mmol, 1.0 eq.) in THF (75 mL) at 0° C. was added a solution of di-tert-butyl dicarbonate (4.14 g, 18.98 mmol, 1.2 eq.) in THF (35 mL) dropwise over 10 minutes. Mixture was allowed to warm to RT and stirred overnight. The mixture was concentrated in vacuo and triturated with diethyl ether to afford the title compound as a yellow powder (3.36 g, 72% yield). $^1$H NMR (400 MHz, DMSO) δ 7.36-7.31 (m, 2H), 7.16 (d, J=8.6 Hz, 2H), 4.53-4.45 (m, 2H), 4.33 (s, 2H), 1.31 (s, 9H).

Step 4: Synthesis of tert-butyl 7-chloro-2-thioxo-1,2,3,5-tetrahydro-4H-benzo[e][1,4]diazepine-4-carboxylate

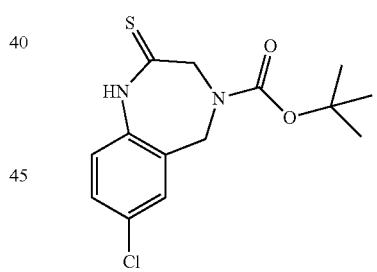

To a suspension of tert-butyl 7-chloro-2-oxo-1,2,3,5-tetrahydro-4H-benzo[e][1,4]diazepine-4-carboxylate (3.36 g, 11.32 mmol, 1.0 eq.) in THF (80 mL) was added 2,4-bis(4-methoxyphenyl)-2,4-dithioxo-1,3,2,4-dithiadiphosphetane (2.75 g, 6.79 mmol, 0.60 eq.) and the mixture was heated to reflux for 90 minutes. The mixture was allowed to cool, concentrated in vacuo, triturated with TBME and filtered. The solid was discarded and the filtrate was concentrated in vacuo to afford the title compound as a pale yellow solid (2.07 g, 58% yield). $^1$H NMR (400 MHz, DMSO) δ 12.08-12.07 (m, 1H), 7.41-7.38 (m, 1H), 7.33 (dd, J=2.5, 8.6 Hz, 1H), 7.20-7.19 (m, 1H), 4.39 (s, 1H), 4.35 (s, 2H), 4.30 (s, 1H), 1.27 (d, J=22.0 Hz, 9H).

Step 5: Synthesis of 7-chloro-1,3,4,5-tetrahydro-2H-benzo[e][1,4]diazepine-2-thione

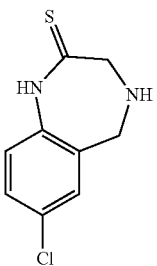 [SMILES: S=C1CNCc2cc(Cl)ccc2N1]

To a solution of tert-butyl 7-chloro-2-thioxo-1,2,3,5-tetrahydro-4H-benzo[e][1,4]diazepine-4-carboxylate (1.08 g, 3.45 mmol, 1.0 eq.) in DCM (30 mL) was added TFA (10 mL) and the mixture was stirred at RT for 1 hour and concentrated in vacuo to afford the title compound as a pale yellow powder (0.737 g, quant. yield). $^1$H NMR (400 MHz, DMSO) δ 12.02 (s, 1H), 7.46-7.40 (m, 2H), 7.27 (d, J=8.3 Hz, 1H), 3.87 (s, 2H), 3.69 (s, 2H), 3.51-3.50 (m, 1H).

Step 6: Synthesis of tert-butyl 6-(8-chloro-5,6-dihydro-4H-benzo[f][1,2,4]triazolo[4,3-a][1,4]diazepin-1-yl)-2-azaspiro[3.3]heptane-2-carboxylate

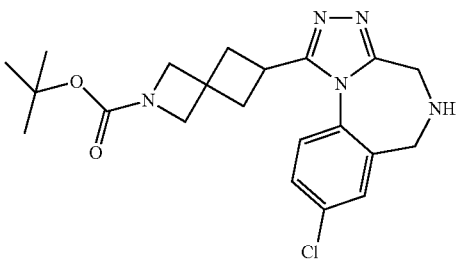 [SMILES: CC(C)(C)OC(=O)N1CC2(CC(c3nnc4n3-c3ccc(Cl)cc3CNC4)C2)C1]

The procedure of Example 1, step 2 was employed to afford the title compound as a foam (1.06 g, 94% yield). $^1$H NMR (400 MHz, CDCl$_3$) δ 7.72 (s, 1H), 7.51-7.47 (m, 1H), 7.12 (d, J=3.9 Hz, 2H), 3.99 (s, 2H), 3.94-3.90 (m, 4H), 3.68 (s, 2H), 3.49-3.40 (m, 1H), 2.76 (dd, J=8.2, 12.8 Hz, 2H), 2.63-2.54 (m, 2H), 1.43 (s, 9H)

Step 7: Synthesis of methyl 1-(2-(tert-butoxycarbonyl)-2-azaspiro[3.3]heptan-6-yl)-8-chloro-4H-benzo[f][1,2,4]triazolo[4,3-a][1,4]diazepine-5(6H)-carboxylate

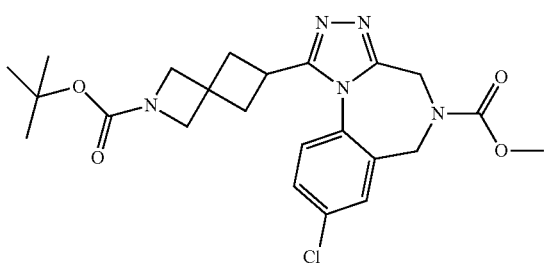 [SMILES: COC(=O)N1Cc2cc(Cl)ccc2-n2c(nnc2C2CC3(C2)CN(C(=O)OC(C)(C)C)C3)C1]

The procedure of Example 11 was employed to afford the title compound which was used without further purification. $^1$H NMR (400 MHz, CDCl$_3$) δ 7.59-7.56 (m, 1H), 7.53 (dd, J=2.4, 8.2 Hz, 1H), 7.15 (d, J=8.5 Hz, 1H), 4.01 (s, 4H), 4.00 (s, 2H), 3.93 (s, 2H), 3.79 (m, 3H), 3.42 (dd, J=8.3, 8.3 Hz, 1H), 2.78 (dd, J=8.1, 12.5 Hz, 2H), 2.62-2.59 (m, 2H), 1.43 (s, 9H).

Step 8: Synthesis of methyl 8-chloro-1-(2-azaspiro[3.3]heptan-6-yl)-4H-benzo[f][1,2,4]-triazole[4,3-a][1,4]diazepine-5(6H)-carboxylate

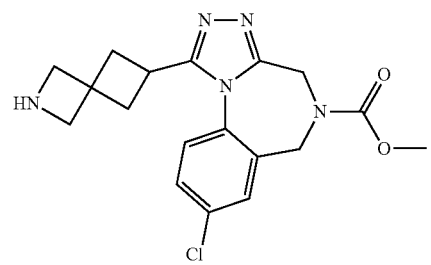 [SMILES: COC(=O)N1Cc2cc(Cl)ccc2-n2c(nnc2C2CC3(CNC3)C2)C1]

The procedure of Example 1, step 3, was employed to afford the title compound (400, mg, 81% yield). $^1$H NMR (400 MHz, CDCl$_3$) δ 7.53-7.51 (m, 2H), 7.19-7.17 (m, 1H), 4.62-4.40 (m, 4H), 3.76 (s, 3H), 3.71 (s, 2H), 3.63 (s, 2H), 3.48-3.46 (m, 1H), 2.75-2.70 (m, 2H), 2.63-2.55 (m, 2H).

Step 9: Synthesis of methyl 8-chloro-1-(2-(6-cyano-pyridin-2-yl)-2-azaspiro[3.3]heptan-6-yl)-4H-benzo[f][1,2,4]triazolo[4,3-a][1,4]diazepine-5(6H)-carboxylate (Compound No. 91)

The procedure of Example 1, step 4 using 6-bromo-2-pyridinecarbonitrile was employed to afford the title compound after preparative HPLC as a yellow film (0.0134 g, 21% yield). $^1$H NMR (400 MHz, DMSO) δ 7.68-7.60 (m, 3H), 7.51 (d, J=8.3 Hz, 1H), 7.10 (d, J=7.2 Hz, 1H), 6.63 (d, J=8.5 Hz, 1H), 4.53 (s, 2H), 4.36 (s, 2H), 4.09 (s, 2H), 4.00 (s, 2H), 3.71 (s, 3H), 3.70-3.68 (m, 1H), 2.65 (d, J=8.0 Hz, 4H). m/z 476 (M+H)$^+$.

Compound Nos. 92 to 94

Compound Nos. 92 to 94 were prepared according to the methods set forth in Example 12. For example, Compound No. 92 of Table 7 lists the method of "Example 12", indicating that this compound was prepared according to the procedure of Example 12 using appropriately substituted intermediates. Analytical data (NMR, mass spectrum) is also presented in Table 7.

TABLE 7

Compound Nos. 92 to 94

| Compound No. | Analytical Data | Synthesis Method |
|---|---|---|
| 92 | $^1$H NMR (400 MHz, DMSO) δ 8.34 (s, 2H), 7.68-7.64 (m, 2H), 7.50 (dd, J = 1.4, 8.0 Hz, 1H), 4.53 (s, 2H), 4.36 (s, 2H), 4.12 (s, 2H), 4.01 (s, 2H), 3.74 (s, 3H), 3.73-3.65 (m, 1H), 2.63 (d, J = 8.0 Hz, 4H). m/z 452 (M + H)$^+$. | Example 12 |
| 93 | $^1$H NMR (400 MHz, DMSO) δ 8.01-7.99 (m, 1H), 7.82-7.79 (m, 3H), 7.66 (dd, J = 2.4, 8.5 Hz, 1H), 7.52 (d, J = 8.5 Hz, 1H), 4.61 (s, | Example 12 |

TABLE 7-continued

Compound Nos. 92 to 94

| Compound No. | Analytical Data | Synthesis Method |
|---|---|---|
|  | 2H), 4.42 (s, 2H), 4.13 (s, 2H), 4.03 (s, 2H), 3.72-3.68 (m, 1H), 2.66 (d, J = 8.2 Hz, 4H), 2.19 (s, 3H). m/z 436 (M + H)+. |  |
| 94 | $^1$H NMR (400 MHz, DMSO) δ 7.98 (d, J = 2.4 Hz, 1H), 7.33-7.19 (m, 4H), 6.24-6.20 (m, 1H), 4.15 (s, 2H), 4.08 (s, 2H), 3.96 (s, 2H), 3.77 (s, 2H), 3.75-3.65 (m, 1H), 2.64-2.59 (m, 4H), 2.39 (s, 3H). m/z 460 (M + H)+. | Example 12 |

Example 13

Compound No. 95

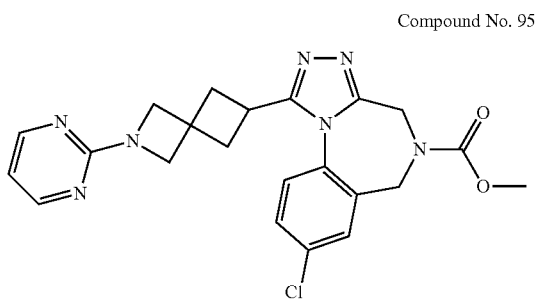 [SMILES: COC(=O)N1Cc2cc(Cl)ccc2-n2c(nnc2C2CC3(C2)CN(c2ncccn2)C3)C1]

A mixture of methyl 8-chloro-1-(2-azaspiro[3.3]heptan-6-yl)-4Hbenzo[f][1,2,4]triazolo[4,3-a][1,4]diazepine-5(6H)-carboxylate (Example 2 step 8 above) (0.030 g, 0.0802 mmol, 1.0 eq.), 2-chloropyrimidine (0.0092 g, 0.0802 mmol, 1.0 eq.), cesium carbonate (0.031 g, 0.0963 mmol, 1.2 eq.) in DMF was heated 80° C. in a reaction tube for 4 hours. The mixture was diluted with water and extracted with EtOAc (×3). The organic phases were combined washed with brine, dried (MgSO4), filtered and concentrated in vacuo to afford the title compound (7.6 mg). $^1$H NMR (400 MHz, DMSO) δ 8.30 (d, J=4.6 Hz, 2H), 7.68-7.64 (m, 2H), 7.51 (d, J=8.7 Hz, 1H), 6.61 (dd, J=4.8, 4.8 Hz, 1H), 4.53 (s, 2H), 4.36 (s, 2H), 4.12 (s, 2H), 4.01 (s, 2H), 3.74 (s, 3H), 3.73-3.65 (m, 1H), 2.64 (d, J=8.0 Hz, 4H). m/z 452 (M+H)+.

Example 14

Compound No. 96

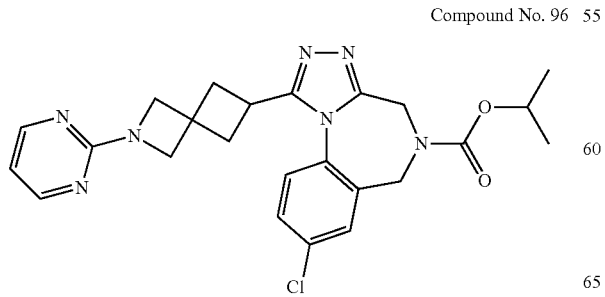

Step 1: Synthesis of isopropyl 7-chloro-2-thioxo-1,2,3,5-tetrahydro-4H-benzo[e][1,4]diazepine-4-carboxylate

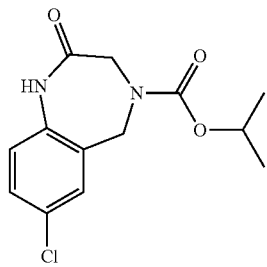 [SMILES: CC(C)OC(=O)N1CC(=O)Nc2ccc(Cl)cc2C1]

To a cooled mixture of 7-chloro-1,3,4,5-tetrahydro-2H-benzo[e][1,4]diazepine-2-thione as prepared by Example 12, step 5 (0.06 g, 0.28 mmol, 1.0 eq.), Et$_3$N (59 µL, 0.42 mmol, 1.5 eq.) at 0° C. in DCM was added isopropyl chloroformate (0.31 mL, 0.31 mmol, 1.10 eq.) and the mixture was stirred at RT overnight. Mixture was diluted with DCM, Sat. NaHCO$_3$ and passed through a phase separator and concentrated in vacuo to afford the title compound as a yellow gum. (90 mg, quant. yield). $^1$H NMR (400 MHz, CDCl$_3$) δ 7.33-7.30 (m, 2H), 6.97 (d, J=8.1 Hz, 1H), 4.97-4.90 (m, 1H), 4.60-4.49 (m, 4H), 1.25-1.18 (m, 6H).

Step 2: Synthesis of isopropyl 8-chloro-1-(2-(pyridin-2-yl)-2-azaspiro[3.3]heptan-6-yl)-4H-benzo[f][1,2,4]triazolo[4,3-a][1,4]diazepine-5(6H)-carboxylate (Compound No. 96)

The procedure of Example 7, step 2 was employed to afford the title compound as a yellow gum. (23 mg). $^1$H NMR (400 MHz, DMSO) δ 8.06-8.04 (m, 1H), 7.68-7.64 (m, 2H), 7.53-7.44 (m, 2H), 6.59 (dd, J=5.0, 6.8 Hz, 1H), 6.33 (d, J=8.4 Hz, 1H), 4.95-4.85 (m, 1H), 4.52 (s, 2H), 4.34 (s, 2H), 4.02 (s, 2H), 3.91 (s, 2H), 3.73-3.65 (m, 1H), 2.63 (d, J=8.2 Hz, 4H), 1.30 (d, J=6.3 Hz, 6H). m/z 479 (M+H)+.

Example 15

Compound No. 97

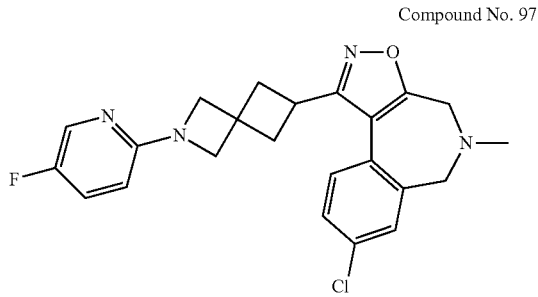 [SMILES: CN1Cc2cc(Cl)ccc2-c2c(C3CC4(C3)CN(c3ccc(F)cn3)C4)noc2C1]

Step 1: Synthesis of tert-butyl (E)-6-(chloro(hydroxyimino)methyl)-2-azaspiro[3.3]heptane-2-carboxylate

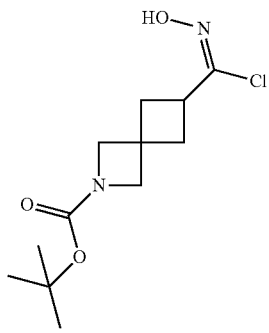 [SMILES: CC(C)(C)OC(=O)N1CC2(CC(/C(Cl)=N\O)C2)C1]

To a cooled solution of tert-butyl 6-formyl-2-azaspiro[3.3]heptane-2-carboxylate (0.8 g, 3.6 mmol, 1.0 eq.) in MeOH (4 mL), water (4 mL) at 0° C. was added Na$_2$CO$_3$ (0.188 g, 1.8 mmol, 0.5 eq.) followed by hydroxylamine hydrochloride (0.283 mg, 4.1 mmol, 1.15 eq.) and stirred at 0° C. for 2 hours. The mixture was then stirred at RT for 3 days, concentrated in vacuo, partitioned between EtOAc and H$_2$O. The organic phase was isolated, concentrated in vacuo the residue dissolved in DMF (8 mL), NCS (0.474 g, 3.6 mmol, 1.0 eq) was added and the mixture was stirred at RT overnight. The mixture was diluted with EtOAc and 4% aq. sol. of LiCl and stirred at RT overnight. The organic layer was separated and concentrated in vacuo to afford the title compound (1.29 g, quant.). $^1$H NMR (400 MHz, CDCl$_3$) δ 8.02 (s, 1H), 3.96 (s, 2H), 3.87 (s, 2H), 3.25-3.16 (m, 1H), 2.96-2.88 (m, 3H), 2.77 (s, 1H), 1.42 (s, 9H).

Step 2: Synthesis of tert-butyl 6-(5-(bromomethyl)isoxazol-3-yl)-2-azaspiro[3.3]heptane-2-carboxylate

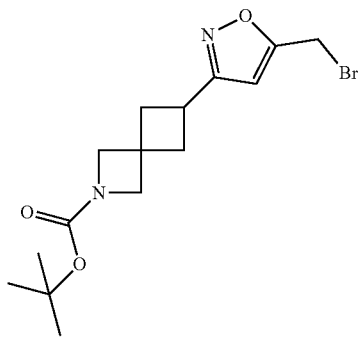 [SMILES: CC(C)(C)OC(=O)N1CC2(CC(c3cc(CBr)on3)C2)C1]

To a cooled mixture of tert-butyl (E)-6-(chloro(hydroxyimino)methyl)-2-azaspiro[3.3]heptane-2-carboxylate (0.989 g, 3.6 mmol, 1.0 eq.), propargyl bromide (80% sol. in toluene, 481.2 μL, 4.3 mmol, 1.2 eq) at 0° C. in DCM (10 mL) was added Et3N (607.1 μL, 4.3 mmol, 1.2 eq) in DCM dropwise. The mixture was allowed to warm to RT and stirred overnight. Mixture was diluted with DCM, washed with water and concentrated in vacuo to afford the title compound as a light brown oil (1.05 g, 81% yield).

Step 3: Synthesis of 1-(5-chloro-2-iodophenyl)-N-methylmethanamine

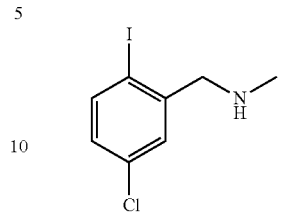

To a solution of 5-chloro-2-iodobenzaldehyde (1.0 g, 3.8 mmol, 1.0 eq.) in anhydrous MeOH (20 mL) was added NaHCO$_3$ (0.95 g, 11.3 mmol, 3.0 eq.), methylamine (33% sol. in EtOH) (0.93 mL, 7.5 mmol, 2.0 eq.) and the mixture was refluxed for 4 hours. Mixture was cooled to 0° C., sodium borohydride (0.17 g, 4.5 mmol, 1.20 eq.) was added portion wise, the mixture was allowed to warm to RT and stirred at RT overnight. The reaction was quenched with H$_2$O (2 mL) and concentrated in vacuo to give a residue. This was partitioned between DCM and brine. The organic phase was separated and the aq. layer was extracted with DCM (×2). The organic phases were combined, dried (MgSO$_4$), concentrated in vacuo to afford the title compound as a light yellow oil (0.97 g, 91% yield). $^1$H NMR (400 MHz, CDCl$_3$) δ 7.68 (d, J=8.3 Hz, 1H), 7.36 (d, J=2.8 Hz, 1H), 6.92 (dd, J=2.5, 8.3 Hz, 1H), 3.69 (s, 2H), 2.44 (s, 3H).

Step 4: Synthesis of tert-butyl 6-(5-(((5-chloro-2-iodobenzyl)(methyl)amino)methyl)isoxazol-3-yl)-2-azaspiro[3.3]heptane-2-carboxylate

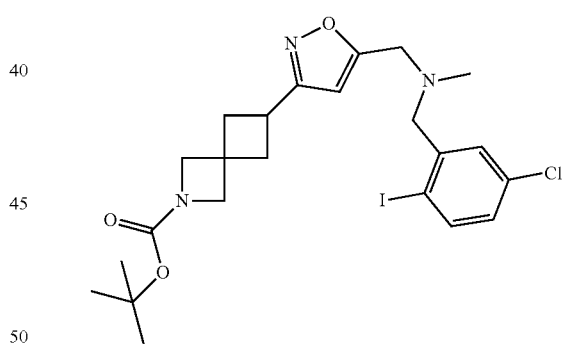

To a solution of tert-butyl 6-(5-(bromomethyl)isoxazol-3-yl)-2-azaspiro[3.3]heptane-2-carboxylate (0.5 g, 1.4 mmol, 1.0 eq) in THF (5 mL) was added 1-(5-chloro-2-iodophenyl)-N-methylmethanamine (0.433 g, 2.1 mmol, 1.1 eq.), potassium carbonate (0.29 g, 2.1 mmol, 1.5 eq.) and stirred at RT for 48 hours. The mixture was diluted with DCM, washed with brine and concentrated in vacuo. The residue was purified using a Biotage® KP-NH cartridge, eluting with isohexane, isohexane:EtOAc (75%:25%) followed by 100% EtOAc, to afford the title compound (0.36 g, 46% yield). $^1$H NMR (400 MHz, CDCl$_3$) δ 7.74 (d, J=8.3 Hz, 1H), 7.46 (d, J=2.5 Hz, 1H), 6.97 (dd, J=2.5, 8.3 Hz, 1H), 6.03 (s, 1H), 4.02 (s, 2H), 3.88 (s, 2H), 3.75 (s, 2H), 3.57 (s, 2H), 3.48-3.39 (m, 1H), 2.63-2.55 (m, 2H), 2.48-2.39 (m, 2H), 2.33 (s, 3H).

Step 5: Synthesis of tert-butyl 6-(8-chloro-5-methyl-5,6-dihydro-4H-benzo[c]isoxazolo[4,5-e]azepin-1-yl)-2-azaspiro[3.3]heptane-2-carboxylate

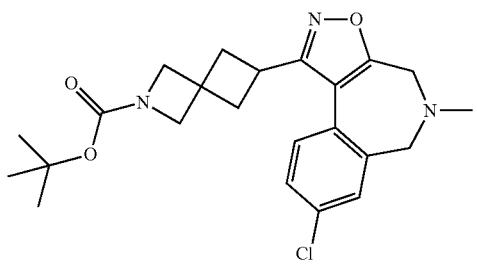 [SMILES: CN1Cc2cc(Cl)ccc2-c2c(C3CC4(C3)CN(C(=O)OC(C)(C)C)C4)noc2C1]

A mixture of tert-butyl 6-(5-(((5-chloro-2-iodobenzyl)(methyl)amino)-methyl)isoxazol-3-yl)-2-azaspiro[3.3]heptane-2-carboxylate (0.18 g, 0.3 mmol, 1.0 eq.), potassium carbonate (0.178 g, 1.3 mmol, 4.0 eq.), pivalic acid (0.0098 g, 0.1 mmol, 0.3 eq.), triphenylphosphine (0.0253 mg, 0.1 mmol, 0.3 eq.) in DMA (2 mL) was degassed using N₂ for 2 hours. Palladium acetate (0.0072 g, 0.0032 mmol, 0.1 eq.) was added and the reaction was heated to 80° C. for 2 hours, 100° C. for 2 hour, and 110° C. for 2 hours. The mixture was allowed to cool overnight. The mixture was filtered through a pad of celite, the filtrate was diluted with EtOAc, washed with 4% aq. sol. of LiCl (×4). The organic phase was concentrated in vacuo, the residue was purified using a Biotage® KP-NH cartridge, eluting with isohexane, isohexane:EtOAc (70%:30%) to afford the title compound (0.71 g, 51% yield). ¹H NMR (400 MHz, CDCl₃) δ 7.31 (dd, J=2.3, 8.3 Hz, 1H), 7.26-7.23 (m, 1H), 7.20 (d, J=2.3 Hz, 1H), 4.17 (s, 2H), 4.03 (s, 2H), 3.89 (s, 2H), 3.73 (s, 2H), 3.61-3.53 (m, 1H), 2.67-2.59 (m, 4H), 2.38 (s, 3H), 1.43 (s, 9H).

Step 6: Synthesis of 8-chloro-1-(2-(5-fluoropyridin-2-yl)-2-azaspiro[3.3]heptan-6-yl)-5-methyl-5,6-dihydro-4H-benzo[c]isoxazolo[4,5-e]azepine (Compound No. 97)

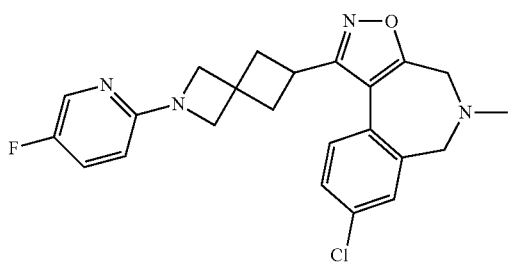 [SMILES: CN1Cc2cc(Cl)ccc2-c2c(C3CC4(C3)CN(c3ccc(F)cn3)C4)noc2C1]

To a solution of tert-butyl 6-(8-chloro-5-methyl-5,6-dihydro-4H-benzo[c]isoxazolo[4,5-e]azepin-1-yl)-2-azaspiro[3.3]heptane-2-carboxylate (0.071 g, 0.2 mmol, 1.0 eq.) in DCM (1 mL) was added TFA (0.3 mL, 3.30 mmol, 20.0 eq.), the mixture was stirred at RT for 30 minutes and concentrated in vacuo. The procedure of Example 1, step 4 was employed to afford the title compound (0.0034 g, 40% yield). ¹H NMR (400 MHz, CDCl₃) δ 7.78-7.73 (m, 1H), 7.65-7.59 (m, 2H), 7.52-7.50 (m, 1H), 7.10-7.08 (m, 1H), 6.64-6.62 (m, 1H), 4.18 (s, 2H), 4.11 (s, 2H), 3.96 (s, 2H), 3.74 (s, 2H), 3.70-3.60 (m, 1H), 2.72 (d, J=7.8 Hz, 4H), 2.19 (s, 3H). m/z 425 (M+H)⁺.

Compound Nos 98 to 106

Compound Nos. 98 to 106 are prepared according to the methods set forth in Table 8 below. In particular, such compound may be prepared according to the procedures of Examples 1, 11, 15, and 16 using appropriately substituted intermediates.

TABLE 8

| Compound Nos. 98 to 106 | |
|---|---|
| Cpd. No. | Synthesis Method |
| 98 | Examples 15 and 1 |
| 99 | Examples 15 and 11 |
| 100 | Examples 15 and 11 |
| 101 | Examples 15 and 11 |
| 102 | Examples 15 and 16 |
| 103 | Examples 15 and 16 |
| 104 | Examples 15 and 16 |
| 105 | Examples 15 and 16 |
| 106 | Examples 15 and 16 |

Example 16

Compound No. 107

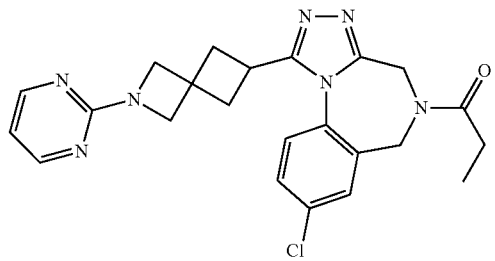

Step 1: Synthesis of tert-butyl 6-(8-chloro-5-propionyl-5,6-dihydro-4H-benzo[f][1,2,4]triazolo[4,3-a][1,4]diazepin-1-yl)-2-azaspiro[3.3]heptane-2-carboxylate

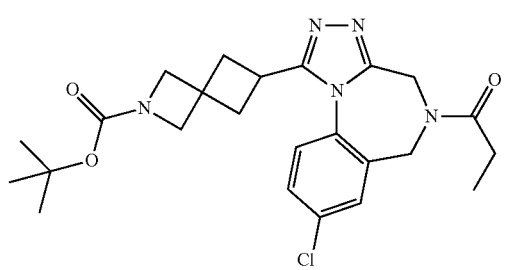 [SMILES: CCC(=O)N1Cc2cc(Cl)ccc2-n2c(nnc2C2CC3(C2)CN(C(=O)OC(C)(C)C)C3)C1]

To a cooled solution of tert-butyl 6-(8-chloro-5,6-dihydro-4H-benzo[f][1,2,4]triazolo[4,3-a][1,4]diazepin-1-yl)-2-azaspiro[3.3]heptane-2-carboxylate (1.0 g, 2.4 mmol, 1.0 eq.), prepared in Example 12, step 6, in DCM (20 mL) at 0° C. was added Et₃N (503 µL, 3.61 mmol, 1.5 eq.), propionyl chloride (231 µL, 2.64 mmol, 1.1 eq.) and the mixture was stirred at 0° C. for 30 minutes. The mixture was diluted with DCM and washed with sat.NaHCO₃, the organic layer was isolated and concentrated in vacuo. The residue was purified using flash column chromatography, eluting with 0-10

MeOH in EtOAc to give the title compound (593 mg, 53% yield). $^1$H NMR (400 MHz, CDCl$_3$) δ 7.60-7.45 (m, 1H), 7.21-7.14 (m, 2H), 4.62-4.40 (m, 4H), 4.00 (s, 2H), 3.94 (s, 2H), 3.50-3.39 (m, 1H), 2.78 (dd, J=8.2, 12.5 Hz, 2H), 2.62-2.60 (m, 2H), 2.49-2.35 (m, 2H), 1.43 (s, 9H), 1.25-1.16 (m, 3H).

Step 2: Synthesis of 1-(8-chloro-1-(2-(pyrimidin-2-yl)-2-azaspiro[3.3]heptan-6-yl)-4H-benzo[f][1,2,4]triazolo[4,3-a][1,4]diazepin-5(6H)-yl)propan-1-one (Compound No. 107)

A solution of tert-butyl 6-(8-chloro-5-propionyl-5,6-dihydro-4H-benzo[f][1,2,4]triazolo[4,3-a][1,4]diazepin-1-yl)-2-azaspiro[3.3]heptane-2-carboxylate (40 mg, 0.11 mmol, 1.0 eq.), 2-chloropyrimidine (15 mg, 0.13 mmol, 1.2 eq.), cesium carbonate (53 mg, 0.16 mmol, 1.5 eq.) in DMF (1 mL) was heated to 80° C. for 3 hours. Mixture was diluted with DCM and concentrated in vacuo. The residue was purified by preparative HPLC to yield the title compound (2.9 mg, 6% yield). $^1$H NMR (400 MHz, DMSO) δ 8.37 (d, J=4.8 Hz, 2H), 7.77-7.68 (m, 1H), 7.63-7.57 (m, 1H), 7.51 (d, J=8.1 Hz, 1H), 6.61 (dd, J=4.7, 4.7 Hz, 1H), 4.60 (s, 2H) 4.42 (s, 2H), 4.12 (s, 2H), 4.01 (s, 2H), 3.72-3.68 (m, 1H), 2.65-2.63 (m, 4H), 2.59-2.57 (m, 2H), 1.14-1.05 (m, 3H). m/z 450 (M+H)$^+$.

Compound Nos 108 to 123, 125, and 127 to 131 Compound Nos. 108 to 116, 122, and 125 were prepared according to the methods set forth in Example 16. For example, Compound No. 108 of Table 9 lists the method of "Example 16", indicating that this compound was prepared according to the procedure of Example 16 using appropriately substituted intermediates. Analytical data (NMR, mass spectrum) is also presented in Table 9. Compound Nos. 117 to 121, 123, and 127 to 131 are prepared according to the procedure of Example 16 using appropriately substituted intermediates.

TABLE 9

Compound Nos. 108 to 116, 122, and 125

| Compound No. | Analytical Data | Synthesis Method |
|---|---|---|
| 108 | $^1$H NMR (400 MHz, DMSO) δ 8.51-8.50 (m, 1H), 7.77-7.75 (m, 1H), 7.67-7.64 (m, 1H), 7.52 (d, J = 8.3 Hz, 1H), 7.30-7.27 (m, 1H), 6.70-6.67 (m, 1H), 4.60 (s, 2H), 4.30 (s, 2H), 4.14 (s, 2H), 4.04 (s, 2H), 3.73-3.69 (m, 1H), 2.57-2.53 (m, 2H), 2.67 (d, J = 8.1 Hz, 4H), 1.10 (t, J = 7.9 Hz, 3H); m/z 450 (M + H)$^+$. | Example 16 |
| 109 | $^1$H NMR (400 MHz, DMSO) δ 7.71-7.64 (m, 1H), 7.67-7.64 (m, 1H), 7.51 (d, J = 7.9 Hz, 1H), 7.37-7.33 (m, 1H), 6.46 (d, J = 7.3 Hz, 1H), 6.12 (d, J = 8.1 Hz, 1H), 4.60 (s, 2H), 4.42 (s, 2H), 3.96 (s, 2H), 3.89 (s, 2H), 3.72-3.63 (m, 1H), 2.62-2.58 (m, 4H), 2.56-2.53 (m, 2H), 2.29 (s, 3H), 1.07-0.98 (m, 3H). m/z 463 (M + H)$^+$. | Example 16 |
| 110 | $^1$H NMR (400 MHz, DMSO) δ 8.06 (dd, J = 1.5, 2.5 Hz, 1H), 7.85-7.83 (m, 2H), 7.77-7.69 (m, 1H), 7.66-7.63 (m, 1H), 7.51 (d, J = 8.3 Hz, 1H), 4.62 (s, 2H), 4.48 (s, 2H), 4.15 (s, 2H), 4.02 (s, 2H), 3.78-3.70 (m, 1H), 2.70-2.59 (m, 4H), 2.56-2.53 (m, 2H), 1.13-1.02 (m, 3H). m/z 450 (M + H)$^+$. | Example 16 |
| 111 | $^1$H NMR (400 MHz, DMSO) δ 8.01 (d, J = 2.3 Hz, 1H), 7.67-7.64 (m, 2H), 7.50 (d, J = 8.2 Hz, 1H), 7.42-7.36 (m, 1H), 6.37-6.34 (m, 1H), 4.93-4.83 (m, 1H), 4.50 (s, 2H), 4.34 (s, 2H), 4.00 (s, 2H), 3.99 (s, 2H), 3.72-3.64 (m, 1H), 2.62 (d, J = 8.1 Hz, 4H), 1.29 (d, J = 6 Hz, 6H). m/z 497 (M + H)$^+$. | Example 16 |
| 112 | $^1$H NMR (400 MHz, DMSO) δ 7.77-7.75 (m, 1H), 7.66-7.63 (m, 1H), 7.52 (d, J = 8.4 Hz, 1H), 7.27-7.24 (m, 1H), 6.98-6.94 (m, 1H), 4.60 (s, 2H), 4.42 (s, 2H), 4.14 (s, 2H), 4.04 (s, 2H), 3.75-3.67 (m, 1H), 2.70-2.65 (m, 4H), 2.56-2.53 (m, 2H), 1.10 (t, J = 7.6 Hz, 3H). m/z 468 (M + H)$^+$. | Example 16 |
| 113 | $^1$H NMR (400 MHz, DMSO) δ 7.67-7.56 (4H, m), 6.21-6.16 (2H, m), 4.60 (2H, s), 4.42 (2H, s), 4.03 (2H, s), 3.93 (2H, s), 3.75-3.66 (1H, m), 2.64 (4H, d, J = 12.4 Hz), 1.10 (3H, dd, J = 7.3, 7.3 Hz); 2H obscured by DMSO peak). m/z 467 (M + H)$^+$. | Example 16 |
| 114 | $^1$H NMR (400 MHz, DMSO) δ 7.99 (d, J = 3.0 Hz, 1H), 7.72 (s, 1H), 7.66 (dd, J = 2.4, 8.5 Hz, 1H), 7.51 (d, J = 8.5 Hz, 1H), 7.42-7.37 (m, 1H), 6.36 (dd, J = 3.5, 9.0 Hz, 1H), 4.52 (s, 2H), 4.34 (s, 2H), 4.01 (s, 2H), 3.90 (s, 2H), 3.71-3.67 (m, 1H), 3.59-3.57 (m, 1H), 2.63 (d, J = 8.2 Hz, 4H), 2.30-2.23 (m, 4H), 2.05-1.93 (m, 1H), 1.90-1.82 (m, 1H). m/z 493 (M + H)$^+$. | Example 16 |
| 115 | $^1$H NMR (400 MHz, DMSO) δ 7.66 (2H, d, J = 7.9 Hz), 7.50 (1H, d, J = 8.0 Hz), 7.35 (1H, dd, J = 7.7, 7.7 Hz), 6.46 (1H, d, J = 7.3 Hz), 6.12 (1H, d, J = 8.3 Hz), 4.53 (2H, s), 4.36 (2H, s), 3.99 (2H, s), 3.89 (2H, s), 3.74 (3H, s), 3.72-3.64 (1H, m), 2.62 (4H, d, J = 8.0 Hz), 2.29 (3H, s); m/z 465 (M + H)$^+$. | Example 16 |
| 116 | $^1$H NMR (400 MHz, DMSO) δ 8.00 (1H, d, J = 3.0 Hz), 7.76-7.76 (1H, m), 7.70 (1H, dd, J = 2.4, 8.5 Hz), 7.54 (1H, d, J = 8.5 Hz), 7.43-7.37 (1H, m), 6.37 (1H, dd, J = 3.3, 9.0 Hz), 4.50 (2H, s), 4.01 (2H, s), 3.91 (2H, s), 2.95 (1H, s), 2.89 (1H, s), 2.64 (4H, d, J = 8.2 Hz), 2.54 (1H, s), 2.49-2.47 (1H, m); m/z 489 (M + H)$^+$. | Example 16 |
| 122 | $^1$H NMR (400 MHz, DMSO) d 8.05 (dd, J = 1.5, 4.9 Hz, 1H), 7.86 (d, J = 2.4 Hz, 1H), 7.73 (ddd, J = 2.5, 4.2, 8.6 Hz, 1H), 7.58 (d, J = 8.7 Hz, 1H), 7.52-7.47 (m, 1H), 7.10-6.81 (m, 1H), 6.62 (dd, J = 5.0, 6.8 Hz, 1H), 6.35 (d, J = 8.3 Hz, 1H), 4.60-4.41 (m, 4H), 4.00 (s, 2H), 3.88 (s, 2H), 3.75-3.66 (m, 1H), 2.64-2.55 (m, 4H). m/z 471 (M + H)$^+$. | Example 16 |
| 125 | $^1$H NMR (400 MHz, DMSO) δ 7.76 (s, 1H), 7.67-7.62 (m, 2H), 7.51 (d, J = 8.0 Hz, 1H), 7.10-7.08 (m, 1H), 6.64-6.62 (m, 1H), 4.60 (s, 2H), 4.42 (s, 2H), 4.09 (s, 2H), 3.99 (s, 2H), 3.72-3.68 (m, 1H), 2.65 (d, J = 8.1 Hz, 4H), 2.57-2.54 (m, 2H), 1.10 (t, J = 7.3 Hz, 3H). m/z 475 (M + H)$^+$. | Example 17 |

Example 17

Compound No. 124

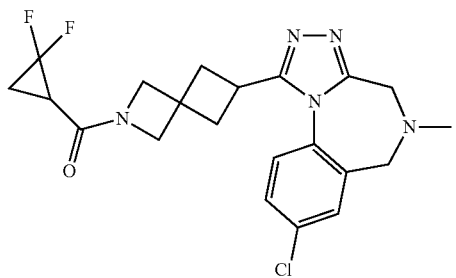

To a solution of 8-chloro-5-methyl-1-(2-azaspiro[3.3]heptan-6-yl)-5,6-dihydro-4H-benzo[f][1,2,4]triazolo[4,3-a][1,4]diazepine bis(2,2,2-trifluoroacetate) (30 mg, 0.09 mmol, 1.0 eq.) in DMF (1.5 mL) was added 2,2-difluorocyclopropane carboxylic acid (13 mg, 0.11 mmol, 1.2 eq.), HOBt (3 mg, 0102 mmol, 0.2 eq.), EDCl.HCl (23 mg, 0.12 mmol, 1.3 eq.), DIPEA (32 µL, 0.14 mmol, 1.5 eq.) and the mixture was stirred at RT overnight. Mixture was diluted with DCM, passed through a phase separator and concentrated in vacuo. The residue was purified by preparative HPLC to give the title compound (15 mg, 37% yield). $^1$H NMR (400 MHz, CDCl$_3$) δ 7.51 (d, J=8.0 Hz, 2H), 7.14-7.09 (m, 1H), 4.35-4.30 (m, 2H), 4.16-4.01 (m, 2H), 3.68 (s, 2H), 3.53-3.44 (m, 1H), 3.35 (s, 2H), 2.94-2.75 (m, 2H), 2.71-2.61 (m, 2H), 2.48 (s, 3H), 2.26-2.09 (m, 2H), 1.67-1.52 (m, 1H). m/z 434 (M+H)$^+$.

Compound Nos 126, 132 to 139, 144 to 155

Compound Nos. 126, 134, 136 to 138, 147, and 153 were prepared according to the methods set forth in Example 17. For example, Compound No. 126 of Table 10 lists the method of "Example 17", indicating that this compound was prepared according to the procedure of Example 17 using appropriately substituted intermediates. Analytical data (NMR, mass spectrum) is also presented in Table 10.

Compound Nos. to 132 to 133, 135, and 139 are prepared according to the methods set forth in Table 11 below. In particular, such compound may be prepared according to the procedures of Examples 11 and 17 using appropriately substituted intermediates.

TABLE 10

Compound Nos. 126, 134, and 136 to 138

| Compound No. | Analytical Data | Synthesis Method |
|---|---|---|
| 126 | $^1$H NMR (400 MHz, CDCl$_3$) δ 7.53-7.49 (m, 2H), 7.13-7.09 (m, 1H), 4.33-4.27 (m, 2H), 4.12-4.05 (m, 2H), 3.96-3.94 (m, 2H), 3.67 (s, 2H), 3.52-3.43 (m, 1H), 3.39 (s, 3H), 3.36 (s, 2H), 2.86-2.78 (m, 2H), 2.69-2.58 (m, 2H), 2.48 (s, 3H). m/z 402 (M + H)$^+$. | Example 17 |
| 134 | $^1$H NMR (400 MHz, CDCl$_3$) d 7.62-7.57 (m, 1H), 7.55 (d, J = 2.1 Hz, 1H), 7.21 (dd, J = 6.5, 8.6 Hz, 1H), 6.20 (t, J = 53 Hz, 1H), 4.53-4.49 (m, 6H), 4.15-4.13 (m, 2H), 3.53-3.43 (m, 1H), 2.86 (dd, J = 8.0, 12.1 Hz, 2H), 2.68 (s, 2H), 1.38-1.16 (m, 4H). m/z 480 (M + H)$^+$. | Example 17 |
| 136 | $^1$H NMR (400 MHz, DMSO) d 7.79-7.79 (m, 1H), 7.72 (dd, J = 2.4, 8.5 Hz, 1H), 7.56 (dd, J = 2.1, 8.5 Hz, 1H), 4.81-4.57 (m, 4H), 4.31 (s, 1H), 4.19 (s, 1H), 3.92 (s, 1H), 3.79 (s, 1H), 3.74-3.65 (m, 1H), 2.63-2.54 (m, 4H), 1.52-1.40 (m, 3H), 1.32-1.24 (m, 2H), 0.71-0.65 (m, 4H). m/z 470 (M + H)$^+$. | Example 17 |
| 137 | $^1$H NMR (400 MHz, DMSO) d 7.72-7.68 (m, 2H), 7.53 (d, J = 8.8 Hz, 1H), 4.90-4.80 (m, 1H), 4.70-4.60 (m, 1H), 4.50 (s, 2H), 4.38 (s, 2H), 4.16 (s, 1H), 4.04 (s, 1H), 3.66 (dd, J = 8.2, 8.2 Hz, 1H), 2.64-2.54 (m, 4H), 2.31-2.10 (m, 1H), 0.87-0.79 (m, 4H). m/z 480 (M + H)$^+$. | Example 17 |
| 138 | $^1$H NMR (400 MHz, CDCl$_3$) d 7.63-7.56 (m, 1H), 7.55 (d, J = 2.1 Hz, 1H), 7.25-7.18 (m, 1H), 6.2 (t, J = 52 Hz, 1H), 4.90-4.75 (m, 2H), 4.74-4.62 (m, 2H), 4.36-4.29 (m, 2H), 4.08 (s, 1H), 4.01 (s, 1H), 3.53-3.44 (m, 1H), 2.89-2.82 (m, 2H), 2.68 (s, 2H), 1.43-1.34 (m, 1H), 0.97-0.91 (m, 2H), 0.77-0.70 (m, 2H). m/z 462 (M + H)$^+$. | Example 17 |
| 147 | $^1$H NMR (400 MHz, DMSO) d 7.74 (d, J = 2.3 Hz, 1H), 7.68 (d, J = 8.7 Hz, 1H), 7.51 (d, J = 8.5 Hz, 1H), 4.90-4.80 (m, 1H), 4.61-4.30 (m, 6H), 4.02 (s, 1H), 3.90 (s, 1H), 3.69-3.60 (m, 1H), 2.52-2.48 (m, 4H), 1.28-1.16 (m, 10H). m/z 488 (M + H)$^+$. | Example 17 |
| 153 | $^1$H NMR (400 MHz, DMSO) d 7.74 (d, J = 2.3 Hz, 1H), 7.68 (d, J = 8.7 Hz, 1H), 7.51 (d, J = 8.5 Hz, 1H), 4.90-4.80 (m, 1H), 4.61-4.30 (m, 6H), 4.02 (s, 1H), 3.90 (s, 1H), 3.69-3.60 (m, 1H), 2.52-2.48 (m, 4H), 1.28-1.16 (m, 10H). m/z 471 (M + H)$^+$. | Example 17 |

TABLE 11

Compound Nos. to 132 to 133, 135, 139, 144 to 146, 148 to 152, 154, 155

| Cpd. No. | Synthesis Method |
|---|---|
| 132 | Example 17 |
| 133 | Example 17 |
| 135 | Example 17 |
| 139 | Example 17 |
| 144 | Examples 17 and 11 |
| 145 | Examples 17 and 11 |
| 146 | Examples 17 and 11 |
| 148 | Examples 17 and 11 |
| 149 | Examples 17 and 11 |
| 150 | Examples 17 and 11 |
| 151 | Examples 17 and 11 |
| 152 | Examples 17 and 11 |
| 154 | Examples 17 and 11 |
| 155 | Examples 17 and 11 |

Example 18

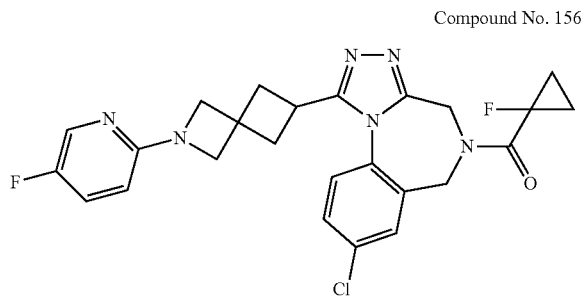 [SMILES: O=C(N1Cc2cc(Cl)ccc2-n2c(nnc2C2CC3(C2)CN(c2ccc(F)cn2)C3)C1)C1(F)CC1]

Compound No. 156

The title compound was prepared by using 8-chloro-1-(2-(5-fluoropyridin-2-yl)-2-azaspiro[3.3]heptan-6-yl)-5,6-dihydro-4H-benzo[f][1,2,4]triazolo[4,3-a][1,4]diazepine from Example 10 and treating in the manner of Example 17 (19.8 mg, 52% yield). $^1$H NMR (400 MHz, DMSO) δ 8.00 (d, J=2.9 Hz, 1H), 7.70-7.67 (m, 2H), 7.56-7.53 (m, 1H), 7.42-7.37 (m, 1H), 6.36 (dd, J=3.5, 9.2 Hz, 1H), 4.71 (s, 2H), 4.55 (s, 2H), 4.01 (s, 2H), 3.91 (s, 2H), 3.75-3.67 (m, 1H), 2.64 (d, J=8.2 Hz, 4H), 1.47-1.27 (m, 4H). m/z 497 (M+H)$^+$.

Compounds 157 to 162

Compound Nos. 157 to 162 were prepared according to the methods set forth in Example 18. For example, Compound No. 157 of Table 12 lists the method of "Example 18", indicating that this compound was prepared according to the procedure of Example 18 using appropriately substituted intermediates. Analytical data (NMR, mass spectrum) is also presented in Table 12.

TABLE 12

Compound Nos. 157 to 162

| Compound No. | Analytical Data | Synthesis Method |
|---|---|---|
| 157 | $^1$H NMR (400 MHz, DMSO) δ 8.35 (2H, d, J = 2.6 Hz), 7.76 (1H, s), 7.66 (1H, dd, J = 3.3, 8.5 Hz), 7.51 (1H, d, J = 9.8 Hz), 4.61 (2H, s), 4.43 (2H, s), 4.13 (2H, s), 4.01 (2H, s), 3.70 (1H, ddd, J = 10.1, 10.1, 10.1 Hz), 2.64 (4H, d, J = 8.5 Hz), 1.11 (3H, t, J = 7.5 Hz); (2H obscured by DMSO peak). m/z 468 (M + H)$^+$ | Example 18 |
| 158 | $^1$H NMR (400 MHz, DMSO) δ 8.00 (d, J = 3.0 Hz, 1H), 7.75 (s, 1H), 7.67 (dd, J = 2.4, 8.5 Hz, 1H), 7.53 (d, J = 8.7 Hz, 1H), 7.43-7.37 (m, 1H), 6.37 (dd, J = 3.4, 8.9 Hz, 1H), 5.12-4.93 (m, 1H), 4.78 (s, 1H), 4.67-4.63 (m, 2H), 4.48-4.45 (m, 1H), 4.01 (s, 2H), 3.91 (s, 2H), 3.72-3.68 (m, 1H), 2.69-2.55 (m, 4H), 2.35-2.32 (m, 1H), 1.70-1.59 (m, 1H), 1.20-1.09 (m, 1H). m/z 497 (M + H)$^+$. | Example 18 |
| 159 | $^1$H NMR (400 MHz, DMSO) δ 8.00 (d, J = 3.0 Hz, 1H), 7.76 (s, 1H), 7.65 (dd, J = 2.2, 8.3 Hz, 1H), 7.52 (d, J = 8.5 Hz, 1H), 7.40-7.37 (m, 1H), 6.36 (dd, J = 3.2, 8.7 Hz, 1H), 4.94-4.79 (m, 1H), 4.78-4.51 (m, 4H), 4.01 (s, 2H), 3.90 (s, 2H), 3.74-3.66 (m, 1H), 2.80-2.69 (m, 1H), 2.65-2.62 (m, 4H), 1.56-1.46 (m, 1H), 1.27-1.20 (m, 1H). m/z 497 (M + H)$^+$. | Example 18 |
| 160 | $^1$H NMR (400 MHz, DMSO) δ 7.99 (d, J = 3.0 Hz, 1H), 7.74-7.74 (m, 1H), 7.66 (dd, J = 2.4, 8.5 Hz, 1H), 7.51 (d, J = 8.7 Hz, 1H), 7.42-7.37 (m, 1H), 6.36 (dd, J = 3.5, 9.0 Hz, 1H), 4.84-4.71 (m, 4H), 4.52-4.49 (m, 2H), 4.36-4.25 (m, 3H), 4.01 (s, 2H), 3.90 (s, 2H), 3.71-3.67 (m, 1H), 2.63 (d, J = 8.0 Hz, 4H). m/z 495 (M + H)$^+$. | Example 18 |
| 161 | $^1$H NMR (400 MHz, DMSO) δ 8.35 (d, J = 2.6 Hz, 2H), 7.76 (s, 1H), 7.66 (dd, J = 3.3, 8.5 Hz, 1H), 7.51 (d, J = 9.8 Hz, 1H), 4.61 (s, 2H), 4.43 (s, 2H), 4.13 (s, 2H), 4.01 (s, 2H), 3.71-3.67 (m, 1H), 2.64 (d, J = 8.5 Hz, 4H), 2.57-2.53 (m, 2H), 1.11 (t, J = 7.5 Hz, 3H). m/z 468 (M + H)$^+$ | Example 18 |
| 162 | $^1$H NMR (400 MHz, DMSO) δ 7.68-7.64 (m, 2H), 7.49 (d, J = 8.3 Hz, 1H), 4.52 (s, 2H), 4.35 (s, 2H), 4.09-4.01 (m, 4H), 3.73 (s, 3H), 3.68-3.63 (m, 1H), 2.60 (d, J = 8.0 Hz, 4H), 1.52-1.45 (m, 1H), 0.71-0.68 (m, 4H); m/z 442 (M + H)$^+$. | Example 18 |

Example 19

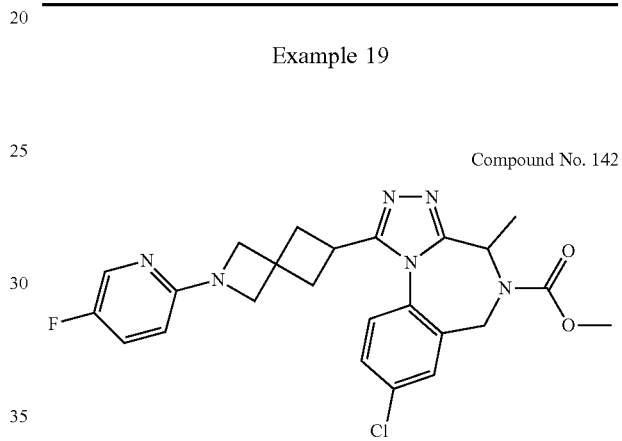

Compound No. 142

Step 1: Synthesis of methyl (5-chloro-2-nitrobenzyl)alaninate

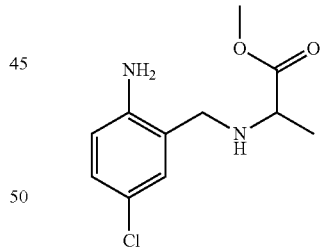

To a solution of 5-chloro-2-nitrobenzaldehyde (2 g, 10.78 mmol, 1.0 eq.) in DCM (30 mL) was added DL-Alanine methyl ester hydrochloride (1.5 g, 10.78 mmol, 1.0 eq.), trimethylamine (1.1 g, 10.78 mmol, 1.0 eq.) and sodium triacetoxyborohydride (4.6 g, 21.56 mmol, 2.0 eq.). The resulting solution was stirred at RT for 1 hour, diluted with DCM, washed with an aq. sol. of sat. NaHCO$_3$, dried, concentrated in vacuo. The residue was purified by flash column chromatography eluting with 50-100% EtOAc in isohexane to give the title compound as a light yellow oil (1.23 g, 42% yield). $^1$H NMR (400 MHz, CDCl$_3$) δ 7.94-7.91 (m, 1H), 7.72 (d, J=2.3 Hz, 1H), 7.40-7.36 (m, 1H), 4.15-4.09 (m, 1H), 3.99-3.94 (m, 1H), 3.73-3.72 (m, 3H), 3.40-3.37 (m, 1H), 1.36-1.33 (m, 3H).

Step 2: Synthesis of 7-chloro-3-methyl-1,3,4,5-tetrahydro-2H-benzo[e][1,4]diazepin-2-one

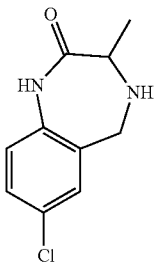

To a solution of methyl (5-chloro-2-nitrobenzyl)alaninate (1.23 g, 4.51 mmol, 1.0 eq.) in acetic acid (30 mL) was added iron (0.63 g, 11.28 mmol, 2.5 eq.). The resulting suspension was heated at 110° C. for 30 minutes, cooled to RT and filtered through celite rinsing with acetic acid. The filtrate was partitioned between aq. sol. of sat. NaHCO$_3$ and EtOAc and the organic phase was dried and concentrated in vacuo. The residue was triturated with diethyl ether to give the title compound as a light brown solid (0.70 g, 57% yield). $^1$H NMR (400 MHz, CDCl$_3$) δ 7.85-7.79 (m, 1H), 7.25-7.23 (m, 1H), 6.93-6.88 (m, 1H), 4.09 (d, J=13.4 Hz, 1H), 3.87 (d, J=13.1 Hz, 1H), 3.57 (q, J=6.6 Hz, 1H), 1.31 (d, J=6.6 Hz, 3H).

Step 3: Synthesis of tert-butyl 7-chloro-3-methyl-2-oxo-1,2,3,5-tetrahydro-4H-benzo[e][1,4]diazepine-4-carboxylate

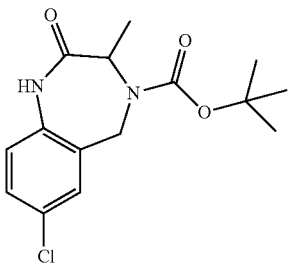 [SMILES: CC1C(=O)Nc2ccc(Cl)cc2CN1C(=O)OC(C)(C)C]

To a cooled suspension of 7-chloro-3-methyl-1,3,4,5-tetrahydro-2H-benzo[e][1,4]diazepin-2-one (2.07 g, 9.82 mmol, 1.0 eq.) in THF (20 mL) at 0° C. was added a solution of di-tert-butyl dicarbonate (3.21 g, 14.73 mmol, 1.5 eq.) in THF (10 mL) dropwise over 10 minutes. Mixture was allowed to warm to RT and stirred overnight. The mixture was concentrated in vacuo and triturated with diisopropyl ether to afford the title compound as a light brown solid (2.93 g, 96% yield). $^1$H NMR (400 MHz, CDCl$_3$) δ 8.02 (s, 1H), 7.23-7.17 (m, 1H), 6.84-6.80 (m, 1H), 5.21-4.19 (m, 3H), 1.54-1.50 (m, 3H), 1.41 (s, 9H).

Step 4: Synthesis of tert-butyl 7-chloro-3-methyl-2-thioxo-1,2,3,5-tetrahydro-4H-benzo[e][1,4]diazepine-4-carboxylate

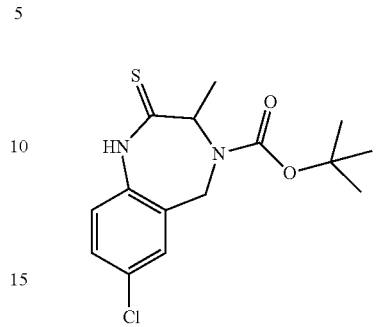

To a suspension of tert-butyl 7-chloro-3-methyl-2-oxo-1,2,3,5-tetrahydro-4H-benzo[e][1,4]diazepine-4-carboxylate (0.95 g, 3.06 mmol, 1.0 eq.) in THF (10 mL) was added 2,4-bis(4-methoxyphenyl)-2,4-dithioxo-1,3,2,4-dithiadiphosphetane (0.74 g, 1.83 mmol, 0.60 eq.) and the mixture was heated to reflux for 90 minutes. The mixture was allowed to cool, concentrated in vacuo. The residue was purified by flash column chromatography eluting with 90-100% EtOAc in isohexane to give the title compound as a light yellow solid (1.02 g, 100% yield). $^1$H NMR (400 MHz, CDCl$_3$) δ 9.34-9.34 (m, 1H), 7.25-7.23 (m, 1H), 6.90-6.87 (m, 1H), 5.52-5.43 (m, 1H), 4.67-4.51 (m, 2H), 1.48-1.41 (m, 12H).

Step 5: Synthesis of tert-butyl 8-chloro-1-(2-(5-fluoropyridin-2-yl)-2-azaspiro[3.3]heptan-6-yl)-4-methyl-4H-benzo[f][1,2,4]triazolo[4,3-a][1,4]diazepine-5(6H)-carboxylate

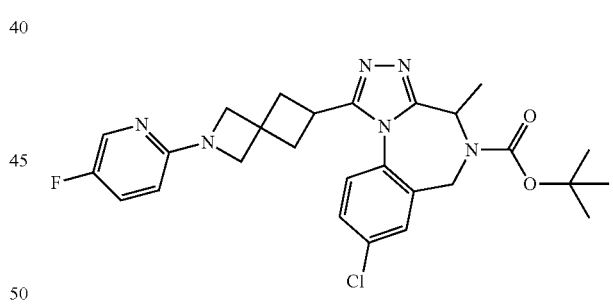

To a solution of tert-butyl 7-chloro-3-methyl-2-thioxo-1,2,3,5-tetrahydro-4H-benzo[e][1,4]diazepine-4-carboxylate (0.3 g, 0.92 mmol, 1.0 eq.), was added 2-(4-fluoropyridin-2-yl)-2-azaspiro[3.3]heptane-6-carbohydrazide (0.25 g, 1.01 mmol, 1.1 eq.) in dioxane (5 mL) and the mixture was heated to 90° C. for 36 hours. The mixture was allowed to cool and was concentrated in vacuo. The residue was purified by flash column chromatography eluting with 90-100% EtOAc in isohexane then 0-10% MeOH in DCM to give the title product as a brown foam (0.31 g, 64% yield). $^1$H NMR (400 MHz, CDCl$_3$) δ 7.99 (d, J=2.5 Hz, 1H), 7.56-7.48 (m, 2H), 7.26-7.16 (m, 2H), 6.23 (dd, J=3.4, 9.0 Hz, 1H), 5.57-5.51 (m, 1H), 5.06-4.75 (m, 1H), 4.14-3.97 (m, 4H), 3.81-3.61 (m, 1H), 3.56-3.45 (m, 1H), 2.93-2.47 (m, 4H), 1.49 (s, 9H), 1.16-1.03 (m, 3H).

Step 6: Synthesis of methyl 8-chloro-1-(2-(5-fluoro-pyridin-2-yl)-2-azaspiro[3.3]heptan-6-yl)-4-methyl-4H-benzo[f][1,2,4]triazolo[4,3-a][1,4]diazepine-5(6H)-carboxylate (Compound No. 142)

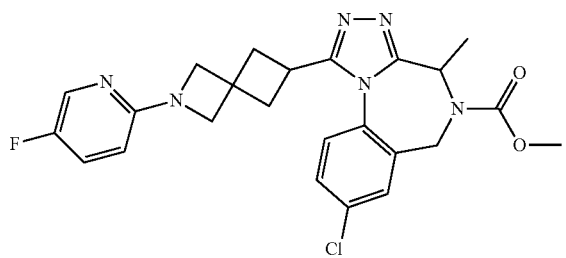 [SMILES: COC(=O)N1Cc2cc(Cl)ccc2-n2c(C3CC4(C3)CN(c3ccc(F)cn3)C4)nnc2C1C]

To a solution of tert-butyl 8-chloro-1-(2-(5-fluoropyridin-2-yl)-2-azaspiro[3.3]heptan-6-yl)-4-methyl-4H-benzo[f][1,2,4]triazolo[4,3-a][1,4]diazepine-5(6H)-carboxylate (1.10 g, 4.31 mmol, 1.0 eq.) in MeOH (3 mL) was added 4 M HCl in dioxane (1.5 mL, 5.90 mmol, 10.0 eq.) and the mixture was stirred at RT for 1 hour. The mixture was concentrated in vacuo to give a light brown solid. To a solution of the light brown solid (137 mg, 0.29 mmol, 1.0 eq.) and Et$_3$N (0.15 mL, 1.04 mmol, 3.5 eq.) at 0° C. in THF (3 mL) was added methyl chloroformate (0.034 mL, 0.45 mmol, 1.5 eq.) dropwise. The resulting solution was stirred at RT for 1 hour, diluted with EtOAc, washed with an aq. sol. of sat. NaHCO$_3$, and dried. The mixture was concentrated in vacuo and the residue was purified by preparative HPLC to give the title compound as an off-white solid (49 mg, 34% yield). $^1$H NMR (400 MHz, DMSO-d$_6$) δ 8.03 (d, J=3.0 Hz, 1H), 7.76-7.72 (m, 1H), 7.70 (dd, J=2.4, 8.5 Hz, 1H), 7.59 (d, J=8.5 Hz, 1H), 7.51-7.45 (m, 1H), 6.39 (dd, J=3.6, 9.1 Hz, 1H), 5.39-5.31 (m, 1H), 4.85-4.72 (m, 1H), 3.98 (m, 3H), 3.88-3.81 (m, 2H), 3.71 (m, 4H), 2.69-2.67 (m, 2H), 2.49-2.41 (m, 2H), 1.10-1.06 (m, 3H); m/z 483 (M+H)$^+$.

Compounds 140, 141, 143, and 163 to 173

Compound Nos. 163 to 173 were prepared according to the methods set forth in Example 19. For example, Compound No. 163 of Table 13 lists the method of "Example 19", indicating that this compound was prepared according to the procedure of Example 19 using appropriately substituted intermediates. Analytical data (NMR, mass spectrum) is also presented in Table 13.

Compound Nos. to 140, 141, and 143 are prepared according to the procedures of Examples 19 using appropriately substituted intermediates.

TABLE 13

Compound Nos. 163 to 173

| Compound No. | Analytical Data | Synthesis Method |
|---|---|---|
| 163 | $^1$H NMR (400 MHz, CDCl$_3$) δ 8.00 (d, J = 2.8 Hz, 1H), 7.57-7.54 (m, 1H), 7.52 (dd, J = 2.0, 8.3 Hz, 1H), 7.25-7.17 (m, 2H), 6.24 (dd, J = 3.4, 9.0 Hz, 1H), 5.65-5.58 (m, 1H), 5.10-5.05 (m, 1H), 5.04-4.94 (m, 1H), 4.10-3.98 (m, 4H), 3.90-3.68 (m, 1H), 3.53-3.45 (m, 1H), 2.95-2.77 (m, 3H), 2.55-2.52 (m, 1H), 1.33-1.27 (m, 6H), 1.13-1.10 (m, 3H); m/z 511 (M + H)$^+$. | Example 19 |
| 164 | $^1$H NMR (400 MHz, CDCl$_3$) δ 8.01 (dd, J = 1.5, 2.6 Hz, 1H), 7.85 (d, J = 2.8 Hz, 1H), 7.77 (d, J = 1.5 Hz, 1H), 7.61-7.52 (m, 2H), 7.18 (d, J = 8.5 Hz, 1H), 5.65-5.55 (m, 1H), 5.11-4.94 (m, 2H), 4.20-4.12 (m, 4H), 3.77-3.72 (m, 1H), 3.55-3.46 (m, 1H), 2.98-2.81 (m, 3H), 2.60-2.51 (m, 1H), 1.34-1.27 (m, 6H), 1.13-1.09 (m, 3H); m/z 494 (M + H)$^+$. | Example 19 |
| 165 | $^1$H NMR (400 MHz, CDCl$_3$) δ 8.01 (dd, J = 1.5, 2.8 Hz, 1H), 7.85 (d, J = 2.8 Hz, 1H), 7.77 (d, J = 1.4 Hz, 1H), 7.53 (dd, J = 1.9, 8.3 Hz, 2H), 7.18 (d, J = 8.5 Hz, 1H), 5.71-5.49 (m, 1H), 5.17-4.91 (m, 1H), 4.20-4.12 (m, 4H), 3.91-3.82 (m, 1H), 3.79 (s, 3H), 3.54-3.46 (m, 1H), 2.97-2.83 (m, 3H), 2.62 (s, 1H), 1.15-1.13 (m, 3H); m/z 466 (M + H)$^+$. | Example 19 |
| 166 | $^1$H NMR (400 MHz, CDCl$_3$) δ 8.30 (d, J = 4.8 Hz, 2H), 7.57-7.51 (m, 2H), 7.20 (d, J = 8.5 Hz, 1H), 6.53 (t, J = 4.8 Hz, 1H), 5.67-5.53 (m, 1H), 5.11-4.93 (m, 1H), 4.24-4.13 (m, 4H), 3.91-3.81 (m, 1H), 3.78 (s, 3H), 3.56-3.46 (m, 1H), 2.97-2.82 (m, 3H), 2.54-2.53 (m, 1H), 1.15-1.12 (m, 3H); m/z 466 (M + H)$^+$. | Example 19 |
| 167 | $^1$H NMR (400 MHz, CDCl$_3$) δ 8.30 (d, J = 4.5 Hz, 2H), 7.56-7.50 (m, 2H), 7.20 (d, J = 8.6 Hz, 1H), 6.53 (dd, J = 4.7, 4.7 Hz, 1H), 5.67-5.61 (m, 1H), 5.19-4.91 (m, 2H), 4.27-4.17 (m, 2H), 4.13 (s, 2H), 3.82-3.75 (m, 1H), 3.56-3.46 (m, 1H), 2.97-2.79 (m, 3H), 2.57-2.49 (m, 1H), 1.32-1.29 (m, 6H), 1.19-1.05 (m, 3H); m/z 494 (M + H)$^+$. | Example 19 |
| 168 | $^1$H NMR (400 MHz, CDCl$_3$) δ 8.32-8.28 (m, 2H), 7.60-7.51 (m, 2H), 7.20 (d, J = 8.1 Hz, 1H), 6.55-6.51 (m, 1H), 5.61-5.55 (m, 1H), 5.10-5.01 (m, 1H), 4.27-4.11 (m, 4H), 4.12 (s, 2H), 3.84-3.80 (m, 1H), 3.51-3.49 (m, 1H), 2.97-2.80 (m, 3H), 2.56-2.53 (m, 1H), 1.32-1.30 (m, 3H), 1.20-1.05 (m, 3H); m/z 480 (M + H)$^+$. | Example 19 |
| 169 | $^1$H NMR (400 MHz, CDCl$_3$) δ 8.00 (d, J = 2.9 Hz, 1H), 7.55-7.50 (m, 2H), 7.25-7.17 (m, 2H), 6.24 (dd, J = 3.3, 9.0 Hz, 1H), 5.61-5.56 (m, 1H), 5.10-5.01 (m, 1H), 4.26-4.18 (m, 2H), 4.10-3.98 (m, 4H), 3.91-3.68 (m, 1H), 3.55-3.45 (m, 1H), 2.94-2.78 (m, 3H), 2.58-2.49 (m, 1H), 1.31 (t, J = 7.1 Hz, 3H), 1.18-1.08 (m, 3H); m/z 497 (M + H)$^+$. | Example 19 |
| 170 | $^1$H NMR (400 MHz, DMSO-d$_6$) δ 8.43 (s, 2H), 7.76-7.72 (m, 1H), 7.69 (dd, J = 2.4, 8.5 Hz, 1H), 7.59 (d, J = 8.5 Hz, 1H), 5.41-5.33 (m, 1H), 4.89-4.68 (m, 1H), 4.14-4.06 (m, 2H), 4.00-3.95 (m, 3H), 3.72-3.69 (m, 4H), 2.73-2.68 (m, 2H), 2.51-2.39 (m, 2H), 1.15-1.05 (m, 3H); m/z 484 (M + H)$^+$. | Example 19 |
| 171 | $^1$H NMR (400 MHz, CDCl$_3$) δ 8.31-8.30 (m, 2H), 7.58-7.51 (m, 2H), 7.21-7.18 (m, 1H), 6.53 (t, J = 4.8 Hz, 1H), 5.56-5.51 (m, 1H), 5.06-4.66 (m, 1H), 4.24-4.12 (m, 5H), 3.80-3.77 (m, 1H), 3.56-3.46 (m, 1H), 2.97-2.53 (m, 4H), 1.31-1.06 (m, 3H), 0.74 (d, J = 5.9 Hz, 4H); m/z 492 (M + H)$^+$. | Example 19 |
| 172 | $^1$H NMR (400 MHz, CDCl$_3$) δ 8.20-8.19 (m, 2H), 7.55-7.50 (m, 2H), 7.21-7.18 (m, 1H), 5.66-5.60 (m, 1H), 5.02-4.77 (m, 1H), 4.24-4.10 (m, 6H), 3.84-3.74 (m, 1H), 3.56-3.45 (m, 1H), 2.96-2.78 | Example 19 |

TABLE 13-continued

Compound Nos. 163 to 173

| Compound No. | Analytical Data | Synthesis Method |
|---|---|---|
| | (m, 3H), 2.54-2.51 (m, 1H), 1.35-1.11 (m, 6H); m/z 498 (M + H)⁺. | |
| 173 | ¹H NMR (400 MHz, CDCl₃) δ 8.19-8.19 (m, 2H), 7.58-7.50 (m, 2H), 7.21-7.16 (m, 1H), 5.58-5.52 (m, 1H), 5.07-4.72 (m, 1H), 4.21-4.09 (m, 4H), 3.78-3.68 (m, 1H), 3.54-3.46 (m, 1H), 2.96-2.77 (m, 3H), 2.52-2.47 (m, 1H), 1.58 (s, 3H), 1.05-0.64 (m, 7H); m/z 524 (M + H)⁺. | Example 19 |

Example 20

Compound No. 174

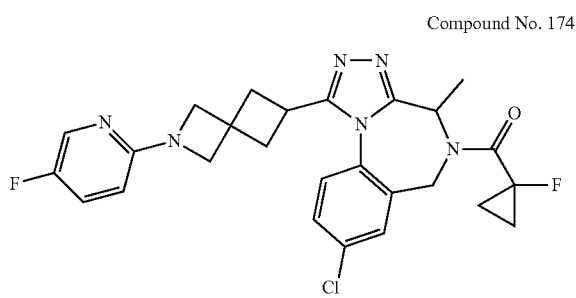 [SMILES: CC1c2nnc(C3CC4(C3)CN(c3ccc(F)cn3)C4)n2-c2ccc(Cl)cc2CN1C(=O)C1(F)CC1]

To a solution of tert-butyl 8-chloro-1-(2-(5-fluoropyridin-2-yl)-2-azaspiro[3.3]heptan-6-yl)-4-methyl-4H-benzo[f][1,2,4]triazolo[4,3-a][1,4]diazepine-5(6H)-carboxylate (1.10 g, 4.31 mmol, 1.0 eq.) in MeOH (3 mL) was added 4 M HCl in dioxane (1.5 mL, 5.90 mmol, 10.0 eq.) and the mixture was stirred at RT for 1 hour. The mixture was concentrated in vacuo to give a light brown solid. To a solution of the light brown solid (137 mg, 0.29 mmol, 1.0 eq.) in DMF (3 mL) was added 1-fluorocyclopropane-1-carboxylic acid (37 mg, 0.36 mmol, 1.2 eq.), HOBt (8 mg, 0.059 mmol, 0.2 eq.), EDCl.HCl (74 mg, 0.39 mmol, 1.3 eq.), DIPEA (181 μL, 1.04 mmol, 3.5 eq.) and the mixture was stirred at RT overnight. The mixture was partitioned between aq. sol. of sat. NaHCO₃ and DCM and the organic phase was dried and concentrated in vacuo. The residue was purified by preparative HPLC to give the title compound as an off-white solid (61 mg, 40% yield). ¹H NMR (400 MHz, DMSO-d₆) δ 8.08 (d, J=3.0 Hz, 1H), 7.79 (dd, J=2.3, 8.5 Hz, 2H), 7.69 (d, J=8.5 Hz, 1H), 7.56-7.50 (m, 1H), 6.45 (dd, J=3.6, 9.1 Hz, 1H), 5.66-5.61 (m, 1H), 5.11-5.07 (m, 1H), 4.28-4.24 (m, 1H), 4.08-3.99 (m, 2H), 3.91 (q, J=8.4 Hz, 2H), 3.82-3.74 (m, 1H), 2.85-2.80 (m, 2H), 2.53-2.43 (m, 2H), 1.56-1.45 (m, 2H), 1.41-1.32 (m, 2H), 1.07-1.03 (m, 3H); m/z 511 (M+H)⁺.

Compound 175

Compound No. 18-2 was prepared according to the methods set forth in Example 20. For example, Compound No. 20-2 of Table 14 lists the method of "Example 20", indicating that this compound was prepared according to the procedure of Example 20 using appropriately substituted intermediates. Analytical data (NMR, mass spectrum): ¹H NMR (400 MHz, CDCl₃) δ 8.30 (d, J=4.9 Hz, 2H), 7.60-7.55 (m, 2H), 7.26-7.23 (m, 1H), 6.54 (t, J=4.8 Hz, 1H), 6.01-5.88 (m, 1H), 5.16-5.13 (m, 1H), 4.27-4.13 (m, 4H), 4.08-3.92 (m, 1H), 3.58-3.50 (m, 1H), 2.97 (dd, J=8.3, 11.7 Hz, 1H), 2.83 (dd, J=8.7, 11.7 Hz, 2H), 2.62-2.49 (m, 1H), 1.53-1.24 (m, 4H), 1.20-1.06 (m, 3H); m/z 494 (M+H)⁺.

Example 21

Compound No. 176

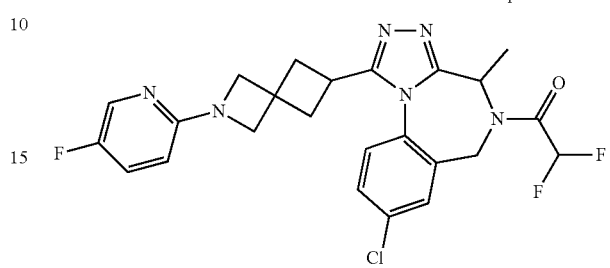

To a solution of tert-butyl 8-chloro-1-(2-(5-fluoropyridin-2-yl)-2-azaspiro[3.3]heptan-6-yl)-4-methyl-4H-benzo[f][1,2,4]triazolo[4,3-a][1,4]diazepine-5(6H)-carboxylate (1.10 g, 4.31 mmol, 1.0 eq.) in MeOH (3 mL) was added 4 M HCl in dioxane (1.5 mL, 5.90 mmol, 10.0 eq.) and the mixture was stirred at RT for 1 hour. The mixture was concentrated in vacuo to give a light brown solid. To a solution of the light brown solid (60 mg, 0.14 mmol, 1.0 eq.) in DMF (1 mL) was added difluoroacetic acid (13 μL, 0.21 mmol, 1.5 eq.), HATU (80 mg, 0.21 mmol, 1.5 eq.), DIPEA (37 μL, 0.21 mmol, 1.5 eq.) and the mixture was stirred at RT overnight. The mixture was partitioned between aq. sol. of sat. NaHCO₃ and DCM and the organic phase was dried and concentrated in vacuo. The residue was purified by preparative HPLC to give the title compound as an off-white solid (11 mg, 15% yield). ¹H NMR (400 MHz, DMSO-d₆) δ 8.04 (d, J=3.0 Hz, 1H), 7.88 (d, J=2.4 Hz, 1H), 7.75 (dd, J=2.4, 8.5 Hz, 1H), 7.63 (d, J=8.5 Hz, 1H), 7.51-7.45 (m, 1H), 7.04 (t, J=52.2 Hz, 1H), 6.40 (dd, J=3.5, 9.0 Hz, 1H), 5.63-5.57 (m, 1H), 4.84 (d, J=14.9 Hz, 1H), 4.15 (d, J=14.2 Hz, 1H), 4.04-3.94 (m, 2H), 3.90-3.82 (m, 2H), 3.78-3.68 (m, 1H), 2.80-2.68 (m, 2H), 2.53-2.48 (m, 1H), 2.39-2.34 (m, 1H), 0.96-0.95 (m, 3H); m/z 503 (M+H)⁺.

Compound Nos. 177 to 178

Compound Nos. 177 to 178 were prepared according to the methods set forth in Example 21. For example, Compound No. 177 of Table 15 lists the method of "Example 21", indicating that this compound was prepared according to the procedure of Example 21 using appropriately substituted intermediates. Analytical data (NMR, mass spectrum) is also presented in Table 15.

TABLE 15

Compound Nos. 177 to 178

| Compound No. | Analytical Data | Synthesis Method |
|---|---|---|
| 177 | ¹H NMR (400 MHz, CDCl₃) δ 8.01 (dd, J = 1.5, 2.8 Hz, 1H), 7.85 (d, J = 2.8 Hz, 1H), 7.78 (d, J = 1.5 Hz, 1H), 7.57 (d, J = 7.0 Hz, 2H), 7.26-7.23 (m, 1H), 6.01-5.97 (m, 1H), 5.19-5.07 (m, 1H), 4.22-4.13 (m, 4H), 4.10-4.01 (m, 1H), 3.57-3.50 (m, 1H), 3.00-2.81 (m, 3H), 2.60-2.52 (m, 1H), 1.60-1.26 (m, 4H), 1.19-1.10 (m, 3H); m/z 494 (M + H)⁺. | Example 21 |

TABLE 15-continued

Compound Nos. 177 to 178

| Compound No. | Analytical Data | Synthesis Method |
|---|---|---|
| 178 | $^1$H NMR (400 MHz, CDCl$_3$) δ 8.00 (d, J = 3.0 Hz, 1H), 7.56 (d, J = 6.9 Hz, 2H), 7.25-7.19 (m, 2H), 6.24 (dd, J = 3.5, 9.0 Hz, 1H), 5.99-5.94 (m, 1H), 5.35-5.29 (m, 1H), 4.12-3.99 (m, 4H), 3.91-3.80 (m, 1H), 3.57-3.49 (m, 1H), 2.97-2.76 (m, 3H), 2.51-2.49 (m, 1H), 1.76-1.65 (m, 6H), 1.13-1.01 (m, 3H); m/z 513 (M + H)$^+$. | Example 21 |

Example 22

Compound No. 179

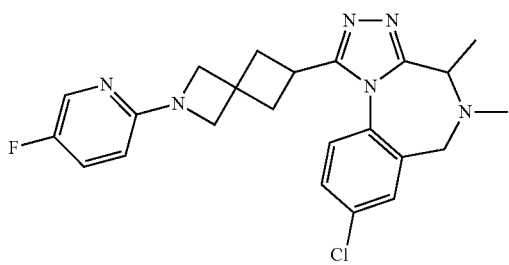

To a solution of 8-chloro-1-(2-(5-fluoropyridin-2-yl)-2-azaspiro[3.3]heptan-6-yl)-4-methyl-5,6-dihydro-4H-benzo[f][1,2,4]triazolo[4,3-a][1,4]diazepine (88 mg, 0.19 mmol, 1.0 eq.) in DCM (2 mL) was added a 37% formaldehyde aq. (0.043 mL, 0.57 mmol, 3.0 eq.), acetic acid (0.1 mL) and sodium triacetoxyborohydride (81 mg, 0.38 mmol, 2.0 eq.). The resulting solution was stirred at RT for 16 hours, diluted with DCM, washed with an aq. sol. of sat. NaHCO$_3$, dried, concentrated in vacuo to give the title compound as an off-white solid (43 mg, 50% yield). $^1$H NMR (400 MHz, CDCl$_3$) δ 7.99 (d, J=2.9 Hz, 1H), 7.49 (dd, J=2.3, 8.4 Hz, 1H), 7.43 (d, J=2.3 Hz, 1H), 7.25-7.19 (m, 1H), 7.15 (d, J=8.4 Hz, 1H), 6.23 (dd, J=3.5, 9.0 Hz, 1H), 4.10-4.03 (m, 2H), 4.00 (s, 2H), 3.51-3.44 (m, 3H), 3.31-3.27 (m, 1H), 2.90-2.76 (m, 3H), 2.55-2.48 (m, 1H), 2.41 (s, 3H); m/z 439 (M+H)$^+$.

Compound Nos. 22 and 23

Compound Nos. 22 and 23 are prepared according to the procedure of Example 22 using appropriately substituted intermediates.

Example 23

Compound No. 180

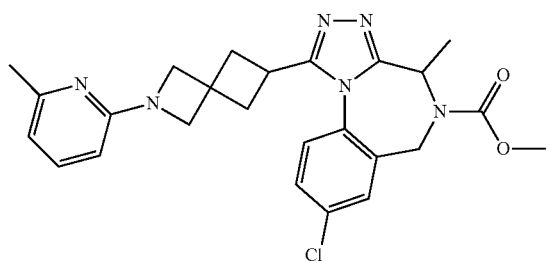

To a solution of methyl 1-(2-(tert-butoxycarbonyl)-2-azaspiro[3.3]heptan-6-yl)-8-chloro-4-methyl-4H-benzo[f][1,2,4]triazolo[4,3-a][1,4]diazepine-5(6H)-carboxylate (0.25 g, 0.51 mmol, 1.0 eq.) in DCM (15 mL) was added TFA (1.1 mL, 14.4 mmol, 28.1 eq.) and the mixture was stirred at RT for 1 hour. Toluene was added and the mixture was concentrated in vacuo to give a light yellow oil. A mixture of the light yellow oil (50 mg, 0.13 mmol, 1.0 eq.), 2-bromo-6-methylpyridine (0.015 mL, 0.13 mmol, 1.0 eq.), RuPhos (12 mg, 0.03 mmol, 0.20 eq.), palladium acetate (3 mg, 0.01 mmol, 0.10 eq.), cesium carbonate (0.126 g, 0.39 mmol, 3.0 eq.) in dioxane (3 mL) was degassed using N$_2$, for 10 minutes and then heated to 80° C. for 2 hours. The mixture was allowed to cool to RT and partitioned between water and EtOAc. The organic phase was dried and concentrated in vacuo and the residue was purified by preparative HPLC to give the title compound as an off-white solid (8 mg, 13% yield). $^1$H NMR (400 MHz, CDCl$_3$) δ 7.55-7.50 (m, 2H), 7.37-7.31 (m, 1H), 7.21-7.17 (m, 1H), 6.46 (d, J=7.4 Hz, 1H), 6.11-6.07 (m, 1H), 5.62-5.54 (m, 1H), 5.01-4.78 (m, 1H), 4.16-4.00 (m, 4H), 3.88-3.79 (m, 4H), 3.53-3.44 (m, 1H), 2.92-2.77 (m, 3H), 2.55-2.49 (m, 1H), 2.39 (s, 3H), 1.13-1.07 (m, 3H); m/z 479 (M+H)$^+$.

Compound Nos 181 to 183

Compound Nos. 181 to 183 were prepared according to the methods set forth in Example 23. For example, Compound No. 181 of Table 16 lists the method of "Example 23", indicating that this compound was prepared according to the procedure of Example 23 using appropriately substituted intermediates. Analytical data (NMR, mass spectrum) is also presented in Table 16.

TABLE 16

Compound Nos. 181 to 183

| Compound No. | Analytical Data | Synthesis Method |
|---|---|---|
| 181 | $^1$H NMR (400 MHz, CDCl$_3$) δ 8.15-8.13 (m, 1H), 7.60-7.55 (m, 2H), 7.48-7.42 (m, 1H), 7.26-7.20 (m, 1H), 6.61 (dd, J = 5.2, 6.7 Hz, 1H), 6.28 (d, J = 8.4 Hz, 1H), 6.05-5.89 (m, 1H), 5.17-5.11 (m, 1H), 4.13 (dd, J = 8.2, 22.2 Hz, 2H), 4.06-4.01 (m, 2H), 3.85-3.79 (m, 1H), 3.56-3.49 (m, 1H), 2.97-2.78 (m, 3H), 2.57-2.48 (m, 1H), 1.61-1.27 (m, 4H), 1.21-1.05 (m, 3H); m/z 493 (M + H)$^+$. | Example 23 |
| 182 | $^1$H NMR (400 MHz, CDCl$_3$) δ 7.91 (d, J = 4.9 Hz, 1H), 7.57-7.51 (m, 2H), 7.21-7.11 (m, 2H), 6.61-6.55 (m, 1H), 5.61-5.59 (m, 1H), 4.98-4.74 (m, 1H), 4.23-4.14 (m, 4H), 3.89-3.77 (m, 4H), 3.53-3.44 (m, 1H), 2.94-2.78 (m, 3H), 2.57-2.50 (m, 1H), 1.20-1.03 (m, 3H); m/z 483 (M + H)$^+$. | Example 23 |
| 183 | $^1$H NMR (400 MHz, DMSO-d$_6$) δ 8.30-8.28 (m, 1H), 8.17 (d, J = 4.8 Hz, 1H), 7.76-7.68 (m, 2H), 7.55-7.52 (m, 1H), 4.66-4.08 (m, 8H), 3.72-3.68 (m, 4H), 2.65-2.57 (m, 4H); m/z 470 (M + H)$^+$. | Example 23 |

Example 24

Compound No. 184

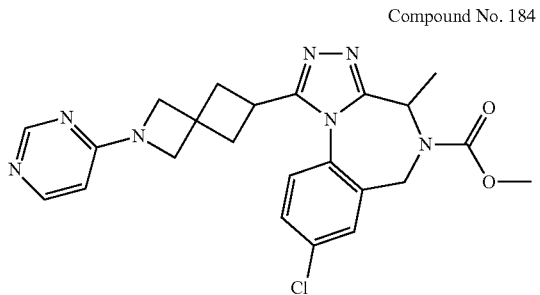 [SMILES: COC(=O)N1Cc2cc(Cl)ccc2-n2c(C3CC4(C3)CN(c3ccncn3)C4)nnc2C1C]

Step 1: Synthesis of methyl 7-chloro-3-methyl-2-oxo-1,2,3,5-tetrahydro-4H-benzo[e][1,4]diazepine-4-carboxylate

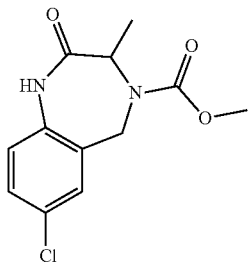 [SMILES: COC(=O)N1Cc2cc(Cl)ccc2NC(=O)C1C]

To a solution 7-chloro-3-methyl-1,3,4,5-tetrahydro-2H-benzo[e][1,4]diazepin-2-one, prepared in example 1 step 2, (1.0 g, 4.75 mmol, 1.0 eq.) and Et₃N (1.3 mL, 9.49 mmol, 2.0 eq.) at 0° C. in THF (20 mL) was added methyl chloroformate (0.55 mL, 7.12 mmol, 1.5 eq.) dropwise. The resulting solution was stirred at RT for 2 hours, diluted with EtOAc, washed with an aq. sol. of sat. NaHCO₃, and dried. The residue was purified by flash column chromatography eluting with 70-100% EtOAc in isohexane to give the title compound as a yellow solid (0.82 g, 64% yield). ¹H NMR (400 MHz, DMSO-d₆) δ 8.57 (s, 1H), 7.26-7.19 (m, 2H), 6.90-6.87 (m, 1H), 5.22-4.95 (m, 1H), 4.60-4.53 (m, 1H), 4.32-4.21 (m, 1H), 3.70 (s, 3H), 1.55 (d, J=6.7 Hz, 3H).

Step 2: Synthesis of methyl 7-chloro-3-methyl-2-thioxo-1,2,3,5-tetrahydro-4H-benzo[e][1,4]diazepine-4-carboxylate

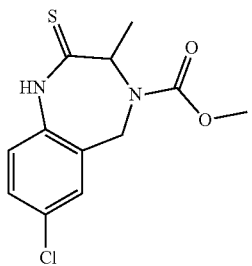 [SMILES: COC(=O)N1Cc2cc(Cl)ccc2NC(=S)C1C]

To a suspension of methyl 7-chloro-3-methyl-2-oxo-1,2,3,5-tetrahydro-4H-benzo[e][1,4]diazepine-4-carboxylate (0.82 g, 3.05 mmol, 1.0 eq.) in THF (10 mL) was added 2,4-bis(4-methoxyphenyl)-2,4-dithioxo-1,3,2,4-dithiadiphosphetane (0.74 g, 1.83 mmol, 0.60 eq.) and the mixture was heated to reflux for 1 hour. The mixture was allowed to cool and was concentrated in vacuo. The residue was purified by flash column chromatography eluting with 90-100% EtOAc in isohexane to give the title compound as a yellow solid (0.67 g, 77% yield). ¹H NMR (400 MHz, CDCl₃) δ 9.46-9.43 (m, 1H), 7.31-7.28 (m, 2H), 6.93-6.90 (m, 1H), 5.60-5.52 (m, 1H), 4.71-4.55 (m, 2H), 3.73 (s, 3H), 1.42 (d, J=6.5 Hz, 3H).

Step 3: Synthesis of methyl 1-(2-(tert-butoxycarbonyl)-2-azaspiro[3.3]heptan-6-yl)-8-chloro-4-methyl-4H-benzo[f][1,2,4]triazolo[4,3-a][1,4]diazepine-5(6H)-carboxylate

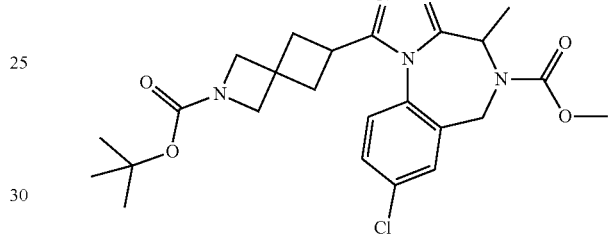

To a solution of methyl 7-chloro-3-methyl-2-thioxo-1,2,3,5-tetrahydro-4H-benzo[e][1,4]diazepine-4-carboxylate (0.3 g, 1.05 mmol, 1.0 eq.), was added tert-butyl 6-(hydrazinecarbonyl)-2-azaspiro[3.3]heptane-2-carboxylate (0.320 g, 1.26 mmol, 1.2 eq.) in dioxane (5 mL) and the mixture was heated to 90° C. for 36 hours. The mixture was allowed to cool and was concentrated in vacuo. The residue was purified by flash column chromatography eluting with 50-100% EtOAc in isohexane then 0-10% MeOH in DCM to give the title product as an off-white solid (0.43 g, 83% yield). ¹H NMR (400 MHz, CDCl₃) δ 7.54-7.49 (m, 2H), 7.16 (dd, J=2.6, 8.5 Hz, 1H), 5.59-5.52 (m, 1H), 5.01-4.58 (m, 1H), 4.04-3.88 (m, 5H), 3.77 (s, 3H), 3.46-3.38 (m, 1H), 2.85-2.70 (m, 3H), 2.51-2.42 (m, 1H), 1.61-1.58 (m, 9H), 1.19-1.05 (m, 3H).

Step 4: Synthesis of methyl 8-chloro-4-methyl-1-(2-(pyrimidin-4-yl)-2-azaspiro[3.3]heptan-6-yl)-4H-benzo[f][1,2,4]triazolo[4,3-a][1,4]diazepine-5(6H)-carboxylate (Compound No. 184)

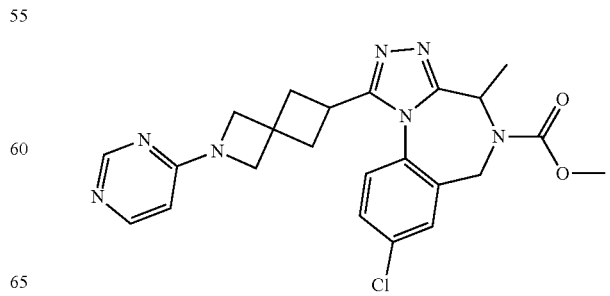

To a solution of methyl 1-(2-(tert-butoxycarbonyl)-2-azaspiro[3.3]heptan-6-yl)-8-chloro-4-methyl-4H-benzo[f][1,2,4]triazolo[4,3-a][1,4]diazepine-5(6H)-carboxylate (0.30 g, 0.62 mmol, 1.0 eq.) in DCM (4 mL) was added TFA (1.3 mL, 17.3 mmol, 28.1 eq.) and the mixture was stirred at RT for 1 hour. The mixture was concentrated in vacuo and was purified using a 5 g SCX-2 cartridge eluting with MeOH then 2.3 M ammonia in MeOH to give a colourless oil. To a solution of the colourless oil (20 mg, 0.052 mmol, 1.0 eq.) in N,N-dimethylformamide (1 mL) was added cesium carbonate (50 mg, 0.155 mmol, 3.0 eq.) and 4-chloropyrimidine hydrochloride (12 mg, 0.077 mmol, 1.50 eq.). The mixture was heated to 80° C. for 16 hours, allowed to cool to RT and partitioned between water and EtOAc. The organic phase was dried and concentrated in vacuo and the residue was purified by preparative HPLC to give the title compound as a white solid (12 mg, 50% yield). $^1$H NMR (400 MHz, CDCl$_3$) δ 8.57 (s, 1H), 8.16 (d, J=6.1 Hz, 1H), 7.56-7.51 (m, 2H), 7.19-7.15 (m, 1H), 6.17-6.15 (m, 1H), 5.64-5.54 (m, 1H), 5.20-4.46 (m, 1H), 4.20-4.10 (m, 4H), 3.90-3.79 (m, 4H), 3.55-3.46 (m, 1H), 2.96-2.56 (m, 4H), 1.20-1.08 (m, 3H); m/z 466 (M+H)$^+$.

Compound Nos. 185 to 190

Compound Nos. 185 to 190 were prepared according to the methods set forth in Example 24. For example, Compound No. 185 of Table 17 lists the method of "Example 24", indicating that this compound was prepared according to the procedure of Example 24 using appropriately substituted intermediates. Analytical data (NMR, mass spectrum) is also presented in Table 17.

TABLE 17

Compound Nos. 185 to 190

| Compound No. | Analytical Data | Synthesis Method |
|---|---|---|
| 185 | $^1$H NMR (400 MHz, CDCl$_3$) δ 8.34 (d, J = 3.1 Hz, 1H), 7.99 (d, J = 4.4 Hz, 1H), 7.59-7.52 (m, 2H), 7.19-7.16 (m, 1H), 5.24-3.60 (m, 9H), 3.55-3.41 (m, 1H), 2.92-2.70 (m, 4H), 1.33-1.26 (m, 6H); m/z 498 (M + H)$^+$. | Example 24 |
| 186 | $^1$H NMR (400 MHz, CDCl$_3$) δ 8.58 (d, J = 1.0 Hz, 1H), 8.18-8.13 (m, 1H), 7.59-7.52 (m, 2H), 7.19-7.15 (m, 1H), 6.17 (d, J = 5.5 Hz, 1H), 4.64-4.13 (m, 8H), 3.78 (s, 3H), 3.55-3.46 (m, 1H), 2.92-2.68 (m, 4H); m/z 452 (M + H)$^+$. | Example 24 |
| 187 | $^1$H NMR (400 MHz, CDCl$_3$) δ 8.58-8.56 (m, 1H), 8.18-8.15 (m, 1H), 7.57-7.49 (m, 2H), 7.18-7.15 (m, 1H), 6.17 (dd, J = 1.2, 6.0 Hz, 1H), 5.66-5.55 (m, 1H), 5.09-4.94 (m, 2H), 4.21-4.11 (m, 4H), 3.85-3.67 (m, 1H), 3.55-3.46 (m, 1H), 2.96-2.57 (m, 4H), 1.33-1.09 (m, 9H); m/z 494 (M + H)$^+$. | Example 24 |
| 188 | $^1$H NMR (400 MHz, CDCl$_3$) δ 8.34 (d, J = 3.1 Hz, 1H), 7.99 (d, J = 4.4 Hz, 1H), 7.58-7.51 (m, 2H), 7.19-7.15 (m, 1H), 5.59-5.54 (m, 1H), 5.04-4.77 (m, 1H), 4.37-4.30 (m, 4H), 3.88-3.79 (m, 4H), 3.52-3.44 (m, 1H), 2.97-2.82 (m, 3H), 2.63-2.54 (m, 1H), 1.15-1.10 (m, 3H); m/z 484 (M + H)$^+$. | Example 24 |
| 189 | $^1$H NMR (400 MHz, CDCl$_3$) δ 8.45-8.43 (m, 1H), 7.55-7.50 (m, 2H), 7.21-7.17 (m, 1H), 6.79 (d, J = 4.9 Hz, 1H), 6.46-6.17 (m, 1H), 5.66-5.57 (m, 1H), 5.07-4.67 (m, 1H), 4.26-4.16(m, 6H), 3.88-3.70 (m, 1H), 3.55-3.45 (m, 1H), 2.95-2.53 | Example 24 |

TABLE 17-continued

Compound Nos. 185 to 190

| Compound No. | Analytical Data | Synthesis Method |
|---|---|---|
|  | (m, 4H), 1.33-1.11 (m, 6H); m/z 530 (M + H)$^+$. |  |
| 190 | $^1$H NMR (400 MHz, CDCl$_3$) δ 8.48 (d, J = 4.6 Hz, 1H), 7.53 (dd, J = 2.2, 8.5 Hz, 2H), 7.20-7.17 (m, 1H), 6.80 (d, J = 4.9 Hz, 1H), 5.66-5.61 (m, 1H), 5.07-4.75 (m, 1H), 4.29-4.18 (m, 6H), 3.86-3.75 (m, 1H), 3.55-3.45 (m, 1H), 2.97-2.53 (m, 4H), 1.33-1.12 (m, 6H); m/z 548 (M + H)$^+$. | Example 24 |

Example 25

Compound No. 191

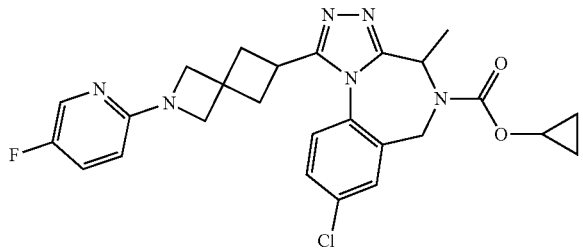

Step 1: Synthesis of 8-chloro-1-(2-(5-fluoropyridin-2-yl)-2-azaspiro[3.3]heptan-6-yl)-4-methyl-5,6-dihydro-4H-benzo[f][1,2,4]triazolo[4,3-a][1,4]diazepine

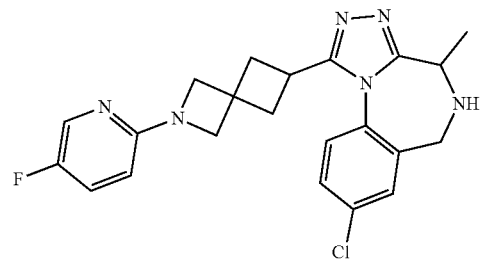 [SMILES: CC1NCc2cc(Cl)ccc2-n2c(C3CC4(C3)CN(c3ccc(F)cn3)C4)nnc21]

To a solution of tert-butyl 8-chloro-1-(2-(5-fluoropyridin-2-yl)-2-azaspiro[3.3]heptan-6-yl)-4-methyl-4H-benzo[f][1,2,4]triazolo[4,3-a][1,4]diazepine-5(6H)-carboxylate (0.28 g, 0.57 mmol, 1.0 eq.) in DCM (4 mL) was added TFA (1.2 mL, 15.4 mmol, 28.1 eq.) and the mixture was stirred at RT for 1 hour. The mixture was concentrated in vacuo and was purified using a 5 g SCX-2 cartridge eluting with MeOH then 2.3 M ammonia in MeOH to give the title compound as a pale yellow oil (0.28 g, 0.55 mmol, 1.0 eq.). $^1$H NMR (400 MHz, CDCl$_3$) δ 7.99 (d, J=2.8 Hz, 1H), 7.50-7.46 (m, 2H), 7.28-7.19 (m, 1H), 7.12 (d, J=9.1 Hz, 1H), 6.23 (dd, J=3.2, 9.0 Hz, 1H), 3.98 (s, 2H), 3.79-3.70 (m, 1H), 3.69 (s, 2H), 3.60 (d, J=12.6 Hz, 1H), 3.54-3.45 (m, 1H), 2.92-2.75 (m, 3H), 2.54-2.46 (m, 1H), 1.63 (d, J=6.6 Hz, 3H).

Step 2: Synthesis of cyclopropyl 8-chloro-1-(2-(5-fluoropyridin-2-yl)-2-azaspiro[3.3]heptan-6-yl)-4-methyl-4H-benzo[f][1,2,4]triazolo[4,3-a][1,4]diazepine-5(6H)-carboxylate (Compound No. 191)

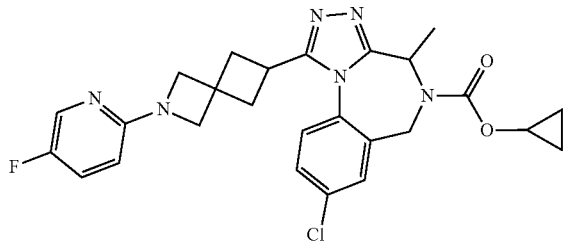 [SMILES: CC1c2nnc(C3CC4(C3)CN(c3ccc(F)cn3)C4)n2-c2ccc(Cl)cc2CN1C(=O)OC1CC1]

To a solution of cyclopropanol (33 mg, 0.57 mmol, 7.0 eq.) in MeCN (1 mL) was added CDI (93 mg, 0.57 mmol, 7.0 eq.) and the mixture stirred for 6 hours. To the mixture was added 8-chloro-1-(2-(5-fluoropyridin-2-yl)-2-azaspiro[3.3]heptan-6-yl)-4-methyl-5,6-dihydro-4H-benzo[f][1,2,4]triazolo[4,3-a][1,4]diazepine (35 mg, 0.082 mmol, 1.0 eq.) and the resulting solution was heated to 80° C. for 16 hours. The mixture was partitioned between aq. sol. of sat. NaHCO$_3$ and DCM and the organic phase was dried and concentrated in vacuo. The residue was purified by preparative HPLC to give the title compound as an off-white solid (32 mg, 76% yield). $^1$H NMR (400 MHz, CDCl$_3$) δ 8.01-7.99 (m, 1H), 7.59-7.52 (m, 2H), 7.25-7.17 (m, 2H), 6.24 (dd, J=3.5, 9.0 Hz, 1H), 5.55-5.50 (m, 1H), 5.08-4.66 (m, 1H), 4.10-3.98 (m, 5H), 3.79-3.74 (m, 1H), 3.54-3.45 (m, 1H), 2.94-2.78 (m, 3H), 2.54-2.50 (m, 1H), 1.11-1.00 (m, 3H), 0.77-0.71 (m, 4H); m/z 509 (M+H)$^+$.

Compound 192

Compound No. 192 was prepared according to the methods set forth in Example 25. For example, Compound No. 192 lists the method of "Example 25", indicating that this compound was prepared according to the procedure of Example 25 using appropriately substituted intermediates. Analytical data (NMR, mass spectrum): $^1$H NMR (400 MHz, CDCl$_3$) δ 8.20-8.19 (m, 2H), 7.59-7.51 (m, 2H), 7.21-7.17 (m, 1H), 5.56-5.47 (m, 1H), 5.09-4.64 (m, 1H), 4.21-4.10 (m, 5H), 3.86-3.68 (m, 1H), 3.53-3.46 (m, 1H), 2.96-2.80 (m, 3H), 2.56-2.49 (m, 1H), 1.11-1.06 (m, 3H), 0.74 (d, J=5.8 Hz, 4H); m/z 510 (M+H)$^+$.

Example 26

Compound No. 193

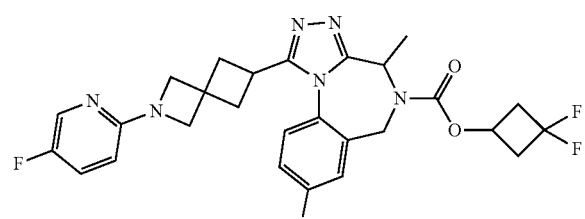

Step 1: Synthesis of 1-((3,3-difluorocyclobutoxy)carbonyl)-3-methyl-1H-imidazol-3-ium

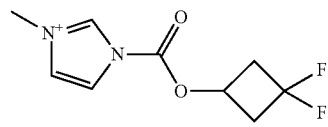

To a solution of 3,3-difluorocyclobutan-1-ol (22 mg, 0.20 mmol, 1.0 eq.) in THF (1 mL) was added CDI (40 mg, 0.24 mmol, 1.20 eq.) and the mixture stirred for 16 hours. The mixture was partitioned between water and EtOAc. The organic phase was dried and concentrated in vacuo. To a solution of the residue in MeCN (1 mL) was added iodomethane (0.038 mL, 0.61 mmol, 3.0 eq.) and the mixture stirred for 16 hours. The mixture was concentrated in vacuo to give the title compound as an orange oil (70 mg, 100% yield). $^1$H NMR (400 MHz, CDCl$_3$) δ 9.40 (s, 1H), 7.53-7.50 (m, 1H), 7.46-7.43 (m, 1H), 5.37-5.24 (m, 1H), 4.10 (s, 3H), 3.27-2.88 (m, 4H).

Step 2: Synthesis of 3,3-difluorocyclobutyl 8-chloro-1-(2-(5-fluoropyridin-2-yl)-2-azaspiro[3.3]heptan-6-yl)-4-methyl-4H-benzo[f][1,2,4]triazolo[4,3-a][1,4]diazepine-5(6H)-carboxylate (Compound No. 193)

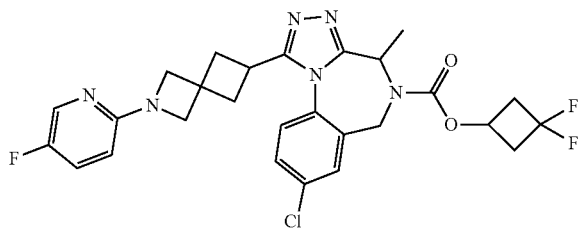 [SMILES: CC1c2nnc(C3CC4(C3)CN(c3ccc(F)cn3)C4)n2-c2ccc(Cl)cc2CN1C(=O)OC1CC(F)(F)C1]

To a solution of tert-butyl 8-chloro-1-(2-(5-fluoropyridin-2-yl)-2-azaspiro[3.3]heptan-6-yl)-4-methyl-4H-benzo[f][1,2,4]triazolo[4,3-a][1,4]diazepine-5(6H)-carboxylate (0.28 g, 0.57 mmol, 1.0 eq.) in DCM (4 mL) was added TFA (1.2 mL, 15.4 mmol, 28.1 eq.) and the mixture was stirred at RT for 1 hour. The mixture was concentrated in vacuo and was purified using a 5 g SCX-2 cartridge eluting with MeOH then 2.3 M ammonia in MeOH to give a pale yellow oil. To a solution of the pale yellow oil (1.0 g, 4.75 mmol, 1.0 eq.) and Et$_3$N (1.3 mL, 9.49 mmol, 2.0 eq.) in MeCN (3 mL) was added a solution of 1-((3,3-difluorocyclobutoxy)carbonyl)-3-methyl-1H-imidazol-3-ium (71 mg, 0.21 mmol, 1.75 eq.) in MeCN (1 mL). The resulting solution was stirred at RT for 2 hours, filtered through celite and concentrated in vacuo. The residue was purified by preparative HPLC to give the title compound as an off-white solid (7 mg, 10% yield). $^1$H NMR (400 MHz, CDCl$_3$) δ 8.00 (d, J=2.9 Hz, 1H), 7.58-7.52 (m, 2H), 7.25-7.18 (m, 2H), 6.24 (dd, J=3.4, 9.0 Hz, 1H), 5.63-5.55 (m, 1H), 5.01-4.56 (m, 2H), 4.11-3.79 (m, 5H), 3.52-3.46 (m, 1H), 3.07-2.53 (m, 8H), 1.13-1.10 (m, 3H); m/z 559 (M+H)$^+$.

Compound Nos. 194 to 196 and 201 to 220

Compound Nos. 194 to 196, 201 to 207, and 215 were prepared according to the methods set forth in Example 26. For example, Compound No. 194 of Table 18 lists the method of "Example 26", indicating that this compound was prepared according to the procedure of Example 26 using appropriately substituted intermediates. Analytical data (NMR, mass spectrum) is also presented in Table 18.

Compound Nos. 207 to 214 and 216 to 217 are prepared according to the procedure of Example 19 using appropriately substituted intermediates.

TABLE 18

Compound Nos. 194 to 196

| Compound No. | Analytical Data | Synthesis Method |
|---|---|---|
| 194 | $^1$H NMR (400 MHz, CDCl$_3$) d 8.20 (s, 2H), 7.58-7.50 (m, 2H), 7.23-7.20 (m, 1H), 5.72-5.63 (m, 1H), 5.26-5.03 (m, 2H), 4.73-4.59 (m, 4H), 4.20-4.11 (m, 4H), 3.87-3.74 (m, 1H), 3.55-3.47 (m, 1H), 2.96-2.79 (m, 3H), 2.57-2.51 (m, 1H), 1.17-1.06 (m, 3H); m/z 548 (M + H)$^+$. | Example 26 |
| 195 | $^1$H NMR (400 MHz, CDCl$_3$) δ 8.00 (d, J = 3.0 Hz, 1H), 7.56-7.50 (m, 2H), 7.21 (d, J = 31.1 Hz, 2H), 6.24 (dd, J = 3.1, 9.0 Hz, 1H), 5.68-5.57 (m, 1H), 5.16-4.84 (m, 2H), 4.12-3.76 (m, 5H), 3.54-3.45 (m, 1H), 2.94-2.78 (m, 3H), 2.56-2.53 (m, 1H), 2.39-2.34 (m, 2H), 2.15-2.03 (m, 2H), 1.86-1.77 (m, 1H), 1.68-1.59 (m, 1H), 1.14-1.06 (m, 3H); m/z 523 (M + H)$^+$. | Example 26 |
| 196 | $^1$H NMR (400 MHz, CDCl$_3$) δ 8.30 (2H, d, J = 4.9 Hz), 7.58 (1H, s), 7.54 (1H, dd, J = 2.4, 8.4 Hz), 7.20 (1H, d, J = 8.5 Hz), 6.53 (1H, dd, J = 4.8, 4.8 Hz), 4.55 (2H, s), 4.50 (2H, s), 4.43 (2H, s), 4.22 (2H, s), 4.14 (2H, s), 3.56-3.47 (1H, m), 2.89 (2H, dd, J = 8.6, 12.1 Hz), 2.67 (2H, s), 1.54 (3H, s), 1.51 (3H, s); m/z 512 (M + H)$^+$. | Example 26 |
| 201 | Enantiomers separated and characterized in Example 29 | Example 26 |
| 202 | Enantiomers separated and characterized in Example 29 | Example 26 |
| 203 | Enantiomers separated and characterized in Example 29 | Example 26 |
| 204 | Enantiomers separated and characterized in Example 29 | Example 26 |
| 205 | Enantiomers separated and characterized in Example 29 | Example 26 |
| 206 | Enantiomers separated and characterized in Example 29 | Example 26 |

Example 27

Compound No. 197

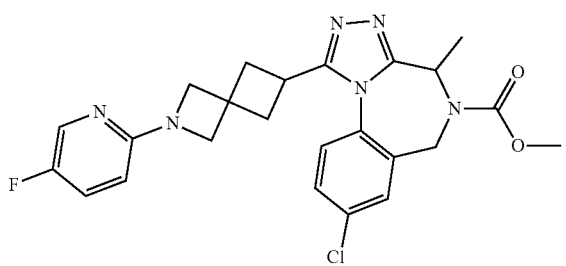

Step 1: Synthesis of methyl 2-((5-chloro-2-nitrobenzyl)amino)butanoate

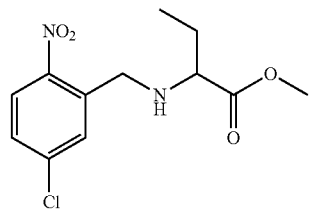 [SMILES: CCC(NCc1cc(Cl)ccc1[N+](=O)[O-])C(=O)OC]

To a solution of 5-chloro-2-nitrobenzaldehyde (0.68 g, 3.66 mmol, 1.0 eq.) in DCM (18 mL) was added methyl-DL-alpha-aminobutyrate hydrochloride (0.69 g, 3.66 mmol, 1.0 eq.), triethylamine (0.51 mL, 3.66 mmol, 1.0 eq.) and sodium triacetoxyborohydride (1.55 g, 7.31 mmol, 2.0 eq.). The resulting solution was stirred at RT for 36 hours, diluted with DCM, washed with an aq. sol. of sat. NaHCO$_3$, dried, concentrated in vacuo to give the title compound as a yellow oil (0.29 g, 28% yield). $^1$H NMR (400 MHz, CDCl$_3$) δ 7.92 (d, J=8.7 Hz, 1H), 7.72 (d, J=2.3 Hz, 1H), 7.37 (dd, J=2.3, 8.7 Hz, 1H), 4.14-4.09 (m, 1H), 3.94 (d, J=15.4 Hz, 1H), 3.72 (s, 3H), 3.19 (t, J=6.6 Hz, 1H), 1.78-1.58 (m, 2H), 0.96 (t, J=7.4 Hz, 3H).

Step 2: Synthesis of 7-chloro-3-ethyl-1,3,4,5-tetrahydro-2H-benzo[e][1,4]diazepin-2-one

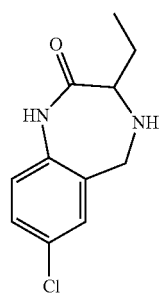

To a solution of methyl 2-((5-chloro-2-nitrobenzyl)amino)butanoate (0.29 g, 1.01 mmol, 1.0 eq.) in acetic acid (10 mL) was added iron (0.14 g, 2.53 mmol, 2.5 eq.). The resulting suspension was heated at 110° C. for 30 minutes, cooled to RT and filtered through celite rinsing with acetic acid. The filtrate was partitioned between aq. sol. of sat. NaHCO$_3$ and EtOAc and the organic phase was dried and concentrated in vacuo. The residue was triturated with diethyl ether to give the title compound as a light brown solid (80 mg, 35% yield). $^1$H NMR (400 MHz, CDCl$_3$) δ 7.45 (d, J=2.0 Hz, 1H), 7.26-7.23 (m, 1H), 6.91-6.86 (m, 1H), 4.08 (d, J=13.3 Hz, 1H), 3.87 (d, J=13.4 Hz, 1H), 3.33 (t, J=6.5 Hz, 1H), 1.95-1.85 (m, 1H), 1.65-1.54 (m, 1H), 0.96-0.91 (m, 3H).

Step 3: Synthesis of methyl 7-chloro-3-ethyl-2-oxo-1,2,3,5-tetrahydro-4H-benzo[e][1,4]diazepine-4-carboxylate

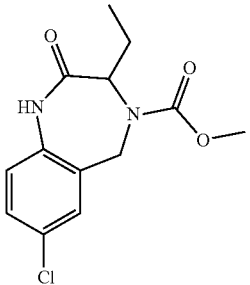 [SMILES: CCC1C(=O)Nc2ccc(Cl)cc2CN1C(=O)OC]

To a solution 7-chloro-3-ethyl-1,3,4,5-tetrahydro-2H-benzo[e][1,4]diazepin-2-one (75 mg, 0.33 mmol, 1.0 eq.) and Et₃N (0.07 mL, 0.50 mmol, 1.5 eq.) at 0° C. in THF (3 mL) was added methyl chloroformate (0.028 mL, 0.36 mmol, 1.1 eq.) dropwise. The resulting solution was stirred at RT for 20 minutes, partitioned between DCM and an aq. sol. of sat. NaHCO₃. The organics were dried, concentrated in vacuo to give the title compound as an off-white solid (0.11 g, 100% yield). $^1$H NMR (400 MHz, CDCl₃) δ 7.99-7.88 (m, 1H), 7.21-7.17 (m, 1H), 6.84-6.79 (m, 1H), 5.07-4.49 (m, 2H), 4.29-4.23 (m, 1H), 3.71-3.68 (m, 3H), 2.24-1.76 (m, 2H), 1.01-0.94 (m, 3H).

Step 4: Synthesis of methyl 7-chloro-3-ethyl-2-thioxo-1,2,3,5-tetrahydro-4H-benzo[e][1,4]diazepine-4-carboxylate

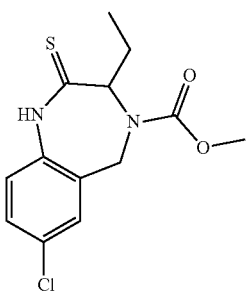 [SMILES: CCC1C(=S)Nc2ccc(Cl)cc2CN1C(=O)OC]

To a suspension of methyl 7-chloro-3-ethyl-2-oxo-1,2,3,5-tetrahydro-4H-benzo[e][1,4]diazepine-4-carboxylate (0.11 g, 0.39 mmol, 1.0 eq.) in THF (4 mL) was added 2,4-bis(4-methoxyphenyl)-2,4-dithioxo-1,3,2,4-dithiadiphosphetane (94 mg, 0.23 mmol, 0.60 eq.) and the mixture was heated to reflux for 1 hour. The mixture was allowed to cool and was concentrated in vacuo to give the title compound as a yellow solid (0.12 g, 100% yield). m/z 299.1 (M+H)⁺.

Step 5: Synthesis of methyl 8-chloro-4-ethyl-1-(2-(5-fluoropyridin-2-yl)-2-azaspiro[3.3]heptan-6-yl)-4H-benzo[f][1,2,4]triazolo[4,3-a][1,4]diazepine-5(6H)-carboxylate (Compound No. 197)

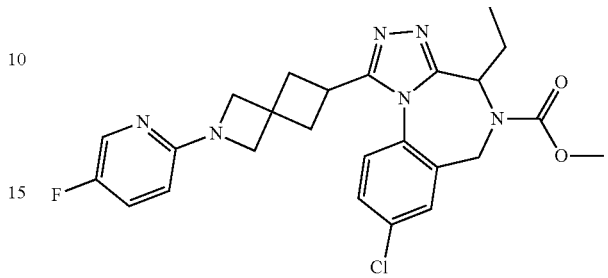

To a solution of methyl 7-chloro-3-ethyl-2-thioxo-1,2,3,5-tetrahydro-4H-benzo[e][1,4]diazepine-4-carboxylate (58 mg, 0.19 mmol, 1.0 eq.), was added 2-(4-fluoropyridin-2-yl)-2-azaspiro[3.3]heptane-6-carbohydrazide (50 mg, 0.21 mmol, 1.1 eq.) in dioxane (1 mL) and the mixture was heated to 100° C. for 16 hours. The mixture was allowed to cool and was concentrated in vacuo. The residue was purified by preparative HPLC to give the title compound to give the title product as an off-white solid (4 mg, 4% yield). $^1$H NMR (400 MHz, CDCl₃) δ 8.01-7.99 (m, 1H), 7.56-7.50 (m, 2H), 7.25-7.17 (m, 2H), 6.24 (dd, J=3.3, 9.0 Hz, 1H), 5.46-5.40 (m, 1H), 5.06-4.83 (m, 1H), 4.12-3.97 (m, 4H), 3.85-3.78 (m, 4H), 3.55-3.47 (m, 1H), 2.96-2.76 (m, 3H), 2.55-2.46 (m, 1H), 1.62-1.53 (m, 1H), 1.03-0.86 (m, 1H), 0.70-0.59 (m, 3H); m/z 497 (M+H)⁺.

Compound Nos. 198 to 199

Compound Nos. 198 to 199 were prepared according to the methods set forth in Example 27. For example, Compound No. 198 of Table 19 lists the method of "Example 27", indicating that this compound was prepared according to the procedure of Example 27 using appropriately substituted intermediates. Analytical data (NMR, mass spectrum) is also presented in Table 19.

TABLE 19

| Compound No. | Analytical Data | Synthesis Method |
|---|---|---|
| 198 | $^1$H NMR (400 MHz, CDCl₃) δ 8.32-8.30 (m, 2H), 7.61-7.58 (m, 2H), 7.19-7.16 (m, 1H), 6.54 (t, J = 4.8 Hz, 1H), 5.37 (dd, J = 5.8, 8.2 Hz, 1H), 4.74-4.62 (m, 3H), 4.24-4.15 (m, 4H), 3.96 (d, J = 13.7 Hz, 1H), 3.59-3.49 (m, 1H), 2.97-2.80 (m, 3H), 2.55-2.48 (m, 1H); m/z 450 (M + H)⁺. | Example 27 |
| 199 | $^1$H NMR (400 MHz, CDCl₃) δ 8.30 (2H, d, J = 4.9 Hz), 7.52-7.47 (2H, m), 7.04 (1H, d, J = 8.3 Hz), 6.53 (1H, dd, J = 4.8, 4.8 Hz), 4.48 (2H, s), 4.23 (2H, s), 4.14 (2H, s), 3.76 (3H, s), 3.62-3.52 (1H, m), 2.95-2.88 (2H, m), 2.71-2.64 (2H, m), 1.31-1.26 (2H, m), 1.17-1.13 (2H, m); m/z 478 (M + H)⁺. | Example 27 |

Example 28

Compound No. 200

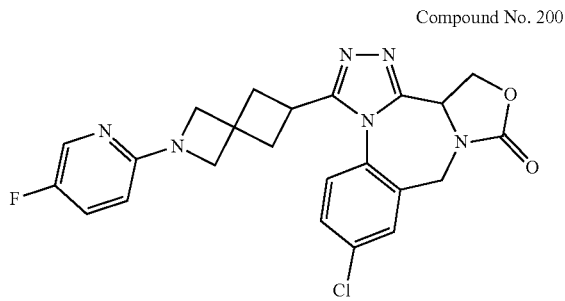 [SMILES: O=C1OCC2c3nnc(C4CC5(C4)CN(c4ccc(F)cn4)C5)n3-c3ccc(Cl)cc3CN12]

Step 1: Synthesis of methyl (5-chloro-2-nitrobenzyl)serinate

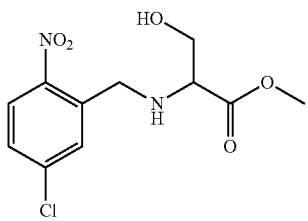 [SMILES: COC(=O)C(CO)NCc1cc(Cl)ccc1[N+](=O)[O-]]

To a solution of 2-(bromomethyl)-4-chloro-1-nitrobenzene (0.97 g, 3.86 mmol, 1.0 eq.) in DMF (10 mL) was added DL-Serine methyl ester hydrochloride (0.6 g, 3.86 mmol, 1.0 eq.) and potassium carbonate (1.07 g, 7.71 mmol, 2.0 eq.). The resulting mixture was stirred at RT for 4 hours, concentrated in vacuo, diluted with EtOAc and washed with an aq. sol. of sat. NaHCO$_3$. The organics were dried, concentrated in vacuo and the residue was purified by flash column chromatography eluting with 5% EtOAc in isohexane to give the title compound as a light yellow oil (0.77 g, 69% yield). $^1$H NMR (400 MHz, CDCl$_3$) δ 7.96-7.93 (m, 1H), 7.64 (d, J=2.3 Hz, 1H), 7.41 (dd, J=2.4, 8.7 Hz, 1H), 4.20-4.05 (m, 2H), 3.86-3.80 (m, 1H), 3.75 (s, 3H), 3.68 (dd, J=6.2, 11.3 Hz, 1H), 3.44 (dd, J=4.4, 6.3 Hz, 1H).

Step 2: Synthesis of methyl 3-(5-chloro-2-nitrobenzyl)-2-oxooxazolidine-4-carboxylate

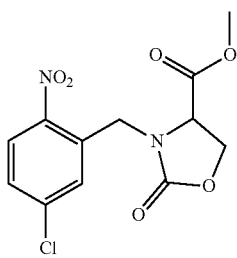 [SMILES: COC(=O)C1COC(=O)N1Cc1cc(Cl)ccc1[N+](=O)[O-]]

To a solution methyl (5-chloro-2-nitrobenzyl)serinate (0.77 g, 2.67 mmol, 1.0 eq.) and Et$_3$N (0.56 mL, 4.0 mmol, 1.5 eq.) at 0° C. in DCM (10 mL) was added triphosgene (0.23 mL, 0.80 mmol, 0.3 eq.) dropwise. The resulting solution was stirred at RT for 30 minutes, partitioned between DCM and an aq. sol. of sat. NaHCO$_3$. The organics were washed with brine, dried and concentrated in vacuo. The residue was purified by flash column chromatography eluting with 20% EtOAc in isohexane to give the title compound as a light yellow solid (0.51 g, 60% yield). $^1$H NMR (400 MHz, CDCl$_3$) δ 8.01-7.97 (m, 1H), 7.64 (d, J=1.8 Hz, 1H), 7.43 (ddd, J=2.2, 8.7, 19.5 Hz, 1H), 4.94 (d, J=16.4 Hz, 1H), 4.79 (d, J=16.2 Hz, 1H), 4.54 (t, J=10.2 Hz, 1H), 4.45-4.38 (m, 2H), 3.80 (s, 3H).

Step 3: Synthesis of 7-chloro-1,5,10,11a-tetrahydro-3H,11H-benzo[e]oxazolo[3,4-a][1,4]diazepine-3,11-dione

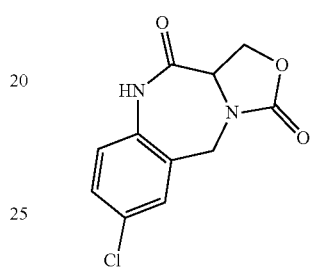

To a solution of methyl 3-(5-chloro-2-nitrobenzyl)-2-oxooxazolidine-4-carboxylate (0.51 g, 1.62 mmol, 1.0 eq.) in acetic acid (15 mL) was added iron (0.23 g, 4.05 mmol, 2.5 eq.). The resulting suspension was heated at 110° C. for 2 hours, cooled to RT and filtered through celite rinsing with acetic acid. The filtrate was partitioned between water and EtOAc and the organic phase was dried and concentrated in vacuo. The residue was triturated with diisopropyl ether to give the title compound as a light brown solid (0.27 g, 66% yield). $^1$H NMR (400 MHz, CDCl$_3$) δ 7.57 (s, 1H), 7.41-7.36 (m, 2H), 6.99 (d, J=8.3 Hz, 1H), 4.94 (dd, J=5.1, 8.3 Hz, 1H), 4.56 (d, J=13.6 Hz, 1H), 4.43-4.29 (m, 3H).

Step 4: Synthesis of 7-chloro-11-thioxo-5,10,11,11a-tetrahydro-1H,3H-benzo[e]oxazolo[3,4-a][1,4]diazepin-3-one

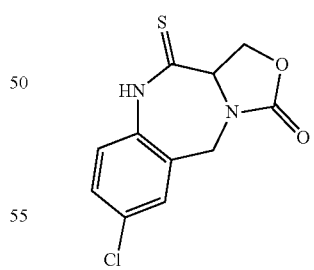

To a suspension of 7-chloro-1,5,10,11a-tetrahydro-3H,11H-benzo[e]oxazolo[3,4-a][1,4]diazepine-3,11-dione (0.27 g, 1.07 mmol, 1.0 eq.) in THF (5 mL) was added 2,4-bis(4-methoxyphenyl)-2,4-dithioxo-1,3,2,4-dithiadiphosphetane (0.26 g, 0.64 mmol, 0.60 eq.) and the mixture was heated to reflux for 2 hours. The mixture was allowed to cool and was concentrated in vacuo. The residue was purified by flash column chromatography eluting with 10-100% EtOAc in isohexane to give the title compound as a light yellow solid (0.31 g, 100% yield). ¹H NMR (400 MHz, DMSO-d₆) δ 9.47-9.43 (m, 1H), 7.42 (d, J=9.6 Hz, 2H), 7.06 (d, J=7.8 Hz, 1H), 5.33 (dd, J=5.3, 8.8 Hz, 1H), 4.59 (d, J=13.9 Hz, 1H), 4.46-4.31 (m, 3H).

Step 5: Synthesis of 7-chloro-3-(2-(5-fluoropyridin-2-yl)-2-azaspiro[3.3]heptan-6-yl)-13,13a-dihydro-9H,11H-benzo[e]oxazolo[3,4-a][1,2,4]triazolo[3,4-c][1,4]diazepin-11-one (Compound No. 200)

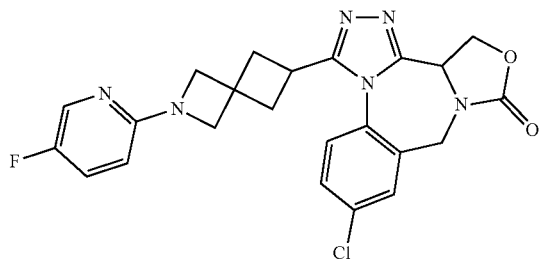 [SMILES: O=C1OCC2c3nnc(C4CC5(C4)CN(c4ccc(F)cn4)C5)n3-c3ccc(Cl)cc3CN12]

To a solution of 7-chloro-11-thioxo-5,10,11,11a-tetrahydro-1H,3H-benzo[e]oxazolo[3,4-a][1,4]diazepin-3-one (40 mg, 0.15 mmol, 1.0 eq.), was added 2-(4-fluoropyridin-2-yl)-2-azaspiro[3.3]heptane-6-carbohydrazide (41 mg, 0.16 mmol, 1.1 eq.) in dioxane (1 mL) and the mixture was heated to 100° C. for 16 hours. The mixture was allowed to cool and was concentrated in vacuo. The residue was purified by preparative HPLC to give the title compound to give the title product as an off-white solid (7 mg, 11% yield). ¹H NMR (400 MHz, CDCl₃) δ 8.01-7.99 (m, 1H), 7.61-7.57 (m, 2H), 7.25-7.14 (m, 2H), 6.24 (dd, J=3.5, 9.0 Hz, 1H), 5.37 (dd, J=5.8, 8.3 Hz, 1H), 4.75-4.61 (m, 3H), 4.10-3.93 (m, 5H), 3.58-3.48 (m, 1H), 2.94-2.76 (m, 3H), 2.56-2.49 (m, 1H); m/z 467 (M+H)⁺.

Example 29

Isomer Separation

Homochiral isomer A and homochiral isomer B were isolated using Supercritical Fluid Chromatography (SFC) chiral separation of the corresponding racemates. Either a Waters Thar Prep100 preparative SFC system (P200 CO2 pump, 2545 modifier pump, 2998 UV/VIS detector, 2767 liquid handler with Stacked Injection Module) or Waters Thar Investigator semi preparative system (Waters Fluid Delivery Module, 2998 UV/VIS detector, Waters Fraction Collection Module) were used. Where the Waters 2767 liquid handler was used it acted as both auto-sampler and fraction collector. The compounds were purified using an appropriate column selected from the following: YMC Amylose-C, YMC Cellulose-C, YMC Cellulose-SC, Phenomenex LUX Cellulose-3 or Phenomenex LUX Cellulose-4. Appropriate isocratic methods were selected based on methanol, ethanol or isopropanol solvent systems under un-modified or basic conditions. The standard method used was modifier/CO2, 100 ml/min (or as appropriate), 120 Bar backpressure, 40° C. column temperature. The modifier used under basic conditions was diethyl amine (0.1% V/V). The purification was controlled either by Waters Fractionlynx or Waters Chromscope software through monitoring at 210-400 nm and triggered a threshold collection value at an appropriate wavelength. Collected fractions were analysed by SFC (Waters/Thar SFC systems with Waters SQD or Waters UPCC with Waters QDa). The fractions that contained the desired product were concentrated by vacuum centrifugation.

The following compounds were purified using SFC chiral separation.

TABLE 20

Compound Separated by Chiral SFC

| Racemate Compound No. | Isomer | Data |
|---|---|---|
| 142 | Isomer A | ¹H NMR (400 MHz, CDCl₃) δ 8.00 (d, J = 2.9 Hz, 1H), 7.55-7.51 (m, 2H), 7.25-7.17 (m, 2H), 6.23 (dd, J = 3.5, 9.0 Hz, 1H), 5.60-5.55 (m, 1H), 5.05-4.98 (m, 1H), 4.11-4.03 (m, 2H), 3.99 (s, 2H), 3.98-3.92 (m, 1H), 3.78 (s, 3H), 3.54-3.45 (m, 1H), 2.94-2.79 (m, 3H), 2.59-2.51 (m, 1H), 1.21-1.03 (m, 3H); m/z 483 (M + H)⁺. |
| 142 | Isomer B | ¹H NMR (400 MHz, CDCl₃) δ 8.00 (d, J = 2.9 Hz, 1H), 7.55-7.51 (m, 2H), 7.25-7.17 (m, 2H), 6.24 (dd, J = 3.4, 9.2 Hz, 1H), 5.61-5.58 (m, 1H), 5.06-4.98 (m, 1H), 4.11-4.03 (m, 2H), 3.99 (s, 2H), 3.98-3.92 (m, 1H), 3.78 (s, 3H), 3.54-3.45 (m, 1H), 2.94-2.79 (m, 3H), 2.56-2.52 (m, 1H), 1.19-1.11 (m, 3H); m/z 483 (M + H)⁺. |
| 174 | Isomer A | ¹H NMR (400 MHz, CDCl₃) δ 8.00 (d, J = 3.0 Hz, 1H), 7.56 (d, J = 7.0 Hz, 2H), 7.25-7.20 (m, 2H), 6.24 (dd, J = 3.4, 9.0 Hz, 1H), 6.00-5.95 (m, 1H), 5.18-5.11 (m, 1H), 4.12-4.08 (m, 2H), 4.02-3.99 (m, 2H), 3.85-3.71 (m, 1H), 3.54-3.49 (m, 1H), 2.98-2.90 (m, 1H), 2.87-2.78 (m, 2H), 2.56-2.50 (m, 1H), 1.51-1.22 (m, 4H), 1.21-1.09 (m, 3H); m/z 511 (M + H)⁺. |
| 184 | Isomer A | ¹H NMR (400 MHz, CDCl₃) δ 8.59-8.56 (m, 1H), 8.21-8.15 (m, 1H), 7.56-7.50 (m, 2H), 7.20 -7.15 (m, 1H), 6.17 (d, J = 5.3 Hz, 1H), 5.65 -5.59 (m, 1H), 5.31-4.37 (m, 1H), 4.22-4.12 (m, 4H), 3.80-3.78 (m, 4H), 3.55-3.47 (m, 1H), 2.98-2.54 (m, 4H), 1.26-1.14 (m, 3H); m/z 466 (M + H)⁺. |
| 184 | Isomer B | ¹H NMR (400 MHz, CDCl₃) δ 8.57 (s, 1H), 8.21-8.15 (m, 1H), 7.60-7.51 (m, 2H), 7.19-7.15 (m, 1H), 6.17 (dd, J = 1.2, 6.1 Hz, 1H), 5.59-5.57 (m, 1H), 5.03-4.74 (m, 1H), 4.21-4.12 (m, 4H), 3.90-3.78 (m, 4H), 3.54-3.46 (m, 1H), 2.97-2.57 (m, 4H), 1.20-1.05 (m, 3H); m/z 466 (M + H)⁺. |
| 191 | Isomer A | ¹H NIVIR (400 MHz, CDCl₃) δ 8.00 (d, J = 2.9 Hz, 1H), 7.55-7.51 (m, 2H), 7.25-7.16 (m, 2H), 6.23 (dd, J = 3.1, 9.0 Hz, 1H), 5.55-5.45 (m, 1H), 5.27-4.33 (m, 1H), 4.09-3.98 (m, 5H), 3.94 -3.64 (m, 1H), 3.54-3.45 (m, 1H), 2.93-2.78 (m, 3H), 2.56-2.53 (m, 1H), 1.11-1.04 (m, 3H), 0.74 (d, J = 6.0 Hz, 4H); m/z 510 (M + H)⁺. |
| 191 | Isomer B | ¹H NMR (400 MHz, CDCl₃) δ 8.00 (d, J = 2.9 Hz, 1H), 7.55-7.51 (m, 2H), 7.25-7.17 (m, 2H), 6.24 (dd, J = 3.4, 9.0 Hz, 1H), 5.56-5.46 (m, 1H), 5.07-4.68 (m, 1H), 4.15-3.79 (m, 6H), 3.54 -3.45 (m, 1H), 2.94-2.53 (m, 4H), 1.14-0.97 (m, 3H), 0.74 (d, J = 6.0 Hz, 4H); m/z 509 (M + H)⁺. |
| 179 | Isomer A | ¹H NMR (400 MHz, CDCl₃) δ 7.99 (d, J = 2.9 Hz, 1H), 7.49 (dd, J = 2.4, 8.4 Hz, 1H), 7.43 (d, J = 2.4 Hz, 1H), 7.25-7.19 (m, 1H), 7.15 (d, J = 8.4 Hz, 1H), 6.23 (dd, J = 3.5, 9.0 Hz, 1H), 4.10-4.03 (m, 2H), 3.99 (s, 2H), 3.51-3.44 (m, 3H), 3.30-3.26 (m, 1H), 2.90-2.76 (m, 3H), 2.56-2.48 (m, 1H), 2.41 (s, 3H); m/z 439 (M + H)⁺. |
| 179 | Isomer B | ¹H NMR (400 MHz, CDCl₃) δ 7.99 (d, J = 2.9 Hz, 1H), 7.52-7.48 (m, 1H), 7.43 (d, J = 2.4 Hz, 1H), 7.25-7.19 (m, 1H), 7.15 (d, J = 8.4 |

TABLE 20-continued

Compound Separated by Chiral SFC

| Racemate Compound No. | Isomer | Data |
|---|---|---|
| | | Hz, 1H), 6.23 (dd, J = 3.6, 8.8 Hz, 1H), 4.10-4.03 (m, 2H), 3.99 (s, 2H), 3.51-3.44 (m, 3H), 3.31-3.27 (m, 1H), 2.90-2.76 (m, 3H), 2.55-2.48 (m, 1H), 2.41 (s, 3H); m/z 439 (M + H)+. |
| 163 | Isomer A | ¹H NMR (400 MHz, CDCl₃) δ 8.00 (d, J = 2.8 Hz, 1H), 7.58-7.55 (m, 1H), 7.52 (dd, J = 2.0, 8.3 Hz, 1H), 7.25-7.17 (m, 2H), 6.24 (dd, J = 3.4, 9.0 Hz, 1H), 5.62-5.57 (m, 1H), 5.12-5.06 (m, 1H), 5.04-4.94 (m, 1H), 4.10-3.98 (m, 4H), 3.90-3.68 (m, 1H), 3.53-3.45 (m, 1H), 2.95-2.77 (m, 3H), 2.55-2.52 (m, 1H), 1.33-1.27 (m, 6H), 1.17-1.10 (m, 3H); m/z 511 (M + H)+. |
| 163 | Isomer B | ¹H NMR (400 MHz, CDCl₃) δ 8.00 (d, J = 2.8 Hz, 1H), 7.58-7.55 (m, 1H), 7.52 (dd, J = 2.0, 8.3 Hz, 1H), 7.25-7.17 (m, 2H), 6.24 (dd, J = 3.4, 9.0 Hz, 1H), 5.64-5.59 (m, 1H), 5.10-5.05 (m, 1H), 5.04-4.94 (m, 1H), 4.10-3.98 (m, 4H), 3.90-3.68 (m, 1H), 3.53-3.45 (m, 1H), 2.95-2.77 (m, 3H), 2.55-2.52 (m, 1H), 1.33-1.27 (m, 6H), 1.16-1.11 (m, 3H); m/z 511 (M + H)+. |
| 165 | Isomer A | ¹H NMR (400 MHz, CDCl₃) δ 8.01 (dd, J = 1.5, 2.8 Hz, 1H), 7.85 (d, J = 2.8 Hz, 1H), 7.77 (d, J = 1.4 Hz, 1H), 7.52 (dd, J = 1.9, 8.3 Hz, 2H), 7.18 (d, J = 8.5 Hz, 1H), 5.68-5.48 (m, 1H), 5.17-4.91 (m, 1H), 4.20-4.12 (m, 4H), 3.91-3.82 (m, 1H), 3.79 (s, 3H), 3.54-3.46 (m, 1H), 2.97-2.83 (m, 3H), 2.62 (s, 1H), 1.16-1.13 (m, 3H); m/z 466 (M + H)+. |
| 165 | Isomer B | ¹H NMR (400 MHz, CDCl₃) δ 8.01 (dd, J = 1.5, 2.8 Hz, 1H), 7.85 (d, J = 2.8 Hz, 1H), 7.77 (d, J = 1.4 Hz, 1H), 7.53 (dd, J = 1.9, 8.3 Hz, 2H), 7.18 (d, J = 8.5 Hz, 1H), 5.71-5.49 (m, 1H), 5.17-4.91 (m, 1H), 4.20-4.12 (m, 4H), 3.90-3.81 (m, 1H), 3.79 (s, 3H), 3.53-3.44 (m, 1H), 2.97-2.83 (m, 3H), 2.62 (s, 1H), 1.17-1.14 (m, 3H); m/z 466 (M + H)+. |
| 166 | Isomer A | ¹H NMR (400 MHz, CDCl₃) δ 8.01 (dd, J = 1.5, 2.8 Hz, 1H), 7.84 (d, J = 2.8 Hz, 1H), 7.77 (d, J = 1.4 Hz, 1H), 7.53 (dd, J = 1.9, 8.3 Hz, 2H), 7.18 (d, J = 8.5 Hz, 1H), 5.71-5.49 (m, 1H), 5.17-4.91 (m, 1H), 4.20-4.12 (m, 4H), 3.90-3.82 (m, 1H), 3.79 (s, 3H), 3.52-3.45 (m, 1H), 2.97-2.83 (m, 3H), 2.62 (s, 1H), 1.17-1.12 (m, 3H); m/z 466 (M + H)+. |
| 166 | Isomer B | ¹H NMR (400 MHz, CDCl₃) δ 8.30 (d, J = 4.8 Hz, 2H), 7.57-7.51 (m, 2H), 7.21 (d, J = 8.5 Hz, 1H), 6.53 (t, J = 4.8 Hz, 1H), 5.67-5.53 (m, 1H), 5.11-4.93 (m, 1H), 4.24-4.13 (m, 4H), 3.92-3.83 (m, 1H), 3.78 (s, 3H), 3.56-3.46 (m, 1H), 2.97-2.82 (m, 3H), 2.54-2.53 (m, 1H), 1.15-1.11 (m, 3H); m/z 466 (M + H)+. |
| 167 | Isomer A | ¹H NMR (400 MHz, CDCl₃) δ 8.30 (d, J = 4.5 Hz, 2H), 7.57-7.50 (m, 2H), 7.20 (d, J = 8.5 Hz, 1H), 6.53 (t, J = 4.8 Hz, 1H), 5.66-5.62 (m, 1H), 5.04-4.94 (m, 2H), 4.27-4.17 (m, 2H), 4.13 (s, 2H), 3.81-3.75 (m, 1H), 3.56-3.47 (m, 1H), 2.97-2.81 (m, 3H), 2.60-2.49 (m, 1H), 1.33-1.27 (m, 6H), 1.14-1.08 (m, 3H); m/z 494 (M + H)+. |
| 167 | Isomer B | ¹H NMR (400 MHz, CDCl₃) δ 8.30 (d, J = 4.8 Hz, 2H), 7.57-7.50 (m, 2H), 7.20 (d, J = 8.5 Hz, 1H), 6.53 (t, J = 4.8 Hz, 1H), 5.69-5.55 (m, 1H), 5.04-4.94 (m, 2H), 4.24-4.13 (m, 4H), 3.81-3.74 (m, 1H), 3.56-3.47 (m, 1H), 2.97-2.81 (m, 3H), 2.60-2.48 (m, 1H), 1.33-1.27 (m, 6H), 1.13-1.09 (m, 3H); m/z 494 (M + H)+. |
| 168 | Isomer A | ¹H NMR (400 MHz, CDCl₃) δ 8.32-8.28 (m, 2H), 7.56-7.51 (m, 2H), 7.20 (d, J = 8.1 Hz, 1H), 6.55-6.51 (m, 1H), 5.70-5.56 (m, 1H), 5.16-4.95 (m, 1H), 4.24-4.13 (m, 4H), 4.11 (s, 2H), 3.95-3.72 (m, 1H), 3.56-3.47 (m, 1H), 2.97-2.81 (m, 3H), 2.60-2.47 (m, 1H), 1.32-1.30 (m, 3H), 1.19-1.04 (m, 3H); m/z 480 (M + H)+. |
| 168 | Isomer B | ¹H NMR (400 MHz, CDCl₃) δ 8.31-8.28 (m, 2H), 7.56-7.51 (m, 2H), 7.20 (d, J = 8.1 Hz, 1H), 6.55-6.51 (m, 1H), 5.68-5.57 (m, 1H), 5.12-4.95 (m, 1H), 4.24-4.13 (m, 4H), 4.12 (s, 2H), 3.85-3.80 (m, 1H), 3.56-3.47 (m, 1H), 2.97-2.82 (m, 3H), 2.59-2.47 (m, 1H), 1.32-1.30 (m, 3H), 1.20-1.05 (m, 3H); m/z 480 (M + H)+. |
| 169 | Isomer A | ¹H NMR (400 MHz, CDCl₃) δ 8.00 (d, J = 2.9 Hz, 1H), 7.55-7.50 (m, 2H), 7.25-7.17 (m, 2H), 6.24 (dd, J = 3.3, 9.0 Hz, 1H), 5.60-5.54 (m, 1H), 5.10-5.03 (m, 1H), 4.26-4.18 (m, 2H), 4.10-3.99 (m, 4H), 3.91-3.67 (m, 1H), 3.55-3.45 (m, 1H), 2.94-2.78 (m, 3H), 2.58-2.49 (m, 1H), 1.31 (t, J = 7.1 Hz, 3H), 1.20-1.04 (m, 3H); m/z 497 (M + H)+. |
| 169 | Isomer B | ¹H NMR (400 MHz, CDCl₃) δ 8.00 (d, J = 2.9 Hz, 1H), 7.55-7.50 (m, 2H), 7.25-7.17 (m, 2H), 6.24 (dd, J = 3.3, 9.0 Hz, 1H), 5.61-5.56 (m, 1H), 5.10-5.01 (m, 1H), 4.26-4.18 (m, 2H), 4.10-3.98 (m, 4H), 3.91-3.68 (m, 1H), 3.55-3.45 (m, 1H), 2.94-2.78 (m, 3H), 2.58-2.49 (m, 1H), 1.31 (t, J = 7.1 Hz, 3H), 1.19-1.05 (m, 3H); m/z 497 (M + H)+. |
| 181 | Isomer A | ¹H NMR (400 MHz, DMSO-d₆) δ 7.96 (dd, J = 1.5, 5.0 Hz, 1H), 7.67-7.65 (m, 2H), 7.56 (d, J = 8.7 Hz, 1H), 7.43-7.37 (m, 1H), 6.53 (dd, J = 5.0, 6.8 Hz, 1H), 6.26 (d, J = 8.3 Hz, 1H), 5.61-5.44 (m, 1H), 5.02-4.95 (m, 1H), 4.14-4.10 (m, 1H), 3.96-3.87 (m, 2H), 3.77 (q, J = 8.4 Hz, 2H), 3.70-3.61 (m, 1H), 2.70 (d, J = 8.0 Hz, 2H), 2.41-2.26 (m, 2H), 1.40-1.13 (m, 4H), 1.00-0.82 (m, 3H); m/z 493 (M + H)+. |
| 181 | Isomer B | ¹H NMR (400 MHz, DMSO-d₆) δ 7.96 (dd, J = 1.5, 5.0 Hz, 1H), 7.67-7.65 (m, 2H), 7.56 (d, J = 8.7 Hz, 1H), 7.43-7.38 (m, 1H), 6.53 (dd, J = 5.0, 6.8 Hz, 1H), 6.26 (d, J = 8.3 Hz, 1H), 5.62-5.46 (m, 1H), 5.01-4.95 (m, 1H), 4.14-4.10 (m, 1H), 3.96-3.87 (m, 2H), 3.78 (q, J = 8.4 Hz, 2H), 3.70-3.61 (m, 1H), 2.70 (d, J = 8.0 Hz, 2H), 2.41-2.26 (m, 2H), 1.41-1.15 (m, 4H), 0.98-0.83 (m, 3H); m/z 493 (M + H)+. |
| 178 | Isomer A | ¹H NMR (400 MHz, DMSO-d₆) δ 7.95 (d, J = 2.9 Hz, 1H), 7.66 (dd, J = 2.1, 8.5 Hz, 1H), 7.59-7.51 (m, 2H), 7.42-7.37 (m, 1H), 6.31 (dd, J = 3.5, 9.0 Hz, 1H), 5.60-5.58 (m, 1H), 5.13-5.06 (m, 1H), 4.02-3.95 (m, 1H), 3.90 (dd, J = 8.3, 23.5 Hz, 2H), 3.77 (dd, J = 8.7, 18.3 Hz, 2H), 3.71-3.62 (m, 1H), 2.73-2.70 (m, 2H), 2.35-2.25 (m, 2H), 1.63-1.55 (m, 6H), 0.85-0.79 (m, 3H); m/z 513 (M + H)+. |
| 178 | Isomer B | ¹H NMR (400 MHz, DMSO-d₆) δ 7.95 (d, J = 2.9 Hz, 1H), 7.66 (dd, J = 2.1, 8.5 Hz, 1H), 7.58-7.51 (m, 2H), 7.42-7.37 (m, 1H), 6.31 (dd, J = 3.4, 9.0 Hz, 1H), 5.59-5.57 (m, 1H), 5.12-5.03 (m, 1H), 4.02-3.94 (m, 1H), 3.90 (dd, J = 8.3, 23.5 Hz, 2H), 3.77 (dd, J = 8.7, 18.3 Hz, 2H), 3.71-3.62 (m, 1H), 2.73-2.70 (m, 2H), 2.35-2.25 (m, 2H), 1.63-1.55 (m, 6H), 0.84-0.78 (m, 3H); m/z 513 (M + H)+. |

TABLE 20-continued

Compound Separated by Chiral SFC

| Racemate Compound No. | Isomer | Data |
|---|---|---|
| 170 | Isomer A | $^1$H NMR (400 MHz, CDCl$_3$) δ 8.20 (d, J = 0.9 Hz, 2H), 7.53 (dd, J = 1.8, 8.3 Hz, 2H), 7.21-7.18 (m, 1H), 5.64-5.54 (m, 1H), 5.19-4.61 (m, 1H), 4.21-4.10 (m, 4H), 4.01-3.64 (m, 4H), 3.55-3.46 (m, 1H), 2.96-2.76 (m, 3H), 2.56-2.49 (m, 1H), 1.18-1.08 (m, 3H); m/z 484 (M + H)$^+$. |
| 170 | Isomer B | $^1$H NMR (400 MHz, CDCl$_3$) δ 8.20 (d, J = 0.8 Hz, 2H), 7.54 (dd, J = 2.0, 8.3 Hz, 2H), 7.21-7.18 (m, 1H), 5.65-5.55 (m, 1H), 5.02-4.76 (m, 1H), 4.21-4.10 (m, 4H), 3.88-3.79 (m, 4H), 3.55-3.46 (m, 1H), 2.96-2.52 (m, 4H), 1.23-1.03 (m, 3H); m/z 484 (M + H)$^+$. |
| 192 | Isomer A | $^1$H NMR (400 MHz, CDCl$_3$) δ 8.20-8.19 (m, 2H), 7.56-7.51 (m, 2H), 7.21-7.17 (m, 1H), 5.59-5.45 (m, 1H), 5.23-4.36 (m, 1H), 4.21-4.10 (m, 4H), 3.80 (s, 1H), 3.55-3.46 (m, 1H), 2.96-2.78 (m, 3H), 2.57-2.48 (m, 1H), 1.10-1.02 (m, 3H), 0.74 (d, J = 5.9 Hz, 4H); m/z 510 (M + H)$^+$. |
| 192 | Isomer B | $^1$H NMR (400 MHz, CDCl$_3$) δ 8.19 (s, 2H), 7.53 (dd, J = 1.6, 8.5 Hz, 2H), 7.21-7.17 (m, 1H), 5.54-5.45 (m, 1H), 5.06-4.65 (m, 1H), 4.21-4.09 (m, 5H), 3.89-3.71 (m, 1H), 3.55-3.46 (m, 1H), 2.96-2.54 (m, 4H), 1.18-0.98 (m, 3H), 0.75-0.71 (m, 4H); m/z 510 (M + H)$^+$. |
| 187 | Isomer A | $^1$H NMR (400 MHz, CDCl$_3$) δ 8.57 (s, 1H), 8.16 (d, J = 5.9 Hz, 1H), 7.58-7.51 (m, 2H), 7.18-7.15 (m, 1H), 6.17-6.15 (m, 1H), 5.66-5.54 (m, 1H), 5.11-4.96 (m, 2H), 4.20-4.10 (m, 4H), 3.83-3.69 (m, 1H), 3.55-3.47 (m, 1H), 2.97-2.58 (m, 4H), 1.35-1.08 (m, 9H); m/z 494 (M + H)$^+$. |
| 187 | Isomer B | $^1$H NMR (400 MHz, CDCl$_3$) δ 8.57-8.56 (m, 1H), 8.18-8.15 (m, 1H), 7.57-7.49 (m, 2H), 7.19-7.15 (m, 1H), 6.16 (dd, J = 1.2, 6.0 Hz, 1H), 5.74-5.39 (m, 1H), 5.25-4.78 (m, 2H), 4.20-4.10 (m, 4H), 3.98-3.60 (m, 1H), 3.55-3.47 (m, 1H), 2.98-2.49 (m, 4H), 1.34-1.26 (m, 9H); m/z 494 (M + H)$^+$. |
| 171 | Isomer A | $^1$H NMR (400 MHz, CDCl$_3$) δ 8.30 (d, J = 4.8 Hz, 2H), 7.58-7.50 (m, 2H), 7.22-7.17 (m, 1H), 6.53 (t, J = 4.8 Hz, 1H), 5.56-5.51 (m, 1H), 5.23-4.36 (m, 1H), 4.28-3.60 (m, 6H), 3.56-3.47 (m, 1H), 2.97-2.81 (m, 3H), 2.53 (d, J = 2.0 Hz, 1H), 1.22-0.87 (m, 3H), 0.77-0.71 (m, 4H); m/z 492 (M + H)$^+$. |
| 171 | Isomer B | $^1$H NMR (400 MHz, CDCl$_3$) δ 8.32-8.28 (m, 2H), 7.58-7.50 (m, 2H), 7.23-7.17 (m, 1H), 6.53 (t, J = 4.7 Hz, 1H), 5.56-5.51 (m, 1H), 5.29-4.34 (m, 1H), 4.25-4.11 (m, 5H), 3.94-3.60 (m, 1H), 3.57-3.47 (m, 1H), 2.98-2.53 (m, 4H), 1.11-0.99 (m, 3H), 0.78-0.70 (m, 4H); m/z 492 (M + H)$^+$. |
| 194 | Isomer A | $^1$H NMR (400 MHz, CDCl$_3$) δ 8.20 (d, J = 0.9 Hz, 2H), 7.59-7.50 (m, 2H), 7.23-7.19 (m, 1H), 5.72-5.61 (m, 1H), 5.29-4.51 (m, 6H), 4.21-4.10 (m, 4H), 3.89-3.70 (m, 1H), 3.55-3.47 (m, 1H), 2.97-2.81 (m, 3H), 2.65-2.44 (m, 1H), 1.22-1.01 (m, 3H); m/z 548 (M + H)$^+$. |
| 194 | Isomer B | $^1$H NMR (400 MHz, CDCl$_3$) δ 8.20 (d, J = 0.8 Hz, 2H), 7.58-7.50 (m, 2H), 7.23-7.19 (m, 1H), 5.72-5.62 (m, 1H), 5.24-4.97 (m, 2H), 4.73-4.59 (m, 4H), 4.22-4.10 (m, 4H), 3.86-3.73 (m, 1H), 3.54-3.47 (m, 1H), 2.97-2.51 (m, 4H), 1.18-1.09 (m, 3H); m/z 548 (M + H)$^+$. |
| 172 | Isomer A | $^1$H NMR (400 MHz, CDCl$_3$) δ 8.20 (m, 2H), 7.56-7.49 (m, 2H), 7.21-7.17 (m, 1H), 5.63-5.61 (m, 1H), 5.23-4.44 (m, 1H), 4.27-3.62 (m, 7H), 3.54-3.46 (m, 1H), 2.96-2.78 (m, 3H), 2.53-2.51 (m, 1H), 1.31 (t, J = 7.1 Hz, 3H), 1.13 (m, 3H); m/z 498 (M + H)$^+$. |
| 172 | Isomer B | $^1$H NMR (400 MHz, CDCl$_3$) δ 8.25-8.19 (m, 2H), 7.56-7.50 (m, 2H), 7.24-7.19 (m, 1H), 5.72-5.56 (m, 1H), 5.06-4.78 (m, 1H), 4.23-3.81 (m, 7H), 3.55-3.47 (m, 1H), 2.98-2.54 (m, 4H), 1.38-1.12 (m, 6H); m/z 498 (M + H)$^+$. |
| 188 | Isomer A | $^1$H NMR (400 MHz, CDCl$_3$) δ 8.35-8.32 (m, 1H), 8.00-7.98 (m, 1H), 7.56-7.50 (m, 2H), 7.19-7.15 (m, 1H), 5.63-5.55 (m, 1H), 5.29-4.55 (m, 1H), 4.37-4.30 (m, 4H), 3.95-3.69 (m, 4H), 3.54-3.44 (m, 1H), 2.98-2.51 (m, 4H), 1.23-1.04 (m, 3H); m/z 484 (M + H)$^+$. |
| 188 | Isomer B | $^1$H NMR (400 MHz, CDCl$_3$) δ 8.37-8.32 (m, 1H), 7.99 (d, J = 4.3 Hz, 1H), 7.53 (d, J = 8.4 Hz, 2H), 7.20-7.15 (m, 1H), 5.60-5.60 (m, 1H), 5.09-4.74 (m, 1H), 4.35-4.31 (m, 4H), 3.81-3.77 (m, 4H), 3.50-3.48 (m, 1H), 2.96-2.82 (m, 3H), 2.69-2.51 (m, 1H), 1.31-1.03 (m, 3H); m/z 484 (M + H)$^+$. |
| 201 | Isomer A | $^1$H NMR (400 MHz, CDCl$_3$) δ 8.20-8.19 (m, 2H), 7.57-7.50 (m, 2H), 7.22-7.16 (m, 1H), 5.63-5.56 (m, 1H), 5.24-4.66 (m, 2H), 4.21-4.10 (m, 4H), 3.77-3.70 (m, 1H), 3.56-3.46 (m, 1H), 2.97-2.79 (m, 3H), 2.55-2.52 (m, 1H), 1.33-1.27 (m, 6H), 1.13-1.07 (m, 3H); m/z 512 (M + H)$^+$. |
| 201 | Isomer B | $^1$H NMR (400 MHz, CDCl$_3$) δ 8.20-8.19 (m, 2H), 7.55-7.50 (m, 2H), 7.21-7.18 (m, 1H), 5.67-5.54 (m, 1H), 5.09-4.94 (m, 2H), 4.21-4.10 (m, 4H), 3.86-3.65 (m, 1H), 3.56-3.46 (m, 1H), 2.97-2.52 (m, 4H), 1.34-1.09 (m, 9H); m/z 512 (M + H)$^+$. |
| 202 | Isomer A | $^1$H NMR (400 MHz, DMSO-d$_6$) δ 8.21 (d, J = 4.8 Hz, 2H), 7.60-7.55 (m, 2H), 7.50-7.45 (m, 1H), 6.54 (t, J = 4.8 Hz, 1H), 5.28-4.51 (m, 7H), 4.02-3.81 (m, 5H), 3.61-3.55 (m, 1H), 2.65-2.53 (m, 2H), 2.36-2.25 (m, 2H), 1.11-0.81 (m, 3H); m/z 530 (M + H)$^+$. |
| 202 | Isomer B | $^1$H NMR (400 MHz, DMSO-d$_6$) δ 8.38-8.35 (m, 2H), 7.79-7.71 (m, 2H), 7.66-7.61 (m, 1H), 6.69 (t, J = 4.8 Hz, 1H), 5.57-4.90 (m, 3H), 4.82-4.76 (m, 2H), 4.73-4.64 (m, 2H), 4.57-3.85 (m, 5H), 3.79-3.70 (m, 1H), 2.73-2.70 (m, 2H), 2.50-2.40 (m, 2H), 1.22-1.02 (m, 3H); m/z 530 (M + H)$^+$. |
| 203 | Isomer A | $^1$H NMR (400 MHz, CDCl$_3$) δ 8.00 (d, J = 2.9 Hz, 1H), 7.58-7.50 (m, 2H), 7.23-7.18 (m, 2H), 6.23 (dd, J = 3.1, 8.9 Hz, 1H), 5.77-5.56 (m, 1H), 5.19-5.18 (m, 2H), 4.71-4.69 (m, 2H), 4.61-4.57 (m, 2H), 4.10-3.99 (m, 4H), 3.87-3.72 (m, 1H), 3.55-3.48 (m, 1H), 2.94-2.80 (m, 3H), 2.56-2.48 (m, 1H), 1.17-1.07 (m, 3H); m/z 547 (M + H)$^+$. |
| 203 | Isomer B | $^1$H NMR (400 MHz, CDCl$_3$) δ 8.00 (d, J = 3.0 Hz, 1H), 7.58-7.51 (m, 2H), 7.25-7.19 (m, 2H), 6.24 (dd, J = 3.4, 9.0 Hz, 1H), 5.72-5.62 (m, 1H), 5.24-5.17 (m, 2H), 4.72-4.57 (m, 4H), 4.10-3.99 (m, 4H), 3.88-3.71 (m, 1H), 3.55-3.46 (m, 1H), 2.94-2.79 (m, 3H), 2.57-2.48 (m, 1H), 1.20-1.04 (m, 3H); m/z 547 (M + H)$^+$. |
| 204 | Isomer A | $^1$H NMR (400 MHz, CDCl$_3$) δ 7.57-7.44 (m, 3H), 7.20-7.15 (m, 1H), 6.99-6.94 (m, 1H), 6.43-6.39 (m, 1H), 5.66-5.56 (m, 1H), 5.26-4.57 (m, 2H), 4.29-3.58 (m, 5H), 3.55-3.46 (m, 1H), 2.97-2.41 (m, 4H), 1.37-1.00 (m, 9H); m/z 518 (M + H)$^+$. |

TABLE 20-continued

Compound Separated by Chiral SFC

| Racemate Compound No. | Isomer | Data |
|---|---|---|
| 204 | Isomer B | ¹H NMR (400 MHz, CDCl₃) δ 7.55-7.45 (m, 3H), 7.19-7.16 (m, 1H), 6.97-6.95 (m, 1H), 6.43 -6.41 (m, 1H), 5.65-5.55 (m, 1H), 5.28-4.29 (m, 2H), 4.23-3.62 (m, 5H), 3.54-3.46 (m, 1H), 2.95-2.79 (m, 3H), 2.60-2.51 (m, 1H), 1.34-1.24 (m, 9H); m/z 518 (M + H)⁺. |
| 205 | Isomer A | ¹H NMR (400 MHz, CDCl₃) δ 8.31-8.29 (m, 2H), 7.58-7.51 (m, 2H), 7.21-7.17 (m, 1H), 6.53 (t, J = 4.8 Hz, 1H), 5.57-5.48 (m, 1H), 5.30 -4.38 (m, 1H), 4.24-4.12 (m, 4H), 3.73-3.69 (m, 1H), 3.55-3.46 (m, 1H), 2.97 -2.51 (m, 4H), 1.58 (s, 3H), 1.04-0.68 (m, 7H); m/z 506 (M + H)⁺. |
| 205 | Isomer B | ¹H NMR (400 MHz, CDCl₃) δ 8.30 (dd, J = 1.4, 4.8 Hz, 2H), 7.59-7.51 (m, 2H), 7.22-7.17 (m, 1H), 6.55-6.52 (m, 1H), 5.59-5.52 (m, 1H), 5.30-4.41 (m, 1H), 4.24-4.12 (m, 4H), 3.97-3.62 (m, 1H), 3.54-3.47 (m, 1H), 2.97 -2.77 (m, 3H), 2.58-2.52 (m, 1H), 1.59 (s, 3H), 1.12-0.84 (m, 5H), 0.70-0.65 (m, 2H); m/z 506 (M + H)⁺. |
| 206 | Isomer A | ¹H NMR (400 MHz, CDCl₃) δ 8.00 (d, J = 2.9 Hz, 1H), 7.56-7.50 (m, 2H), 7.25-7.17 (m, 2H), 6.23 (dd, J = 3.1, 9.0 Hz, 1H), 5.60-5.56 (m, 1H), 5.04 (s, 1H), 4.52-4.45 (m, 2H), 4.09 (d, J = 7.8 Hz, 1H), 4.05 (d, J = 7.9 Hz, 1H), 3.99 (dd, J = 8.4, 10.4 Hz, 2H), 3.70 (s, 1H), 3.55 -3.45 (m, 1H), 2.91 (t, J = 9.7 Hz, 1H), 2.81 (dd, J = 8.6, 11.9 Hz, 2H), 2.54-2.51 (m, 1H), 1.54 (s, 3H), 1.52 (s, 3H), 1.11-1.08 (m, 3H); m/z 543 (M + H)⁺. |
| 206 | Isomer B | ¹H NMR (400 MHz, CDCl₃) δ 8.00 (d, J = 2.9 Hz, 1H), 7.56-7.50 (m, 2H), 7.25-7.17 (m, 2H), 6.24 (dd, J = 3.1, 9.0 Hz, 1H), 5.54-5.53 (m, 1H), 5.04 (s, 1H), 4.53-4.49 (m, 2H), 4.10 (d, J = 7.7 Hz, 1H), 4.05 (d, J = 7.9 Hz, 1H), 3.99 (dd, J = 8.4, 10.3 Hz, 2H), 3.70 (s, 1H), 3.55-3.45 (m, 1H), 2.91 (t, J = 9.8 Hz, 1H), 2.81 (dd, J = 7.7, 12.2 Hz, 2H), 2.53-2.51 (m, 1H), 1.54 (s, 3H), 1.52 (s, 3H), 1.13-1.09 (m, 3H); m/z 543 (M + H)⁺. |

Example 30

Compound No. 217

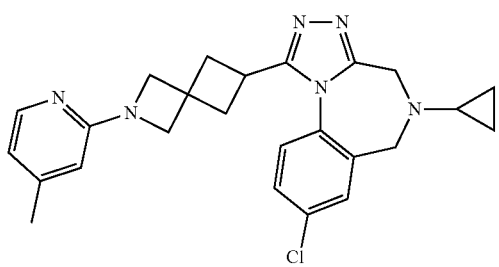

Step 1: Synthesis of tert-butyl 6-(hydrazinecarbonyl)-2-azaspiro[3.3]heptane-2-carboxylate

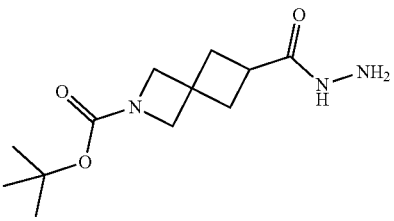

To a stirred solution of 2-(tert-butoxycarbonyl)-2-azaspiro[3.3]heptane-6-carboxylic acid (0.26 g, 1 mmol, 1 eq.) in THF (5 mL) was added 1-1'-Carbonyldiimidazole (0.19 g, 1.2 mmol, 1.2 eq.) and the mixture was stirred at RT overnight. The resulting mixture was added to a solution of hydrazine monohydrate (0.07 mL, 1.4 mmol, 1.4 eq.) in THF (10 mL) and stirred at RT overnight. The mixture was diluted with brine and extracted with ethyl acetate. The organic phase was separated, washed with brine, dried (MgSO₄), filtered and concentrated under reduced pressure to afford the title compound as a white solid (0.29 g, 100% yield). This material was used without further purification. ¹H NMR (400 MHz, CDCl₃) δ 6.61-6.59 (m, 1H), 3.91-3.80 (m, 6H), 2.81-2.73 (m, 1H), 2.48-2.43 (m, 2H), 2.35-2.30 (m, 2H), 1.40 (s, 9H).

Step 2: Synthesis of tert-butyl (4-chloro-2-((cyclopropylamino)methyl)phenyl)carbamate

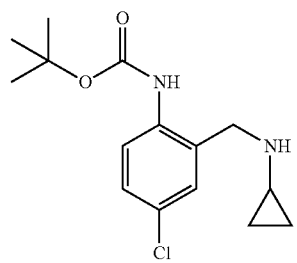 [SMILES: CC(C)(C)OC(=O)Nc1ccc(Cl)cc1CNC1CC1]

A mixture of tert-butyl (4-chloro-2-formylphenyl)carbamatee (5.122 g, 20.03 mmol, 1 eq.) and cyclopropanamine (2.08 mL, 30.05 mmol, 1.5 eq.) in MeOH (65.2 mL) was stirred for 5 h at 60° C., allowed to cool to RT, and then stirred 18 h. THF (30 mL) was added to the reaction mixture, followed by solid NaCNBH₃ (2.517 g, 40.06 mmol, 2 eq.). The reaction mixture was stirred at RT for 2 hours. Acetic acid (2.29 mL, 40.06 mmol, 2 eq) was added and stirring was continued for 20 min. The reaction mixture was concentrated under reduced pressure, and the resultant crude residue was diluted with EtOAc (150 mL) and washed with sat. aq. NaHCO₃ (100 mL). The aqueous later was collected, and the organic layer was further washed with sat. aq. NaHCO₃ (2×50 mL). The combined aqueous washes were back-extracted with EtOAc (1×100 mL) and the combined organic phases were dried over MgSO₄, filtered to remove solid material, and concentrated under reduced pressure. The residue was purified by column chromatography (SiO₂, 0-30% EtOAc/Hex-2% DCM additive) to afford tert-butyl (4-chloro-2-((cyclopropylamino)methyl)phenyl)carbamate (5.4 g, 91% yield) as a white solid. LCMS (ESI): m/z 297.1 (M+H); Retention time: 3.40 min (50-100% ACN/H$_2$O, method 3).

Step 3: Synthesis of tert-butyl (4-chloro-2-(((cyanomethyl)(cyclopropyl)amino)methyl)phenyl) carbamate

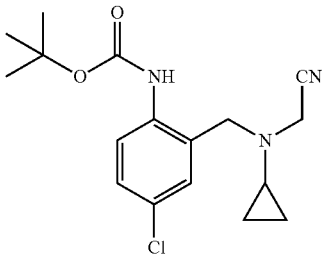 [SMILES: CC(C)(C)OC(=O)Nc1ccc(Cl)cc1CN(CC#N)C1CC1]

A mixture of K$_2$CO$_3$ (1.87 g, 13.5 mmol, 2 eq.), KI (0.671 g, 4.04 mmol, 0.6 eq.), 2-chloroacetonitrile (0.855 mL, 13.5 mmol, 2 eq.), and tert-butyl (4-chloro-2-((cyclopropylamino)methyl)phenyl)carbamate (2.00 g, 6.74 mmol, 1 eq.), added in sequence, was stirred in ACN (15 mL) under an atmosphere of N2 for 18 h at 75° C. The reaction mixture was allowed to cool to RT, diluted with EtOAc (100 mL), and washed with sat aq. NaHCO$_3$ (100 mL). The organic phase was collected, and the aq. phase was extracted with EtOAc (2×100 mL). The combined organic extracts were washed with 15% aq. Na$_2$S$_2$O$_3$ (2×100 mL), brine (1×100 mL), and dried over MgSO4. Solids were removed by vacuum filtration and the filtrate was concentrated under reduced pressure to afford tert-butyl (4-chloro-2-(((cyanomethyl)(cyclopropyl)amino) methyl)phenyl) carbamate (2.548 g, 88% pure, 99% yield) as a brown oil. The crude material was taken on to the next step without further purification. LCMS (ESI): m/z 336.1 (M+H); Retention time: 3.80 min (50-100% ACN/H$_2$O, method 3).

Step 4: Synthesis of 7-chloro-4-cyclopropyl-4,5-dihydro-3H-benzo[e][1,4]diazepin-2-amine

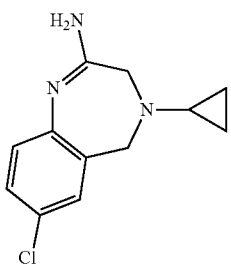 [SMILES: NC1=Nc2ccc(Cl)cc2CN(C2CC2)C1]

A solution of acetyl chloride (9.64 mL, 134.6 mmol, 20 eq.) in isopropanol (55.6 mL) was stirred for 20 min prior to slow addition to a solution of tert-butyl (4-chloro-2-(((cyanomethyl)(cyclopropyl)amino) methyl)phenyl) carbamate (2.26 g, 6.730 mmol, 1 eq.) in isopropanol (67.3 mL) and stirred for 60 h at 50° C. The reaction mixture was concentrated under reduced pressure and the crude residue was diluted with EtOAc (125 mL). The crude mixture was washed with sat aq. NaHCO$_3$ (1×125 mL). The organic phase was collected, and the aqueous phase was extracted with EtOAc (3×50 mL). The combined organics were washed with brine (1×50 mL), dried over MgSO$_4$, and solids were removed by vacuum filtration. The filtrate was concentrated under reduced pressure, and the crude residue was purified by column chromatography (SiO$_2$, 0-100% EtOAc/Hex, 0-100% DCM/EtOAc, 0-12% MeOH/DCM) to afford 7-chloro-4-cyclopropyl-4,5-dihydro-3H-benzo[e][1,4]diazepin-2-amine (0.721 g, 45.5% yield) as a light brown solid. LCMS (ESI): m/z 236.0 (M+H); Retention time: 1.37 min (50-100% ACN/H$_2$O, method 3).

Step 5: Synthesis of tert-butyl 6-(8-chloro-5-cyclopropyl-5,6-dihydro-4H-benzo[f][1,2,4]triazolo[4,3-a][1,4]diazepin-1-yl)-2-azaspiro[3.3]heptane-2-carboxylate

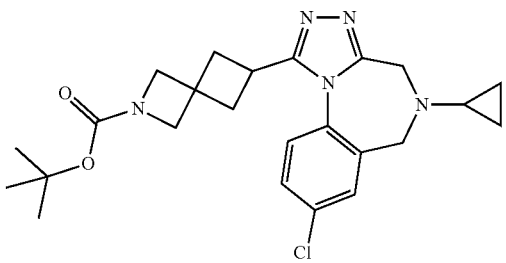 [SMILES: CC(C)(C)OC(=O)N1CC2(CC(c3nnc4n3-c3ccc(Cl)cc3CN(C3CC3)C4)C2)C1]

A mixture of 7-chloro-4-(2-methoxyethyl)-4,5-dihydro-3H-benzo[e][1,4]diazepin-2-amine (0.200 g, 0.848 mmol, 1.0 eq.), tert-butyl 6-(hydrazinecarbonyl)-2-azaspiro[3.3]heptane-2-carboxylate (0.227 g, 0.890 mmol, 1.05 eq.) from Example 32, Step 1, and AcOH (0.097 mL, 1.70 mmol, 2.0 eq.) in 2-propanol (10 mL) was heated to 80° C. for 2 h. The reaction mixture was concentrated under reduced pressure, the crude residue was diluted with DCM (10 mL) and washed with sat. aq. NaHCO$_3$ (10 mL). The organic phase was collected, and the aq. phase was extracted with DCM (3×10 mL). The combined organics were dried over MgSO$_4$, solids were removed by vacuum filtration, and the filtrate was concentrated under reduced pressure. The crude residue was purified by column chromatography (SiO$_2$, 0-10% MeOH/DCM) to afford tert-butyl 6-(8-chloro-5-cyclopropyl-5,6-dihydro-4H-benzo[f][1,2,4]triazolo[4,3-a][1,4]diazepin-1-yl)-2-azaspiro[3.3]heptane-2-carboxylate (0.385 g, 99%) as a light brown solid. LCMS (ESI): m/z 456.1 (M+H); Retention time: 2.30 min (50-100% ACN/H$_2$O, method 3).

Step 6: Synthesis of 8-chloro-5-cyclopropyl-1-(2-azaspiro[3.3]heptan-2-ium-6-yl)-5,6-dihydro-4H-benzo[f][1,2,4]triazolo[4,3-a][1,4]diazepin-5-ium 2,2,2-trifluoroacetate

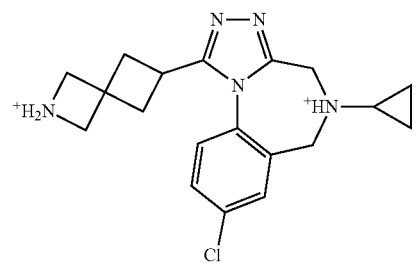

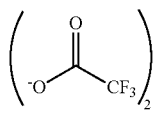

A solution of tert-butyl 6-(8-chloro-5-methyl-5,6-dihydro-4H-benzo[f][1,2,4]triazolo[4,3-a][1,4]diazepin-1-yl)-2-azaspiro[3.3]heptane-2-carboxylate (0.421 g, 0.923 mmol, 1.0 eq.) in DCM (10 mL) was stirred at 0° C. Trifluoroacetic acid (2.11 mL, 27.7 mmol, 30 eq.) was added dropwise. The reaction mixture was allowed to warm to RT and stirred for 60 min. The mixture was concentrated under reduced pressure, and the crude residue was azeotroped with toluene (4×20 mL). After 6 h under high vacuum, 8-chloro-5-cyclopropyl-1-(2-azaspiro[3.3]heptan-2-ium-6-yl)-5,6-dihydro-4H-benzo[f][1,2,4]triazolo[4,3-a][1,4]diazepin-5-ium 2,2,2-trifluoroacetate (0.539 g, 100%) was isolated as a brown solid. LCMS (ESI): m/z 356.1 (M+H); Retention time: 1.41 min (50-100% ACN/H$_2$O, method 3).

Step 7: Synthesis of 8-chloro-5-cyclopropyl-1-(2-(4-methylpyridin-2-yl)-2-azaspiro[3.3]heptan-6-yl)-5,6-dihydro-4H-benzo[f][1,2,4]triazolo[4,3-a][1,4]diazepine (Compound No. 217)

A mixture of 8-chloro-5-cyclopropyl-1-(2-azaspiro[3.3]heptan-2-ium-6-yl)-5,6-dihydro-4H-benzo[f][1,2,4]triazolo[4,3-a][1,4]diazepin-5-ium 2,2,2-trifluoroacetate (0.045 g, 0.0771 mmol, 1.0 eq), 2-chloro-4-methylpyridine (0.020 g, 0.157 mmol, 2.0 eq.), NaO$^t$Bu (0.0371 g, 0.386 mmol, 5.0 eq.), and RuPhos Pd G3 (0.007 g, 0.0077 mmol, 0.1 eq.) was stirred in 1,4-dioxane (1.0 mL) under a N$_2$ atmosphere for 2.5 h at 155° C. The reaction mixture was diluted with EtOAc (3 mL) and filtered through a pad of celite. The filter cake was washed with EtOAc (2×2 mL) and the combined filtrates were concentrated under reduced pressure. The crude residue was purified by reverse phase chromatography (5-85% ACN/H$_2$O, 20 min method). 8-chloro-5-cyclopropyl-1-(2-(4-methylpyridin-2-yl)-2-azaspiro[3.3]heptan-6-yl)-5,6-dihydro-4H-benzo[f][1,2,4]triazolo[4,3-a][1,4]diazepine (0.012 g, >98% pure, 34.1%) was isolated as a white solid after lyophilization of pure fractions. LCMS (ESI): m/z 447.4 (M+H); Retention time: 4.82 min (5-95% ACN/H$_2$O, method 5).

Compound Nos. 218 to 225, 227 to 229, 232 to 235, 247 to 250, and 270 to 278

Compound Nos. 218 to 225, 227 to 229, 232 to 235, 247 to 250, and 270 to 278 were prepared according to the methods set forth in Example 30 using appropriately substituted intermediates. Analytical data (LCMS) is also presented in Table 21.

Compound Nos. 279 to 1072 are prepared according to the procedure of Example 30 using appropriately substituted intermediates.

TABLE 21

| Compound Nos. 218 to 225, 227 to 229, 232 to 235, 247 to 250, and 270 to 278 | | |
|---|---|---|
| Compound No. | Analytical Data | Synthesis Method |
| 218 | LCMS (ESI): m/z 447.4 (M + H); Retention time: 4.67 min (5-95% ACN/H$_2$O, method 5); 98% | Examples 30 |
| 219 | LCMS (ESI): m/z 434.3 (M + H); Retention time: 6.37 min (5-95% ACN/H$_2$O, method 5); 98.5% | Examples 30 |
| 220 | LCMS (ESI): m/z 466.3 (M + H); Retention time: 7.97 min (5-95% ACN/H$_2$O, method 5); 98% | Examples 30 |
| 221 | LCMS (ESI): m/z 448.4 (M + H); Retention time: 6.65 min (5-95% ACN/H$_2$O, method 5); 98.5% | Examples 30 |
| 222 | LCMS (ESI): m/z 448.4 (M + H); Retention time: 6.65 min (5-95% ACN/H$_2$O, method 5); 98% | Examples 30 |
| 223 | LCMS (ESI): m/z 451.3 (M + H); Retention time: 6.10 min (5-95% ACN/H$_2$O, method 5); 98% | Examples 30 |
| 224 | LCMS (ESI): m/z 452.3 (M + H); Retention time: 7.43 min (5-95% ACN/H$_2$O, method 5); 98% | Examples 30 |
| 225 | LCMS (ESI): m/z 434.3 (M + H); Retention time: 7.43 min (5-95% ACN/H$_2$O, method 5); 98% | Examples 30 |
| 226 | LCMS (ESI): m/z 447.3 (M + H); Retention time: 4.78 min (5-95% ACN/H$_2$O, method 5); 98% | Examples 30 |
| 228 | LCMS (ESI): m/z 458.3 (M + H); Retention time: 9.84 min (5-95% ACN/H$_2$O, method 5); 98% | Examples 30 |
| 229 | LCMS (ESI): m/z 465.3 (M + H); Retention time: 6.52 min (5-95% ACN/H$_2$O, method 5); 98% | Examples 30 |
| 232 | LCMS (ESI): m/z 458.0 (M + H); Retention time: 7.49 min (5-95% ACN/H$_2$O, method 5); 98% | Examples 30 |
| 233 | LCMS (ESI): m/z 434.0 (M + H); Retention time: 3.69 min (5-95% ACN/H$_2$O, method 5); 98% | Examples X-32 |
| 234 | LCMS (ESI): m/z 447.9 (M + H); Retention time: 6.16 min (5-95% ACN/H$_2$O, method 5); 98% | Examples 30 |
| 237 | LCMS (ESI): m/z 465.2 (M + H); Retention time: 5.78 min (5-95% ACN/H$_2$O, method 5); 98% | Examples 30 |
| 247 | LCMS (ESI): m/z 452.1 (M + H); Retention time: 5.03 min (5-95% ACN/H$_2$O, method 5); 98% | Examples 30 |
| 248 | LCMS (ESI): m/z 459.2 (M + H); Retention time: 8.17 min (5-95% ACN/H$_2$O, method 5); 98% | Examples 30 |
| 249 | LCMS (ESI): m/z 481.2 (M + H); Retention time: 5.07 min (5-95% ACN/H$_2$O, method 5); 98% | Examples 30 |
| 250 | LCMS (ESI): m/z 487.2 (M + H); Retention time: 7.38 min (5-95% ACN/H$_2$O, method 5); 98% | Examples 30 |
| 270 | LCMS (ESI): m/z 448.2 (M + H); Retention time: 4.01 min (5-95% ACN/H$_2$O, method 5); 98% | Examples 30 |
| 271 | LCMS (ESI): m/z 519.2 (M + H); Retention time: 11.62 min (5-95% ACN/H$_2$O, method 5); 98% | Examples 30 |
| 272 | LCMS (ESI): m/z 517.2 (M + H); Retention time: 9.23 min (5-95% ACN/H$_2$O, method 5); 98% | Examples 30 |
| 273 | LCMS (ESI): m/z 465.2 (M + H); Retention time: 6.27 min (5-95% ACN/H$_2$O, method 5); 96% | Examples 30 |
| 274 | LCMS (ESI): m/z 477.2 (M + H); Retention time: 5.50 min (5-95% ACN/H$_2$O, method 5); 97.7% | Examples 30 |
| 275 | LCMS (ESI): m/z 461.4 (M + H); Retention time: 5.32 min (5-95% ACN/H$_2$O, method 5); 97.6% | Examples 30 |

561

TABLE 21-continued

Compound Nos. 218 to 225, 227 to 229, 232 to 235, 247 to 250, and 270 to 278

| Compound No. | Analytical Data | Synthesis Method |
|---|---|---|
| 276 | LCMS (ESI): m/z 501.3 (M + H); Retention time: 12.95 min (5-95% ACN/H$_2$O, method 5); 97.9% | Examples 30 |
| 277 | LCMS (ESI): m/z 469.2 (M + H); Retention time: 10.73 min (5-95% ACN/H$_2$O, method 5); 97.1% | Examples 30 |
| 278 | LCMS (ESI): m/z 519.3 (M + H); Retention time: 13.60 min (5-95% ACN/H$_2$O, method 5); 98.3% | Examples 30 |

Example 31

Compound No. 226

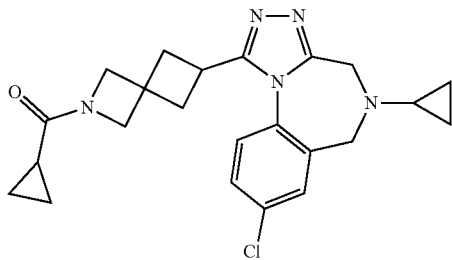

A mixture of 8-chloro-5-cyclopropyl-1-(2-azaspiro[3.3]heptan-2-ium-6-yl)-5,6-dihydro-4H-benzo[f][1,2,4]triazolo[4,3-a][1,4]diazepin-5-ium 2,2,2-trifluoroacetate (0.060 g, 0.103 mmol, 1.0 eq) from Example X-32, Step 6, DIPEA (0.090 mL, 0.515 mmol, 5 eq.), and cyclopropanecarbonyl chloride (0.014 mL, 0.154 mmol, 1.5 eq.) in DCM (1.0 mL) was stirred for 60 h at RT. The reaction mixture was concentrated under reduced pressure and the crude residue was purified by reverse phase chromatography (5-85% ACN/H$_2$O, 20 min method). (6-(8-chloro-5-cyclopropyl-5,6-dihydro-4H-benzo[1,2,4]triazolo[4,3-a][1,4]diazepin-1-yl)-2-azaspiro[3.3]heptan-2-yl)(cyclopropyl)methanone (0.010 g, 98% pure, 22.4% yield) was isolated as a white solid. LCMS (ESI): m/z 424.3 (M+H); Retention time: 6.34 min (5-95% ACN/H$_2$O, method 5).

Example 32

Compound No. 268

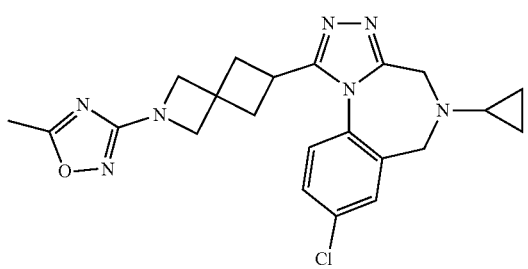

562

Step 1: 6-(8-chloro-5-cyclopropyl-5,6-dihydro-4H-benzo[f][1,2,4]triazolo[4,3-a][1,4]diazepin-1-yl)-2-azaspiro[3.3]heptane-2-carbonitrile

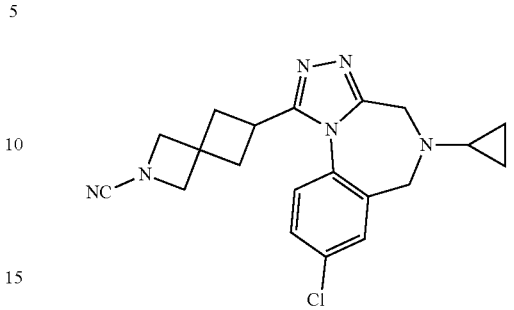

A mixture of 8-chloro-5-cyclopropyl-1-(2-azaspiro[3.3]heptan-2-ium-6-yl)-5,6-dihydro-4H-benzo[f][1,2,4]triazolo[4,3-a][1,4]diazepin-5-ium 2,2,2-trifluoroacetate (0.438 g, 0.750 mmol, 1.0 eq) from Example X-32, Step 7, DIPEA (0.654 mL, 3.76 mmol, 5 eq.), and cyanogen bromide (0.159 g, 1.50 mmol, 2 eq.) was stirred in DCM (2.5 mL) for 60 min at 0° C. The reaction mixture was diluted with EtOAc (10 mL) and washed with sat. aq. NaHCO$_3$ (2×10 mL), brine (1×10 mL) and dried over MgSO$_4$. Solids were removed by vacuum filtration, and the filtrate was concentrated under reduced pressure. The crude residue was purified by column chromatography (SiO$_2$, 0-10% MeOH/DCM) to afford 6-(8-chloro-5-cyclopropyl-5,6-dihydro-4H-benzo[f][1,2,4]triazolo[4,3-a][1,4]diazepin-1-yl)-2-azaspiro[3.3]heptane-2-carbonitrile (0.385 g, 99%) as a light brown solid. LCMS (ESI): m/z 381.1 (M+H); Retention time: 1.66 min (50-100% ACN/H$_2$O, method 3).

Step 2: (E)-6-(8-chloro-5-cyclopropyl-5,6-dihydro-4H-benzo[f][1,2,4]triazolo[4,3-a][1,4]diazepin-1-yl)-N-hydroxy-2-azaspiro[3.3]heptane-2-carboximidamide

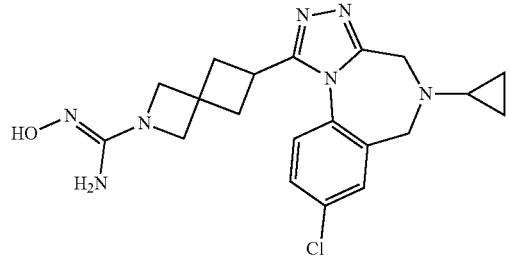 [SMILES: N/C(=N\O)N1CC2(CC(c3nnc4n3-c3ccc(Cl)cc3CN(C3CC3)C4)C2)C1]

A suspension of 6-(7-chloro-3,4-dihydro-2H-benzo[b][1,4]oxazine-4-carbonyl)-2,6-diazaspiro[3.3]heptane-2-carbonitrile (100 mg, 0.263 mmol, 1.0 eq.), TEA (0.0385 mL, 0.276 mmol, 1.05 eq.) and hydroxylamine hydrochloride (19.2 mg, 0.276 mmol, 1.05 eq.) in EtOH (1 mL) was heated at 80° C. for 1 hour. The mixture was concentrated under reduced pressure to afford (E)-6-(8-chloro-5-cyclopropyl-5,6-dihydro-4H-benzo[1,2,4]triazolo[4,3-a][1,4]diazepin-1-yl)-N-hydroxy-2-azaspiro[3.3]heptane-2-carboximidamide (0.109 g, 100%) as a light brown solid. The crude product was carried forward without further purification. LCMS (ESI): m/z 414.1 (M+H); Retention time: 1.46 min (50-100% ACN/H$_2$O, method 3).

Step 3: 3-(6-(8-chloro-5-cyclopropyl-5,6-dihydro-4H-benzo[f][1,2,4]triazolo[4,3-a][1,4]diazepin-1-yl)-2-azaspiro[3.3]heptan-2-yl)-5-methyl-1,2,4-oxadiazole (Compound No. 268)

A mixture of (E)-6-(8-chloro-5-cyclopropyl-5,6-dihydro-4H-benzo[f][1,2,4]triazolo[4,3-a][1,4]diazepin-1-yl)-N-hydroxy-2-azaspiro[3.3]heptane-2-carboximidamide (0.055 g, 0.133 mmol, 1 eq.) and acetic anhydride (0.027 mL, 0.28 mmol, 1.05 eq.) in pyridine (1 mL) was stirred for 1 h at 80° C. The reaction mixture was concentrated under reduced pressure and the crude residue was purified by reverse phase chromatography (5-85% ACN/H2O, 20 min method). 3-(6-(8-chloro-5-cyclopropyl-5,6-dihydro-4H-benzo[f][1,2,4]triazolo[4,3-a][1,4]diazepin-1-yl)-2-azaspiro[3.3]heptan-2-yl)-5-methyl-1,2,4-oxadiazole (0.011 g, 95.2% pure, 18% yield) was isolated as a white solid. LCMS (ESI): m/z 438.3 (M+H); Retention time: 7.11 min (5-95% ACN/H2O, method 5).

Compound No. 269

Compound No. 269 was prepared according to the methods set forth in Example 32 using appropriately substituted intermediates. Analytical data (LCMS) LCMS (ESI): m/z 464.4 (M+H); Retention time: 8.72 min (5-95% ACN/H2O, method 5); 97.0%.

Example 33

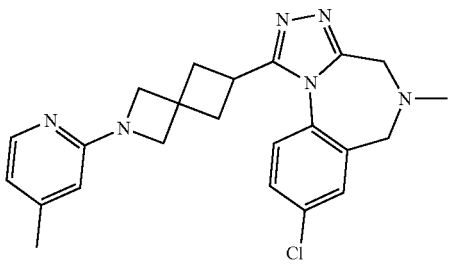

Compound No. 241

Step 1: tert-butyl (4-chloro-2-(((cyanomethyl)(methyl)amino)methyl)phenyl)carbamate

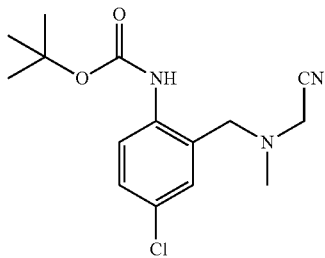 [SMILES: CN(CC#N)Cc1cc(Cl)ccc1NC(=O)OC(C)(C)C]

tert-butyl (4-chloro-2-formylphenyl)carbamate (3.00 g, 11.7 mmol, 1 eq.), 2-(methylamino)-acetonitrile hydrochloride (3.74 g, 35.1 mmol, 3 eq.), and DIPEA (6.16 g, 35.1 mmol, 3 eq.) were mixed in DCE (76 mL) and stirred for 15 min at 25° C. Acetic acid (2.1 mL, 35.1 mmol, 3 eq.)) and MgSO4 (4.32 g, 35.1 mmol, 3 eq.) were added, and the suspension was stirred for 2 h at 60° C. After the reaction mixture was cooled to 25° C., sodium triacetoxyborohydride (6.21 g, 29.3 mmol, 2.5 eq.) was added in two portions, and the reaction was stirred for 18 h at 25° C. The reaction was quenched with methanol and sodium bicarbonate (sat. aq.) to pH 8, and the aqueous layer was extracted with ethyl acetate twice. The organic layers were combined, dried over MgSO4, and evaporated under reduced pressure. The residue was purified by column chromatography (SiO2, 0-30% EtOAc/Hex) to give tert-butyl (4-chloro-2-(((cyanomethyl)(methyl)amino)methyl)phenyl)carbamate (1.33 g, 37% yield) as a white solid. LCMS (ESI): m/z 310 (M+H); Retention time: 3.36 min (50-100% ACN/H2O, method 3).

Step 2: 7-chloro-4-methyl-4,5-dihydro-3H-benzo[e][1,4]diazepin-2-amine

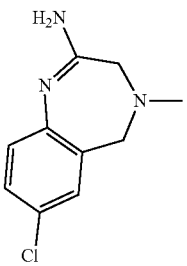

To a solution of tert-butyl (4-chloro-2-(((cyanomethyl)(methyl) amino)methyl)phenyl)carbamate (0.140 g, 0.45 mmol, 1 eq.) in dioxane (1.0 mL) was added hydrogen chloride solution in 1,4-dioxane (4.0 M, 2.25 mL, 9.0 mmol, 9 eq.) dropwise, and the reaction was stirred at 25° C. for 2 h. 2-Propanol (2.0 mL) was added. The solution was stirred for 18 h at 65° C., resulting in a light brown suspension. Na2CO3 (2.0 M, aq.) was added to the suspension, and the final pH was 11. The mixture was extracted with EtOAc three times, and the organic layers were combined, dried over MgSO4, and evaporated under reduced pressure. 7-chloro-4-methyl-4,5-dihydro-3H-benzo[e][1,4]diazepin-2-amine (125 mg, crude) was isolated as a brown solid, and used in the next step without further purification.

Step 3: tert-butyl 6-(8-chloro-5-methyl-5,6-dihydro-4H-benzo[f][1,2,4]triazolo[4,3-a][1,4]-diazepin-1-yl)-2-azaspiro[3.3]heptane-2-carboxylate

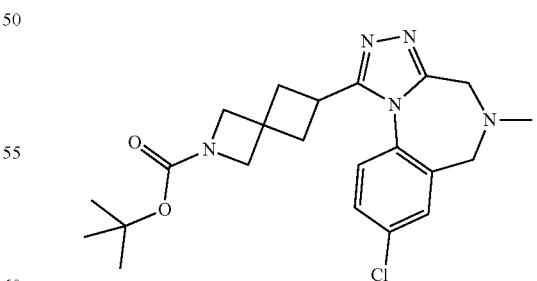

7-chloro-4-methyl-4,5-dihydro-3H-benzo[e][1,4]diazepin-2-amine (1.36 g, 6.5 mmol) and tert-butyl 6-(hydrazinecarbonyl)-2-azaspiro[3.3]heptane-2-carboxylate (1.65 mg, 6.5 mmol) were mixed in isopropanol (35 mL) and acetic acid (0.38 mL, 6.5 mmol), and the solution was stirred at 80° C. for 2 h. The reaction solution was diluted with EtOAc, washed by Na₂CO₃ (twice) and brine, dried over MgSO₄, and evaporated under reduced pressure. The brown residue was purified by column chromatography (SiO₂, 0-15% MeOH/DCM) to afford tert-butyl 6-(8-chloro-5-methyl-5,6-dihydro-4H-benzo[f][1,2,4]triazolo[4,3-a][1,4]diazepin-1-yl)-2-azaspiro[3.3]hept-ane-2-carboxylate (1.80 g, 65% yield) as white foam solid. LCMS (ESI): m/z 430 (M+H); Retention time: 1.42 min (50-100% ACN/H₂O, method 3).

Step 4: 8-chloro-5-methyl-1-(2-azaspiro[3.3]heptan-6-yl)-5,6-dihydro-4H-benzo[f][1,2,4]-triazolo[4,3-a][1,4]diazepine TFA Salt

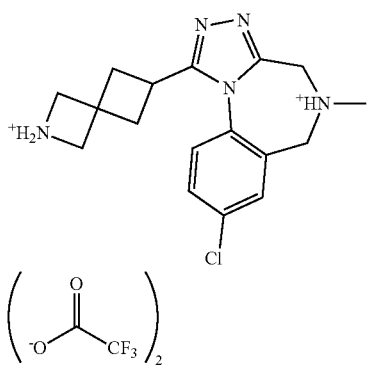

To a solution of tert-butyl 6-(8-chloro-5-methyl-5,6-di-hydro-4H-benzo[f][1,2,4]triazolo-[4,3-a][1,4]diazepin-1-yl)-2-azaspiro[3.3]heptane-2-carboxylate (1.53 g, 3.56 mmol) in DCM (21 mL) was added trifluoroacetic acid (5.5 mL, 71 mmol) at 0° C., and the solution was stirred at 25° C. for 2 h. The reaction mixture was evaporated under reduced pressure, and azeotropic evaporation was done with acetonitrile (twice) and toluene (once). 8-chloro-5-methyl-1-(2-azaspiro[3.3]heptan-6-yl)-5,6-dihydro-4H-benzo[f][1,2,4]triazolo[4,3-a][1,4]-diazepine TFA salt (4.03 g) was obtained as brown oil, and used without further treatment. LCMS (ESI): m/z 330 (M+H); Retention time: 1.40 min (50-100% ACN/H₂O, method 3).

Step 5: 8-chloro-5-methyl-1-(2-(4-methylpyridin-2-yl)-2-azaspiro[3.3]heptan-6-yl)-5,6-dihydro-4H-benzo[f][1,2,4]triazolo[4,3-a][1,4]diazepine (Compound No. 241)

8-Chloro-5-methyl-1-(2-azaspiro[3.3]heptan-6-yl)-5,6-dihydro-4H-benzo[f][1,2,4]triazolo[4,3-a][1,4]diazepine TFA salt (50 mg, 0.090 mmol, crude from Step 4), 2-bromo-4-methylpyridine (31 mg, 0.18 mmol), sodium tert-butoxide (43 mg, 0.45 mmol), RuPhos (4.2 mg, 9.0 umol) and RuPhos-Palladacycle-G3 (7.5 mg, 9.0 umol) were mixed in 1,4-dioxane (1.0 mL) and N-methylpyrrolidine (0.1 mL), and the mixture was stirred at 120° C. for 5 h. The reaction mixture was diluted with EtOAc, washed by NaHCO₃ (sat. aq.) and brine, dried over MgSO₄, filtered and evaporated under reduced pressure. The residue was purified by RP-HPLC (5-85% ACN/H₂O) to give 8-chloro-5-methyl-1-(2-(4-methylpyridin-2-yl)-2-azaspiro[3.3]heptan-6-yl)-5,6-di-hydro-4H-benzo[f][1,2,4]triazolo[4,3-a][1,4]diazepine (10.5 mg, 28% yield) as white solid. LCMS (ESI): m/z 421 (M+H); Retention time: 2.12 min (10-100% ACN/H₂O, method 4).

Compound Nos. 231, 237 to 240, 242 to 243, 251 to 252, and 256 to 258

Compound Nos. 231, 237 to 240, 242 to 243, 251 to 252, and 256 to 258 were prepared according to the methods set forth in Example 33 using appropriately substituted intermediates. Analytical data (LCMS) is also presented in Table 22.

TABLE 22

Compound Nos. 231, 237 to 240, 242 to 243, 251 to 252, and 256 to 258

| Compound No. | Analytical Data | Synthesis Method |
|---|---|---|
| 231 | LCMS (ESI): m/z 461.1 (M + H); Retention time: 4.0 min (5-95% ACN/H₂O, method 5) | Examples 33 |
| 237 | LCMS (ESI): m/z 422 (M + H); Retention time: 2.75 min (10-100% ACN/H₂O, method 4) | Examples 33 |
| 238 | LCMS (ESI): m/z 426 (M + H); Retention time: 2.06 min (10-100% ACN/H₂O, method 4) | Examples 33 |
| 239 | LCMS (ESI): m/z 422 (M + H); Retention time: 2.52 min (10-100% ACN/H₂O, method 4) | Examples 33 |
| 240 | LCMS (ESI): m/z 440 (M + H); Retention time: 3.18 min (10-100% ACN/H₂O, method 4) | Examples 33 |
| 242 | LCMS (ESI): m/z 439 (M + H); Retention time: 2.53 min (10-100% ACN/H₂O, method 4) | Examples 33 |
| 243 | LCMS (ESI): m/z 408 (M + H); Retention time: 1.70 min (10-100% ACN/H₂O, method 4) | Examples 33 |
| 251 | LCMS (ESI): m/z 422 (M + H); Retention time: 1.75 min (10-100% ACN/H₂O, method 4 | Examples 33 |
| 252 | LCMS (ESI): m/z 439 (M + H); Retention time: 2.49 min (10-100% ACN/H₂O, method 4) | Examples 33 |
| 256 | LCMS (ESI): m/z 447.1 (M + H); Retention time: 6.8 min (5-95% ACN/H₂O, method 5) | Examples 33 |
| 257 | LCMS (ESI): m/z 461.2 (M + H); Retention time: 1.8 min (5-95% ACN/H₂O, method 5) | Examples 33 |
| 258 | LCMS (ESI): m/z 461.2 (M + H); Retention time: 1.0 min (5-95% ACN/H₂O, method 5) | Examples 33 |

Example 34

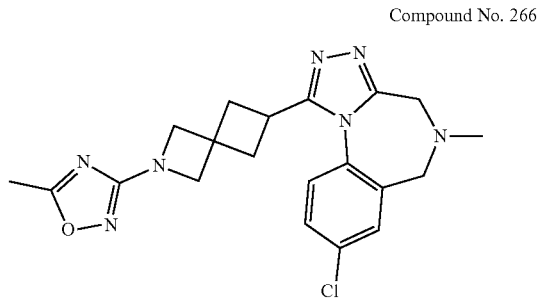

Compound No. 266

Step 1: 6-(8-chloro-5-methyl-5,6-dihydro-4H-benzo[f][1,2,4]triazolo[4,3-a][1,4]diazepin-1-yl)-2-azaspiro[3.3]heptane-2-carbonitrile

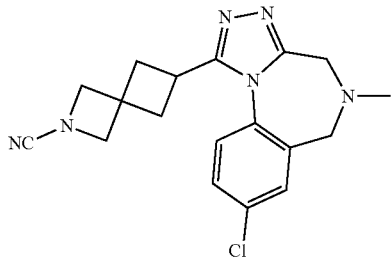 [SMILES: CN1Cc2cc(Cl)ccc2-n2c(nnc2C2CC3(C2)CN(C#N)C3)C1]

To a solution of 8-chloro-5-methyl-1-(2-azaspiro[3.3]heptan-6-yl)-5,6-dihydro-4H-benzo[f][1,2,4]triazolo[4,3-a][1,4]diazepine TFA salt (100 mg, 0.18 mmol) and DIPEA (0.16 mL) in DCM (0.5 mL) was added cyanogen bromide (38 mg) at 0° C., and the reaction was stirred at 0° C. for 1 h. The reaction mixture was diluted with EtOAc, washed by NaHCO₃ (sat. aq.) and brine. The organic layer was dried over MgSO₄ and evaporated under reduced pressure. The residue was purified by column chromatography (SiO₂, 0-10% MeOH/DCM) to give 6-(8-chloro-5-methyl-5,6-dihydro-4H-benzo[f][1,2,4]triazolo[4,3-a][1,4]diazepin-1-yl)-2-azaspiro[3.3]-heptane-2-carbonitrile (36 mg, 33% yield) as yellow film. LCMS (ESI): m/z 355 (M+H); Retention time: 2.31 min (10-100% ACN/H₂O, method 4).

Step 2: 6-(8-chloro-5-methyl-5,6-dihydro-4H-benzo[f][1,2,4]triazolo[4,3-a][1,4]diazepin-1-yl)-N-hydroxy-2-azaspiro[3.3]heptane-2-carboximidamide

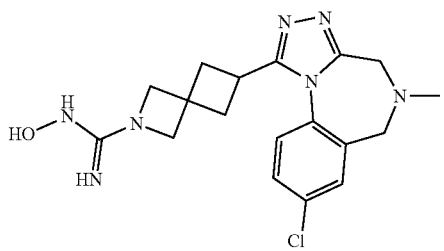 [SMILES: CN1Cc2cc(Cl)ccc2-n2c(nnc2C2CC3(C2)CN(C(=N)NO)C3)C1]

To a suspension of 6-(8-chloro-5-methyl-5,6-dihydro-4H-benzo[f][1,2,4]triazolo-[4,3-a][1,4]diazepin-1-yl)-2-azaspiro[3.3]heptane-2-carbonitrile (147 mg, 0.41 mmol) and hydroxyamine hydrochloride (30 mg, 0.43 mmol) in ethanol (1.5 mL) was added triethylamine (60 uL, 0.43 mmol), and the reaction was stirred at 80° C. for 1 h, resulting in a yellow solution. Ethanol was evaporated under reduced pressure, and the crude 6-(8-chloro-5-methyl-5,6-dihydro-4H-benzo[f][1,2,4]triazolo[4,3-a][1,4]diazepin-1-yl)-N-hydroxy-2-azaspiro[3.3]heptane-2-carboximidamide was diluted with pyridine (1.2 mL) and used without further treatment. LCMS (ESI): m/z 388 (M+H); Retention time: 1.44 min (50-100% ACN/H₂O, method 3).

Step 3: 3-(6-(8-chloro-5-methyl-5,6-dihydro-4H-benzo[f][1,2,4]triazolo[4,3-a][1,4]diazepin-1-yl)-2-azaspiro[3.3]heptan-2-yl)-5-methyl-1,2,4-oxadiazole (Compound No. 266)

To a solution of 6-(8-chloro-5-methyl-5,6-dihydro-4H-benzo[f][1,2,4]triazolo[4,3-a][1,4]diazepin-1-yl)-N-hydroxy-2-azaspiro[3.3]heptane-2-carboximidamide (46 mg, 0.12 mmol) in pyridine (0.4 mL) was added acetic anhydride (13 uL, 0.14 mmol) at 0° C., and the reaction was stirred at 0° C. for 30 min, then at 80° C. for 1 h. The reaction solution was diluted with EtOAc and washed by NaHCO₃ (sat. aq.) and brine. The organic layer was dried over MgSO₄ and evaporated under reduced pressure. The residue was purified by RP-HPLC (5-85% ACN/H₂O) to give 3-(6-(8-chloro-5-methyl-5,6-dihydro-4H-benzo[f][1,2,4]triazolo[4,3-a][1,4]diazepin-1-yl)-2-azaspiro[3.3]heptan-2-yl)-5-methyl-1,2,4-oxadiazole (4.8 mg, 9% yield) as white solid. LCMS (ESI): m/z 412; Retention time: 2.67 min (10-100% ACN/H₂O, method 4).

Compound No. 267

Compound No. 267 was prepared according to the methods set forth in Example 34 using appropriately substituted intermediates. Analytical data (LCMS): LCMS (ESI): m/z 438 (M+H); Retention time: 2.93 min (10-100% ACN/H₂O, method 4).

Example 35

Compound No. 236

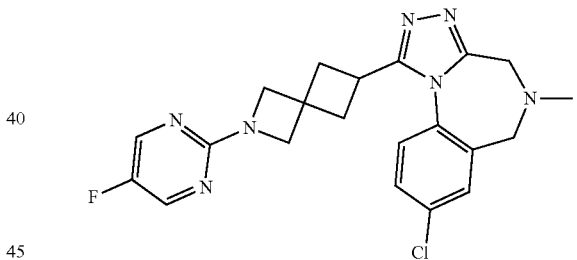

8-chloro-5-methyl-1-(2-(pyrimidin-2-yl)-2-azaspiro[3.3]heptan-6-yl)-5,6-dihydro-4H-benzo[f][1,2,4]triazolo[4,3-a][1,4]diazepine (Compound No. 236)

To a solution of 7-chloro-4-methyl-4,5-dihydro-3H-benzo[e][1,4]diazepin-2-amine (20 mg, 0.095 mmol) and 2-(5-fluoropyrimidin-2-yl)-2-azaspiro[3.3]heptane-6-carbohydrazide (25 mg, 0.11 mmol) in 2-propanol (1 mL) was added acetic acid (6 uL), and the reaction was stirred at 80° C. for 4 h. The reaction solution was diluted with EtOAc and washed by NaHCO₃ (sat. aq.) and brine. The organic layer was dried over MgSO4 and evaporated under reduced pressure. The residue was purified by RP-HPLC (5-85% ACN/H₂O) to give 8-chloro-5-methyl-1-(2-(5-fluoropyrimidin-2-yl)-2-azaspiro[3.3]heptan-6-yl)-5,6-dihydro-4H-benzo[f][1,2,4]triazolo[4,3-a][1,4]diazepine (20 mg, 70% yield) as white solid. LCMS (ESI): m/z 426 (M+H); Retention time: 2.82 min (10-100% ACN/H₂O, method 4).

Example 36

Compound No. 259

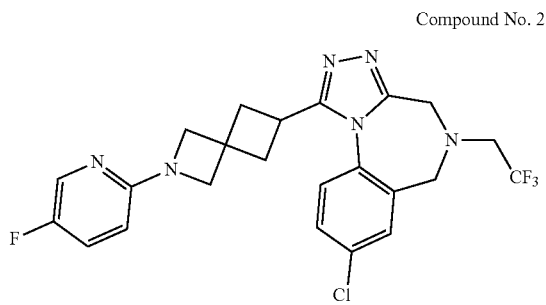

8-chloro-1-(2-(5-fluoropyridin-2-yl)-2-azaspiro[3.3]
heptan-6-yl)-5-(2,2,2-trifluoroethyl)-5,6-dihydro-
4H-benzo[f][1,2,4]triazolo[4,3-a][1,4]diazepine
(Compound No. 259)

To a mixture of 2,2,2-trifluoroethyl trifluoromethanesulfonate (56 mg, 0.244 mg, 2 eq.) and 8-chloro-1-(2-(5-fluoropyridin-2-yl)-2-azaspiro[3.3]heptan-6-yl)-5,6-dihydro-4H-benzo[f][1,2,4]triazolo[4,3-a][1,4]diazepine from Example 10, step 3 (50 mg, 0.122 mmol, 1.0 eq.) in anhydrous MeCN (0.75 mL) was added K₂CO₃ (35 mg, 0.13 mmol, 2.1 eq.) and the resultant mixture was stirred at room temperature for 0.5 hours and then at 75° C. for 3 hours. The mixture was cooled and partitioned between sodium bicarbonate solution and DCM. The organic fraction was collected, concentrated to a residue, and purified by reverse phase HPLC, eluting with a gradient of 5-85% CH₃CN in water, to give the title compound as a white solid (23.2 mg, 38% yield). LCMS (ESI): m/z 493.1 (M+H), Retention time: 9.0 min (5-95% ACN/H₂O with 0.1% formic acid, method 5).

Example 37

Compound No. 246

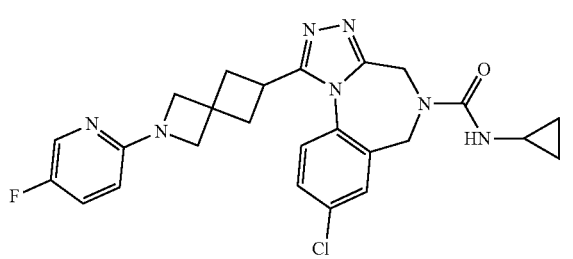

8-chloro-N-cyclopropyl-1-(2-(5-fluoropyridin-2-yl)-
2-azaspiro[3.3]heptan-6-yl)-4H-benzo[f][1,2,4]triazolo[4,3-a][1,4]diazepine-5(6H)-carboxamide
(Compound No. 246)

To a solution of 8-chloro-1-(2-(5-fluoropyridin-2-yl)-2-azaspiro[3.3]heptan-6-yl)-5,6-dihydro-4H-benzo[f][1,2,4]triazolo[4,3-a][1,4]diazepine from Example 10, step 3 (35 mg, 0.085 mmol, 1.0 eq.) in 0.5 ml anhydrous THF and 30 μL DMF was added isocyanatocyclopropane (9 μL, 0.128 mmol, 1.5 eq.) and the mixture was heated at 45° C. in a sealed tube for 18 hours. The solution was diluted with methanol, concentrated under vacuum, and purified by reverse phase HPLC, eluting with a gradient of 5-85% CH₃CN in water, to give 18.7 mg of white solid (44.5% yield). LCMS (ESI): m/z 494.1 (M+H), Retention time: 6.2 min (5-95% ACN/H₂O with 0.1% formic acid, method 5).

Example 38

Compound No. 230

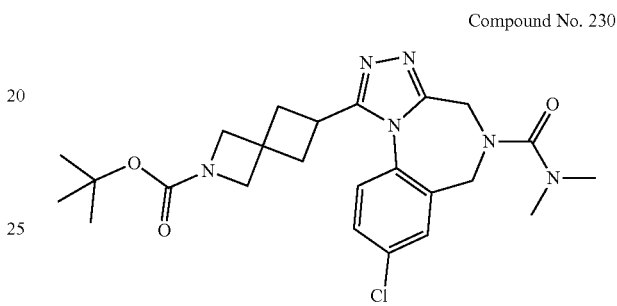

Step 1: Synthesis of tert-butyl 6-(8-chloro-5-(dimethylcarbamoyl)-5,6-dihydro-4H-benzo[f][1,2,4]triazolo[4,3-a][1,4]diazepin-1-yl)-2-azaspiro[3.3]heptane-2-carboxylate

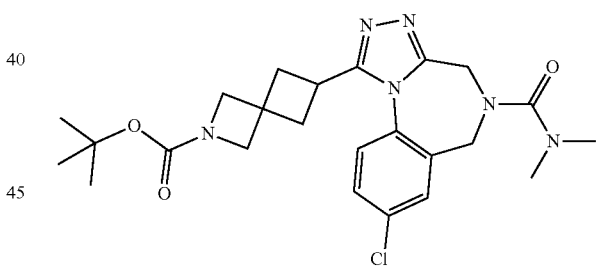

To a cooled 0° C. solution of 4-nitrophenyl chloroformate (29 mg, 0.143 mmol, 1.1 eq.) and triethylamine (36 μL, 0.26 mmol, 2 eq.) in anhydrous DCM (300 μL) was slowly added a solution of tert-butyl 6-(8-chloro-5,6-dihydro-4H-benzo[f][1,2,4]triazolo[4,3-a][1,4]diazepin-1-yl)-2-azaspiro[3.3]heptane-2-carboxylate from Example 12, step 6 (54 mg, 0.13 mmol, 1.0 eq.) in DCM (1 mL). The mixture was stirred for three hours at 0° C., then allowed to warm to room temperature and stirred for 1 hour. A solution of 2M dimethylamine in THF (500 μL, 1.0 mmol, 7.7 eq) and the mixture was stirred at 45° C. for 72 hours. The reaction mixture was diluted with DCM and successively washed with water, 1M citric acid soln., and brine. The organic fraction was dried over sodium sulfate and concentrated to 52 mg of clear residue, which was used in the next step without further purification (82% yield). MS (ESI): m/z 487.2 (M+H)

Step 2: 6-(8-chloro-5-(dimethylcarbamoyl)-5,6-dihydro-4H-benzo[f][1,2,4]triazolo[4,3-a][1,4]diazepin-1-yl)-2-azaspiro[3.3]heptan-2-ium 2,2,2-trifluoroacetate

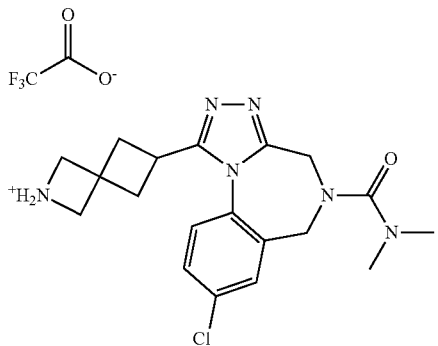

To a solution of tert-butyl 6-(8-chloro-5-(dimethylcarbamoyl)-5,6-dihydro-4H-benzo[f][1,2,4]triazolo[4,3-a][1,4]diazepin-1-yl)-2-azaspiro[3.3]heptane-2-carboxylate (52 mg, 0.10 mmol, 1 eq.) in 3 mL of DCM was added 1 mL of TFA, and the solution was stirred at room temperature for 2 hours. The solution was concentrated under vacuum, and the residue suspended in toluene and concentrated under vacuum to give the title compound as 55 mg of a clear oil (100% yield). MS (ESI): m/z 387.1 (M+H)

Step 3: 8-chloro-1-(2-(5-fluoropyridin-2-yl)-2-azaspiro[3.3]heptan-6-yl)-N,N-dimethyl-4H-benzo[j][1,2,4]triazolo[4,3-a][1,4]diazepine-5(6H)-carboxamide (Compound No. 230)

A vial was charged with 6-(8-chloro-5-(dimethylcarbamoyl)-5,6-dihydro-4H-benzo[f][1,2,4]triazolo[4,3-a][1,4]diazepin-1-yl)-2-azaspiro[3.3]heptan-2-ium 2,2,2-trifluoroacetate (55 mg, 0.11 mmol, 1.0 eq.), 2-bromo-5-fluoropyridine (39 mg, 0.22 mmol, 2 eq.), sodium tert-butoxide (53 mg, 0.55 mmol, 5 eq.), and 1 ml of a 9:1 mixture of 1,4-dioxane: NMP. The resultant suspension was degassed, placed under a nitrogen atmosphere, and heated at 85° C. for 5 hours. The mixture was cooled, filtered through celite (washing with DCM and EtOAc) and concentrated to a brown oil. The crude product was dissolved in methanol and purified by reverse phase chromatography, eluting from a C18 column with a gradient of 5-85% CH₃CN in water to give the title compound as 9.7 mg of a white solid (18.3% yield). LCMS (ESI): m/z 482.5 (M+H), Retention time: 6.9 min (5-95% ACN/H₂O with 0.1% formic acid, method 5).

Example 39

Compound No. 255

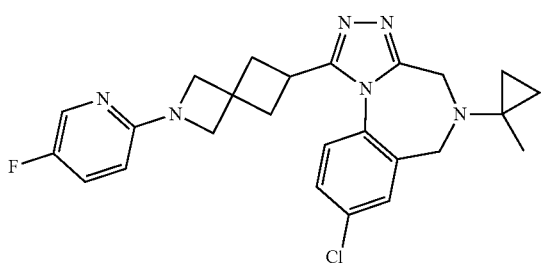

Step 1: Synthesis of tert-butyl (4-chloro-2-(((1-methylcyclopropyl)amino)methyl)phenyl)-carbamate

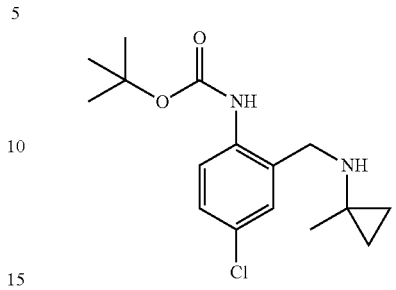

To a stirred solution of tert-butyl (4-chloro-2-formylphenyl)carbamate (0.5 g, 1.955 mmol, 1.0 eq) in MeOH (10 mL) was added 1-methylcyclopropan-1-amine (0.2781 g, 3.910 mmol, 2.0 eq) and the mixture was stirred at 43° C. for 16 h. THF (6.0 mL) was added to the reaction mixture, followed by the addition of sodium triacetoxyborohydride (2.08 g, 9.80 mmol, 5.0 eq) and acetic acid (0.35 g, 5.89 mmol, 3.0 eq), and stirred at RT for 20 h. The reaction mixture was diluted with EtOAc (20 mL) and sat. aq. NaHCO₃ (20 mL). The organic phase was collected, and the aqueous phase was extracted with EtOAc (2×10 mL). Combined organics were washed with brine, dried over MgSO₄, filtered, and concentrated under reduced pressure. The residue was purified by column chromatography (SiO2, 0-20% EtOAc/Hex) to afford tert-butyl (4-chloro-2-(((1-methylcyclopropyl)amino)methyl)phenyl)-carbamate (0.520 g, 85%) as a white solid. LCMS (ESI): m/z=311.4 (M+H), retention time; 1.40 min (50-100% ACN/H₂O, method 3).

Step 2: Synthesis of tert-butyl (4-chloro-2-(((cyanomethyl)(1-methylcyclopropyl)amino)methyl)-phenyl)carbamate

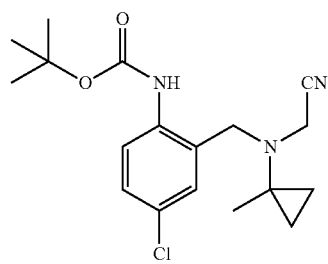 [SMILES: CC(C)(C)OC(=O)Nc1ccc(Cl)cc1CN(CC#N)C1(C)CC1]

To a mixture of tert-butyl (4-chloro-2-(((1-methylcyclopropyl)amino)methyl)-phenyl)carbamate (0.510 g, 1.64 mmol, 1.0 eq), K₂CO₃ (0.453 g, 3.28 mmol, 2.0 eq), and KI (0.164 g, 0.988 mmol, 0.6 eq) in ACN (2.0 mL) and 1,4-dioxane (3.0 mL) was added 2-chloroacetonitrile (0.248 g, 3.28 mmol, 2.0 eq). The mixture was stirred at 80° C. for 22 h under an atmosphere of N₂. The reaction mixture was then cooled to RT, diluted with (1:1) mixture of EtOAc and sat. aq. NaHCO₃ (20 mL). The organic phase was collected, and the aqueous phase was extracted with EtOAc (2×20 mL). The combined organics were washed with sat. aq Na₂S₂O₃ solution, brine, dried over MgSO₄, filtered, and concentrated under reduced pressure. The residue was purified by column chromatography (SiO2, 0-20% EtOAc/Hex) to afford tert-butyl (4-chloro-2-(((cyanomethyl)(1-methylcyclopropyl)amino)methyl)-phenyl)carbamate (0.50 g, 87%) as a white solid. LCMS (ESI): m/z=350.1 (M+1), retention time; 4.15 min (50-100% ACN/H₂O, method 3).

Step 3: Synthesis of 7-chloro-4-(1-methylcyclopropyl)-4,5-dihydro-3H-benzo[e][1,4]diazepin-2-amine

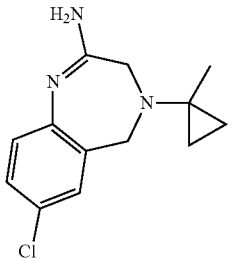 [SMILES: CC1(N2CC(N)=Nc3ccc(Cl)cc3C2)CC1]

A solution of acetyl chloride (3.17 g, 40.4 mmol, 20.0 eq) in isopropanol (15 mL) was stirred for 20 min at RT prior to slow addition to a solution of tert-butyl (4-chloro-2-(((cyanomethyl)(1-methylcyclopropyl)amino)-methyl)-phenyl) carbamate (0.705 g, 2.02 mmol, 1.0 eq) in isopropanol (15 mL) and stirred for 60 h at 50° C. The reaction mixture was concentrated under reduced pressure and the crude was mixed vigorously with a (1:1) mixture of EtOAc/satd aq NaHCO₃ (60 mL). The organic phase was collected, and the aqueous phase was extracted with EtOAc (3×15 mL). Combined organics were washed with brine, dried over MgSO₄, filtered, and concentrated under reduced pressure. The crude residue was purified by column chromatography (SiO₂, 0-100% EtOAc/Hex, 0-100% DCM/EtOAc, 0-12% MeOH/DCM) to afford 7-chloro-4-(1-methylcyclopropyl)-4,5-dihydro-3H-benzo[e][1,4]diazepin-2-amine (0.433 g, 86% yield) as a light brown solid. LCMS (ESI): m/z 250.1 (M+H); Retention time: 1.39 min (50-100% ACN/H₂O, method 3).

Step 4: Synthesis of tert-butyl 6-(hydrazinecarbonyl)-2-azaspiro[3.3]heptane-2-carboxylate

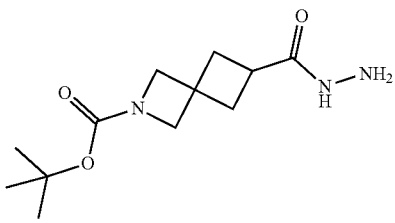

To a stirred solution of 2-(tert-butoxycarbonyl)-2-azaspiro[3.3]heptane-6-carboxylic acid (0.26 g, 1 mmol, 1 eq.) in THF (5 mL) was added 1-1'-Carbonyldiimidazole (0.19 g, 1.2 mmol, 1.2 eq.) and the mixture was stirred at RT overnight. The resulting mixture was added to a solution of hydrazine monohydrate (0.07 mL, 1.4 mmol, 1.4 eq.) in THF (10 mL) and stirred at RT overnight. The mixture was diluted with brine and extracted with ethyl acetate. The organic phase was separated, washed with brine, dried (MgSO₄), filtered and concentrated in vacuo to afford tert-butyl 6-(hydrazinecarbonyl)-2-azaspiro[3.3]heptane-2-car-boxylate as a white solid (0.29 g, 100% yield). This material was used without further purification. (TLC rf: 0.4; 10% MeOH in DCM).

Step 5: Synthesis of tert-butyl 6-(8-chloro-5-(1-methylcyclopropyl)-5,6-dihydro-4H-benzo[f]-[1,2,4]triazolo[4,3-a][1,4]diazepin-1-yl)-2-azaspiro[3.3]heptane-2-carboxylate

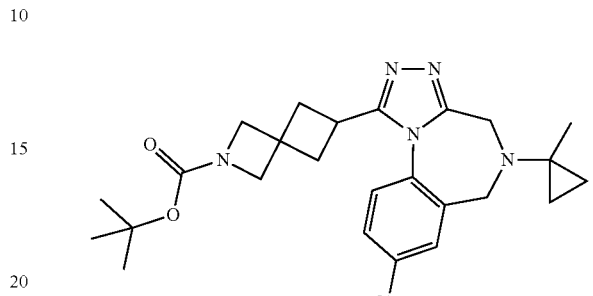

A mixture of 7-chloro-4-(1-methylcyclopropyl)-4,5-dihydro-3H-benzo[e][1,4]-diazepin-2-amine (0.058 g, 0.232 mmol, 1.0 eq), 2-(5-fluoro-4-methylpyridin-2-yl)-2-azaspiro-[3.3]heptane-6-carbohydrazide (0.089 g, 0.348 mmol, 1.5 eq), and AcOH (2 drops) in 2-propanol (1 mL) was stirred for 20 h at 80° C. The reaction mixture was then concentrated under reduced pressure, and the crude was diluted with DCM (5 mL) and satd aq NaHCO₃ (5 mL). Organic phase was collected, and the aqueous phase was extracted with DCM (3×5 mL). Combined organics were washed with brine, dried over MgSO4, filtered, and concentrated under reduced pressure. The crude residue was purified by column chromatography (SiO₂, 0-10% MeOH/DCM) to afford tert-butyl 6-(8-chloro-5-(1-methylcyclopropyl)-5,6-dihydro-4H-benzo[f][1,2,4]triazolo[4,3-a]-[1,4]diazepin-1-yl)-2-azaspiro[3.3]heptane-2-carboxylate (0.082 g, 74%) as a light brown solid. LCMS (ESI): m/z 470.2 (M+H); Retention time: 2.48 min (50-100% ACN/H₂O, method 3).

Step 6: Synthesis of 8-chloro-5-(1-methylcyclopropyl)-1-(2-azaspiro[3.3]heptan-2-ium-6-yl)-5,6-dihydro-4H-benzo[f][1,2,4]triazolo[4,3-a][1,4]diazepin-5-ium-6-ylium 2,2,2-trifluoroacetate

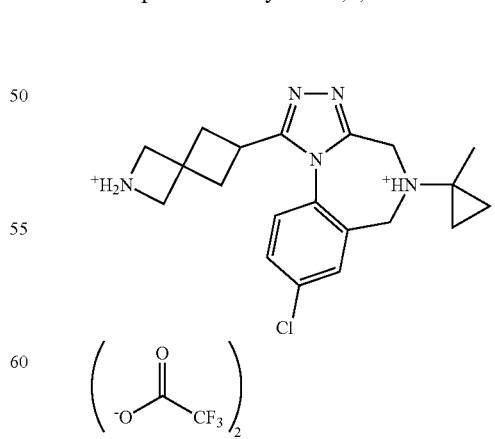

To a solution of tert-butyl 8-chloro-5-(1-methylcyclopropyl)-1-(2-azaspiro[3.3]heptan-2-ium-6-yl)-5,6-dihydro-4H-benzo[f][1,2,4]triazolo[4,3-a][1,4]diazepin-5-ium 2,2,2-trifluoroacetate (0.279 g, 0.594 mmol, 1.0 eq) in DCM (20 mL) at 0° C., TFA (6 mL) was added dropwise. The reaction mixture was allowed to warm to RT and stirred 60 min. The mixture was concentrated under reduced pressure, and the crude residue was azeotroped with toluene (4×20 mL). After 6 h under high vacuum, 8-chloro-5-(1-methylcyclopropyl)-1-(2-azaspiro[3.3]heptan-2-ium-6-yl)-5,6-dihydro-4H-benzo[f][1,2,4]triazolo[4,3-a][1,4]diazepin-5-ium-6-ylium 2,2,2-trifluoroacetate (0.353 g, 100%) was isolated as a brown solid. LCMS (ESI): m/z 370.1 (M+H); Retention time: 1.41 min (50-100% ACN/H$_2$O, method 3).

Step 7: Synthesis of 8-chloro-1-(2-(5-fluoropyridin-2-yl)-2-azaspiro[3.3]heptan-6-yl)-5-(1-methylcyclopropyl)-5,6-dihydro-4H-benzo[f][1,2,4]triazolo[4,3-a][1,4]diazepine (Compound No. 255)

A mixture of 8-chloro-5-(1-methylcyclopropyl)-1-(2-azaspiro[3.3]heptan-2-ium-6-yl)-5,6-dihydro-4H-benzo[f][1,2,4]triazolo[4,3-a][1,4]diazepin-5-ium-6-ylium 2,2,2-trifluoroacetate (0.025 g, 0.043 mmol, 1.0 eq), 2-chloro-5-fluoropyridine (0.012 g, 0.087 mmol, 2.0 eq), NaO$^t$Bu (0.021 g, 0.218 mmol, 5.0 eq.), and RuPhos Pd G3 (0.004 g, 0.004 mmol, 0.1 eq) was stirred in 1,4-dioxane (1.0 mL) and few drops of NMP under a N$_2$ atmosphere for 16 h at 90° C. The reaction mixture was diluted with EtOAc (3 mL) and filtered through a pad of celite. The filter cake was washed with EtOAc (2×2 mL) and the combined filtrates were concentrated under reduced pressure. The crude residue was purified by reverse phase chromatography (5-85% ACN/H$_2$O, 20 min method). 8-chloro-1-(2-(5-fluoropyridin-2-yl)-2-azaspiro[3.3]heptan-6-yl)-5-(1-methylcyclopropyl)-5,6-dihydro-4H-benzo[f][1,2,4]triazolo[4,3-a][1,4]diazepine (0.0085 g, >97% pure, 41.1%) was isolated as a white solid after lyophilization of pure fractions. LCMS (ESI): m/z 465.2 (M+H); Retention time: 7.35 min (5-95% ACN/H$_2$O, method 5).

Compound Nos. 244 to 245, 253 to 254, and 260 to 265

Compound Nos. 244 to 245, 253 to 254, and 260 to 265 were prepared according to the methods set forth in Example 38 using appropriately substituted intermediates. Analytical data (LCMS) is also presented in Table 23.

TABLE 23

Compound Nos. 244 to 245, 253 to 254, and 260 to 265

| Compound No. | Analytical Data | Synthesis Method |
|---|---|---|
| 244 | LCMS (ESI): m/z 462.0 (M + H); Retention time: 6.75 min (10-100% ACN/H$_2$O, method 5) | Example 39 |
| 245 | LCMS (ESI): m/z 479.0 (M + H); Retention time: 6.03 min (10-100% ACN/H$_2$O, method 5) | Example 39 |
| 253 | LCMS (ESI): m/z 462.3 (M + H); Retention time: 7.95 min (10-100% ACN/H$_2$O, method 5) | Example 39 |
| 254 | LCMS (ESI): m/z 448.2 (M + H); Retention time: 4.10 min (10-100% ACN/H$_2$O, method 5) | Example 39 |
| 260 | LCMS (ESI): m/z 479.1 (M + H); Retention time: 6.27 min (10-100% ACN/H$_2$O, method 5) | Example 39 |
| 261 | LCMS (ESI): m/z 466.3 (M + H); Retention time: 8.48 min (10-100% ACN/H$_2$O, method 5) | Example 39 |
| 262 | LCMS (ESI): m/z 472.2 (M + H); Retention time: 10.75 min (10-100% ACN/H$_2$O, method 5) | Example 39 |
| 263 | LCMS (ESI): m/z 473.1 (M + H); Retention time: 9.41 min (10-100% ACN/H$_2$O, method 5) | Example 39 |
| 264 | LCMS (ESI): m/z 448.1 (M + H); Retention time: 6.77 min (10-100% ACN/H$_2$O, method 5) | Example 39 |
| 265 | LCMS (ESI): m/z 461.2 (M + H); Retention time: 5.10 min (10-100% ACN/H$_2$O, method 5) | Example 39 |

In Vitro Activity

Example B1

Vasopressin V1A Receptor Antagonist Assay

The purpose of this assay was to determine the inhibitory effect of synthesized compounds on the Vasopressin V1a receptor. The assay as performed in Chinese Hamster Ovary (CHO) cells expressing the human Arginine Vasopressin Receptor 1a (AVPR1a). Arginine Vasopressin (AVP) evokes an increase in intracellular calcium in CHO-AVPR1a cells which is measured in a fluorescence assay on the FLIPR$^{TETRA}$ using calcium sensitive dyes. Test compounds were assessed for their ability to affect the magnitude of the response to AVP, with antagonists showing a concentration-dependent reduction in the AVP-mediated fluorescence. Compounds were tested in duplicate in a 10-point, 1:3 dilution series starting at a nominal concentration of 3 μM in the assay.

CHO-AVPR1a cells were maintained in routine culture in T175 Flasks at 37° C., 5% CO2. The growth medium consists of Ham's F12 media supplemented with 10% v/v fetal bovine serum, 1× non-essential amino acids, and 0.4 mg/ml Geneticin G418.

On day one, cells were harvested from T175 flasks when they are 80-90% confluent by first washing the cell monolayer with PBS and then dissociated using trypsin 0.05%/EDTA (3 mL for a T175 Flask). The flasks were incubated at room temperature until the cells detached. To the cell suspension, 10 ml of growth media was added and the cell density determined using the Vi-Cell automated cell counter. The cells were spun at 1000 rpm for 3 minutes, then the supernatant was carefully removed and discarded. The cell pellet was re-suspended at 6.0e$^5$ cells/ml in growth media. 25 μL of cells in growth media was dispensed into each well (15,000 cells per well) of a poly-D-lysine coated black, clear bottomed, 384-well plate. The plates were incubated at 37° C., 5% CO$_2$ overnight.

At the start of each assay day, the potency of AVP was assessed and an EC$_{80}$ concentration determined for subsequent compound profiling. Assays were performed using a two-step addition protocol on the FLIPR$^{TETRA}$; first addition of 5 μl of control or test compound at 10× final in assay buffer with 15 min incubation at 37° C., 5% CO$_2$ followed by 10 μl of AVP at 6× final concentration in assay buffer. Changes in fluorescence were monitored for 3 min after both additions on the FLIPR$^{TETRA}$ using 470-495 nm excitation and 515-575 nm emission wavelengths. The assay buffer consisted of HBSS (+Ca/+Mg) supplemented with 20 mM HEPES, and for the preparation of the AVP agonist only, 0.1% w/v bovine serum albumin. The assay was initiated by the removal of growth media from the cells and replacement with 45 μl of Calcium-6 dye (Molecular Devices) prepared at 1× in assay buffer. Cells are loaded with dye for 60-90 min at 37° C., 5% CO$_2$ before initiation of the FLIPR$^{TETRA}$ protocol. For the AVP potency determination, the first addition consisted of assay buffer containing 3% v/v DMSO and the second addition, a 10-point dilution series of AVP (1:3 dilutions from 1 μM) in assay buffer supplemented with 0.1% BSA. For compound profiling, test compounds were first serially diluted in DMSO (10-point curve, 1:3 dilutions) then diluted 33.3-fold in assay buffer prior to addition to the dye loaded cells on the FLIPR$^{TETRA}$. At the end of the incubation period, 10 μl of AVP in assay buffer containing 0.1% BSA was added at the previously determined EC$_{80}$ concentration.

In-plate controls for the assay include Ro5028442 and PF-184563 concentration-response curves as reference V1a antagonists and an AVP concentration-response curve to confirm the reproducibility of the $EC_{80}$ used for the compound challenge.

MAX-MIN raw data is normalised to in-plate assay controls comprising DMSO matched solutions of 300 nM SR49059 (100% inhibition) and AVP $EC_{80}$ (0% inhibition).

Selectivity profiling of certain example compounds was determined against Vasopressin V1b and V2 receptors.

Example B2

Vasopressin V1B Receptor Antagonist Assay

The purpose of the assay is to determine the inhibitory effect of synthesized compounds on the Vasopressin V1b receptor. The assay was performed in Chinese Hamster Ovary (CHO) cells expressing the human Arginine Vasopressin Receptor 1b (AVPR1b). Arginine Vasopressin (AVP) evokes an increase in intracellular calcium in CHO-AVPR1b cells which is measured in a fluorescence assay on the FLIPR$^{TETRA}$ using calcium sensitive dyes. Test compounds were assessed for their ability to affect the magnitude of the response to AVP, with antagonists showing a concentration-dependent reduction in the AVP-mediated fluorescence.

CHO-AVPR1b cells were maintained in routine culture in T175 Flasks at 37° C., 5% CO2. The growth medium consisted of Ham's F12 media supplemented with 10% v/v fetal bovine serum, 1× non-essential amino acids, and 0.4 mg/ml Geneticin G418.

Cells were harvested from T175 flasks when they were 80-90% confluent by first washing the cell monolayer with PBS and then dissociated using trypsin 0.05%/EDTA (3 mL for a T175 Flask). The flasks were incubated at room temperature until the cells detached. To the cell suspension, 10 ml of growth media was added and the cell density determined using the Vi-Cell automated cell counter. The cells were spun at 1000 rpm for 3 minutes, then the supernatant was carefully removed and discarded. The cell pellet was re-suspended at $6.0e^5$ cells/ml in growth media. 25 µL of cells in growth media was dispensed into each well (15,000 cells per well) of a poly-D-lysine coated black, clear bottomed, 384-well plate. The plates were incubated at 37° C., 5% $CO_2$ overnight.

At the start of each assay day, the potency of AVP is assessed and an $EC_{80}$ concentration determined for subsequent compound profiling. Assays were performed using a two-step addition protocol on the FLIPR$^{TETRA}$; first addition of 5 µl of control or test compound at 10× final in assay buffer with 15 min incubation at 37° C., 5% $CO_2$ followed by 10 µl of AVP at 6× final concentration in assay buffer. Changes in fluorescence were monitored for 3 min after both additions on the FLIPR$^{TETRA}$ using 470-495 nm excitation and 515-575 nm emission wavelengths. The assay buffer consisted of HBSS (+Ca/+Mg) supplemented with 20 mM HEPES, and for the preparation of the AVP agonist only, 0.1% w/v bovine serum albumin. The assay was initiated by the removal of growth media from the cells and replacement with 45 µl of Calcium-6 dye (Molecular Devices) prepared at 1× in assay buffer. Cells were loaded with dye for 60-90 min at 37° C., 5% $CO_2$ before initiation of the FLIPR$^{TETRA}$ protocol. For the AVP potency determination, the first addition consisted of assay buffer containing 3% v/v DMSO and the second addition a 10-point dilution series of AVP (1:3 dilutions from 1 µM) in assay buffer supplemented with 0.1% BSA. For compound profiling, test compounds were first serially diluted in DMSO (10-point curve, 1:3 dilutions) then diluted 33.3-fold in assay buffer prior to addition to the dye loaded cells on the FLIPR$^{TETRA}$. At the end of the incubation period 10 µl of AVP in assay buffer containing 0.1% BSA was added at the previously determined $EC_{80}$ concentration.

In-plate controls for the assay include a Nelivaptan concentration-response curve as the reference V1b antagonist and an AVP concentration-response curve to confirm the reproducibility of the $EC_{80}$ used for the compound challenge.

MAX-MIN raw data is normalised to in-plate assay controls comprising DMSO matched solutions of 3 µM nelivaptan (100% inhibition) and AVP $EC_{80}$ (0% inhibition).

Example B3

Vasopressin V2 Receptor Antagonist Assay

The purpose of the assay was to determine the inhibitory effect of synthesized compounds on the Vasopressin receptor 2. The assay was performed in commercially available 1321N1 cells expressing the human Arginine Vasopressin Receptor V2 (AVPR2) (Perkin Elmer #ES-363-CF). Arginine Vasopressin (AVP) evokes an increase in intracellular cAMP in these cells which is measured in a TR-FRET assay using a Europium cAMP tracer and ULight labelled antibody reagents contained in a LANCE Ultra cAMP kit (Perkin Elmer #TRF0263). Increases in cAMP in the assay result in a reduction in TR-FRET as the cAMP produced by the stimulated cells competes with the Eu-cAMP tracer for binding sites on the ULight labelled antibody. Test compounds were assessed for their ability to affect the magnitude of the response to AVP, with antagonists showing a concentration-dependent decrease in the AVP-mediated reduction in TR-FRET signal.

cAMPZen V2 assay ready cells were thawed at 37° C. and resuspended directly from frozen in 9 ml growth medium consisting of DMEM supplemented with 10% v/v fetal bovine serum, 1× non-essential amino acids, and 1 mM sodium pyruvate. Cells were spun at 1000 rpm for 3 minutes and the supernatant was carefully removed and discarded. The pellet was resuspended in 5 ml stimulation buffer and the cell density determined using the Vi-Cell automated cell counter. The cell suspension was diluted to a $0.2\times10^6$/ml suspension ready for plating. To all wells of a white 384-well Optiplate (Perkin Elmer #6007299) 5 µL of cells in stimulation buffer were dispensed (1,000 cells per well). Stimulation buffer consisted of HBSS (+Ca/+Mg) supplemented with 5 mM HEPES, 0.1% BSA stabiliser and 0.5 mM IBMX.

At the start of each assay day the potency of AVP was assessed and an $EC_{80}$ concentration determined for subsequent compound profiling. Assays were performed by first an addition of 2.5 µl of control or test compound at 4× final concentration in stimulation buffer followed by 2.5 µl of AVP at 4× final concentration in stimulation buffer. After a 1 hour reaction, detection reagents were added by first an addition of 5 µl EU-cAMP tracer, followed by 5 µl ULight-anti-cAMP both diluted as per the manufacturer's instructions. After a one hour incubation, plates were ready to be read (signals then remained stable for up to 24 hours). Changes in time resolved fluorescence were monitored with excitation via a laser (337 nm) measuring both 615 nm and 665 nm emission wavelengths. For the AVP potency determination the first addition consisted of stimulation buffer containing 3% v/v DMSO and the second addition a 10-point dilution series of AVP (1:3 dilutions from 0.1 nM) in stimulation buffer. For compound profiling, test compounds were dispensed by the Labcyte Echo (10-point curve, 1:3 dilutions) in a target 0.1 μl volume then diluted 750-fold in stimulation buffer containing 3% DMSO prior to addition to the cells. At the end of the incubation period, 2.5 μl of AVP in stimulation buffer was added at the previously determined $EC_{80}$ concentration.

In-plate controls for the assay include a Tolvaptan concentration-response curve as the reference V2 antagonist and an AVP concentration-response curve to confirm the reproducibility of the $EC_{80}$ used for the compound challenge.

Data for fluorescence at 665 nm is normalised to in-plate assay controls comprising DMSO matched solutions of assay buffer without agonist (100% inhibition) and AVP $EC_{80}$ (0% inhibition).

Example B4

Oxytocin Receptor Antagonist Assay

This assay was performed in CHEM-1 cells expressing the human Oxytocin Receptor (hOTR) to determine the inhibitory effect of the compounds of the invention on the human Oxytocin receptor. Oxytocin evokes an increase in intracellular calcium in CHEM-1-hOTR cells which is measured in a fluorescence assay on the FLIPR$^{TETRA}$ using calcium sensitive dyes. Test compounds were assessed for their ability to affect the magnitude of the response to oxytocin, with antagonists showing a concentration-dependent reduction in the oxytocin-mediated fluorescence. Compounds displaying potency at the vasopressin V1a receptor of <100 nM were progressed to selectivity testing against hOTR and were tested in triplicate in a 10-point, 1:3 dilution series starting at a nominal concentration of 3 μM in the assay.

CHEM-1-hOTR ready was used to assay frozen cells (Eurofins #HTS090RTA) which are supplied with a proprietary Media Component.

Day 1 of the Assay:

Cells were thawed in a 37° C. water bath and diluted with the supplied Media Component to a final volume of 10 ml. The cell suspension was centrifuged at 1000 rpm for 3 min at room temperature and the supernatant was discarded. The cell pellet was resuspended in Media Component (10.5 ml) and the cells (25 μL) were dispensed into a poly-D-lysine coated black, clear bottomed, 384-well plate. The plates were incubated overnight at 37° C., 5% $CO_2$.

Day 2:

At the start of each assay day the potency of oxytocin was assessed and an $EC_{80}$ concentration was determined for subsequent compound profiling. Assays were performed using a two-step addition protocol on the FLIPR$^{TETRA}$; first addition of 5 μl of control or test compound at 10× final in assay buffer with 15 min incubation at 37° C., 5% $CO_2$ followed by 10 μl of oxytocin at 6× final concentration in assay buffer. Changes in fluorescence were monitored for 3 min after both additions on the FLIPR$^{TETRA}$ using 470-495 nm excitation and 515-575 nm emission wavelengths. The assay buffer consisted of HBSS (+Ca/+Mg) supplemented with 20 mM HEPES, and for the preparation of the oxytocin agonist only, 0.1% w/v bovine serum albumin. The assay was initiated by the removal of growth media from the cells and replaced with 45 μl of Calcium-6 dye (Molecular Devices) prepared at 1× in assay buffer. Cells were loaded with dye for 60-90 min at 37° C., 5% $CO_2$ before initiation of the FLIPR$^{TETRA}$ protocol. For the oxytocin potency determination the first addition consisted of assay buffer containing 3% v/v DMSO and the second addition involved a 10-point dilution series of oxytocin (1:3 dilutions from 1 μM) in assay buffer supplemented with 0.1% BSA. For compound profiling, test compounds were first serially diluted in DMSO (10-point curve, 1:3 dilutions) then diluted 33.3-fold in assay buffer prior to addition to the dye loaded cells on the FLIPR$^{TETRA}$. At the end of the incubation period 10 μl of oxytocin in assay buffer containing 0.1% BSA was added at the previously determined $EC_{80}$ concentration.

In-plate controls for the assay include a L-368,899 concentration-response curve as the reference OTR antagonist and an oxytocin concentration-response curve to confirm the reproducibility of the $EC_{80}$ used for the compound challenge.

MAX-MIN raw data is normalised to in-plate assay controls comprising DMSO matched solutions of assay buffer without agonist (100% inhibition) and oxytocin $EC_{80}$ (0% inhibition).

Activity expressed as $IC_{50}$ of representative compounds against the V1a, V1b, V2, and OT receptors is provided in Table 24 below. With respect to V1a, V1b, V2, and OT activity: "++++" denotes an $IC_{50}$ of less than 100 nM; "+++" denotes an $IC_{50}$ of from 100 nM to less than 500 nM; "++" denotes an $IC_{50}$ of from 500 nM to less than 1000 nM; and "+" denotes an $IC_{50}$ of 1000 nM or more. Reference compounds were assessed in the in vitro antagonist assay with the following results: balovaptan—V1A (++++), V1B (+), V2 (+), OT (+); relcovaptan—V1A (++++), V1B (−), V2 (−), OT (−); JNJ-17308616—V1A (++++), V1B (+), V2 (+++), OT (+).

TABLE 24

Activity of Representative Compounds

| Cpd No. | V1a $IC_{50}$ | V1b $IC_{50}$ | V2 $IC_{50}$ | OT $IC_{50}$ |
|---|---|---|---|---|
| 1 | ++++ | + | + | + |
| 2 | ++++ | + | + | + |
| 3 | ++++ | + | + | + |
| 4 | ++++ | + | + | + |
| 5 | +++ | − | − | + |
| 6 | ++++ | − | − | + |
| 7 | +++ | − | − | + |
| 8 | ++++ | + | + | + |
| 9 | +++ | − | − | ++ |
| 10 | +++ | − | − | + |
| 11 | ++ | − | − | + |
| 12 | +++ | − | − | + |
| 13 | +++ | − | − | + |
| 14 | + | − | − | + |
| 15 | + | − | − | + |
| 16 | ++++ | − | − | + |
| 24 | + | − | − | − |
| 25 | + | − | − | − |
| 26 | +++ | − | − | − |
| 27 | + | − | − | − |
| 28 | ++++ | + | + | + |
| 29 | + | − | − | − |
| 30 | +++ | − | − | − |
| 31 | +++ | − | − | − |
| 32 | + | − | − | − |
| 33 | + | − | − | − |
| 34 | ++ | − | − | − |
| 35 | +++ | − | − | − |
| 36 | ++++ | − | − | − |
| 37 | ++++ | − | − | + |
| 38 | ++++ | − | − | − |
| 39 | ++++ | + | + | + |
| 40 | ++++ | − | − | − |
| 41 | ++++ | + | ++++ | ++ |
| 42 | ++++ | + | ++++ | ++ |
| 43 | ++++ | − | − | − |

TABLE 24-continued

Activity of Representative Compounds

| Cpd No. | V1a IC$_{50}$ | V1b IC$_{50}$ | V2 IC$_{50}$ | OT IC$_{50}$ |
|---|---|---|---|---|
| 44 | ++++ | − | − | − |
| 45 | ++++ | + | +++ | + |
| 46 | ++++ | + | + | + |
| 47 | ++++ | + | + | + |
| 48 | ++++ | + | ++ | + |
| 49 | ++++ | + | +++ | + |
| 50 | ++++ | + | +++ | + |
| 51 | +++ | − | − | − |
| 52 | ++++ | + | +++ | ++ |
| 53 | ++++ | − | − | − |
| 54 | ++++ | + | ++ | + |
| 55 | +++ | − | − | − |
| 56 | ++++ | + | +++ | ++ |
| 57 | ++++ | + | + | + |
| 58 | ++++ | + | ++ | + |
| 59 | ++++ | + | ++ | + |
| 60 | +++ | − | − | − |
| 61 | ++++ | + | +++ | ++ |
| 62 | ++++ | − | − | − |
| 63 | ++++ | + | ++ | + |
| 64 | ++++ | + | +++ | + |
| 65 | ++++ | − | − | + |
| 66 | +++ | − | − | − |
| 67 | ++++ | + | + | + |
| 68 | ++++ | − | − | + |
| 69 | ++++ | + | +++ | +++ |
| 70 | ++++ | + | +++ | ++ |
| 71 | ++++ | + | + | + |
| 72 | ++++ | + | +++ | + |
| 73 | ++++ | − | − | + |
| 74 | ++++ | − | − | + |
| 75 | ++++ | − | − | − |
| 78 | ++++ | + | +++ | +++ |
| 79 | ++++ | + | ++ | +++ |
| 81 | ++++ | + | + | + |
| 82 | ++++ | − | − | − |
| 90 | ++++ | + | + | +++ |
| 91 | ++++ | − | − | ++ |
| 92 | ++++ | − | − | + |
| 93 | ++++ | − | − | + |
| 94 | ++++ | − | − | + |
| 95 | ++++ | − | − | ++ |
| 96 | ++++ | − | − | +++ |
| 97 | ++++ | − | − | − |
| 107 | ++++ | − | − | + |
| 108 | ++++ | − | − | + |
| 109 | ++++ | − | − | + |
| 110 | ++++ | − | − | + |
| 111 | ++++ | − | − | +++ |
| 112 | ++++ | − | − | + |
| 113 | ++++ | − | − | + |
| 114 | ++++ | − | − | + |
| 115 | ++++ | − | − | − |
| 116 | ++++ | − | − | + |
| 122 | ++++ | + | +++ | + |
| 124 | +++ | − | − | − |
| 125 | ++++ | − | − | + |
| 126 | + | − | − | − |
| 134 | ++++ | + | + | + |
| 136 | ++++ | + | + | + |
| 137 | ++++ | − | − | − |
| 138 | ++++ | − | − | + |
| 142 | ++++ | + | + | ++ |
| 142A | ++++ | + | + | + |
| 142B | ++ | + | + | ++ |
| 147 | ++++ | − | − | − |
| 153 | ++++ | + | + | + |
| 156 | ++++ | − | − | + |
| 157 | ++++ | − | − | + |
| 158 | ++++ | − | − | − |
| 159 | ++++ | − | − | − |
| 160 | ++++ | − | − | − |
| 161 | ++++ | − | − | + |
| 162 | ++++ | − | − | − |
| 163 | ++++ | − | − | − |
| 163A | ++++ | + | + | +++ |
| 163B | ++ | − | − | − |
| 164 | ++++ | + | + | +++ |
| 165 | ++++ | + | + | ++ |
| 165A | ++++ | + | + | ++ |
| 165B | ++ | − | − | − |
| 166 | ++++ | + | + | + |
| 166A | ++++ | + | + | + |
| 166B | ++ | − | − | − |
| 167 | ++++ | + | + | + |
| 167A | +++ | + | + | ++ |
| 167B | + | − | − | − |
| 168 | ++++ | + | + | + |
| 168A | ++++ | + | + | ++ |
| 168B | +++ | − | − | − |
| 169 | ++++ | + | + | +++ |
| 169A | ++++ | + | + | +++ |
| 169B | +++ | − | − | − |
| 170 | ++++ | + | + | + |
| 170A | ++++ | + | ++ | + |
| 170B | ++ | − | − | − |
| 171 | ++++ | + | + | + |
| 171A | ++++ | + | + | + |
| 171B | ++ | + | + | + |
| 172 | ++++ | + | + | + |
| 172A | ++++ | − | − | − |
| 172B | + | − | − | − |
| 173 | ++++ | + | + | +++ |
| 174 | ++++ | + | + | ++ |
| 174A | ++++ | + | + | +++ |
| 175 | ++++ | + | + | + |
| 176 | ++++ | − | − | − |
| 177 | ++++ | + | + | + |
| 178 | ++++ | − | − | − |
| 178A | ++++ | + | +++ | +++ |
| 178B | +++ | − | − | − |
| 179 | +++ | − | − | − |
| 179A | ++++ | + | + | + |
| 179B | +++ | − | − | − |
| 180 | ++++ | + | +++ | +++ |
| 181 | ++++ | − | − | − |
| 181A | ++++ | + | +++ | +++ |
| 181B | +++ | − | − | − |
| 182 | ++++ | + | ++ | ++ |
| 183 | +++ | − | − | +++ |
| 184 | +++ | − | − | − |
| 184A | ++++ | − | − | − |
| 184B | + | − | − | − |
| 185 | ++++ | − | − | ++ |
| 186 | +++ | − | − | − |
| 187 | +++ | − | − | − |
| 187A | ++++ | − | − | − |
| 187B | + | − | − | − |
| 188 | ++++ | − | − | +++ |
| 188A | ++++ | − | − | − |
| 188B | + | − | − | − |
| 189 | ++++ | − | − | + |
| 190 | ++++ | − | − | − |
| 191 | ++++ | − | − | ++ |
| 191A | ++++ | + | + | +++ |
| 191B | + | − | − | − |
| 192 | ++++ | − | − | − |
| 192A | ++++ | + | + | + |
| 192B | + | − | − | − |
| 193 | ++++ | − | − | + |
| 194 | ++++ | + | + | + |
| 194A | ++++ | − | − | − |
| 194B | + | − | − | − |
| 105 | ++++ | + | + | +++ |
| 196 | ++++ | + | − | + |
| 197 | +++ | − | − | − |
| 198 | +++ | − | − | − |
| 199 | ++++ | + | − | + |
| 200 | +++ | − | − | − |
| 201A | ++++ | + | + | − |

TABLE 24-continued

Activity of Representative Compounds

| Cpd No. | V1a IC$_{50}$ | V1b IC$_{50}$ | V2 IC$_{50}$ | OT IC$_{50}$ |
|---|---|---|---|---|
| 201B | ++ | − | − | − |
| 202A | ++++ | + | + | + |
| 202B | + | − | − | + |
| 203A | ++++ | + | ++ | +++ |
| 203B | + | − | − | + |
| 204A | ++++ | + | — | +++ |
| 204B | +++ | + | — | + |
| 205A | ++++ | + | — | ++ |
| 205B | + | + | — | + |
| 206A | ++++ | + | — | +++ |
| 206B | +++ | + | — | + |
| 217 | ++++ | − | − | − |
| 218 | ++++ | − | − | − |
| 219 | ++++ | − | − | − |
| 220 | ++++ | − | − | − |
| 221 | ++++ | − | − | − |
| 222 | ++++ | − | − | − |
| 223 | ++++ | − | ++++ | + |
| 224 | ++++ | − | − | − |
| 225 | ++++ | − | − | − |
| 226 | ++++ | − | − | − |
| 227 | ++++ | − | − | − |
| 228 | ++++ | − | − | − |
| 229 | ++++ | − | ++++ | ++ |
| 230 | ++++ | − | − | − |
| 231 | +++ | − | − | − |
| 232 | ++++ | − | − | − |
| 233 | ++++ | − | − | − |
| 234 | +++ | − | − | − |
| 235 | ++++ | − | − | − |
| 236 | ++++ | − | − | − |
| 237 | ++++ | − | − | − |
| 238 | ++++ | − | − | − |
| 239 | +++ | − | − | − |
| 240 | ++++ | − | − | − |
| 241 | ++++ | − | − | − |
| 242 | ++++ | − | − | − |
| 243 | +++ | − | − | − |
| 244 | ++++ | − | − | − |
| 245 | ++++ | − | − | − |
| 246 | ++++ | − | − | − |
| 247 | ++++ | − | − | − |
| 248 | ++++ | − | − | − |
| 249 | ++++ | − | − | − |
| 250 | ++++ | − | − | − |
| 251 | +++ | − | − | − |
| 252 | ++++ | − | − | − |
| 253 | +++ | − | − | − |
| 254 | +++ | − | − | − |
| 255 | ++++ | − | +++ | + |
| 256 | ++++ | − | − | − |
| 257 | ++ | − | − | − |
| 258 | + | − | − | − |
| 259 | ++++ | − | − | − |
| 260 | ++++ | − | − | − |
| 261 | ++++ | − | − | − |
| 262 | ++++ | − | − | − |
| 263 | ++++ | − | − | − |
| 264 | ++++ | − | − | − |
| 265 | +++ | − | − | − |
| 266 | ++ | − | − | − |
| 267 | + | − | − | − |
| 268 | +++ | − | − | − |
| 269 | ++ | − | − | − |
| 270 | +++ | − | − | − |
| 271 | ++++ | − | − | − |
| 272 | ++++ | − | − | − |
| 273 | ++++ | − | − | − |
| 274 | ++++ | − | − | − |
| 275 | ++++ | − | − | − |
| 276 | ++++ | − | − | − |
| 277 | +++ | − | − | − |
| 278 | ++++ | − | − | − |

Example B5

MDCK-MDR1 Effective Efflux Ratio

The MDR1-MDCK effective efflux assay was performed as described in the BioFocus Standard Operating Procedure, ADME-SOP-56. Both wild-type (WT) and MDR1-MDCK cells (Solvo Biotechnology) were seeded onto 24-well Transwell plates at 2.35×105 cells per well and used in confluent monolayers after a 3 day culture at 37° C. under 5% CO2. For both cell types, test and control compounds (propranolol, vinblastine) were added (10 μM, 0.1% DMSO final, n=2) to donor compartments of the Transwell plate assembly in assay buffer (Hanks balanced salt solution supplemented with 25 mM HEPES, adjusted to pH 7.4) for both apical to basolateral (A>B) and basolateral to apical (B>A) measurements. Incubations were performed at 37° C., with samples removed from both donor and acceptor chambers at T=0 and 1 hour and compound analysed by mass spectrometry (LC-MS/MS) including an analytical internal standard.

Apparent permeability (Papp) values were determined from the relationship:

$$\text{Papp} = [\text{Compound Acceptor } T=\text{end}] \times V \text{ Acceptor}/([\text{Compound Donor } T=0] \times V \text{ Donor})/\text{incubation time} \times V \text{ Donor/Area} \times 60 \times 10^{-6} \text{ cm/s}$$

Where V is the volume of each Transwell compartment (apical 125 basolateral 600 and concentrations are the relative MS responses for compound (normalized to internal standard) in the donor chamber before incubation and acceptor chamber at the end of the incubation. Area=area of cells exposed for drug transfer (0.33 cm2).

Efflux ratios (Papp B>A/Papp A>B) were calculated for each compound from the mean Papp values in each direction for both wild-type and MDR1-MDCK cells. The MDR1-MDCK cell line has been engineered to over-express the efflux transporter, MDR1 (P-glycoprotein), and a finding of good permeability B>A, but poor permeability A>B, suggests that a compound is a substrate for this transporter.

In order to confirm the involvement of MDR1 in any efflux seen, an "effective efflux ratio" (EER) was calculated by comparing compound efflux ratios (ER) in the two cell types, i.e.

$$\text{EER} = \text{ER(MDR1-MDCK)}/\text{ER(wild-type MDCK)}$$

This ratio illustrates the effect of the over-expressed MDR1 normalised for the background movement of compound through the wild-type cells.

Lucifer Yellow (LY) was added to the apical buffer in all wells to assess viability of the cell layer. Compound recovery from the wells was determined from MS responses (normalized to internal standard) in donor and acceptor chambers at the end of incubation compared to response in the donor chamber pre-incubation.

TABLE 25

Papp (10^−6 cm/sec), Efflux ratio, and Effective efflux ratio

| Compound No. | Papp AB MDR1 | MDR1 ER | MDR1 EER | Papp AB WT | WT ER |
|---|---|---|---|---|---|
| 1 | ++ | + | + | ++++ | ++ |
| 8 | ++++ | +++ | +++ | ++++ | ++++ |
| 16 | + | + | ++ | + | + |
| 19 | + | + | + | ++++ | +++ |
| 36 | + | + | + | +++ | ++ |
| 52 | +++ | + | + | ++++ | ++++ |
| 56 | ++++ | + | +++ | ++++ | ++ |
| 57 | + | + | + | ++++ | +++ |

TABLE 25-continued

Papp (10^-6 cm/sec), Efflux ratio, and Effective efflux ratio

| Compound No. | Papp AB MDR1 | MDR1 ER | MDR1 EER | Papp AB WT | WT ER |
|---|---|---|---|---|---|
| 59 | ++ | + | + | ++++ | ++++ |
| 61 | +++ | + | + | ++++ | +++ |
| 63 | + | + | + | ++++ | ++++ |
| 64 | + | + | + | +++ | + |
| 65 | + | + | + | ++++ | ++++ |
| 67 | + | + | + | ++++ | +++ |
| 69 | ++++ | +++ | ++ | ++++ | ++++ |
| 70 | +++ | + | + | ++++ | ++++ |
| 71 | + | + | + | ++++ | ++++ |
| 72 | + | + | + | ++++ | +++ |
| 73 | + | + | + | +++ | + |
| 74 | + | + | + | ++++ | +++ |
| 75 | + | + | + | +++ | + |
| 75 | ++ | + | + | ++++ | ++++ |
| 78 | ++++ | ++ | ++ | ++++ | ++++ |
| 79 | +++ | + | + | ++++ | +++ |
| 81 | ++ | + | + | ++++ | +++ |
| 90 | ++++ | ++ | + | ++++ | ++++ |
| 91 | + | + | + | ++++ | ++++ |
| 92 | ++ | + | + | ++++ | +++ |
| 93 | + | + | + | + | + |
| 94 | + | + | + | +++ | + |
| 95 | + | + | + | ++++ | +++ |
| 96 | ++++ | +++ | +++ | ++++ | ++++ |
| 107 | + | + | + | +++ | + |
| 110 | + | + | + | +++ | + |
| 111 | ++++ | +++ | ++ | ++++ | ++++ |
| 113 | + | + | + | ++++ | +++ |
| 114 | + | + | + | + | + |
| 115 | +++ | + | + | ++++ | +++ |
| 116 | + | + | + | ++++ | ++++ |
| 122 | ++ | + | + | ++++ | ++++ |
| 125 | + | + | + | ++++ | +++ |
| 136 | + | + | + | +++ | + |
| 137 | + | + | + | + | + |
| 142 | ++++ | ++ | + | ++++ | ++++ |
| 142A | ++++ | ++ | ++ | ++++ | ++++ |
| 147 | + | + | + | + | + |
| 153 | + | + | + | ++++ | ++ |
| 156 | +++ | + | ++ | ++++ | +++ |
| 160 | + | + | + | + | + |
| 162 | + | + | + | + | + |
| 163 | ++++ | +++ | +++ | ++++ | ++++ |
| 163A | ++++ | +++ | +++ | ++++ | ++++ |
| 165 | ++ | + | + | ++++ | +++ |
| 165A | + | + | + | ++++ | +++ |
| 165B | + | + | + | ++++ | +++ |
| 166 | + | + | + | ++++ | +++ |
| 166A | + | + | + | ++++ | +++ |
| 166B | + | + | + | ++++ | +++ |
| 167 | ++++ | +++ | +++ | ++++ | +++ |
| 167A | ++++ | ++++ | -- | ++++ | ++++ |
| 168 | ++ | + | + | ++++ | +++ |
| 168A | ++++ | ++++ | -- | ++++ | ++++ |
| 169 | ++++ | +++ | +++ | ++++ | +++ |
| 169A | ++++ | ++++ | -- | ++++ | ++++ |
| 170 | +++ | + | + | ++++ | ++++ |
| 171 | +++ | + | + | ++++ | ++++ |
| 171A | + | + | + | ++++ | +++ |
| 172 | ++++ | ++ | ++ | ++++ | ++++ |
| 172A | ++++ | ++ | ++ | ++++ | +++ |
| 173 | ++++ | +++ | +++ | ++++ | ++++ |
| 174 | ++++ | +++ | ++ | ++++ | ++++ |
| 174A | ++++ | +++ | +++ | ++++ | ++++ |
| 175A | + | + | + | ++++ | ++++ |
| 175B | + | + | + | ++++ | ++++ |
| 176 | ++ | + | + | ++++ | ++++ |
| 177 | + | + | + | ++++ | +++ |
| 178A | ++++ | ++++ | -- | ++++ | ++++ |
| 179 | ++++ | + | ++ | ++++ | +++ |
| 180 | ++++ | +++ | -- | ++++ | ++++ |
| 181A | ++++ | ++++ | ++ | ++++ | ++++ |
| 182 | ++++ | +++ | +++ | ++++ | +++ |
| 184A | ++ | + | + | ++++ | ++++ |
| 185 | ++++ | +++ | ++ | ++++ | ++++ |
| 187 | ++++ | ++ | -- | ++++ | ++++ |
| 191A | ++++ | +++ | +++ | ++++ | +++ |
| 192 | ++++ | +++ | +++ | ++++ | +++ |
| 192A | ++++ | ++ | ++ | ++++ | +++ |
| 193 | ++++ | +++ | +++ | ++++ | +++ |
| 194 | +++ | + | + | +++ | ++++ |
| 194A | +++ | + | + | ++++ | +++ |
| 195 | ++++ | +++ | ++++ | +++ | +++ |
| 197 | ++++ | ++ | + | ++++ | ++++ |
| 200 | + | + | + | ++++ | ++ |
| 201A | ++++ | +++ | +++ | ++++ | ++++ |
| 202 | + | + | + | ++++ | ++++ |
| 202A | + | + | + | ++++ | +++ |
| 202B | + | + | + | ++++ | +++ |
| 203 | +++ | ++ | +++ | ++++ | +++ |

MDCK II Cell Permeability Assay Procedure

MDCK II cell culture media was prepared using Dulbecco's modified eagle medium (DMEM), fetal bovine serum (FBS) 10%, Glutamax 1% and PenStrep 1% and was sterile-filtered. Transwell 24-well plates of MDCK II_WT or MDCK II-MDR1 cells were prepared and the plates were fed every alternate day until the day of use. Plates were used on 5th day after cell plating. Preparation for changing the media of the basal plate was conducted by filling all wells of a 24 well sterile plate with 900 µl of culture media and placing it in an incubator until use. Then the apical section of plate was lifted out and lowered onto an empty basal plate, followed by aspiration of 200 µl of the culture media from the apical compartment and replacement with 200 µl of fresh culture media. This step was repeated twice for a total of 3 washes followed by removal of the basal plate from the incubator and placement of the plate in the hood. The apical section of plate was then added to the basal plate and returned to incubator.

On the day of the assay, approximately 3 ml of 1000-fold diluted compound solution (required concentration for the assay) was prepared in transport buffer using the following volumes: 200 µl/insert/well (apical application) and 780 µl/insert/well (basal application). The basal assay plate was prepared by adding 750 µl of transport buffer (Hank's Balanced Salt Solution) to A-B wells, and 780 µl of diluted compound solution to B-A wells. Triplicate samples of 10 µl each were collected from basal compartments of B-A wells for T0, and then basal assay plates were placed in the incubator. MDCK plates were placed in the hood and the apical section of the plates were lifted out and lowered onto empty basal plates. 200 µl of the media was removed from the apical wells and replaced with 200 µl of fresh transport media, and this step was repeated twice for a total of 3 washes. 200 µl of the media was removed from the apical wells and replaced with 200 µl of the diluted compound (for A-B wells) or 200 µl of fresh transport buffer (for B-A wells). Triplicate samples were collected (10 µl each) from apical compartments of A-B wells for T0. Basal plates were removed from the incubator and transferred to the apical section of the plate to the basal plate and the assay plates were covered and returned to the incubator. The T0 samples were diluted with 40 µl transport buffer and 100 µl of room temperature quench solution was added to the diluted T0 samples. 50 µl of all T0 samples were mixed and transferred to T0 sample plates and diluted with 1000 of MilliQ water for bioanalysis. At T-2 hrs, 3 replicate 10 µl samples from all apical compartments and B-A basal compartments were collected; and, 3 replicate 50 µl samples from A-B basal compartments were collected. The 10 µl samples were diluted with 40 µl transport buffer. 100 µl of quench solution was added to all T-2 hrs samples. 50 µl of all T-2 hrs samples were mixed and transferred to sample plates and diluted with 1000 of MilliQ water for bioanalysis.

Analyte levels (peak area ratios) were measured on apical (A) and basolateral (B) sides at T0 and T2 hrs. A-to-B and B-to-A fluxes were calculated (mean of n=3 measurements). Apparent permeability (Papp, 10^-6 cm/sec) was calculated as dQ (flux)/(dt×Area×Concentration).

The efflux ratio was (B-to-A)/(A-to-B) ratio [i.e., Papp (B-A)/Papp(B-A)]. A ratio >2-3 was determined as evidence of efflux, and compounds that demonstrate efflux ratios in or above this range PGP efflux can be confirmed by testing+/−pgp inhibitor (dosing solutions prepared with and without verapamil at a final assay concentration of 25

The ability of a test compound to penetrate the blood brain barrier and avoid efflux by transporters expressed in the brain, can be roughly correlated with the Papp(A-B) and the efflux ratio (as defined above), respectively, the results are provided in Table 26. (+) denotes an apparent permeability <7 (10^-6 cm/sec); (++) denotes >7 (10^-6 cm/sec) but <10 (10^-6 cm/sec; (+++) denotes >10 (10^-6 cm/sec) but <20 (10^-6 cm/sec); and (++++) denotes >20 (10^-6 cm/sec). PGP efflux can be confirmed by testing+/−pgp inhibitor (dosing solutions prepared with and without verapamil at a final assay concentration of 25 µM). Reference compounds were assessed in the in vitro MDCK apparent permeability, efflux ratio, and effective efflux ratio assays (MDR1 and WT) with the following results: balovaptan—MDR1AB (++++), MDR1ER (++), MDR1EER (++), WTAB (+++), WTER (++++); JNJ-17308616—MDR1AB (+), MDR1ER (+), MDR1EER (+), WTAB (+++), WTER (+).

TABLE 26

Papp (10^-6 cm/sec) and Efflux ratio

| Compound No. | Papp AB MDR1 | MDR1 ER |
|---|---|---|
| 218 | ++++ | ++++ |
| 220 | ++++ | +++ |
| 223 | ++++ | +++ |
| 224 | ++++ | ++++ |
| 225 | ++++ | +++ |
| 226 | + | + |
| 242 | ++++ | ++ |
| 255 | ++++ | +++ |
| 259 | ++++ | ++++ |

In Vivo Activity

Example B6

Evaluation of Behavioral, Biochemical and/or Neurophysiological Characteristics in the Valproate Model Valproate (VPA) is an anticonvulsant drug commonly prescribed for patients with epilepsy. During pregnancy, administration of VPA elevates the risk of neurodevelopmental disorders in the offspring and this effect has been modeled similarly in rodents to better understand the mechanisms underlying the VPA-induced neurodevelopmental changes. V1a antagonists are assessed for preventative and/or restorative effects in rodents following the administration of a single injection of valproate acid (600 mg/kg) or vehicle (sham) to pregnant females dams on gestational day 13 (embryonic day 13). Pregnant dams are monitored on a daily basis for changes in weight and health, or in their feeding patterns. After birth, pups are monitored for any signs of physical abnormalities (e.g., weights, food and water intake, postnatal day of eye opening).

Selective studies are conducted to evaluate behavioral, biochemical and/or neurophysiological characteristics of the valproate treated animals as compared to control animals. More specifically, the effects of V1 antagonists administered to VPA treated animals are assessed using standard methodology for behavioral changes such as anxiety (e.g., ultrasonic vocalizations, elevated plus maze), learning and memory (e.g., Morris water maze, novel object recognition), social interactions, sensorimotor gating and locomotor activity. Biochemical changes are measured by assessing synaptic proteins and mRNA (e.g., gamma-aminobutyric acid [GABA] synthesis, glutamic acid decarboxylase [GAD], brain derived neurotrophic factor [BDNF]). Neurophysiological characteristics are assessed by whole cell recordings of the electrophysiological properties of neurons from VPA- and sham-treated animals to identify differences in neuronal function with and without V1 antagonists.

Activity and/or Telemetry Studies in Rodents and Non-Human Primates to Assess Sleep/Wake Cycles and Circadian Rhythms:

The vasopressin system is important in regulating biological circadian rhythms and re-entrainment following environmental alterations. In these studies, animals are housed on a 12 hour light/dark cycle and activity is monitored using an infrared beam break system or by wheel running (rodents) or by activity monitors attached to the collar of the animal (non-human primates). Activity data is collected for up to 30 days to establish circadian rhythms and changes induced by phase shifting the light/dark cycle by e.g., 4, 8 or 12 hours is recorded and analyzed. V1a antagonist is administered to improve re-entrainment as measured by re-establishment of the regular activity patterns. Additional endpoints may include cognitive assessment (e.g., spatial working memory).

Implantation of a telemetry device with electrodes to record electroencephalography/electromoyography/electroculography (EEG/EMG/EOG) for staging sleep/wake cycles is used. In this case, EEG/EMG electrodes and transmitters are implanted in fully anesthetized animals by trained surgeons. The transmitter module is implanted subcutaneously below the scapular region or into the abdomen. Biopotential leads are guided subcutaneously from the back to the head via a midline incision. Using a stereotaxic approach, stainless steel screws are implanted into the skull over areas of interest until the tips are on the surface of the dura mater. The biopotential leads are wrapped around the screws and referenced. The EMG or EOG leads are sutured into the temporalis muscle or intra-ocular muscle, respectively. Animals receive postoperative analgesia and antibiotics and recover for a minimum of 21-days before testing. Receiver boards are placed in close proximity to the animal to facilitate real-time EEG/EMG/EOG recordings during testing.

Physiological Measures

Vasopressin is an important regulator of water conservation and blood pressure in the body and its release into the peripheral blood supply can be induced by an increase in plasma osmolality. In healthy adults, a rise in plasma osmolality of 1-2% above basal level produces thirst that promotes water intake and normalization of osmolality. Intravenous administration of a hyperosmolic solution to rodents or humans increases the plasma vasopressin concentration and other measures (e.g., thirst, urine output and vasoconstriction). V1a antagonist is evaluated for its ability to alter plasma vasopressin concentrations, vasoconstriction and/or urine output following administration of a hyperosmolic solution.

Example B7

Arginine-Vasopressin (AVP) Induced Phospho-Erk Measurement in Native Tissue

When V1a receptors are coupled to phospholipase C (PLC), they increase intracellular Ca2+ concentrations and protein kinase C (PKC) activity, and transactivate the mitogen-activated protein kinases/extracellular signal-regulated kinase (MAPK/Erk) and PI3 kinase/Akt pathways upon activation (Chen et al., J Neuroendocrinol. 2010). Rat choroid plexus (RCP) cell lines express functional V1a receptors measured by increased calcium concentrations in response to V1a receptor agonists (Battle et al., Biochem Biophys Res Comm 2000). In these studies, RCP were stimulated with AVP and V1a receptor antagonists reference compounds relcovaptan and balovaptan and test compound 142A were evaluated.

RCP P9(18) cells were seeded 30K/well, in 100 µl growth medium containing 10% FBS in polystyrene 96-well plates and incubated at 37° C., 5% CO2 and incubated overnight. The following day, the growth medium was replaced with 50 µl pre-warmed HBSS containing 20 mM HEPES and the cells were incubated at 37° C., 5% CO2 for 1.5 hrs. 1 mM AVP (Sigma V9879) was freshly prepared in distilled water in a glass vial, and diluted to 3× concentrations in HBSS containing 20 mM HEPES and 0.1% BSA in glass vials and kept on ice. Cells were treated with 25 µl 3× vehicle, 3× eBioscience Cell Stimulation Cocktail (Thermo Fisher Scientific 00-4970-93) or 3×AVP and incubated at 37° C., 5% CO2 for 5, 10 or 20 min. Final concentrations of AVP: 10, 100 or 1000 nM. Final concentrations of components in Cell Stimulation Cocktail: 81 nM PMA, 1.34 µM ionomycin, 0.2% ethanol. Cells were lysed with 25 µl 4×CST lysis buffer containing protease and phosphatase inhibitors, PMSF and SDS and then stored at −80° C., for 48 h. The lysates were thawed, centrifuged at 2000 g for 30 min at 4° C. and 40 µl supernatants assayed for pERK1/2 (Thr202/Tyr204; Thr185/Tyr187) and total ERK1/2 using MSD kit K15107D. The MSD ECL data for the lysates were corrected for no cell blanks, then phospho-protein levels expressed as a ratio to the total ERK1/2 level. The ratios were expressed as fold-change from the vehicle-treated control at each timepoint. In study 1, the $IC_{50}$ values for the compounds tested, ralcovaptan, 142A and balovaptan were: 0.03 nM, 16.0 nM, 85.6 nM and 10.9 nM, respectively. In the second study, the $IC_{50}$ values for the compounds tested, ralcovaptan, 142A and balovaptan were: 0.08 nM, 20.0 nM, 56.7 nM and 13.6 nM, respectively. Ralcovaptan and balovaptan are purchased commercially.

Example B8

Arginine-Vasopressin (AVP) Induced Behavior in Mouse

Administration of Arginine-Vasopressin (AVP) intracerebroventricularly (i.c.v.) elicits characteristic scratching, digging and grooming behavior in mice that can be measured readily and is sensitive to blockade with vasopressin antagonists (Meisenberg, 1988; Bleickart et al., 2009).

Male CD-1 mice (Charles River Germany) weighing 22-25 g upon the study in-life are used for this study. Animals are housed in groups of 4-5 per cage in standard temperature (22±1° C.) and light-controlled environment (lights on from 7 am to 8 µm), with ad libitum access to food and water. Prior to commencing any procedures to the mice, they are allowed to habituate in the vivarium for a minimum of 7 days.

Anesthesia is induced in a plexiglass chamber for 2-3 min with 5% isoflurane, and maintained through a snout mask with 1-2% isoflurane thereafter. A homeothermic blanket system with a rectal probe is used to monitor and maintain the animal's body temperature at 37.0° C.±1.5° C. during the operation. Anesthetized mice are placed in a stereotaxic apparatus and skin between the ears shaved and disinfected with povidone-iodine solution (Betadine). A 10-µl Hamilton syringe with 28-gauge needle is used for the i.c.v. injections. All animals receive identical AVP injections (3.689 µM) or sterile saline (0.9% sodium chloride solution) into the right lateral ventricle at the following coordinates: AP=+0.5 mm; ML=+1.0 mm; DV=−2.5 mm (approximately from bregma). The actual coordinates are calculated by the distance from the point in midline between the eyes and no skin incision is made. After the needle is placed in the ventricle and the AVP is delivered, the needle is left in place for 3 minutes before withdrawal. Finally, the mouse is detached from the anesthesia mask and immediately placed in a clean cage to commence the observation.

Mice are observed and video-recorded for 15 minutes following AVP/saline administration and behaviors are measured (in seconds) and a cumulative time is calculated. The following behaviors are considered as AVP-related: scratching of limbs or torso, digging, licking and face washing (swiping of face).

Using this assay, balovaptan (100 and 300 mg/kg, po) and JNJ-17308616 (30, 100 mg/kg, po) were evaluated for antagonist activity to AVP-induced scratching behaviors. Balovaptan was effective at 100 mg/kg and JNJ-17308616 showed weak effects at 100 mg/kg.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure

We claim:
1. A compound having the following structure:

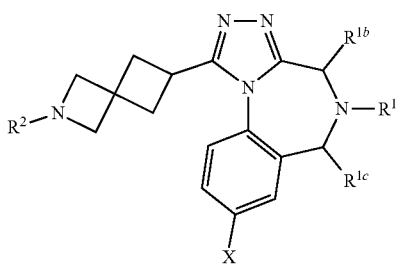

or a pharmaceutically acceptable isomer, racemate, hydrate, solvate, isotope, or salt thereof:
wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ and $R^{1c}$ are independently hydrogen, lower alkyl, or spiroalkyl;
$R^2$ is -Q-$(R^4)_n$, —S(=O)$_2R^5$, or —C(=O)$R^5$;
$R^3$ is lower alkyl, lower haloalkyl, lower alkoxy, lower haloalkoxy, -cycloalkyl-$R^6$, —O-cycloalkyl-$R^6$, —O-heterocyclyl-$R^6$, —NH$R^5$, or —N$R^5R^5$;
or $R^{1b}$ and $R^1$ or $R^{1b}$ and $R^3$, together with the atoms to which they are attached, form a ring;
Q is aryl or heteroaryl;
each $R^4$ is independently halogen, hydroxy, lower alkyl, lower haloalkyl, lower alkoxy, lower haloalkoxyalkyl, or cyano;
each $R^5$ is independently cycloalkyl, lower alkyl, lower haloalkyl, cycloalkylalkyl, lower alkoxy, heterocyclyl, or —O-heterocyclyl;
$R^6$ is hydrogen, halo, alkyl, lower haloalkyl, or cyano; and
n is 0, 1, or 2.

2. The compound of claim 1 having the structure of Formula

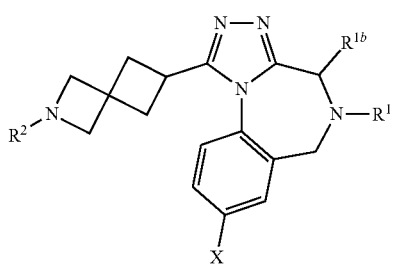

or a pharmaceutically acceptable isomer, racemate, hydrate, solvate, isotope, or salt thereof:
wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^2$ is -Q-$(R^4)_n$, —S(=O)$_2R^5$, or —C(=O)$R^5$;
$R^3$ lower alkyl, lower haloalkyl, alkoxy, lower haloalkoxy, -cycloalkyl-$R^6$, —O-cycloalkyl-$R^6$, or —O-heterocyclyl-$R^6$;
or $R^{1b}$ and $R^1$ or $R^{1b}$ and $R^3$, together with the atoms to which they are attached, form a ring
Q is aryl or heteroaryl;
each $R^4$ is independently halogen, hydroxy, lower alkyl, lower haloalkyl, lower alkoxy, lower haloalkoxyalkyl, or cyano;
$R^5$ is cycloalkyl, lower alkyl, lower haloalkyl, cycloalkylalkyl, lower alkoxy, lower haloalkoxy, heterocyclyl, or —O-heterocyclyl;
$R^6$ is hydrogen, halo, alkyl, lower haloalkyl, or cyano; and
n is 0, 1, or 2.

3. The compound of claim 2 or a pharmaceutically acceptable isomer, racemate, hydrate, solvate, isotope, or salt thereof, wherein
Q is heteroaryl; and
$R^5$ is cycloalkyl, lower alkyl, lower haloalkyl, cycloalkylalkyl, lower alkoxy, heterocyclyl, or —O-heterocyclyl.

4. The compound of claim 1 having the structure of Formula (IV):

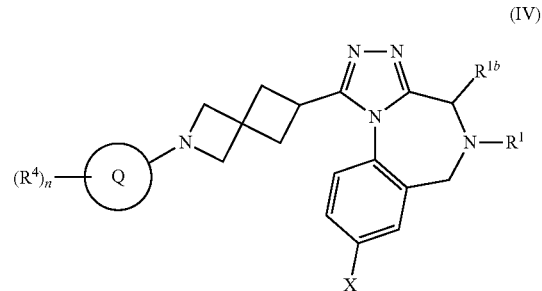

or a pharmaceutically acceptable isomer, racemate, hydrate, solvate, isotope, or salt thereof:
wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^3$ is lower alkyl, lower haloalkyl, alkoxy, lower haloalkoxy, -cycloalkyl-$R^6$, —O-cycloalkyl-$R^6$, or —O-heterocyclyl-$R^6$;
or $R^{1b}$ and $R^1$ or $R^{1b}$ and $R^3$, together with the atoms to which they are attached, form a ring;
Q is heteroaryl;
each $R^4$ is independently halogen, hydroxy, lower alkyl, lower haloalkyl, lower alkoxy, lower haloalkoxyalkyl, or cyano;
$R^6$ is hydrogen, halo, alkyl, lower haloalkyl, or cyano; and
n is 0, 1, or 2.

5. The compound of claim 1 having the structure of Formula (V):

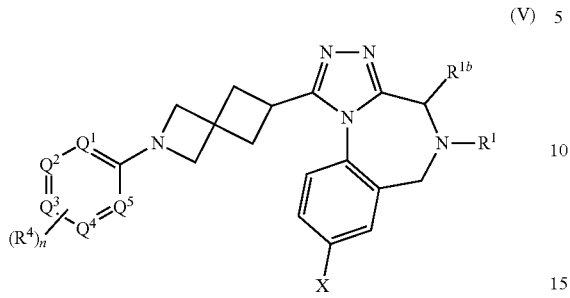

(V)

or a pharmaceutically acceptable isomer, racemate, hydrate, solvate, isotope, or salt thereof:
wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^3$ is lower alkyl, lower haloalkyl, alkoxy, lower haloalkoxy, -cycloalkyl-$R^6$, —O-cycloalkyl-$R^6$, or —O-heterocyclyl-$R^6$;
or $R^{1b}$ and $R^1$ or $R^{1b}$ and $R^3$, together with the atoms to which they are attached, form a ring;
$Q^1$, $Q^2$, $Q^3$, $Q^4$, and $Q^5$ are independently N, CH, or $CR^4$;
each $R^4$ is independently halogen, hydroxy, lower alkyl, lower haloalkyl, lower alkoxy, lower haloalkoxyalkyl, or cyano;
$R^6$ is hydrogen, halo, alkyl, lower haloalkyl, or cyano; and
n is 0, 1, or 2.

6. The compound of claim 1 having the structure of Formula (VI):

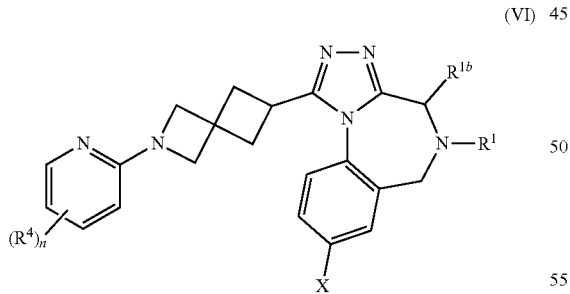

(VI)

or a pharmaceutically acceptable isomer, racemate, hydrate, solvate, isotope, or salt thereof:
wherein
X is halogen, lower alkyl, lower haloalkyl, lower alkoxy, or cyano;
$R^1$ is hydrogen, lower alkyl-$R^6$, haloalkyl, lower alkoxyalkyl, -cycloalkyl-$R^6$, -alkyl-cycloalkyl-$R^6$, -aryl-$R^6$, -alkyl-aryl-$R^6$, -heterocyclyl-$R^6$, -alkyl-heterocyclyl-$R^6$, lower haloalkyl, -alkyl-C(=O)$R^3$, or —C(=O)$R^3$;
$R^{1b}$ is hydrogen or lower alkyl;
$R^3$ is lower alkyl, lower haloalkyl, alkoxy, lower haloalkoxy, -cycloalkyl-$R^6$, —O-cycloalkyl-$R^6$, or —O-heterocyclyl-$R^6$;
or $R^{1b}$ and $R^1$ or $R^{1b}$ and $R^3$, together with the atoms to which they are attached, form a ring;
each $R^4$ is independently halogen, hydroxy, lower alkyl, lower haloalkyl, lower alkoxy, lower haloalkoxyalkyl, or cyano;
$R^6$ is hydrogen, halo, alkyl, lower haloalkyl, or cyano; and
n is 0, 1, or 2.

7. The compound of claim 1, or a pharmaceutically acceptable isomer, racemate, hydrate, solvate, isotope, or salt thereof, wherein $R^1$ is lower alkyl.

8. The compound of claim 1, or a pharmaceutically acceptable isomer, racemate, hydrate, solvate, isotope, or salt thereof, wherein n is 0.

9. The compound of claim 1, or a pharmaceutically acceptable isomer, racemate, hydrate, solvate, isotope, or salt thereof, wherein X is halogen.

10. The compound of claim 1, or a pharmaceutically acceptable isomer, racemate, hydrate, solvate, isotope, or salt thereof, having the structure of any of the compounds of Table 1.

11. A composition comprising a compound of claim 1, or a pharmaceutically acceptable isomer, racemate, hydrate, solvate, isotope, or salt thereof, and a pharmaceutically acceptable carrier, diluent, or excipient.

* * * * *